(12) United States Patent
Shelton, IV et al.

(10) Patent No.: US 11,744,604 B2
(45) Date of Patent: Sep. 5, 2023

(54) SURGICAL INSTRUMENT WITH A HARDWARE-ONLY CONTROL CIRCUIT

(71) Applicant: Cilag GmbH International, Zug (CH)

(72) Inventors: Frederick E. Shelton, IV, Hillsboro, OH (US); David C. Yates, Morrow, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 200 days.

(21) Appl. No.: 16/220,281

(22) Filed: Dec. 14, 2018

(65) Prior Publication Data
US 2019/0201025 A1 Jul. 4, 2019

Related U.S. Application Data

(60) Provisional application No. 62/778,571, filed on Dec. 12, 2018, provisional application No. 62/750,529, (Continued)

(51) Int. Cl.
*A61B 34/00* (2016.01)
*A61B 17/295* (2006.01)
(Continued)

(52) U.S. Cl.
CPC ............ *A61B 17/295* (2013.01); *A61B 5/065* (2013.01); *A61B 17/0469* (2013.01); *A61B 17/072* (2013.01); *A61B 17/07207* (2013.01); *A61B 17/1285* (2013.01); *A61B 17/29* (2013.01); *A61B 17/320068* (2013.01); *A61B 18/1445* (2013.01); *A61B 34/30* (2016.02); *A61B 34/76* (2016.02); *A61B 90/98* (2016.02); *G01S 17/04* (2020.01); *H03K 3/033* (2013.01); *H03K 3/355* (2013.01); *H03K 17/945* (2013.01); *H03K 17/9622* (2013.01); *A61B 17/0467* (2013.01); *A61B 17/12013* (2013.01); (Continued)

(58) Field of Classification Search
CPC ............................................. A61B 2017/00017
See application file for complete search history.

(56) References Cited

U.S. PATENT DOCUMENTS 1,853,416 A 4/1932 Hall
2,222,125 A 11/1940 Stehlik
(Continued)

FOREIGN PATENT DOCUMENTS

AU 2015201140 A1 3/2015
CA 2795323 A1 5/2014
(Continued)

OTHER PUBLICATIONS

US 10,504,709 B2, 12/2019, Karancsi et al. (withdrawn)
(Continued)

*Primary Examiner* — John R Downey

(57) ABSTRACT

A surgical instrument is disclosed. The surgical instrument includes an electric motor and a control circuit. The control circuit includes a plurality of logic gates and a monostable multivibrator. The monostable multivibrator is connected to a first one of the logic gates. The control circuit is configured to alter a rate of action of a function of the surgical instrument by controlling a speed of rotation of the electric motor based on a sensed parameter.

22 Claims, 130 Drawing Sheets

Related U.S. Application Data filed on Oct. 25, 2018, provisional application No. 62/750,539, filed on Oct. 25, 2018, provisional application No. 62/750,555, filed on Oct. 25, 2018, provisional application No. 62/665,129, filed on May 1, 2018, provisional application No. 62/665,177, filed on May 1, 2018, provisional application No. 62/665,134, filed on May 1, 2018, provisional application No. 62/665,128, filed on May 1, 2018, provisional application No. 62/665,192, filed on May 1, 2018, provisional application No. 62/665,139, filed on May 1, 2018, provisional application No. 62/659,900, filed on Apr. 19, 2018, provisional application No. 62/649,320, filed on Mar. 28, 2018, provisional application No. 62/649,307, filed on Mar. 28, 2018, provisional application No. 62/649,294, filed on Mar. 28, 2018, provisional application No. 62/649,309, filed on Mar. 28, 2018, provisional application No. 62/649,310, filed on Mar. 28, 2018, provisional application No. 62/649,313, filed on Mar. 28, 2018, provisional application No. 62/649,327, filed on Mar. 28, 2018, provisional application No. 62/649,315, filed on Mar. 28, 2018, provisional application No. 62/649,323, filed on Mar. 28, 2018, provisional application No. 62/649,300, filed on Mar. 28, 2018, provisional application No. 62/649,291, filed on Mar. 28, 2018, provisional application No. 62/649,296, filed on Mar. 28, 2018, provisional application No. 62/649,302, filed on Mar. 28, 2018, provisional application No. 62/649,333, filed on Mar. 28, 2018, provisional application No. 62/611,341, filed on Dec. 28, 2017, provisional application No. 62/611,339, filed on Dec. 28, 2017, provisional application No. 62/611,340, filed on Dec. 28, 2017.

(51) Int. Cl.

| | | |
|---|---|---|
| *A61B 17/128* | (2006.01) | |
| *A61B 17/29* | (2006.01) | |
| *A61B 17/072* | (2006.01) | |
| *H03K 17/96* | (2006.01) | |
| *H03K 3/033* | (2006.01) | |
| *H03K 17/945* | (2006.01) | |
| *A61B 18/14* | (2006.01) | |
| *A61B 5/06* | (2006.01) | |
| *A61B 17/32* | (2006.01) | |
| *H03K 3/355* | (2006.01) | |
| *A61B 90/98* | (2016.01) | |
| *G01S 17/04* | (2020.01) | |
| *A61B 34/30* | (2016.01) | |
| *A61B 17/04* | (2006.01) | |
| *A61B 18/12* | (2006.01) | |
| *A61B 18/00* | (2006.01) | |
| *A61B 17/00* | (2006.01) | |
| *A61B 90/00* | (2016.01) | |
| *A61B 34/20* | (2016.01) | |
| *H03K 17/97* | (2006.01) | |
| *A61B 17/12* | (2006.01) | |
| *A61B 17/3205* | (2006.01) | |

(52) U.S. Cl.

CPC . *A61B 17/32056* (2013.01); *A61B 2017/0003* (2013.01); *A61B 2017/00017* (2013.01); *A61B 2017/00022* (2013.01); *A61B 2017/00039* (2013.01); *A61B 2017/0046* (2013.01); *A61B 2017/00075* (2013.01); *A61B 2017/00084* (2013.01); *A61B 2017/00115* (2013.01); *A61B 2017/00123* (2013.01); *A61B 2017/00154* (2013.01); *A61B 2017/00176* (2013.01); *A61B 2017/00199* (2013.01); *A61B 2017/00221* (2013.01); *A61B 2017/00358* (2013.01); *A61B 2017/00398* (2013.01); *A61B 2017/00464* (2013.01); *A61B 2017/00473* (2013.01); *A61B 2017/00477* (2013.01); *A61B 2017/00482* (2013.01); *A61B 2017/00734* (2013.01); *A61B 2017/00876* (2013.01); *A61B 2017/07285* (2013.01); *A61B 2017/2901* (2013.01); *A61B 2017/2903* (2013.01); *A61B 2017/2927* (2013.01); *A61B 2017/2931* (2013.01); *A61B 2018/0091* (2013.01); *A61B 2018/00178* (2013.01); *A61B 2018/00303* (2013.01); *A61B 2018/00678* (2013.01); *A61B 2018/00702* (2013.01); *A61B 2018/00797* (2013.01); *A61B 2018/00875* (2013.01); *A61B 2018/00988* (2013.01); *A61B 2018/00994* (2013.01); *A61B 2018/1253* (2013.01); *A61B 2034/2051* (2016.02); *A61B 2034/301* (2016.02); *A61B 2034/305* (2016.02); *A61B 2090/065* (2016.02); *A61B 2090/0803* (2016.02); *A61B 2090/0807* (2016.02); *A61B 2090/0808* (2016.02); *A61B 2090/0809* (2016.02); *A61B 2562/0257* (2013.01); *A61B 2562/08* (2013.01); *H03K 2017/9706* (2013.01)

(56) References Cited

U.S. PATENT DOCUMENTS

| | | | | |
|---|---|---|---|---|
| 3,082,426 | A | | 3/1963 | Miles |
| 3,503,396 | A | | 3/1970 | Pierie et al. |
| 3,584,628 | A | | 6/1971 | Green |
| 3,626,457 | A | * | 12/1971 | Duerr ................ B23D 36/0041 |
| | | | | 83/74 |
| 3,633,584 | A | | 1/1972 | Farrell |
| 3,759,017 | A | | 9/1973 | Young |
| 3,863,118 | A | * | 1/1975 | Lander ...................... H02P 8/24 |
| | | | | 318/685 |
| 3,898,545 | A | * | 8/1975 | Coppa ..................... H02P 23/22 |
| | | | | 388/811 |
| 3,912,121 | A | * | 10/1975 | Steffen ................... A01C 7/105 |
| | | | | 221/13 |
| 3,915,271 | A | * | 10/1975 | Harper ................... B63H 23/30 |
| | | | | 477/5 |
| 3,932,812 | A | * | 1/1976 | Milligan ................. G01P 1/106 |
| | | | | 324/161 |
| 4,041,362 | A | * | 8/1977 | Ichiyanagi ............... H02P 6/06 |
| | | | | 318/269 |
| 4,052,649 | A | * | 10/1977 | Greenwell ............. H02P 23/03 |
| | | | | 318/765 |
| 4,087,730 | A | * | 5/1978 | Goles ........................ A61F 4/00 |
| | | | | 318/603 |
| 4,157,859 | A | * | 6/1979 | Terry ..................... G02B 21/20 |
| | | | | 351/212 |
| 4,171,700 | A | | 10/1979 | Farin |
| 4,202,722 | A | | 5/1980 | Paquin |
| 4,412,539 | A | | 11/1983 | Jarvik |
| 4,448,193 | A | | 5/1984 | Ivanov |
| 4,523,695 | A | | 6/1985 | Braun et al. |
| 4,608,160 | A | | 8/1986 | Zoch |
| 4,614,366 | A | | 9/1986 | North et al. |
| 4,633,874 | A | | 1/1987 | Chow et al. |
| 4,701,193 | A | | 10/1987 | Robertson et al. |
| 4,735,603 | A | | 4/1988 | Goodson et al. |
| 4,788,977 | A | | 12/1988 | Farin et al. |
| 4,849,752 | A | | 7/1989 | Bryant |
| D303,787 | S | | 10/1989 | Messenger et al. |
| 4,892,244 | A | | 1/1990 | Fox et al. |
| 4,976,173 | A | | 12/1990 | Yang |
| 5,010,341 | A | | 4/1991 | Huntley et al. |

(56) References Cited

U.S. PATENT DOCUMENTS

| | | |
|---|---|---|
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,217,003 A | 6/1993 | Wilk |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,385,544 A | 1/1995 | Edwards et al. |
| 5,391,144 A | 2/1995 | Sakurai et al. |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,507,773 A | 4/1996 | Huitema et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A * | 9/1996 | Young ............... H02P 6/15 318/400.32 |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A * | 10/1997 | Roos ............... A61B 6/10 192/129 A |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,796,188 A | 8/1998 | Bays |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,139,561 A | 10/2000 | Shibata et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,482,217 B1 | 11/2002 | Pintor et al. |
| 6,524,307 B1 | 2/2003 | Palmerton et al. |
| 6,530,933 B1 | 3/2003 | Yeung et al. |
| 6,551,243 B2 | 4/2003 | Bocionek et al. |

(56) References Cited

U.S. PATENT DOCUMENTS

| | | |
|---|---|---|
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,695,199 B2 | 2/2004 | Whitman |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,071 B2 | 2/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,094,231 B1 | 8/2006 | Ellman et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,413,541 B2 | 8/2008 | Konishi |
| 7,422,136 B1 | 9/2008 | Marczyk |
| 7,422,139 B2 | 9/2008 | Shelton, IV et al. |
| 7,422,586 B2 | 9/2008 | Morris et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,772 B2 | 4/2010 | Pauker et al. |
| 7,699,860 B2 | 4/2010 | Huitema et al. |
| 7,717,312 B2 | 5/2010 | Beetel |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,722,603 B2 | 5/2010 | McPherson |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |

(56) References Cited

U.S. PATENT DOCUMENTS

| | | |
|---|---|---|
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,950,560 B2 | 5/2011 | Zemlok et al. |
| 7,951,148 B2 | 5/2011 | McClurken |
| 7,954,682 B2 | 6/2011 | Giordano et al. |
| 7,954,687 B2 | 6/2011 | Zemlok et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,993,354 B1 | 8/2011 | Brecher et al. |
| 7,993,954 B2 | 8/2011 | Wieting |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,095,327 B2 | 1/2012 | Tahara et al. |
| 8,096,459 B2 | 1/2012 | Ortiz et al. |
| 8,116,848 B2 | 2/2012 | Shahidi |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| 8,146,149 B2 | 3/2012 | Steinkogler et al. |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,453,906 B2 | 6/2013 | Huang et al. |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,473,066 B2 | 6/2013 | Aghassian et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |

(56) References Cited

U.S. PATENT DOCUMENTS

| | | |
|---|---|---|
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,533,475 B2 | 9/2013 | Frikart et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,568,411 B2 | 10/2013 | Falkenstein et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,663,222 B2 | 3/2014 | Anderson et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| 8,708,213 B2 | 4/2014 | Shelton, IV et al. |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,607 B2 | 9/2014 | Marczyk |
| 8,820,608 B2 | 9/2014 | Miyamoto |
| 8,827,134 B2 | 9/2014 | Viola et al. |
| 8,827,136 B2 | 9/2014 | Hessler |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,864,747 B2 | 10/2014 | Merchant et al. |
| 8,875,973 B2 | 11/2014 | Whitman |
| 8,876,857 B2 | 11/2014 | Burbank |
| 8,882,662 B2 | 11/2014 | Charles |
| 8,885,032 B2 | 11/2014 | Igarashi et al. |
| 8,886,790 B2 | 11/2014 | Harrang et al. |
| 8,893,946 B2 | 11/2014 | Boudreaux et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,934,684 B2 | 1/2015 | Mohamed |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |

(56) References Cited

U.S. PATENT DOCUMENTS

| | | | |
|---|---|---|---|
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 * | 8/2015 | Mah | B25H 1/0092 |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,259,282 B2 | 2/2016 | Azizian et al. |
| 9,265,429 B2 | 2/2016 | St. Pierre et al. |
| 9,265,585 B2 | 2/2016 | Wingardner et al. |
| 9,265,959 B2 | 2/2016 | Drew et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,299,138 B2 | 3/2016 | Zellner et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,544 B2 | 5/2016 | Hourtash et al. |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Durie |
| 9,364,200 B2 | 6/2016 | Whitman et al. |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,404,868 B2 | 8/2016 | Yamanaka et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |

(56) References Cited

U.S. PATENT DOCUMENTS

| | | |
|---|---|---|
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,219 B2 | 11/2016 | Moore et al. |
| 9,498,231 B2 | 11/2016 | Haider et al. |
| 9,498,291 B2 | 11/2016 | Balaji et al. |
| 9,509,566 B2 | 11/2016 | Chu et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,580 B2 | 12/2016 | Humayun et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,585,658 B2 | 3/2017 | Shelton, IV |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| 9,603,609 B2 | 3/2017 | Kawashima et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,096 B1 | 5/2017 | Heaton, II et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,614 B2 | 5/2017 | Swensgard et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,737,371 B2 | 8/2017 | Romo et al. |
| 9,740,826 B2 | 8/2017 | Raghavan et al. |
| 9,743,016 B2 | 8/2017 | Res et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,560 B2 | 9/2017 | Ballakur et al. |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |

(56) References Cited

U.S. PATENT DOCUMENTS

| | | |
|---|---|---|
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondon et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,943,964 B2 | 4/2018 | Hares |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |

(56) References Cited

U.S. PATENT DOCUMENTS

| | | |
|---|---|---|
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,130,432 B2 | 11/2018 | Auld et al. |
| 10,133,248 B2 | 11/2018 | Fitzsimmons et al. |
| 10,135,242 B2 | 11/2018 | Baber et al. |
| 10,136,246 B2 | 11/2018 | Yamada |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonitas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,610 B2 | 5/2019 | Srivastava |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,868 B2 | 5/2019 | Tsuboi et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,042 B2 | 7/2019 | Schoenle et al. |

(56) References Cited

U.S. PATENT DOCUMENTS

| | | |
|---|---|---|
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,344 B2 | 10/2019 | Notz et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,684 B2 | 11/2019 | Toth et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,507,278 B2 | 12/2019 | Gao et al. |
| 10,510,267 B2 | 12/2019 | Jarc et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,509 B2 | 12/2019 | Bowling et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,537,396 B2 | 1/2020 | Zingaretti et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,349 B2 | 2/2020 | Wedekind et al. |
| 10,561,422 B2 | 2/2020 | Schellin et al. |
| 10,561,470 B2 | 2/2020 | Hourtash et al. |
| 10,561,471 B2 | 2/2020 | Nichogi |
| 10,561,560 B2 | 2/2020 | Boutoussov et al. |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savaii et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,962 B2 | 3/2020 | Friedrichs et al. |
| 10,582,964 B2 | 3/2020 | Weinberg et al. |

(56) References Cited

U.S. PATENT DOCUMENTS

| | | |
|---|---|---|
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,498 B2 | 8/2020 | Watanabe et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,499 B2 | 10/2020 | Castaneda et al. |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sedeh et al. |
| 10,828,028 B2 | 11/2020 | Harris et al. |
| 10,828,030 B2 | 11/2020 | Weir et al. |
| 10,835,206 B2 | 11/2020 | Bell et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |

(56) References Cited

U.S. PATENT DOCUMENTS

| | | |
|---|---|---|
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,898,256 B2 | 1/2021 | Yates et al. |
| 10,902,944 B1 | 1/2021 | Casey et al. |
| 10,905,418 B2 | 2/2021 | Shelton, IV et al. |
| 10,905,420 B2 | 2/2021 | Jasemian et al. |
| 10,912,567 B2 | 2/2021 | Shelton, IV et al. |
| 10,916,415 B2 | 2/2021 | Karancsi et al. |
| D914,878 S | 3/2021 | Shelton, IV et al. |
| 10,932,784 B2 | 3/2021 | Mozdzierz et al. |
| 10,950,982 B2 | 3/2021 | Regnier et al. |
| 10,952,732 B2 | 3/2021 | Binmoeller et al. |
| 10,959,729 B2 | 3/2021 | Ehrenfels et al. |
| 10,962,449 B2 | 3/2021 | Unuma et al. |
| 10,966,590 B2 | 4/2021 | Takahashi et al. |
| 10,980,595 B2 | 4/2021 | Wham |
| 10,987,102 B2 | 4/2021 | Gonzalez et al. |
| 10,992,698 B2 | 4/2021 | Patel et al. |
| 11,000,276 B2 | 5/2021 | Shelton, IV et al. |
| 11,051,817 B2 | 7/2021 | Shelton, IV et al. |
| 11,051,902 B2 | 7/2021 | Kruecker et al. |
| 11,058,501 B2 | 7/2021 | Tokarchuk et al. |
| 11,071,595 B2 | 7/2021 | Johnson et al. |
| 11,141,213 B2 | 10/2021 | Yates et al. |
| 11,185,325 B2 | 11/2021 | Shelton, IV et al. |
| 11,273,290 B2 | 3/2022 | Kowshik |
| D950,728 S | 5/2022 | Bakos et al. |
| D952,144 S | 5/2022 | Boudreaux |
| 11,322,248 B2 | 5/2022 | Grantcharov et al. |
| 11,350,932 B2 | 6/2022 | Shelton, IV et al. |
| 11,373,755 B2 | 6/2022 | Shelton, IV et al. |
| 11,376,098 B2 | 7/2022 | Shelton, IV et al. |
| 11,382,715 B2 | 7/2022 | Arai et al. |
| D964,564 S | 9/2022 | Boudreaux |
| 11,464,514 B2 | 10/2022 | Yates et al. |
| 11,504,191 B2 | 11/2022 | Mccloud et al. |
| 11,571,212 B2 | 2/2023 | Yates et al. |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0144147 A1 | 10/2002 | Basson et al. |
| 2002/0169584 A1 | 11/2002 | Fu et al. |
| 2002/0194023 A1 | 12/2002 | Turley et al. |
| 2003/0009111 A1 | 1/2003 | Cory et al. |
| 2003/0009154 A1 | 1/2003 | Whitman |
| 2003/0018329 A1 | 1/2003 | Hooven |
| 2003/0046109 A1 | 3/2003 | Uchikubo |
| 2003/0050654 A1 | 3/2003 | Whitman et al. |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0120284 A1 | 6/2003 | Palacios et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0092992 A1 | 5/2004 | Adams et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0229496 A1 | 11/2004 | Robinson et al. |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0070800 A1 | 3/2005 | Takahashi |
| 2005/0100867 A1 | 5/2005 | Hilscher et al. |
| 2005/0131390 A1 | 6/2005 | Heinrich et al. |
| 2005/0139629 A1 | 6/2005 | Schwemberger et al. |
| 2005/0143759 A1 | 6/2005 | Kelly |
| 2005/0148854 A1 | 7/2005 | Ito et al. |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0213832 A1 | 9/2005 | Schofield et al. |
| 2005/0222631 A1 | 10/2005 | Dalal et al. |
| 2005/0228246 A1 | 10/2005 | Lee et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2005/0288425 A1 | 12/2005 | Lee et al. |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0142739 A1 | 6/2006 | DiSilestro et al. |
| 2006/0184160 A1 | 8/2006 | Ozaki et al. |
| 2006/0241399 A1 | 10/2006 | Fabian |
| 2006/0282009 A1 | 12/2006 | Oberg et al. |
| 2006/0287645 A1 | 12/2006 | Tashiro et al. |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175951 A1 | 8/2007 | Shelton et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0192139 A1 | 8/2007 | Cookson et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0019393 A1 | 1/2008 | Yamaki |

(56) References Cited

U.S. PATENT DOCUMENTS

| | | |
|---|---|---|
| 2008/0033404 A1 | 2/2008 | Romoda et al. |
| 2008/0039742 A1 | 2/2008 | Hashimshony et al. |
| 2008/0040151 A1 | 2/2008 | Moore |
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0164296 A1 | 7/2008 | Shelton et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0223904 A1 | 9/2008 | Marczyk |
| 2008/0234708 A1 | 9/2008 | Houser et al. |
| 2008/0235052 A1 | 9/2008 | Node-Langlois et al. |
| 2008/0245841 A1 | 10/2008 | Smith et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Llkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0157072 A1 | 6/2009 | Wham et al. |
| 2009/0182577 A1 | 7/2009 | Squilla et al. |
| 2009/0188094 A1 | 7/2009 | Cunningham et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0259489 A1 | 10/2009 | Kimura et al. |
| 2009/0270678 A1 | 10/2009 | Scott et al. |
| 2009/0281541 A1 | 11/2009 | Ibrahim et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0066939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0244929 A1* | 9/2010 | Jalbout ............... H05B 45/37 327/427 |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0022032 A1 | 1/2011 | Zemlok et al. |
| 2011/0036890 A1* | 2/2011 | Ma ............... A61B 17/07207 227/175.2 |
| 2011/0043612 A1 | 2/2011 | Keller et al. |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0105277 A1 | 5/2011 | Shauli |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0155781 A1* | 6/2011 | Swensgard ...... A61B 17/07207 227/176.1 |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0218526 A1 | 9/2011 | Mathur |
| 2011/0237883 A1 | 9/2011 | Chun |
| 2011/0238079 A1 | 9/2011 | Hannaford et al. |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0265311 A1 | 11/2011 | Kondo et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |

(56) References Cited

U.S. PATENT DOCUMENTS

| | | |
|---|---|---|
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0090755 A1 | 4/2013 | Kiryu et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0131845 A1 | 5/2013 | Guilleminot |
| 2013/0144284 A1 | 6/2013 | Behnke, II et al. |
| 2013/0153635 A1 | 6/2013 | Hodgkinson |
| 2013/0165776 A1 | 6/2013 | Blomqvist |
| 2013/0178853 A1 | 7/2013 | Hyink et al. |
| 2013/0191647 A1 | 7/2013 | Ferrara, Jr. et al. |
| 2013/0193188 A1 | 8/2013 | Shelton, IV et al. |
| 2013/0196703 A1 | 8/2013 | Masoud et al. |
| 2013/0197531 A1 | 8/2013 | Boukhny et al. |
| 2013/0201356 A1 | 8/2013 | Kennedy et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0006943 A1 | 1/2014 | Robbins et al. |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0058407 A1 | 2/2014 | Tsekos et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R. et al. |
| 2014/0117256 A1 | 5/2014 | Mueller et al. |
| 2014/0121669 A1 | 5/2014 | Claus |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0176576 A1 | 6/2014 | Spencer |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276748 A1 | 9/2014 | Ku et al. |
| 2014/0276749 A1 | 9/2014 | Johnson |
| 2014/0287393 A1 | 9/2014 | Kumar et al. |
| 2014/0296694 A1 | 10/2014 | Jaworski |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0057675 A1 | 2/2015 | Akeel et al. |
| 2015/0062316 A1 | 3/2015 | Haraguchi et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0099458 A1 | 4/2015 | Weisner et al. |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0141980 A1 | 5/2015 | Jadhav et al. |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0201918 A1 | 7/2015 | Kumar et al. |
| 2015/0202014 A1* | 7/2015 | Kim ............... B25J 9/1676 |
| | | 606/130 |
| 2015/0208934 A1 | 7/2015 | Sztrubel et al. |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282733 A1 | 10/2015 | Fielden et al. |
| 2015/0282821 A1 | 10/2015 | Look et al. |
| 2015/0282825 A1* | 10/2015 | Trees ............... A61B 18/1445 |
| | | 606/170 |
| 2015/0289925 A1 | 10/2015 | Voegele et al. |
| 2015/0296042 A1 | 10/2015 | Aoyama |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0305828 A1 | 10/2015 | Park et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |

(56) References Cited

U.S. PATENT DOCUMENTS

| | | |
|---|---|---|
| 2016/0015471 A1 | 1/2016 | Piron et al. |
| 2016/0022374 A1 | 1/2016 | Haider et al. |
| 2016/0034648 A1 | 2/2016 | Mohlenbrock et al. |
| 2016/0038224 A1 | 2/2016 | Couture et al. |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |
| 2016/0066913 A1 | 3/2016 | Swayze et al. |
| 2016/0078190 A1 | 3/2016 | Greene et al. |
| 2016/0100837 A1 | 4/2016 | Huang et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0157717 A1 | 6/2016 | Gaster |
| 2016/0158468 A1 | 6/2016 | Tang et al. |
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0182637 A1 | 6/2016 | Adriaens et al. |
| 2016/0184054 A1 | 6/2016 | Lowe |
| 2016/0192960 A1 | 7/2016 | Bueno et al. |
| 2016/0203599 A1 | 7/2016 | Gillies et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0256153 A1* | 9/2016 | Shelton, IV ......... A61B 17/295 |
| 2016/0270732 A1 | 9/2016 | Källbäck et al. |
| 2016/0270861 A1 | 9/2016 | Guru et al. |
| 2016/0275259 A1 | 9/2016 | Nolan et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | McHenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0324537 A1 | 11/2016 | Green et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0354160 A1 | 12/2016 | Crowley et al. |
| 2016/0354162 A1* | 12/2016 | Yen ........................ A61B 34/20 |
| 2016/0361070 A1 | 12/2016 | Ardel et al. |
| 2016/0367305 A1 | 12/2016 | Hareland |
| 2016/0367401 A1 | 12/2016 | Claus |
| 2016/0374665 A1 | 12/2016 | DiNardo et al. |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0005911 A1 | 1/2017 | Kasargod et al. |
| 2017/0007247 A1 | 1/2017 | Shelton, IV et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0105787 A1 | 4/2017 | Witt et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0156076 A1 | 6/2017 | Eom et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0172674 A1 | 6/2017 | Hanuschik et al. |
| 2017/0172676 A1 | 6/2017 | Itkowitz et al. |
| 2017/0173262 A1 | 6/2017 | Veltz |
| 2017/0177807 A1 | 6/2017 | Fabian |
| 2017/0178069 A1 | 6/2017 | Paterra et al. |
| 2017/0185732 A1 | 6/2017 | Niklewski et al. |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202607 A1 | 7/2017 | Shelton, IV et al. |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231553 A1 | 8/2017 | Igarashi et al. |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0289617 A1 | 10/2017 | Song et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0319268 A1 | 11/2017 | Akagane |
| 2017/0325876 A1 | 11/2017 | Nakadate et al. |
| 2017/0325878 A1 | 11/2017 | Messerly et al. |
| 2017/0333152 A1 | 11/2017 | Wade |
| 2017/0337043 A1 | 11/2017 | Brincat et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367697 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0014764 A1 | 1/2018 | Bechtel et al. |
| 2018/0021058 A1 | 1/2018 | Meglan |
| 2018/0042659 A1 | 2/2018 | Rupp et al. |

(56) References Cited

U.S. PATENT DOCUMENTS

| | | |
|---|---|---|
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098049 A1 | 4/2018 | Sugano et al. |
| 2018/0098816 A1 | 4/2018 | Govari et al. |
| 2018/0108438 A1 | 4/2018 | Ryan et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0153436 A1 | 6/2018 | Olson |
| 2018/0153574 A1 | 6/2018 | Faller et al. |
| 2018/0153628 A1 | 6/2018 | Grover et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168586 A1 | 6/2018 | Shelton, IV et al. |
| 2018/0168590 A1 | 6/2018 | Overmyer et al. |
| 2018/0168592 A1 | 6/2018 | Overmyer et al. |
| 2018/0168593 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168601 A1 | 6/2018 | Bakos et al. |
| 2018/0168603 A1 | 6/2018 | Morgan et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168628 A1 | 6/2018 | Hunter et al. |
| 2018/0168632 A1 | 6/2018 | Harris et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0172420 A1 | 6/2018 | Hein et al. |
| 2018/0177383 A1 | 6/2018 | Noonan et al. |
| 2018/0182475 A1 | 6/2018 | Cossler et al. |
| 2018/0183684 A1 | 6/2018 | Jacobson et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0250825 A1 | 9/2018 | Hashimoto et al. |
| 2018/0263699 A1 | 9/2018 | Murphy et al. |
| 2018/0263710 A1 | 9/2018 | Sakaguchi et al. |
| 2018/0263717 A1 | 9/2018 | Kopp |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0296289 A1 | 10/2018 | Rodriguez-Navarro et al. |
| 2018/0303552 A1 | 10/2018 | Ryan et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0315492 A1 | 11/2018 | Bishop et al. |
| 2018/0317826 A1 | 11/2018 | Muhsin et al. |
| 2018/0317915 A1 | 11/2018 | McDonald, II |
| 2018/0317916 A1 | 11/2018 | Wixey |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0353186 A1 | 12/2018 | Mozdzierz et al. |
| 2018/0357383 A1 | 12/2018 | Allen et al. |
| 2018/0360449 A1 | 12/2018 | Shelton, IV et al. |
| 2018/0360454 A1 | 12/2018 | Shelton, IV et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2018/0369511 A1 | 12/2018 | Zergiebel et al. |
| 2019/0000446 A1 | 1/2019 | Shelton, IV et al. |
| 2019/0000448 A1 | 1/2019 | Shelton, IV et al. |
| 2019/0000478 A1 | 1/2019 | Messerly et al. |
| 2019/0000530 A1 | 1/2019 | Yates et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0029712 A1 | 1/2019 | Stoddard et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0045515 A1 | 2/2019 | Kwasnick et al. |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0090969 A1 | 3/2019 | Jarc et al. |
| 2019/0099221 A1 | 4/2019 | Schmidt et al. |
| 2019/0099226 A1 | 4/2019 | Hallen |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0122330 A1 | 4/2019 | Saget et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125337 A1 | 5/2019 | Shelton, IV et al. |
| 2019/0125338 A1 | 5/2019 | Shelton, IV et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |

(56) References Cited

U.S. PATENT DOCUMENTS

| | | |
|---|---|---|
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125383 A1 | 5/2019 | Scheib et al. |
| 2019/0125384 A1 | 5/2019 | Scheib et al. |
| 2019/0125385 A1 | 5/2019 | Scheib et al. |
| 2019/0125386 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0162179 A1 | 5/2019 | O'Shea et al. |
| 2019/0163875 A1 | 5/2019 | Allen et al. |
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201076 A1 | 7/2019 | Honda et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201088 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201144 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206216 A1 | 7/2019 | Shelton, IV et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0207773 A1 | 7/2019 | Shelton, IV et al. |
| 2019/0207857 A1 | 7/2019 | Shelton, IV et al. |
| 2019/0207911 A1 | 7/2019 | Wiener et al. |
| 2019/0208641 A1 | 7/2019 | Yates et al. |

(56) References Cited

U.S. PATENT DOCUMENTS

| | | |
|---|---|---|
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cut et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054327 A1 | 2/2020 | Harris et al. |
| 2020/0054328 A1 | 2/2020 | Harris et al. |
| 2020/0054330 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0348662 A1 | 11/2020 | Cella et al. |
| 2020/0352664 A1 | 11/2020 | King et al. |
| 2020/0405304 A1 | 12/2020 | Mozdzierz et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |

(56) References Cited

U.S. PATENT DOCUMENTS

| | | |
|---|---|---|
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0157306 A1 | 5/2022 | Albrecht et al. |
| 2022/0160438 A1 | 5/2022 | Shelton, IV et al. |
| 2022/0175374 A1 | 6/2022 | Shelton, IV et al. |
| 2022/0230738 A1 | 7/2022 | Shelton, IV et al. |
| 2022/0241027 A1 | 8/2022 | Shelton, IV et al. |
| 2022/0249097 A1 | 8/2022 | Shelton, IV et al. |
| 2022/0323092 A1 | 10/2022 | Shelton, IV et al. |
| 2022/0323095 A1 | 10/2022 | Nott et al. |
| 2022/0323150 A1 | 10/2022 | Yates et al. |
| 2022/0331011 A1 | 10/2022 | Shelton, IV et al. |
| 2022/0331018 A1 | 10/2022 | Parihar et al. |
| 2022/0346792 A1 | 11/2022 | Shelton, IV et al. |
| 2022/0370117 A1 | 11/2022 | Messerly et al. |
| 2022/0370126 A1 | 11/2022 | Shelton, IV et al. |
| 2022/0374414 A1 | 11/2022 | Shelton, IV et al. |
| 2022/0395276 A1 | 12/2022 | Yates et al. |
| 2022/0401099 A1 | 12/2022 | Shelton, IV et al. |
| 2022/0406452 A1 | 12/2022 | Shelton, IV |
| 2022/0409302 A1 | 12/2022 | Shelton, IV et al. |
| 2023/0000518 A1 | 1/2023 | Nott et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 107811710 A | 3/2018 |
| CN | 108652695 A | 10/2018 |
| DE | 2037167 A1 | 7/1980 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2509523 A | 7/2014 |
| JP | S5373315 A | 6/1978 |
| JP | S57185848 A | 11/1982 |
| JP | S58207752 A | 12/1983 |
| JP | S63315049 A | 12/1988 |
| JP | H06142113 A | 5/1994 |
| JP | H07132122 A | 5/1995 |
| JP | H08332169 A | 12/1996 |
| JP | H11197159 A | 7/1999 |
| JP | 2000058355 A | 2/2000 |
| JP | 2001029353 A | 2/2001 |
| JP | 2001195686 A | 7/2001 |
| JP | 2001314411 A | 11/2001 |
| JP | 2001340350 A | 12/2001 |
| JP | 2002272758 A | 9/2002 |
| JP | 2003153918 A | 5/2003 |
| JP | 2006117143 A | 5/2006 |
| JP | 2006288431 A | 10/2006 |
| JP | 2007123394 A | 5/2007 |
| JP | 2007139822 A | 6/2007 |
| JP | 2007300312 A | 11/2007 |
| JP | 2009039515 A | 2/2009 |
| JP | 2010057642 A | 3/2010 |
| JP | 2010131265 A | 6/2010 |
| JP | 2012065698 A | 4/2012 |
| JP | 2012239669 A | 12/2012 |
| JP | 2012533346 A | 12/2012 |
| JP | 2013081282 A | 5/2013 |
| JP | 2013144057 A | 7/2013 |
| JP | 2014155207 A | 8/2014 |
| JP | 2016174836 A | 10/2016 |
| JP | 2017047022 A | 3/2017 |
| JP | 2017513561 A | 6/2017 |
| JP | 2017526510 A | 9/2017 |
| JP | 2017532168 A | 11/2017 |
| KR | 20140104587 A | 8/2014 |
| KR | 101587721 B1 | 1/2016 |
| WO | WO-9734533 A1 | 9/1997 |
| WO | WO-9808449 A1 | 3/1998 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2006001264 A1 | 1/2006 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014116961 A1 | 7/2014 |
| WO | WO-2014134196 A1 | 9/2014 |
| WO | WO-2015054665 A1 | 4/2015 |
| WO | WO-2015129395 A1 | 9/2015 |
| WO | WO-2016093049 A1 | 6/2016 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |

(56) References Cited

FOREIGN PATENT DOCUMENTS

| WO | WO-2017058695 A1 | 4/2017 |
| WO | WO-2017151996 A1 | 9/2017 |
| WO | WO-2017183353 A1 | 10/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Cengiz, et al., "A Tale of Two Compartments: Interstitial Versus Blood Glucose Monitoring," Article, Jun. 2009, Pages S11-S16, vol. 11, Supplement 1, Diabetes Technology & Therapeutics.

Nabil Simaan et al., "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021,9 pages.

Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

"ATM-MPLS Network Interworking Version 2.0, af-aic-0178.001" ATM Standard, The ATM Forum Technical Committe, published Aug. 2003.

Lalys, et al., "Automatic knowledge-based recognition of low-level tasks in ophthalmological procedures", Int J Cars, vol. 8, No. 1, pp. 1-49, Apr. 19, 2012.

Flores et al., "Large-scale Offloading in the Internet of Things," 2017 IEEE International Conference on Pervasive Computing and Communications Workshops (Percom Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey, " Artificial Intelligence in Medicine, vol. 39, No. 1, pp. 1-24 (2006).

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Zoccali, Bruno, "A Method for Approximating Component Temperatures at Altitude Conditions Based on CFD Analysis at Sea Level Conditions," (white paper), www.tdminginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

(56) References Cited

OTHER PUBLICATIONS

Jiang, "Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

Dottorato, "Analysis and Design of the Rectangular Microstrip Patch Antennas for TM0n0 operating mode,"Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Hsiao-Wei Tang, "ARCM", Video, Sep. 2012, YouTube, 5 screenshots, Retrieved from Internet: <https://www.youtube.com/watch?v=UldQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

IEEE Std No. 177, "Standard Definitions and Methods of Measurement for Piezoelectric Vibrators," published May 1966, The Institute of Electrical and Electronics Engineers, Inc., New York, N.Y.

Shi et al., An intuitive control console for robotic syrgery system, 2014, IEEE, p. 404-407 (Year: 2014).

Choi et al., A haptic augmented reality surgeon console for a laparoscopic surgery robot system, 2013, IEEE, p. 355-357 (Year: 2013).

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1735-1759 (Year: 2010).

Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.

Draijer, Matthijs et al., "Review of laser pseckle contrast techniques for visualizing tissue perfusion," Lasers in Medical Science, Springer-Verlag, LO, vol. 24, No. 4, Dec. 3, 2008, pp. 639-651.

Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.

"Surgical instrumentation: the true cost of instrument trays and a potential strategy for optimization"; Mhlaba et al.; Sep. 23, 2015 (Year: 2015).

Hu, Jinwen, Stimulations of adaptive temperature control with self-focused hyperthermia system for tumor treatment, Jan. 9, 2012, Ultrasonics 53, pp. 171-177, (Year: 2012).

Hussain et al., "A survey on resource allocation in high performance distributed computing systems", Parallel Computing, vol. 39, No. 11, pp. 709-736 (2013).

Anonymous: "Quality of service—Wikipedia", Dec. 7, 2017, Retrieved from the Internet: URL:https://en.wikipedia.org/w/index.php?title=Quality_of_service&oldid=814298744#Applications [retrieved on Feb. 14, 2023], pp. 1-12.

Anonymous: "Differentiated services—Wikipedia", Dec. 14, 2017, Retrieved from the Internet: URL:https://en.wikipedia.org/w/index.php?title=Differentiated_services&oldid=815415620 [retrieved on Feb. 14, 2023], pp. 1-7.

Anonymous: "Cloud computing—Wikipedia", Dec. 19, 2017, Retrieved from the Internet: URL:https://en.wikipedia.org/w/index.php?title=Cloud_computing&oldid=816206558 [retrieved Feb. 14, 2023], pp. 1-21.

* cited by examiner

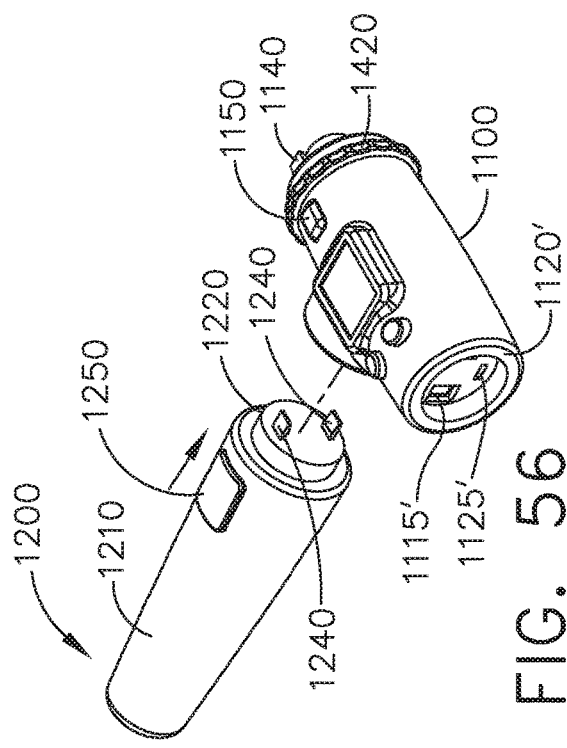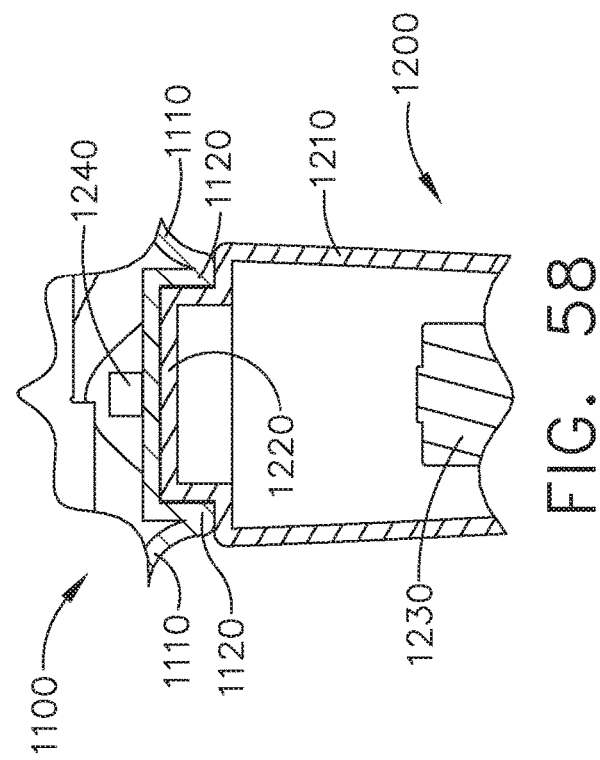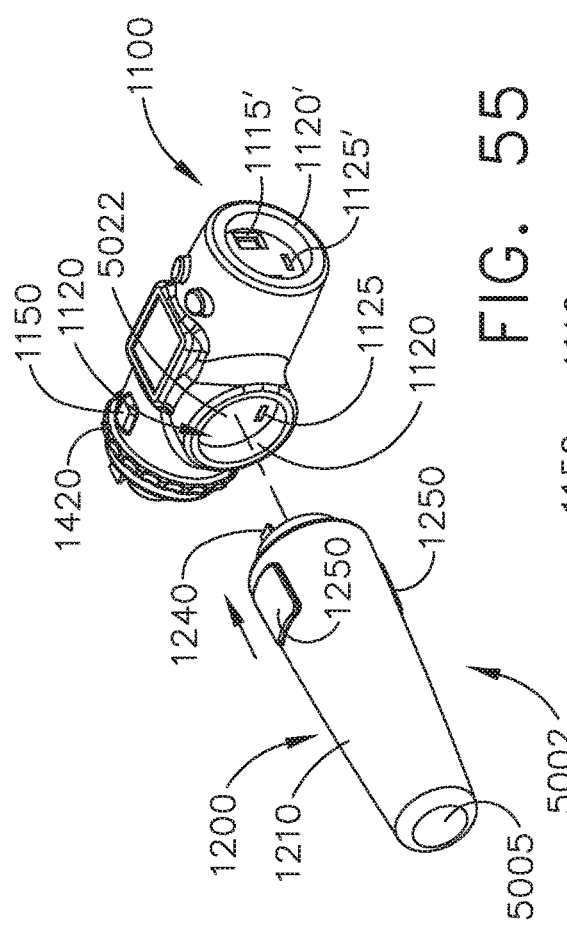

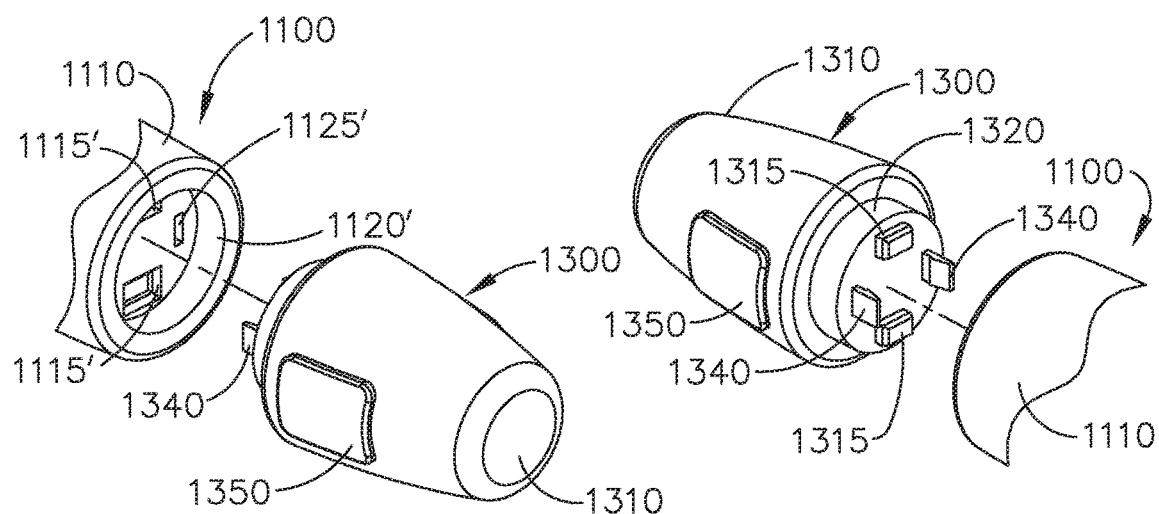
FIG. 63
FIG. 64
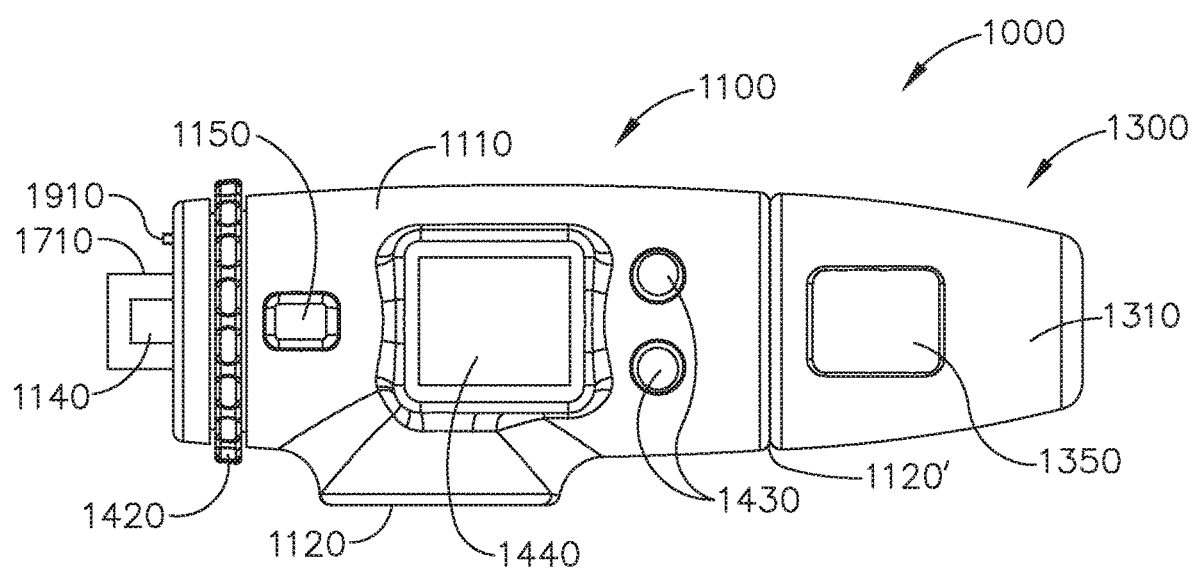
FIG. 65

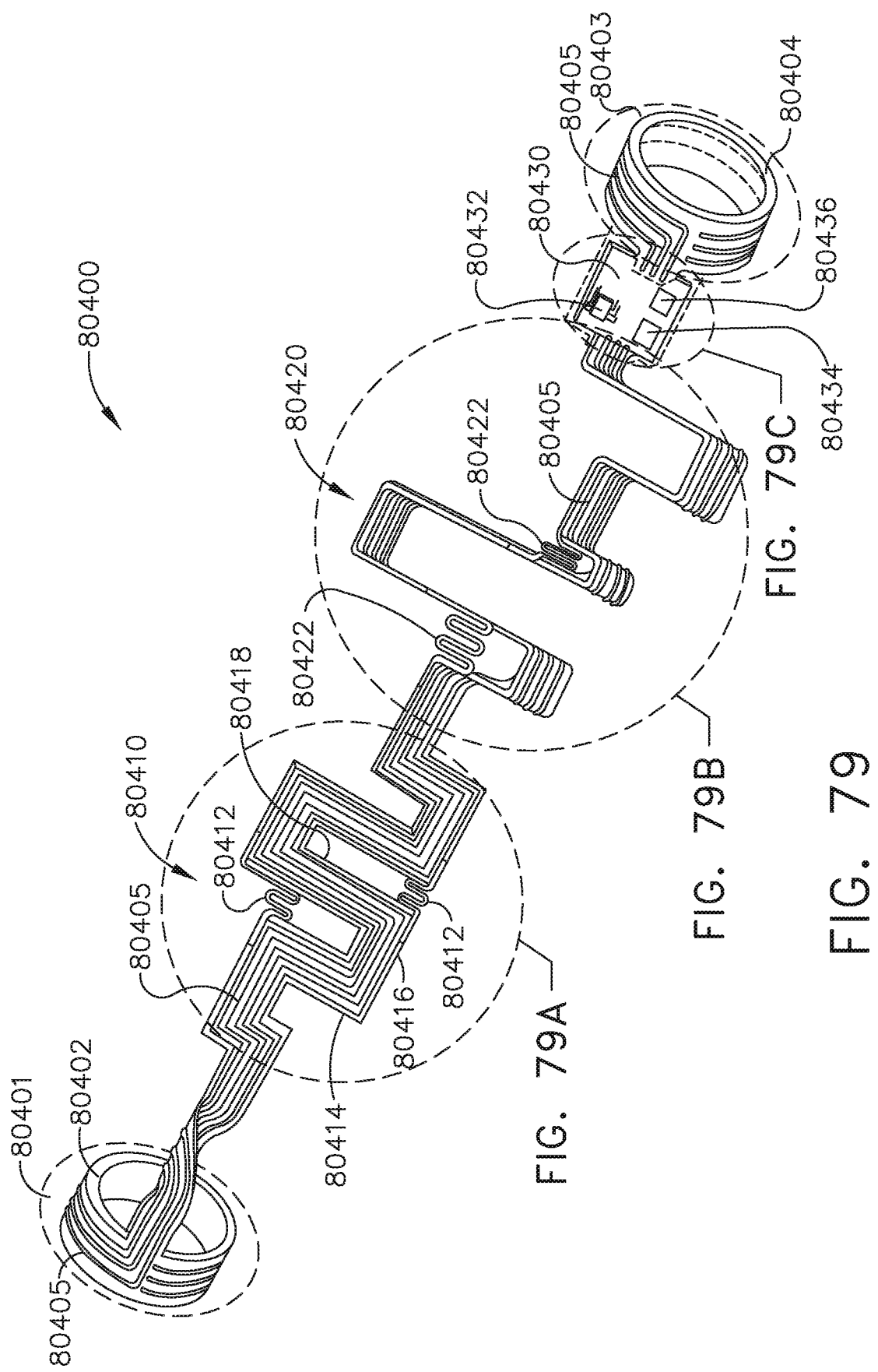

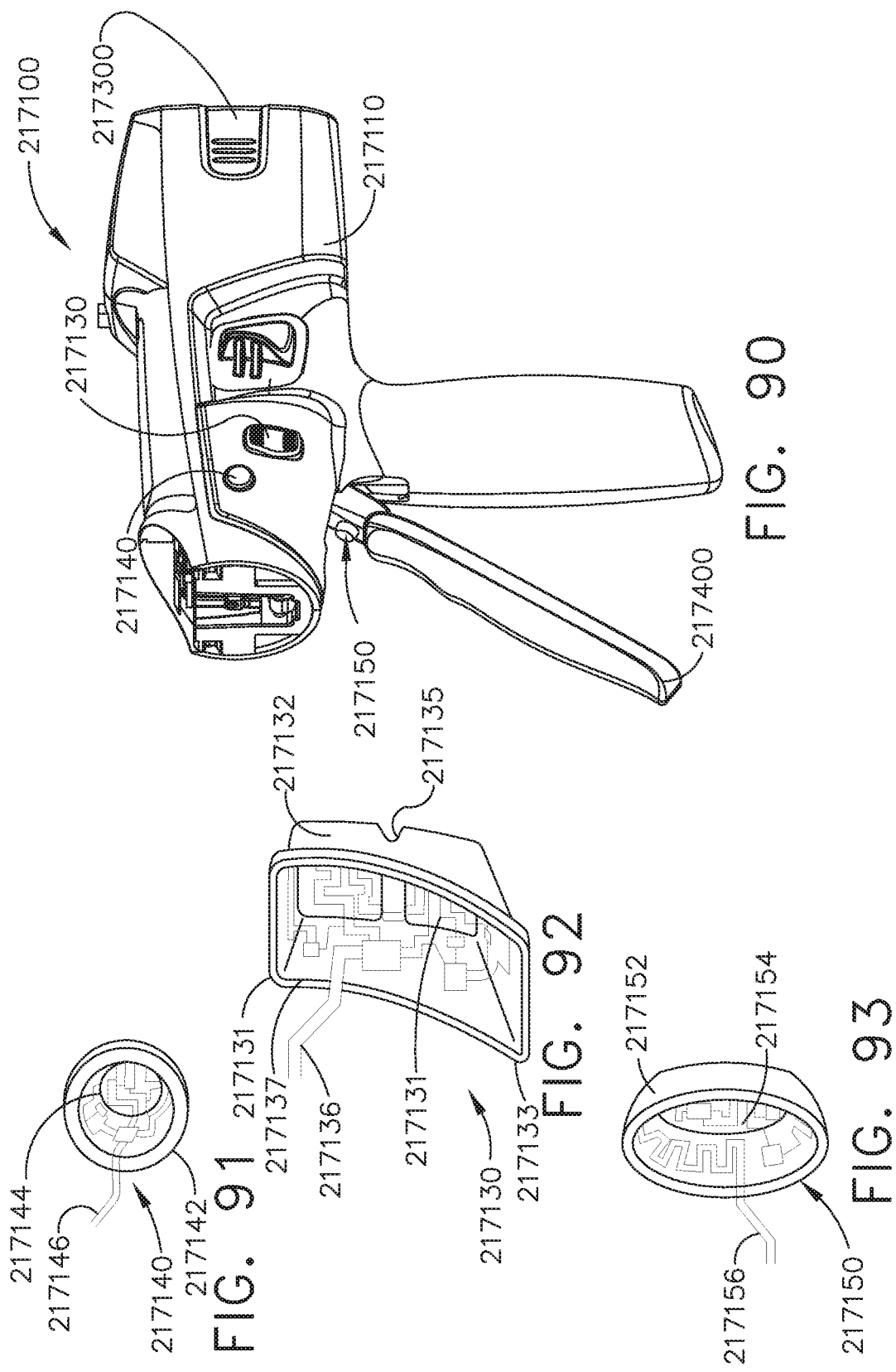

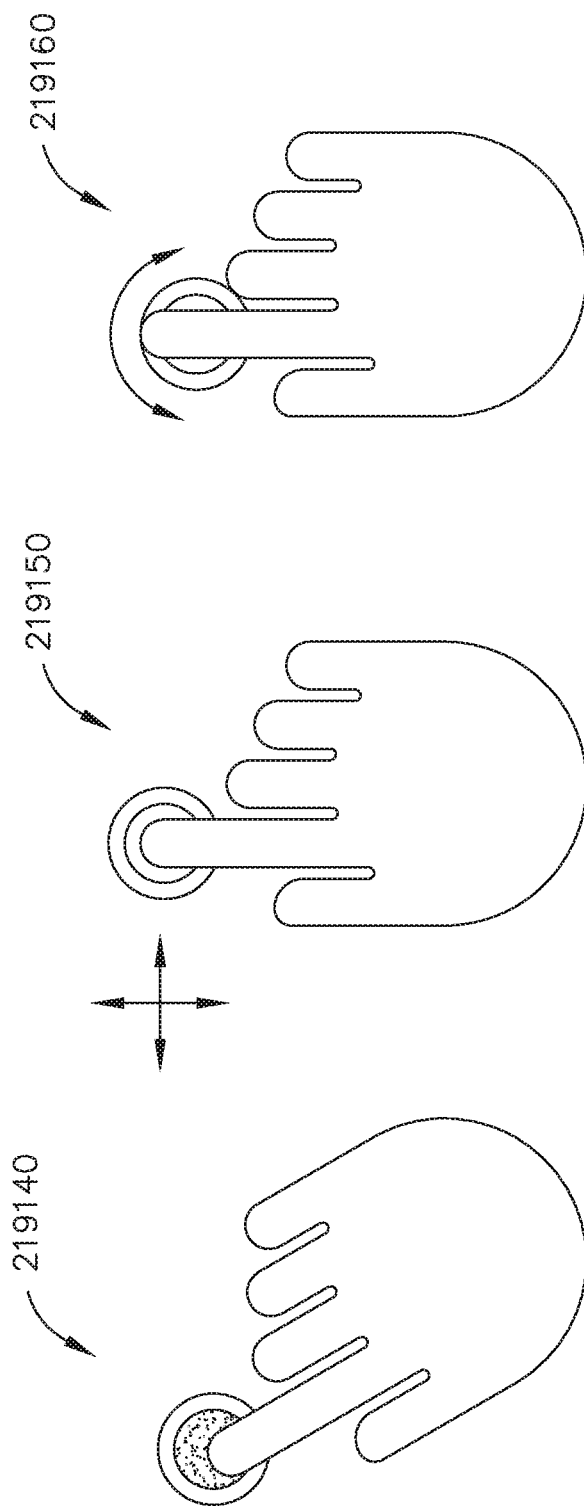

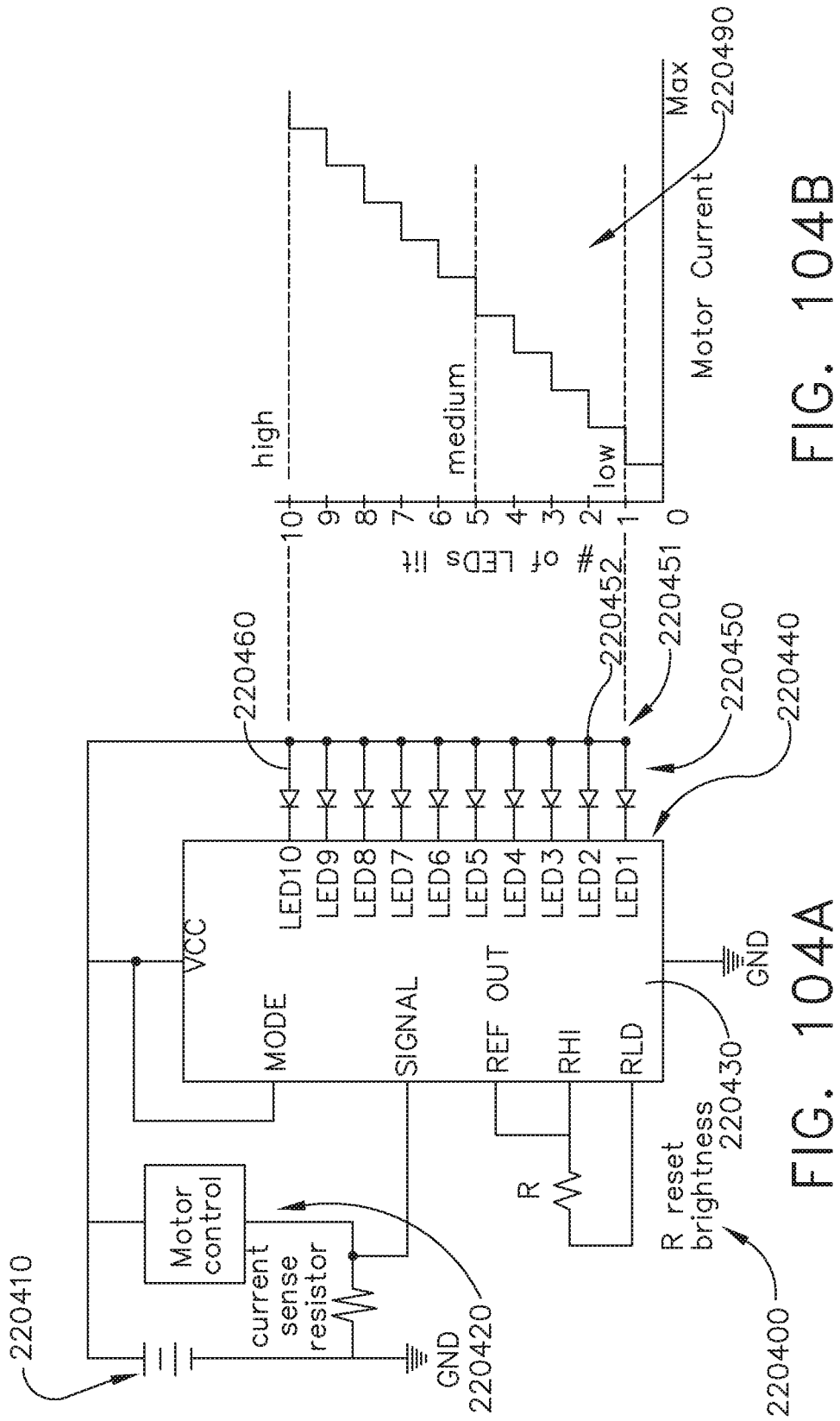

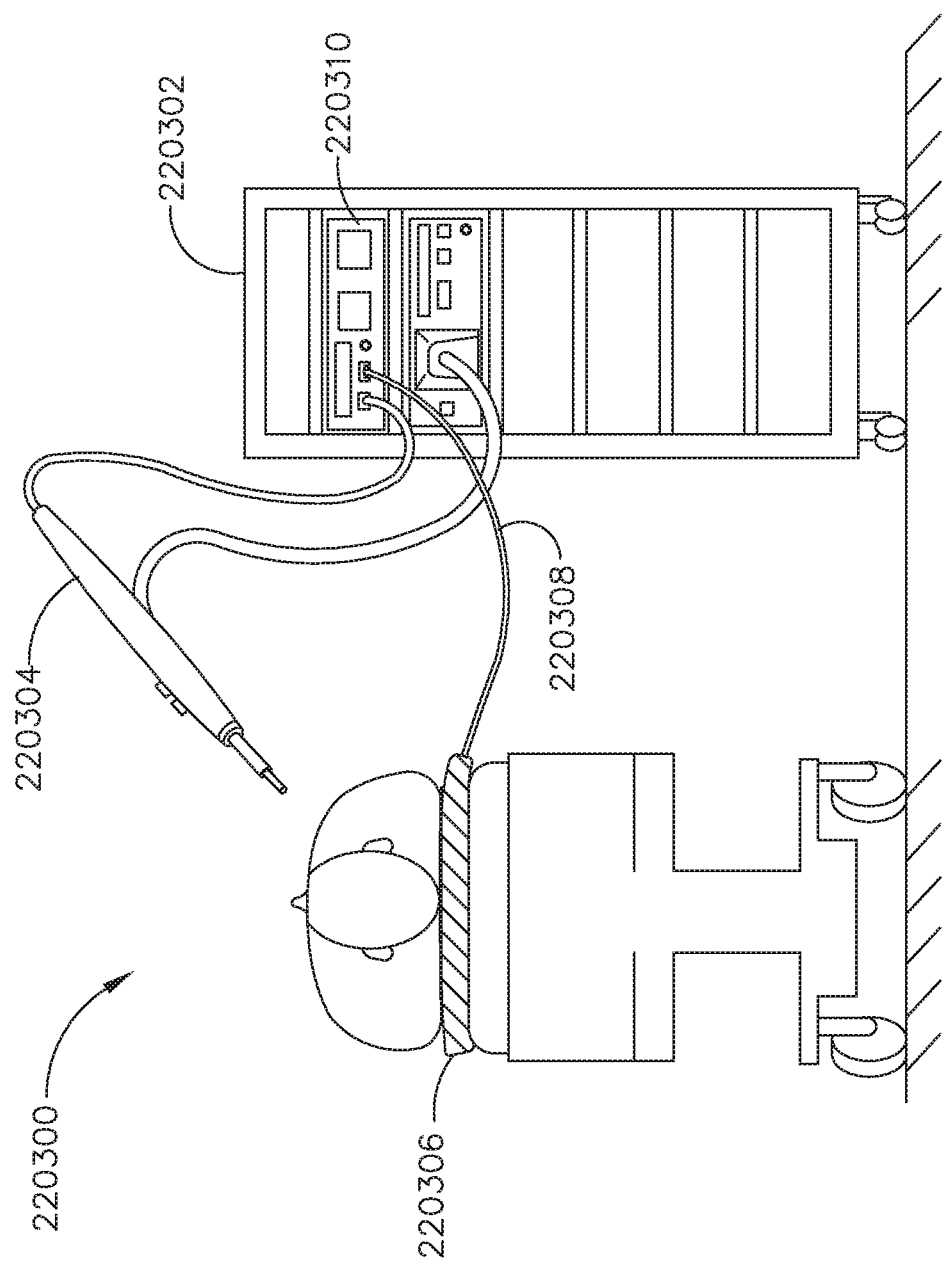

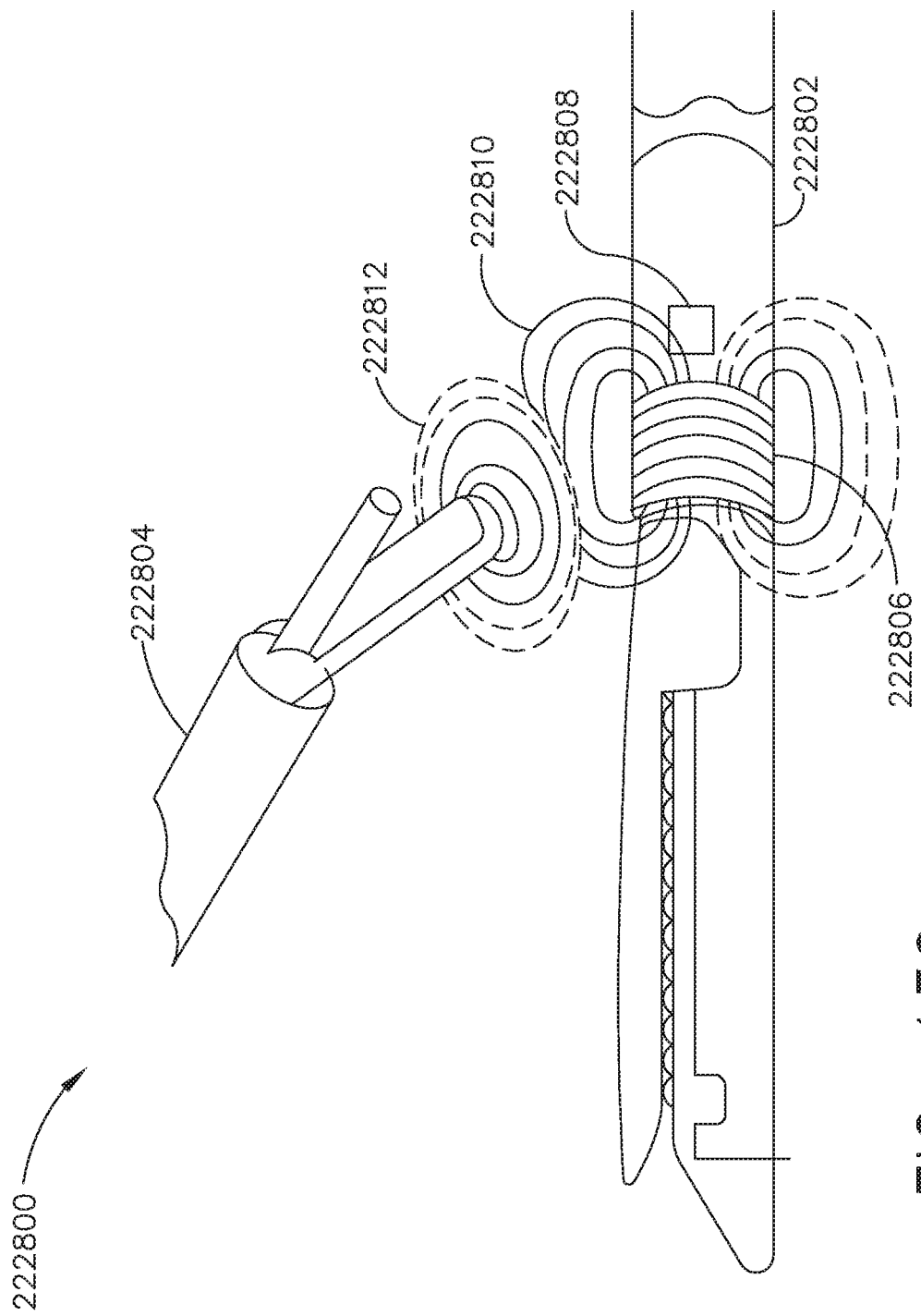

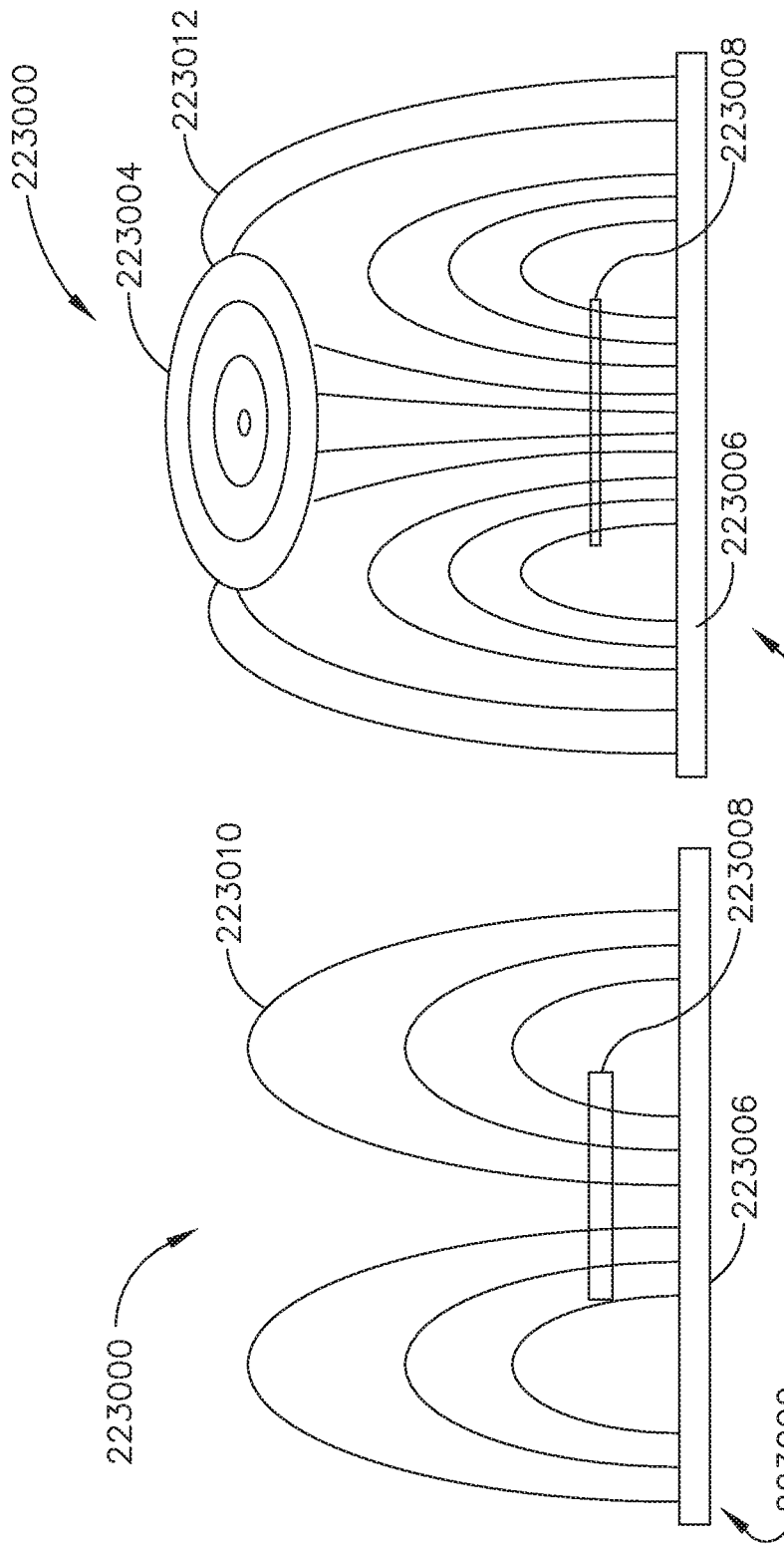

SURGICAL INSTRUMENT WITH A HARDWARE-ONLY CONTROL CIRCUIT

CROSS-REFERENCE TO RELATED APPLICATIONS

This application claims the benefit of U.S. Provisional Patent Application Ser. No. 62/778,571, entitled SURGICAL INSTRUMENT SYSTEMS, filed Dec. 12, 2018, the disclosure of which is incorporated by reference herein in its entirety. This application claims the benefit of U.S. Provisional Patent Application Ser. No. 62/750,529, entitled METHOD FOR OPERATING A POWERED ARTICULATING MULTI-CLIP APPLIER, filed Oct. 25, 2018, of U.S. Provisional Patent Application Ser. No. 62/750,539, entitled SURGICAL CLIP APPLIER, filed Oct. 25, 2018, and of U.S. Provisional Patent Application Ser. No. 62/750,555, entitled SURGICAL CLIP APPLIER, filed Oct. 25, 2018, the disclosures of which are incorporated by reference herein in their entireties. This application claims the benefit of U.S. Provisional Patent Application Ser. No. 62/659,900, entitled METHOD OF HUB COMMUNICATION, filed Apr. 19, 2018, the disclosure of which is incorporated by reference herein in its entirety. This application claims the benefit of U.S. Provisional Patent Application Ser. No. 62/665,128, entitled MODULAR SURGICAL INSTRUMENTS, filed May 1, 2018, of U.S. Provisional Patent Application Ser. No. 62/665,129, entitled SURGICAL SUTURING SYSTEMS, filed May 1, 2018, of U.S. Provisional Patent Application Ser. No. 62/665,134, entitled SURGICAL CLIP APPLIER, filed May 1, 2018, of U.S. Provisional Patent Application Ser. No. 62/665,139, entitled SURGICAL INSTRUMENTS COMPRISING CONTROL SYSTEMS, filed May 1, 2018, of U.S. Provisional Patent Application Ser. No. 62/665,177, entitled SURGICAL INSTRUMENTS COMPRISING HANDLE ARRANGEMENTS, filed May 1, 2018, and of U.S. Provisional Patent Application Ser. No. 62/665,192, entitled SURGICAL DISSECTORS, filed May 1, 2018, the disclosures of which are incorporated by reference herein in their entireties. This application claims the benefit of U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT, filed Mar. 28, 2018, of U.S. Provisional Patent Application Ser. No. 62/649,294, entitled DATA STRIPPING METHOD TO INTERROGATE PATIENT RECORDS AND CREATE ANONYMIZED RECORD, filed Mar. 28, 2018, of U.S. Provisional Patent Application Ser. No. 62/649,296, entitled ADAPTIVE CONTROL PROGRAM UPDATES FOR SURGICAL DEVICES, filed Mar. 28, 2018, of U.S. Provisional Patent Application Ser. No. 62/649,300, entitled SURGICAL HUB SITUATIONAL AWARENESS, filed Mar. 28, 2018, of U.S. Provisional Patent Application Ser. No. 62/649,302, entitled INTERACTIVE SURGICAL SYSTEMS WITH ENCRYPTED COMMUNICATION CAPABILITIES, filed Mar. 28, 2018, of U.S. Provisional Patent Application Ser. No. 62/649,307, entitled AUTOMATIC TOOL ADJUSTMENTS FOR ROBOT-ASSISTED SURGICAL PLATFORMS, filed Mar. 28, 2018, of U.S. Provisional Patent Application Ser. No. 62/649,309, entitled SURGICAL HUB SPATIAL AWARENESS TO DETERMINE DEVICES IN OPERATING THEATER, filed Mar. 28, 2018, of U.S. Provisional Patent Application Ser. No. 62/649,310, entitled COMPUTER IMPLEMENTED INTERACTIVE SURGICAL SYSTEMS, filed Mar. 28, 2018, of U.S. Provisional Patent Application Ser. No. 62/649,313, entitled CLOUD INTERFACE FOR COUPLED SURGICAL DEVICES, filed Mar. 28, 2018, of U.S. Provisional Patent Application Ser. No. 62/649,315, entitled DATA HANDLING AND PRIORITIZATION IN A CLOUD ANALYTICS NETWORK, filed Mar. 28, 2018, of U.S. Provisional Patent Application Ser. No. 62/649,320, entitled DRIVE ARRANGEMENTS FOR ROBOT-ASSISTED SURGICAL PLATFORMS, filed Mar. 28, 2018, of U.S. Provisional Patent Application Ser. No. 62/649,323, entitled SENSING ARRANGEMENTS FOR ROBOT-ASSISTED SURGICAL PLATFORMS, filed Mar. 28, 2018, of U.S. Provisional Patent Application Ser. No. 62/649,327, entitled CLOUD-BASED MEDICAL ANALYTICS FOR SECURITY AND AUTHENTICATION TRENDS AND REACTIVE MEASURES, filed Mar. 28, 2018, and of U.S. Provisional Patent Application Ser. No. 62/649,333, entitled CLOUD-BASED MEDICAL ANALYTICS FOR CUSTOMIZATION AND RECOMMENDATIONS TO A USER, filed Mar. 28, 2018, the disclosures of which are incorporated by reference herein in their entireties. This application claims the benefit of U.S. Provisional Patent Application Ser. No. 62/611,339, entitled ROBOT ASSISTED SURGICAL PLATFORM, filed Dec. 28, 2017, of U.S. Provisional Patent Application Ser. No. 62/611,340, entitled CLOUD-BASED MEDICAL ANALYTICS, filed Dec. 28, 2017, and of U.S. Provisional Patent Application Ser. No. 62/611,341, entitled INTERACTIVE SURGICAL PLATFORM, filed Dec. 28, 2017, the disclosures of which are incorporated by reference herein in their entireties.

BACKGROUND

The present disclosure relates to surgical systems and, in various arrangements, to grasping instruments that are designed to grasp the tissue of a patient, dissecting instruments configured to manipulate the tissue of a patient, clip appliers configured to clip the tissue of a patient, and suturing instruments configured to suture the tissue of a patient, among others.

BRIEF DESCRIPTION OF THE DRAWINGS

Various features of the embodiments described herein, together with advantages thereof, may be understood in accordance with the following description taken in conjunction with the accompanying drawings as follows:

FIG. 55 is a perspective view of the drive module of FIG. 7 and a power module of FIG. 1;

FIG. 56 is a perspective view of the drive module of FIG. 7 and the power module of FIG. 55;

FIG. 57 is an elevational view of the drive module of FIG. 7 and the power module of FIG. 55 attached to a side battery port of the drive module;

FIG. 58 is a partial cross-sectional view of the connection between the side battery port of the drive module of FIG. 7 and the power module of FIG. 55;

FIG. 63 is a perspective view of the power module of FIG. 45 detached from the drive module of FIG. 7;

FIG. 64 is another perspective view of the power module of FIG. 45 detached from the drive module of FIG. 7;

FIG. 65 is an elevational view of the power module of FIG. 45 attached to the proximal battery port of the drive module of FIG. 7;

FIG. 79 is a perspective view of a flex circuit for use in the surgical instrument of FIG. 73 in accordance with at least one aspect of the present disclosure;

FIG. 90 is a perspective view of a handle in accordance with at least one embodiment;

FIG. 91 is a perspective view of a button shell of the handle of FIG. 90;

FIG. 92 is a perspective view of another button shell of the handle of FIG. 90;

FIG. 93 is a perspective view of another button shell of the handle of FIG. 90;

FIG. 99 is an icon displayable on a surgical instrument in accordance with at least one embodiment;

FIG. 100 is an icon displayable on a surgical instrument in accordance with at least one embodiment;

FIG. 101 is an icon displayable on a surgical instrument in accordance with at least one embodiment;

FIG. 104B illustrates a graduated display in communication with the control circuit of FIG. 104A, in accordance with at least one embodiment;

FIG. 104C illustrates a surgical instrument comprising a handle, in accordance with at least one embodiment;

FIG. 105 illustrates a surgical system, in accordance with at least one embodiment;

FIG. 106 illustrates a schematic diagram representative of current and signal paths of the surgical system of FIG. 105, in accordance with at least one embodiment;

FIG. 107 illustrates a graph showing a relationship between a continuity level of a patient and a level of electrosurgical power supplied by the surgical system of FIG. 105, in accordance with at least one embodiment;

FIG. 108 illustrates a flexible circuit of a surgical instrument, in accordance with at least one embodiment;

FIG. 109 illustrates a cross-section of the flexible circuit of FIG. 108;

FIG. 110 illustrates a flexible circuit of a surgical instrument, in accordance with at least one embodiment;

FIG. 111 illustrates a cross-section of the flexible circuit of FIG. 110;

FIG. 111A illustrates a flexible circuit of a surgical instrument, in accordance with at least one embodiment;

FIG. 112 illustrates a control circuit of a surgical instrument, in accordance with at least one embodiment;

FIG. 113 illustrates a method for identifying a degradation or failure of components of a surgical instrument, in accordance with at least one embodiment;

Figure 114:
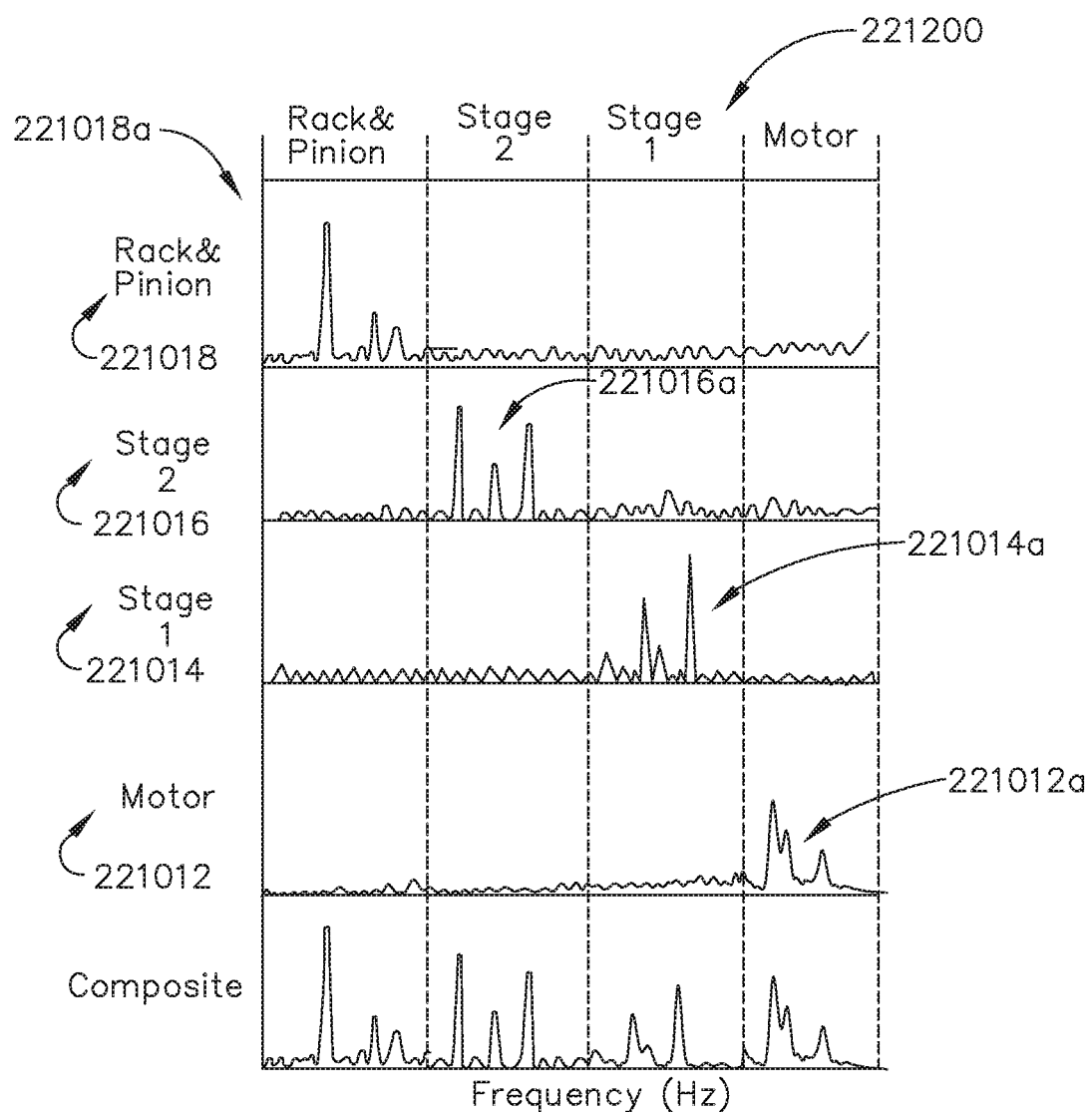
Figure 115:
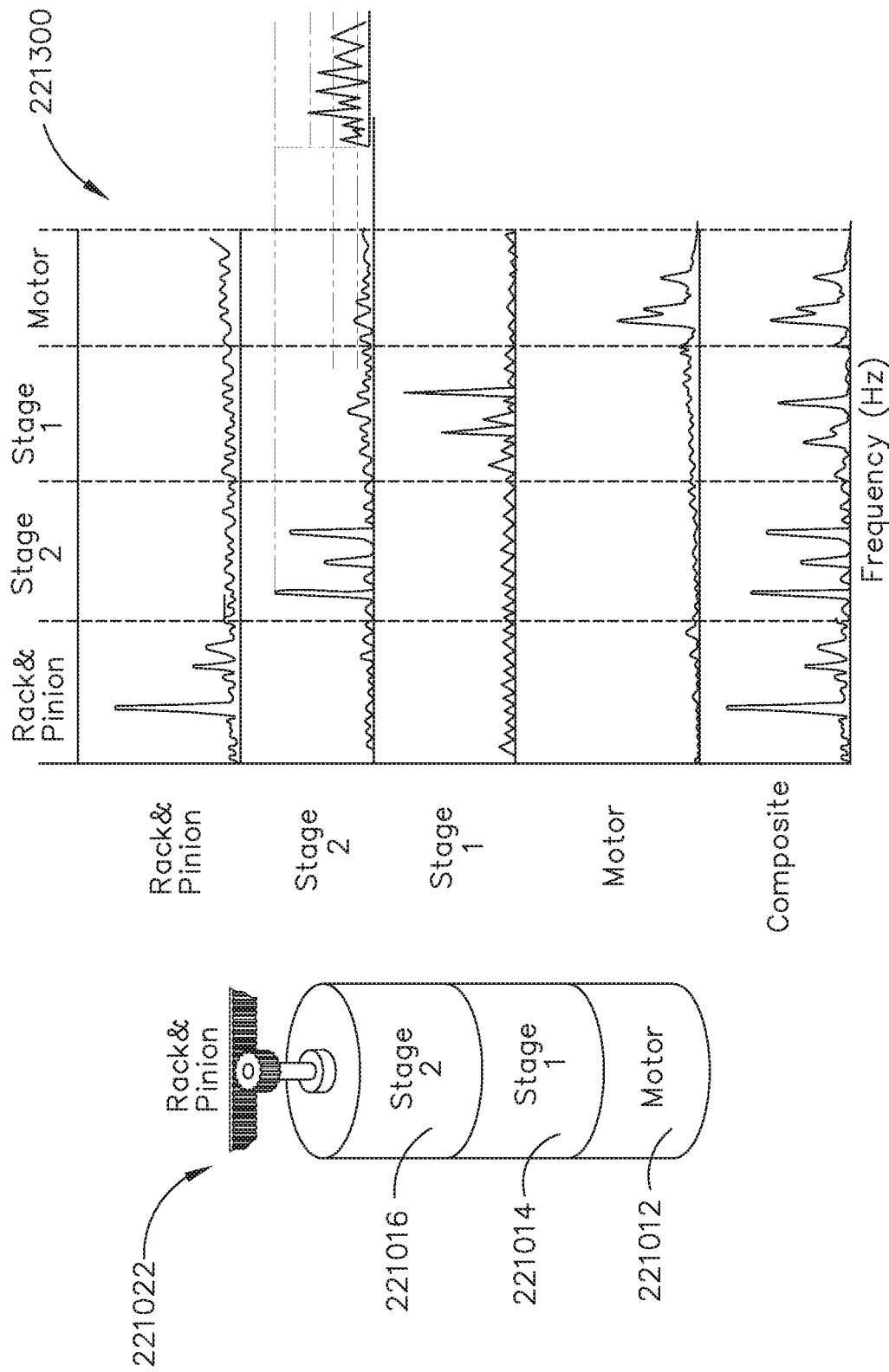
Figure 116:
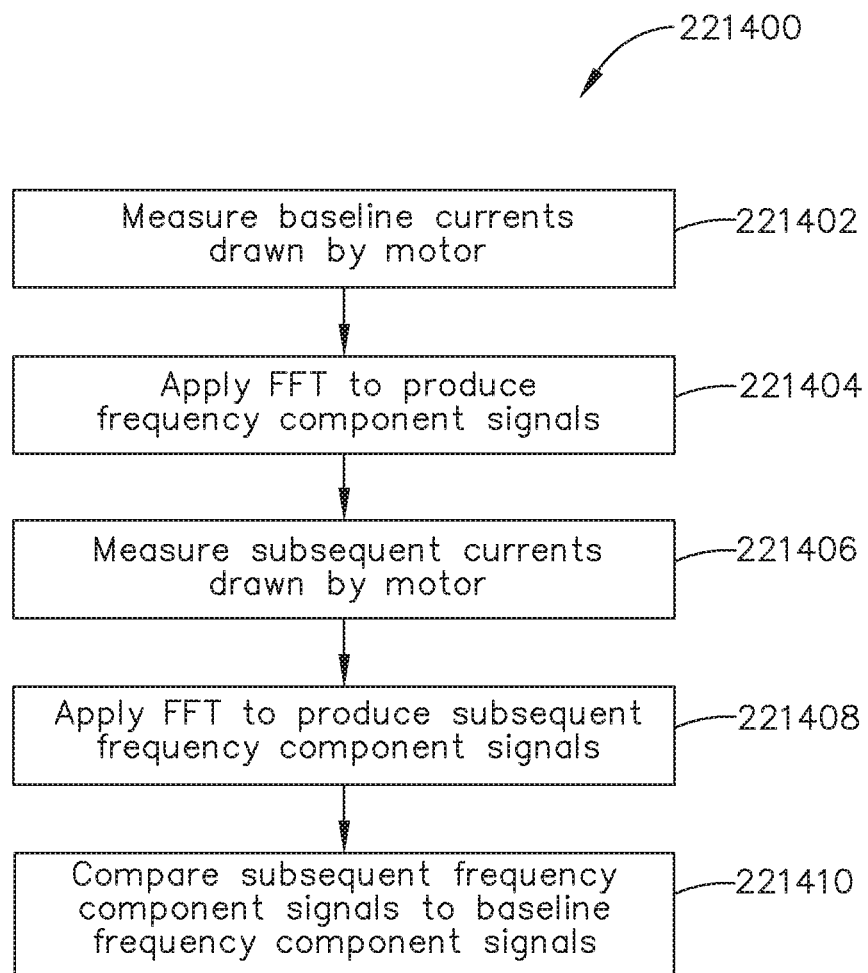
Figure 117:
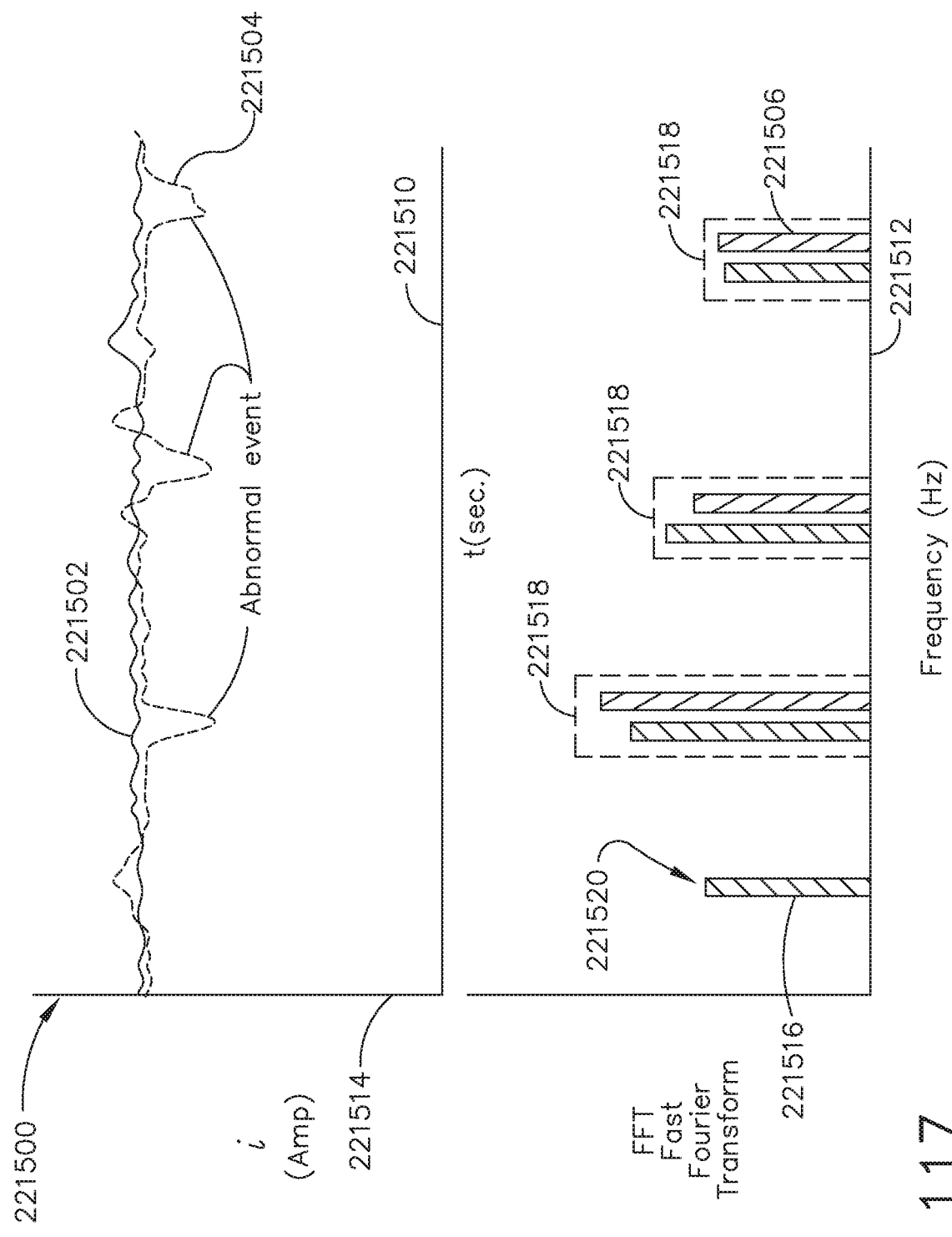
Figure 118:
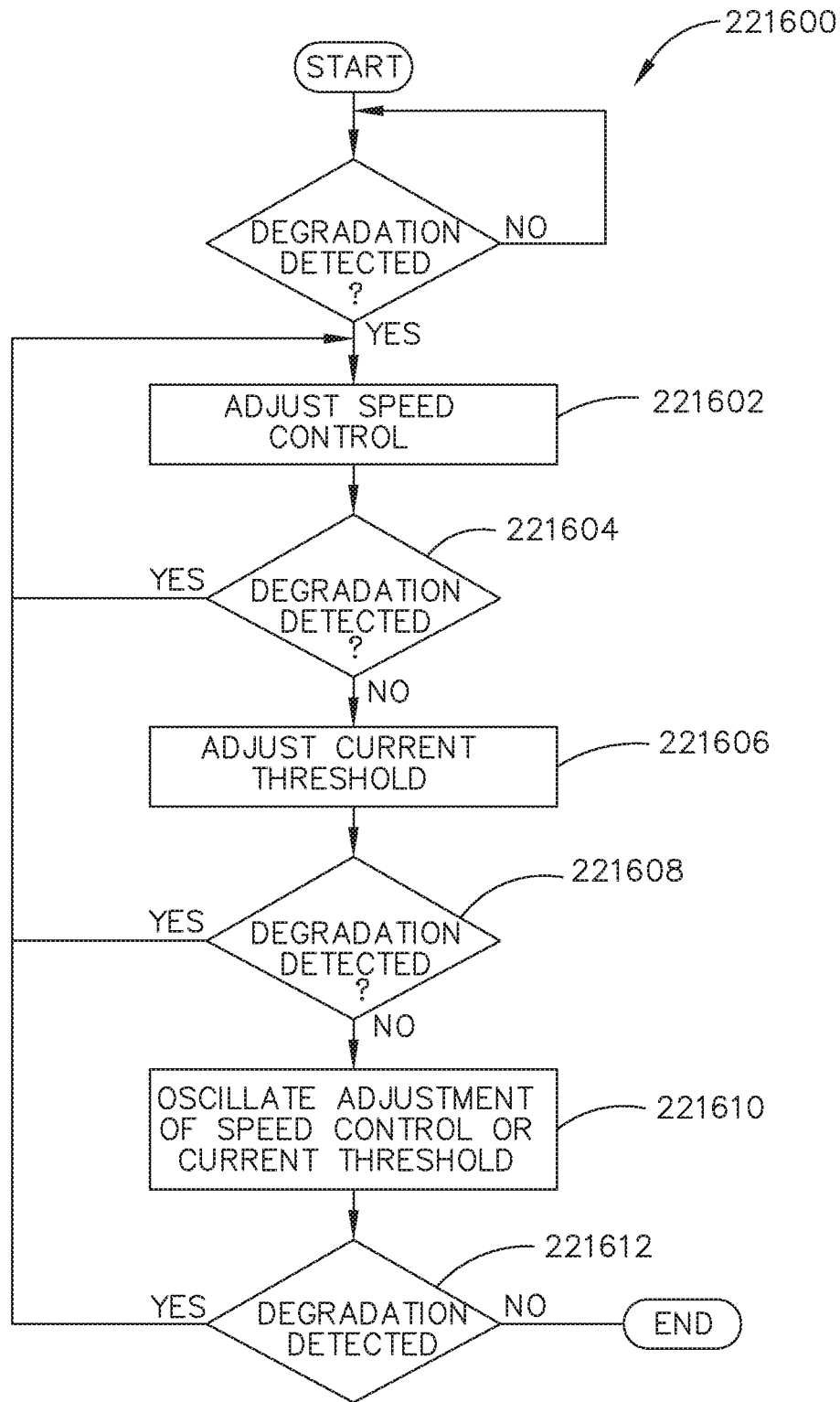
Figure 119:
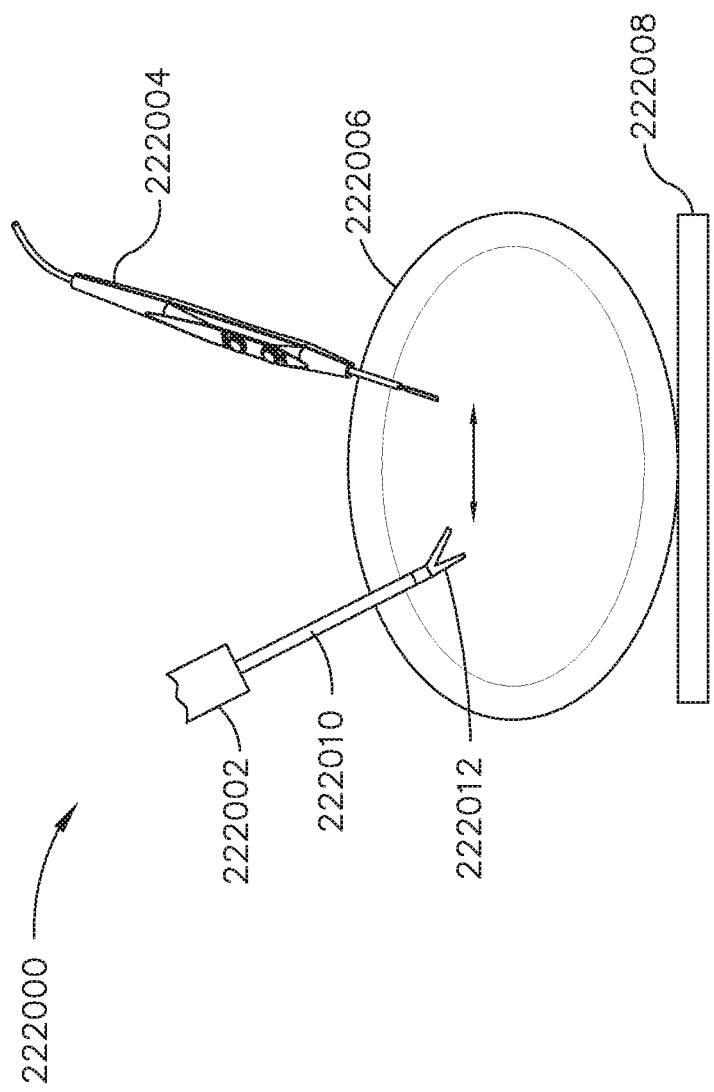
Figure 120:
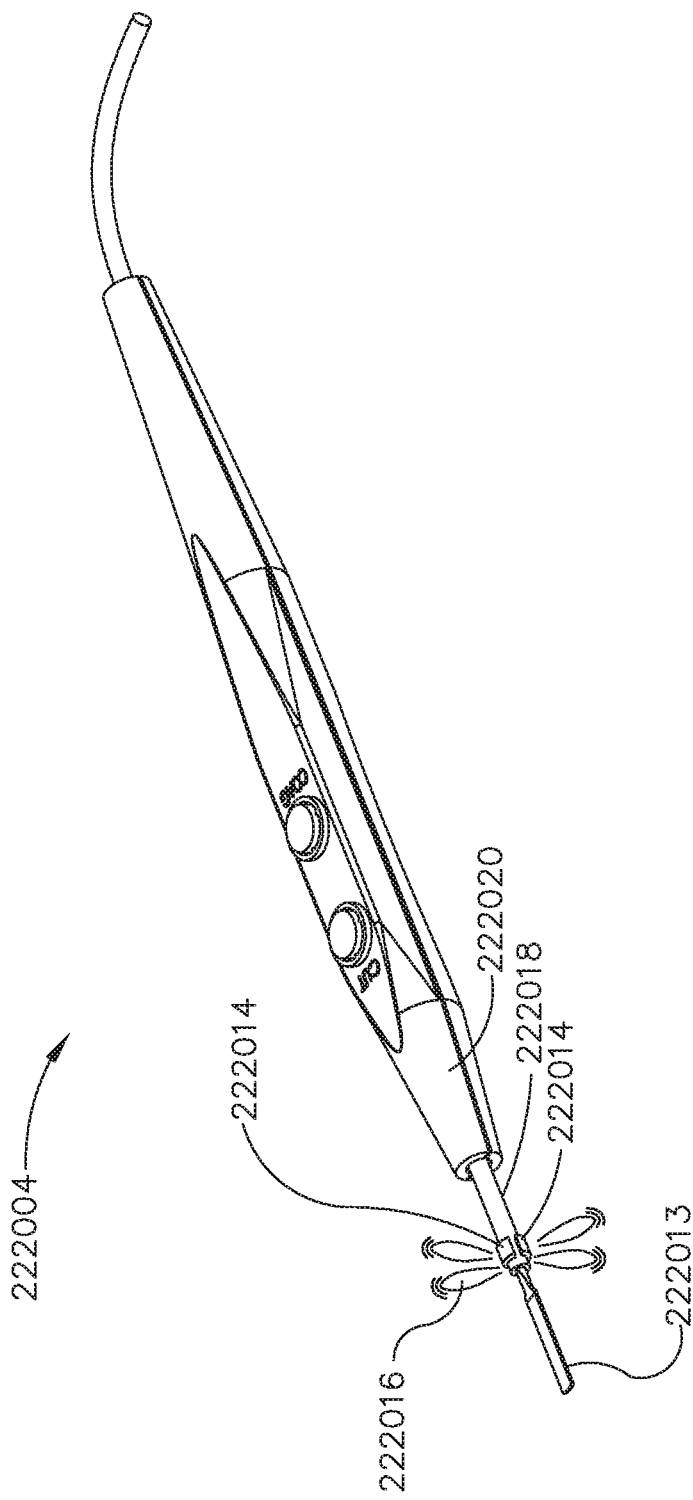
Figures 121, 122:
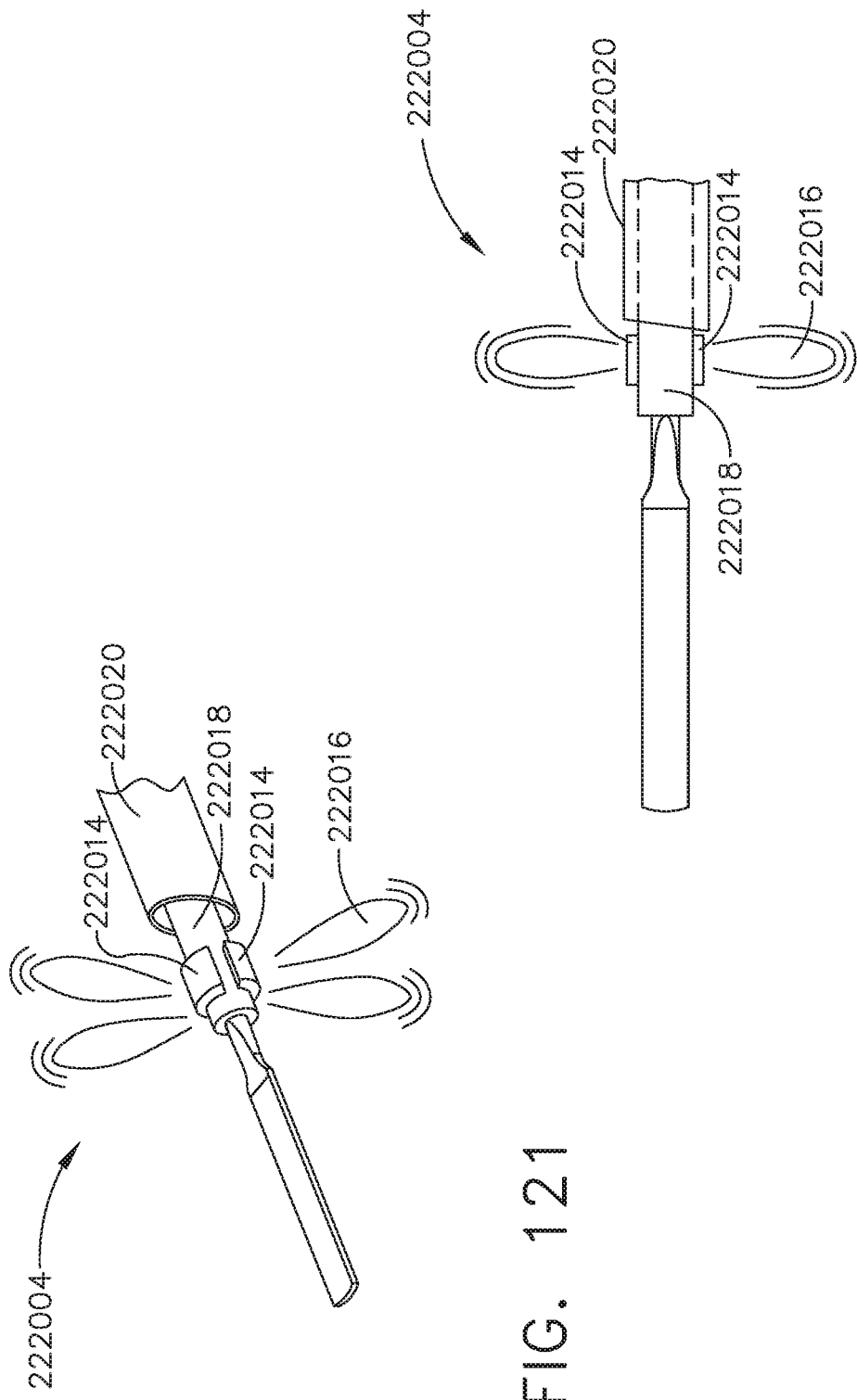
Figure 123:
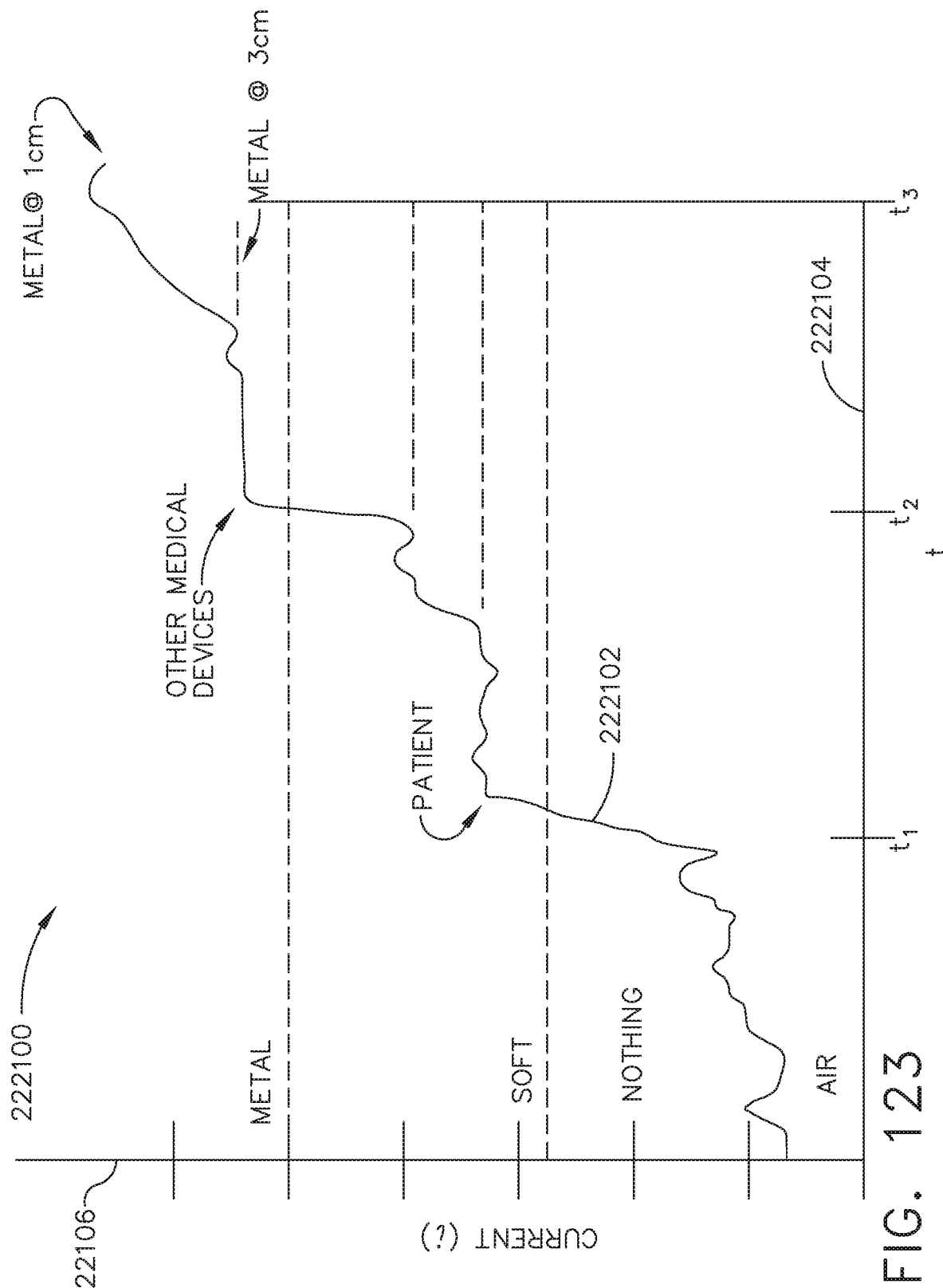
Figure 124:
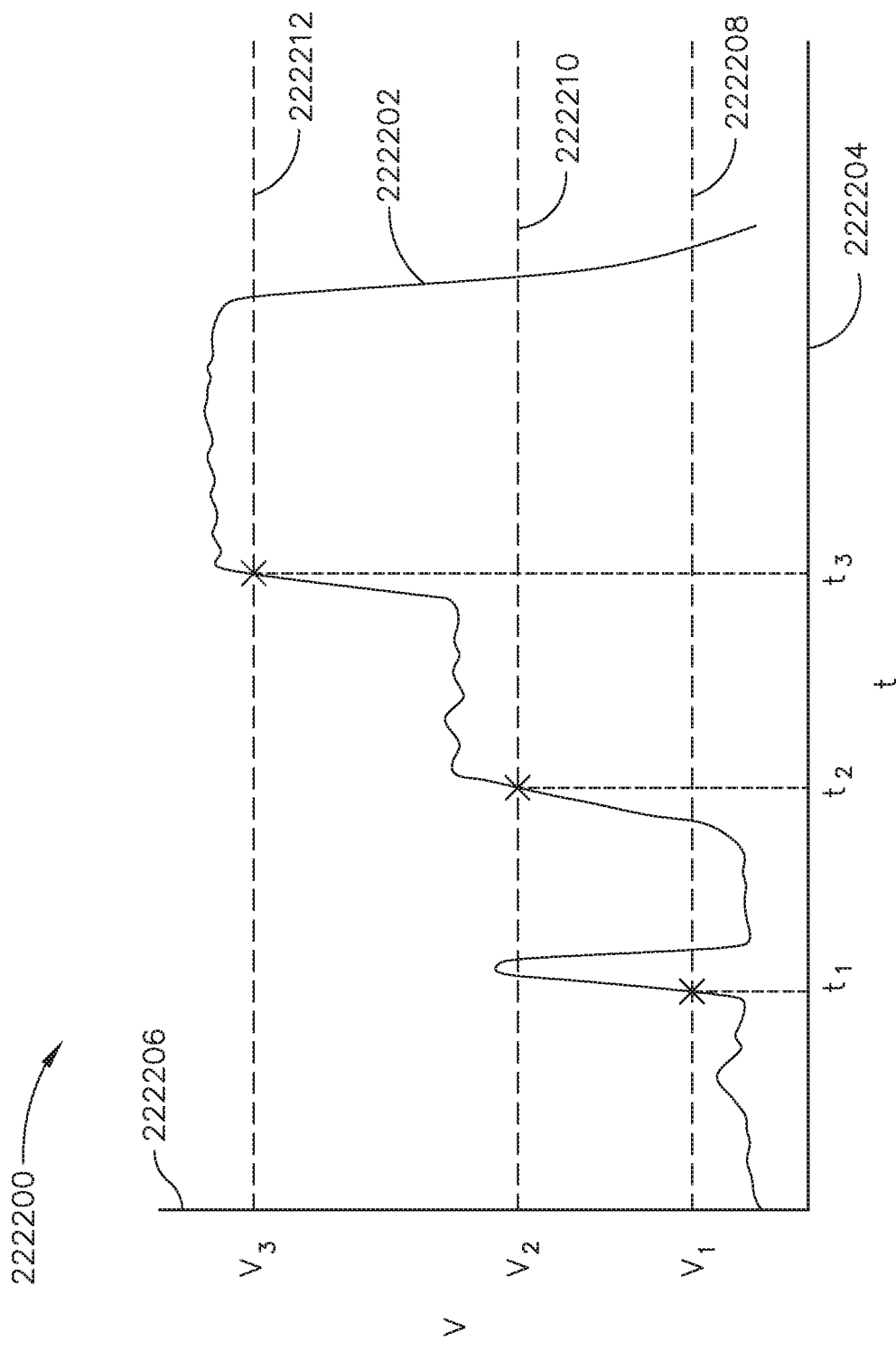
Figure 125:
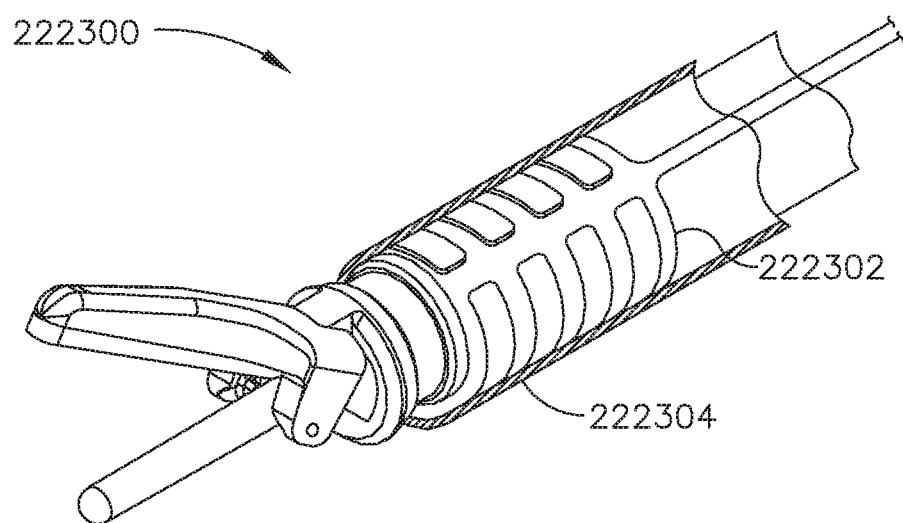
Figure 126:
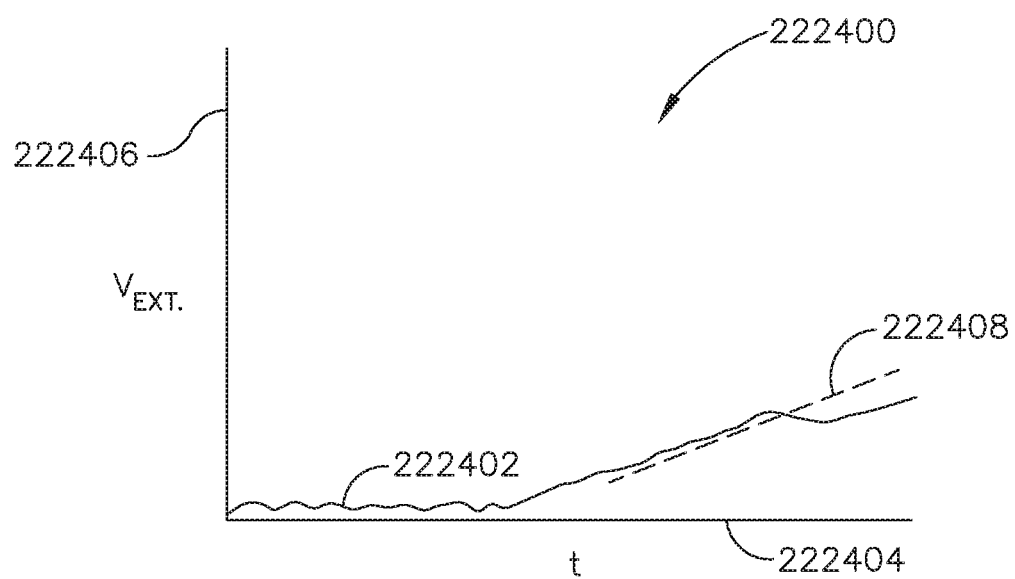
Figure 127:
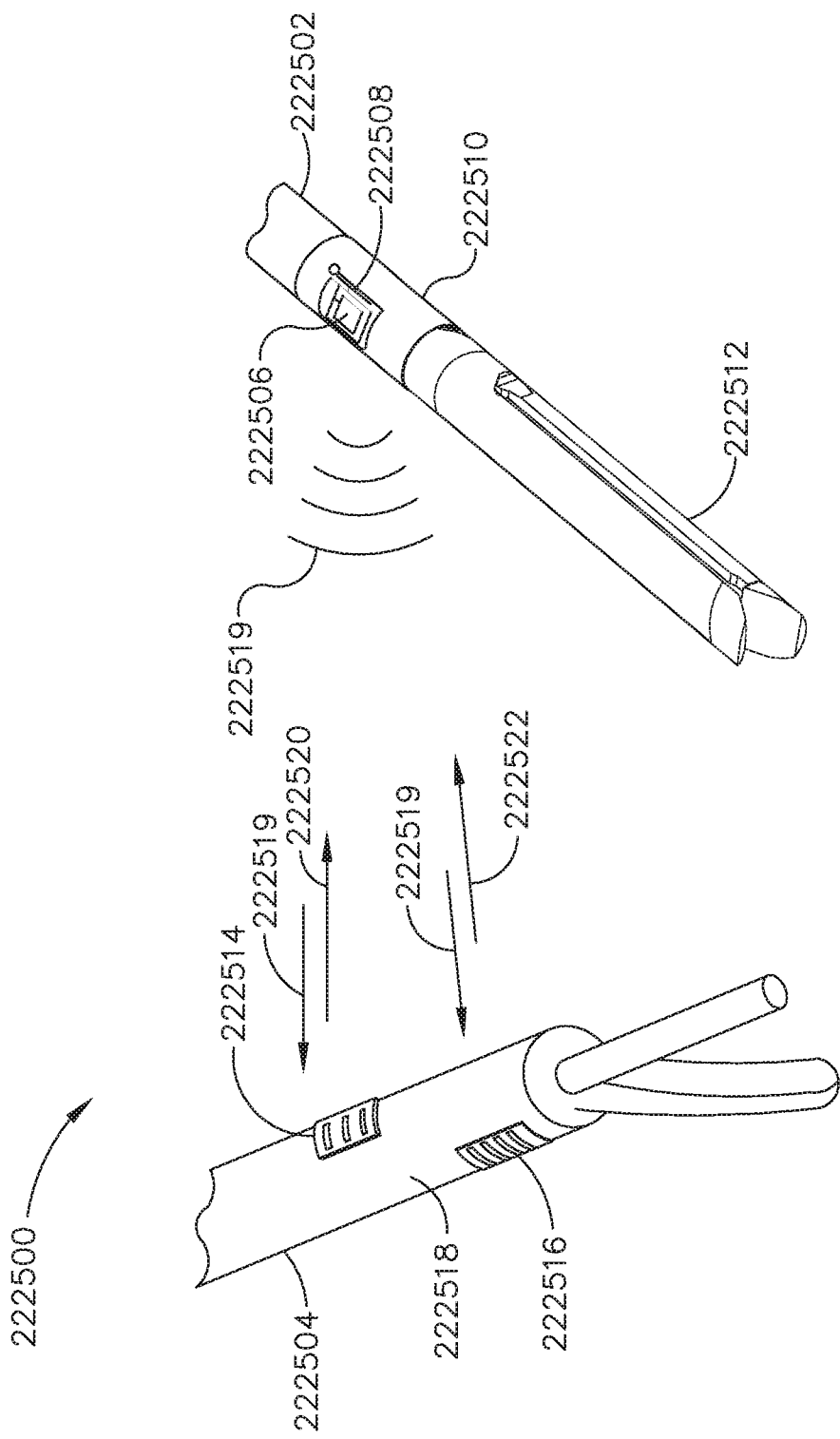
Figure 128:
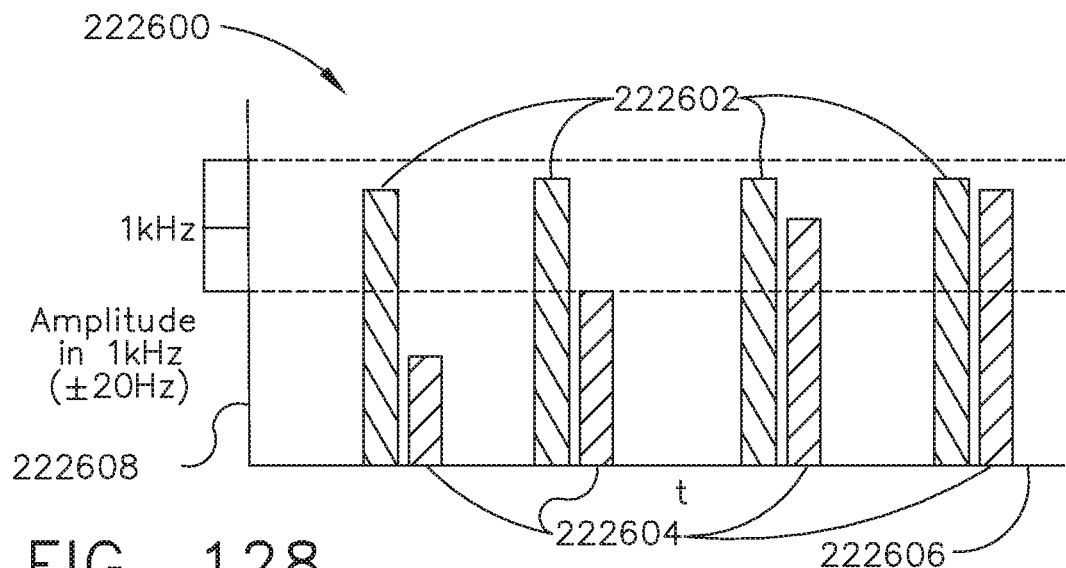
Figure 129:
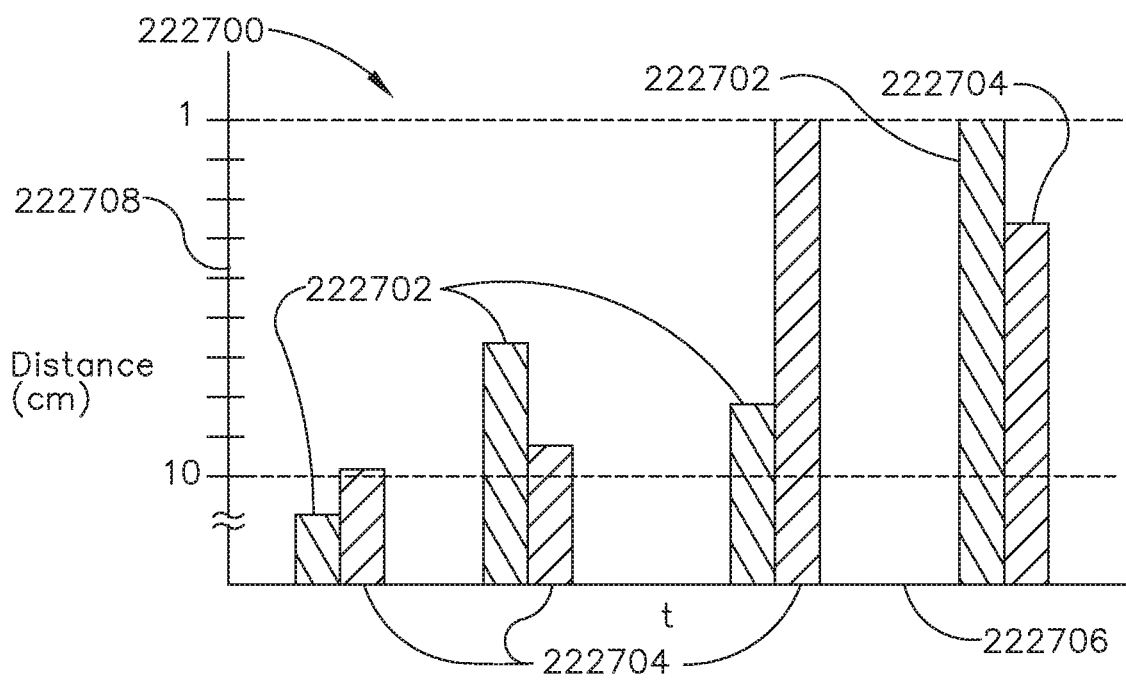
Figure 132:
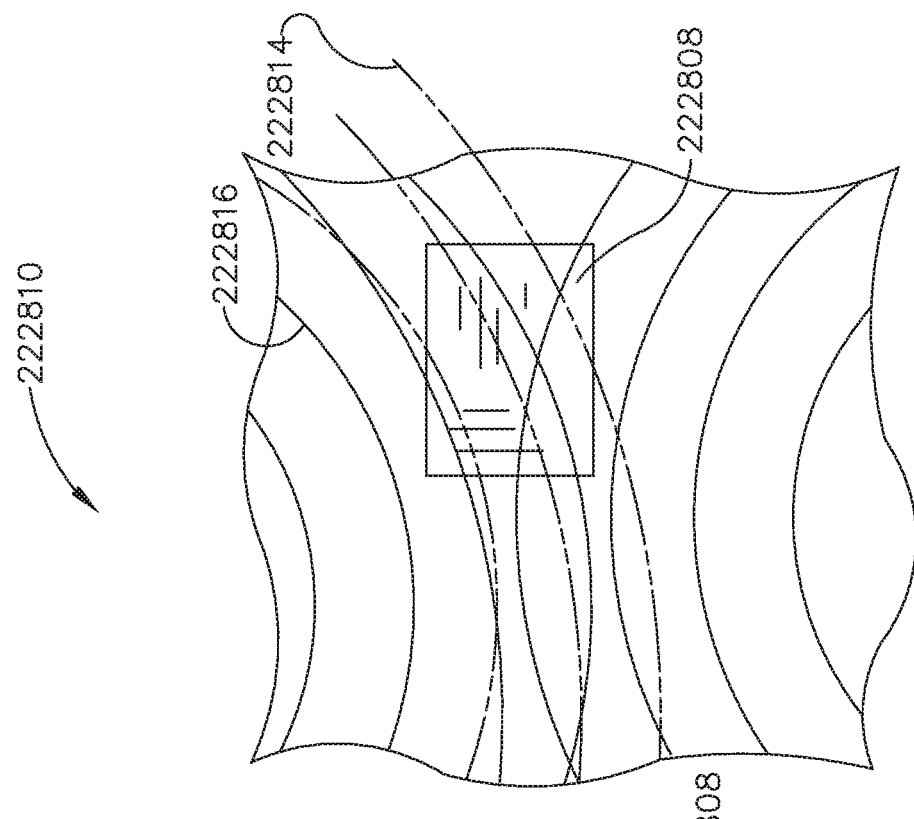
Figure 131:
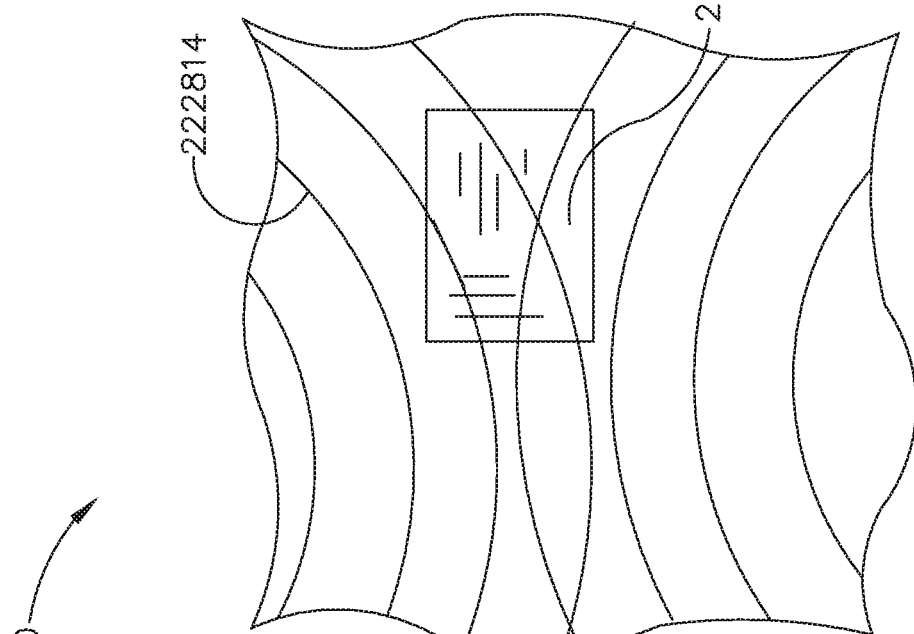
Figure 133:
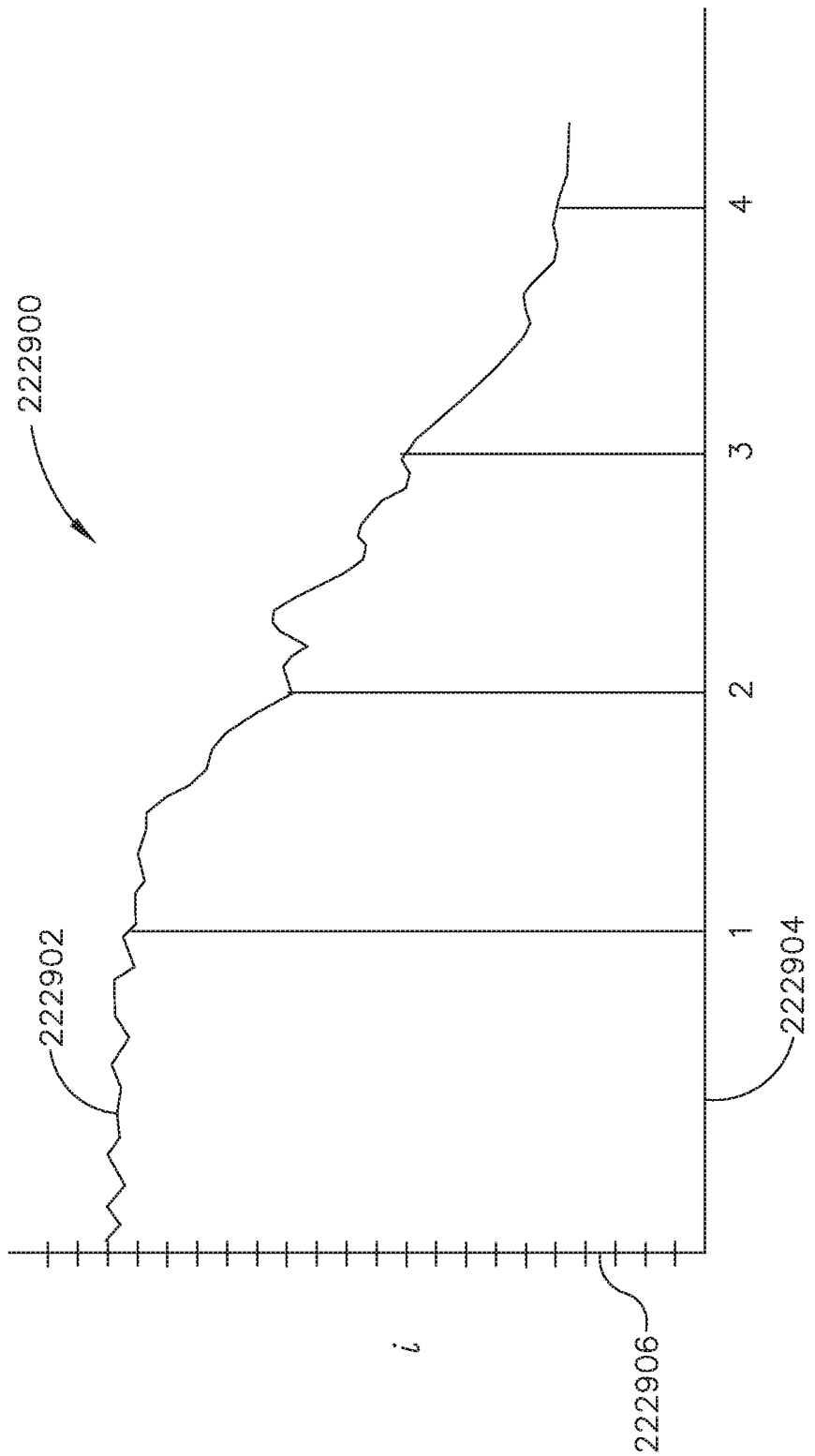
Figure 137:
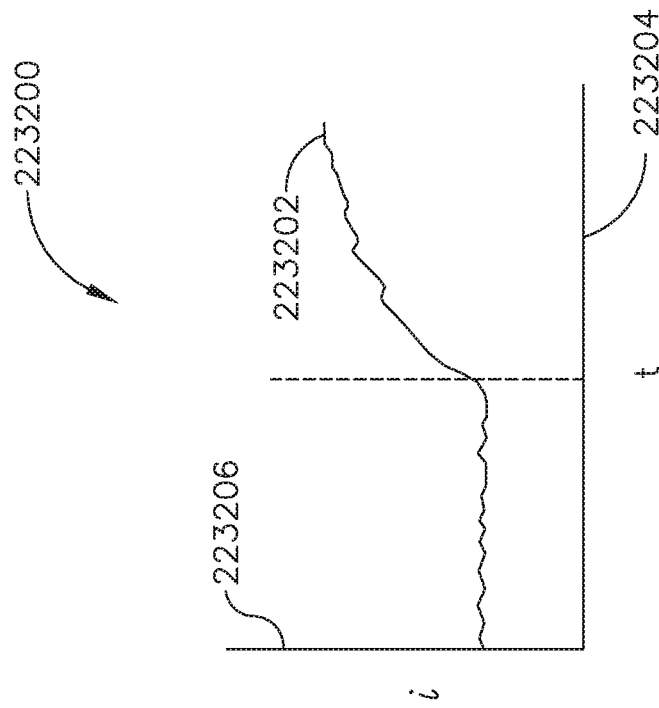
Figure 136:
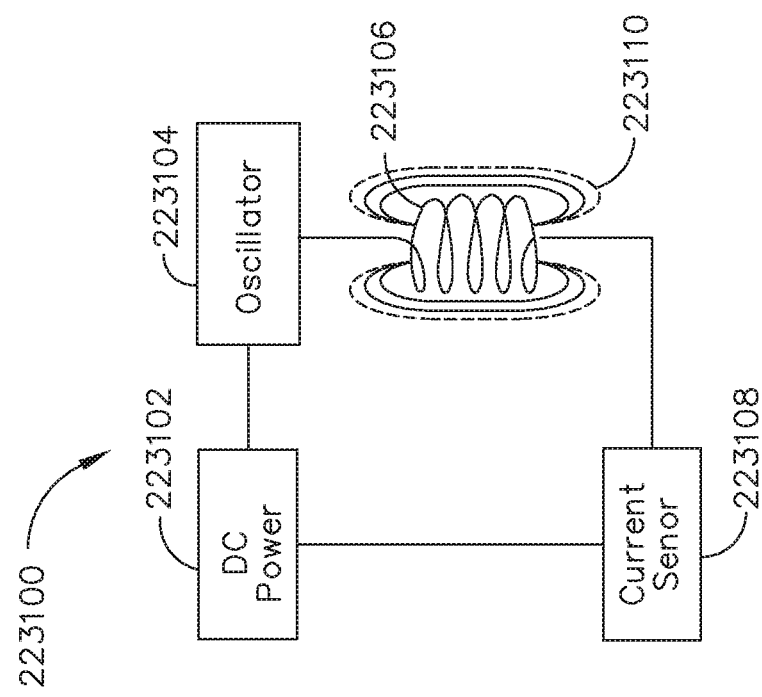
Figure 138:
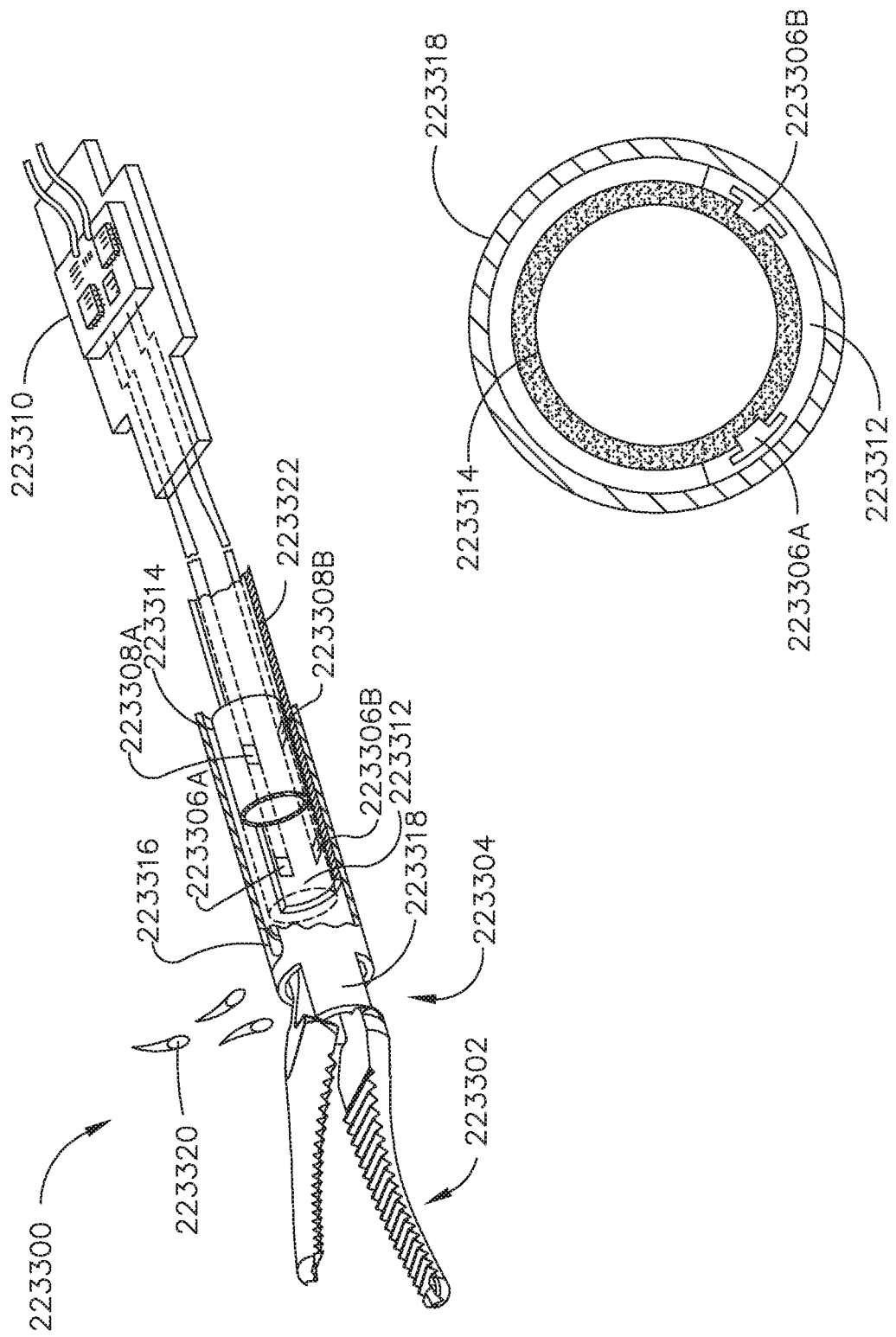
Figure 139:
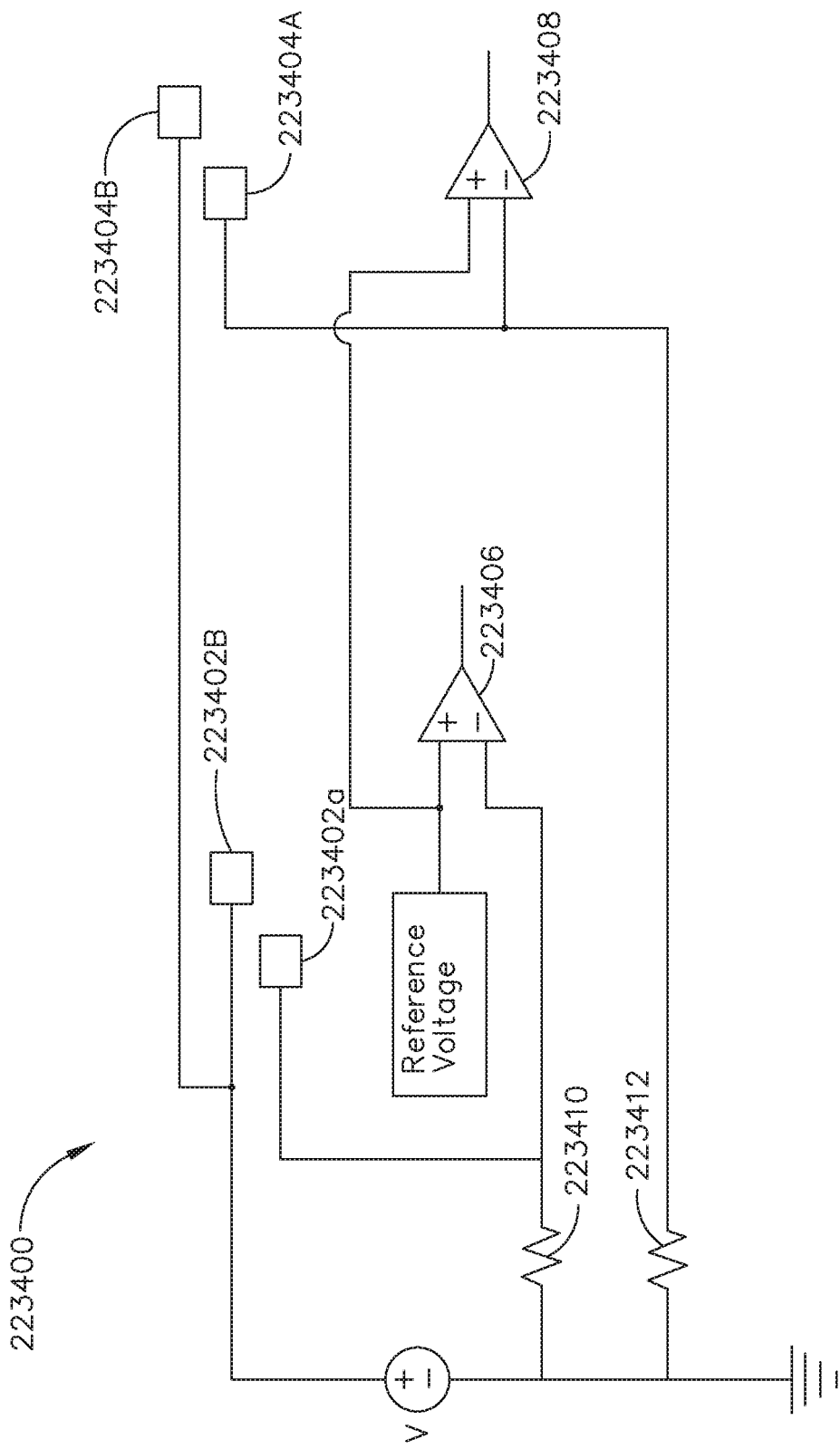
Figure 140:
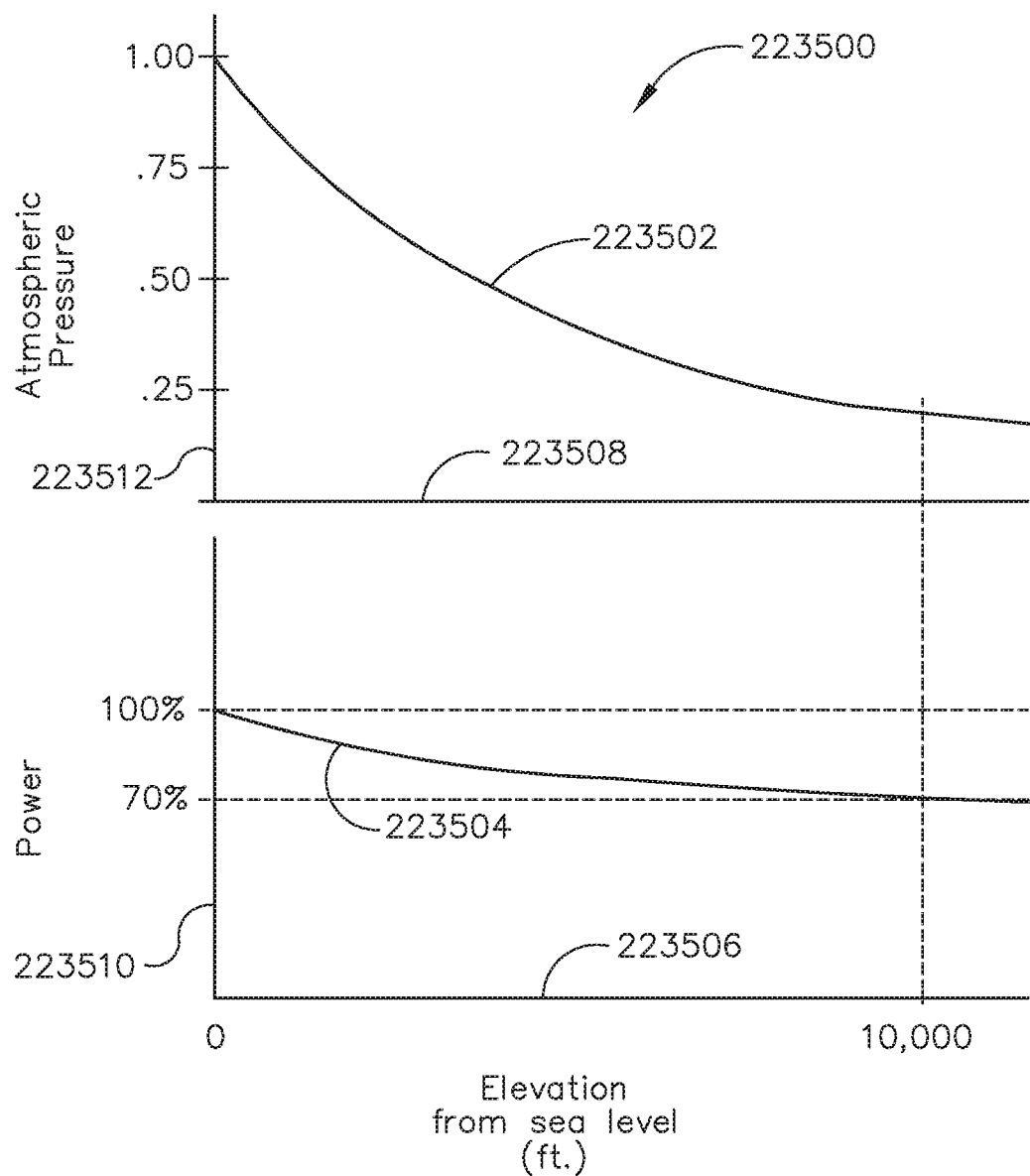
Figure 141:
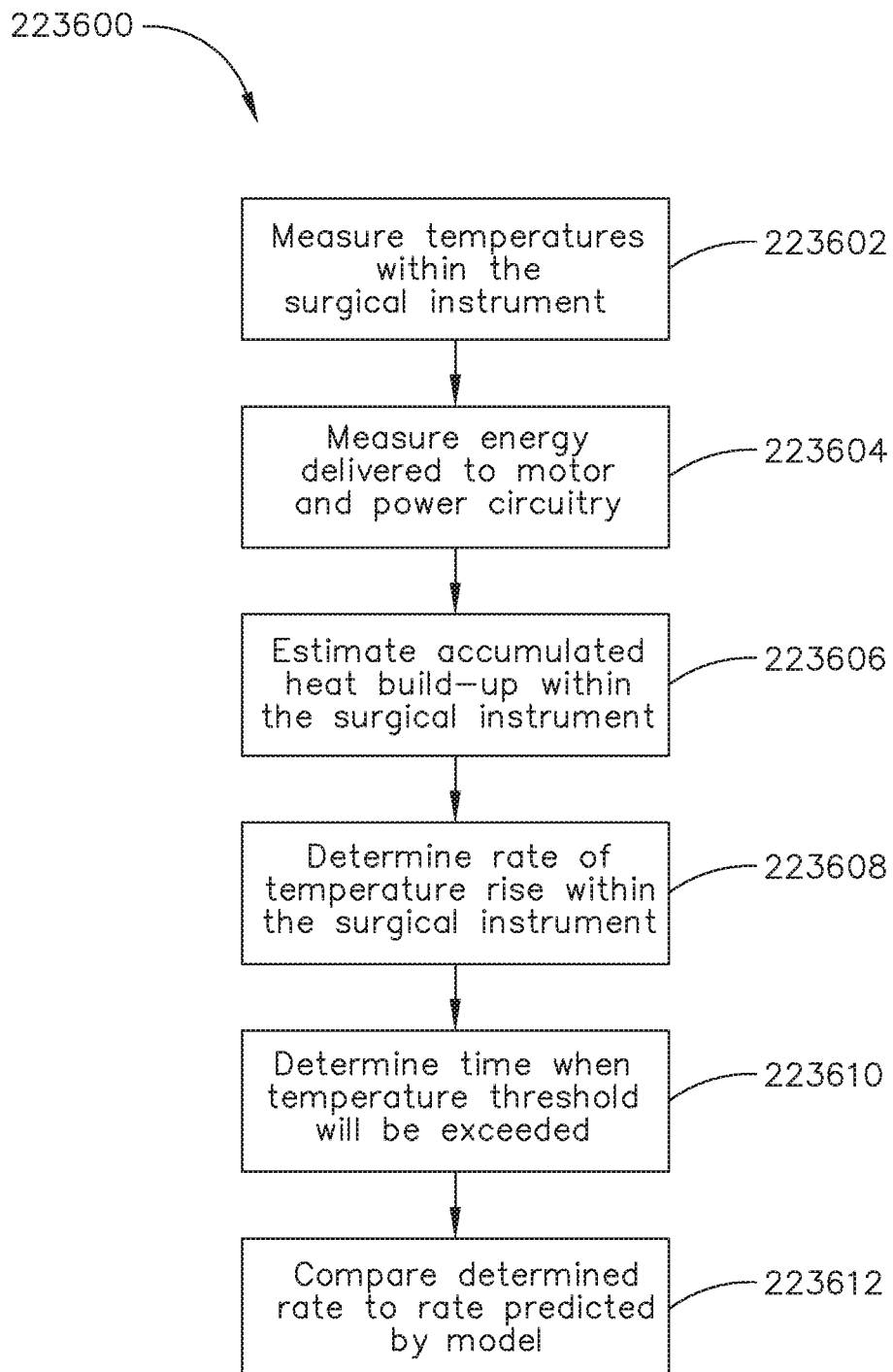
Figure 142:
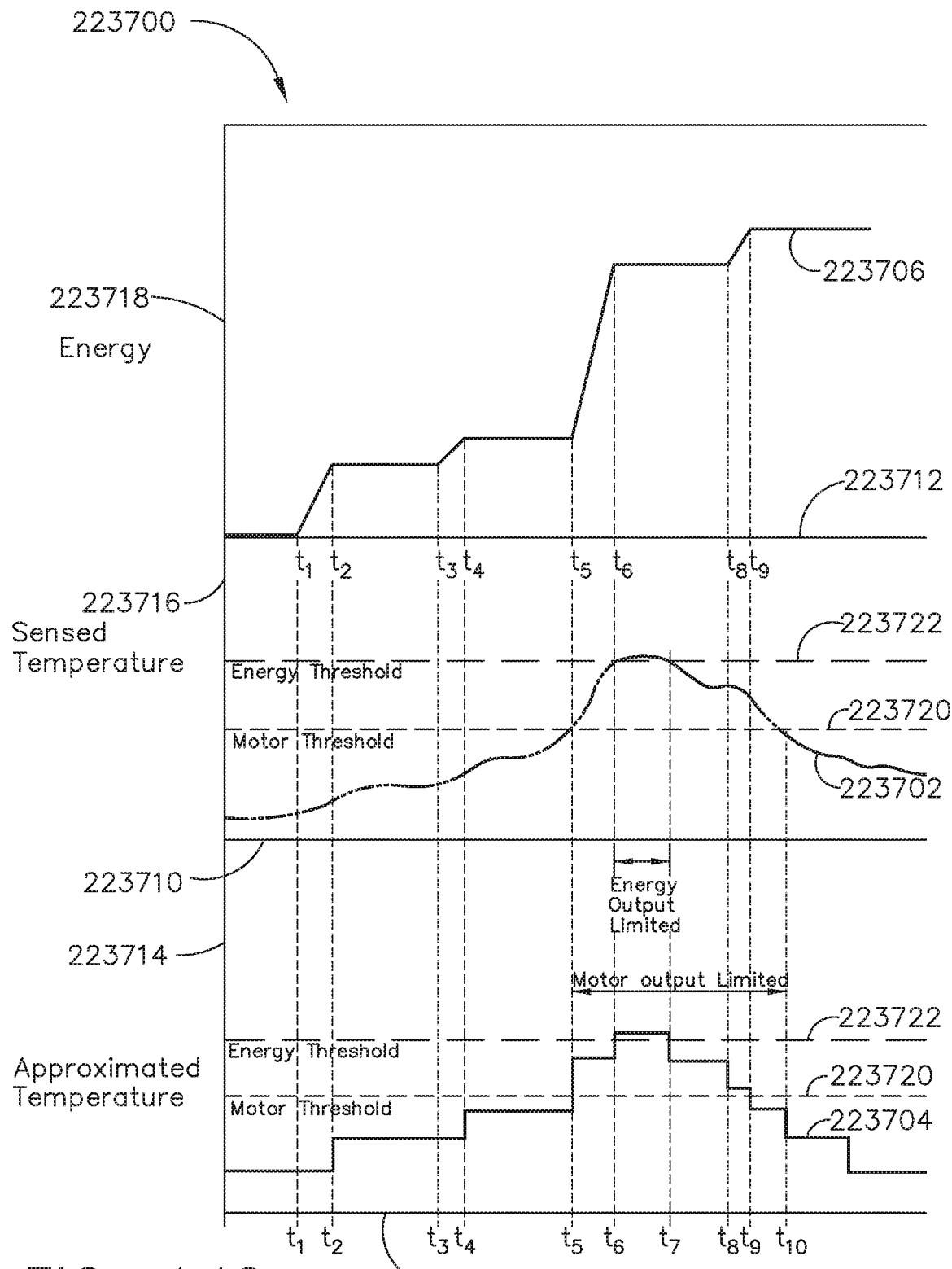

FIG. 114 illustrates a graph showing frequency component signals of acoustical signatures of components of a surgical instrument, in accordance with at least one embodiment;

FIG. 115 illustrates components associated with the frequency component signals of FIG. 114;

FIG. 116 illustrates a method for identifying a degradation or failure of drive components of a surgical instrument, in accordance with at least one embodiment;

FIG. 117 illustrates a graph showing a relationship between motor current draw and frequency component signals of the motor of a surgical instrument, in accordance with at least one embodiment;

FIG. 118 illustrates a method for adjusting a motor control algorithm of a surgical instrument, in accordance with at least one embodiment;

FIG. 119 illustrates an environment of a surgical procedure, in accordance with at least one embodiment;

FIG. 120 illustrates a monopolar surgical instrument, in accordance with at least one embodiment;

FIGS. 121 and 122 illustrate electrical terminations of the monopolar surgical instrument of FIG. 120;

FIG. 123 illustrates a graph showing a relationship between leakage current and distances between surgical instruments, in accordance with at least one aspect of the present disclosure;

FIG. 124 illustrates a graph showing direct current (DC) output voltage thresholds for different types of surgical instrument contact, in accordance with at least one embodiment;

FIG. 125 illustrates a powered surgical instrument, in accordance with at least one embodiment;

FIG. 126 illustrates a graph showing electrical potential associated with the powered surgical instrument of FIG. 125, in accordance with at least one embodiment;

FIG. 127 illustrates an active transmission and sensing scheme utilized by a surgical instrument, in accordance with at least one embodiment;

FIG. 128 illustrates a graph showing signals transmitted and received by the surgical instrument of FIG. 127;

FIG. 129 illustrates a graph showing proximity measurements associated with the surgical instrument of FIG. 127;

FIG. 130 illustrates a passive sensing scheme utilized by a surgical instrument, in accordance with at least one embodiment;

FIG. 131 illustrates a primary magnetic field associated with the surgical instrument of FIG. 130 in an unaffected condition;

FIG. 132 illustrates a primary magnetic field associated with the surgical instrument of FIG. 130 in an affected condition;

FIG. 133 illustrates a graph which showing Hall current associated with the surgical instrument of FIG. 130, in accordance with at least one embodiment;

FIGS. 134 and 135 illustrate a passive sensing scheme utilized by a surgical instrument, in accordance with at least one embodiment;

FIG. 136 illustrates a schematic of a surgical instrument, in accordance with at least one embodiment;

FIG. 137 illustrates a graph which showing induced current measured by a current sensor of the surgical instrument of FIG. 136, in accordance with at least one embodiment;

FIG. 138 illustrates a surgical instrument in accordance with at least one embodiment illustrated with components removed;

FIG. 139 illustrates an electrical circuit of the surgical instrument of FIG. 138;

FIG. 140 illustrates a graph showing relationships between altitude, atmospheric pressure and electrical power utilized by a surgical instrument, in accordance with at least one embodiment;

FIG. 141 illustrates a method for predicting an occurrence of a predefined temperature threshold being exceeded, in accordance with at least one embodiment; and FIG. 142 illustrates a graph showing a relationship between a sensed temperature, an approximated temperature, and an energy usage of a surgical instrument, in accordance with at least one embodiment.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. patent applications that were filed on Dec. 14, 2018 which are each herein incorporated by reference in their respective entireties:
- U.S. patent application Ser. No. 16/220,301, entitled SURGICAL INSTRUMENT WITH ACOUSTIC-BASED MOTOR CONTROL, now U.S. Patent Application Publication No. 2019/0201027;
- U.S. patent application Ser. No. 16/220,313, entitled SURGICAL INSTRUMENT COMPRISING A PLURALITY OF DRIVE SYSTEMS, now U.S. Patent Application Publication No. 2019/0201030;
- U.S. patent application Ser. No. 16/220,296, entitled SURGICAL INSTRUMENT COMPRISING A CONTROL CIRCUIT, now U.S. Patent Application Publication No. 2019/0201026;
- U.S. patent application Ser. No. 16,220,309, entitled SURGICAL INSTRUMENTS COMPRISING BUTTON CIRCUITS, now U.S. Patent Application Publication No. 2019/0201028;
- U.S. patent application Ser. No. 16/220,318, entitled SURGICAL INSTRUMENT COMPRISING A CONTROL SYSTEM THAT USES INPUT FROM A STRAIN GAGE CIRCUIT, now U.S. Patent Application Publication No. 2019/0201029;
- U.S. patent application Ser. No. 16/220,273, entitled SURGICAL INSTRUMENT WITH A SENSING ARRAY, now U.S. Patent Application Publication No. 2019/0201023; and
- U.S. patent application Ser. No. 16/220,280, entitled SURGICAL INSTRUMENT WITH ENVIRONMENT SENSING, now U.S. Patent Application Publication No. 2019/0201024.

Applicant of the present application owns the following U.S. Provisional patent applications, filed on Dec. 12, 2018, each of which is herein incorporated by reference in its entirety:
- U.S. Provisional Patent Application Ser. No. 62/778,571, entitled SURGICAL INSTRUMENT SYSTEMS;
- U.S. Provisional Patent Application Ser. No. 62/778,572, entitled SURGICAL INSTRUMENT SYSTEMS; and
- U.S. Provisional Patent Application Ser. No. 62/778,573, entitled SURGICAL INSTRUMENT SYSTEMS.

Applicant of the present application owns the following U.S. patent applications that were filed on Oct. 26, 2018 which are each herein incorporated by reference in their respective entireties:
- U.S. patent application Ser. No. 16/172,130, entitled CLIP APPLIER COMPRISING INTERCHANGEABLE CLIP RELOADS;
- U.S. patent application Ser. No. 16/172,066, entitled CLIP APPLIER COMPRISING A MOVABLE CLIP MAGAZINE;
- U.S. patent application Ser. No. 16/172,078, entitled CLIP APPLIER COMPRISING A ROTATABLE CLIP MAGAZINE;
- U.S. patent application Ser. No. 16/172,087, entitled CLIP APPLIER COMPRISING CLIP ADVANCING SYSTEMS;
- U.S. patent application Ser. No. 16/172,094, entitled CLIP APPLIER COMPRISING A CLIP CRIMPING SYSTEM;
- U.S. patent application Ser. No. 16/172,128, entitled CLIP APPLIER COMPRISING A RECIPROCATING CLIP ADVANCING MEMBER;
- U.S. patent application Ser. No. 16/172,168, entitled CLIP APPLIER COMPRISING A MOTOR CONTROLLER;
- U.S. patent application Ser. No. 16/172,164, entitled SURGICAL SYSTEM COMPRISING A SURGICAL TOOL AND A SURGICAL HUB; and
- U.S. patent application Ser. No. 16/172,303, entitled METHOD FOR OPERATING A POWERED ARTICULATING MULTI-CLIP APPLIER.

Applicant of the present application owns the following U.S. patent applications that were filed on Oct. 26, 2018 which are each herein incorporated by reference in their respective entireties:
- U.S. patent application Ser. No. 16/172,328, entitled METHOD OF HUB COMMUNICATION WITH SURGICAL INSTRUMENT SYSTEMS;
- U.S. patent application Ser. No. 16/172,280, entitled METHOD FOR PRODUCING A SURGICAL INSTRUMENT COMPRISING A SMART ELECTRICAL SYSTEM;
- U.S. patent application Ser. No. 16/172,219, entitled METHOD OF HUB COMMUNICATION WITH SURGICAL INSTRUMENT SYSTEMS;
- U.S. patent application Ser. No. 16/172,248, entitled METHOD FOR COMMUNICATING WITH SURGICAL INSTRUMENT SYSTEMS;
- U.S. patent application Ser. No. 16/172,198, entitled METHOD OF HUB COMMUNICATION WITH SURGICAL INSTRUMENT SYSTEMS; and
- U.S. patent application Ser. No. 16/172,155, entitled METHOD OF HUB COMMUNICATION WITH SURGICAL INSTRUMENT SYSTEMS.

Applicant of the present application owns the following U.S. patent applications that were filed on Aug. 24, 2018 which are each herein incorporated by reference in their respective entireties:
- U.S. patent application Ser. No. 16/112,129, entitled SURGICAL SUTURING INSTRUMENT CONFIGURED TO MANIPULATE TISSUE USING MECHANICAL AND ELECTRICAL POWER;
- U.S. patent application Ser. No. 16/112,155, entitled SURGICAL SUTURING INSTRUMENT COMPRISING A CAPTURE WIDTH WHICH IS LARGER THAN TROCAR DIAMETER;
- U.S. patent application Ser. No. 16/112,168, entitled SURGICAL SUTURING INSTRUMENT COMPRISING A NON-CIRCULAR NEEDLE;
- U.S. patent application Ser. No. 16/112,180, entitled ELECTRICAL POWER OUTPUT CONTROL BASED ON MECHANICAL FORCES;
- U.S. patent application Ser. No. 16/112,193, entitled REACTIVE ALGORITHM FOR SURGICAL SYSTEM;
- U.S. patent application Ser. No. 16/112,099, entitled SURGICAL INSTRUMENT COMPRISING AN ADAPTIVE ELECTRICAL SYSTEM;
- U.S. patent application Ser. No. 16/112,112, entitled CONTROL SYSTEM ARRANGEMENTS FOR A MODULAR SURGICAL INSTRUMENT;
- U.S. patent application Ser. No. 16/112,119, entitled ADAPTIVE CONTROL PROGRAMS FOR A SURGICAL SYSTEM COMPRISING MORE THAN ONE TYPE OF CARTRIDGE;
- U.S. patent application Ser. No. 16/112,097, entitled SURGICAL INSTRUMENT SYSTEMS COMPRISING BATTERY ARRANGEMENTS;

U.S. patent application Ser. No. 16/112,109, entitled SURGICAL INSTRUMENT SYSTEMS COMPRISING HANDLE ARRANGEMENTS;

U.S. patent application Ser. No. 16/112,114, entitled SURGICAL INSTRUMENT SYSTEMS COMPRISING FEEDBACK MECHANISMS;

U.S. patent application Ser. No. 16/112,117, entitled SURGICAL INSTRUMENT SYSTEMS COMPRISING LOCKOUT MECHANISMS;

U.S. patent application Ser. No. 16/112,095, entitled SURGICAL INSTRUMENTS COMPRISING A LOCKABLE END EFFECTOR SOCKET;

U.S. patent application Ser. No. 16/112,121, entitled SURGICAL INSTRUMENTS COMPRISING A SHIFTING MECHANISM;

U.S. patent application Ser. No. 16/112,151, entitled SURGICAL INSTRUMENTS COMPRISING A SYSTEM FOR ARTICULATION AND ROTATION COMPENSATION;

U.S. patent application Ser. No. 16/112,154, entitled SURGICAL INSTRUMENTS COMPRISING A BIASED SHIFTING MECHANISM;

U.S. patent application Ser. No. 16/112,226, entitled SURGICAL INSTRUMENTS COMPRISING AN ARTICULATION DRIVE THAT PROVIDES FOR HIGH ARTICULATION ANGLES;

U.S. patent application Ser. No. 16/112,062, entitled SURGICAL DISSECTORS AND MANUFACTURING TECHNIQUES;

U.S. patent application Ser. No. 16/112,098, entitled SURGICAL DISSECTORS CONFIGURED TO APPLY MECHANICAL AND ELECTRICAL ENERGY;

U.S. patent application Ser. No. 16/112,237, entitled SURGICAL CLIP APPLIER CONFIGURED TO STORE CLIPS IN A STORED STATE;

U.S. patent application Ser. No. 16/112,245, entitled SURGICAL CLIP APPLIER COMPRISING AN EMPTY CLIP CARTRIDGE LOCKOUT;

U.S. patent application Ser. No. 16/112,249, entitled SURGICAL CLIP APPLIER COMPRISING AN AUTOMATIC CLIP FEEDING SYSTEM;

U.S. patent application Ser. No. 16/112,253, entitled SURGICAL CLIP APPLIER COMPRISING ADAPTIVE FIRING CONTROL; and U.S. patent application Ser. No. 16/112,257, entitled SURGICAL CLIP APPLIER COMPRISING ADAPTIVE CONTROL IN RESPONSE TO A STRAIN GAUGE CIRCUIT.

Applicant of the present application owns the following U.S. patent applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; and U.S. Provisional Patent Application Ser. No. 62/665,134, entitled SURGICAL CLIP APPLIER.

Applicant of the present application owns the following U.S. patent applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. patent applications that were filed on Oct. 30, 2017 and which are each herein incorporated by reference in their respective entireties:

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional patent applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional patent applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. patent applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. patent applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. patent applications, filed on Mar. 29, 2018, each of which is herein incorporated by reference in its entirety:
  U.S. patent application Ser. No. 15/940,627, entitled DRIVE ARRANGEMENTS FOR ROBOT-ASSISTED SURGICAL PLATFORMS;
  U.S. patent application Ser. No. 15/940,637, entitled COMMUNICATION ARRANGEMENTS FOR ROBOT-ASSISTED SURGICAL PLATFORMS;
  U.S. patent application Ser. No. 15/940,642, entitled CONTROLS FOR ROBOT-ASSISTED SURGICAL PLATFORMS;
  U.S. patent application Ser. No. 15/940,676, entitled AUTOMATIC TOOL ADJUSTMENTS FOR ROBOT-ASSISTED SURGICAL PLATFORMS;
  U.S. patent application Ser. No. 15/940,680, entitled CONTROLLERS FOR ROBOT-ASSISTED SURGICAL PLATFORMS;
  U.S. patent application Ser. No. 15/940,683, entitled COOPERATIVE SURGICAL ACTIONS FOR ROBOT-ASSISTED SURGICAL PLATFORMS;
  U.S. patent application Ser. No. 15/940,690, entitled DISPLAY ARRANGEMENTS FOR ROBOT-ASSISTED SURGICAL PLATFORMS; and
  U.S. patent application Ser. No. 15/940,711, entitled SENSING ARRANGEMENTS FOR ROBOT-ASSISTED SURGICAL PLATFORMS.

Applicant of the present application owns the following U.S. Provisional patent applications, filed on Mar. 30, 2018, each of which is herein incorporated by reference in its entirety:
  U.S. Provisional Patent Application Ser. No. 62/650,887, entitled SURGICAL SYSTEMS WITH OPTIMIZED SENSING CAPABILITIES;
  U.S. Provisional Patent Application Ser. No. 62/650,877, entitled SURGICAL SMOKE EVACUATION SENSING AND CONTROLS;
  U.S. Provisional Patent Application Ser. No. 62/650,882, entitled SMOKE EVACUATION MODULE FOR INTERACTIVE SURGICAL PLATFORM; and
  U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional patent application, filed on Apr. 19, 2018, which is herein incorporated by reference in its entirety:
  U.S. Provisional Patent Application Ser. No. 62/659,900, entitled METHOD OF HUB COMMUNICATION.

Applicant of the present application owns the following U.S. Provisional patent applications, filed on Oct. 25, 2018, each of which is herein incorporated by reference in its entirety:
  U.S. Provisional Patent Application Ser. No. 62/750,529, entitled METHOD FOR OPERATING A POWERED ARTICULATING MULTI-CLIP APPLIER;
  U.S. Provisional Patent Application Ser. No. 62/750,539, entitled SURGICAL CLIP APPLIER; and
  U.S. Provisional Patent Application Ser. No. 62/750,555, entitled SURGICAL CLIP APPLIER.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical instrument, such as a grasper, for example, can comprise a handle, a shaft extending from the handle, and an end effector extending from the shaft. In various instances, the end effector comprises a first jaw and a second jaw, wherein one or both of the jaws are movable relative to the other to grasp the tissue of a patient. That said, an end effector of a surgical instrument can comprise any suitable arrangement and can perform any suitable function. For instance, an end effector can comprise first and second jaws configured to dissect or separate the tissue of a patient. Also, for instance, an end effector can be configured to suture and/or clip the tissue of a patient. In various instances, the end effector and/or shaft of the surgical instrument are configured to be inserted into a patient through a trocar, or cannula, and can have any suitable diameter, such as approximately 5 mm, 8 mm, and/or 12 mm, for example. U.S. patent application Ser. No. 11/013,924, entitled TROCAR SEAL ASSEMBLY, now U.S. Pat. No. 7,371,227, is incorporated by reference in its entirety. The shaft can define a longitudinal axis and at least a portion of the end effector can be rotatable about the longitudinal axis. Moreover, the surgical instrument can further comprise an articulation joint which can permit at least a portion of the end effector to be articulated relative to the shaft. In use, a clinician can rotate and/or articulate the end effector in order to maneuver the end effector within the patient.

Figure 1:
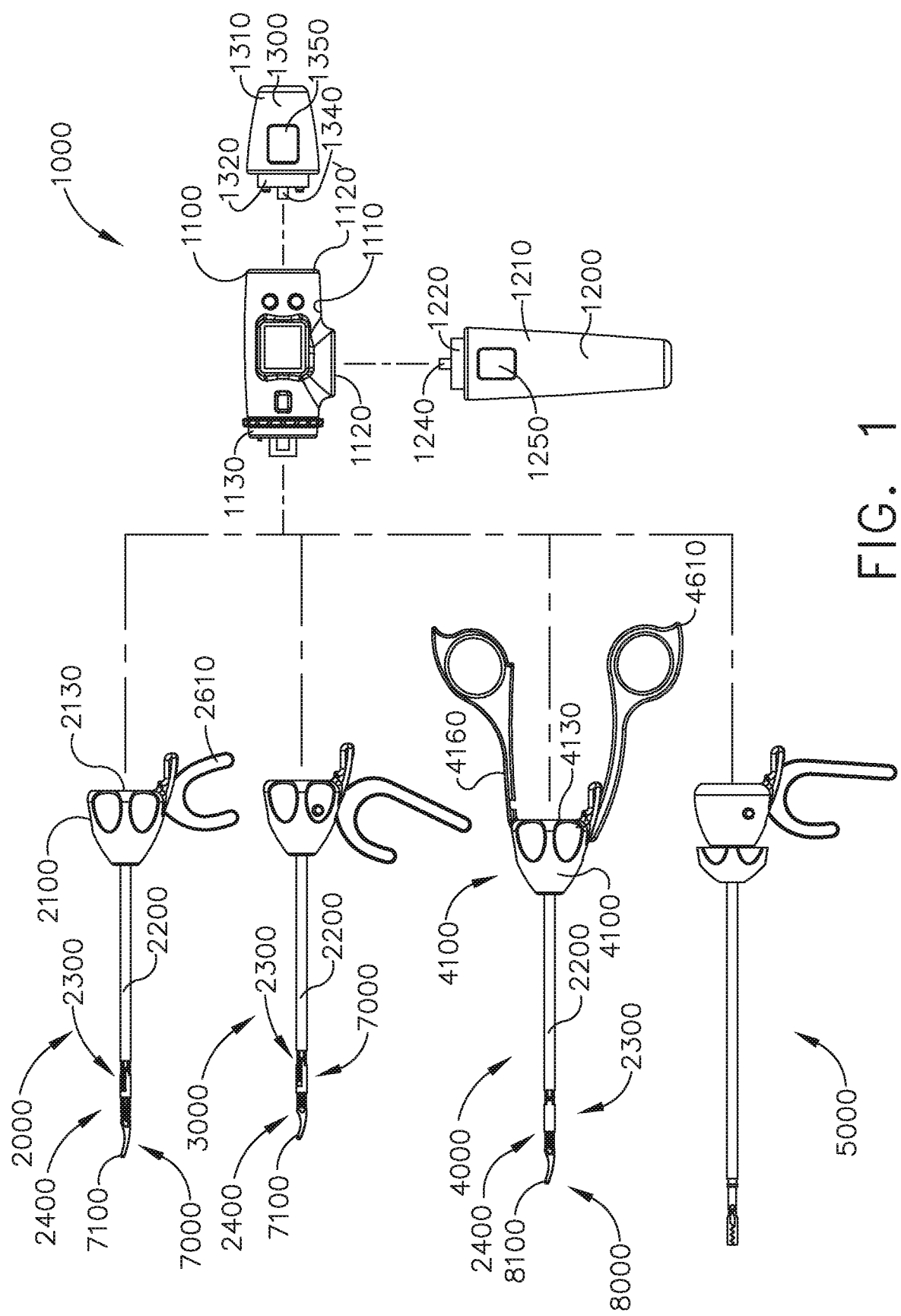
FIG. 1 illustrates a surgical system comprising a handle and several shaft assemblies—each of which are selectively attachable to the handle in accordance with at least one embodiment.
Figure 2:
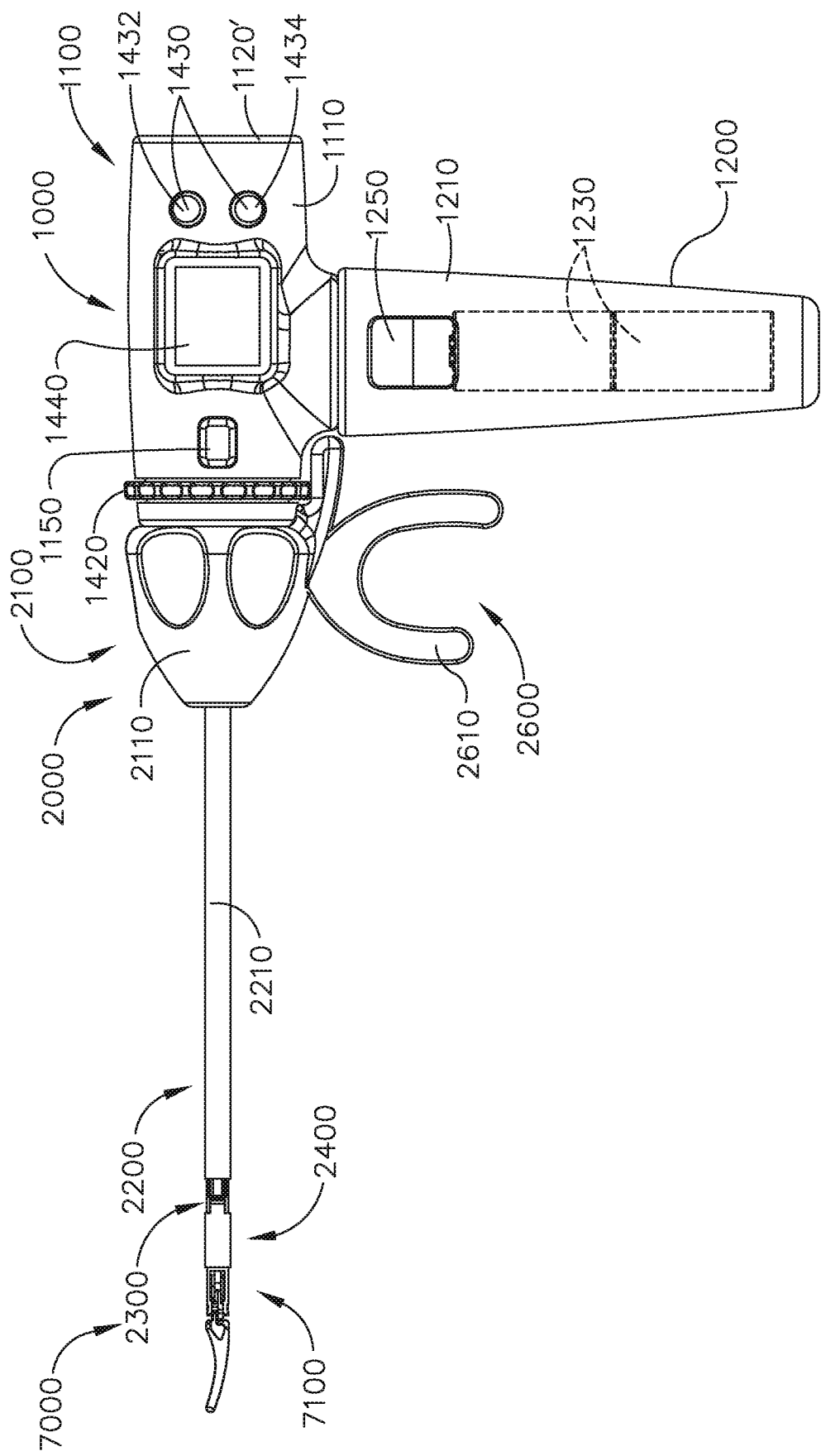
FIG. 2 is an elevational view of the handle and one of the shaft assemblies of the surgical system of FIG. 1.
Figure 3:
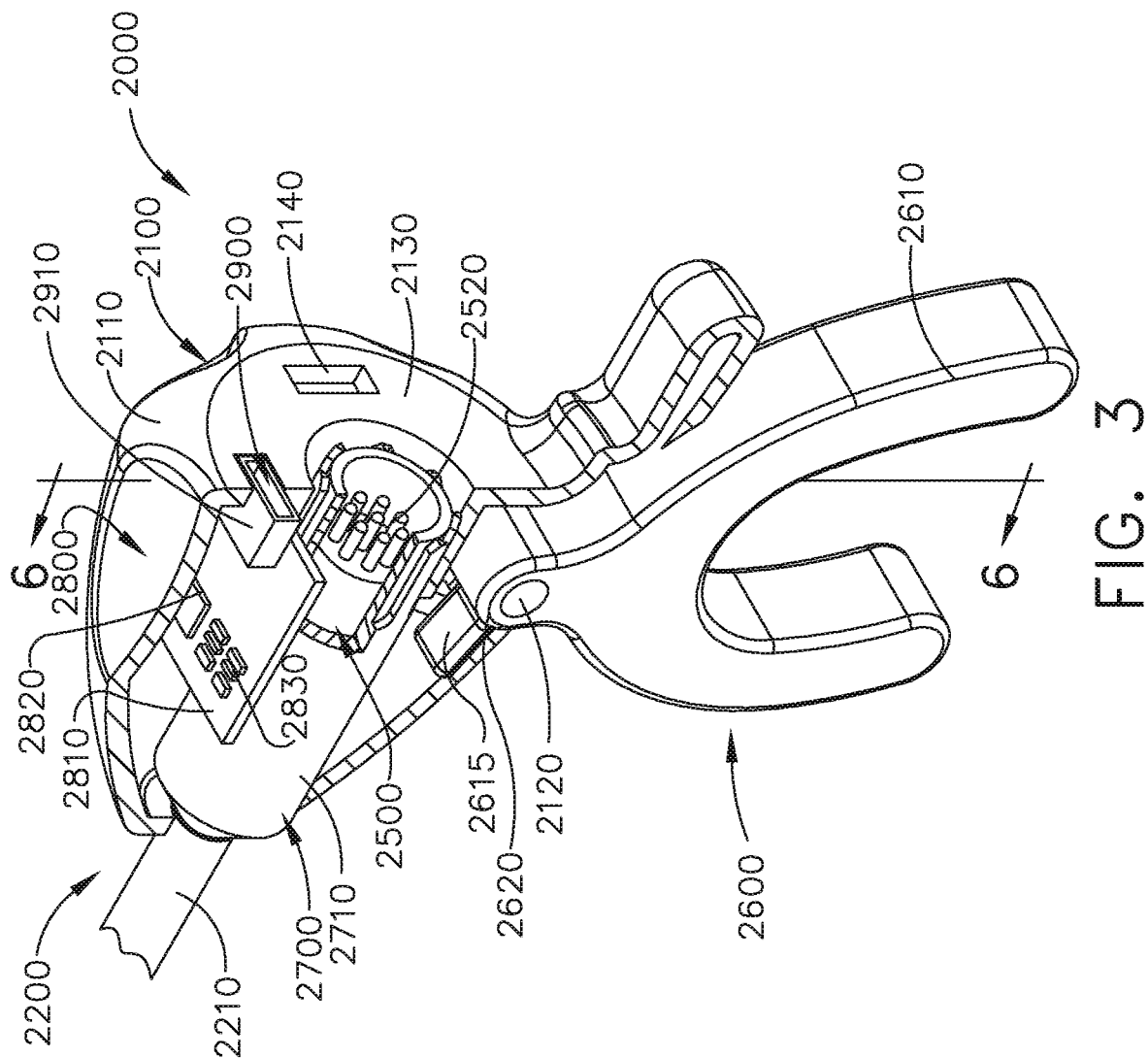
FIG. 3 is a partial cross-sectional perspective view of the shaft assembly of FIG. 2.
Figure 4:
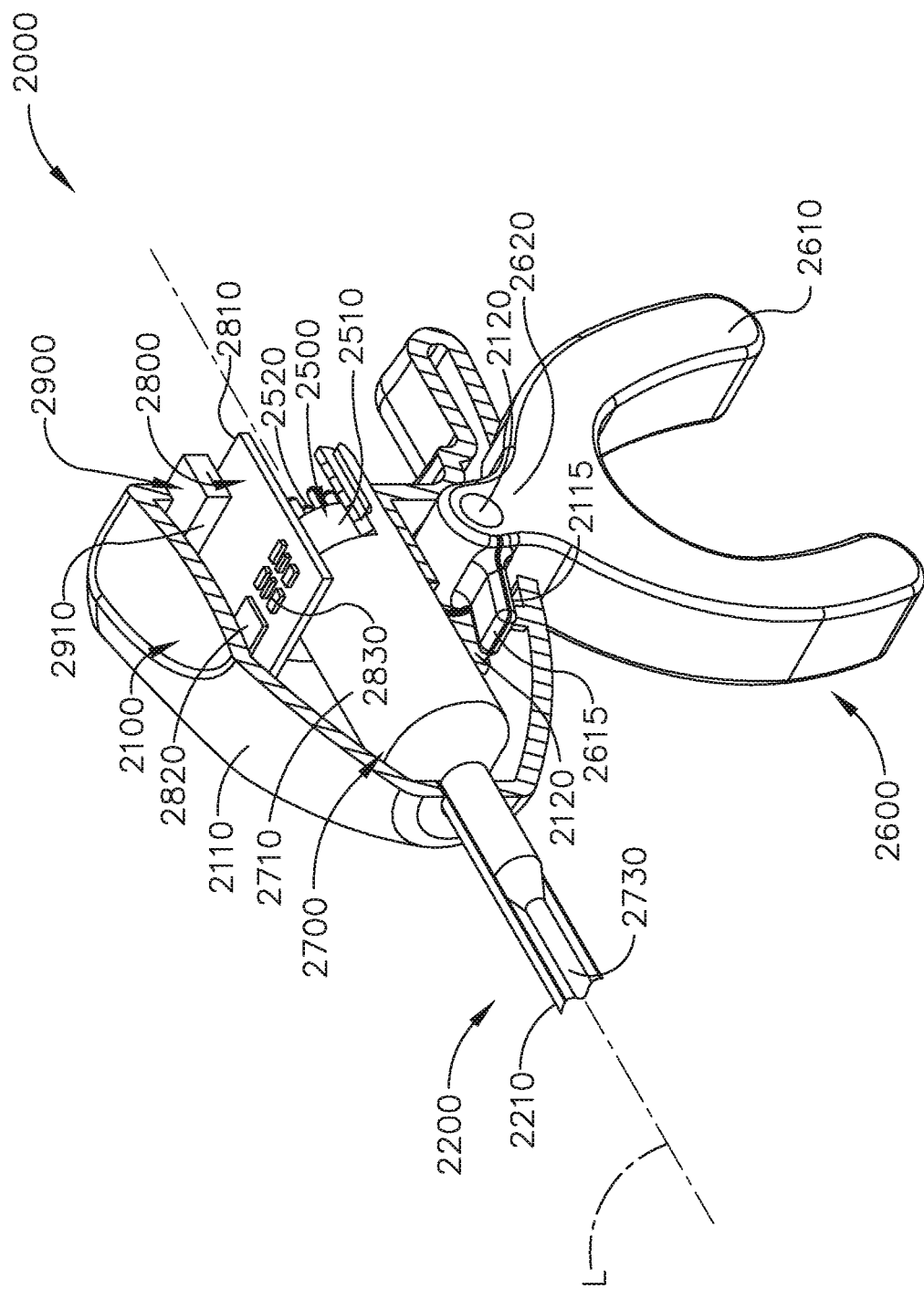
FIG. 4 is another partial cross-sectional perspective view of the shaft assembly of FIG. 2.
Figure 45:
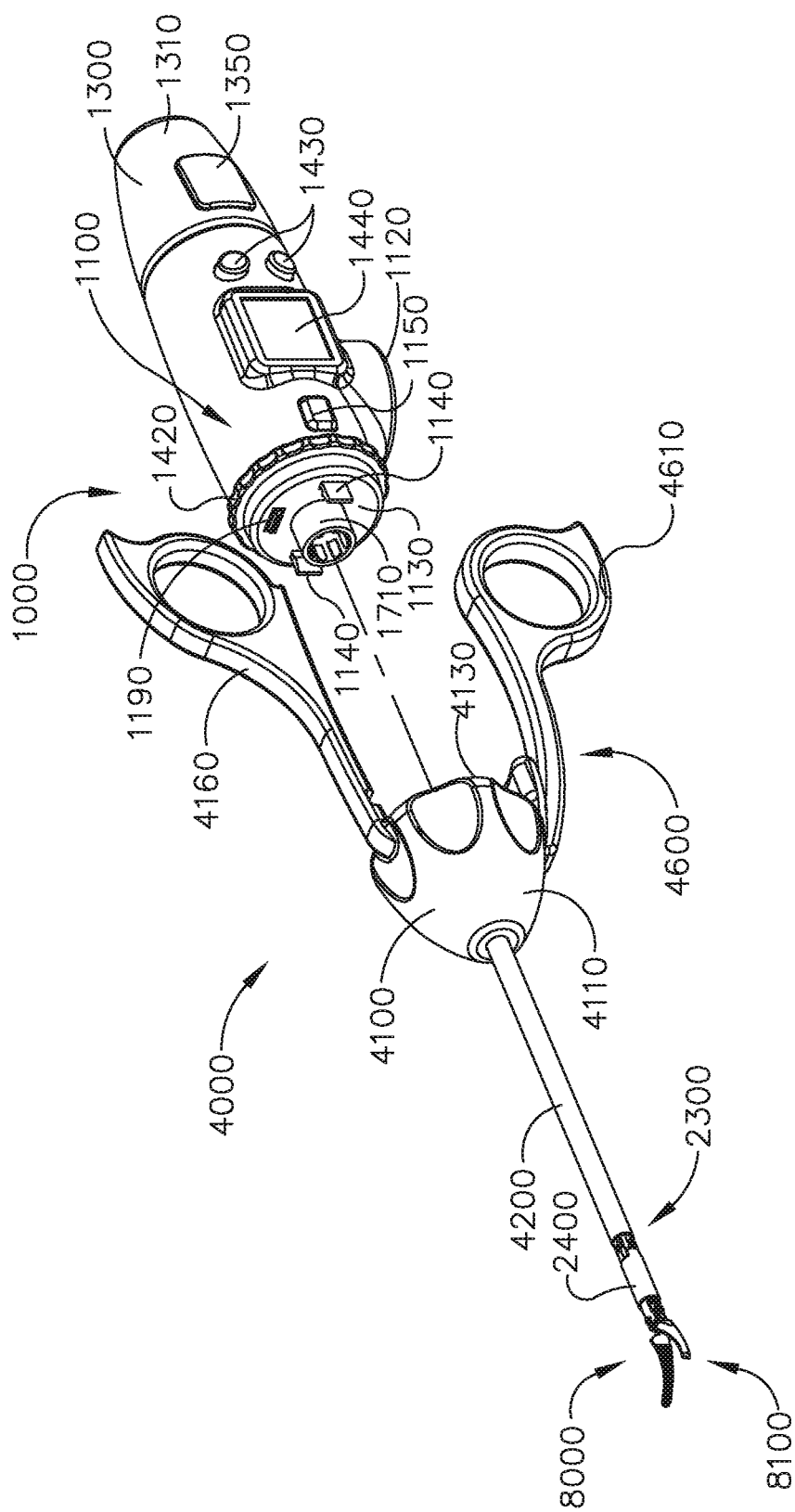
FIG. 45 is a perspective view of the handle drive module of FIG. 7 and one of the shaft assemblies of the surgical system of FIG. 1.
Figure 46:
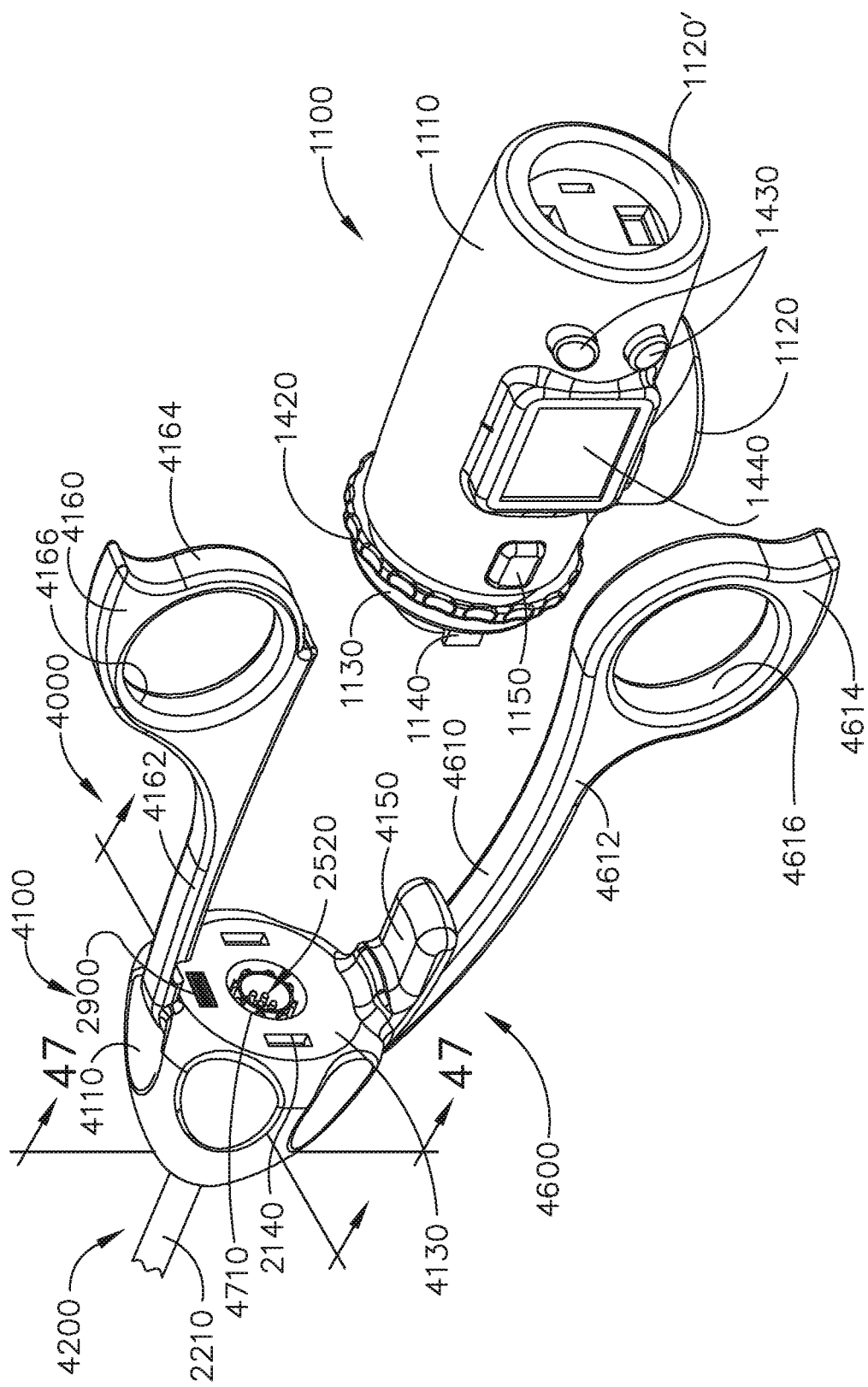
FIG. 46 is another perspective view of the handle drive module of FIG. 7 and the shaft assembly of FIG. 45.

A surgical instrument system is depicted in FIG. 1. The surgical instrument system comprises a handle assembly 1000 which is selectively usable with a shaft assembly 2000, a shaft assembly 3000, a shaft assembly 4000, a shaft assembly 5000, and/or any other suitable shaft assembly. The shaft assembly 2000 is attached to the handle assembly 1000 in FIG. 2 and the shaft assembly 4000 is attached to the handle assembly 1000 in FIG. 45. The shaft assembly 2000 comprises a proximal portion 2100, an elongate shaft 2200 extending from the proximal portion 2100, a distal attachment portion 2400, and an articulation joint 2300 rotatably connecting the distal attachment portion 2400 to the elongate shaft 2200. The shaft assembly 2000 further comprises a replaceable end effector assembly 7000 attached to the distal attachment portion 2400. The replaceable end effector assembly 7000 comprises a jaw assembly 7100 configured to be opened and closed to clamp and/or manipulate the tissue of a patient. In use, the end effector assembly 7000 can be articulated about the articulation joint 2300 and/or rotated relative to the distal attachment portion 2400 about a longitudinal axis to better position the jaw assembly 7100 within the patient, as described in greater detail further below.

Referring again to FIG. 1, the handle assembly 1000 comprises, among other things, a drive module 1100. As described in greater detail below, the drive module 1100 comprises a distal mounting interface which permits a clinician to selectively attach one of the shaft assemblies 2000, 3000, 4000, and 5000, for example, to the drive module 1100. Thus, each of the shaft assemblies 2000, 3000, 4000, and 5000 comprises an identical, or an at least similar, proximal mounting interface which is configured to engage the distal mounting interface of the drive module 1100. As also described in greater detail below, the mounting interface of the drive module 1100 mechanically secures and electrically couples the selected shaft assembly to the drive module 1100. The drive module 1100 further comprises at least one electric motor, one or more controls and/or displays, and a controller configured to operate the electric motor—the rotational output of which is transmitted to a drive system of the shaft assembly attached to the drive module 1100. Moreover, the drive module 1100 is usable with one or more power modules, such as power modules 1200 and 1300, for example, which are operably attachable to the drive module 1100 to supply power thereto.

Further to the above, referring again to FIGS. 1 and 2, the handle drive module 1100 comprises a housing 1110, a first module connector 1120, and a second module connector 1120'. The power module 1200 comprises a housing 1210, a connector 1220, one or more release latches 1250, and one or more batteries 1230. The connector 1220 is configured to be engaged with the first module connector 1120 of the drive module 1100 in order to attach the power module 1200 to the drive module 1100. The connector 1220 comprises one or more latches 1240 which mechanically couple and fixedly secure the housing 1210 of the power module 1200 to the housing 1110 of the drive module 1100. The latches 1240 are movable into disengaged positions when the release latches 1250 are depressed so that the power module 1200 can be detached from the drive module 1100. The connector 1220 also comprises one or more electrical contacts which place the batteries 1230, and/or an electrical circuit including the batteries 1230, in electrical communication with an electrical circuit in the drive module 1100.

Figure 47:
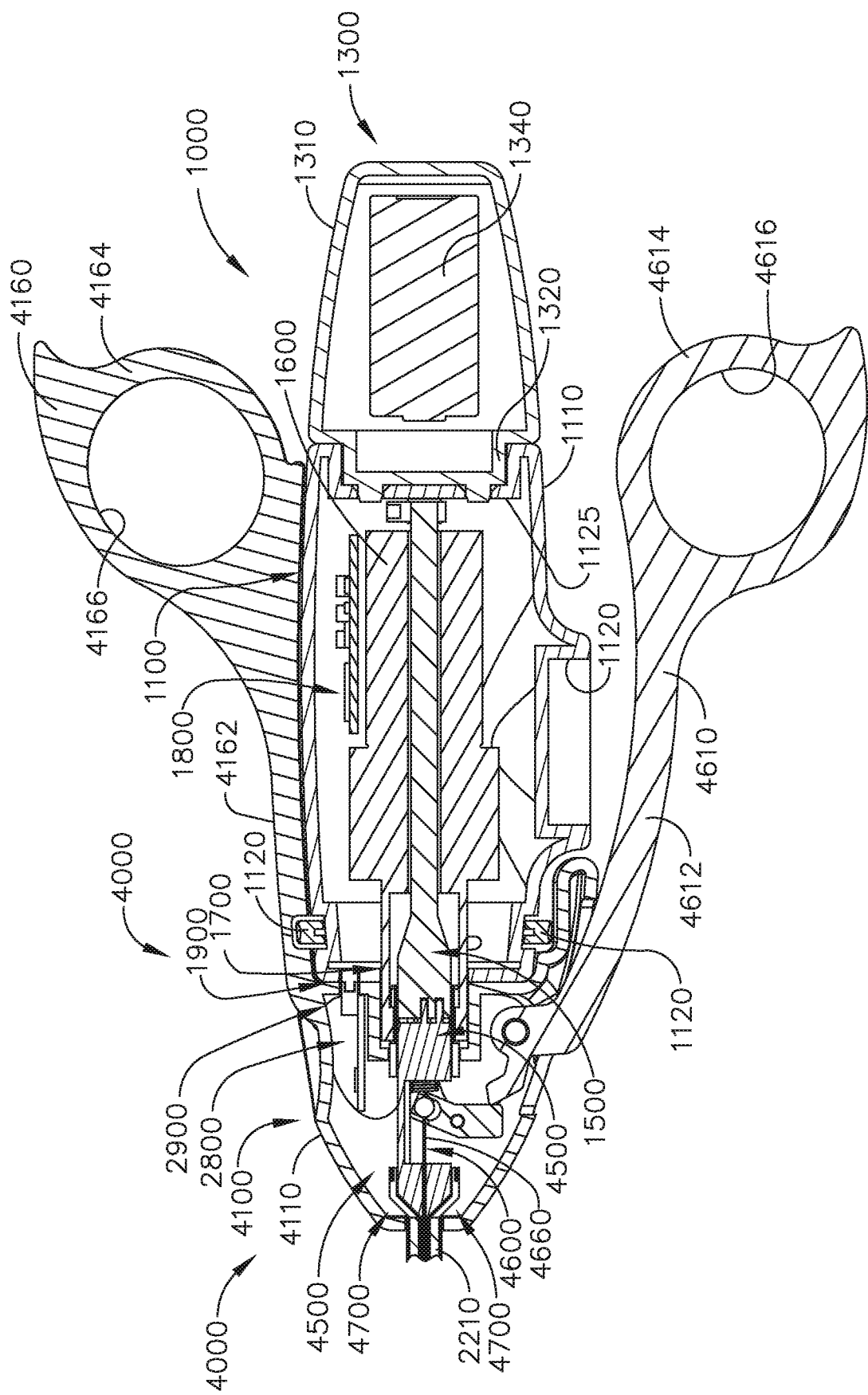
FIG. 47 is a partial cross-sectional view of the shaft assembly of FIG. 45 attached to the handle of FIG. 1.

Further to the above, referring again to FIGS. 1 and 2, the power module 1300 comprises a housing 1310, a connector 1320, one or more release latches 1350, and one or more batteries 1330 (FIG. 47). The connector 1320 is configured to be engaged with the second module connector 1120' of the drive module 1100 to attach the power module 1300 to the drive module 1100. The connector 1320 comprises one or more latches 1340 which mechanically couple and fixedly secure the housing 1310 of the power module 1300 to the housing 1110 of the drive module 1100. The latches 1340 are movable into disengaged positions when the release latches 1350 are depressed so that the power module 1300 can be detached from the drive module 1100. The connector 1320 also comprises one or more electrical contacts which place the batteries 1330 of the power module 1300, and/or an electrical power circuit including the batteries 1330, in electrical communication with an electrical power circuit in the drive module 1100.

Further to the above, the power module 1200, when attached to the drive module 1100, comprises a pistol grip which can allow a clinician to hold the handle 1000 in a manner which places the drive module 1100 on top of the clinician's hand. The power module 1300, when attached to the drive module 1100, comprises an end grip which allows a clinician to hold the handle 1000 like a wand. The power module 1200 is longer than the power module 1300, although the power modules 1200 and 1300 can comprise any suitable length. The power module 1200 has more battery cells than the power module 1300 and can suitably accommodate these additional battery cells owing to its length. In various instances, the power module 1200 can provide more power to the drive module 1100 than the power module 1300 while, in some instances, the power module 1200 can provide power for a longer period of time. In some instances, the housing 1110 of the drive module 1100 comprises keys, and/or any other suitable features, which prevent the power module 1200 from being connected to the second module connector 1120' and, similarly, prevent the power module 1300 from being connected to the first module connector 1120. Such an arrangement can assure that the longer power module 1200 is used in the pistol grip arrangement and that the shorter power module 1300 is used in the wand grip arrangement. In alternative embodiments, the power module 1200 and the power module 1300 can be selectively coupled to the drive module 1100 at either the first module connector 1120 or the second module connector 1120'. Such embodiments provide a clinician with more options to customize the handle 1000 in a manner suitable to them.

In various instances, further to the above, only one of the power modules 1200 and 1300 is coupled to the drive module 1100 at a time. In certain instances, the power module 1200 can be in the way when the shaft assembly 4000, for example, is attached to the drive module 1100. Alternatively, both of the power modules 1200 and 1300 can be operably coupled to the drive module 1100 at the same time. In such instances, the drive module 1100 can have access to power provided by both of the power modules 1200 and 1300. Moreover, a clinician can switch between a pistol grip and a wand grip when both of the power modules 1200 and 1300 are attached to the drive module 1100. Moreover, such an arrangement allows the power module 1300 to act as a counterbalance to a shaft assembly, such as shaft assemblies 2000, 3000, 4000, or 5000, for example, attached to the drive module 1100.

Figure 7:
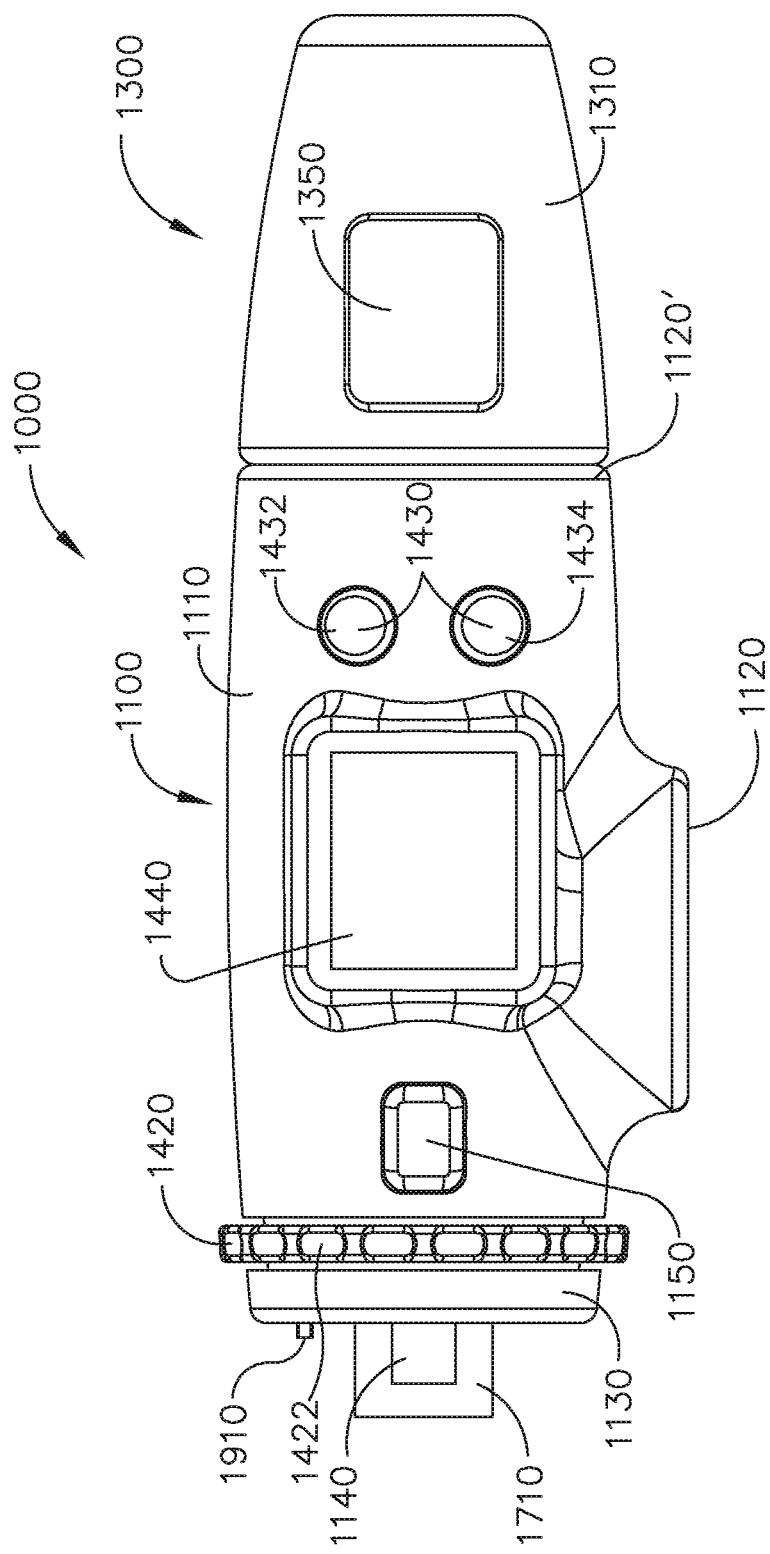
FIG. 7 is an elevational view of a drive module of the handle of FIG. 1.
Figure 8:
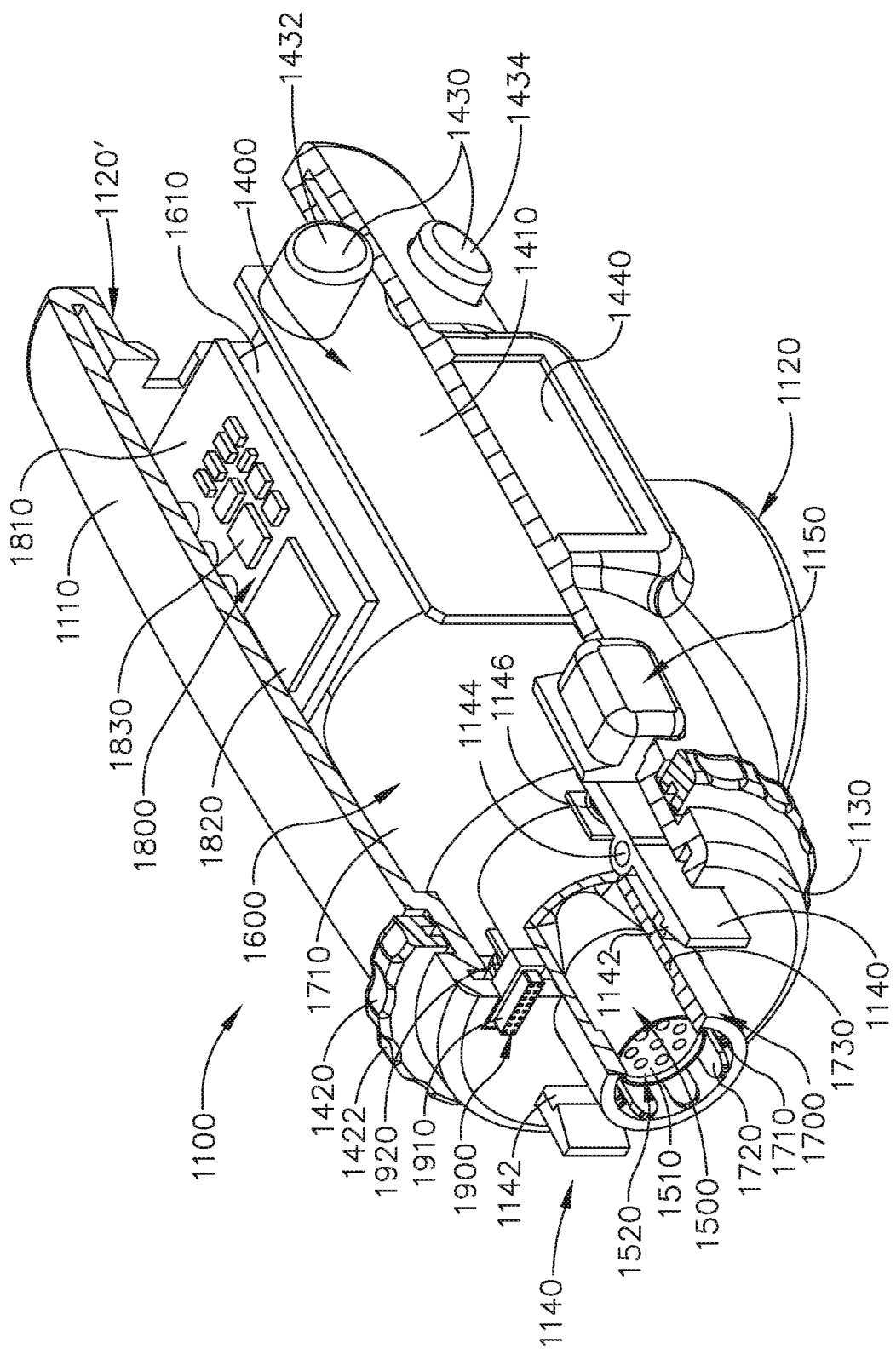
FIG. 8 is a cross-sectional perspective view of the drive module of FIG. 7.
Figure 9:
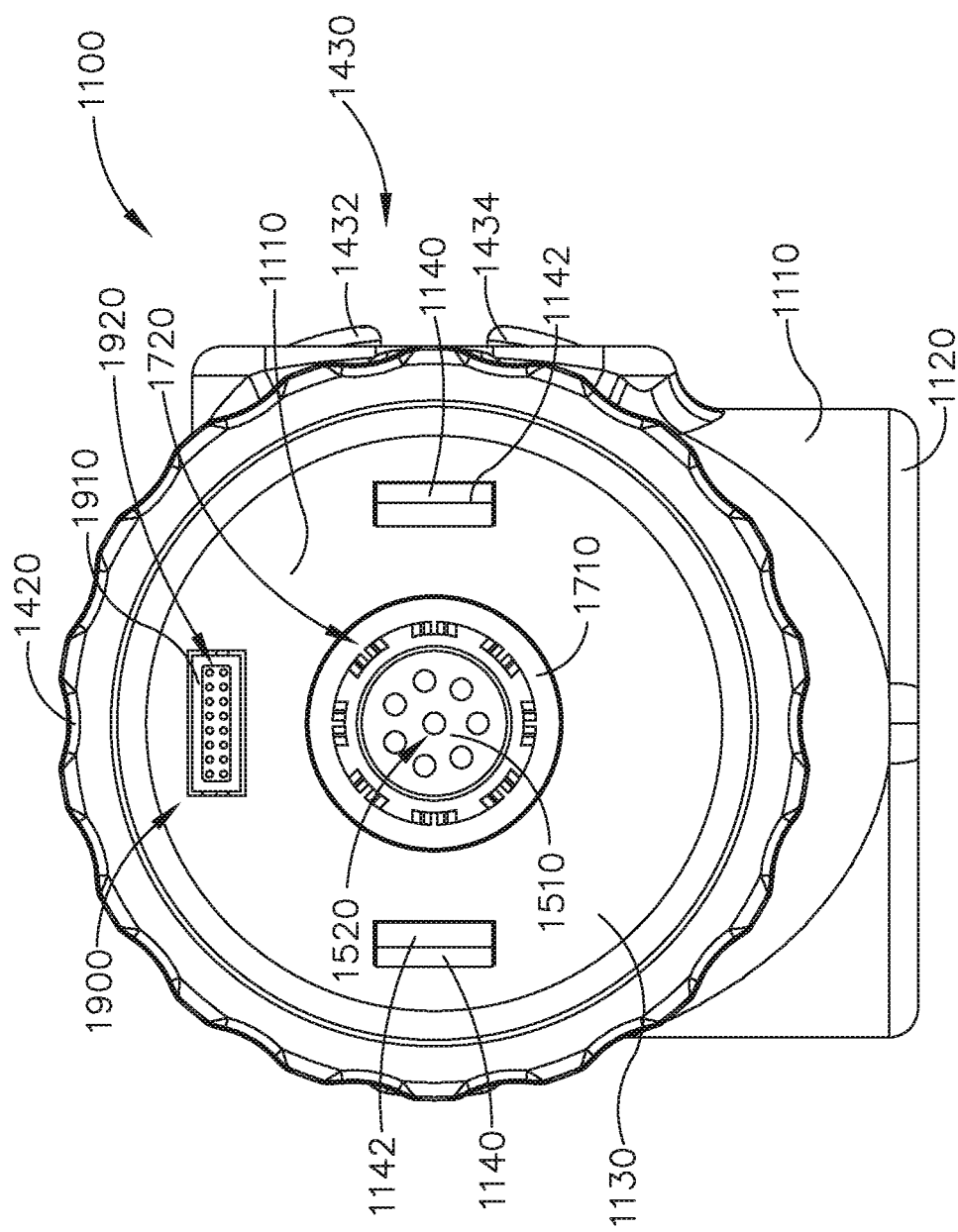
FIG. 9 is an end view of the drive module of FIG. 7.

Referring to FIGS. 7 and 8, the handle drive module 1100 further comprises a frame 1500, a motor assembly 1600, a drive system 1700 operably engaged with the motor assembly 1600, and a control system 1800. The frame 1500 comprises an elongate shaft that extends through the motor assembly 1600. The elongate shaft comprises a distal end 1510 and electrical contacts, or sockets, 1520 defined in the distal end 1510. The electrical contacts 1520 are in electrical communication with the control system 1800 of the drive module 1100 via one or more electrical circuits and are configured to convey signals and/or power between the control system 1800 and the shaft assembly, such as the shaft assembly 2000, 3000, 4000, or 5000, for example, attached to the drive module 1100. The control system 1800 comprises a printed circuit board (PCB) 1810, at least one microprocessor 1820, and at least one memory device 1830. The board 1810 can be rigid and/or flexible and can comprise any suitable number of layers. The microprocessor 1820 and the memory device 1830 are part of a control circuit defined on the board 1810 which controls the operation of the motor assembly 1600, as described in greater detail below.

Figure 12:
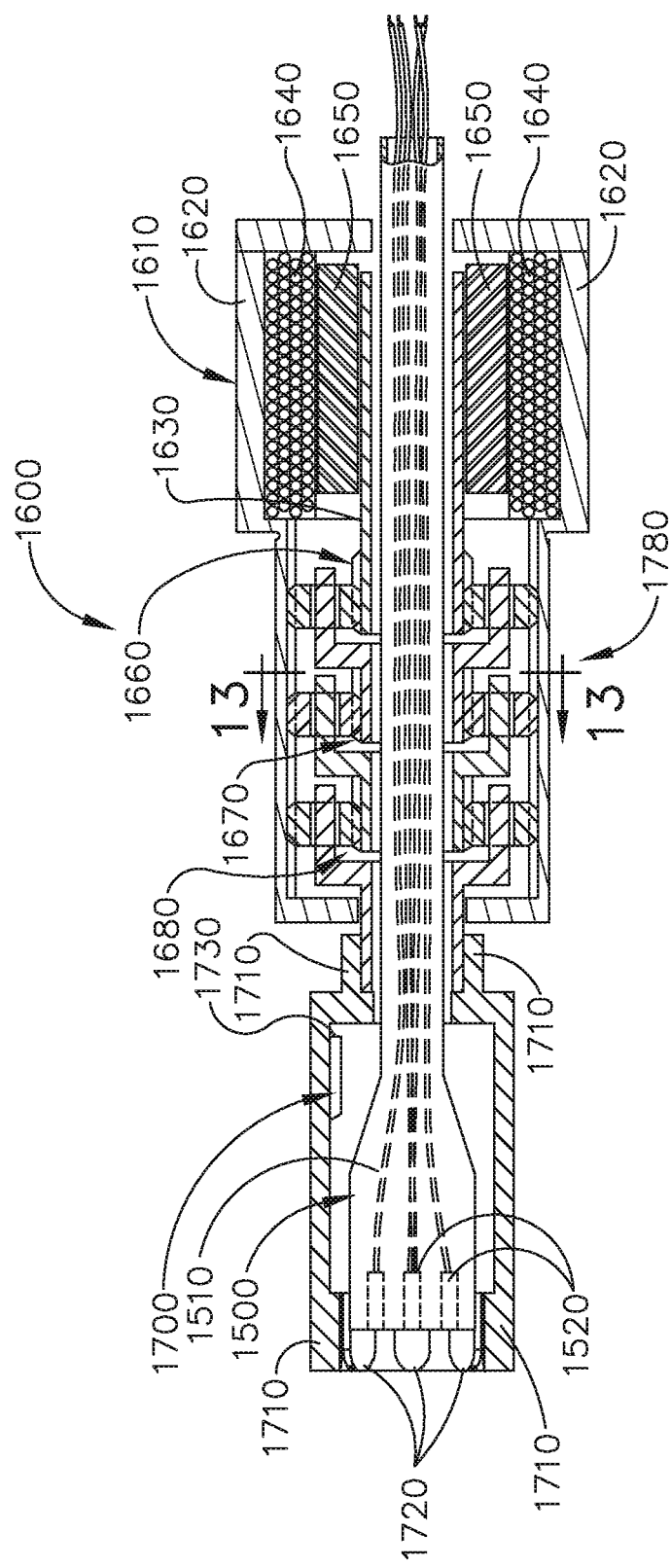
FIG. 12 is a cross-sectional perspective view of a motor and a speed reduction gear assembly of the drive module of FIG. 7.
Figure 13:
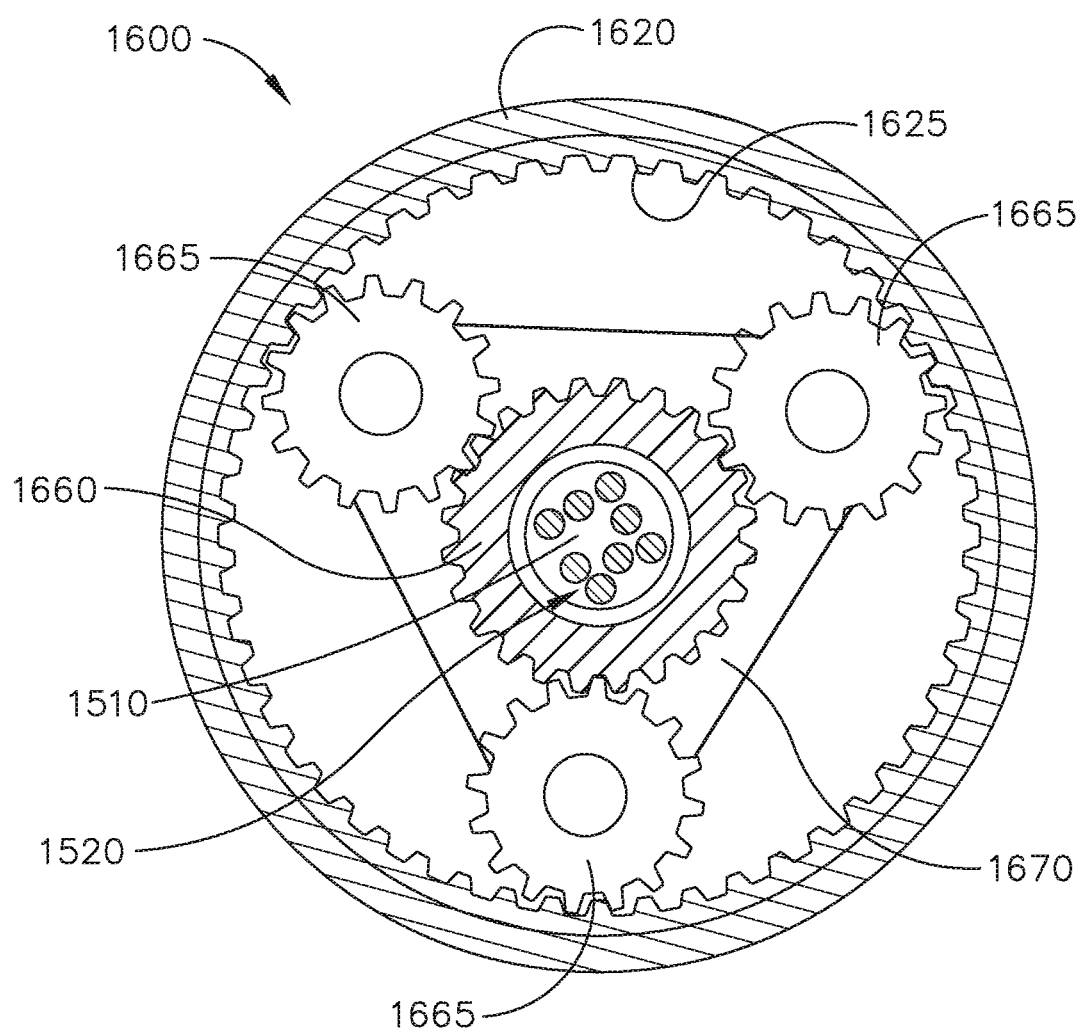
FIG. 13 is an end view of the speed reduction gear assembly of FIG. 12.
Figure 14:
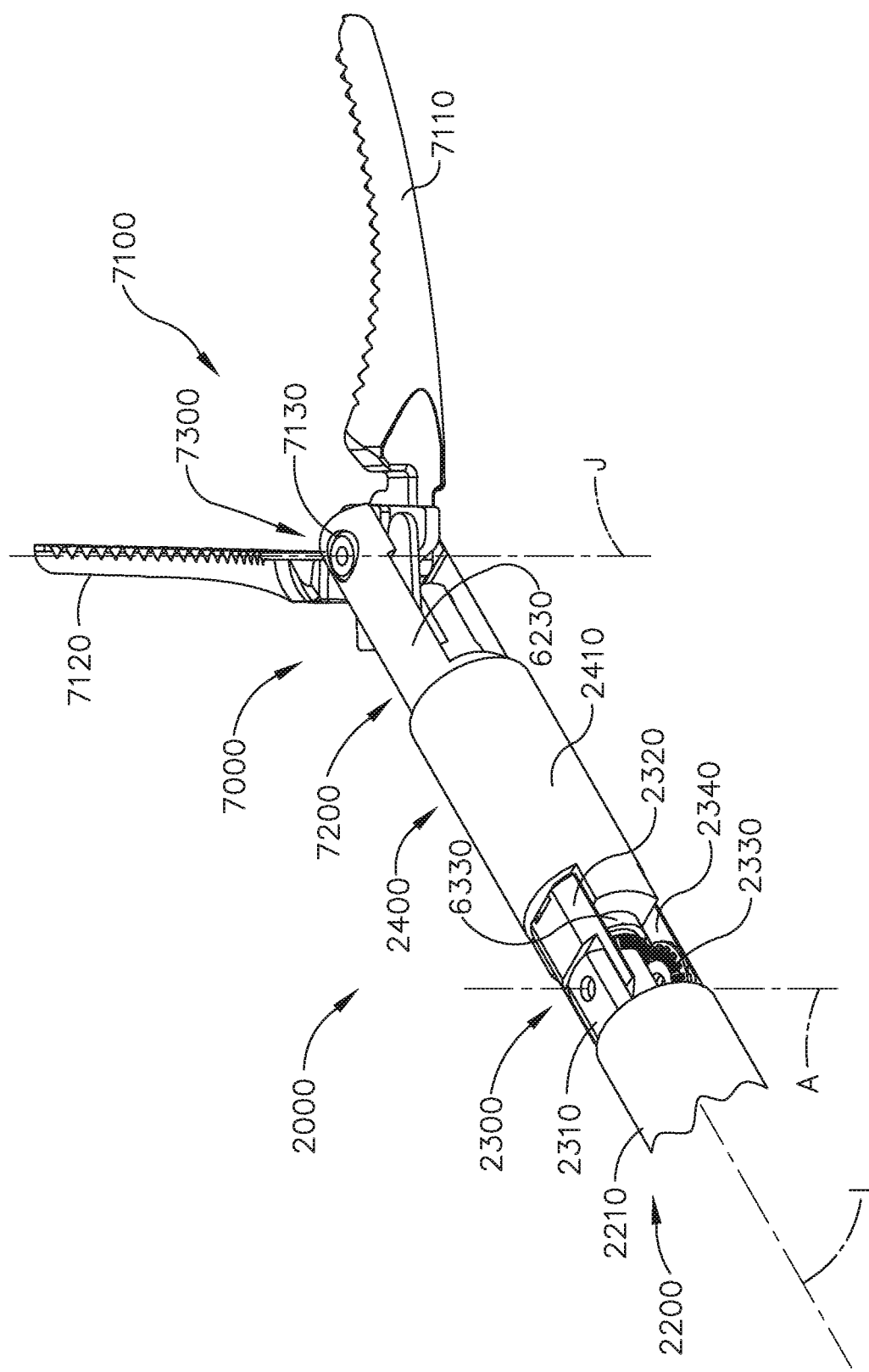
FIG. 14 is a partial perspective view of an end effector of the shaft assembly of FIG. 2 in an open configuration.

Referring to FIGS. 12 and 13, the motor assembly 1600 comprises an electric motor 1610 including a housing 1620, a drive shaft 1630, and a gear reduction system. The electric motor 1610 further comprises a stator including windings 1640 and a rotor including magnetic elements 1650. The stator windings 1640 are supported in the housing 1620 and the rotor magnetic elements 1650 are mounted to the drive shaft 1630. When the stator windings 1640 are energized with an electric current controlled by the control system 1800, the drive shaft 1630 is rotated about a longitudinal axis. The drive shaft 1630 is operably engaged with a first planetary gear system 1660 which includes a central sun gear and several planetary gears operably intermeshed with the sun gear. The sun gear of the first planetary gear system 1660 is fixedly mounted to the drive shaft 1630 such that it rotates with the drive shaft 1630. The planetary gears of the first planetary gear system 1660 are rotatably mounted to the sun gear of a second planetary gear system 1670 and, also, intermeshed with a geared or splined inner surface 1625 of the motor housing 1620. As a result of the above, the rotation of the first sun gear rotates the first planetary gears which rotate the second sun gear. Similar to the above, the second planetary gear system 1670 further comprises planetary gears 1665 (FIG. 13) which drive a third planetary gear system and, ultimately, the drive shaft 1710. The planetary gear systems 1660, 1670, and 1680 co-operate to gear down the speed applied to the drive shaft 1710 by the motor shaft 1620. Various alternative embodiments are envisioned without a speed reduction system. Such embodiments are suitable when it is desirable to drive the end effector functions quickly. Notably, the drive shaft 1630 comprises an aperture, or hollow core, extending therethrough through which wires and/or electrical circuits can extend.

The control system 1800 is in communication with the motor assembly 1600 and the electrical power circuit of the drive module 1100. The control system 1800 is configured to control the power delivered to the motor assembly 1600 from the electrical power circuit. The electrical power circuit is configured to supply a constant, or at least nearly constant, direct current (DC) voltage. In at least one instance, the electrical power circuit supplies 3 VDC to the control system 1800. The control system 1800 comprises a pulse width modulation (PWM) circuit which is configured to deliver voltage pulses to the motor assembly 1600. The duration or width of the voltage pulses, and/or the duration or width between the voltage pulses, supplied by the PWM circuit can be controlled in order to control the power applied to the motor assembly 1600. By controlling the power applied to the motor assembly 1600, the PWM circuit can control the speed of the output shaft of the motor assembly 1600. In addition to or in lieu of a PWM circuit, the control system 1800 can include a frequency modulation (FM) circuit. As discussed in greater detail below, the control system 1800 is operable in more than one operating mode and, depending on the operating mode being used, the control system 1800 can operate the motor assembly 1600 at a speed, or a range of speeds, which is determined to be appropriate for that operating mode.

Further to the above, referring again to FIGS. 7 and 8, the drive system 1700 comprises a rotatable shaft 1710 comprising a splined distal end 1720 and a longitudinal aperture 1730 defined therein. The rotatable shaft 1710 is operably mounted to the output shaft of the motor assembly 1600 such that the rotatable shaft 1710 rotates with the motor output shaft. The handle frame 1510 extends through the longitudinal aperture 1730 and rotatably supports the rotatable shaft 1710. As a result, the handle frame 1510 serves as a bearing for the rotatable shaft 1710. The handle frame 1510 and the rotatable shaft 1710 extend distally from a mounting interface 1130 of the drive module 1110 and are coupled with corresponding components on the shaft assembly 2000 when the shaft assembly 2000 is assembled to the drive module 1100. Referring primarily to FIGS. 3-6, the shaft assembly 2000 further comprises a frame 2500 and a drive system 2700. The frame 2500 comprises a longitudinal shaft 2510 extending through the shaft assembly 2000 and a plurality of electrical contacts, or pins, 2520 extending proximally from the shaft 2510. When the shaft assembly 2000 is attached to the drive module 1100, the electrical contacts 2520 on the shaft frame 2510 engage the electrical contacts 1520 on the handle frame 1510 and create electrical pathways therebetween.

Similar to the above, the drive system 2700 comprises a rotatable drive shaft 2710 which is operably coupled to the rotatable drive shaft 1710 of the handle 1000 when the shaft assembly 2000 is assembled to the drive module 1100 such that the drive shaft 2710 rotates with the drive shaft 1710. To this end, the drive shaft 2710 comprises a splined proximal end 2720 which mates with the splined distal end 1720 of the drive shaft 1710 such that the drive shafts 1710 and 2710 rotate together when the drive shaft 1710 is rotated by the motor assembly 1600. Given the nature of the splined interconnection between the drive shafts 1710 and 2710 and the electrical interconnection between the frames 1510 and 2510, the shaft assembly 2000 is assembled to the handle 1000 along a longitudinal axis; however, the operable interconnection between the drive shafts 1710 and 2710 and the electrical interconnection between the frames 1510 and 2510 can comprise any suitable configuration which can allow a shaft assembly to be assembled to the handle 1000 in any suitable manner.

Figure 10:
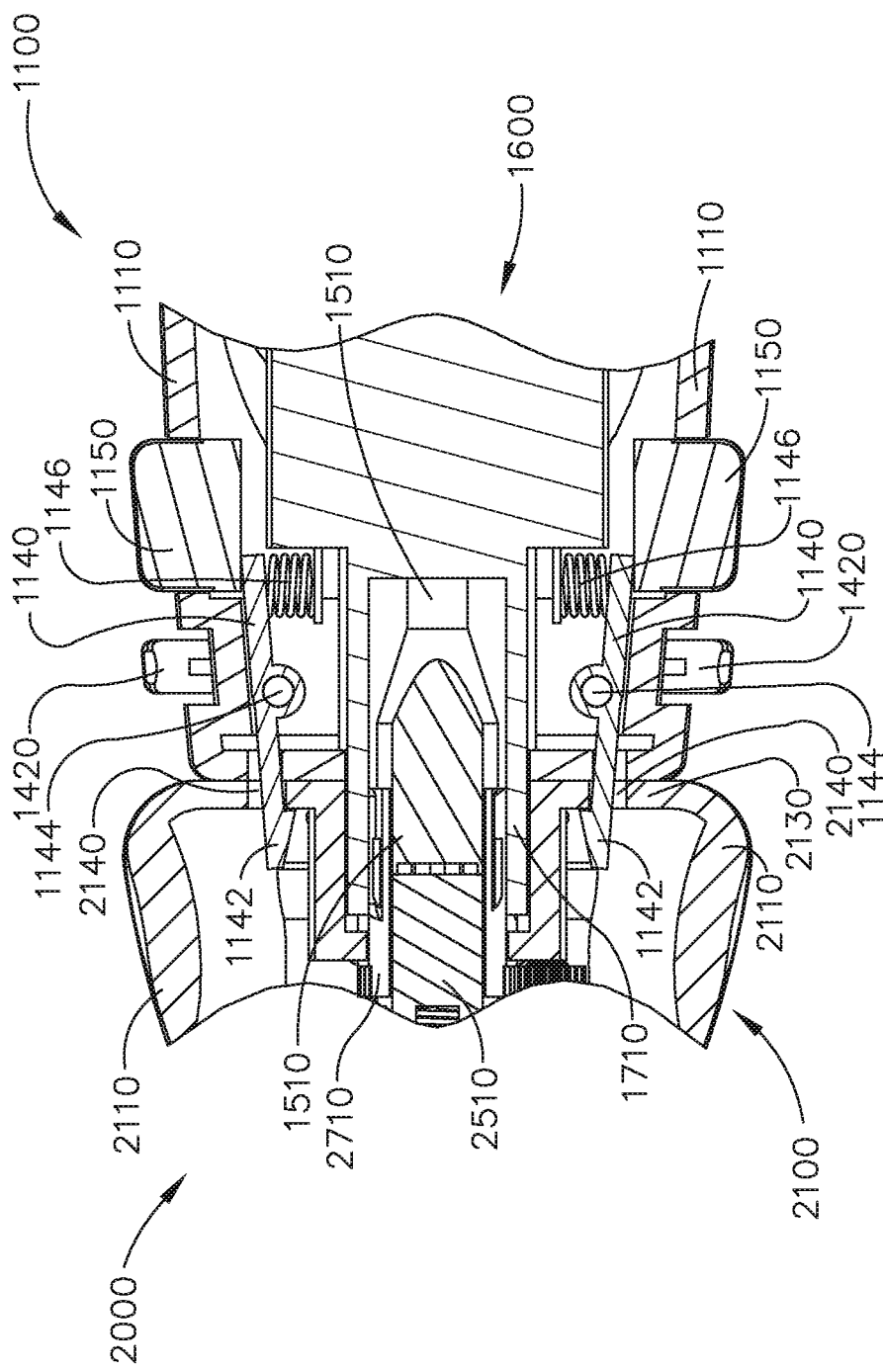
FIG. 10 is a partial cross-sectional view of the interconnection between the handle and shaft assembly of FIG. 2 in a locked configuration.
Figure 11:
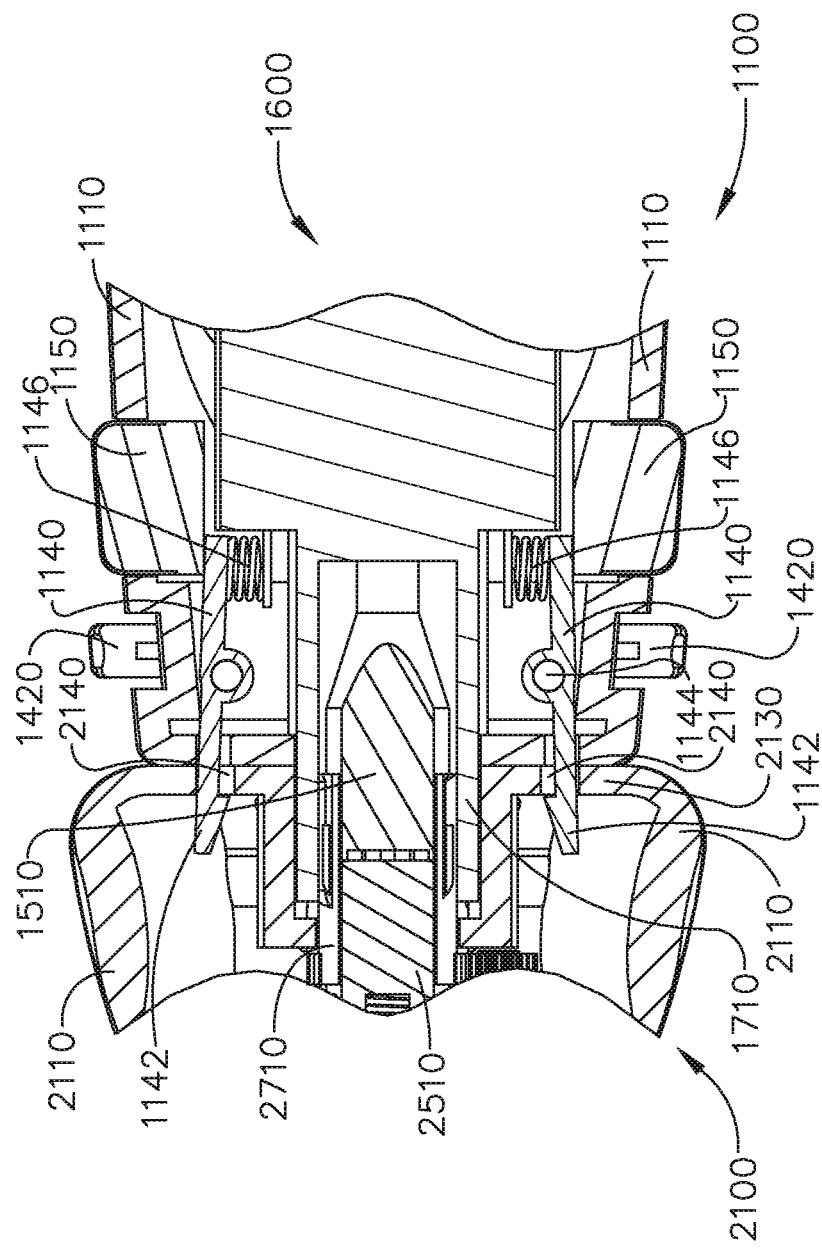
FIG. 11 is a partial cross-sectional view of the interconnection between the handle and shaft assembly of FIG. 2 in an unlocked configuration.

As discussed above, referring to FIGS. 3-8, the mounting interface 1130 of the drive module 1110 is configured to be coupled to a corresponding mounting interface on the shaft assemblies 2000, 3000, 4000, and 5000, for example. For instance, the shaft assembly 2000 comprises a mounting interface 2130 configured to be coupled to the mounting interface 1130 of the drive module 1100. More specifically, the proximal portion 2100 of the shaft assembly 2000 comprises a housing 2110 which defines the mounting interface 2130. Referring primarily to FIG. 8, the drive module 1100 comprises latches 1140 which are configured to releasably hold the mounting interface 2130 of the shaft assembly 2000 against the mounting interface 1130 of the drive module 1100. When the drive module 1100 and the shaft assembly 2000 are brought together along a longitudinal axis, as described above, the latches 1140 contact the mounting interface 2130 and rotate outwardly into an unlocked position. Referring primarily to FIGS. 8, 10, and 11, each latch 1140 comprises a lock end 1142 and a pivot portion 1144. The pivot portion 1144 of each latch 1140 is rotatably coupled to the housing 1110 of the drive module 1100 and, when the latches 1140 are rotated outwardly, as mentioned above, the latches 1140 rotate about the pivot portions 1144. Notably, each latch 1140 further comprises a biasing spring 1146 configured to bias the latches 1140 inwardly into a locked position. Each biasing spring 1146 is compressed between a latch 1140 and the housing 1110 of the drive module 1100 such that the biasing springs 1146 apply biasing forces to the latches 1140; however, such biasing forces are overcome when the latches 1140 are rotated outwardly into their unlocked positions by the shaft assembly 2000. That said, when the latches 1140 rotate outwardly after contacting the mounting interface 2130, the lock ends 1142 of the latches 1140 can enter into latch windows 2140 defined in the mounting interface 2130. Once the lock ends 1142 pass through the latch windows 2140, the springs 1146 can bias the latches 1140 back into their locked positions. Each lock end 1142 comprises a lock shoulder, or surface, which securely holds the shaft assembly 2000 to the drive module 1100.

Further to the above, the biasing springs 1146 hold the latches 1140 in their locked positions. The distal ends 1142 are sized and configured to prevent, or at least inhibit, relative longitudinal movement, i.e., translation along a longitudinal axis, between the shaft assembly 2000 and the drive module 1100 when the latches 1140 are in their locked positions. Moreover, the latches 1140 and the latch windows 1240 are sized and configured to prevent relative lateral movement, i.e., translation transverse to the longitudinal axis, between the shaft assembly 2000 and the drive module 1100. In addition, the latches 1140 and the latch windows 2140 are sized and configured to prevent the shaft assembly 2000 from rotating relative to the drive module 1100. The drive module 1100 further comprises release actuators 1150 which, when depressed by a clinician, move the latches 1140 from their locked positions into their unlocked positions. The drive module 1100 comprises a first release actuator 1150 slideably mounted in an opening defined in the first side of the handle housing 1110 and a second release actuator 1150 slideably mounted in an opening defined in a second, or opposite, side of the handle housing 1110. Although the release actuators 1150 are actuatable separately, both release actuators 1150 typically need to be depressed to completely unlock the shaft assembly 2000 from the drive module 1100 and allow the shaft assembly 2000 to be detached from the drive module 1100. That said, it is possible that the shaft assembly 2000 could be detached from the drive module 1100 by depressing only one release actuator 1150.

Once the shaft assembly 2000 has been secured to the handle 1000 and the end effector 7000, for example, has been assembled to the shaft 2000, the clinician can maneuver the handle 1000 to insert the end effector 7000 into a patient. In at least one instance, the end effector 7000 is inserted into the patient through a trocar and then manipulated in order to position the jaw assembly 7100 of the end effector assembly 7000 relative to the patient's tissue. Oftentimes, the jaw assembly 7100 must be in its closed, or clamped, configuration in order to fit through the trocar. Once through the trocar, the jaw assembly 7100 can be opened so that the patient tissue fit between the jaws of the jaw assembly 7100. At such point, the jaw assembly 7100 can be returned to its closed configuration to clamp the patient tissue between the jaws. The clamping force applied to the patient tissue by the jaw assembly 7100 is sufficient to move or otherwise manipulate the tissue during a surgical procedure. Thereafter, the jaw assembly 7100 can be reopened to release the patient tissue from the end effector 7000. This process can be repeated until it is desirable to remove the end effector 7000 from the patient. At such point, the jaw assembly 7100 can be returned to its closed configuration and retracted through the trocar. Other surgical techniques are envisioned in which the end effector 7000 is inserted into a patient through an open incision, or without the use of the trocar. In any event, it is envisioned that the jaw assembly 7100 may have to be opened and closed several times throughout a surgical technique.

Referring again to FIGS. 3-6, the shaft assembly 2000 further comprises a clamping trigger system 2600 and a control system 2800. The clamping trigger system 2600 comprises a clamping trigger 2610 rotatably connected to the proximal housing 2110 of the shaft assembly 2000. As discussed below, the clamping trigger 2610 actuates the motor 1610 to operate the jaw drive of the end effector 7000 when the clamping trigger 2610 is actuated. The clamping trigger 2610 comprises an elongate portion which is graspable by the clinician while holding the handle 1000. The clamping trigger 2610 further comprises a mounting portion 2620 which is pivotably connected to a mounting portion 2120 of the proximal housing 2110 such that the clamping trigger 2610 is rotatable about a fixed, or an at least substantially fixed, axis. The closure trigger 2610 is rotatable between a distal position and a proximal position, wherein the proximal position of the closure trigger 2610 is closer to the pistol grip of the handle 1000 than the distal position. The closure trigger 2610 further comprises a tab 2615 extending therefrom which rotates within the proximal housing 2110. When the closure trigger 2610 is in its distal position, the tab 2615 is positioned above, but not in contact with, a switch 2115 mounted on the proximal housing 2110. The switch 2115 is part of an electrical circuit configured to detect the actuation of the closure trigger 2610 which is in an open condition the closure trigger 2610 is in its open position. When the closure trigger 2610 is moved into its proximal position, the tab 2615 comes into contact with the switch 2115 and closes the electrical circuit. In various instances, the switch 2115 can comprise a toggle switch, for example, which is mechanically switched between open and closed states when contacted by the tab 2615 of the closure trigger 2610. In certain instances, the switch 2115 can comprise a proximity sensor, for example, and/or any suitable type of sensor. In at least one instance, the switch 2115 comprises a Hall Effect sensor which can detect the amount in which the closure trigger 2610 has been rotated and, based on the amount of rotation, control the speed in which the motor 1610 is operated. In such instances, larger rotations of the closure trigger 2610 result in faster speeds of the motor 1610 while smaller rotations result in slower speeds, for example. In any event, the electrical circuit is in communication with the control system 2800 of the shaft assembly 2000, which is discussed in greater detail below.

Further to the above, the control system 2800 of the shaft assembly 2000 comprises a printed circuit board (PCB) 2810, at least one microprocessor 2820, and at least one memory device 2830. The board 2810 can be rigid and/or flexible and can comprise any suitable number of layers. The microprocessor 2820 and the memory device 2830 are part of a control circuit defined on the board 2810 which communicates with the control system 1800 of the handle 1000. The shaft assembly 2000 further comprises a signal communication system 2900 and the handle 1000 further comprises a signal communication system 1900 which are configured to convey data between the shaft control system 2800 and the handle control system 1800. The signal communication system 2900 is configured to transmit data to the signal communication system 1900 utilizing any suitable analog and/or digital components. In various instances, the communication systems 2900 and 1900 can communicate using a plurality of discrete channels which allows the input gates of the microprocessor 1820 to be directly controlled, at least in part, by the output gates of the microprocessor 2820. In some instances, the communication systems 2900 and 1900 can utilize multiplexing. In at least one such instance, the control system 2900 includes a multiplexing device that sends multiple signals on a carrier channel at the same time in the form of a single, complex signal to a multiplexing device of the control system 1900 that recovers the separate signals from the complex signal.

The communication system 2900 comprises an electrical connector 2910 mounted to the circuit board 2810. The electrical connector 2910 comprises a connector body and a plurality of electrically-conductive contacts mounted to the connector body. The electrically-conductive contacts comprise male pins, for example, which are soldered to electrical traces defined in the circuit board 2810. In other instances, the male pins can be in communication with circuit board traces through zero-insertion-force (ZIF) sockets, for example. The communication system 1900 comprises an electrical connector 1910 mounted to the circuit board 1810. The electrical connector 1910 comprises a connector body and a plurality of electrically-conductive contacts mounted to the connector body. The electrically-conductive contacts comprise female pins, for example, which are soldered to electrical traces defined in the circuit board 1810. In other instances, the female pins can be in communication with circuit board traces through zero-insertion-force (ZIF) sockets, for example. When the shaft assembly 2000 is assembled to the drive module 1100, the electrical connector 2910 is operably coupled to the electrical connector 1910 such that the electrical contacts form electrical pathways therebetween. The above being said, the connectors 1910 and 2910 can comprise any suitable electrical contacts. Moreover, the communication systems 1900 and 2900 can communicate with one another in any suitable manner. In various instances, the communication systems 1900 and 2900 communicate wirelessly. In at least one such instance, the communication system 2900 comprises a wireless signal transmitter and the communication system 1900 comprises a wireless signal receiver such that the shaft assembly 2000 can wirelessly communicate data to the handle 1000. Likewise, the communication system 1900 can comprise a wireless signal transmitter and the communication system 2900 can comprise a wireless signal receiver such that the handle 1000 can wirelessly communicate data to the shaft assembly 2000.

As discussed above, the control system 1800 of the handle 1000 is in communication with, and is configured to control, the electrical power circuit of the handle 1000. The handle control system 1800 is also powered by the electrical power circuit of the handle 1000. The handle communication system 1900 is in signal communication with the handle control system 1800 and is also powered by the electrical power circuit of the handle 1000. The handle communication system 1900 is powered by the handle electrical power circuit via the handle control system 1800, but could be directly powered by the electrical power circuit. As also discussed above, the handle communication system 1900 is in signal communication with the shaft communication system 2900. That said, the shaft communication system 2900 is also powered by the handle electrical power circuit via the handle communication system 1900. To this end, the electrical connectors 1910 and 2010 connect both one or more signal circuits and one or more power circuits between the handle 1000 and the shaft assembly 2000. Moreover, the shaft communication system 2900 is in signal communication with the shaft control system 2800, as discussed above, and is also configured to supply power to the shaft control system 2800. Thus, the control systems 1800 and 2800 and the communication systems 1900 and 2900 are all powered by the electrical power circuit of the handle 1000; however, alternative embodiments are envisioned in which the shaft assembly 2000 comprises its own power source, such as one or more batteries, for example, an and electrical power circuit configured to supply power from the batteries to the handle systems 2800 and 2900. In at least one such embodiment, the handle control system 1800 and the handle communication system 1900 are powered by the handle electrical power system and the shaft control system 2800 and the handle communication system 2900 are powered by the shaft electrical power system.

Further to the above, the actuation of the clamping trigger 2610 is detected by the shaft control system 2800 and communicated to the handle control system 1800 via the communication systems 2900 and 1900. Upon receiving a signal that the clamping trigger 2610 has been actuated, the handle control system 1800 supplies power to the electric motor 1610 of the motor assembly 1600 to rotate the drive shaft 1710 of the handle drive system 1700, and the drive shaft 2710 of the shaft drive system 2700, in a direction which closes the jaw assembly 7100 of the end effector 7000. The mechanism for converting the rotation of the drive shaft 2710 to a closure motion of the jaw assembly 7100 is discussed in greater detail below. So long as the clamping trigger 2610 is held in its actuated position, the electric motor 1610 will rotate the drive shaft 1710 until the jaw assembly 7100 reaches its fully-clamped position. When the jaw assembly 7100 reaches its fully-clamped position, the handle control system 1800 cuts the electrical power to the electric motor 1610. The handle control system 1800 can determine when the jaw assembly 7100 has reached its fully-clamped position in any suitable manner. For instance, the handle control system 1800 can comprise an encoder system which monitors the rotation of, and counts the rotations of, the output shaft of the electric motor 1610 and, once the number of rotations reaches a predetermined threshold, the handle control system 1800 can discontinue supplying power to the electric motor 1610. In at least one instance, the end effector assembly 7000 can comprise one or more sensors configured to detect when the jaw assembly 7100 has reached its fully-clamped position. In at least one such instance, the sensors in the end effector 7000 are in signal communication with the handle control system 1800 via electrical circuits extending through the shaft assembly 2000 which can include the electrical contacts 1520 and 2520, for example.

When the clamping trigger 2610 is rotated distally out of its proximal position, the switch 2115 is opened which is detected by the shaft control system 2800 and communicated to the handle control system 1800 via the communication systems 2900 and 1900. Upon receiving a signal that the clamping trigger 2610 has been moved out of its actuated position, the handle control system 1800 reverses the polarity of the voltage differential being applied to the electric motor 1610 of the motor assembly 1600 to rotate the drive shaft 1710 of the handle drive system 1700, and the drive shaft 2710 of the shaft drive system 2700, in an opposite direction which, as a result, opens the jaw assembly 7100 of the end effector 7000. When the jaw assembly 7100 reaches its fully-open position, the handle control system 1800 cuts the electrical power to the electric motor 1610. The handle control system 1800 can determine when the jaw assembly 7100 has reached its fully-open position in any suitable manner. For instance, the handle control system 1800 can utilize the encoder system and/or the one or more sensors described above to determine the configuration of the jaw assembly 7100. In view of the above, the clinician needs to be mindful about holding the clamping trigger 2610 in its actuated position in order to maintain the jaw assembly 7100 in its clamped configuration as, otherwise, the control system 1800 will open jaw assembly 7100. With this in mind, the shaft assembly 2000 further comprises an actuator latch 2630 configured to releasably hold the clamping trigger 2610 in its actuated position to prevent the accidental opening of the jaw assembly 7100. The actuator latch 2630 can be manually released, or otherwise defeated, by the clinician to allow the clamping trigger 2610 to be rotated distally and open the jaw assembly 7100.

The clamping trigger system 2600 further comprises a resilient biasing member, such as a torsion spring, for example, configured to resist the closure of the clamping trigger system 2600. The torsion spring can also assist in reducing and/or mitigating sudden movements and/or jitter of the clamping trigger 2610. Such a torsion spring can also automatically return the clamping trigger 2610 to its unactuated position when the clamping trigger 2610 is released. The actuator latch 2630 discussed above can suitably hold the clamping trigger 2610 in its actuated position against the biasing force of the torsion spring.

As discussed above, the control system 1800 operates the electric motor 1610 to open and close the jaw assembly 7100. The control system 1800 is configured to open and close the jaw assembly 7100 at the same speed. In such instances, the control system 1800 applies the same voltage pulses to the electric motor 1610, albeit with different voltage polarities, when opening and closing the jaw assembly 7100. That said, the control system 1800 can be configured to open and close the jaw assembly 7100 at different speeds. For instance, the jaw assembly 7100 can be closed at a first speed and opened at a second speed which is faster than the first speed. In such instances, the slower closing speed affords the clinician an opportunity to better position the jaw assembly 7100 while clamping the tissue. Alternatively, the control system 1800 can open the jaw assembly 7100 at a slower speed. In such instances, the slower opening speed reduces the possibility of the opening jaws colliding with adjacent tissue. In either event, the control system 1800 can decrease the duration of the voltage pulses and/or increase the duration between the voltage pulses to slow down and/or speed up the movement of the jaw assembly 7100.

As discussed above, the control system 1800 is configured to interpret the position of the clamping trigger 2610 as a command to position the jaw assembly 7100 in a specific configuration. For instance, the control system 1800 is configured to interpret the proximal-most position of the clamping trigger 2610 as a command to close the jaw assembly 7100 and any other position of the clamping trigger as a command to open the jaw assembly 7100. That said, the control system 1800 can be configured to interpret the position of the clamping trigger 2610 in a proximal range of positions, instead of a single position, as a command to close the jaw assembly 7100. Such an arrangement can allow the jaw assembly 7000 to be better responsive to the clinician's input. In such instances, the range of motion of the clamping trigger 2610 is divided into ranges—a proximal range which is interpreted as a command to close the jaw assembly 7100 and a distal range which is interpreted as a command to open the jaw assembly 7100. In at least one instance, the range of motion of the clamping trigger 2610 can have an intermediate range between the proximal range and the distal range. When the clamping trigger 2610 is in the intermediate range, the control system 1800 can interpret the position of the clamping trigger 2610 as a command to neither open nor close the jaw assembly 7100. Such an intermediate range can prevent, or reduce the possibility of, jitter between the opening and closing ranges. In the instances described above, the control system 1800 can be configured to ignore cumulative commands to open or close the jaw assembly 7100. For instance, if the closure trigger 2610 has already been fully retracted into its proximal-most position, the control assembly 1800 can ignore the motion of the clamping trigger 2610 in the proximal, or clamping, range until the clamping trigger 2610 enters into the distal, or opening, range wherein, at such point, the control system 1800 can then actuate the electric motor 1610 to open the jaw assembly 7100.

In certain instances, further to the above, the position of the clamping trigger 2610 within the clamping trigger range, or at least a portion of the clamping trigger range, can allow the clinician to control the speed of the electric motor 1610 and, thus, the speed in which the jaw assembly 7100 is being opened or closed by the control assembly 1800. In at least one instance, the sensor 2115 comprises a Hall Effect sensor, and/or any other suitable sensor, configured to detect the position of the clamping trigger 2610 between its distal, unactuated position and its proximal, fully-actuated position. The Hall Effect sensor is configured to transmit a signal to the handle control system 1800 via the shaft control system 2800 such that the handle control system 1800 can control the speed of the electric motor 1610 in response to the position of the clamping trigger 2610. In at least one instance, the handle control system 1800 controls the speed of the electric motor 1610 proportionately, or in a linear manner, to the position of the clamping trigger 2610. For example, if the clamping trigger 2610 is moved half way through its range, then the handle control system 1800 will operate the electric motor 1610 at half of the speed in which the electric motor 1610 is operated when the clamping trigger 2610 is fully-retracted. Similarly, if the clamping trigger 2610 is moved a quarter way through its range, then the handle control system 1800 will operate the electric motor 1610 at a quarter of the speed in which the electric motor 1610 is operated when the clamping trigger 2610 is fully-retracted. Other embodiments are envisioned in which the handle control system 1800 controls the speed of the electric motor 1610 in a non-linear manner to the position of the clamping trigger 2610. In at least one instance, the control system 1800 operates the electric motor 1610 slowly in the distal portion of the clamping trigger range while quickly accelerating the speed of the electric motor 1610 in the proximal portion of the clamping trigger range.

As described above, the clamping trigger 2610 is movable to operate the electric motor 1610 to open or close the jaw assembly 7100 of the end effector 7000. The electric motor 1610 is also operable to rotate the end effector 7000 about a longitudinal axis and articulate the end effector 7000 relative to the elongate shaft 2200 about the articulation joint 2300 of the shaft assembly 2000. Referring primarily to FIGS. 7 and 8, the drive module 1100 comprises an input system 1400 including a rotation actuator 1420 and an articulation actuator 1430. The input system 1400 further comprises a printed circuit board (PCB) 1410 which is in signal communication with the printed circuit board (PCB) 1810 of the control system 1800. The drive module 1100 comprises an electrical circuit, such as a flexible wiring harness or ribbon, for example, which permits the input system 1400 to communicate with the control system 1800. The rotation actuator 1420 is rotatably supported on the housing 1110 and is in signal communication with the input board 1410 and/or control board 1810, as described in greater detail below. The articulation actuator 1430 is supported by and in signal communication with the input board 1410 and/or control board 1810, as also described in greater detail below.

Referring primarily to FIGS. 8, 10, and 11, further to the above, the handle housing 1110 comprises an annular groove or slot defined therein adjacent the distal mounting interface 1130. The rotation actuator 1420 comprises an annular ring 1422 rotatably supported within the annular groove and, owing to the configuration of the sidewalls of the annular groove, the annular ring 1422 is constrained from translating longitudinally and/or laterally with respect to the handle housing 1110. The annular ring 1422 is rotatable in a first, or clockwise, direction and a second, or counter-clockwise, direction, about a longitudinal axis extending through the frame 1500 of the drive module 1100. The rotation actuator 1420 comprises one or more sensors configured to detect the rotation of the annular ring 1422. In at least one instance, the rotation actuator 1420 comprises a first sensor positioned on a first side of the drive module 1100 and a second sensor positioned on a second, or opposite, side of the drive module 1100 and the annular ring 1422 comprises a detectable element which is detectable by the first and second sensors. The first sensor is configured to detect when the annular ring 1422 is rotated in the first direction and the second sensor is configured to detect when the annular ring 1422 is rotated in the second direction. When the first sensor detects that the annular ring 1422 is rotated in the first direction, the handle control system 1800 rotates the handle drive shaft 1710, the drive shaft 2710, and the end effector 7000 in the first direction, as described in greater detail below. Similarly, the handle control system 1800 rotates the handle drive shaft 1710, the drive shaft 2710, and the end effector 7000 in the second direction when the second sensor detects that the annular ring 1422 is rotated in the second direction. In view of the above, the reader should appreciate that the clamping trigger 2610 and the rotation actuator 1420 are both operable to rotate the drive shaft 2710.

In various embodiments, further to the above, the first and second sensors comprise switches which are mechanically closable by the detectable element of the annular ring 1422. When the annular ring 1422 is rotated in the first direction from a center position, the detectable element closes the switch of the first sensor. When the switch of the first sensor is closed, the control system 1800 operates the electric motor 1610 to rotate the end effector 7000 in the first direction. When the annular ring 1422 is rotated in the second direction toward the center position, the detectable element is disengaged from the first switch and the first switch is re-opened. Once the first switch is re-opened, the control system 1800 cuts the power to the electric motor 1610 to stop the rotation of the end effector 7000. Similarly, the detectable element closes the switch of the second sensor when the annular ring 1422 is rotated in the second direction from the center position. When the switch of the second sensor is closed, the control system 1800 operates the electric motor 1610 to rotate the end effector 7000 in the second direction. When the annular ring 1422 is rotated in the first direction toward the center position, the detectable element is disengaged from the second switch and the second switch is re-opened. Once the second switch is re-opened, the control system 1800 cuts the power to the electric motor 1610 to stop the rotation of the end effector 7000.

In various embodiments, further to the above, the first and second sensors of the rotation actuator 1420 comprise proximity sensors, for example. In certain embodiments, the first and second sensors of the rotation actuator 1420 comprise Hall Effect sensors, and/or any suitable sensors, configured to detect the distance between the detectable element of the annular ring 1422 and the first and second sensors. If the first Hall Effect sensor detects that the annular ring 1422 has been rotated in the first direction, then, as discussed above, the control system 1800 will rotate the end effector 7000 in the first direction. In addition, the control system 1800 can rotate the end effector 7000 at a faster speed when the detectable element is closer to the first Hall Effect sensor than when the detectable element is further away from the first Hall Effect sensor. If the second Hall Effect sensor detects that the annular ring 1422 has been rotated in the second direction, then, as discussed above, the control system 1800 will rotate the end effector 7000 in the second direction. In addition, the control system 1800 can rotate the end effector 7000 at a faster speed when the detectable element is closer to the second Hall Effect sensor than when the detectable element is further away from the second Hall Effect sensor. As a result, the speed in which the end effector 7000 is rotated is a function of the amount, or degree, in which the annular ring 1422 is rotated. The control system 1800 is further configured to evaluate the inputs from both the first and second Hall Effect sensors when determining the direction and speed in which to rotate the end effector 7000. In various instances, the control system 1800 can use the closest Hall Effect sensor to the detectable element of the annular ring 1422 as a primary source of data and the Hall Effect sensor furthest away from the detectable element as a confirmational source of data to double-check the data provided by the primary source of data. The control system 1800 can further comprise a data integrity protocol to resolve situations in which the control system 1800 is provided with conflicting data. In any event, the handle control system 1800 can enter into a neutral state in which the handle control system 1800 does not rotate the end effector 7000 when the Hall Effect sensors detect that the detectable element is in its center position, or in a position which is equidistant between the first Hall Effect sensor and the second Hall Effect sensor. In at least one such instance, the control system 1800 can enter into its neutral state when the detectable element is in a central range of positions. Such an arrangement would prevent, or at least reduce the possibility of, rotational jitter when the clinician is not intending to rotate the end effector 7000.

Further to the above, the rotation actuator 1420 can comprise one or more springs configured to center, or at least substantially center, the rotation actuator 1420 when it is released by the clinician. In such instances, the springs can act to shut off the electric motor 1610 and stop the rotation of the end effector 7000. In at least one instance, the rotation actuator 1420 comprises a first torsion spring configured to rotate the rotation actuator 1420 in the first direction and a second torsion spring configured to rotate the rotation actuator 1420 in the second direction. The first and second torsion springs can have the same, or at least substantially the same, spring constant such that the forces and/or torques applied by the first and second torsion springs balance, or at least substantially balance, the rotation actuator 1420 in its center position.

In view of the above, the reader should appreciate that the clamping trigger 2610 and the rotation actuator 1420 are both operable to rotate the drive shaft 2710 and either, respectively, operate the jaw assembly 7100 or rotate the end effector 7000. The system that uses the rotation of the drive shaft 2710 to selectively perform these functions is described in greater detail below.

Referring to FIGS. 7 and 8, the articulation actuator 1430 comprises a first push button 1432 and a second push button 1434. The first push button 1432 is part of a first articulation control circuit and the second push button 1434 is part of a second articulation circuit of the input system 1400. The first push button 1432 comprises a first switch that is closed when the first push button 1432 is depressed. The handle control system 1800 is configured to sense the closure of the first switch and, moreover, the closure of the first articulation control circuit. When the handle control system 1800 detects that the first articulation control circuit has been closed, the handle control system 1800 operates the electric motor 1610 to articulate the end effector 7000 in a first articulation direction about the articulation joint 2300. When the first push button 1432 is released by the clinician, the first articulation control circuit is opened which, once detected by the control system 1800, causes the control system 1800 to cut the power to the electric motor 1610 to stop the articulation of the end effector 7000.

In various instances, further to the above, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the first direction. In addition to or in lieu of the encoder system, the shaft assembly 2000 can comprise a first sensor configured to detect when the end effector 7000 has reached the limit of its articulation in the first direction. In any event, when the control system 1800 determines that the end effector 7000 has reached the limit of articulation in the first direction, the control system 1800 can cut the power to the electric motor 1610 to stop the articulation of the end effector 7000.

Similar to the above, the second push button 1434 comprises a second switch that is closed when the second push button 1434 is depressed. The handle control system 1800 is configured to sense the closure of the second switch and, moreover, the closure of the second articulation control circuit. When the handle control system 1800 detects that the second articulation control circuit has been closed, the handle control system 1800 operates the electric motor 1610 to articulate the end effector 7000 in a second direction about the articulation joint 2300. When the second push button 1434 is released by the clinician, the second articulation control circuit is opened which, once detected by the control system 1800, causes the control system 1800 to cut the power to the electric motor 1610 to stop the articulation of the end effector 7000.

In various instances, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the second direction. In addition to or in lieu of the encoder system, the shaft assembly 2000 can comprise a second sensor configured to detect when the end effector 7000 has reached the limit of its articulation in the second direction. In any event, when the control system 1800 determines that the end effector 7000 has reached the limit of articulation in the second direction, the control system 1800 can cut the power to the electric motor 1610 to stop the articulation of the end effector 7000.

Figure 15:
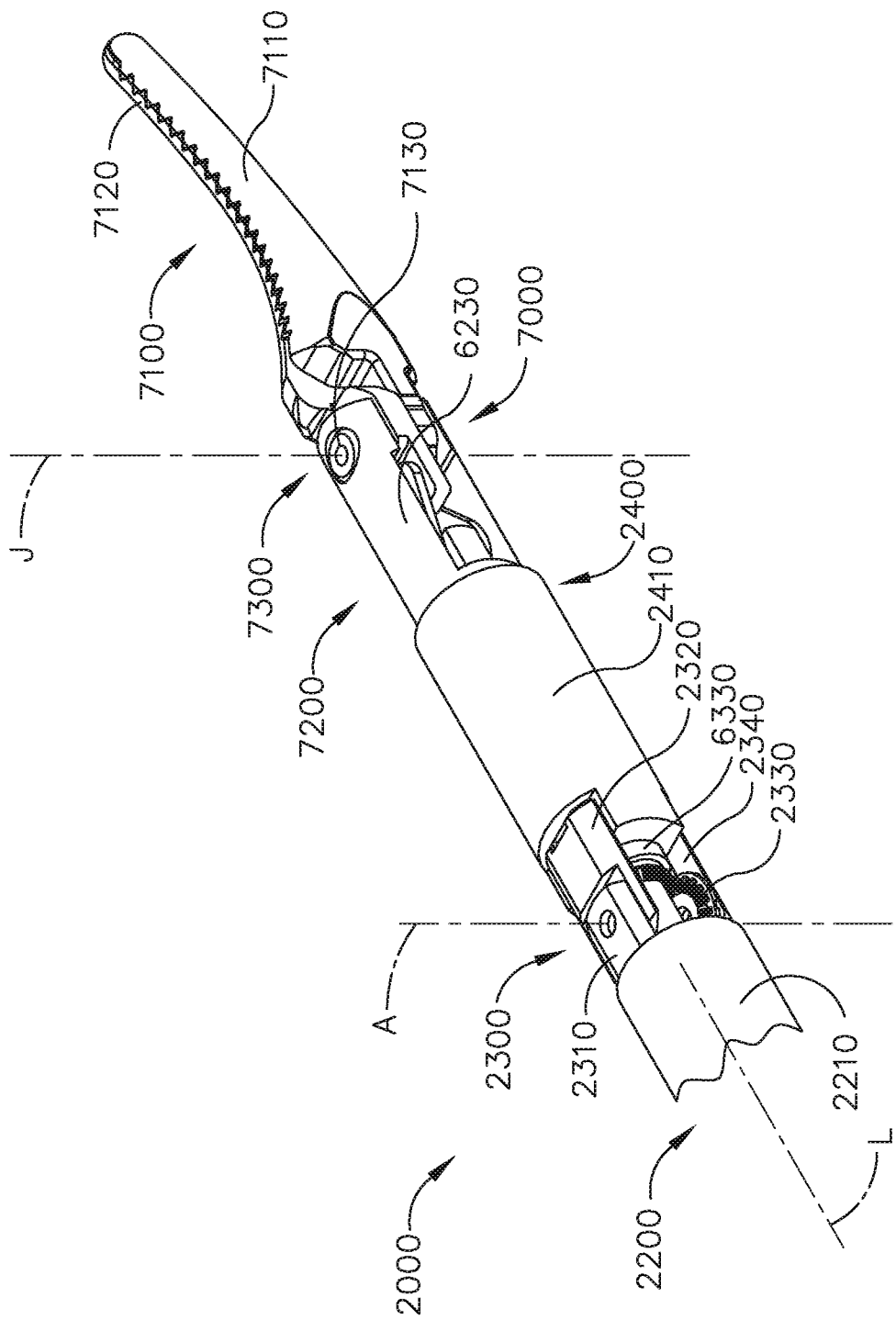
FIG. 15 is a partial perspective view of the end effector of FIG. 14 in a closed configuration.

As described above, the end effector 7000 is articulatable in a first direction (FIG. 16) and/or a second direction (FIG. 17) from a center, or unarticulated, position (FIG. 15). Once the end effector 7000 has been articulated, the clinician can attempt to re-center the end effector 7000 by using the first and second articulation push buttons 1432 and 1434. As the reader can appreciate, the clinician may struggle to re-center the end effector 7000 as, for instance, the end effector 7000 may not be entirely visible once it is positioned in the patient. In some instances, the end effector 7000 may not fit back through a trocar if the end effector 7000 is not re-centered, or at least substantially re-centered. With that in mind, the control system 1800 is configured to provide feedback to the clinician when the end effector 7000 is moved into its unarticulated, or centered, position. In at least one instance, the feedback comprises audio feedback and the handle control system 1800 can comprise a speaker which emits a sound, such as a beep, for example, when the end effector 7000 is centered. In certain instances, the feedback comprises visual feedback and the handle control system 1800 can comprise a light emitting diode (LED), for example, positioned on the handle housing 1110 which flashes when the end effector 7000 is centered. In various instances, the feedback comprises haptic feedback and the handle control system 1800 can comprise an electric motor comprising an eccentric element which vibrates the handle 1000 when the end effector 7000 is centered. Manually re-centering the end effector 7000 in this way can be facilitated by the control system 1800 slowing the motor 1610 when the end effector 7000 is approaching its centered position. In at least one instance, the control system 1800 slows the articulation of the end effector 7000 when the end effector 7000 is within approximately 5 degrees of center in either direction, for example.

In addition to or in lieu of the above, the handle control system 1800 can be configured to re-center the end effector

7000. In at least one such instance, the handle control system 1800 can re-center the end effector 7000 when both of the articulation buttons 1432 and 1434 of the articulation actuator 1430 are depressed at the same time. When the handle control system 1800 comprises an encoder system configured to monitor the rotational output of the electric motor 1610, for example, the handle control system 1800 can determine the amount and direction of articulation needed to re-center, or at least substantially re-center, the end effector 7000. In various instances, the input system 1400 can comprise a home button, for example, which, when depressed, automatically centers the end effector 7000.

Figure 5:
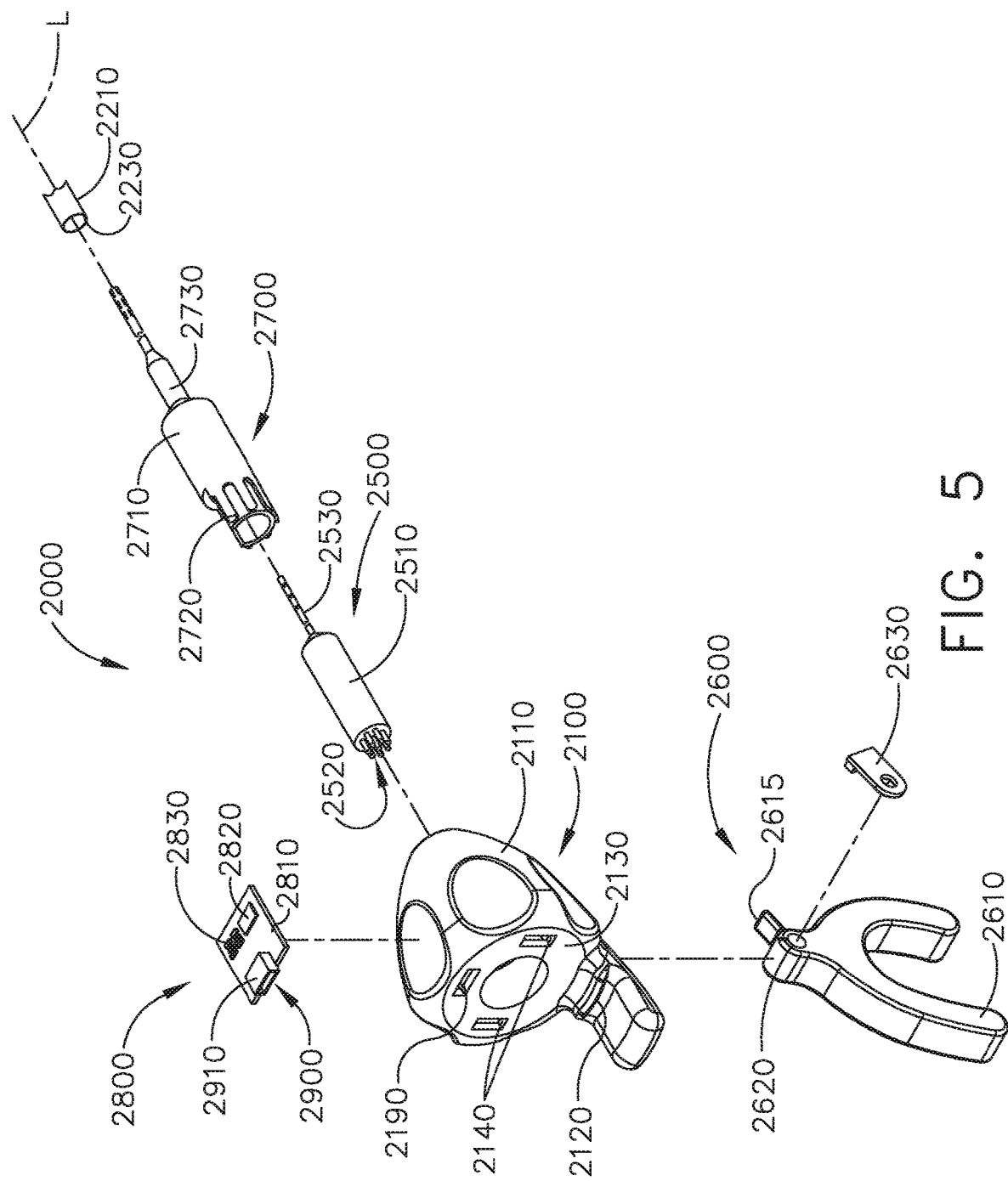
FIG. 5 is a partial exploded view of the shaft assembly of FIG. 2.
Figure 6:
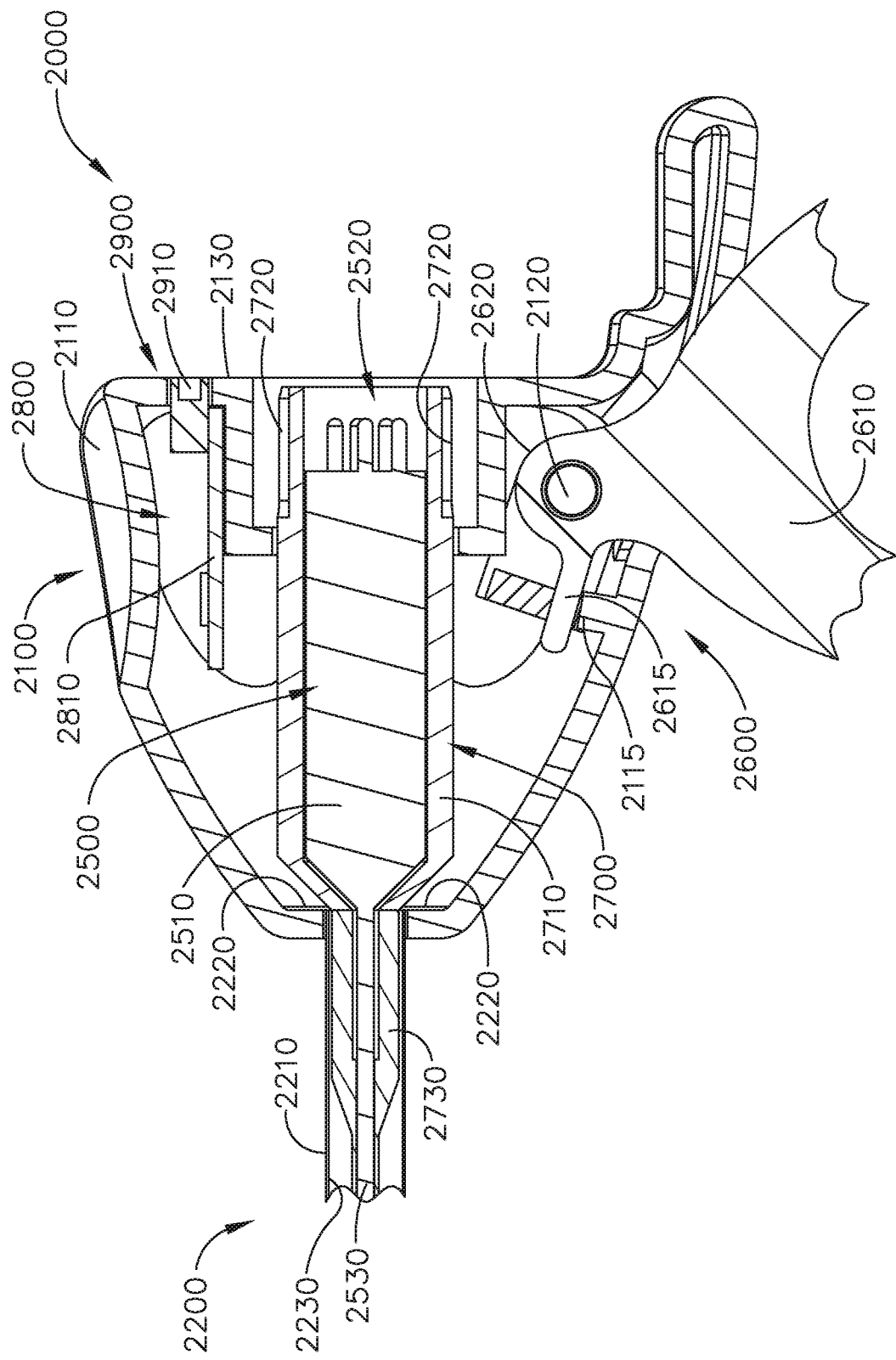
FIG. 6 is a partial cross-sectional elevational view of the shaft assembly of FIG. 2.

Referring primarily to FIGS. 5 and 6, the elongate shaft 2200 of the shaft assembly 2000 comprises an outer housing, or tube, 2210 mounted to the proximal housing 2110 of the proximal portion 2100. The outer housing 2210 comprises a longitudinal aperture 2230 extending therethrough and a proximal flange 2220 which secures the outer housing 2210 to the proximal housing 2110. The frame 2500 of the shaft assembly 2000 extends through the longitudinal aperture 2230 of the elongate shaft 2200. More specifically, the shaft 2510 of the shaft frame 2500 necks down into a smaller shaft 2530 which extends through the longitudinal aperture 2230. That said, the shaft frame 2500 can comprise any suitable arrangement. The drive system 2700 of the shaft assembly 2000 also extends through the longitudinal aperture 2230 of the elongate shaft 2200. More specifically, the drive shaft 2710 of the shaft drive system 2700 necks down into a smaller drive shaft 2730 which extends through the longitudinal aperture 2230. That said, the shaft drive system 2700 can comprise any suitable arrangement.

Figure 20:
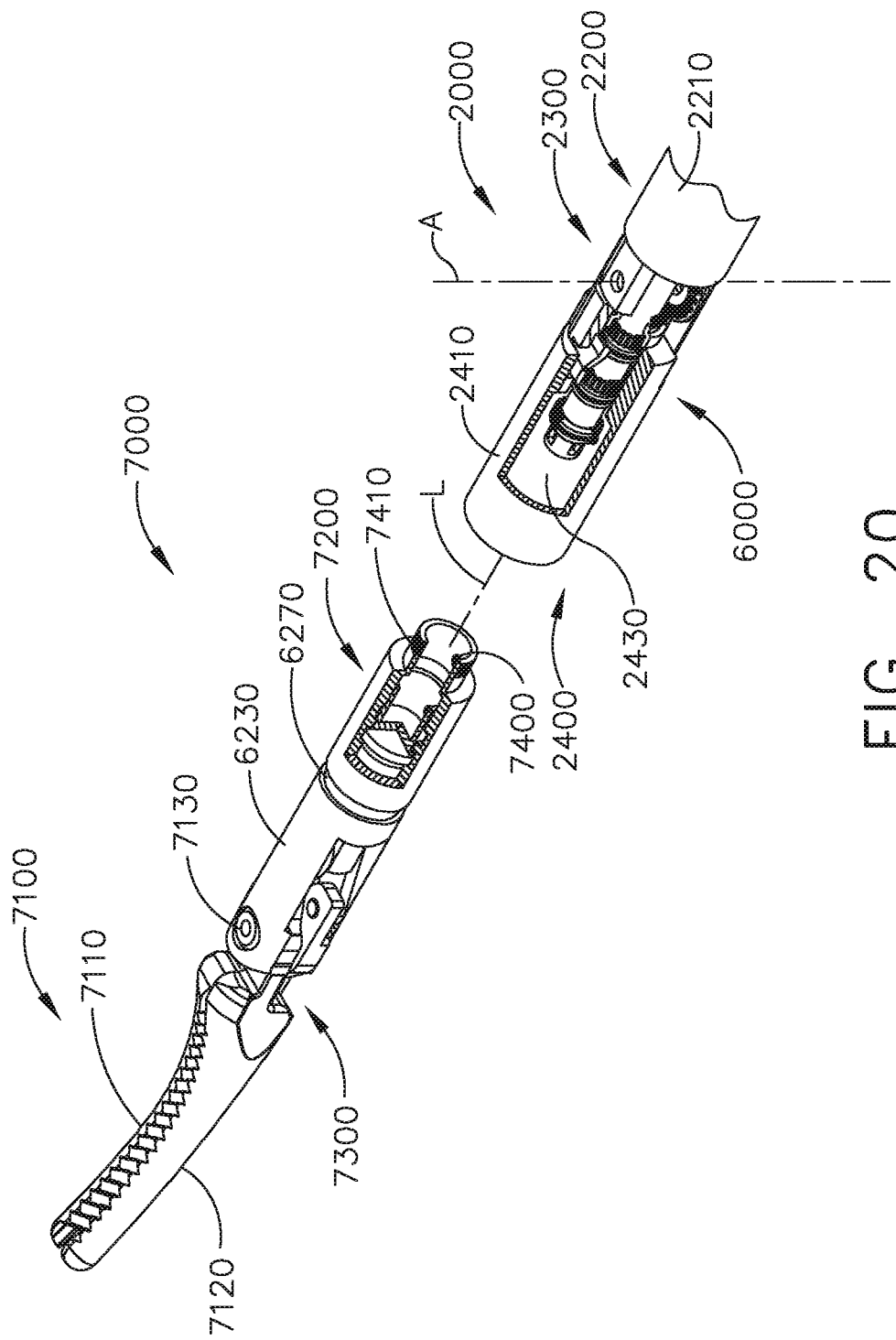
FIG. 20 is a partial cross-sectional perspective view of the end effector of FIG. 14 detached from the shaft assembly of FIG. 2.
Figure 22:
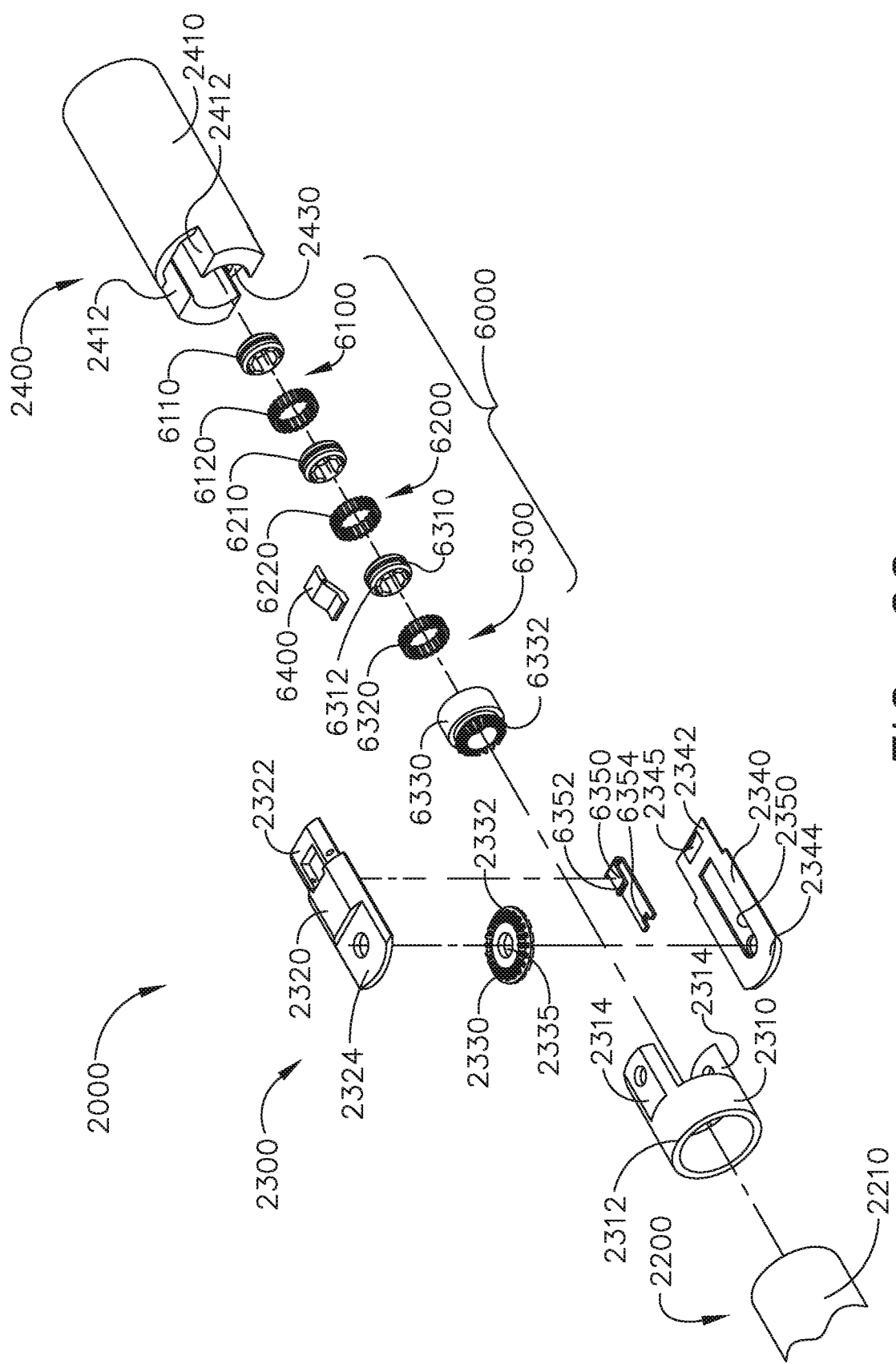
FIG. 22 is an exploded view of a distal attachment portion of the shaft assembly of FIG. 2.
Figure 23:
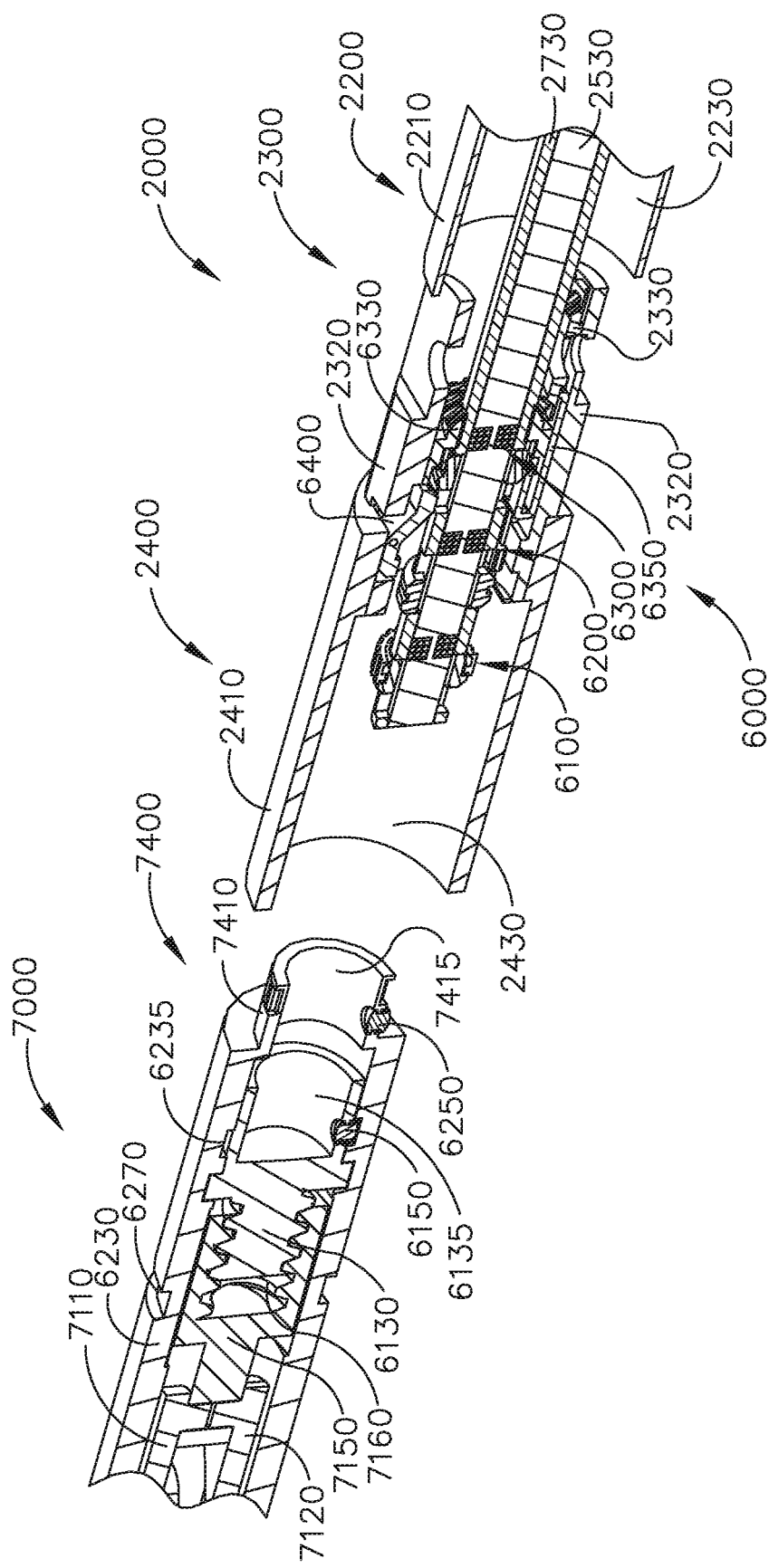
FIG. 23 is another partial cross-sectional perspective view of the end effector of FIG. 14 detached from the shaft assembly of FIG. 2.
Figure 24:
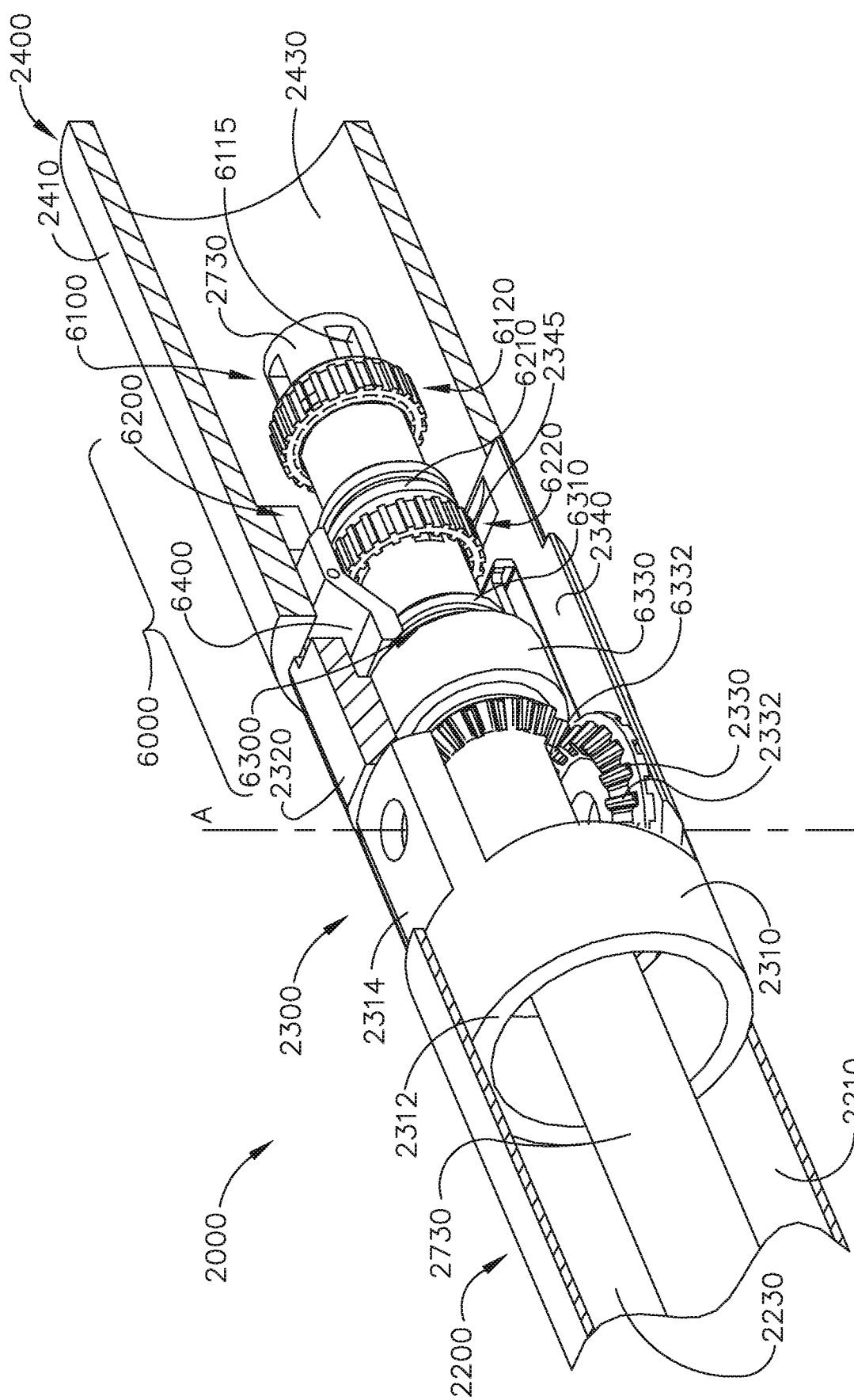
FIG. 24 is a partial cross-sectional perspective view of the end effector of FIG. 14 attached to the shaft assembly of FIG. 2.

Referring primarily to FIGS. 20, 23, and 24, the outer housing 2210 of the elongate shaft 2200 extends to the articulation joint 2300. The articulation joint 2300 comprises a proximal frame 2310 mounted to the outer housing 2210 such that there is little, if any, relative translation and/or rotation between the proximal frame 2310 and the outer housing 2210. Referring primarily to FIG. 22, the proximal frame 2310 comprises an annular portion 2312 mounted to the sidewall of the outer housing 2210 and tabs 2314 extending distally from the annular portion 2312. The articulation joint 2300 further comprises links 2320 and 2340 which are rotatably mounted to the frame 2310 and mounted to an outer housing 2410 of the distal attachment portion 2400. The link 2320 comprises a distal end 2322 mounted to the outer housing 2410. More specifically, the distal end 2322 of the link 2320 is received and fixedly secured within a mounting slot 2412 defined in the outer housing 2410. Similarly, the link 2340 comprises a distal end 2342 mounted to the outer housing 2410. More specifically, the distal end 2342 of the link 2340 is received and fixedly secured within a mounting slot defined in the outer housing 2410. The link 2320 comprises a proximal end 2324 rotatably coupled to a tab 2314 of the proximal articulation frame 2310. Although not illustrated in FIG. 22, a pin extends through apertures defined in the proximal end 2324 and the tab 2314 to define a pivot axis therebetween. Similarly, the link 2340 comprises a proximal end 2344 rotatably coupled to a tab 2314 of the proximal articulation frame 2310. Although not illustrated in FIG. 22, a pin extends through apertures defined in the proximal end 2344 and the tab 2314 to define a pivot axis therebetween. These pivot axes are collinear, or at least substantially collinear, and define an articulation axis A of the articulation joint 2300.

Referring primarily to FIGS. 20, 23, and 24, the outer housing 2410 of the distal attachment portion 2400 comprises a longitudinal aperture 2430 extending therethrough. The longitudinal aperture 2430 is configured to receive a proximal attachment portion 7400 of the end effector 7000. The end effector 7000 comprises an outer housing 6230 which is closely received within the longitudinal aperture 2430 of the distal attachment portion 2400 such that there is little, if any, relative radial movement between the proximal attachment portion 7400 of the end effector 7000 and the distal attachment portion 2400 of the shaft assembly 2000. The proximal attachment portion 7400 further comprises an annular array of lock notches 7410 defined on the outer housing 6230 which is releasably engaged by an end effector lock 6400 in the distal attachment portion 2400 of the shaft assembly 2000. When the end effector lock 6400 is engaged with the array of lock notches 7410, the end effector lock 6400 prevents, or at least inhibits, relative longitudinal movement between the proximal attachment portion 7400 of the end effector 7000 and the distal attachment portion 2400 of the shaft assembly 2000. As a result of the above, only relative rotation between the proximal attachment portion 7400 of the end effector 7000 and the distal attachment portion 2400 of the shaft assembly 2000 is permitted. To this end, the outer housing 6230 of the end effector 7000 is closely received within the longitudinal aperture 2430 defined in the distal attachment portion 2400 of the shaft assembly 2000.

Figure 21:
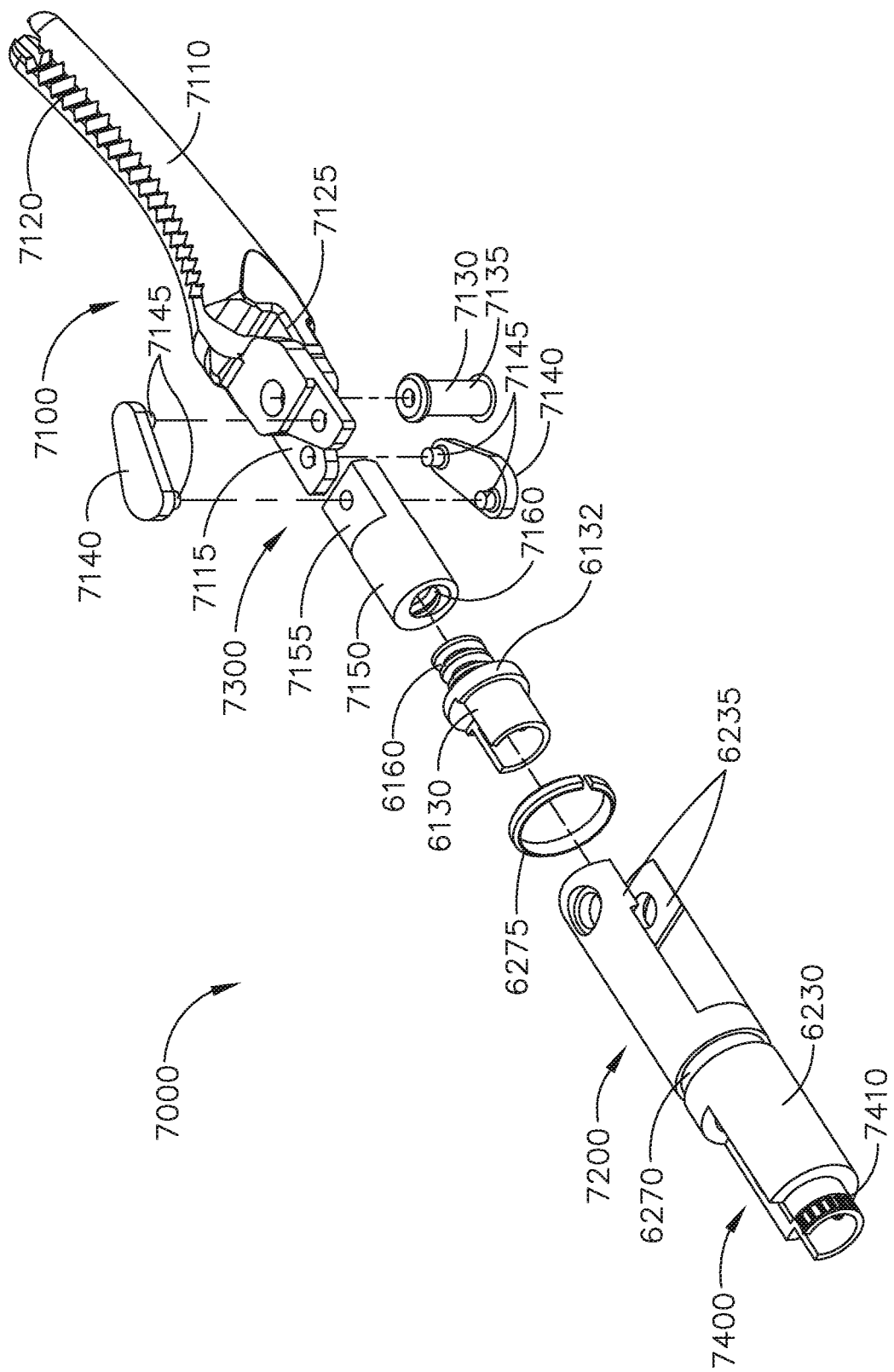
FIG. 21 is an exploded view of the end effector of FIG. 14 illustrated with some components removed.

Further to the above, referring to FIG. 21, the outer housing 6230 further comprises an annular slot, or recess, 6270 defined therein which is configured to receive an O-ring 6275 therein. The O-ring 6275 is compressed between the outer housing 6230 and the sidewall of the longitudinal aperture 2430 when the end effector 7000 is inserted into the distal attachment portion 2400. The O-ring 6275 is configured to resist, but permit, relative rotation between the end effector 7000 and the distal attachment portion 2400 such that the O-ring 6275 can prevent, or reduce the possibility of, unintentional relative rotation between the end effector 7000 and the distal attachment portion 2400. In various instances, the O-ring 6275 can provide a seal between the end effector 7000 and the distal attachment portion 2400 to prevent, or at least reduce the possibility of, fluid ingress into the shaft assembly 2000, for example.

Referring to FIGS. 14-21, the jaw assembly 7100 of the end effector 7000 comprises a first jaw 7110 and a second jaw 7120. Each jaw 7110, 7120 comprises a distal end which is configured to assist a clinician in dissecting tissue with the end effector 7000. Each jaw 7110, 7120 further comprises a plurality of teeth which are configured to assist a clinician in grasping and holding onto tissue with the end effector 7000. Moreover, referring primarily to FIG. 21, each jaw 7110, 7120 comprises a proximal end, i.e., proximal ends 7115, 7125, respectively, which rotatably connect the jaws 7110, 7120 together. Each proximal end 7115, 7125 comprises an aperture extending therethrough which is configured to closely receive a pin 7130 therein. The pin 7130 comprises a central body 7135 closely received within the apertures defined in the proximal ends 7115, 7125 of the jaws 7110, 7120 such that there is little, if any, relative translation between the jaws 7110, 7120 and the pin 7130. The pin 7130 defines a jaw axis J about which the jaws 7110, 7120 can be rotated and, also, rotatably mounts the jaws 7110, 7120 to the outer housing 6230 of the end effector 7000. More specifically, the outer housing 6230 comprises distally-extending tabs 6235 having apertures defined therein which are also configured to closely receive the pin 7130 such that the jaw assembly 7100 does not translate relative to a shaft portion 7200 of the end effector 7000. The pin 7130 further comprises enlarged ends which prevent the jaws 7110, 7120 from becoming detached from the pin 7130 and also prevents the jaw assembly 7100 from becoming detached from the shaft portion 7200. This arrangement defines a rotation joint 7300.

Referring primarily to FIGS. 21 and 23, the jaws 7110 and 7120 are rotatable between their open and closed positions by a jaw assembly drive including drive links 7140, a drive nut 7150, and a drive screw 6130. As described in greater detail below, the drive screw 6130 is selectively rotatable by the drive shaft 2730 of the shaft drive system 2700. The drive screw 6130 comprises an annular flange 6132 which is closely received within a slot, or groove, 6232 (FIG. 25) defined in the outer housing 6230 of the end effector 7000. The sidewalls of the slot 6232 are configured to prevent, or at least inhibit, longitudinal and/or radial translation between the drive screw 6130 and the outer housing 6230, but yet permit relative rotational motion between the drive screw 6130 and the outer housing 6230. The drive screw 6130 further comprises a threaded end 6160 which is threadably engaged with a threaded aperture 7160 defined in the drive nut 7150. The drive nut 7150 is constrained from rotating with the drive screw 6130 and, as a result, the drive nut 7150 is translated when the drive screw 6130 is rotated. In use, the drive screw 6130 is rotated in a first direction to displace the drive nut 7150 proximally and in a second, or opposite, direction to displace the drive nut 7150 distally. The drive nut 7150 further comprises a distal end 7155 comprising an aperture defined therein which is configured to closely receive pins 7145 extending from the drive links 7140. Referring primarily to FIG. 21, a first drive link 7140 is attached to one side of the distal end 7155 and a second drive link 7140 is attached to the opposite side of the distal end 7155. The first drive link 7140 comprises another pin 7145 extending therefrom which is closely received in an aperture defined in the proximal end 7115 of the first jaw 7110 and, similarly, the second drive link 7140 comprises another pin extending therefrom which is closely received in an aperture defined in the proximal end 7125 of the second jaw 7120. As a result of the above, the drive links 7140 operably connect the jaws 7110 and 7120 to the drive nut 7150. When the drive nut 7150 is driven proximally by the drive screw 6130, as described above, the jaws 7110, 7120 are rotated into the closed, or clamped, configuration. Correspondingly, the jaws 7110, 7120 are rotated into their open configuration when the drive nut 7150 is driven distally by the drive screw 6130.

Figure 16:
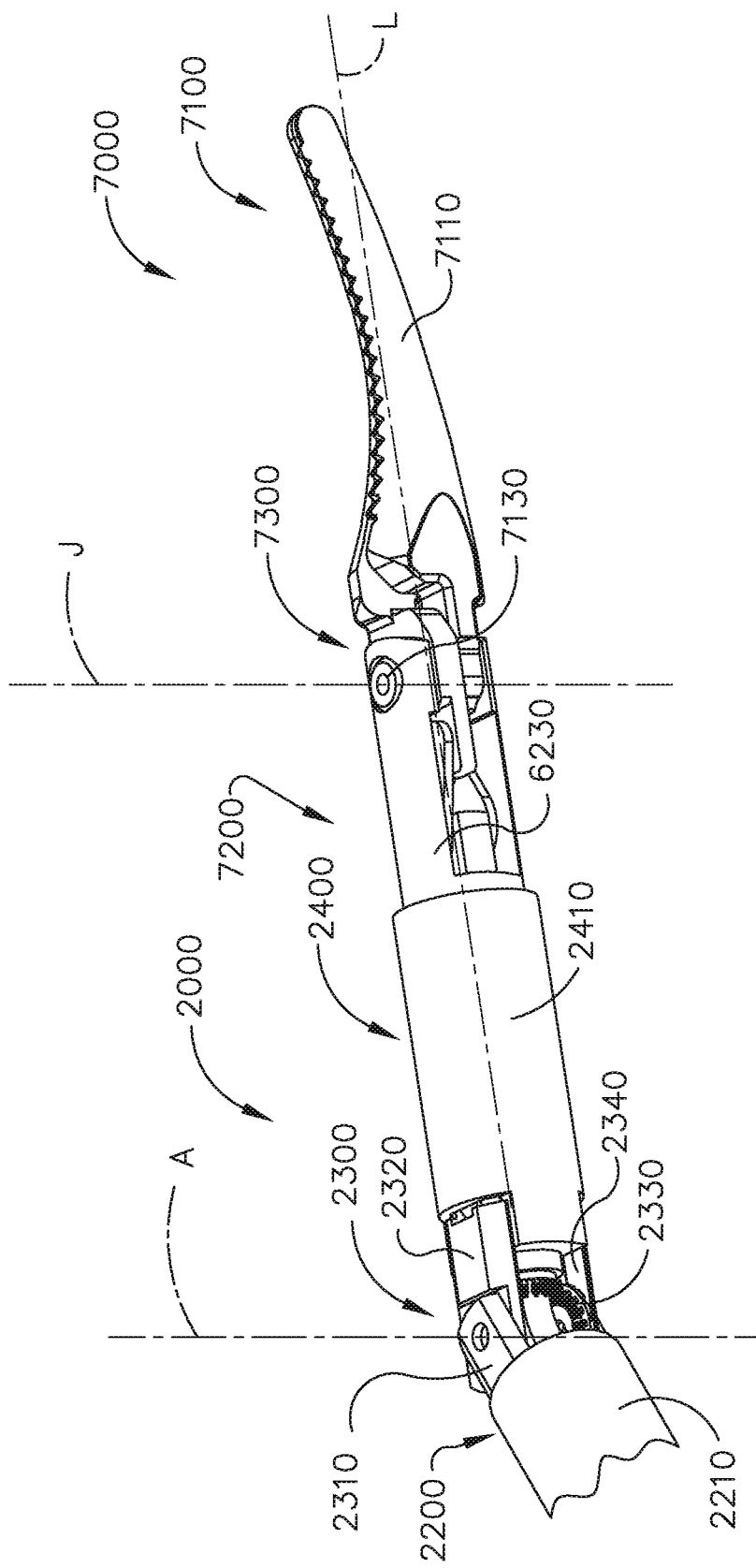
FIG. 16 is a partial perspective view of the end effector of FIG. 14 articulated in a first direction.
Figure 17:
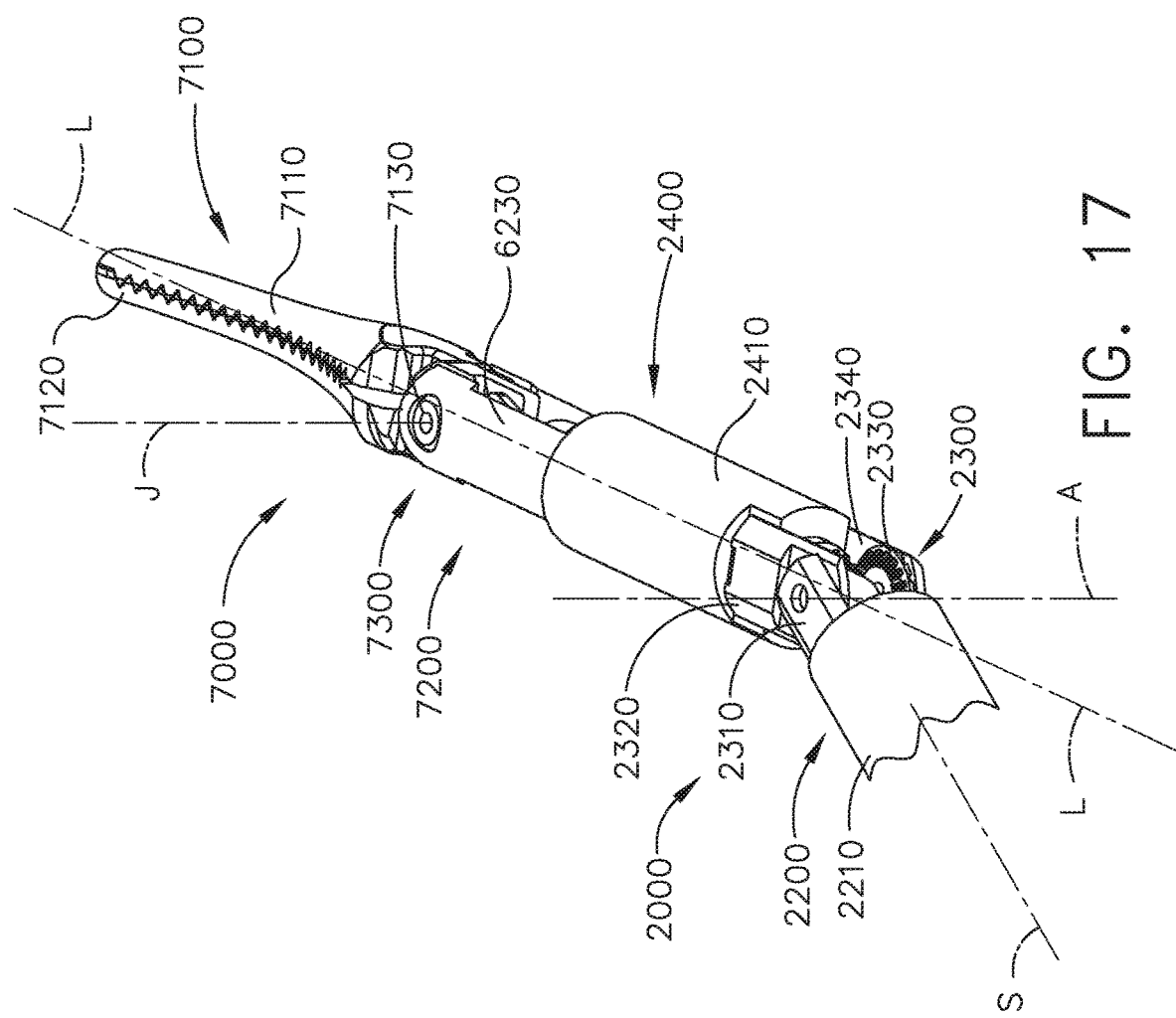
FIG. 17 is a partial perspective view of the end effector of FIG. 14 articulated in a second direction.
Figure 18:
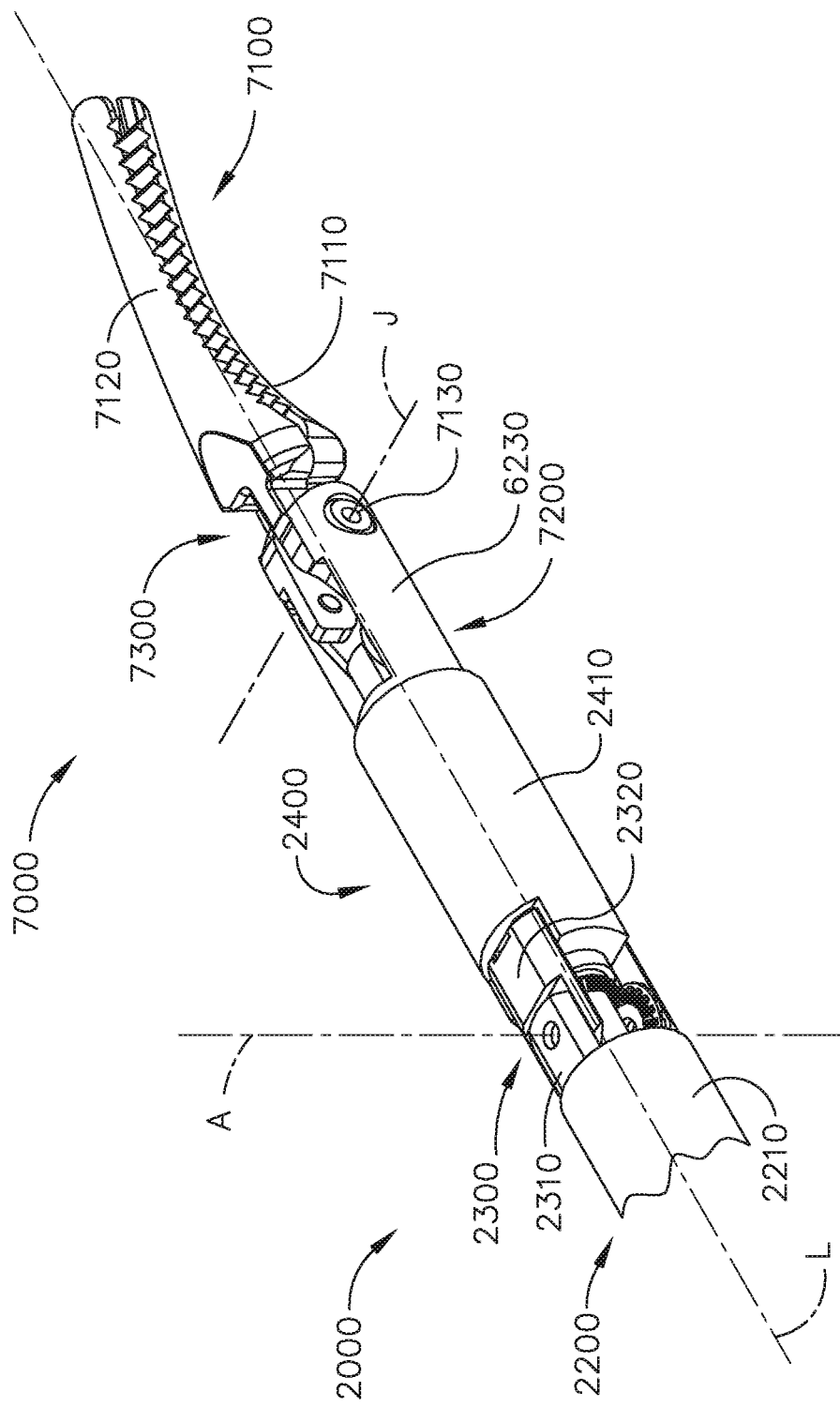
FIG. 18 is a partial perspective view of the end effector of FIG. 14 rotated in a first direction.
Figure 19:
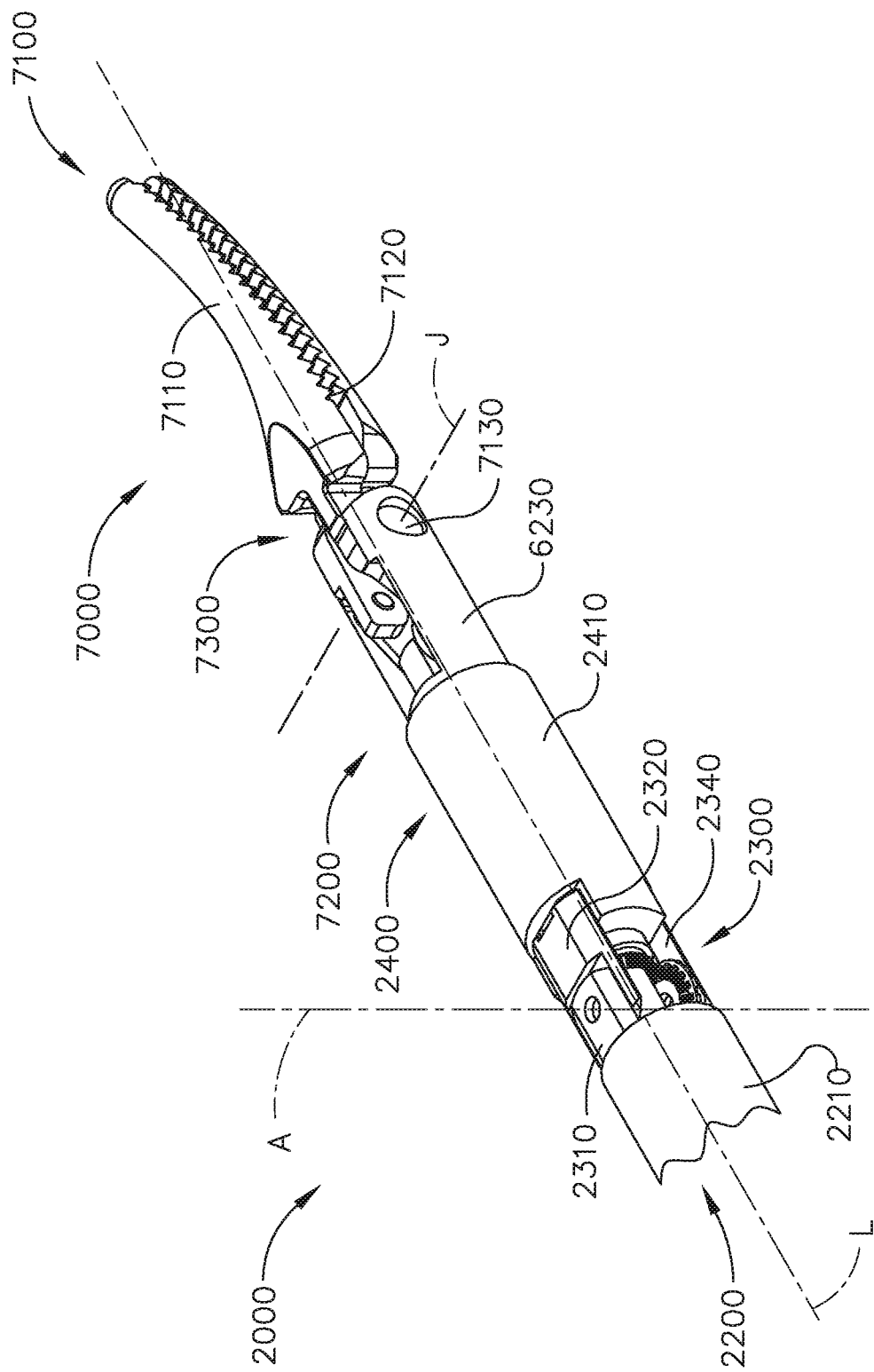
FIG. 19 is a partial perspective view of the end effector of FIG. 14 rotated in a second direction.
Figure 26:
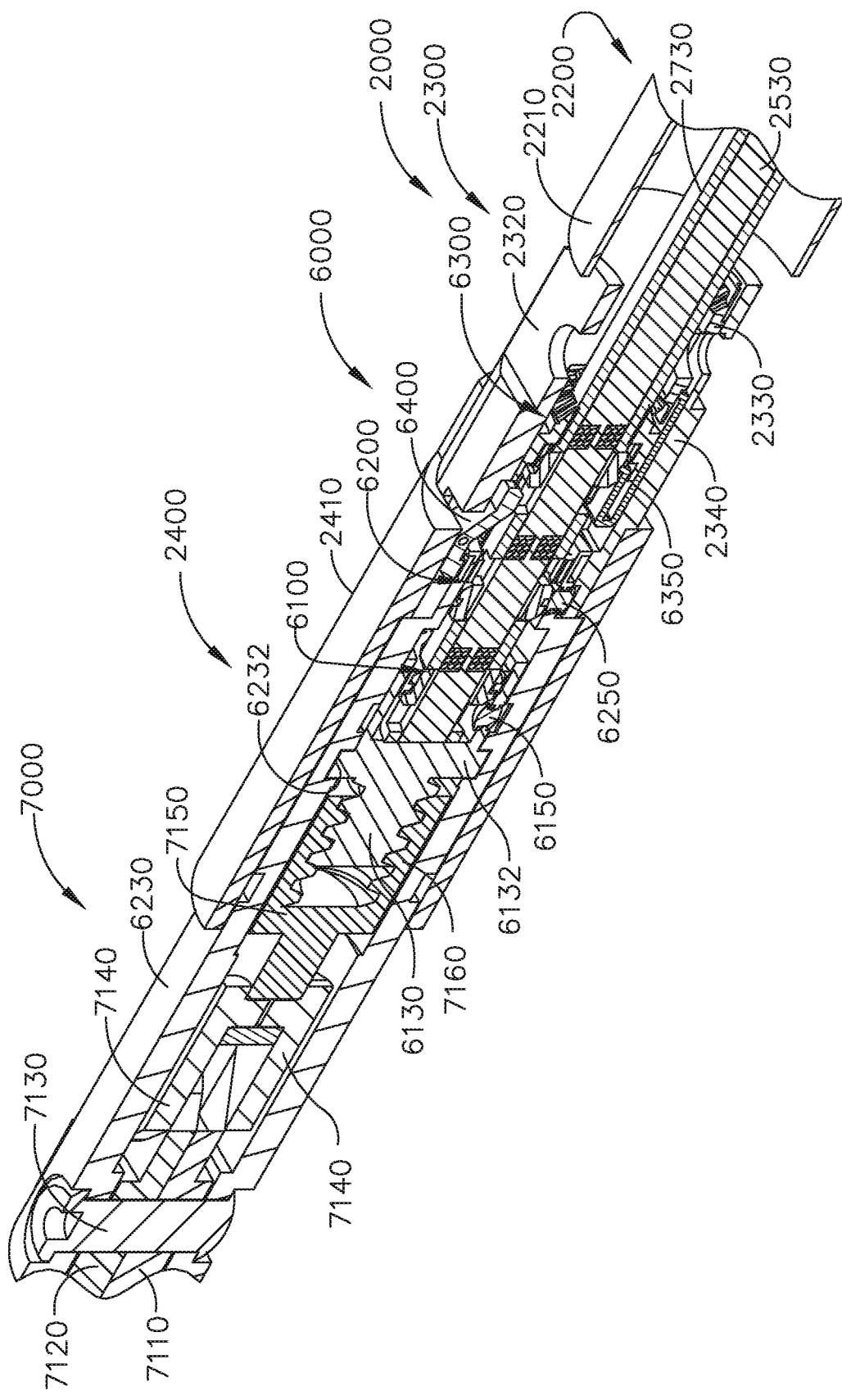
FIG. 26 is another partial cross-sectional perspective view of the end effector of FIG. 14 attached to the shaft assembly of FIG. 2.
Figure 27:
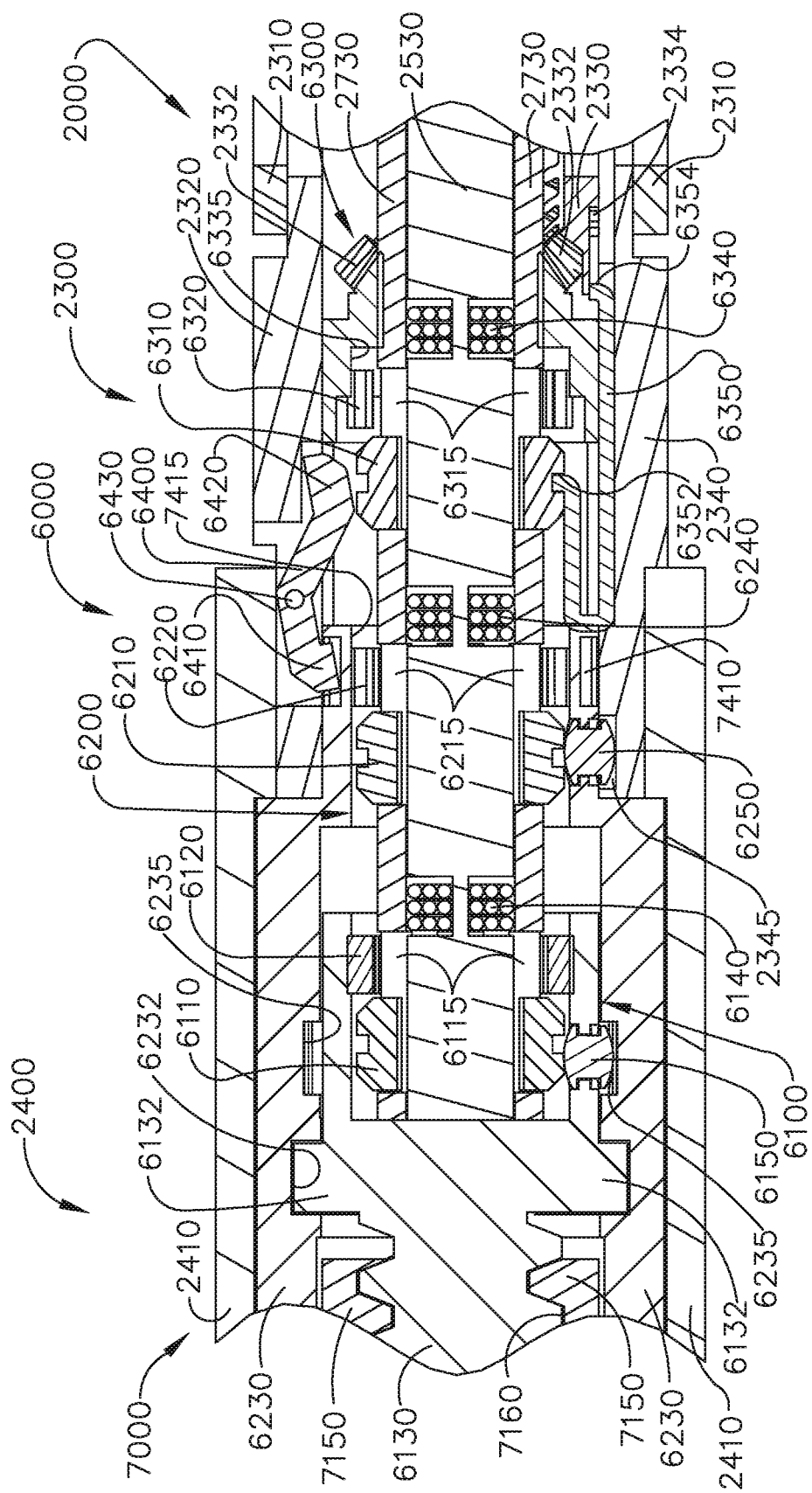
FIG. 27 is a partial cross-sectional view of the end effector of FIG. 14 attached to the shaft assembly of FIG. 2 depicting a first, second, and third clutch of the end effector.

As discussed above, the control system 1800 is configured to actuate the electric motor 1610 to perform three different end effector functions—clamping/opening the jaw assembly 7100 (FIGS. 14 and 15), rotating the end effector 7000 about a longitudinal axis (FIGS. 18 and 19), and articulating the end effector 7000 about an articulation axis (FIGS. 16 and 17). Referring primarily to FIGS. 26 and 27, the control system 1800 is configured to operate a transmission 6000 to selectively perform these three end effector functions. The transmission 6000 comprises a first clutch system 6100 configured to selectively transmit the rotation of the drive shaft 2730 to the drive screw 6130 of the end effector 7000 to open or close the jaw assembly 7100, depending on the direction in which the drive shaft 2730 is rotated. The transmission 6000 further comprises a second clutch system 6200 configured to selectively transmit the rotation of the drive shaft 2730 to the outer housing 6230 of the end effector 7000 to rotate the end effector 7000 about the longitudinal axis L. The transmission 6000 also comprises a third clutch system 6300 configured to selectively transmit the rotation of the drive shaft 2730 to the articulation joint 2300 to articulate the distal attachment portion 2400 and the end effector 7000 about the articulation axis A. The clutch systems 6100, 6200, and 6300 are in electrical communication with the control system 1800 via electrical circuits extending through the shaft 2510, the connector pins 2520, the connector pins 1520, and the shaft 1510, for example. In at least one instance, each of these clutch control circuits comprises two connector pins 2520 and two connector pins 1520, for example.

In various instances, further to the above, the shaft 2510 and/or the shaft 1510 comprise a flexible circuit including electrical traces which form part of the clutch control circuits. The flexible circuit can comprise a ribbon, or substrate, with conductive pathways defined therein and/or thereon. The flexible circuit can also comprise sensors and/or any solid state component, such as signal smoothing capacitors, for example, mounted thereto. In at least one instance, each of the conductive pathways can comprise one or more signal smoothing capacitors which can, among other things, even out fluctuations in signals transmitted through the conductive pathways. In various instances, the flexible circuit can be coated with at least one material, such as an elastomer, for example, which can seal the flexible circuit against fluid ingress.

Figure 22A:
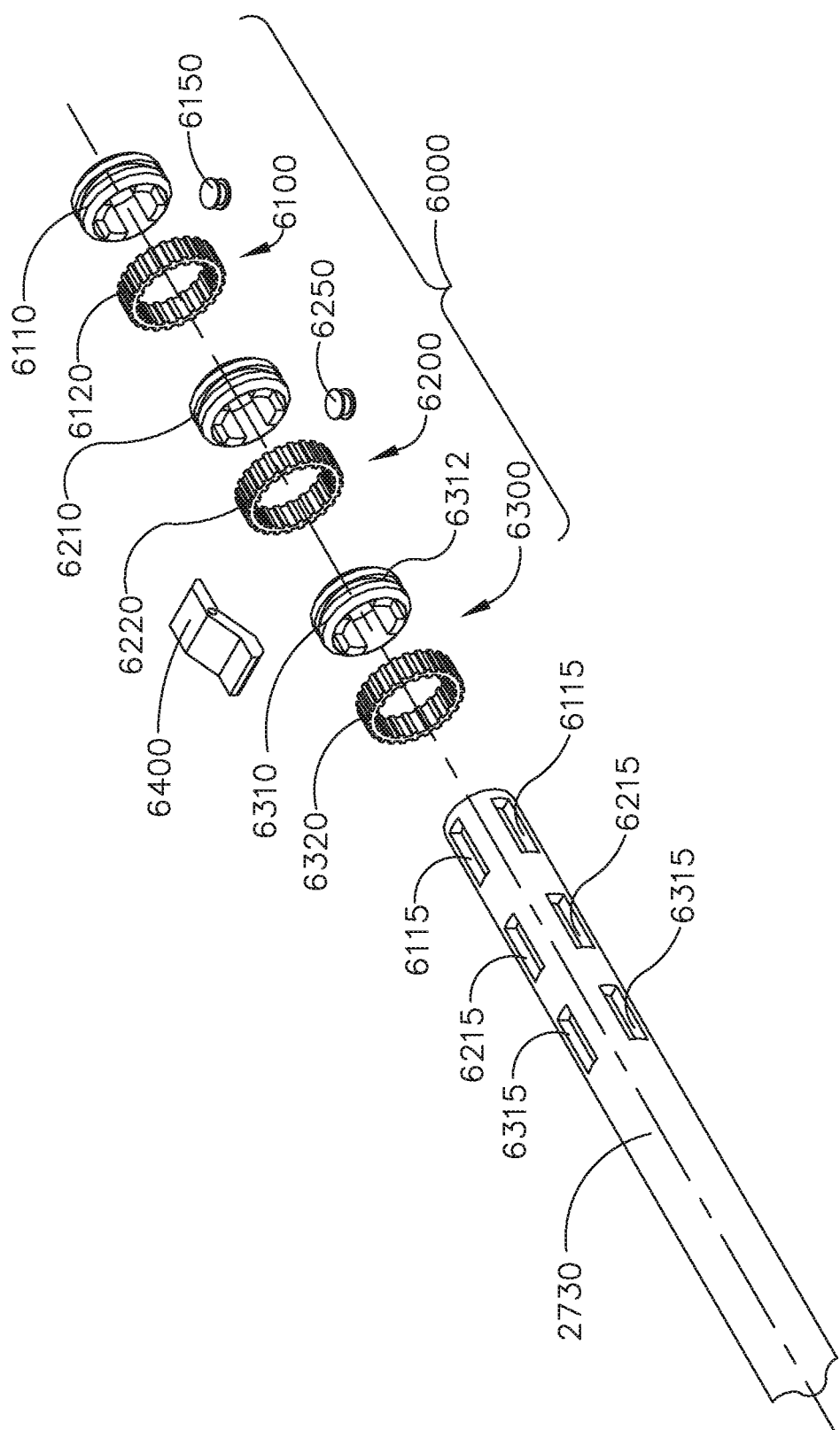
FIG. 22A is an exploded view of the distal portion of the shaft assembly of FIG. 2 illustrated with some components removed.
Figure 28:
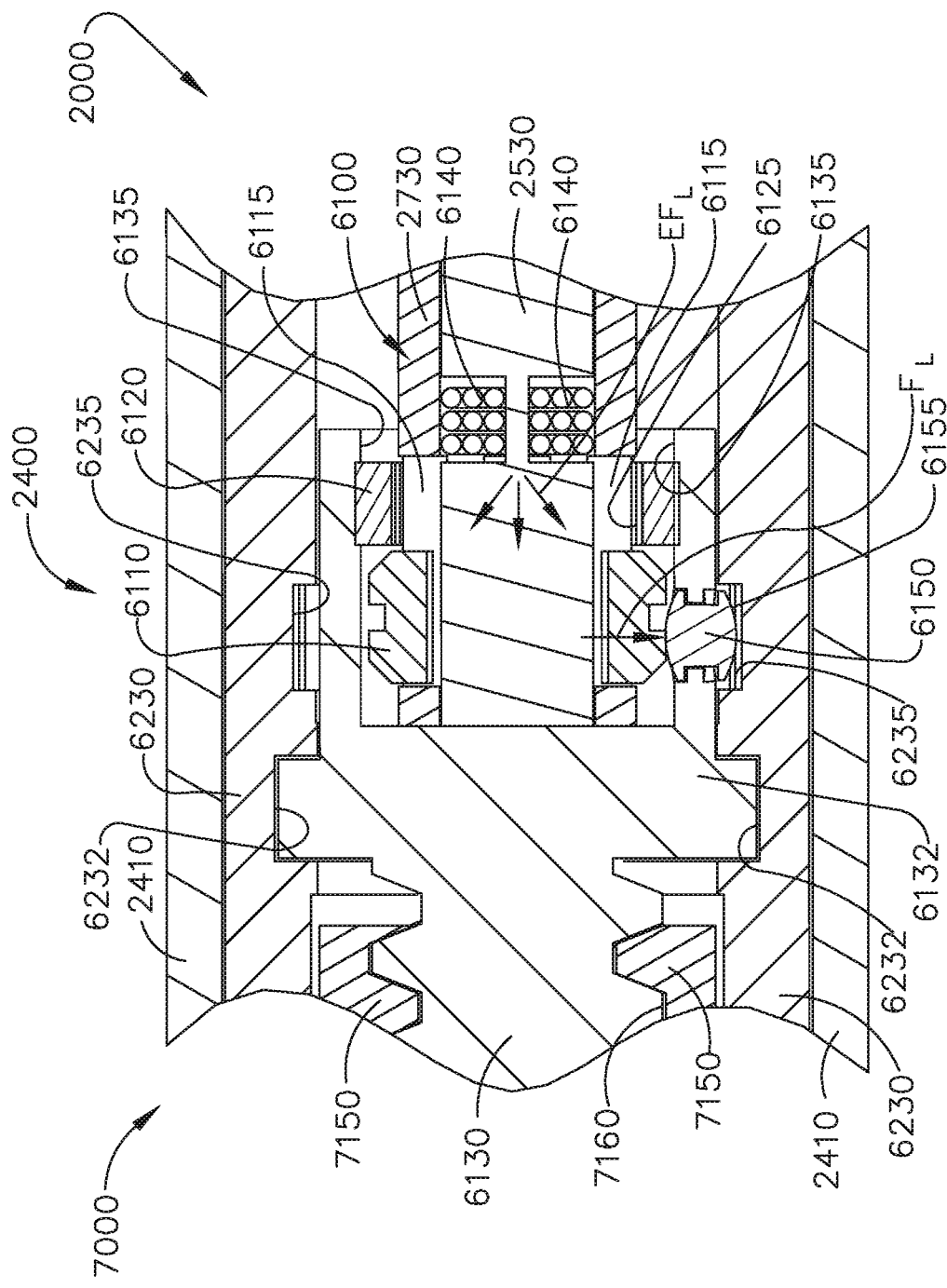
FIG. 28 depicts the first clutch of FIG. 27 in an unactuated condition.

Referring primarily to FIG. 28, the first clutch system 6100 comprises a first clutch 6110, an expandable first drive ring 6120, and a first electromagnetic actuator 6140. The first clutch 6110 comprises an annular ring and is slideably disposed on the drive shaft 2730. The first clutch 6110 is comprised of a magnetic material and is movable between a disengaged, or unactuated, position (FIG. 28) and an engaged, or actuated, position (FIG. 29) by electromagnetic fields EF generated by the first electromagnetic actuator 6140. In various instances, the first clutch 6110 is at least partially comprised of iron and/or nickel, for example. In at least one instance, the first clutch 6110 comprises a permanent magnet. As illustrated in FIG. 22A, the drive shaft 2730 comprises one or more longitudinal key slots 6115 defined therein which are configured to constrain the longitudinal movement of the clutch 6110 relative to the drive shaft 2730. More specifically, the clutch 6110 comprises one or more keys extending into the key slots 6115 such that the distal ends of the key slots 6115 stop the distal movement of the clutch 6110 and the proximal ends of the key slots 6115 stop the proximal movement of the clutch 6110.

Figure 29:
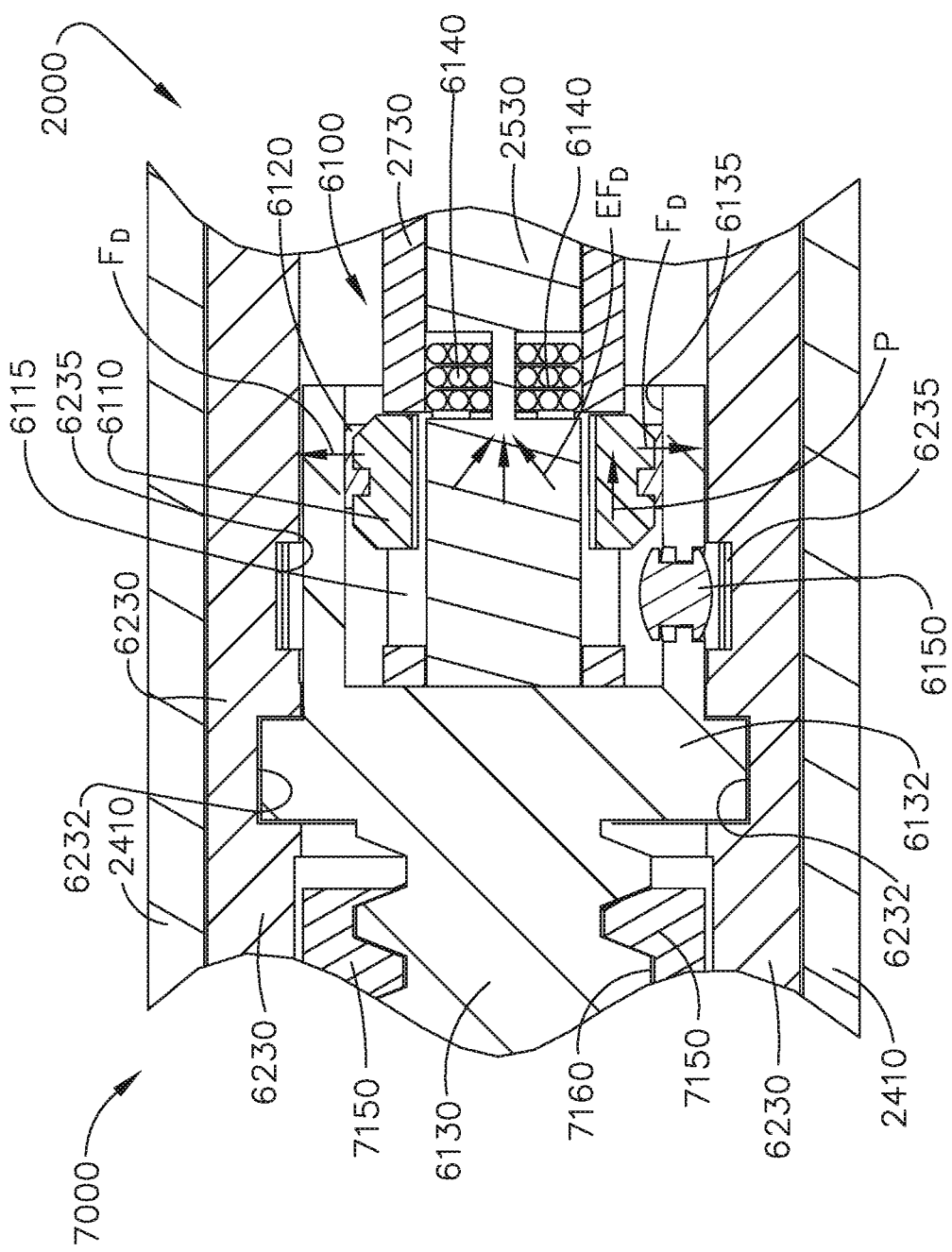
FIG. 29 depicts the first clutch of FIG. 27 in an actuated condition.

When the first clutch 6110 is in its disengaged position (FIG. 28), the first clutch 6110 rotates with the drive shaft 2130 but does not transmit rotational motion to the first drive ring 6120. As can be seen in FIG. 28, the first clutch 6110 is separated from, or not in contact with, the first drive ring 6120. As a result, the rotation of the drive shaft 2730 and the first clutch 6110 is not transmitted to the drive screw 6130 when the first clutch assembly 6100 is in its disengaged state. When the first clutch 6110 is in its engaged position (FIG. 29), the first clutch 6110 is engaged with the first drive ring 6120 such that the first drive ring 6120 is expanded, or stretched, radially outwardly into contact with the drive screw 6130. In at least one instance, the first drive ring 6120 comprises an elastomeric band, for example. As can be seen in FIG. 29, the first drive ring 6120 is compressed against an annular inner sidewall 6135 of the drive screw 6130. As a result, the rotation of the drive shaft 2730 and the first clutch 6110 is transmitted to the drive screw 6130 when the first clutch assembly 6100 is in its engaged state. Depending on the direction in which the drive shaft 2730 is rotated, the first clutch assembly 6100 can move the jaw assembly 7100 into its open and closed configurations when the first clutch assembly 6100 is in its engaged state.

As described above, the first electromagnetic actuator 6140 is configured to generate magnetic fields to move the first clutch 6110 between its disengaged (FIG. 28) and engaged (FIG. 29) positions. For instance, referring to FIG. 28, the first electromagnetic actuator 6140 is configured to emit a magnetic field $EF_L$ which repulses, or drives, the first clutch 6110 away from the first drive ring 6120 when the first clutch assembly 6100 is in its disengaged state. The first electromagnetic actuator 6140 comprises one or more wound coils in a cavity defined in the shaft frame 2530 which generate the magnetic field $EF_L$ when current flows in a first direction through a first electrical clutch circuit including the wound coils. The control system 1800 is configured to apply a first voltage polarity to the first electrical clutch circuit to create the current flowing in the first direction. The control system 1800 can continuously apply the first voltage polarity to the first electric shaft circuit to continuously hold the first clutch 6110 in its disengaged position. While such an arrangement can prevent the first clutch 6110 from unintentionally engaging the first drive ring 6120, such an arrangement can also consume a lot of power. Alternatively, the control system 1800 can apply the first voltage polarity to the first electrical clutch circuit for a sufficient period of time to position the first clutch 6110 in its disengaged position and then discontinue applying the first voltage polarity to the first electric clutch circuit, thereby resulting in a lower consumption of power. That being said, the first clutch assembly 6100 further comprises a first clutch lock 6150 mounted in the drive screw 6130 which is configured to releasably hold the first clutch 6110 in its disengaged position. The first clutch lock 6150 is configured to prevent, or at least reduce the possibility of, the first clutch 6110 from becoming unintentionally engaged with the first drive ring 6120. When the first clutch 6110 is in its disengaged position, as illustrated in FIG. 28, the first clutch lock 6150 interferes with the free movement of the first clutch 6110 and holds the first clutch 6110 in position via a friction force and/or an interference force therebetween. In at least one instance, the first clutch lock 6150 comprises an elastomeric plug, seat, or detent, comprised of rubber, for example. In certain instances, the first clutch lock 6150 comprises a permanent magnet which holds the first clutch 6110 in its disengaged position by an electromagnetic force. In any event, the first electromagnetic actuator 6140 can apply an electromagnetic pulling force to the first clutch 6110 that overcomes these forces, as described in greater detail below.

Further to the above, referring to FIG. 29, the first electromagnetic actuator 6140 is configured to emit a magnetic field $EF_D$ which pulls, or drives, the first clutch 6110 toward the first drive ring 6120 when the first clutch assembly 6100 is in its engaged state. The coils of the first electromagnetic actuator 6140 generate the magnetic field $EF_D$ when current flows in a second, or opposite, direction through the first electrical clutch circuit. The control system 1800 is configured to apply an opposite voltage polarity to the first electrical clutch circuit to create the current flowing in the opposite direction. The control system 1800 can continuously apply the opposite voltage polarity to the first electrical clutch circuit to continuously hold the first clutch 6110 in its engaged position and maintain the operable engagement between the first drive ring 6120 and the drive screw 6130. Alternatively, the first clutch 6110 can be configured to become wedged within the first drive ring 6120 when the first clutch 6110 is in its engaged position and, in such instances, the control system 1800 may not need to continuously apply a voltage polarity to the first electrical clutch circuit to hold the first clutch assembly 6100 in its engaged state. In such instances, the control system 1800 can discontinue applying the voltage polarity once the first clutch 6110 has been sufficiently wedged in the first drive ring 6120.

Notably, further to the above, the first clutch lock 6150 is also configured to lockout the jaw assembly drive when the first clutch 6110 is in its disengaged position. More specifically, referring again to FIG. 28, the first clutch 6110 pushes the first clutch lock 6150 in the drive screw 6130 into engagement with the outer housing 6230 of the end effector 7000 when the first clutch 6110 is in its disengaged position such that the drive screw 6130 does not rotate, or at least substantially rotate, relative to the outer housing 6230. The outer housing 6230 comprises a slot 6235 defined therein which is configured to receive the first clutch lock 6150. When the first clutch 6110 is moved into its engaged position, referring to FIG. 29, the first clutch 6110 is no longer engaged with the first clutch lock 6150 and, as a result, the first clutch lock 6150 is no longer biased into engagement with the outer housing 6230 and the drive screw 6130 can rotate freely with respect to the outer housing 6230. As a result of the above, the first clutch 6110 can do at least two things—operate the jaw drive when the first clutch 6110 is in its engaged position and lock out the jaw drive when the first clutch 6110 is in its disengaged position.

Moreover, further to the above, the threads of the threaded portions 6160 and 7160 can be configured to prevent, or at least resist, backdriving of the jaw drive. In at least one instance, the thread pitch and/or angle of the threaded portions 6160 and 7160, for example, can be selected to prevent the backdriving, or unintentional opening, of the jaw assembly 7100. As a result of the above, the possibility of the jaw assembly 7100 unintentionally opening or closing is prevented, or at least reduced.

Figure 30:
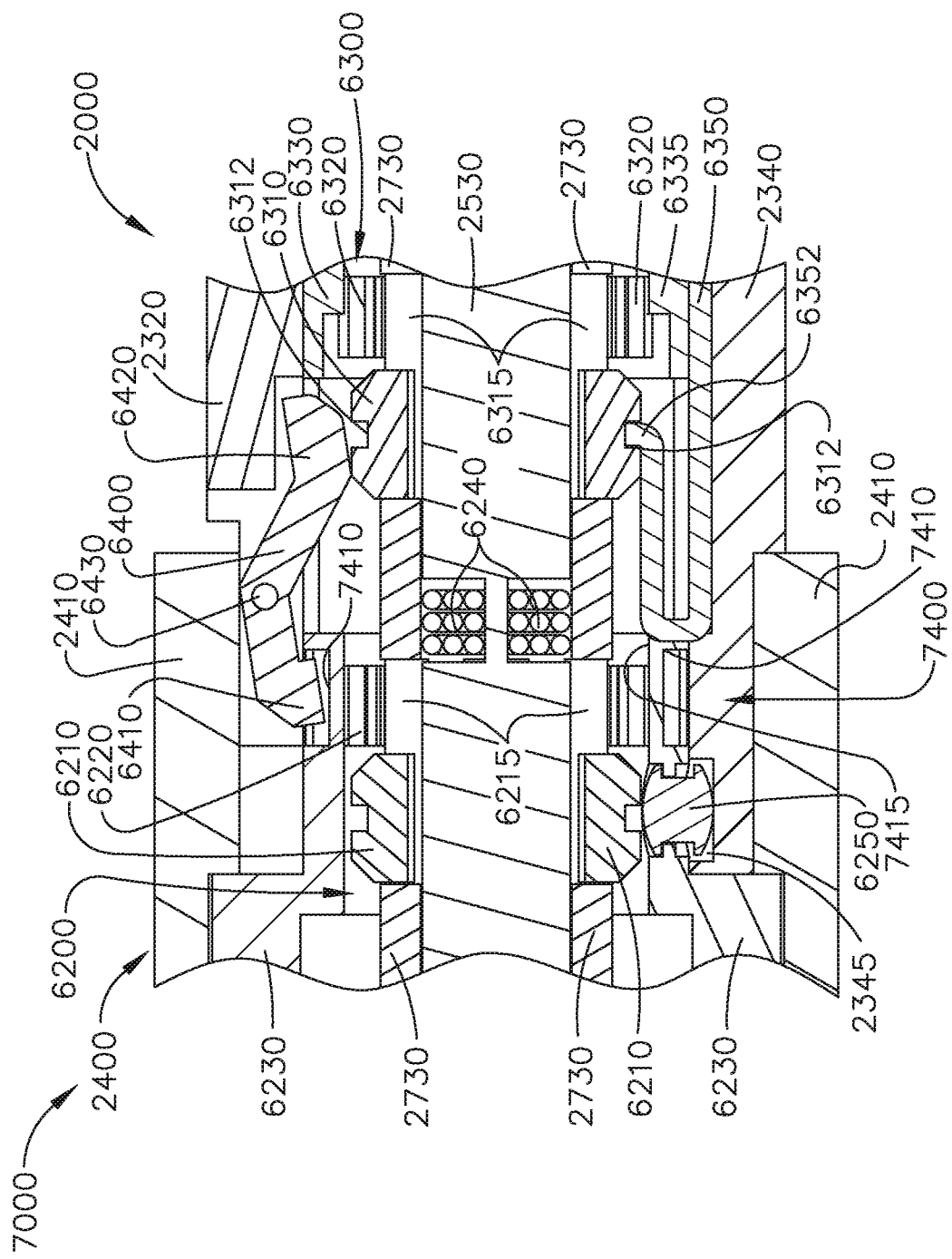
FIG. 30 depicts the second clutch of FIG. 27 in an unactuated condition.

Referring primarily to FIG. 30, the second clutch system 6200 comprises a second clutch 6210, an expandable second drive ring 6220, and a second electromagnetic actuator 6240. The second clutch 6210 comprises an annular ring and is slideably disposed on the drive shaft 2730. The second clutch 6210 is comprised of a magnetic material and is movable between a disengaged, or unactuated, position (FIG. 30) and an engaged, or actuated, position (FIG. 31) by electromagnetic fields EF generated by the second electromagnetic actuator 6240. In various instances, the second clutch 6210 is at least partially comprised of iron and/or nickel, for example. In at least one instance, the second clutch 6210 comprises a permanent magnet. As illustrated in FIG. 22A, the drive shaft 2730 comprises one or more longitudinal key slots 6215 defined therein which are configured to constrain the longitudinal movement of the second clutch 6210 relative to the drive shaft 2730. More specifically, the second clutch 6210 comprises one or more keys extending into the key slots 6215 such that the distal ends of the key slots 6215 stop the distal movement of the second clutch 6210 and the proximal ends of the key slots 6215 stop the proximal movement of the second clutch 6210.

Figure 31:
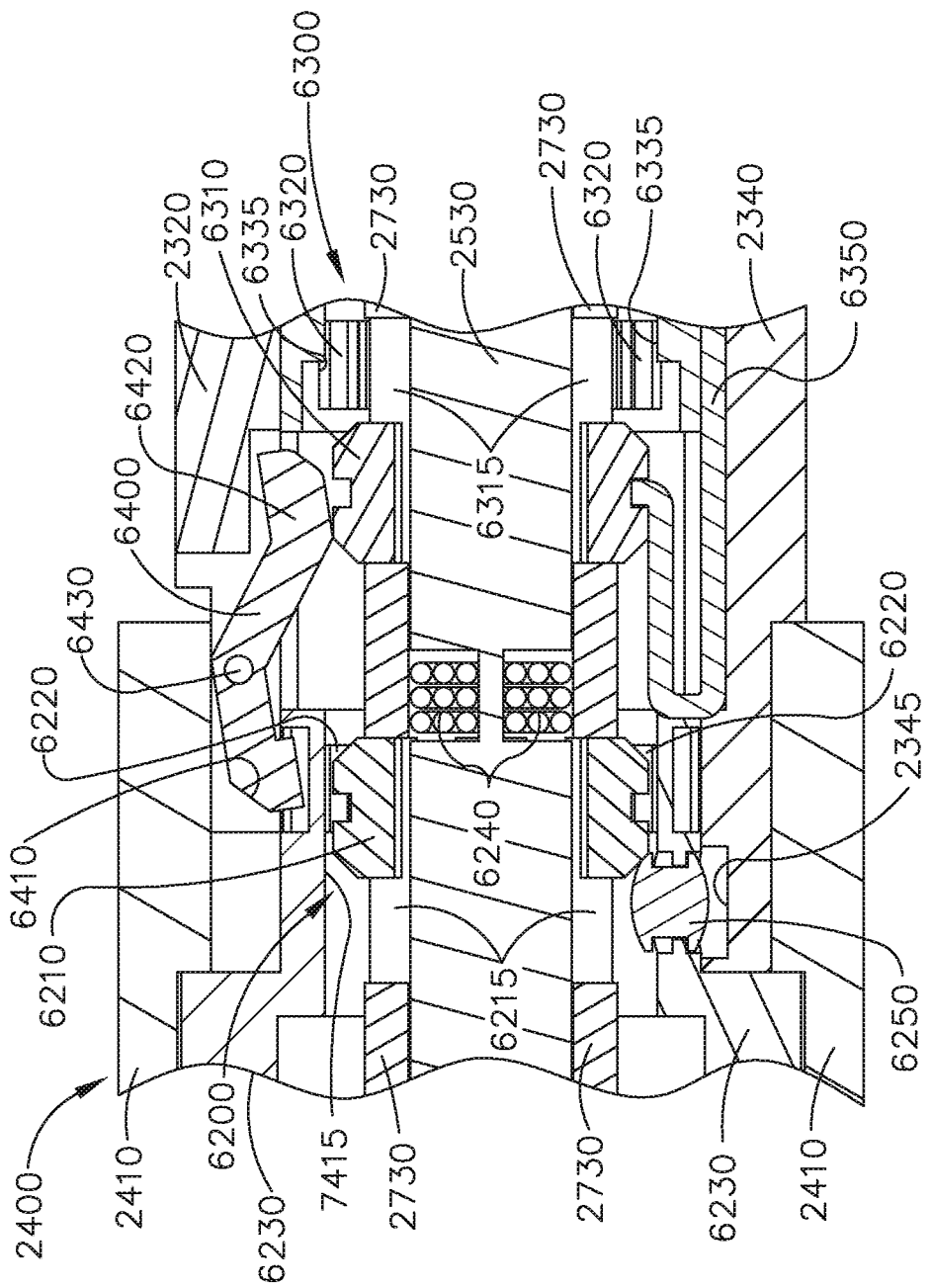
FIG. 31 depicts the second clutch of FIG. 27 in an actuated condition.

When the second clutch 6210 is in its disengaged position, referring to FIG. 30, the second clutch 6210 rotates with the drive shaft 2730 but does not transmit rotational motion to the second drive ring 6220. As can be seen in FIG. 30, the second clutch 6210 is separated from, or not in contact with, the second drive ring 6220. As a result, the rotation of the drive shaft 2730 and the second clutch 6210 is not transmitted to the outer housing 6230 of the end effector 7000 when the second clutch assembly 6200 is in its disengaged state. When the second clutch 6210 is in its engaged position (FIG. 31), the second clutch 6210 is engaged with the second drive ring 6220 such that the second drive ring 6220 is expanded, or stretched, radially outwardly into contact with the outer housing 6230. In at least one instance, the second drive ring 6220 comprises an elastomeric band, for example. As can be seen in FIG. 31, the second drive ring 6220 is compressed against an annular inner sidewall 7415 of the outer housing 6230. As a result, the rotation of the drive shaft 2730 and the second clutch 6210 is transmitted to the outer housing 6230 when the second clutch assembly 6200 is in its engaged state. Depending on the direction in which the drive shaft 2730 is rotated, the second clutch assembly 6200 can rotate the end effector 7000 in a first direction or a second direction about the longitudinal axis L when the second clutch assembly 6200 is in its engaged state.

As described above, the second electromagnetic actuator 6240 is configured to generate magnetic fields to move the second clutch 6210 between its disengaged (FIG. 30) and engaged (FIG. 31) positions. For instance, the second electromagnetic actuator 6240 is configured to emit a magnetic field $EF_L$ which repulses, or drives, the second clutch 6210 away from the second drive ring 6220 when the second clutch assembly 6200 is in its disengaged state. The second electromagnetic actuator 6240 comprises one or more wound coils in a cavity defined in the shaft frame 2530 which generate the magnetic field $EF_L$ when current flows in a first direction through a second electrical clutch circuit including the wound coils. The control system 1800 is configured to apply a first voltage polarity to the second electrical clutch circuit to create the current flowing in the first direction. The control system 1800 can continuously apply the first voltage polarity to the second electric clutch circuit to continuously hold the second clutch 6120 in its disengaged position. While such an arrangement can prevent the second clutch 6210 from unintentionally engaging the second drive ring 6220, such an arrangement can also consume a lot of power. Alternatively, the control system 1800 can apply the first voltage polarity to the second electrical clutch circuit for a sufficient period of time to position the second clutch 6210 in its disengaged position and then discontinue applying the first voltage polarity to the second electric clutch circuit, thereby resulting in a lower consumption of power. That being said, the second clutch assembly 6200 further comprises a second clutch lock 6250 mounted in the outer housing 6230 which is configured to releasably hold the second clutch 6210 in its disengaged position. Similar to the above, the second clutch lock 6250 can prevent, or at least reduce the possibility of, the second clutch 6210 from becoming unintentionally engaged with the second drive ring 6220. When the second clutch 6210 is in its disengaged position, as illustrated in FIG. 30, the second clutch lock 6250 interferes with the free movement of the second clutch 6210 and holds the second clutch 6210 in position via a friction and/or interference force therebetween. In at least one instance, the second clutch lock 6250 comprises an elastomeric plug, seat, or detent, comprised of rubber, for example. In certain instances, the second clutch lock 6250 comprises a permanent magnet which holds the second clutch 6210 in its disengaged position by an electromagnetic force. That said, the second electromagnetic actuator 6240 can apply an electromagnetic pulling force to the second clutch 6210 that overcomes these forces, as described in greater detail below.

Further to the above, referring to FIG. 31, the second electromagnetic actuator 6240 is configured to emit a magnetic field $EF_D$ which pulls, or drives, the second clutch 6210 toward the second drive ring 6220 when the second clutch assembly 6200 is in its engaged state. The coils of the second electromagnetic actuator 6240 generate the magnetic field $EF_D$ when current flows in a second, or opposite, direction through the second electrical shaft circuit. The control system 1800 is configured to apply an opposite voltage polarity to the second electrical shaft circuit to create the current flowing in the opposite direction. The control system 1800 can continuously apply the opposite voltage polarity to the second electric shaft circuit to continuously hold the second clutch 6210 in its engaged position and maintain the operable engagement between the second drive ring 6220 and the outer housing 6230. Alternatively, the second clutch 6210 can be configured to become wedged within the second drive ring 6220 when the second clutch 6210 is in its engaged position and, in such instances, the control system 1800 may not need to continuously apply a voltage polarity to the second shaft electrical circuit to hold the second clutch assembly 6200 in its engaged state. In such instances, the control system 1800 can discontinue applying the voltage polarity once the second clutch 6210 has been sufficiently wedged in the second drive ring 6220.

Notably, further to the above, the second clutch lock 6250 is also configured to lockout the rotation of the end effector 7000 when the second clutch 6210 is in its disengaged position. More specifically, referring again to FIG. 30, the second clutch 6210 pushes the second clutch lock 6250 in the outer shaft 6230 into engagement with the articulation link 2340 when the second clutch 6210 is in its disengaged position such that the end effector 7000 does not rotate, or at least substantially rotate, relative to the distal attachment portion 2400 of the shaft assembly 2000. As illustrated in FIG. 27, the second clutch lock 6250 is positioned or wedged within a slot, or channel, 2345 defined in the articulation link 2340 when the second clutch 6210 is in its disengaged position. As a result of the above, the possibility of the end effector 7000 unintentionally rotating is prevented, or at least reduced. Moreover, as a result of the above, the second clutch 6210 can do at least two things—operate the end effector rotation drive when the second clutch 6210 is in its engaged position and lock out the end effector rotation drive when the second clutch 6210 is in its disengaged position.

Figure 25:
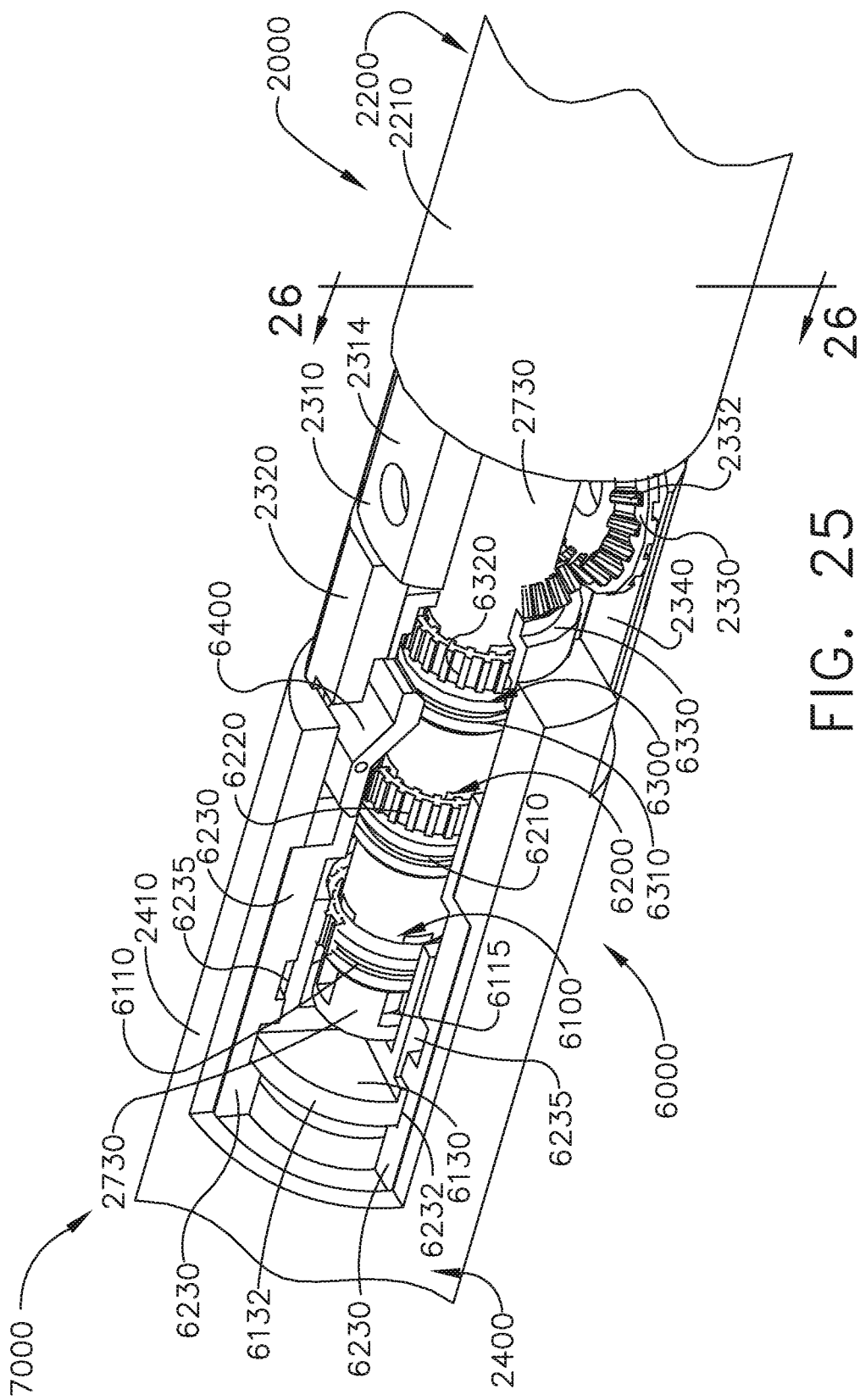
FIG. 25 is a partial cross-sectional perspective view of the end effector of FIG. 14 attached to the shaft assembly of FIG. 2.

Referring primarily to FIGS. 22, 24, and 25, the shaft assembly 2000 further comprises an articulation drive system configured to articulate the distal attachment portion 2400 and the end effector 7000 about the articulation joint 2300. The articulation drive system comprises an articulation drive 6330 rotatably supported within the distal attachment portion 2400. That said, the articulation drive 6330 is closely received within the distal attachment portion 2400 such that the articulation drive 6330 does not translate, or at least substantially translate, relative to the distal attachment portion 2400. The articulation drive system of the shaft assembly 2000 further comprises a stationary gear 2330 fixedly mounted to the articulation frame 2310. More specifically, the stationary gear 2330 is fixedly mounted to a pin connecting a tab 2314 of the articulation frame 2310 and the articulation link 2340 such that the stationary gear 2330 does not rotate relative to the articulation frame 2310. The stationary gear 2330 comprises a central body 2335 and an annular array of stationary teeth 2332 extending around the perimeter of the central body 2335. The articulation drive 6330 comprises an annular array of drive teeth 6332 which is meshingly engaged with the stationary teeth 2332. When the articulation drive 6330 is rotated, the articulation drive 6330 pushes against the stationary gear 2330 and articulates the distal attachment portion 2400 of the shaft assembly 2000 and the end effector 7000 about the articulation joint 2300.

Figure 32:
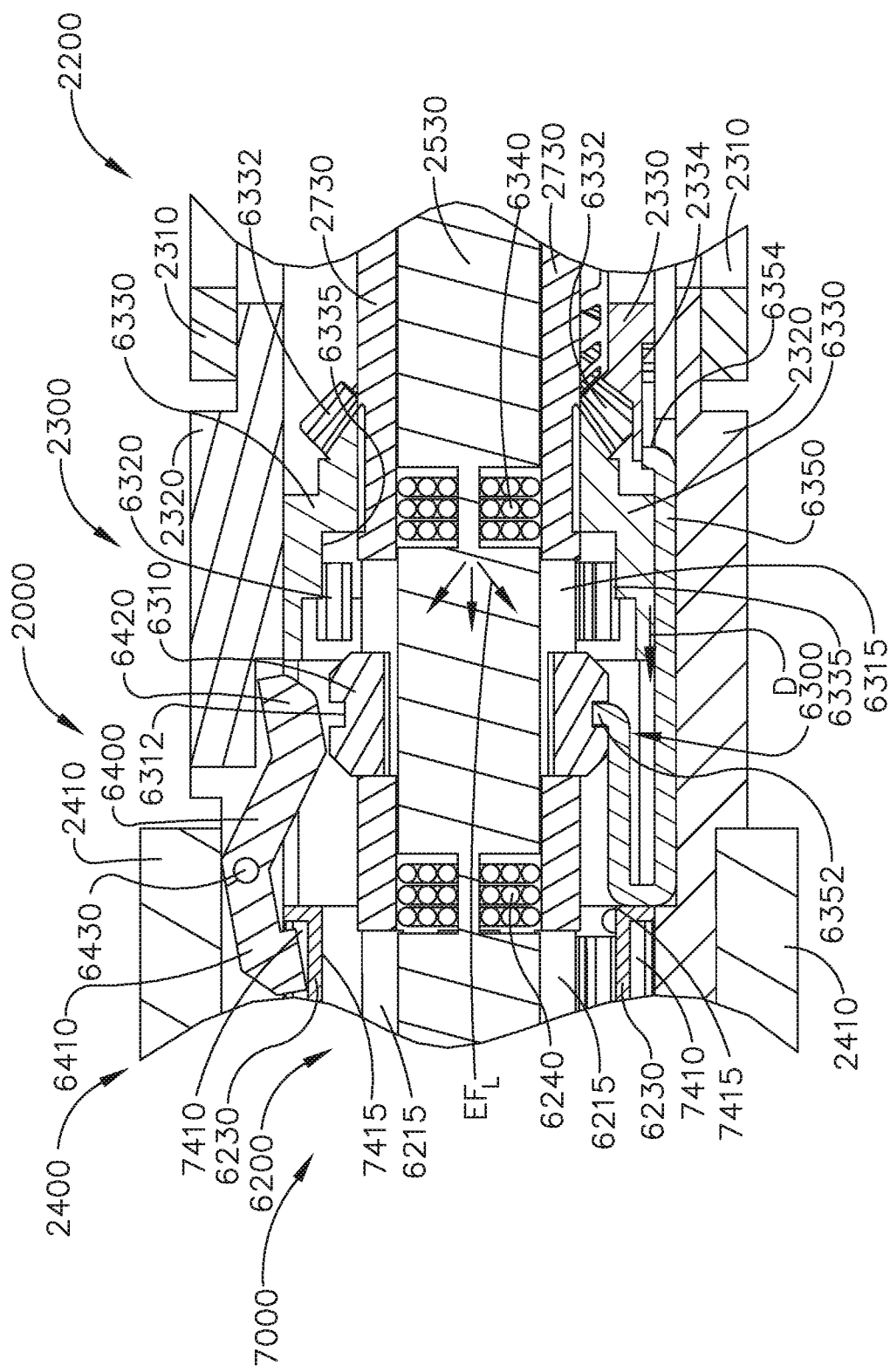
FIG. 32 depicts the third clutch of FIG. 27 in an unactuated condition.

Referring primarily to FIG. 32, the third clutch system 6300 comprises a third clutch 6310, an expandable third drive ring 6320, and a third electromagnetic actuator 6340. The third clutch 6310 comprises an annular ring and is slideably disposed on the drive shaft 2730. The third clutch 6310 is comprised of a magnetic material and is movable between a disengaged, or unactuated, position (FIG. 32) and an engaged, or actuated, position (FIG. 33) by electromagnetic fields EF generated by the third electromagnetic actuator 6340. In various instances, the third clutch 6310 is at least partially comprised of iron and/or nickel, for example. In at least one instance, the third clutch 6310 comprises a permanent magnet. As illustrated in FIG. 22A, the drive shaft 2730 comprises one or more longitudinal key slots 6315 defined therein which are configured to constrain the longitudinal movement of the third clutch 6310 relative to the drive shaft 2730. More specifically, the third clutch 6310 comprises one or more keys extending into the key slots 6315 such that the distal ends of the key slots 6315 stop the distal movement of the third clutch 6310 and the proximal ends of the key slots 6315 stop the proximal movement of the third clutch 6310.

Figure 33:
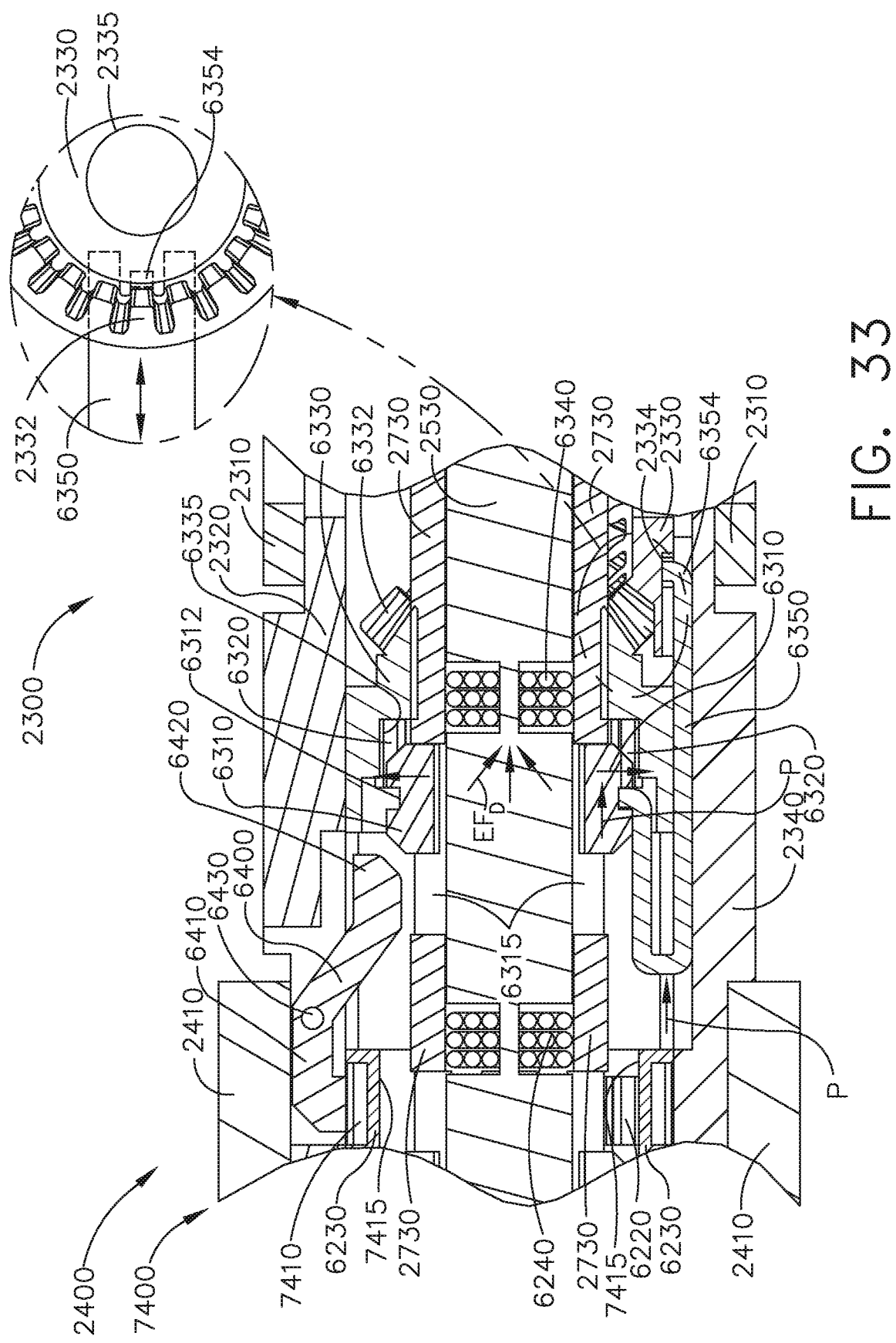
FIG. 33 depicts the third clutch of FIG. 27 in an actuated condition.

When the third clutch 6310 is in its disengaged position, referring to FIG. 32, the third clutch 6310 rotates with the drive shaft 2730 but does not transmit rotational motion to the third drive ring 6320. As can be seen in FIG. 32, the third clutch 6310 is separated from, or not in contact with, the third drive ring 6320. As a result, the rotation of the drive shaft 2730 and the third clutch 6310 is not transmitted to the articulation drive 6330 when the third clutch assembly 6300 is in its disengaged state. When the third clutch 6310 is in its engaged position, referring to FIG. 33, the third clutch 6310 is engaged with the third drive ring 6320 such that the third drive ring 6320 is expanded, or stretched, radially outwardly into contact with the articulation drive 6330. In at least one instance, the third drive ring 6320 comprises an elastomeric band, for example. As can be seen in FIG. 33, the third drive ring 6320 is compressed against an annular inner sidewall 6335 of the articulation drive 6330. As a result, the rotation of the drive shaft 2730 and the third clutch 6310 is transmitted to the articulation drive 6330 when the third clutch assembly 6300 is in its engaged state. Depending on the direction in which the drive shaft 2730 is rotated, the third clutch assembly 6300 can articulate the distal attachment portion 2400 of the shaft assembly 2000 and the end effector 7000 in a first or second direction about the articulation joint 2300.

As described above, the third electromagnetic actuator 6340 is configured to generate magnetic fields to move the third clutch 6310 between its disengaged (FIG. 32) and engaged (FIG. 33) positions. For instance, referring to FIG. 32, the third electromagnetic actuator 6340 is configured to emit a magnetic field $EF_L$ which repulses, or drives, the third clutch 6310 away from the third drive ring 6320 when the third clutch assembly 6300 is in its disengaged state. The third electromagnetic actuator 6340 comprises one or more wound coils in a cavity defined in the shaft frame 2530 which generate the magnetic field $EF_L$ when current flows in a first direction through a third electrical clutch circuit including the wound coils. The control system 1800 is configured to apply a first voltage polarity to the third electrical clutch circuit to create the current flowing in the first direction. The control system 1800 can continuously apply the first voltage polarity to the third electric clutch circuit to continuously hold the third clutch 6310 in its disengaged position. While such an arrangement can prevent the third clutch 6310 from unintentionally engaging the third drive ring 6320, such an arrangement can also consume a lot of power. Alternatively, the control system 1800 can apply the first voltage polarity to the third electrical clutch circuit for a sufficient period of time to position the third clutch 6310 in its disengaged position and then discontinue applying the first voltage polarity to the third electric clutch circuit, thereby resulting in a lower consumption of power.

Further to the above, the third electromagnetic actuator 6340 is configured to emit a magnetic field $EF_D$ which pulls, or drives, the third clutch 6310 toward the third drive ring 6320 when the third clutch assembly 6300 is in its engaged state. The coils of the third electromagnetic actuator 6340 generate the magnetic field $EF_D$ when current flows in a second, or opposite, direction through the third electrical clutch circuit. The control system 1800 is configured to apply an opposite voltage polarity to the third electrical shaft circuit to create the current flowing in the opposite direction. The control system 1800 can continuously apply the opposite voltage polarity to the third electric shaft circuit to continuously hold the third clutch 6310 in its engaged position and maintain the operable engagement between the third drive ring 6320 and the articulation drive 6330. Alternatively, the third clutch 6210 can be configured to become wedged within the third drive ring 6320 when the third clutch 6310 is in its engaged position and, in such instances, the control system 1800 may not need to continuously apply a voltage polarity to the third shaft electrical circuit to hold the third clutch assembly 6300 in its engaged state. In such instances, the control system 1800 can discontinue applying the voltage polarity once the third clutch 6310 has been sufficiently wedged in the third drive ring 6320. In any event, the end effector 7000 is articulatable in a first direction or a second direction, depending on the direction in which the drive shaft 2730 is rotated, when the third clutch assembly 6300 is in its engaged state.

Further to the above, referring to FIGS. 22, 32, and 33, the articulation drive system further comprises a lockout 6350 which prevents, or at least inhibits, the articulation of the distal attachment portion 2400 of the shaft assembly 2000 and the end effector 7000 about the articulation joint 2300 when the third clutch 6310 is in its disengaged position (FIG. 32). Referring primarily to FIG. 22, the articulation link 2340 comprises a slot, or groove, 2350 defined therein wherein the lockout 6350 is slideably positioned in the slot 2350 and extends at least partially under the stationary articulation gear 2330. The lockout 6350 comprises at attachment hook 6352 engaged with the third clutch 6310. More specifically, the third clutch 6310 comprises an annular slot, or groove, 6312 defined therein and the attachment hook 6352 is positioned in the annular slot 6312 such that the lockout 6350 translates with the third clutch 6310. Notably, however, the lockout 6350 does not rotate, or at least substantially rotate, with the third clutch 6310. Instead, the annular groove 6312 in the third clutch 6310 permits the third clutch 6310 to rotate relative to the lockout 6350. The lockout 6350 further comprises a lockout hook 6354 slideably positioned in a radially-extending lockout slot 2334 defined in the bottom of the stationary gear 2330. When the third clutch 6310 is in its disengaged position, as illustrated in FIG. 32, the lockout 6350 is in a locked position in which the lockout hook 6354 prevents the end effector 7000 from rotating about the articulation joint 2300. When the third clutch 6310 is in its engaged position, as illustrated in FIG. 33, the lockout 6350 is in an unlocked position in which the lockout hook 6354 is no longer positioned in the lockout slot 2334. Instead, the lockout hook 6354 is positioned in a clearance slot defined in the middle or body 2335 of the stationary gear 2330. In such instances, the lockout hook 6354 can rotate within the clearance slot when the end effector 7000 rotates about the articulation joint 2300.

Further to the above, the radially-extending lockout slot 2334 depicted in FIGS. 32 and 33 extends longitudinally, i.e., along an axis which is parallel to the longitudinal axis of the elongate shaft 2200. Once the end effector 7000 has been articulated, however, the lockout hook 6354 is no longer aligned with the longitudinal lockout slot 2334. With this in mind, the stationary gear 2330 comprises a plurality, or an array, of radially-extending lockout slots 2334 defined in the bottom of the stationary gear 2330 such that, when the third clutch 6310 is deactuated and the lockout 6350 is pulled distally after the end effector 7000 has been articulated, the lockout hook 6354 can enter one of the lockout slots 2334 and lock the end effector 7000 in its articulated position. Thus, as a result, the end effector 7000 can be locked in an unarticulated and an articulated position. In various instances, the lockout slots 2334 can define discrete articulated positions for the end effector 7000. For instance, the lockout slots 2334 can be defined at 10 degree intervals, for example, which can define discrete articulation orientations for the end effector 7000 at 10 degree intervals. In other instances, these orientations can be at 5 degree intervals, for example. In alternative embodiments, the lockout 6350 comprises a brake that engages a circumferential shoulder defined in the stationary gear 2330 when the third clutch 6310 is disengaged from the third drive ring 6320. In such an embodiment, the end effector 7000 can be locked in any suitable orientation. In any event, the lockout 6350 prevents, or at least reduces the possibility of, the end effector 7000 unintentionally articulating. As a result of the above, the third clutch 6310 can do things—operate the articulation drive when it is in its engaged position and lock out the articulation drive when it is in its disengaged position.

Referring primarily to FIGS. 24 and 25, the shaft frame 2530 and the drive shaft 2730 extend through the articulation joint 2300 into the distal attachment portion 2400. When the end effector 7000 is articulated, as illustrated in FIGS. 16 and 17, the shaft frame 2530 and the drive shaft 2730 bend to accommodate the articulation of the end effector 7000. Thus, the shaft frame 2530 and the drive shaft 2730 are comprised of any suitable material which accommodates the articulation of the end effector 7000. Moreover, as discussed above, the shaft frame 2530 houses the first, second, and third electromagnetic actuators 6140, 6240, and 6340. In various instances, the first, second, and third electromagnetic actuators 6140, 6240, and 6340 each comprise wound wire coils, such as copper wire coils, for example, and the shaft frame 2530 is comprised of an insulative material to prevent, or at least reduce the possibility of, short circuits between the first, second, and third electromagnetic actuators 6140, 6240, and 6340. In various instances, the first, second, and third electrical clutch circuits extending through the shaft frame 2530 are comprised of insulated electrical wires, for example. Further to the above, the first, second, and third electrical clutch circuits place the electromagnetic actuators 6140, 6240, and 6340 in communication with the control system 1800 in the drive module 1100.

As described above, the clutches 6110, 6210, and/or 6310 can be held in their disengaged positions so that they do not unintentionally move into their engaged positions. In various arrangements, the clutch system 6000 comprises a first biasing member, such as a spring, for example, configured to bias the first clutch 6110 into its disengaged position, a second biasing member, such as a spring, for example, configured to bias the second clutch 6210 into its disengaged position, and/or a third biasing member, such as a spring, for example, configured to bias the third clutch 6110 into its disengaged position. In such arrangements, the biasing forces of the springs can be selectively overcome by the electromagnetic forces generated by the electromagnetic actuators when energized by an electrical current. Further to the above, the clutches 6110, 6210, and/or 6310 can be retained in their engaged positions by the drive rings 6120, 6220, and/or 6320, respectively. More specifically, in at least one instance, the drive rings 6120, 6220, and/or 6320 are comprised of an elastic material which grips or frictionally holds the clutches 6110, 6210, and/or 6310, respectively, in their engaged positions. In various alternative embodiments, the clutch system 6000 comprises a first biasing member, such as a spring, for example, configured to bias the first clutch 6110 into its engaged position, a second biasing member, such as a spring, for example, configured to bias the second clutch 6210 into its engaged position, and/or a third biasing member, such as a spring, for example, configured to bias the third clutch 6110 into its engaged position. In such arrangements, the biasing forces of the springs can be overcome by the electromagnetic forces applied by the electromagnetic actuators 6140, 6240, and/or 6340, respectively, as needed to selectively hold the clutches 6110, 6210, and 6310 in their disengaged positions. In any one operational mode of the surgical system, the control assembly 1800 can energize one of the electromagnetic actuators to engage one of the clutches while energizing the other two electromagnetic actuators to disengage the other two clutches.

Although the clutch system 6000 comprises three clutches to control three drive systems of the surgical system, a clutch system can comprise any suitable number of clutches to control any suitable number of systems. Moreover, although the clutches of the clutch system 6000 slide proximally and distally between their engaged and disengaged positions, the clutches of a clutch system can move in any suitable manner. In addition, although the clutches of the clutch system 6000 are engaged one at a time to control one drive motion at a time, various instances are envisioned in which more than one clutch can be engaged to control more than one drive motion at a time.

In view of the above, the reader should appreciate that the control system 1800 is configured to, one, operate the motor system 1600 to rotate the drive shaft system 2700 in an appropriate direction and, two, operate the clutch system 6000 to transfer the rotation of the drive shaft system 2700 to the appropriate function of the end effector 7000. Moreover, as discussed above, the control system 1800 is responsive to inputs from the clamping trigger system 2600 of the shaft assembly 2000 and the input system 1400 of the handle 1000. When the clamping trigger system 2600 is actuated, as discussed above, the control system 1800 activates the first clutch assembly 6100 and deactivates the second clutch assembly 6200 and the third clutch assembly 6300. In such instances, the control system 1800 also supplies power to the motor system 1600 to rotate the drive shaft system 2700 in a first direction to clamp the jaw assembly 7100 of the end effector 7000. When the control system 1800 detects that the jaw assembly 7100 is in its clamped configuration, the control system 1800 stops the motor assembly 1600 and deactivates the first clutch assembly 6100. When the control system 1800 detects that the clamping trigger system 2600 has been moved to, or is being moved to, its unactuated position, the control system 1800 activates, or maintains the activation of, the first clutch assembly 6100 and deactivates, or maintains the deactivation of, the second clutch assembly 6200 and the third clutch assembly 6300. In such instances, the control system 1800 also supplies power to the motor system 1600 to rotate the drive shaft system 2700 in a second direction to open the jaw assembly 7100 of the end effector 7000.

When the rotation actuator 1420 is actuated in a first direction, further to the above, the control system 1800 activates the second clutch assembly 6200 and deactivates the first clutch assembly 6100 and the third clutch assembly 6300. In such instances, the control system 1800 also supplies power to the motor system 1600 to rotate the drive shaft system 2700 in a first direction to rotate the end effector 7000 in a first direction. When the control system 1800 detects that the rotation actuator 1420 has been actuated in a second direction, the control system 1800 activates, or maintains the activation of, the second clutch assembly 6200 and deactivates, or maintains the deactivation of, the first clutch assembly 6100 and the third clutch assembly 6300. In such instances, the control system 1800 also supplies power to the motor system 1600 to rotate the drive shaft system 2700 in a second direction to rotate the drive shaft system 2700 in a second direction to rotate the end effector 7000 in a second direction. When the control system 1800 detects that the rotation actuator 1420 is not actuated, the control system 1800 deactivates the second clutch assembly 6200.

When the first articulation actuator 1432 is depressed, further to the above, the control system 1800 activates the third clutch assembly 6300 and deactivates the first clutch assembly 6100 and the second clutch assembly 6200. In such instances, the control system 1800 also supplies power to the motor system 1600 to rotate the drive shaft system 2700 in a first direction to articulate the end effector 7000 in a first direction. When the control system 1800 detects that the second articulation actuator 1434 is depressed, the control system 1800 activates, or maintains the activation of, the third clutch assembly 6200 and deactivates, or maintains the deactivation of, the first clutch assembly 6100 and the second clutch assembly 6200. In such instances, the control system 1800 also supplies power to the motor system 1600 to rotate the drive shaft system 2700 in a second direction to articulate the end effector 7000 in a second direction. When the control system 1800 detects that neither the first articulation actuator 1432 nor the second articulation actuator 1434 are actuated, the control system 1800 deactivates the third clutch assembly 6200.

Further to the above, the control system 1800 is configured to change the operating mode of the stapling system based on the inputs it receives from the clamping trigger system 2600 of the shaft assembly 2000 and the input system 1400 of the handle 1000. The control system 1800 is configured to shift the clutch system 6000 before rotating the shaft drive system 2700 to perform the corresponding end effector function. Moreover, the control system 1800 is configured to stop the rotation of the shaft drive system 2700 before shifting the clutch system 6000. Such an arrangement can prevent the sudden movements in the end effector 7000. Alternatively, the control system 1800 can shift the clutch system 600 while the shaft drive system 2700 is rotating. Such an arrangement can allow the control system 1800 to shift quickly between operating modes.

Figure 34:
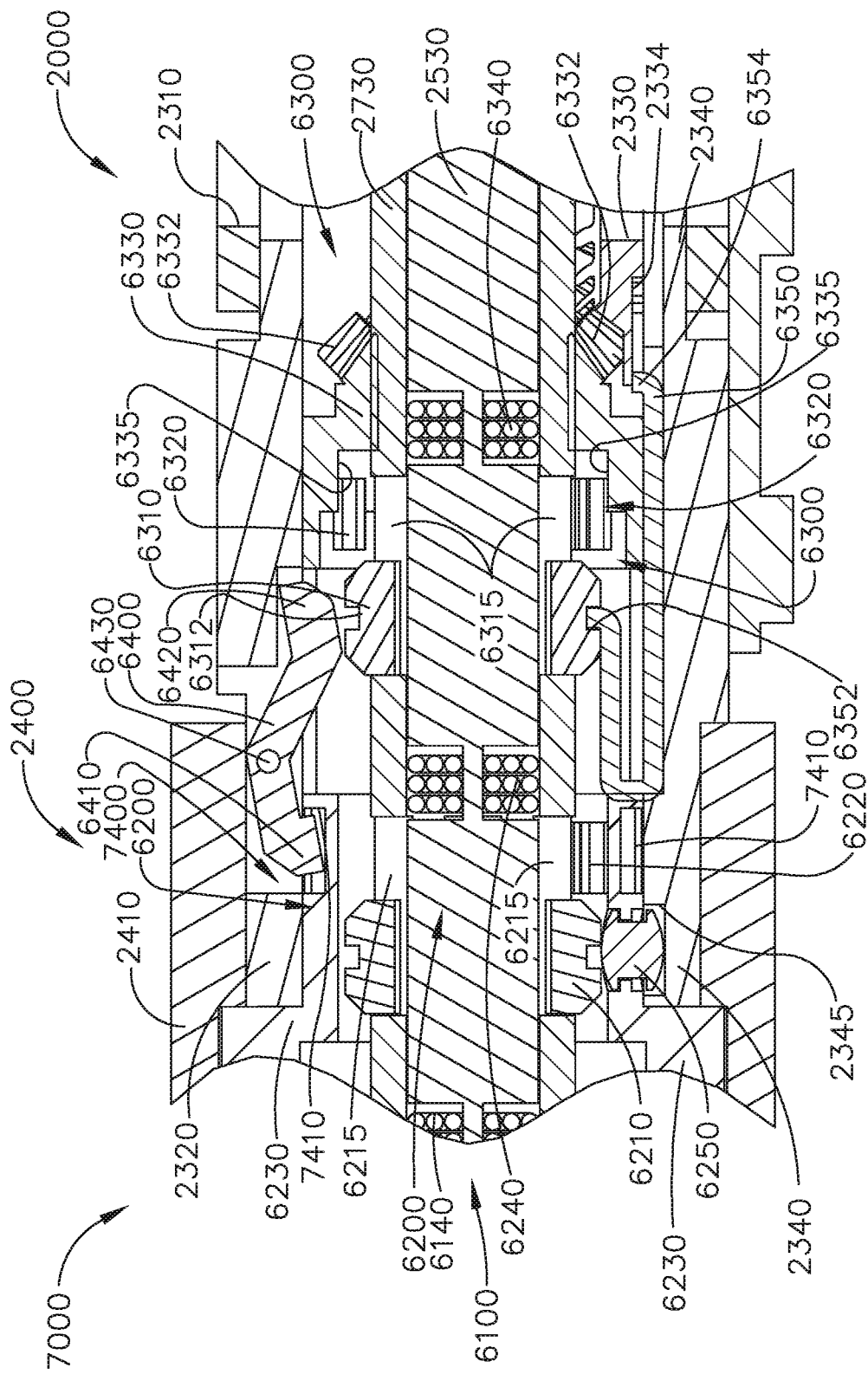
FIG. 34 depicts the second and third clutches of FIG. 27 in their unactuated conditions and the end effector of FIG. 14 locked to the shaft assembly of FIG. 2.
Figure 35:
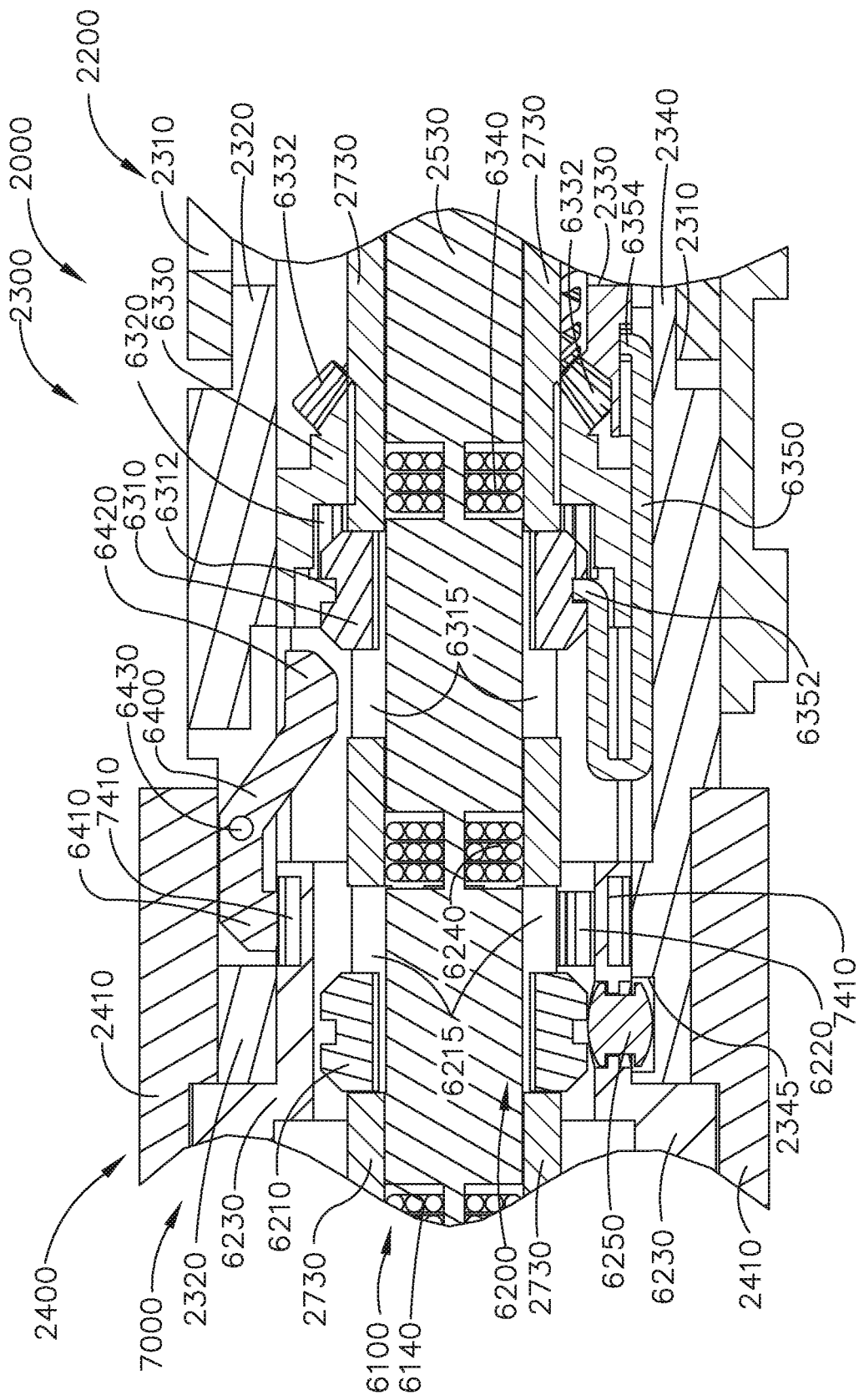
FIG. 35 depicts the second clutch of FIG. 27 in its unactuated condition and the third clutch of FIG. 27 in its actuated condition.
Figure 36:
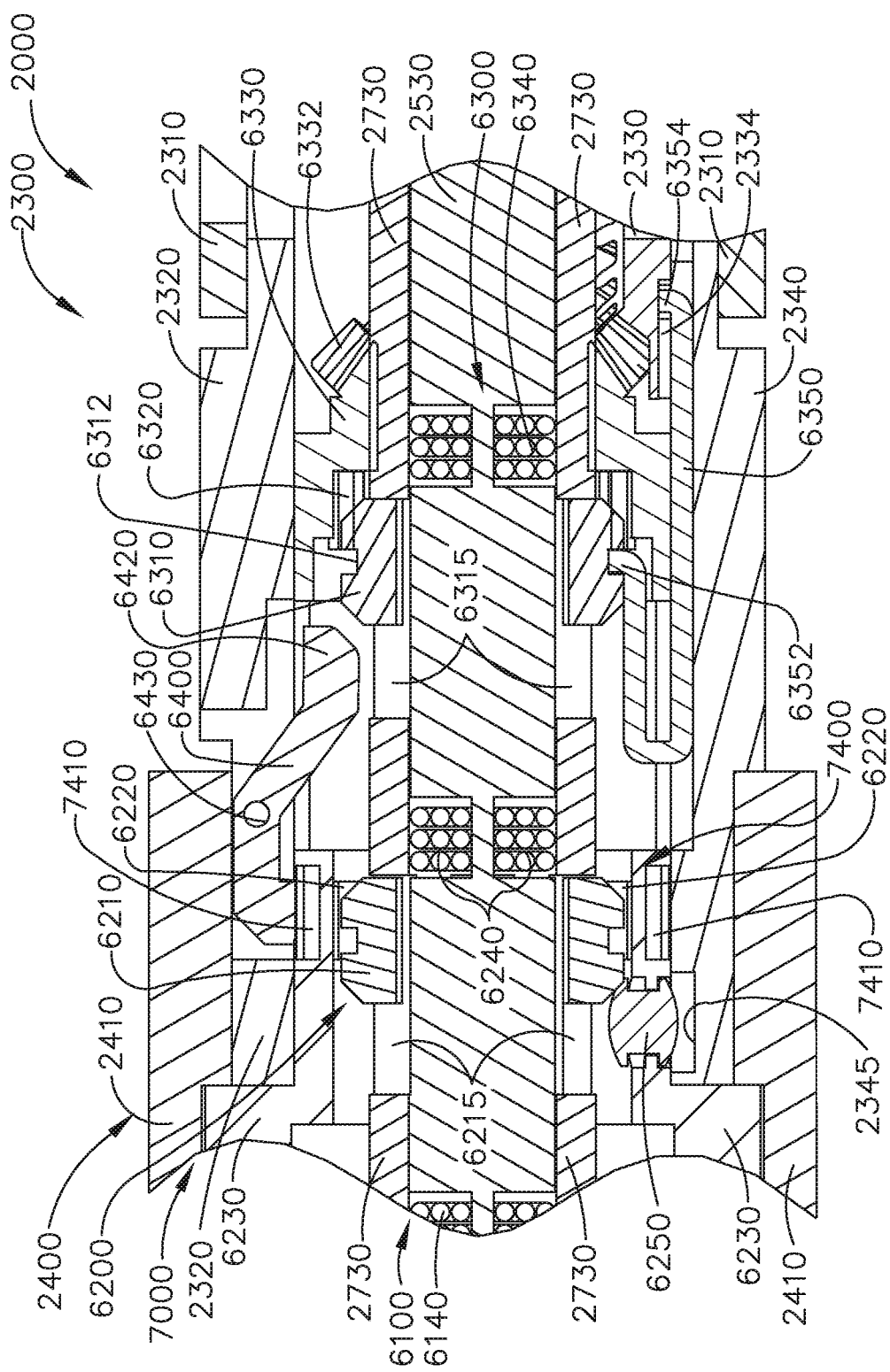
FIG. 36 depicts the second and third clutches of FIG. 27 in their actuated conditions and the end effector of FIG. 14 unlocked from the shaft assembly of FIG. 2.

As discussed above, referring to FIG. 34, the distal attachment portion 2400 of the shaft assembly 2000 comprises an end effector lock 6400 configured to prevent the end effector 7000 from being unintentionally decoupled from the shaft assembly 2000. The end effector lock 6400 comprises a lock end 6410 selectively engageable with the annular array of lock notches 7410 defined on the proximal attachment portion 7400 of the end effector 7000, a proximal end 6420, and a pivot 6430 rotatably connecting the end effector lock 6400 to the articulation link 2320. When the third clutch 6310 of the third clutch assembly 6300 is in its disengaged position, as illustrated in FIG. 34, the third clutch 6310 is contact with the proximal end 6420 of the end effector lock 6400 such that the lock end 6410 of the end effector lock 6400 is engaged with the array of lock notches 7410. In such instances, the end effector 7000 can rotate relative to the end effector lock 6400 but cannot translate relative to the distal attachment portion 2400. When the third clutch 6310 is moved into its engaged position, as illustrated in FIG. 35, the third clutch 6310 is no longer engaged with the proximal end 6420 of the end effector lock 6400. In such instances, the end effector lock 6400 is free to pivot upwardly and permit the end effector 7000 to be detached from the shaft assembly 2000.

The above being said, referring again to FIG. 34, it is possible that the second clutch 6210 of the second clutch assembly 6200 is in its disengaged position when the clinician detaches, or attempts to detach, the end effector 7000 from the shaft assembly 2000. As discussed above, the second clutch 6210 is engaged with the second clutch lock 6250 when the second clutch 6210 is in its disengaged position and, in such instances, the second clutch lock 6250 is pushed into engagement with the articulation link 2340. More specifically, the second clutch lock 6250 is positioned in the channel 2345 defined in the articulation 2340 when the second clutch 6210 is engaged with the second clutch lock 6250 which may prevent, or at least impede, the end effector 7000 from being detached from the shaft assembly 2000. To facilitate the release of the end effector 7000 from the shaft assembly 2000, the control system 1800 can move the second clutch 6210 into its engaged position in addition to moving the third clutch 6310 into its engaged position. In such instances, the end effector 7000 can clear both the end effector lock 6400 and the second clutch lock 6250 when the end effector 7000 is removed.

In at least one instance, further to the above, the drive module 1100 comprises an input switch and/or sensor in communication with the control system 1800 via the input system 1400, and/or the control system 1800 directly, which, when actuated, causes the control system 1800 to unlock the end effector 7000. In various instances, the drive module 1100 comprises an input screen 1440 in communication with the board 1410 of the input system 1400 which is configured to receive an unlock input from the clinician. In response to the unlock input, the control system 1800 can stop the motor system 1600, if it is running, and unlock the end effector 7000 as described above. The input screen 1440 is also configured to receive a lock input from the clinician in which the input system 1800 moves the second clutch assembly 6200 and/or the third clutch assembly 6300 into their unactuated states to lock the end effector 7000 to the shaft assembly 2000.

Figure 37:
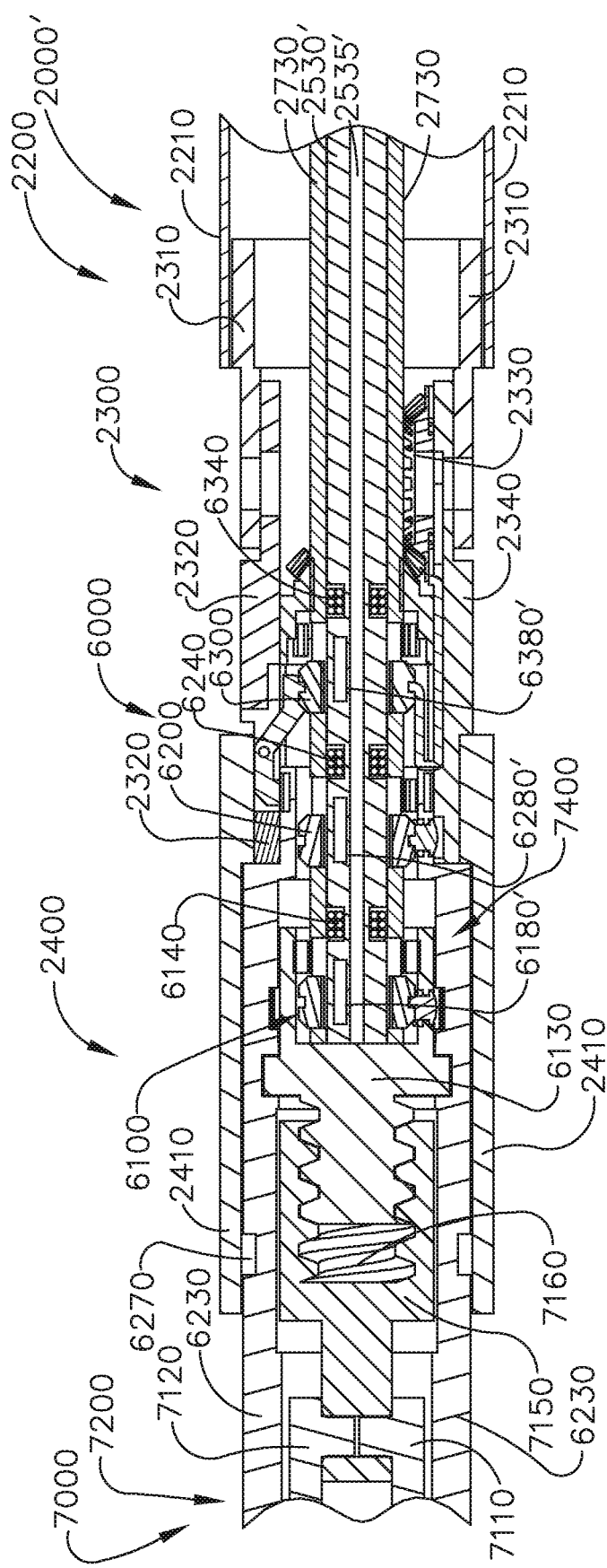
FIG. 37 is a partial cross-sectional view of a shaft assembly in accordance with at least one alternative embodiment comprising sensors configured to detect the conditions of the first, second, and third clutches of FIG. 27.

FIG. 37 depicts a shaft assembly 2000' in accordance with at least one alternative embodiment. The shaft assembly 2000' is similar to the shaft assembly 2000 in many respects, most of which will not be repeated herein for the sake of brevity. Similar to the shaft assembly 2000, the shaft assembly 2000' comprises a shaft frame, i.e., shaft frame 2530'. The shaft frame 2530' comprises a longitudinal passage 2535' and, in addition, a plurality of clutch position sensors, i.e., a first sensor 6180', a second sensor 6280', and a third sensor 6380' positioned in the shaft frame 2530'. The first sensor 6180' is in signal communication with the control system 1800 as part of a first sensing circuit. The first sensing circuit comprises signal wires extending through the longitudinal passage 2535'; however, the first sensing circuit can comprise a wireless signal transmitter and receiver to place the first sensor 6180' in signal communication with the control system 1800. The first sensor 6180' is positioned and arranged to detect the position of the first clutch 6110 of the first clutch assembly 6100. Based on data received from the first sensor 6180', the control system 1800 can determine whether the first clutch 6110 is in its engaged position, its disengaged position, or somewhere in-between. With this information, the control system 1800 can assess whether or not the first clutch 6110 is in the correct position given the operating state of the surgical instrument. For instance, if the surgical instrument is in its jaw clamping/opening operating state, the control system 1800 can verify whether the first clutch 6110 is properly positioned in its engaged position. In such instances, further to the below, the control system 1800 can also verify that the second clutch 6210 is in its disengaged position via the second sensor 6280' and that the third clutch 6310 is in its disengaged position via the third sensor 6380'. Correspondingly, the control system 1800 can verify whether the first clutch 6110 is properly positioned in its disengaged position if the surgical instrument is not in its jaw clamping/opening state. To the extent that the first clutch 6110 is not in its proper position, the control system 1800 can actuate the first electromagnetic actuator 6140 in an attempt to properly position the first clutch 6110. Likewise, the control system 1800 can actuate the electromagnetic actuators 6240 and/or 6340 to properly position the clutches 6210 and/or 6310, if necessary.

The second sensor 6280' is in signal communication with the control system 1800 as part of a second sensing circuit. The second sensing circuit comprises signal wires extending through the longitudinal passage 2535'; however, the second sensing circuit can comprise a wireless signal transmitter and receiver to place the second sensor 6280' in signal communication with the control system 1800. The second sensor 6280' is positioned and arranged to detect the position of the second clutch 6210 of the first clutch assembly 6200. Based on data received from the second sensor 6280', the control system 1800 can determine whether the second clutch 6210 is in its engaged position, its disengaged position, or somewhere in-between. With this information, the control system 1800 can assess whether or not the second clutch 6210 is in the correct position given the operating state of the surgical instrument. For instance, if the surgical instrument is in its end effector rotation operating state, the control system 1800 can verify whether the second clutch 6210 is properly positioned in its engaged position. In such instances, the control system 1800 can also verify that the first clutch 6110 is in its disengaged position via the first sensor 6180' and, further to the below, the control system 1800 can also verify that the third clutch 6310 is in its disengaged position via the third sensor 6380'. Correspondingly, the control system 1800 can verify whether the second clutch 6110 is properly positioned in its disengaged position if the surgical instrument is not in its end effector rotation state. To the extent that the second clutch 6210 is not in its proper position, the control system 1800 can actuate the second electromagnetic actuator 6240 in an attempt to properly position the second clutch 6210. Likewise, the control system 1800 can actuate the electromagnetic actuators 6140 and/or 6340 to properly position the clutches 6110 and/or 6310, if necessary.

The third sensor 6380' is in signal communication with the control system 1800 as part of a third sensing circuit. The third sensing circuit comprises signal wires extending through the longitudinal passage 2535'; however, the third sensing circuit can comprise a wireless signal transmitter and receiver to place the third sensor 6380' in signal communication with the control system 1800. The third sensor 6380' is positioned and arranged to detect the position of the third clutch 6310 of the third clutch assembly 6300. Based on data received from the third sensor 6380', the control system 1800 can determine whether the third clutch 6310 is in its engaged position, its disengaged position, or somewhere in-between. With this information, the control system 1800 can assess whether or not the third clutch 6310 is in the correct position given the operating state of the surgical instrument. For instance, if the surgical instrument is in its end effector articulation operating state, the control system 1800 can verify whether the third clutch 6310 is properly positioned in its engaged position. In such instances, the control system 1800 can also verify that the first clutch 6110 is in its disengaged position via the first sensor 6180' and that the second clutch 6210 is in its disengaged position via the second sensor 6280'. Correspondingly, the control system 1800 can verify whether the third clutch 6310 is properly positioned in its disengaged position if the surgical instrument is not in its end effector articulation state. To the extent that the third clutch 6310 is not in its proper position, the control system 1800 can actuate the third electromagnetic actuator 6340 in an attempt to properly position the third clutch 6310. Likewise, the control system 1800 can actuate the electromagnetic actuators 6140 and/or 6240 to properly position the clutches 6110 and/or 6210, if necessary.

Further to the above, the clutch position sensors, i.e., the first sensor 6180', the second sensor 6280', and the third sensor 6380' can comprise any suitable type of sensor. In various instances, the first sensor 6180', the second sensor 6280', and the third sensor 6380' each comprise a proximity sensor. In such an arrangement, the sensors 6180', 6280', and 6380' are configured to detect whether or not the clutches 6110, 6210, and 6310, respectively, are in their engaged positions. In various instances, the first sensor 6180', the second sensor 6280', and the third sensor 6380' each comprise a Hall Effect sensor, for example. In such an arrangement, the sensors 6180', 6280', and 6380' can not only detect whether or not the clutches 6110, 6210, and 6310, respectively, are in their engaged positions but the sensors 6180', 6280', and 6380' can also detect how close the clutches 6110, 6210, and 6310 are with respect to their engaged or disengaged positions.

Figure 38:
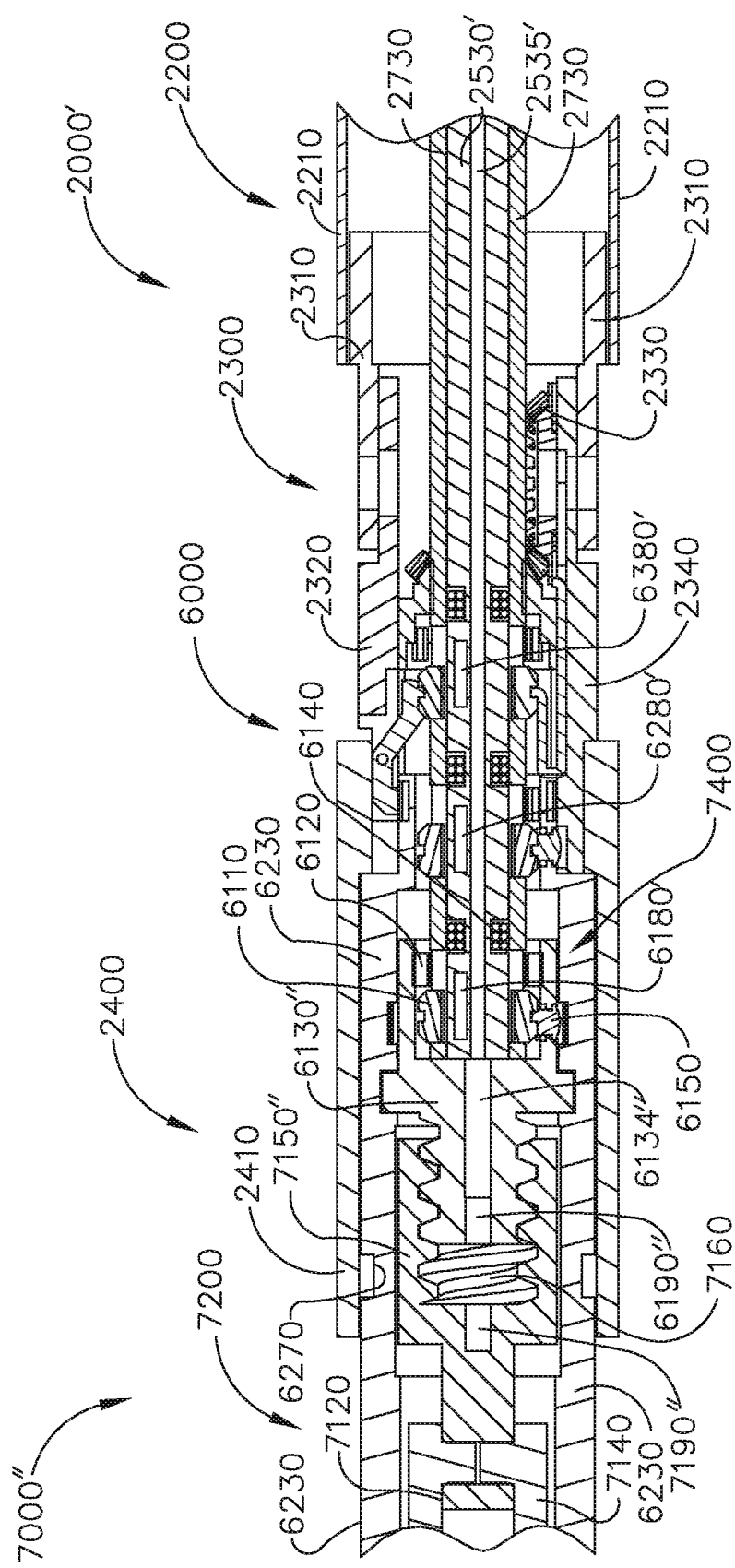
FIG. 38 is a partial cross-sectional view of a shaft assembly in accordance with at least one alternative embodiment comprising sensors configured to detect the conditions of the first, second, and third clutches of FIG. 27.

FIG. 38 depicts the shaft assembly 2000' and an end effector 7000" in accordance with at least one alternative embodiment. The end effector 7000" is similar to the end effector 7000 in many respects, most of which will not be repeated herein for the sake of brevity. Similar to the end effector 7000, the shaft assembly 7000" comprises a jaw assembly 7100 and a jaw assembly drive configured to move the jaw assembly 7100 between its open and closed configurations. The jaw assembly drive comprises drive links 7140, a drive nut 7150", and a drive screw 6130". The drive nut 7150" comprises a sensor 7190" positioned therein which is configured to detect the position of a magnetic element 6190" positioned in the drive screw 6130". The magnetic element 6190" is positioned in an elongate aperture 6134" defined in the drive screw 6130" and can comprise a permanent magnet and/or can be comprised of iron, nickel, and/or any suitable metal, for example. In various instances, the sensor 7190" comprises a proximity sensor, for example, which is in signal communication with the control system 1800. In certain instances, the sensor 7190" comprises a Hall Effect sensor, for example, in signal communication with the control system 1800. In certain instances, the sensor 7190" comprises an optical sensor, for example, and the detectable element 6190" comprises an optically detectable element, such as a reflective element, for example. In either event, the sensor 7190" is configured to communicate wirelessly with the control system 1800 via a wireless signal transmitter and receiver and/or via a wired connection extending through the shaft frame passage 2532', for example.

The sensor 7190", further to the above, is configured to detect when the magnetic element 6190" is adjacent to the sensor 7190" such that the control system 1800 can use this data to determine that the jaw assembly 7100 has reached the end of its clamping stroke. At such point, the control system 1800 can stop the motor assembly 1600. The sensor 7190" and the control system 1800 are also configured to determine the distance between where the drive screw 6130" is currently positioned and where the drive screw 6130" should be positioned at the end of its closure stroke in order to calculate the amount of closure stroke of the drive screw 6130" that is still needed to close the jaw assembly 7100. Moreover, such information can be used by the control system 1800 to assess the current configuration of the jaw assembly 7100, i.e., whether the jaw assembly 7100 is in its open configuration, its closed configuration, or a partially closed configuration. The sensor system could be used to determine when the jaw assembly 7100 has reached its fully open position and stop the motor assembly 1600 at that point. In various instances, the control system 1800 could use this sensor system to confirm that the first clutch assembly 6100 is in its actuated state by confirming that the jaw assembly 7100 is moving while the motor assembly 1600 is turning. Similarly, the control system 1800 could use this sensor system to confirm that the first clutch assembly 6100 is in its unactuated state by confirming that the jaw assembly 7100 is not moving while the motor assembly 1600 is turning.

Figure 39:
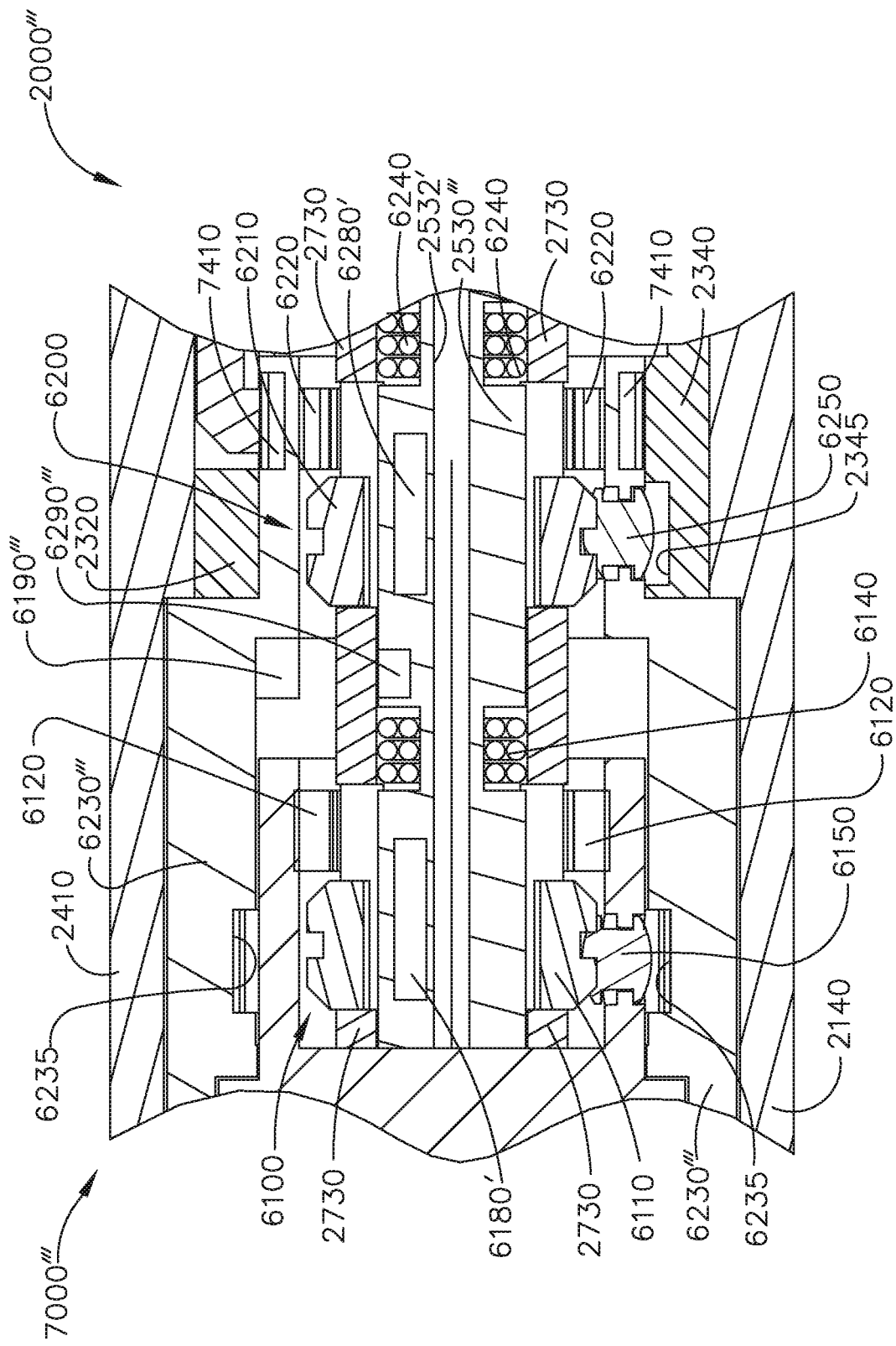
FIG. 39 depicts the first and second clutches of FIG. 38 in their unactuated conditions and a sensor in accordance with at least one alternative embodiment.

FIG. 39 depicts a shaft assembly 2000''' and an end effector 7000''' in accordance with at least one alternative embodiment. The shaft assembly 2000''' is similar to the shaft assemblies 2000 and 2000' in many respects, most of which will not be repeated herein for the sake of brevity. The end effector 7000''' is similar to the end effectors 7000 and 7000" in many respects, most of which will not be repeated herein for the sake of brevity. Similar to the end effector 7000, the end effector 7000''' comprises a jaw assembly 7100 and a jaw assembly drive configured to move the jaw assembly 7100 between its open and closed configurations and, in addition, an end effector rotation drive that rotates the end effector 7000''' relative to the distal attachment portion 2400 of the shaft assembly 2000'. The end effector rotation drive comprises an outer housing 6230''' that is rotated relative to a shaft frame 2530''' of the end effector 7000''' by the second clutch assembly 6200. The shaft frame 2530''' comprises a sensor 6290''' positioned therein which is configured to detect the position of a magnetic element 6190''' positioned in and/or on the outer housing 6230'''. The magnetic element 6190''' can comprise a permanent magnet and/or can be comprised of iron, nickel, and/or any suitable metal, for example. In various instances, the sensor 6290''' comprises a proximity sensor, for example, in signal communication with the control system 1800. In certain instances, the sensor 6290''' comprises a Hall Effect sensor, for example, in signal communication with the control system 1800. In either event, the sensor 6290''' is configured to communicate wirelessly with the control system 1800 via a wireless signal transmitter and receiver and/or via a wired connection extending through the shaft frame passage 2532', for example. In various instances, the control system 1800 can use the sensor 6290''' to confirm whether the magnetic element 6190''' is rotating and, thus, confirm that the second clutch assembly 6200 is in its actuated state. Similarly, the control system 1800 can use the sensor 6290''' to confirm whether the magnetic element 6190''' is not rotating and, thus, confirm that the second clutch assembly 6200 is in its unactuated state. The control system 1800 can also use the sensor 6290''' to confirm that the second clutch assembly 6200 is in its unactuated state by confirming that the second clutch 6210 is positioned adjacent the sensor 6290'''.

Figure 40:
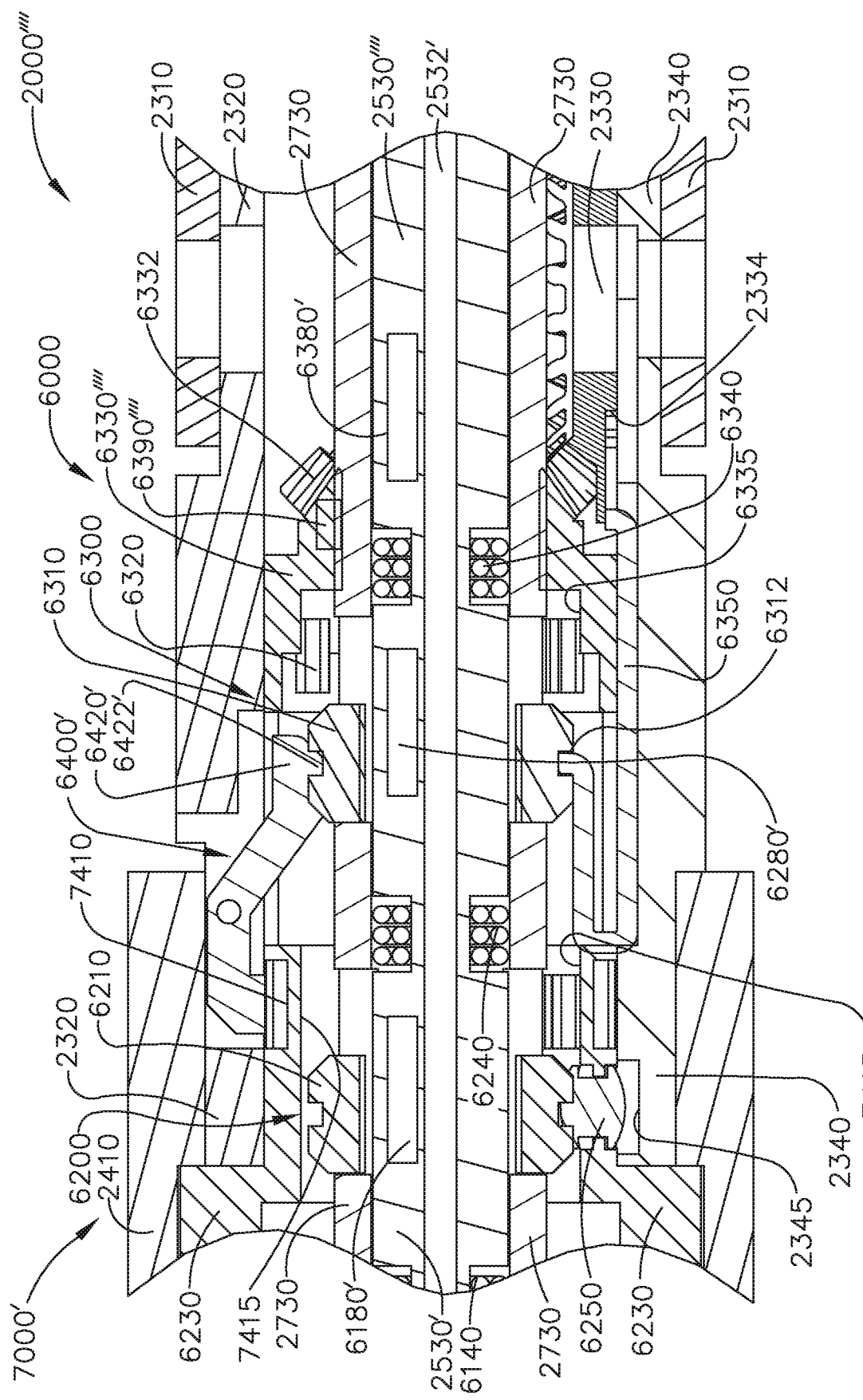
FIG. 40 depicts the second and third clutches of FIG. 38 in their unactuated conditions and a sensor in accordance with at least one alternative embodiment.

FIG. 40 depicts a shaft assembly 2000'''' in accordance with at least one alternative embodiment. The shaft assembly 2000'''' is similar to the shaft assemblies 2000, 2000', and 2000''' in many respects, most of which will not be repeated herein for the sake of brevity. Similar to the shaft assembly 2000, the shaft assembly 2000'''' comprises, among other things, an elongate shaft 2200, an articulation joint 2300, and a distal attachment portion 2400 configured to receive an end effector, such as end effector 7000', for example. Similar to the shaft assembly 2000, the shaft assembly 2000'''' comprises an articulation drive, i.e., articulation drive 6330'''' configured to rotate the distal attachment portion 2400 and the end effector 7000' about the articulation joint 2300. Similar to the above, a shaft frame 2530'''' comprises a sensor positioned therein configured to detect the position, and/or rotation, of a magnetic element 6390'''' positioned in and/or on the articulation drive 6330''''. The magnetic element 6390'''' can comprise a permanent magnet and/or can be comprised of iron, nickel, and/or any suitable metal, for example. In various instances, the sensor comprises a proximity sensor, for example, in signal communication with the control system 1800. In certain instances, the sensor comprises a Hall Effect sensor, for example, in signal communication with the control system 1800. In either event, the sensor is configured to communicate wirelessly with the control system 1800 via a wireless signal transmitter and receiver and/or via a wired connection extending through the shaft frame passage 2532', for example. In various instances, the control system 1800 can use the sensor to confirm whether the magnetic element 6390'''' is rotating and, thus, confirm that the third clutch assembly 6300 is in its actuated state. Similarly, the control system 1800 can use the sensor to confirm whether the magnetic element 6390'''' is not rotating and, thus, confirm that the third clutch assembly 6300 is in its unactuated state. In certain instances, the control system 1800 can use the sensor to confirm that the third clutch assembly 6300 is in its unactuated state by confirming that the third clutch 6310 is positioned adjacent the sensor.

Referring to FIG. 40 once again, the shaft assembly 2000'''' comprises an end effector lock 6400' configured to releasably lock the end effector 7000', for example, to the shaft assembly 2000''''. The end effector lock 6400' is similar to the end effector lock 6400 in many respects, most of which will not be discussed herein for the sake of brevity. Notably, though, a proximal end 6420' of the lock 6400' comprises a tooth 6422' configured to engage the annular slot 6312 of the third clutch 6310 and releasably hold the third clutch 6310 in its disengaged position. That said, the actuation of the third electromagnetic assembly 6340 can disengage the third clutch 6310 from the end effector lock 6400'. Moreover, in such instances, the proximal movement of the third clutch 6310 into its engaged position rotates the end effector lock 6400' into a locked position and into engagement with the lock notches 7410 to lock the end effector 7000' to the shaft assembly 2000''''. Correspondingly, the distal movement of the third clutch 6310 into its disengaged position unlocks the end effector 7000' and allows the end effector 7000' to be disassembled from the shaft assembly 2000''''.

Further to the above, an instrument system including a handle and a shaft assembly attached thereto can be configured to perform a diagnostic check to assess the state of the clutch assemblies 6100, 6200, and 6300. In at least one instance, the control system 1800 sequentially actuates the electromagnetic actuators 6140, 6240, and/or 6340—in any suitable order—to verify the positions of the clutches 6110, 6210, and/or 6310, respectively, and/or verify that the clutches are responsive to the electromagnetic actuators and, thus, not stuck. The control system 1800 can use sensors, including any of the sensors disclosed herein, to verify the movement of the clutches 6110, 6120, and 6130 in response to the electromagnetic fields created by the electromagnetic actuators 6140, 6240, and/or 6340. In addition, the diagnostic check can also include verifying the motions of the drive systems. In at least one instance, the control system 1800 sequentially actuates the electromagnetic actuators 6140, 6240, and/or 6340—in any suitable order—to verify that the jaw drive opens and/or closes the jaw assembly 7100, the rotation drive rotates the end effector 7000, and/or the articulation drive articulates the end effector 7000, for example. The control system 1800 can use sensors to verify the motions of the jaw assembly 7100 and end effector 7000.

The control system 1800 can perform the diagnostic test at any suitable time, such as when a shaft assembly is attached to the handle and/or when the handle is powered on, for example. If the control system 1800 determines that the instrument system passed the diagnostic test, the control system 1800 can permit the ordinary operation of the instrument system. In at least one instance, the handle can comprise an indicator, such as a green LED, for example, which indicates that the diagnostic check has been passed. If the control system 1800 determines that the instrument system failed the diagnostic test, the control system 1800 can prevent and/or modify the operation of the instrument system. In at least one instance, the control system 1800 can limit the functionality of the instrument system to only the functions necessary to remove the instrument system from the patient, such as straightening the end effector 7000 and/or opening and closing the jaw assembly 7100, for example. In at least one respect, the control system 1800 enters into a limp mode. The limp mode of the control system 1800 can reduce a current rotational speed of the motor 1610 by any percentage selected from a range of about 75% to about 25%, for example. In one example, the limp mode reduces a current rotational speed of the motor 1610 by 50%. In one example, the limp mode reduces the current rotational speed of the motor 1610 by 75%. The limp mode may cause a current torque of the motor 1610 to be reduced by any percentage selected from a range of about 75% to about 25%, for example. In one example, the limp mode reduces a current torque of the motor 1610 by 50%. The handle can comprise an indicator, such as a red LED, for example, which indicates that the instrument system failed the diagnostic check and/or that the instrument system has entered into a limp mode. The above being said, any suitable feedback can be used to warn the clinician that the instrument system is not operating properly such as, for example, an audible warning and/or a tactile or vibratory warning, for example.

Figure 41:
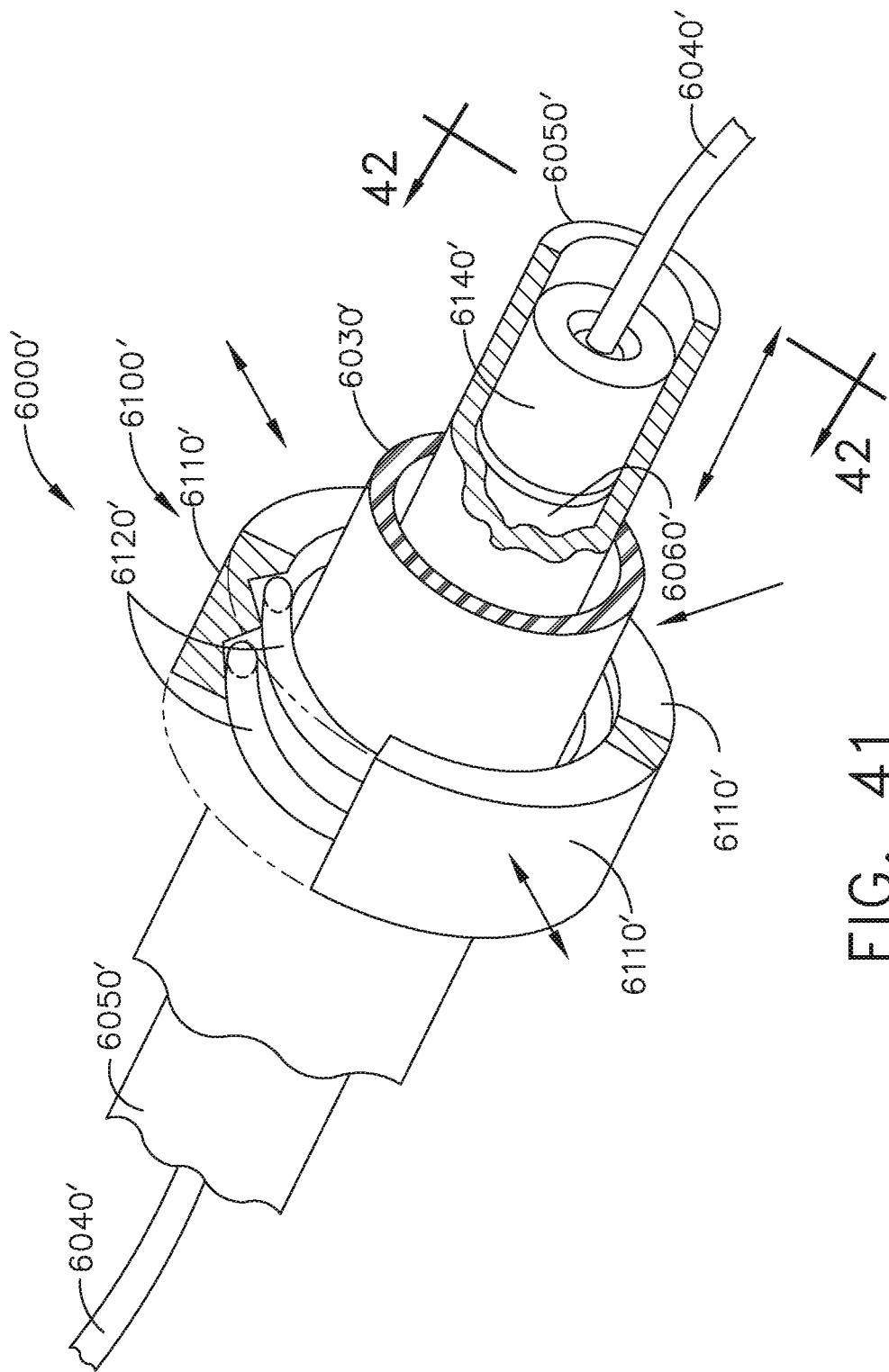
FIG. 41 is a partial cross-sectional view of a shaft assembly in accordance with at least one embodiment.
Figure 42:
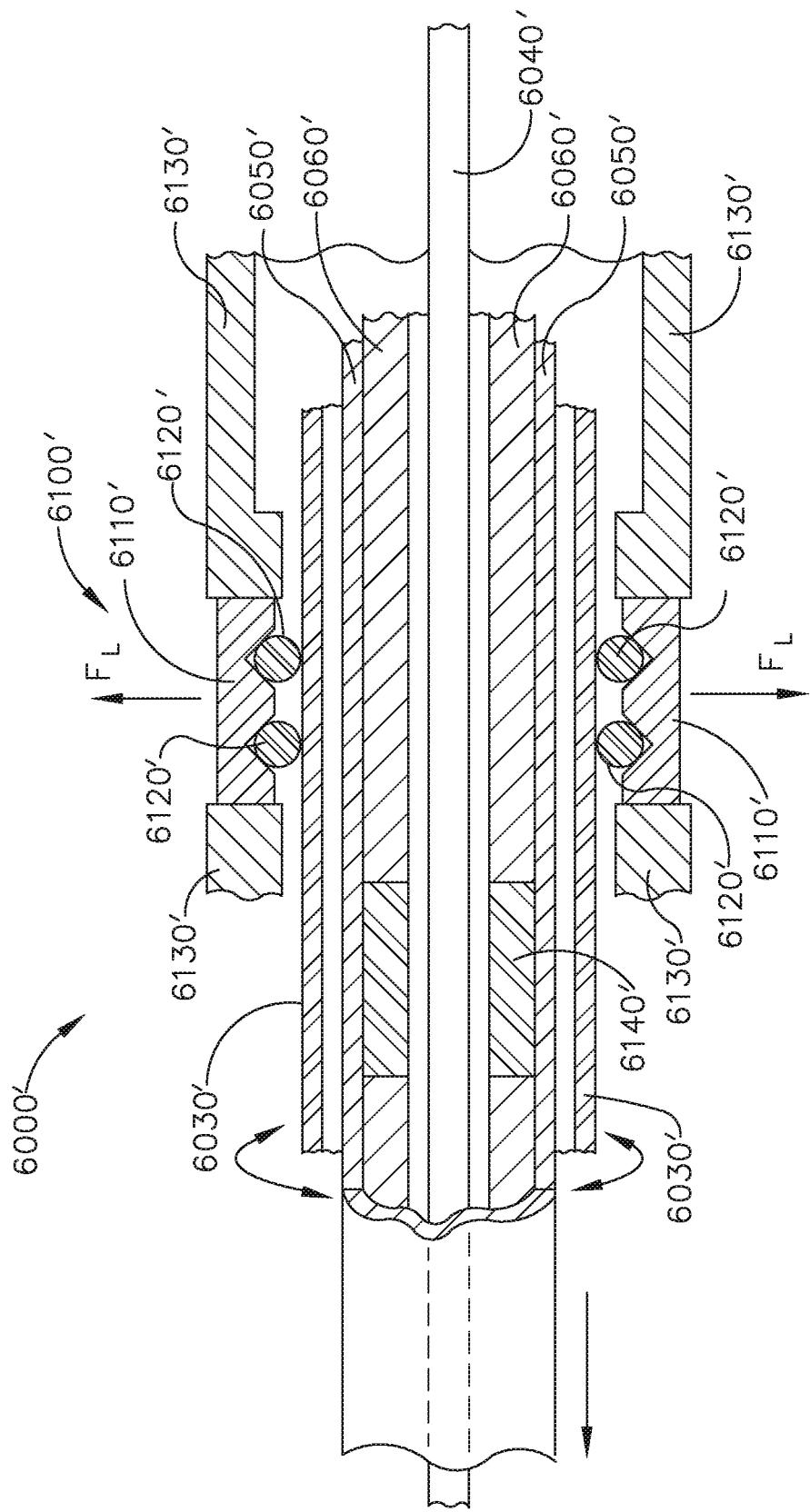
FIG. 42 is a partial cross-sectional view of the shaft assembly of FIG. 41 comprising a clutch illustrated in an unactuated condition.
Figure 43:
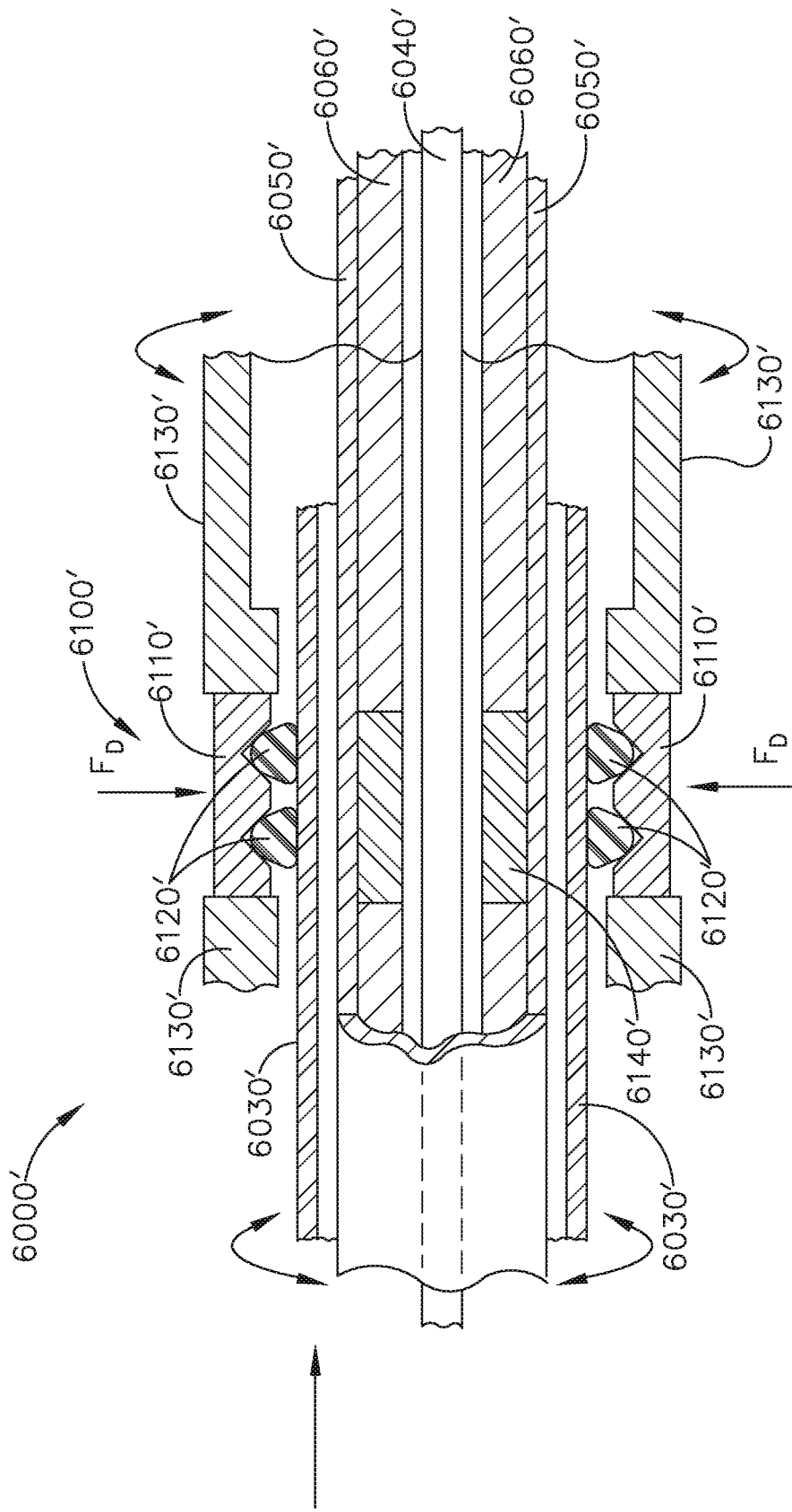
FIG. 43 is a partial cross-sectional view of the shaft assembly of FIG. 41 illustrating the clutch in an actuated condition.

FIGS. 41-43 depict a clutch system 6000' in accordance with at least one alternative embodiment. The clutch system 6000' is similar to the clutch system 6000 in many respects, most of which will not be repeated herein for the sake of brevity. Similar to the clutch system 6000, the clutch system 6000' comprises a clutch assembly 6100' which is actuatable to selectively couple a rotatable drive input 6030' with a rotatable drive output 6130'. The clutch assembly 6100' comprises clutch plates 6110' and drive rings 6120'. The clutch plates 6110' are comprised of a magnetic material, such as iron and/or nickel, for example, and can comprise a permanent magnet. As described in greater detail below, the clutch plates 6110' are movable between unactuated positions (FIG. 42) and actuated positions (FIG. 43) within the drive output 6130'. The clutch plates 6110' are slideably positioned in apertures defined in the drive output 6130' such that the clutch plates 6110' rotate with the drive output 6130' regardless of whether the clutch plates 6110' are in their unactuated or actuated positions.

When the clutch plates 6110' are in their unactuated positions, as illustrated in FIG. 42, the rotation of the drive input 6030' is not transferred to the drive output 6130'. More specifically, when the drive input 6030' is rotated, in such instances, the drive input 6030' slides past and rotates relative to the drive rings 6120' and, as a result, the drive rings 6120' do not drive the clutch plates 6110' and the drive output 6130'. When the clutch plates 6110' are in their actuated positions, as illustrated in FIG. 43, the clutch plates 6110' resiliently compress the drive rings 6120' against the drive input 6030'. The drive rings 6120' are comprised of any suitable compressible material, such as rubber, for example. In any event, in such instances, the rotation of the drive input 6030' is transferred to the drive output 6130' via the drive rings 6120' and the clutch plates 6110'. The clutch system 6000' comprises a clutch actuator 6140' configured to move the clutch plates 6110' into their actuated positions. The clutch actuator 6140' is comprised of a magnetic material such as iron and/or nickel, for example, and can comprise a permanent magnet. The clutch actuator 6140' is slideably positioned in a longitudinal shaft frame 6050' extending through the drive input 6030' and can be moved between an unactuated position (FIG. 42) and an actuated position (FIG. 43) by a clutch shaft 6060'. In at least one instance, the clutch shaft 6060' comprises a polymer cable, for example. When the clutch actuator 6140' is in its actuated position, as illustrated in FIG. 43, the clutch actuator 6140' pulls the clutch plates 6110' inwardly to compress the drive rings 6120', as discussed above. When the clutch actuator 6140' is moved into its unactuated position, as illustrated in FIG. 42, the drive rings 6120' resiliently expand and push the clutch plates 6110' away from the drive input 6030'. In various alternative embodiments, the clutch actuator 6140' can comprise an electromagnet. In such an arrangement, the clutch actuator 6140' can be actuated by an electrical circuit extending through a longitudinal aperture defined in the clutch shaft 6060', for example. In various instances, the clutch system 6000' further comprises electrical wires 6040', for example, extending through the longitudinal aperture.

Figure 44:
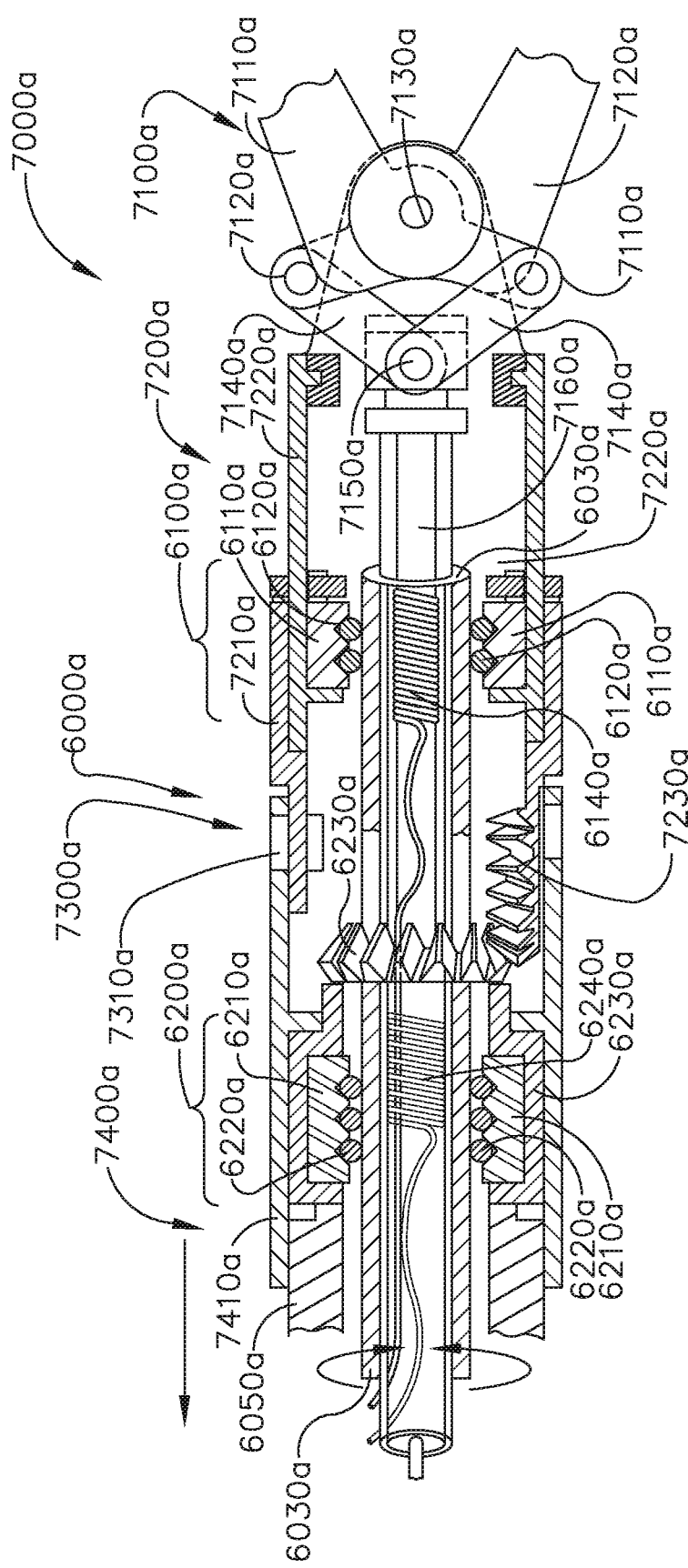
FIG. 44 is a partial cross-sectional view of a shaft assembly in accordance with at least one embodiment comprising first and second clutches illustrated in an unactuated condition.

FIG. 44 depicts an end effector 7000a including a jaw assembly 7100a, a jaw assembly drive, and a clutch system 6000a in accordance with at least one alternative embodiment. The jaw assembly 7100a comprises a first jaw 7110a and a second jaw 7120a which are selectively rotatable about a pivot 7130a. The jaw assembly drive comprises a translatable actuator rod 7160a and drive links 7140a which are pivotably coupled to the actuator rod 7160a about a pivot 7150a. The drive links 7140a are also pivotably coupled to the jaws 7110a and 7120a such that the jaws 7110a and 7120a are rotated closed when the actuator rod 7160a is pulled proximally and rotated open when the actuator rod 7160a is pushed distally. The clutch system 6000a is similar to the clutch systems 6000 and 6000' in many respects, most of which will not be repeated herein for the sake of brevity. The clutch system 6000a comprises a first clutch assembly 6100a and a second clutch assembly 6200a which are configured to selectively transmit the rotation of a drive input 6030a to rotate the jaw assembly 7100a about a longitudinal axis and articulate the jaw assembly 7100a about an articulation joint 7300a, respectively, as described in greater detail below.

The first clutch assembly 6100a comprises clutch plates 6110a and drive rings 6120a and work in a manner similar to the clutch plates 6110' and drive rings 6120' discussed above. When the clutch plates 6110a are actuated by an electromagnetic actuator 6140a, the rotation of the drive input 6030a is transferred to an outer shaft housing 7200a. More specifically, the outer shaft housing 7200a comprises a proximal outer housing 7210a and a distal outer housing 7220a which is rotatably supported by the proximal outer housing 7210a and is rotated relative to the proximal outer housing 7210a by the drive input 6030a when the clutch plates 6110a are in their actuated position. The rotation of the distal outer housing 7220a rotates the jaw assembly 7100a about the longitudinal axis owing to fact that the pivot 7130a of the jaw assembly 7100a is mounted to the distal outer housing 7220a. As a result, the outer shaft housing 7200a rotates the jaw assembly 7100a in a first direction when the outer shaft housing 7200a is rotated in a first direction by the drive input 6030a. Similarly, the outer shaft housing 7200a rotates the jaw assembly 7100a in a second direction when the outer shaft housing 7200a is rotated in a second direction by the drive input 6030a. When the electromagnetic actuator 6140a is de-energized, the drive rings 6120a expand and the clutch plates 6110a are moved into their unactuated positions, thereby decoupling the end effector rotation drive from the drive input 6030a.

The second clutch assembly 6200a comprises clutch plates 6210a and drive rings 6220a and work in a manner similar to the clutch plates 6110' and drive rings 6120' discussed above. When the clutch plates 6210a are actuated by an electromagnetic actuator 6240a, the rotation of the drive input 6030a is transferred to an articulation drive 6230a. The articulation drive 6230a is rotatably supported within an outer shaft housing 7410a of an end effector attachment portion 7400a and is rotatably supported by a shaft frame 6050a extending through the outer shaft housing 7410a. The articulation drive 6230a comprises a gear face defined thereon which is operably intermeshed with a stationary gear face 7230a defined on the proximal outer housing 7210a of the outer shaft housing 7200a. As a result, the articulation drive 6230a articulates the outer shaft housing 7200a and the jaw assembly 7100a in a first direction when the articulation drive 6230a is rotated in a first direction by the drive input 6030a. Similarly, the articulation drive 6230a articulates the outer shaft housing 7200a and the jaw assembly 7100a in a second direction when the articulation drive 6230a is rotated in a second direction by the drive input 6030a. When the electromagnetic actuator 6240a is de-energized, the drive rings 6220a expand and the clutch plates 6210a are moved into their unactuated positions, thereby decoupling the end effector articulation drive from the drive input 6030a.

Further to the above, the shaft assembly 4000 is illustrated in FIGS. 45-49. The shaft assembly 4000 is similar to the shaft assemblies 2000, 2000', 2000''', and 2000'''' in many respects, most of which will not be repeated herein for the sake of brevity. The shaft assembly 4000 comprises a proximal portion 4100, an elongate shaft 4200, a distal attachment portion 2400, and an articulate joint 2300 which rotatably connects the distal attachment portion 2040 to the elongate shaft 4200. The proximal portion 4100, similar to the proximal portion 2100, is operably attachable to the drive module 1100 of the handle 1000. The proximal portion 4100 comprises a housing 4110 including an attachment interface 4130 configured to mount the shaft assembly 4000 to the attachment interface 1130 of the handle 1000. The shaft assembly 4000 further comprises a frame 4500 including a shaft 4510 configured to be coupled to the shaft 1510 of the handle frame 1500 when the shaft assembly 4000 is attached to the handle 1000. The shaft assembly 4000 also comprises a drive system 4700 including a rotatable drive shaft 4710 configured to be operably coupled to the drive shaft 1710 of the handle drive system 1700 when the shaft assembly 4000 is attached to the handle 1000. The distal attachment portion 2400 is configured to receive an end effector, such as end effector 8000, for example. The end effector 8000 is similar to the end effector 7000 in many respects, most of which will not be repeated herein for the sake of brevity. That said, the end effector 8000 comprises a jaw assembly 8100 configured to, among other things, grasp tissue.

Figure 48:
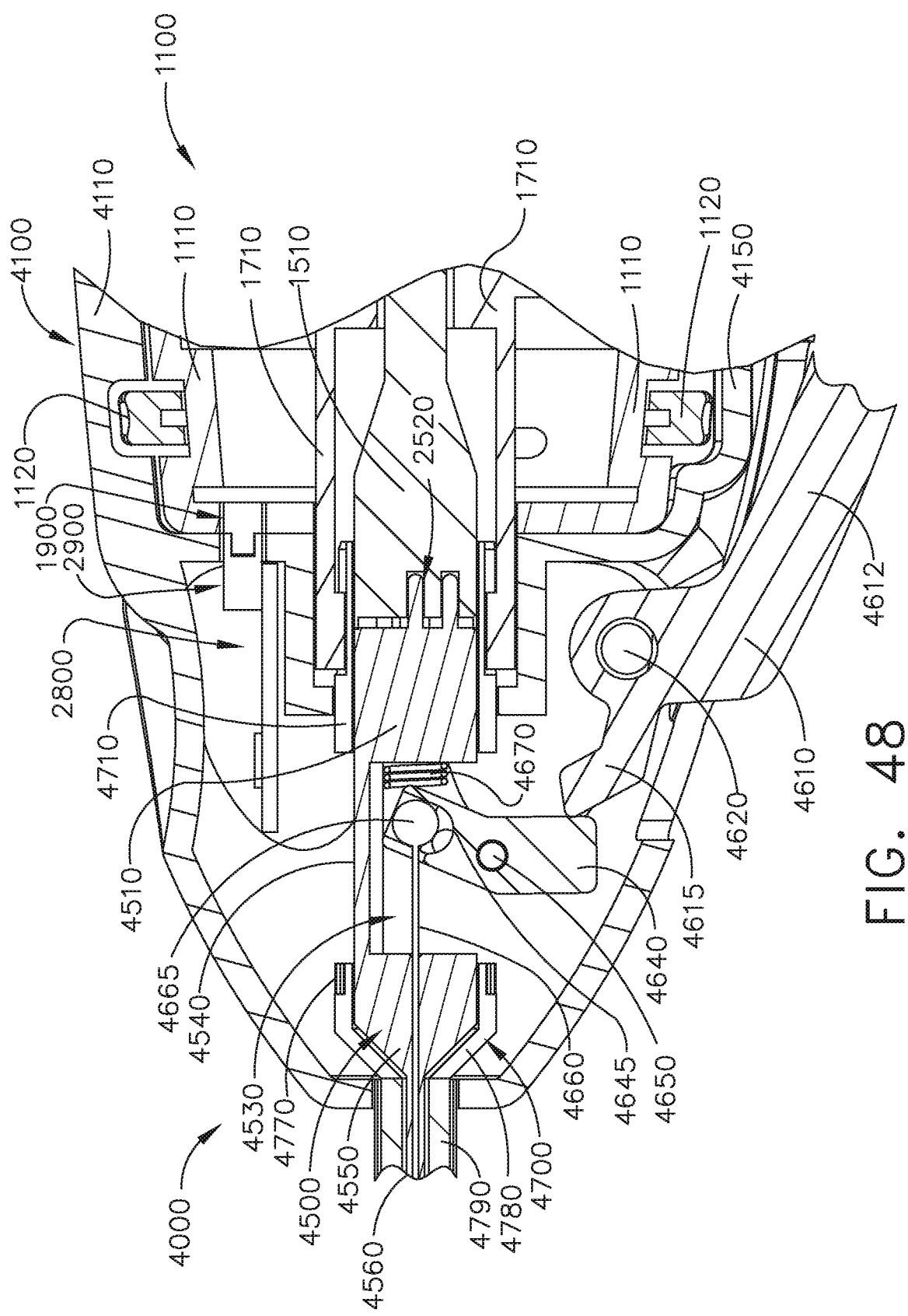
FIG. 48 is another partial cross-sectional view of the shaft assembly of FIG. 45 attached to the handle of FIG. 1.
Figure 49:
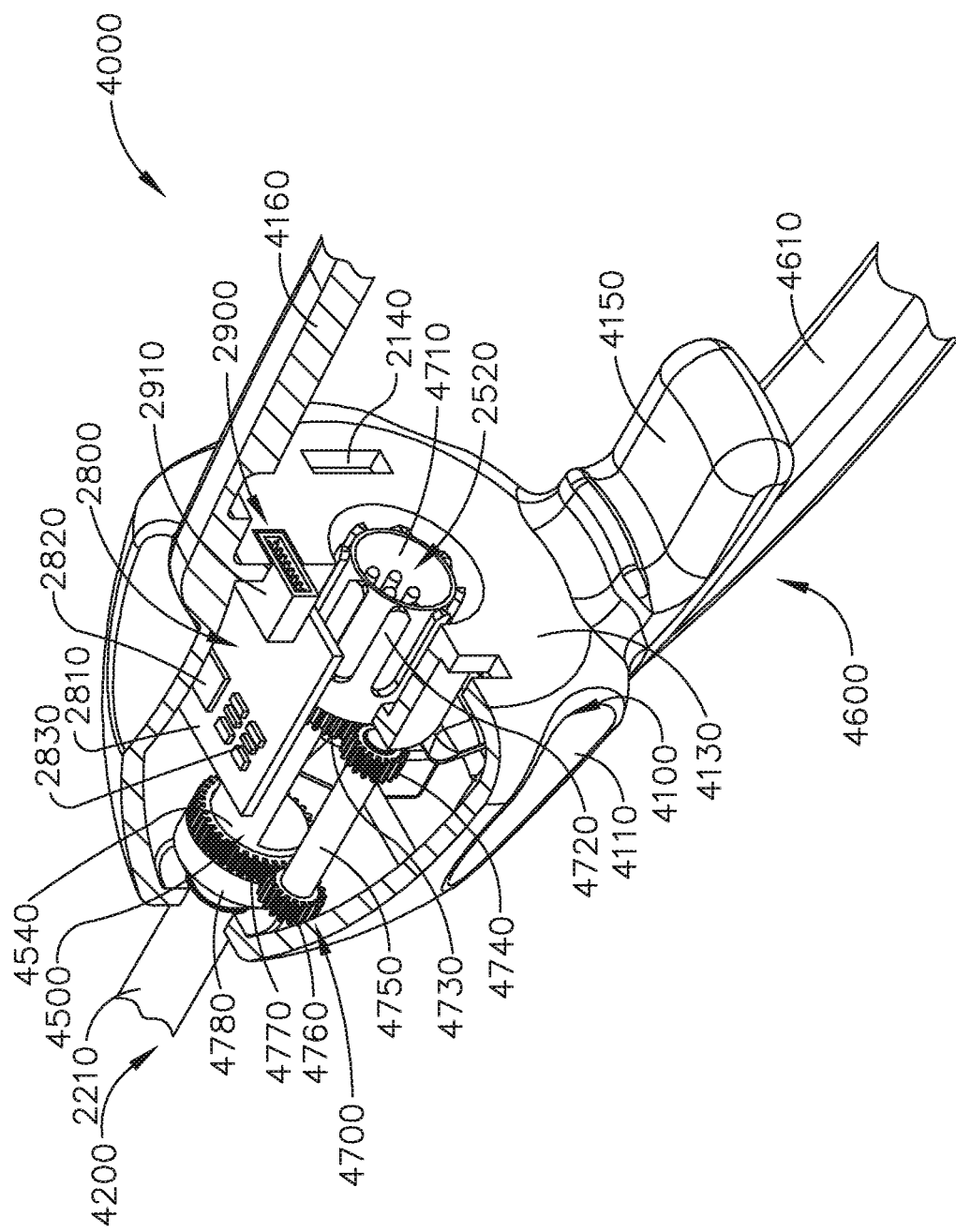
FIG. 49 is a partial cross-sectional perspective view of the shaft assembly of FIG. 45.

As discussed above, referring primarily to FIGS. 47-49, the frame 4500 of the shaft assembly 4000 comprises a frame shaft 4510. The frame shaft 4510 comprises a notch, or cut-out, 4530 defined therein. As discussed in greater detail below, the cut-out 4530 is configured to provide clearance for a jaw closure actuation system 4600. The frame 4500 further comprises a distal portion 4550 and a bridge 4540 connecting the distal portion 4550 to the frame shaft 4510. The frame 4500 further comprises a longitudinal portion 4560 extending through the elongate shaft 4200 to the distal attachment portion 2400. Similar to the above, the frame shaft 4510 comprises one or more electrical traces defined thereon and/or therein. The electrical traces extend through the longitudinal portion 4560, the distal portion 4550, the bridge 4540, and/or any suitable portion of the frame shaft 4510 to the electrical contacts 2520. Referring primarily to FIG. 48, the distal portion 4550 and longitudinal portion 4560 comprise a longitudinal aperture defined therein which is configured to receive a rod 4660 of the jaw closure actuation system 4600, as described in greater detail below.

As also discussed above, referring primarily to FIGS. 48 and 49, the drive system 4700 of the shaft assembly 4000 comprises a drive shaft 4710. The drive shaft 4710 is rotatably supported within the proximal shaft housing 4110 by the frame shaft 4510 and is rotatable about a longitudinal axis extending through the frame shaft 4510. The drive system 4700 further comprises a transfer shaft 4750 and an output shaft 4780. The transfer shaft 4750 is also rotatably supported within the proximal shaft housing 4110 and is rotatable about a longitudinal axis extending parallel to, or at least substantially parallel to, the frame shaft 4510 and the longitudinal axis defined therethrough. The transfer shaft 4750 comprises a proximal spur gear 4740 fixedly mounted thereto such that the proximal spur gear 4740 rotates with the transfer shaft 4750. The proximal spur gear 4740 is operably intermeshed with an annular gear face 4730 defined around the outer circumference of the drive shaft 4710 such that the rotation of the drive shaft 4710 is transferred to the transfer shaft 4750. The transfer shaft 4750 further comprises a distal spur gear 4760 fixedly mounted thereto such that the distal spur gear 4760 rotates with the transfer shaft 4750. The distal spur gear 4760 is operably intermeshed with an annular gear 4770 defined around the outer circumference of the output shaft 4780 such that the rotation of the transfer shaft 4750 is transferred to the output shaft 4780. Similar to the above, the output shaft 4780 is rotatably supported within the proximal shaft housing 4110 by the distal portion 4550 of the shaft frame 4500 such that the output shaft 4780 rotates about the longitudinal shaft axis. Notably, the output shaft 4780 is not directly coupled to the input shaft 4710; rather, the output shaft 4780 is operably coupled to the input shaft 4710 by the transfer shaft 4750. Such an arrangement provides room for the manually-actuated jaw closure actuation system 4600 discussed below.

Further to the above, referring primarily to FIGS. 47 and 48, the jaw closure actuation system 4600 comprises an actuation, or scissors, trigger 4610 rotatably coupled to the proximal shaft housing 4110 about a pivot 4620. The actuation trigger 4610 comprises an elongate portion 4612, a proximal end 4614, and a grip ring aperture 4616 defined in the proximal end 4614 which is configured to be gripped by the clinician. The shaft assembly 4000 further comprises a stationary grip 4160 extending from the proximal housing 4110. The stationary grip 4160 comprises an elongate portion 4162, a proximal end 4164, and a grip ring aperture 4166 defined in the proximal end 4164 which is configured to be gripped by the clinician. In use, as described in greater detail below, the actuation trigger 4610 is rotatable between an unactuated position and an actuated position (FIG. 48), i.e., toward the stationary grip 4160, to close the jaw assembly 8100 of the end effector 8000.

Referring primarily to FIG. 48, the jaw closure actuation system 4600 further comprises a drive link 4640 rotatably coupled to the proximal shaft housing 4110 about a pivot 4650 and, in addition, an actuation rod 4660 operably coupled to the drive link 4640. The actuation rod 4660 extends through an aperture defined in the longitudinal frame portion 4560 and is translatable along the longitudinal axis of the shaft frame 4500. The actuation rod 4660 comprises a distal end operably coupled to the jaw assembly 8100 and a proximal end 4665 positioned in a drive slot 4645 defined in the drive link 4640 such that the actuation rod 4660 is translated longitudinally when the drive link 4640 is rotated about the pivot 4650. Notably, the proximal end 4665 is rotatably supported within the drive slot 4645 such that the actuation rod 4660 can rotate with the end effector 8000.

Further to the above, the actuation trigger 4610 further comprises a drive arm 4615 configured to engage and rotate the drive link 4640 proximally, and translate the actuation rod 4660 proximally, when the actuation trigger 4610 is actuated, i.e., moved closer to the proximal shaft housing 4110. In such instances, the proximal rotation of the drive link 4640 resiliently compresses a biasing member, such as a coil spring 4670, for example, positioned intermediate the drive link 4640 and the frame shaft 4510. When the actuation trigger 4610 is released, the compressed coil spring 4670 re-expands and pushes the drive link 4640 and the actuation rod 4660 distally to open the jaw assembly 8100 of the end effector 8000. Moreover, the distal rotation of the drive link 4640 drives, and automatically rotates, the actuation trigger 4610 back into its unactuated position. That being said, the clinician could manually return the actuation trigger 4610 back into its unactuated position. In such instances, the actuation trigger 4610 could be opened slowly. In either event, the shaft assembly 4000 further comprises a lock configured to releasably hold the actuation trigger 4610 in its actuated position such that the clinician can use their hand to perform another task without the jaw assembly 8100 opening unintentionally.

In various alternative embodiments, further to the above, the actuation rod 4660 can be pushed distally to close the jaw assembly 8100. In at least one such instance, the actuation rod 4660 is mounted directly to the actuation trigger 4610 such that, when the actuation trigger 4610 is actuated, the actuation trigger 4610 drives the actuation rod 4660 distally. Similar to the above, the actuation trigger 4610 can compress a spring when the actuation trigger 4610 is closed such that, when the actuation trigger 4610 is released, the actuation rod 4660 is pushed proximally.

Further to the above, the shaft assembly 4000 has three functions—opening/closing the jaw assembly of an end effector, rotating the end effector about a longitudinal axis, and articulating the end effector about an articulation axis. The end effector rotation and articulation functions of the shaft assembly 4000 are driven by the motor assembly 1600 and the control system 1800 of the drive module 1100 while the jaw actuation function is manually-driven by the jaw closure actuation system 4600. The jaw closure actuation system 4600 could be a motor-driven system but, instead, the jaw closure actuation system 4600 has been kept a manually-driven system such that the clinician can have a better feel for the tissue being clamped within the end effector. While motorizing the end effector rotation and actuation systems provides certain advantages for controlling the position of the end effector, motorizing the jaw closure actuation system 4600 may cause the clinician to lose a tactile sense of the force being applied to the tissue and may not be able to assess whether the force is insufficient or excessive. Thus, the jaw closure actuation system 4600 is manually-driven even though the end effector rotation and articulation systems are motor-driven.

Figure 50:
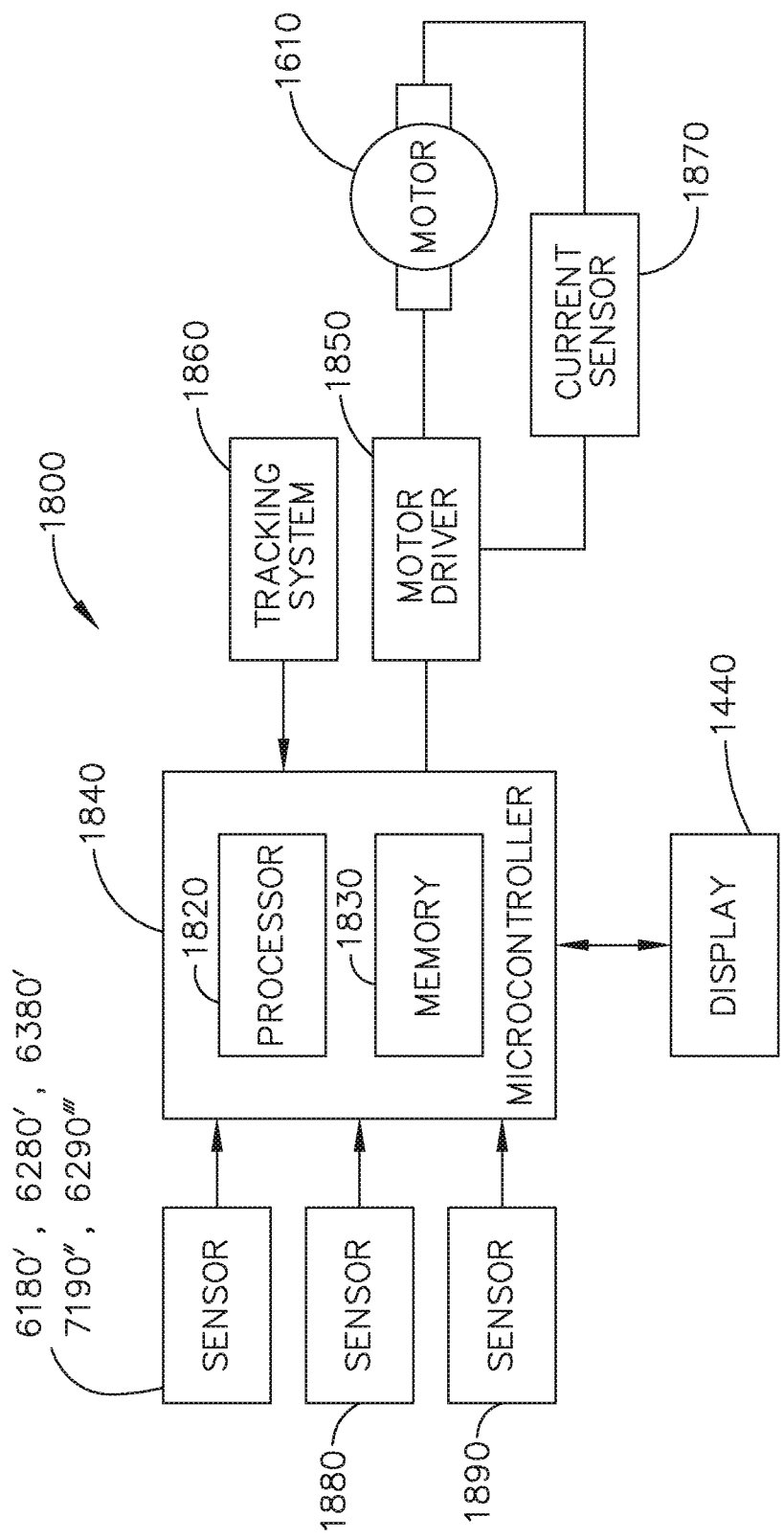
FIG. 50 is a schematic of the control system of the surgical system of FIG. 1.

FIG. 50 is a logic diagram of the control system 1800 of the surgical system depicted in FIG. 1 in accordance with at least one embodiment. The control system 1800 comprises a control circuit. The control circuit includes a microcontroller 1840 comprising a processor 1820 and a memory 1830. One or more sensors, such as sensors 1880, 1890, 6180', 6280', 6380', 7190'', and/or 6290''', for example, provide real time feedback to the processor 1820. The control system 1800 further comprises a motor driver 1850 configured to control the electric motor 1610 and a tracking system 1860 configured to determine the position of one or more longitudinally movable components in the surgical instrument, such as the clutches 6110, 6120, and 6130 and/or the longitudinally-movable drive nut 7150 of the jaw assembly drive, for example. The tracking system 1860 is also configured to determine the position of one or more rotational components in the surgical instrument, such as the drive shaft 2530, the outer shaft 6230, and/or the articulation drive 6330, for example. The tracking system 1860 provides position information to the processor 1820, which can be programmed or configured to, among other things, determine the position of the clutches 6110, 6120, and 6130 and the drive nut 7150 as well as the orientation of the jaws 7110 and 7120. The motor driver 1850 may be an A3941 available from Allegro Microsystems, Inc., for example; however, other motor drivers may be readily substituted for use in the tracking positioning system 1860. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 1840 may be any single core or multicore processor such as those known under the trade name ARM Cortex by Texas Instruments, for example. In at least one instance, the microcontroller 1840 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 1840 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 1840 is programmed to perform various functions such as precisely controlling the speed and/or position of the drive nut 7150 of the jaw closure assembly, for example. The microcontroller 1840 is also programmed to precisely control the rotational speed and position of the end effector 7000 and the articulation speed and position of the end effector 7000. In various instances, the microcontroller 1840 computes a response in the software of the microcontroller 1840. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 1610 is controlled by the motor driver 1850. In various forms, the motor 1610 is a DC brushed driving motor having a maximum rotational speed of approximately 25,000 RPM, for example. In other arrangements, the motor 1610 includes a brushless motor, a cordless motor, a synchronous motor, a stepper motor, or any other suitable electric motor. The motor driver 1850 may comprise an H-bridge driver comprising field-effect transistors (FETs), for example. The motor driver 1850 may be an A3941 available from Allegro Microsystems, Inc., for example. The A3941 driver 1850 is a full-bridge controller for use with external N-channel power metal oxide semiconductor field effect transistors (MOSFETs) specifically designed for inductive loads, such as brush DC motors. In various instances, the driver 1850 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted.

The tracking system 1860 comprises a controlled motor drive circuit arrangement comprising one or more position sensors, such as sensors 1880, 1890, 6180', 6280', 6380', 7190", and/or 6290''', for example. The position sensors for an absolute positioning system provide a unique position signal corresponding to the location of a displacement member. As used herein, the term displacement member is used generically to refer to any movable member of the surgical system. In various instances, the displacement member may be coupled to any position sensor suitable for measuring linear displacement. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall Effect sensors, a magnetic sensing system comprising a fixed magnet and a series of movable linearly arranged Hall Effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 1880, 1890, 6180', 6280', 6380', 7190", and/or 6290''', for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 1860 comprise a magnetic rotary absolute positioning system. Such position sensors may be implemented as an AS5055EQFT single-chip magnetic rotary position sensor available from Austria Microsystems, AG and can be interfaced with the controller 1840 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 1840. The position sensors can provide 12 or 14 bits of resolution, for example. The position sensors can be an AS5055 chip provided in a small QFN 16-pin 4×4×0.85 mm package, for example.

The tracking system 1860 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 1610 has taken to infer the position of a device actuator, drive bar, knife, and the like.

A sensor 1880 comprising a strain gage or a micro-strain gage, for example, is configured to measure one or more parameters of the end effector, such as, for example, the strain experienced by the jaws 7110 and 7120 during a clamping operation. The measured strain is converted to a digital signal and provided to the processor 1820. In addition to or in lieu of the sensor 1880, a sensor 1890 comprising a load sensor, for example, can measure the closure force applied by the closure drive system to the jaws 7110 and 7120. In various instances, a current sensor 1870 can be employed to measure the current drawn by the motor 1610. The force required to clamp the jaw assembly 7100 can correspond to the current drawn by the motor 1610, for example. The measured force is converted to a digital signal and provided to the processor 1820. A magnetic field sensor can be employed to measure the thickness of the captured tissue. The measurement of the magnetic field sensor can also be converted to a digital signal and provided to the processor 1820.

The measurements of the tissue compression, the tissue thickness, and/or the force required to close the end effector on the tissue as measured by the sensors can be used by the controller 1840 to characterize the position and/or speed of the movable member being tracked. In at least one instance, a memory 1830 may store a technique, an equation, and/or a look-up table which can be employed by the controller 1840 in the assessment. In various instances, the controller 1840 can provide the user of the surgical instrument with a choice as to the manner in which the surgical instrument should be operated. To this end, the display 1440 can display a variety of operating conditions of the instrument and can include touch screen functionality for data input. Moreover, information displayed on the display 1440 may be overlaid with images acquired via the imaging modules of one or more endoscopes and/or one or more additional surgical instruments used during the surgical procedure.

As discussed above, the drive module 1100 of the handle 1000 and/or the shaft assemblies 2000, 3000, 4000, and/or 5000, for example, attachable thereto comprise control systems. Each of the control systems can comprise a circuit board having one or more processors and/or memory devices. Among other things, the control systems are configured to store sensor data, for example. They are also configured to store data which identifies the shaft assembly to the handle 1000. Moreover, they are also configured to store data including whether or not the shaft assembly has been previously used and/or how many times the shaft assembly has been used. This information can be obtained by the handle 1000 to assess whether or not the shaft assembly is suitable for use and/or has been used less than a predetermined number of times, for example.

Figure 67:
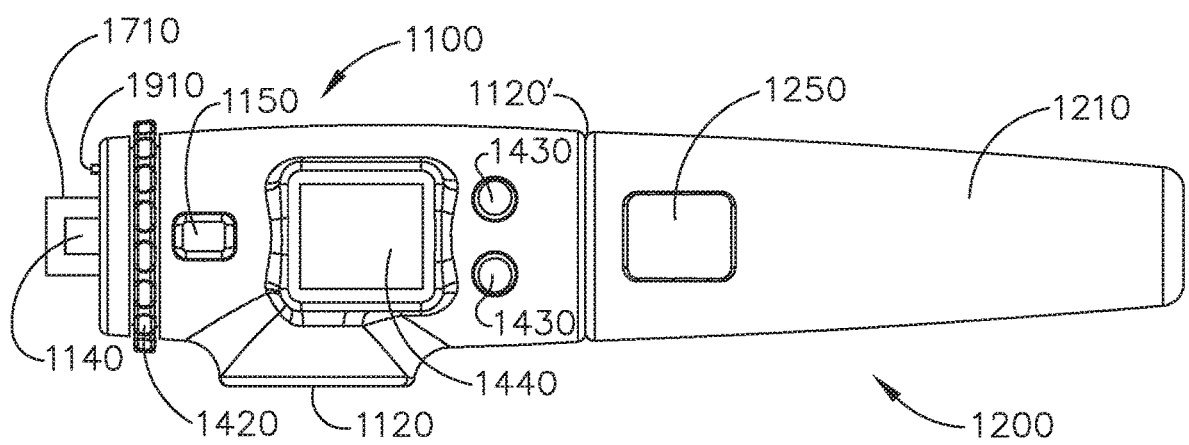
FIG. 67 is an elevational view of the power module of FIG. 55 attached to the proximal battery port of the drive module of FIG. 7.
Figure 68:
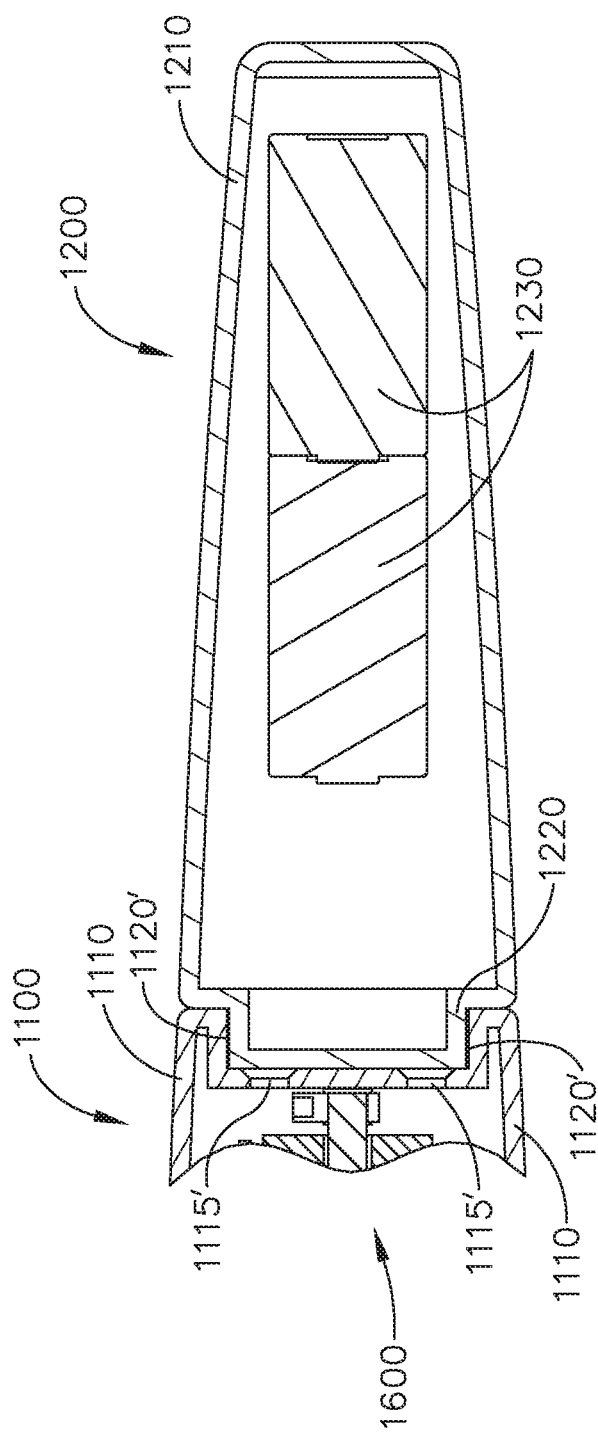
FIG. 68 is a partial cross-sectional view of the connection between the proximal battery port of the drive module of FIG. 7 and the power module of FIG. 55.

Further to the above, the first module connector 1120 of the drive module 1100 comprises a side battery port defined in the side of the drive module 1100. Similarly, the second module connector 1120' comprises a proximal battery port defined in the proximal end of the drive module 1100. That said, a drive module can comprise a battery port at any suitable location. In any event, the power module 1200 is operably attachable to the drive module 1100 at the side battery port 1120, as illustrated in FIGS. 54-58, or the proximal battery port 1120', as illustrated in FIGS. 67 and 68. This is possible because the connector 1220 of the power module 1200 is compatible with the side battery port 1120 and the proximal battery port 1120'. Among other things, the connector 1220 comprises a substantially circular, or substantially cylindrical, configuration that matches, or at least substantially matches, the substantially circular, or substantially cylindrical, configurations of the battery ports 1120 and 1120'. In various instances, the connector 1220 comprises a frustoconical, or an at least substantially frustoconical, shape having a bottom portion which is larger than the top portion and an angled, or tapered, side extending therebetween. The above being said, the connector 1220 of the power module 1200 does not comprise keys, or projections, extending therefrom which interfere with the assembly of the power module 1200 to the battery ports 1120 and 1120'.

Referring primarily to FIGS. 55 and 56, the connector 1220 comprises two latches 1240 extending therefrom. The latches 1240 are positioned on opposite sides of the connector 1220 such that they comprise opposing latch shoulders which releasably hold the power module 1200 to the handle module 1100. The side battery port 1120 comprises latch openings 1125 defined in the housing 1100 which are configured to receive the latches 1240 of the power module 1200 and, similarly, the proximal battery port 1120' comprises latch openings 1125' defined in the housing 1100 which are also configured to receive the latches 1240 of the power module 1200. While the latch openings 1125 in the side battery port 1120 and the latch openings 1125' in the proximal battery port 1120' limit the orientations in which the power module 1200 can be assembled to each battery port 1120 and 1120', i.e., two orientations for each battery port, the power module 1200 is nonetheless operably attachable to both battery ports 1120 and 1120'.

Further to the above, the latches 1240 of the power module 1200 are configured to engage the drive module 1100 in a snap-fit manner. In various instances, the latches 1240 resiliently flex radially outwardly when the power module 1200 is assembled to the drive module 1100 and then resiliently move, or snap, radially inwardly once the power module 1200 is fully seated within one of the ports 1120 and 1120' to lock the power module 1200 to the drive module 1100. In various instances, the latches 1240 comprise flexible arms which deflect radially inwardly and outwardly as described above while, in some instances, the latches 1240 comprise one or more biasing members, such as springs, for example, configured to resiliently push the latches 1240 into their inward, or locked, positions. In various embodiments, the power module 1200 can comprise members which are press-fit into apertures defined in the ports 1120 and 1120' to retain the power module 1200 to the drive module 1100.

Further to the above, the electrical contacts of the power module 1200 are defined on the top portion, or face, of the connector 1220. As discussed above, the electrical contacts of the power module 1200 engage corresponding electrical contacts defined in the ports 1120 and 1120' when the power module 1200 is attached to the drive module 1100 to place the power module 1200 in electrical communication with the drive module 1100. In various instances, the electrical contacts of the power module 1200 are compressed against the electrical contacts of the drive module 1100 when the power module 1200 is attached to the drive module 1100. In at least one such instance, the power module contacts and/or the drive module contacts comprise resilient members which are configured to elastically deflect when the power module 1200 is attached to the drive module 1100. Such resilient members, along with the latches 1240, can assure that there is an adequate electrical interface between the power module 1200 and the drive module 1100. In alternative embodiments, the power module 1200 can comprise annular electrical contacts extending around the perimeter thereof which engage electrical contacts on the sides of the ports 1120 and 1120'. Such an arrangement could permit relative rotation between the power module 1200 and the drive module 1100.

Figure 69:
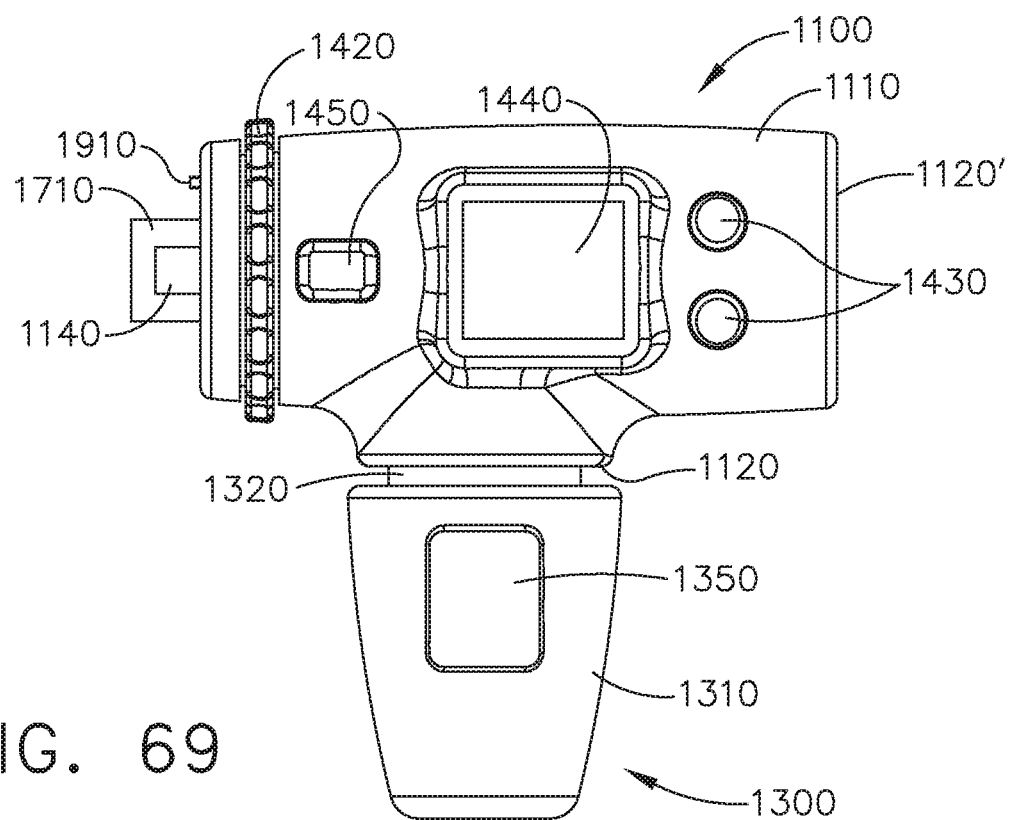
FIG. 69 is an elevational view of an attempt to connect the power module of FIG. 45 to the side battery port of the drive module of FIG. 7.
Figure 70:
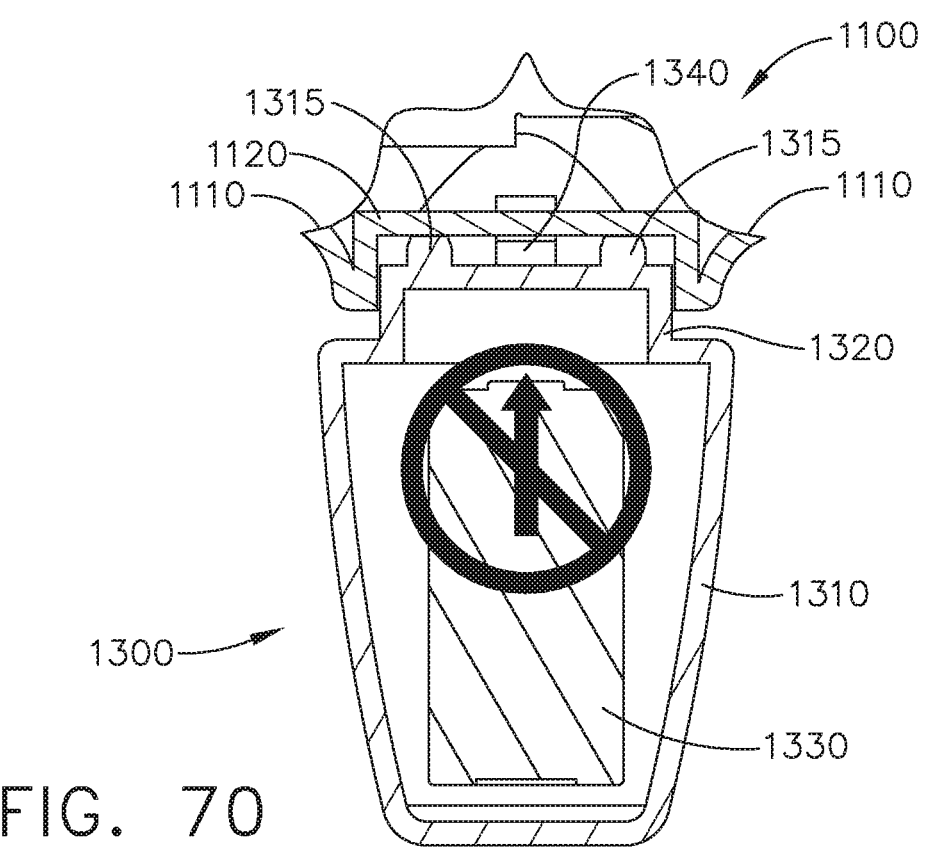
FIG. 70 is a cross-sectional detail view of an attempt to connect the power module of FIG. 45 to the side battery port of the drive module of FIG. 7.

Further to the above, the power module 1300 is operably attachable to the drive module 1100 at the proximal battery port 1120', as illustrated in FIGS. 59-66, but not the side battery port 1120, as illustrated in FIGS. 69 and 70. This is the case because the connector 1320 of the power module 1300 is compatible with the proximal battery port 1120', but not the side battery port 1120. Although the connector 1320 comprises a substantially circular, or substantially cylindrical, configuration that matches, or at least substantially matches, the substantially circular, or substantially cylindrical, configurations of the battery ports 1120 and 1120', the connector 1320 of the power module 1300 comprises keys, or projections, 1315 extending therefrom which interfere with the assembly of the power module 1300 to the side battery port 1120, but not the proximal battery port 1120'.

When a clinician attempts to assembly the power module 1300 to the side battery port 1120', the projections 1315 contact the housing 1110 and prevent the latches 1340 of the power module 1300 from locking the power module 1300 to the drive module 1100 and prevent the power module 1300 from being electrically coupled to the drive module 1100. That being said, referring primarily to FIGS. 63 and 64, the proximal battery port 1120' comprises clearance apertures 1115' defined therein configured to receive the projections 1315 of the power module 1300 and permit the power module 1300 to be assembled to the proximal battery port 1120'. Similar to the above, the latch openings 1125' and the clearance apertures 1115' in the proximal battery port 1120' limit the orientations in which the power module 1300 can be assembled to the proximal battery port 1120' to two orientations.

Figure 51:
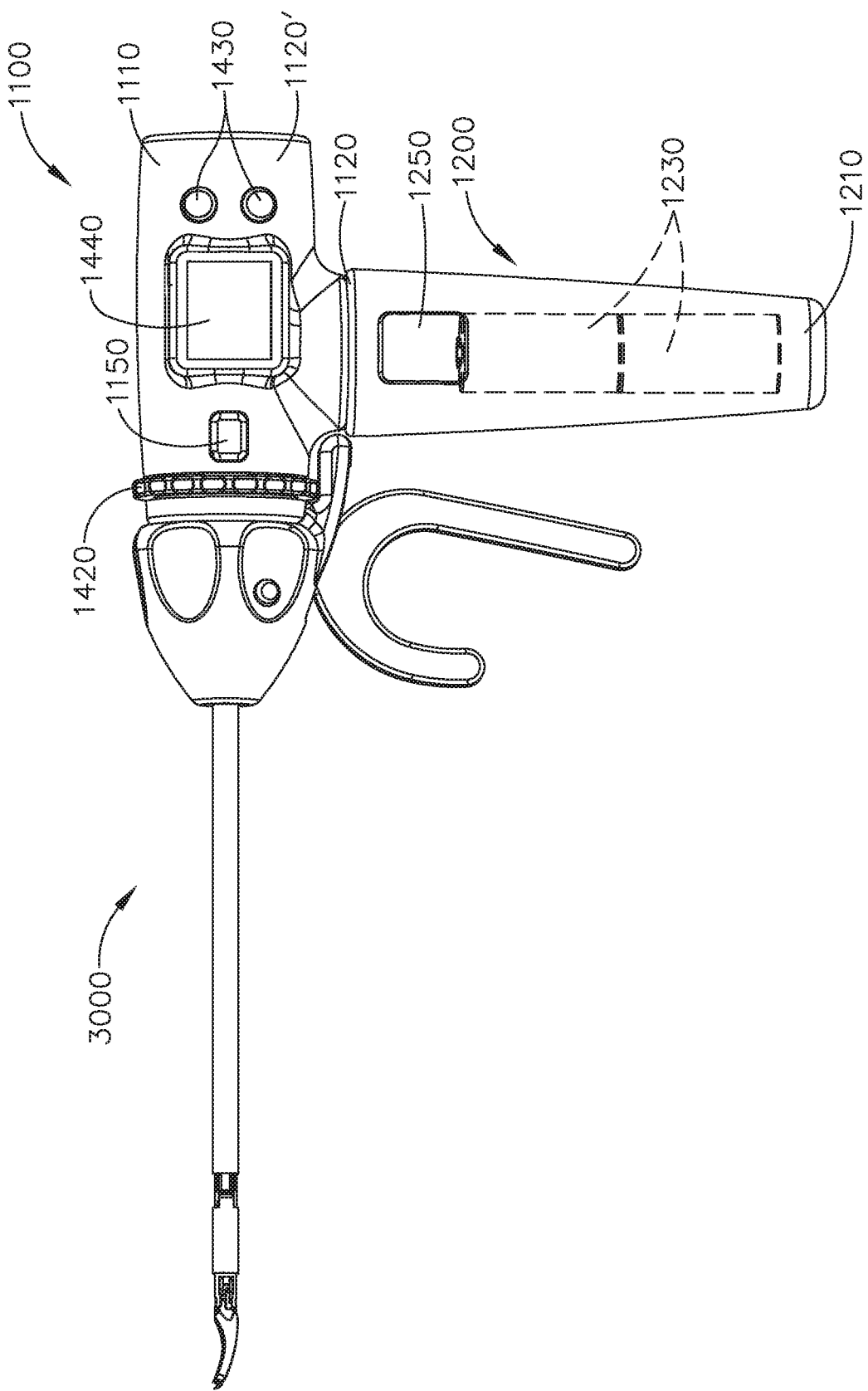
FIG. 51 is an elevational view of the handle and one of the shaft assemblies of the surgical system of FIG. 1.
Figure 52:
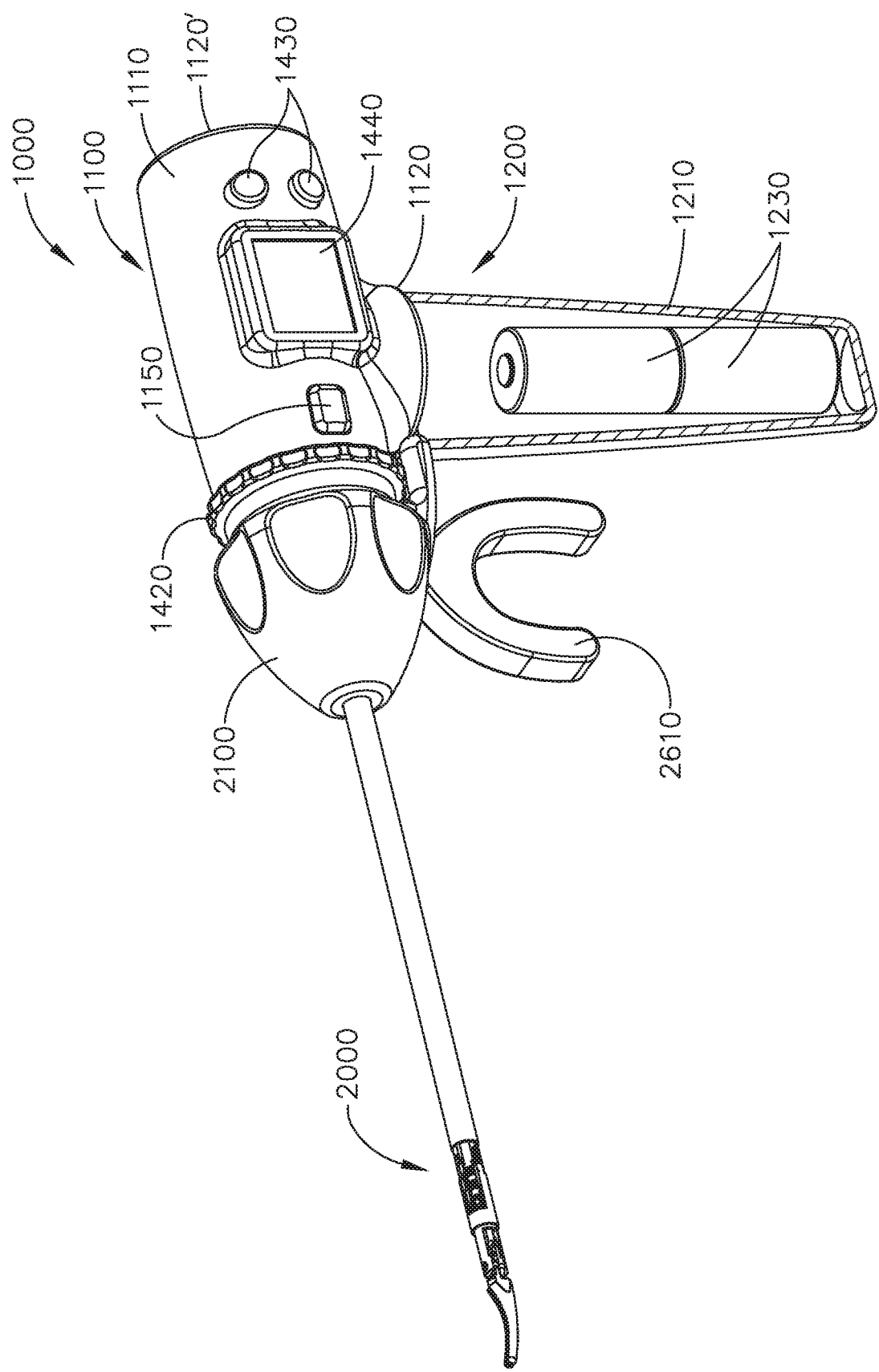
FIG. 52 is a perspective view of the handle of FIG. 1 and the shaft assembly of FIG. 2.
Figure 53:
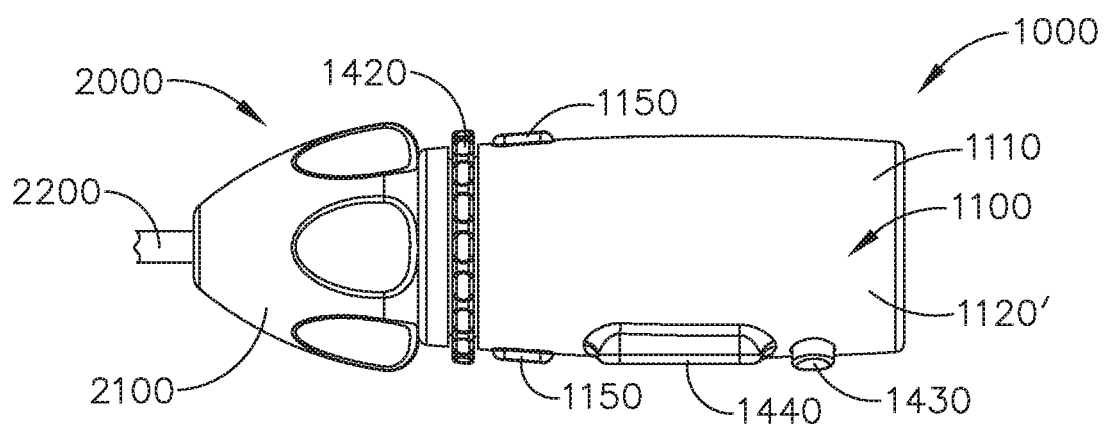
FIG. 53 is a partial top plan view of the handle of FIG. 1 and the shaft assembly of FIG. 2.
Figure 54:
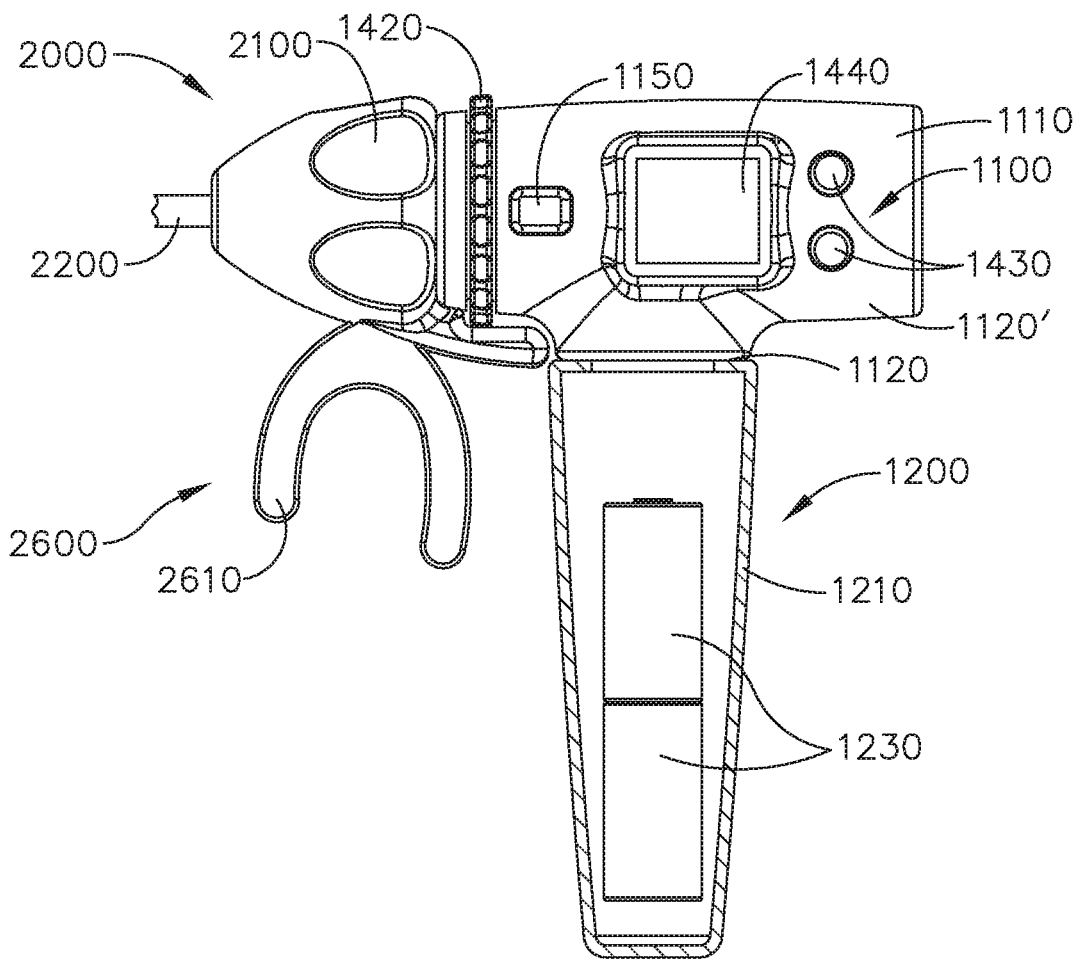
FIG. 54 is a partial elevational view of the handle of FIG. 1 and the shaft assembly of FIG. 2.
Figure 59:
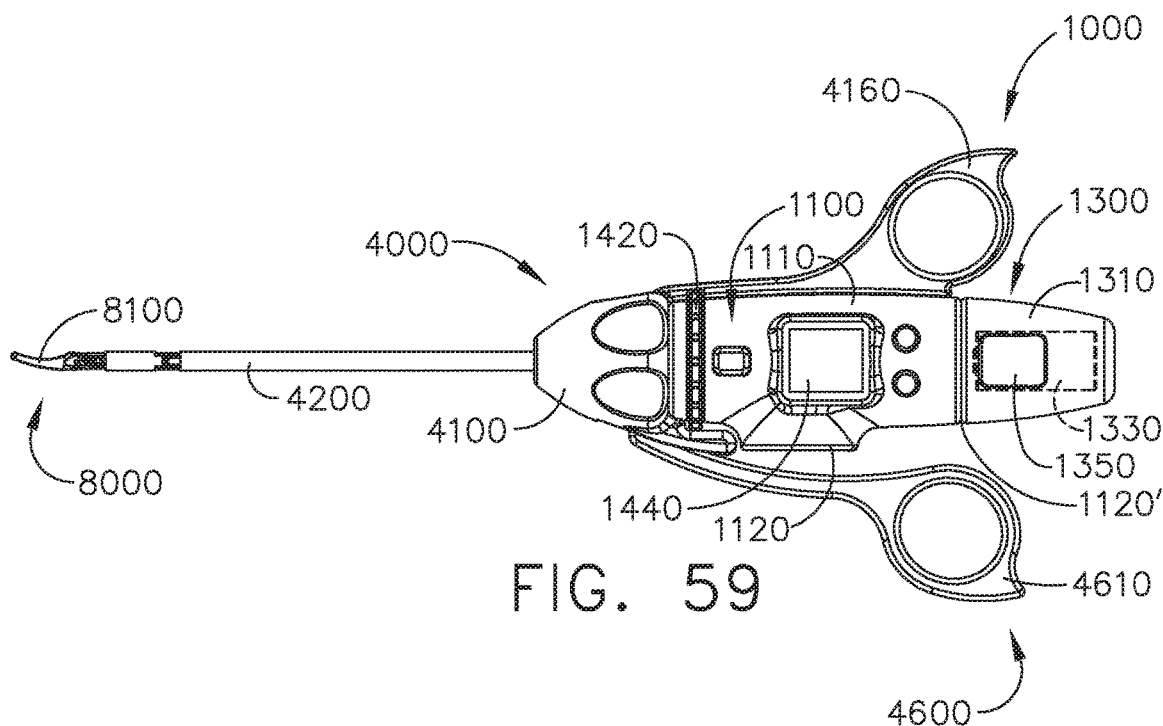
FIG. 59 is an elevational view of the handle drive module of FIG. 7, the power module of FIG. 45 attached to a proximal battery port of the handle drive module, and the shaft assembly of FIG. 45 attached to the drive module.
Figure 60:
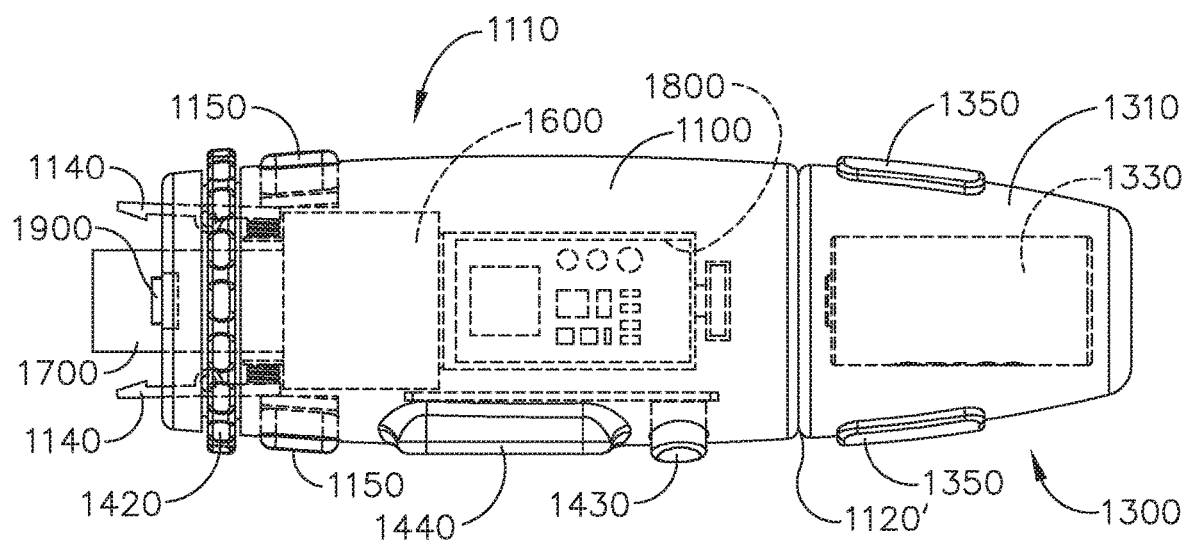
FIG. 60 is a top view of the drive module of FIG. 7 and the power module of FIG. 45 attached to the proximal battery port.
Figure 61:
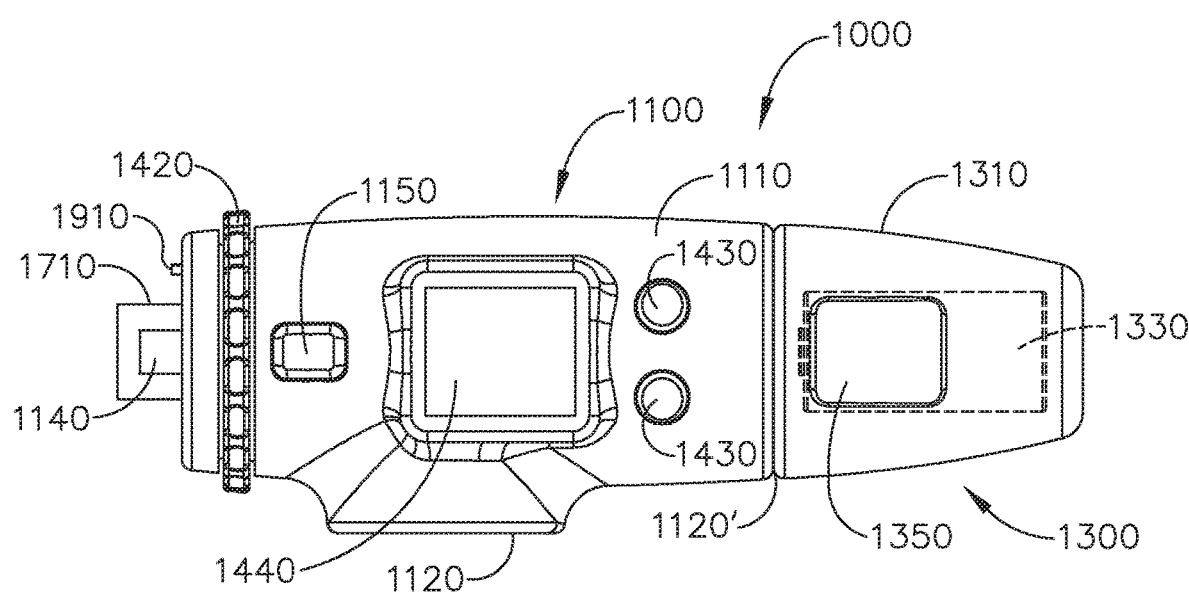
FIG. 61 is an elevational view of the drive module of FIG. 7 and the power module of FIG. 45 attached to the proximal battery port.
Figure 62:
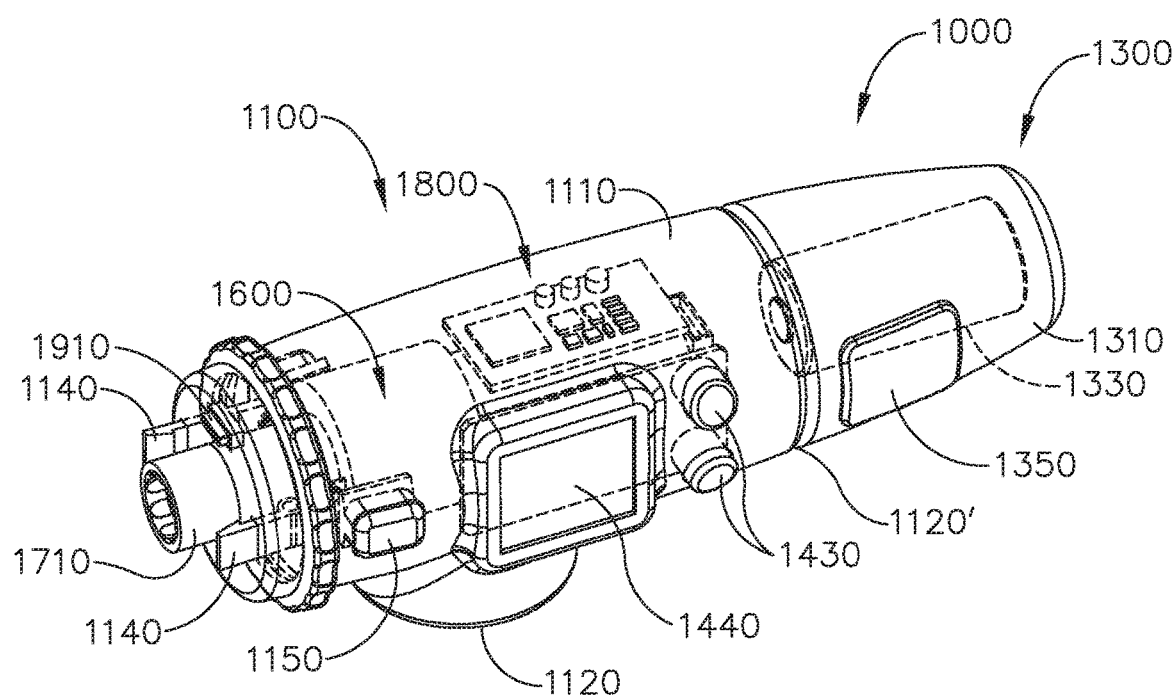
FIG. 62 is a perspective view of the drive module of FIG. 7 and the power module of FIG. 45 attached to the proximal battery port.
Figure 66:
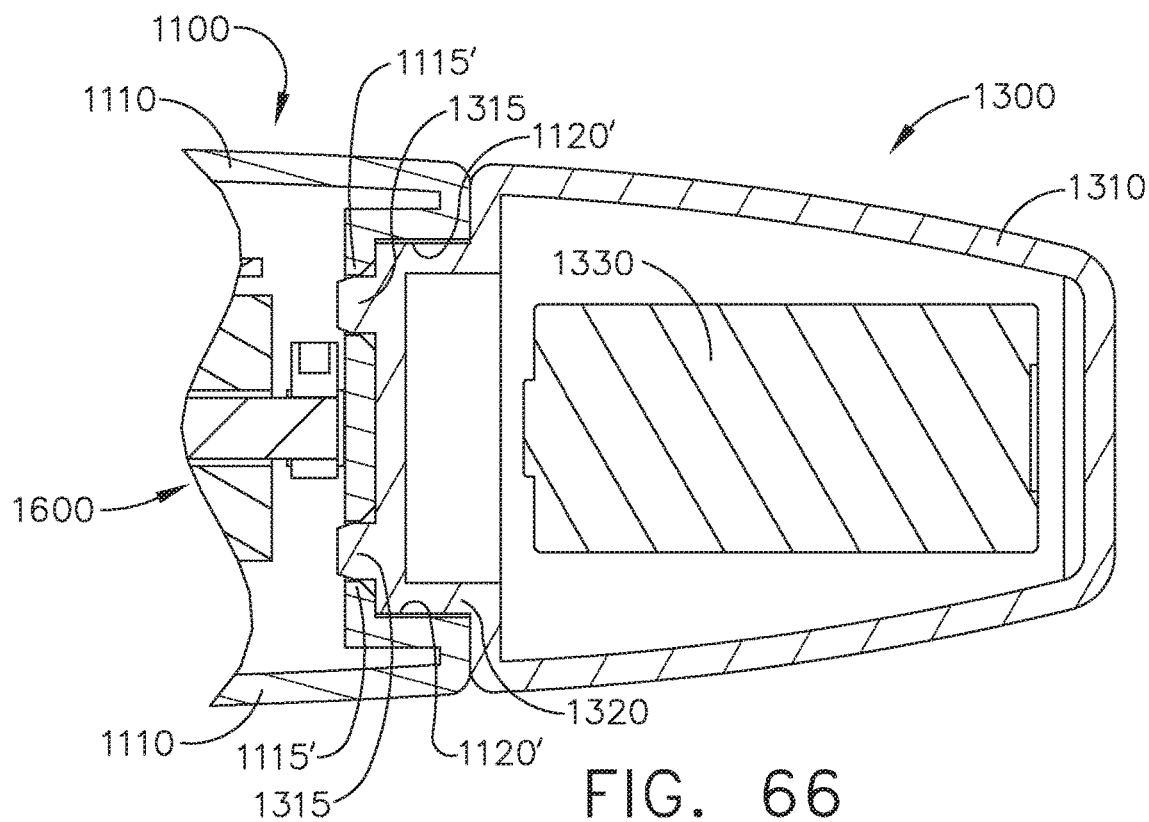
FIG. 66 is a partial cross-sectional view of the connection between proximal battery port of the drive module of FIG. 7 and the power module of FIG. 45.
Figure 71:
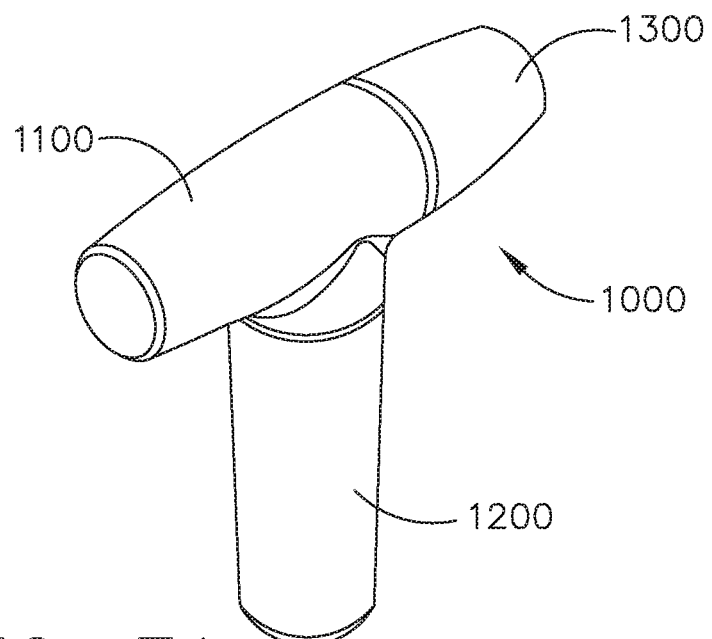
FIG. 71 is a perspective view of the power module of FIG. 45 attached to the proximal battery port of the drive module of FIG. 7 and the power module of FIG. 55 attached to the side battery port.
Figure 72:
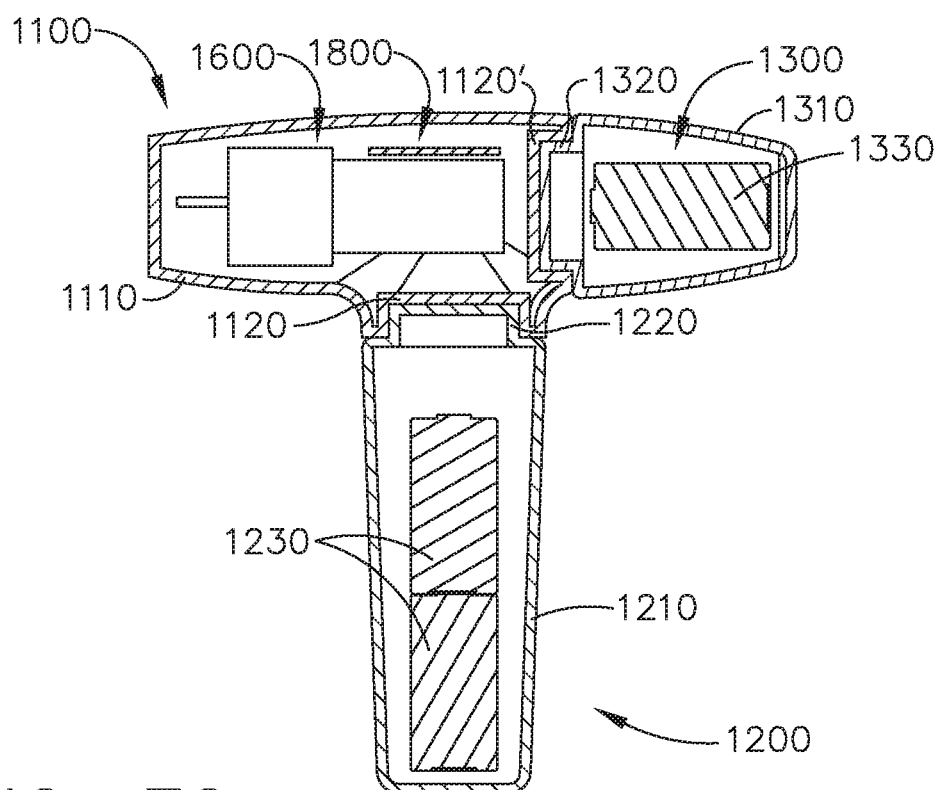
FIG. 72 is a cross-sectional view of the power module of FIG. 45 attached to the proximal battery port of the drive module of FIG. 7 and the power module of FIG. 55 attached to the side battery port.

Further to the above, other circumstances can prevent the attachment of a power module to one of the battery ports 1120 and 1120'. For instance, one of the battery ports can have an asymmetrical geometry which is configured to receive a complementary geometry of only one of the power modules. In at least one such instance, the side battery port 1120 can comprise a semicircular cavity and the proximal battery port 1120' can comprise a circular cavity, wherein the connector 1220 of the power module 1200 comprises a semicircular geometry which can be received in both of the battery ports 1120 and 1120' while the connector 1320 of the power module 1300 comprises a circular geometry which can be received in the proximal battery port 1120', but not the side battery port 1120. In some instances, the configuration of the shaft assembly attached to the drive module 1100 can prevent the assembly of one of the power modules to the drive module 1100. For instance, referring to FIG. 59, the shaft assembly 4000, for example, can prevent the assembly of the power module 1300 to the side battery port 1120 as the actuation trigger 4610 interferes with its assembly thereto. Notably, such an arrangement would also prevent the power module 1200 from being assembled to the side battery port 1120. As a result, the clinician would be required to use the proximal battery port 1120' to couple a power module to the drive module 1100 when using the shaft assembly 4000. The configuration of certain shaft assemblies, referring to FIGS. 71 and 72, would permit both of the power modules 1200 and 1300 to be assembled to the drive module 1100 at the same time. For instance, referring to FIG. 51, the shaft assembly 3000 of FIG. 1 would permit both of the power modules 1200 and 1300 to be used to supply power to the drive module 1100 simultaneously.

The power modules 1200 and 1300 are configured to supply power to the drive module 1100 at the same, or at least substantially the same, voltage. For instance, each power module 1200 and 1300 is configured to supply power to the drive module 1100 at 3 VDC, for example. The control system 1800 of the drive module 1100 comprises one or more power inverters, for example, configured to convert the DC current to AC current to the extent that AC current is needed. That said, the power modules 1200 and 1300 can be configured to deliver power to the drive module 1100 at any suitable voltage. In at least one instance, the power modules 1200 and/or 1300 are configured to deliver AC power to the drive module. In at least one such instance, the power modules 1200 and/or 1300 each comprise one or more power inverters. In alternative embodiments, the power modules 1200 and 1300 are configured to supply power to the drive module 1100 at different voltages. In such embodiments, the configurations of the ports 1120 and 1120', discussed above, can prevent a power module having a higher voltage from being attached to a lower voltage port. Likewise, the configurations of the ports 1120 and 1120' can prevent a power module having a lower voltage from being attached to a higher voltage port, if desired.

In various instances, the power modules 1200 and 1300 are configured to provide the same, or at least substantially the same, current to the drive module. In at least one instance, the power modules 1200 and 1300 supply the same, or at least substantially the same, magnitude of current to the drive module 1100. In alternative embodiments, the power modules 1200 and 1300 are configured to provide different currents to the drive module 1100. In at least one instance, the power module 1200 provides a current to the drive module 1100 having a magnitude which is twice that of the current provided by the power module 1300, for example. In at least one such instance, the battery cells of the power module 1200 are arranged in parallel to provide the same voltage as the power module 1300 but at twice the current. Similar to the above, the configurations of the ports 1120 and 1120', discussed above, can prevent a power module having a higher current from being attached to a lower current port. Likewise, the configurations of the ports 1120 and 1120' can prevent a power module having a lower current from being attached to a higher current port, if desired.

Further to the above, the control system 1800 is configured to adaptively manage the power provided by the power modules 1200 and 1300. In various instances, the control system 1800 comprises one or more transformer circuits configured to step up and/or step down the voltage provided to it by a power module. For instance, if a higher voltage power module is attached to a lower voltage port, the control system 1800 can activate, or switch on, a transformer circuit to step down the voltage from the higher voltage power module. Similarly, if a lower voltage power module is attached to a higher voltage port, the control system 1800 can activate, or switch on, a transformer circuit to step up the voltage from the lower voltage power module. In various embodiments, the control system 1800 is configured to switch a power module off if a power module having an inappropriate voltage is attached to a port in the drive module 1100. In at least one instance, the control system 1800 comprises one or more voltmeter circuits configured to evaluate the voltage of a power module attached to the drive module and, if the voltage of the power module is incorrect or outside of an appropriate voltage range, the control system 1800 can switch off the power module such that the power module does not supply power to the drive module 1100. In at least one such instance, the drive module 1100 has a voltmeter circuit for each port 1120 and 1120'. In at least one instance, the control system 1800 comprises one or more ammeter circuits configured to evaluate the current of a power module attached to the drive module and, if the current of the power module is incorrect or outside of an appropriate current range, the control system 1800 can switch off the power module such that the power module does not supply power to the drive module 1100. In at least one such instance, the drive module 1100 has an ammeter circuit for each port 1120 and 1120'. In at least one instance, each power module 1200 and 1300 comprises a switch circuit which, when opened by the control system 1800, prevents power from being supplied to the drive module 1100. If a power module comprises the correct voltage or a voltage within an appropriate voltage range for the port in which the power module is attached, the switch circuit remains closed and/or is closed by the control system 1800. In at least one such instance, the drive module 1100 has a switch circuit for each port 1120 and 1120'.

In various instances, a power module can comprise a switch which is selectively actuatable by the clinician to prevent the power module from supplying power to the drive module 1100. In at least one instance, the switch comprises a mechanical switch, for example, in the power supply circuit of the power module. A power module that has been switched off, however, can still provide other benefits. For instance, a switched-off power module 1200 can still provide a pistol grip and a switched-off power module 1300 can still provide a wand grip. Moreover, in some instances, a switched-off power module can provide a power reserve that can be selectively actuated by the clinician.

In addition to or in lieu of the above, each of the power modules 1200 and 1300 comprises an identification memory device. The identification memory devices can comprise a solid state chip, for example, having data stored thereon which can be accessed by and/or transmitted to the control system 1800 when a power module is assembled to the drive module 1100. In at least one instance, the data stored on the identification memory device can comprise data regarding the voltage that the power module is configured to supply to the drive module 1100, for example.

Further to the above, each of the shaft assemblies 2000, 3000, 4000, and/or 5000 comprise an identification memory device, such as memory device 2830, for example. The identification memory device of a shaft assembly can comprise a solid state chip, for example, having data stored thereon which can be accessed by and/or transmitted to the control system 1800 when the shaft assembly is assembled to the drive module 1100. In at least one instance, the data stored on the identification memory device can comprise data regarding the power required to operate the drive systems of the shaft assembly. The shaft assembly 2000 comprises three systems driven by the drive module 1100—the end effector articulation drive system, the end effector rotation drive system, and the jaw drive system—each of which having their own power requirement. The jaw drive system, for instance, may require more power than the end effector articulation and rotation drive systems. To this end, the control system 1800 is configured to verify that the power provided by the power module, or power modules, attached to the drive module 1100 is sufficient to power all of the drive systems—including the jaw drive system—of the shaft assembly 2000 assembled to the drive module 1100. As such, the control system 1800 is configured to assure that the power module arrangement attached to the drive module 1100 is properly paired with the shaft assembly attached to the drive module 1100. If the power provided by the power module arrangement is insufficient, or below a required power threshold, the control system 1800 can inform the clinician that a different and/or an additional power module is required. In at least one instance, the drive module 1100 comprises a low-power indicator on the housing 1110 and/or on the display screen 1440, for example. Notably, the jaw drive system of the shaft assembly 4000 is not driven by the drive module 1100; rather, it is manually powered by the clinician. As such, the power required to operate the shaft assembly 4000 can be less than the power required to operate the shaft assembly 2000, for example, and the control system 1800 can lower the required power threshold for the shaft assembly 4000 when evaluating the power module arrangement.

Further to the above, an end effector configured to grasp and/or dissect tissue may require less power than an end effector configured to clip the tissue of a patient. As a result, an end effector and/or shaft assembly comprising a clip applier may have a larger power requirement than an end effector and/or shaft assembly comprising grasping and/or dissecting jaws. In such instances, the control system 1800 of the drive module 1100 is configured to verify that the power module, or modules, attached to the drive module 1100 can provide sufficient power to the drive module 1100. The control system 1800 can be configured to interrogate the identification chips on the power modules attached to the drive module 1100 and/or evaluate the power sources within the power modules to assess whether the power modules comprise sufficiently-available voltage and/or current to properly power the drive module 1100 to operate the clip applier.

Further to the above, an end effector configured to grasp and/or dissect tissue may require less power than an end effector configured to suture the tissue of a patient, for example. As a result, an end effector and/or shaft assembly comprising a suturing device may have a larger power requirement than an end effector and/or shaft assembly comprising grasping and/or dissecting jaws. In such instances, the control system 1800 of the drive module 1100 is configured to verify that the power module, or modules, attached to the drive module 1100 can provide sufficient power to the drive module 1100 based on the shaft assembly attached to the drive module 1100. The control system 1800 can be configured to interrogate the identification chips on the power modules attached to the drive module 1100 and/or evaluate the power sources within the power modules to assess whether the power modules comprise sufficiently-available voltage and/or current to properly power the drive module 1100 to operate the suturing device.

In addition to or in lieu of the above, an end effector, such as end effector 7000, for example, comprises an identification memory device. The identification memory device of an end effector can comprise a solid state chip, for example, having data stored thereon which can be accessed by and/or transmitted to the control system 1800 when the end effector is assembled to the drive module 1100 by way of a shaft assembly. In at least one instance, the data stored on the identification memory device can comprise data regarding the power required to operate the drive systems of the end effector. The end effector can be in communication with the drive module 1100 through electrical pathways, or circuits, extending through the shaft assembly. Similar to the above, the end effector can identify itself to the drive module 1100 and, with this information, the drive module 1100 can adapt its operation to properly operate the end effector.

As described above, the power modules 1200 and 1300 each comprise one or more battery cells. That said, the power modules 1200 and 1300 can comprise any suitable means for storing and delivering power. In at least one instance, the power modules 1200 and 1300 comprise capacitors and/or supercapacitors configured to store energy and deliver energy to the drive module 1100. The capacitors and/or supercapacitors can be part of the same electrical circuit as the battery cells or a different electrical circuit. A supercapacitor can comprise electrostatic double-layer capacitance and/or electrochemical pseudocapacitance, both of which can contribute to the total capacitance of the supercapacitor. In various instances, electrostatic double-layer capacitors use carbon electrodes or derivatives with much higher electrostatic double-layer capacitance than electrochemical pseudocapacitance, achieving separation of charge in a Helmholtz double layer at the interface between the surface of a conductive electrode and an electrolyte. The separation of charge is often of the order of a few angstroms (0.3-0.8 nm), much smaller than in a conventional capacitor. Electrochemical pseudocapacitors use metal oxide or conducting polymer electrodes with a high amount of electrochemical pseudocapacitance additional to the double-layer capacitance. Pseudocapacitance is achieved by Faradaic electron charge-transfer with redox reactions, intercalation, and/or electrosorption. Hybrid capacitors, such as a lithium-ion capacitor, for example, could also be used which comprise electrodes with differing characteristics—one exhibiting mostly electrostatic capacitance and the other mostly electrochemical capacitance.

The power modules 1200 and 1300 can be rechargeable or non-rechargeable. When the power modules 1200 and 1300 are not rechargeable, they are disposed of after a single use. In such instances, it is desirable for the power modules 1200 and 1300 to be completely drained, or at least substantially drained, of power when they are disposed of. To this end, each power module comprises a drain which is engaged, or actuated, when the power module is assembled to the drive module 1100. In various instances, the drain comprises a resistance circuit inside the power module that includes the battery cells. Once actuated, the drain slowly discharges the battery cells of the power module, but at a rate which still permits the power module to provide sufficient power to the drive module 1100 during the surgical procedure. After the surgical procedure is completed, however, the drain continues to discharge the battery cells even though the power module may no longer be assembled to the drive module 1100. As such, the drain discharges the battery cells whether or not the power module is supplying power to, or attached to, the drive module 1100. The entire disclosures of U.S. Pat. No. 8,632,525, entitled POWER CONTROL ARRANGEMENTS FOR SURGICAL INSTRUMENTS AND BATTERIES, which issued on Jan. 21, 2014, and U.S. Pat. No. 9,289,212, entitled SURGICAL INSTRUMENTS AND BATTERIES FOR SURGICAL INSTRUMENTS, which issued on Mar. 22, 2016, are incorporated by reference herein.

Multiple surgical instruments, including various handheld instruments, are used by a clinician during a particular surgical procedure to perform different functions. Each surgical instrument may comprise different handle and/or grip configurations in addition to different user control mechanisms. Switching between various handheld instruments may cause delay and/or discomfort, as the clinician regains control over the surgical instrument and actuates the user control mechanism(s). The use of numerous powered surgical instruments may require a user to ensure that, prior to the start of every surgical procedure, numerous power sources are charged and/or functional, as power sources may vary and/or may not compatible with all powered surgical instruments.

A modular surgical instrument comprising a universal handle and power source may provide a clinician with a sense of familiarity in using a universal handle configuration. The modular surgical instrument is configured for use with numerous surgical tool attachments. Instead of having to charge a plurality of different power sources, the modular surgical instrument is configured for use with a replaceable power source that can be discarded after each surgical procedure. Furthermore, the use of one universal handle with a plurality of surgical tool attachments may reduce the clutter and/or volume of surgical instruments within the surgical arena.

Figure 73:
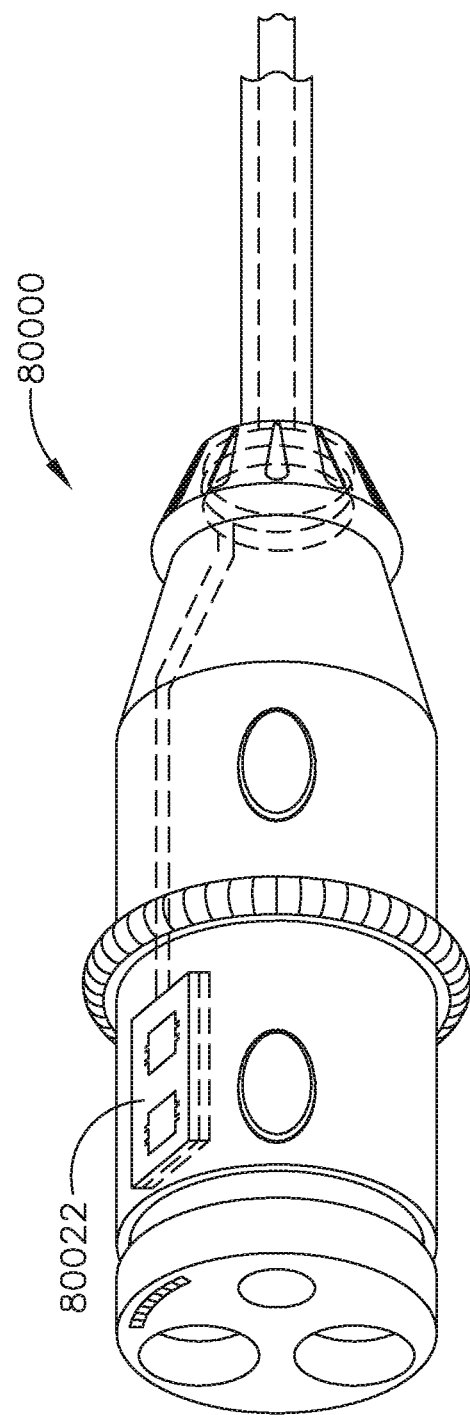
FIG. 73 is a perspective view of a portion of a surgical instrument comprising selectively attachable modular components in accordance with at least one aspect of the present disclosure.
Figure 74:
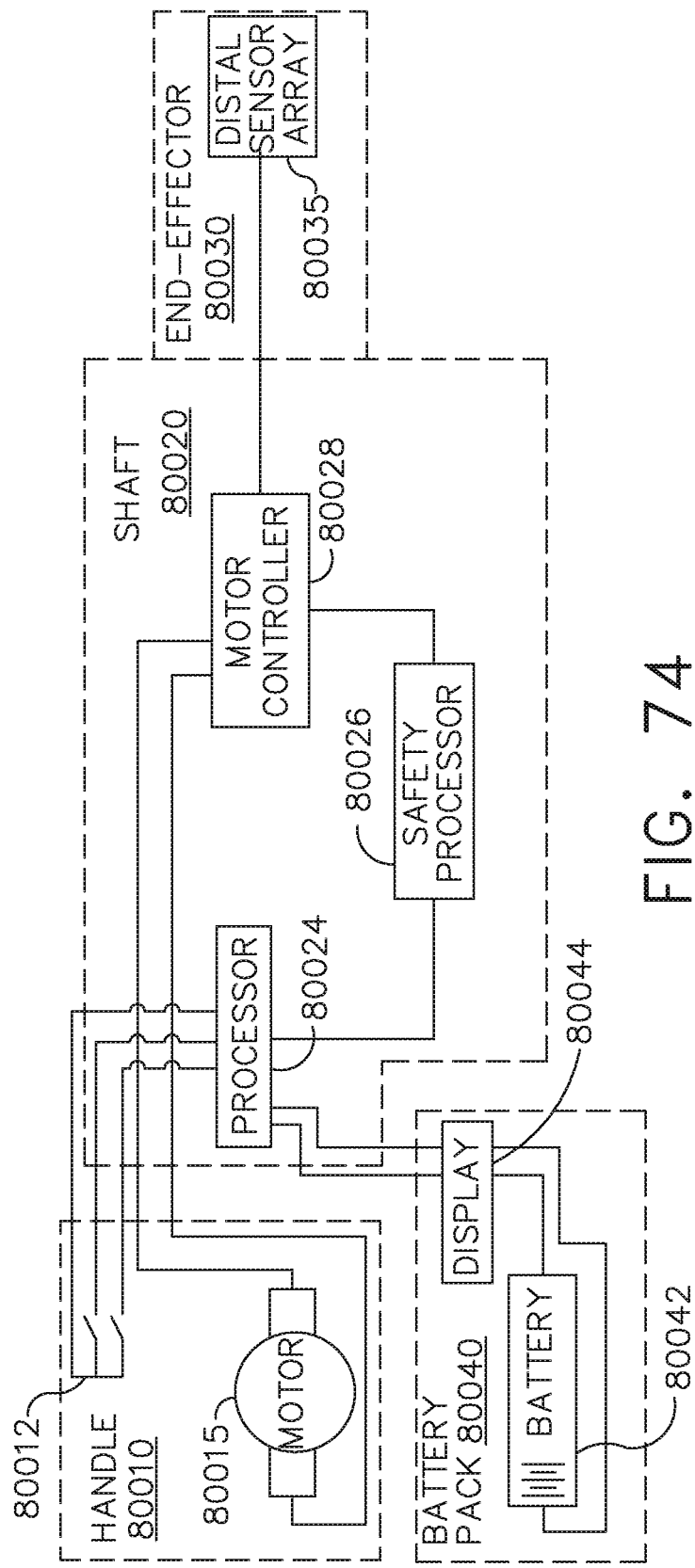
FIG. 74 illustrates an electrical architecture of the surgical instrument of FIG. 73 in accordance with at least one aspect of the present disclosure.

FIG. 73 illustrates a portion of a modular surgical instrument 80000 and FIG. 74 illustrates an electrical architecture of the modular surgical instrument 80000. The configuration of the modular surgical instrument 80000 is similar in many respects to the surgical instrument 1000 in FIG. 1 discussed above. The modular surgical instrument 80000 comprises a plurality of modular components, including, for example: a drive module 80010, a shaft 80020, an end effector 80030, and a power source 80040. In various instances, the drive module 80010 comprises a handle. The drive module 80010 comprises one or more control switches 80012 and a motor 80015.

The shaft 80020 comprises a control circuit 80022 configured to facilitate communication between the modular components 80010, 80020, 80030, 80040 of the surgical instrument 80000. The operation and functionality of the modular components 80010, 80020, 80030, 80040 of the surgical instrument 80000 are described in greater detail above in connection with other surgical instruments.

In various instances, the one or more control switches 80012 correspond to the rotation actuator 1420 and the articulation actuator 1430 of the input system 1400 as described in greater detail with respect to FIGS. 7 and 8 above. As shown in FIGS. 7 and 8, the articulation actuator 1430 comprises a first push button 1432 and a second push button 1434. The first push button 1432 comprises a first switch that is closed when the first push button 1434 is depressed. Similar in many aspects to the articulation actuator 1430 and the rotation actuator 1420 shown in FIGS. 7 and 8, the one or more control switches 80012 may comprise push buttons. When a user input depresses the push button, a switch is closed that sends a signal to the control circuit 80022 indicative of a user command. In various instances, a first push button can initiate articulation or rotation in a first direction while a second push button can initiate articulation or rotation in a second direction. The operation and functionality of these control switches 80012 are described in greater detail above.

In various instances, the shaft 80020 is configured to be disposable after being used to treat a patient. In such instances, the shaft 80020 is usable more than once on the same patient. As discussed in more detail below, the shaft 80020 comprises a processor 80024 and a memory storing instructions for one or more control programs. The disposable shaft 80020 comprises any signal processing circuits required to interface with the end effector 80030, the power source 80040, and/or the drive module 80010 when the modular surgical instrument 80000 is fully configured, or assembled. The end effector 80030 comprises a sensor array 80035 configured to monitor a parameter of the end effector 80030. Such a sensor array 80035 can detect, for example, information pertaining to the identity of the end effector 80030, an operating status of the end effector 80030, and/or information regarding the environment of the surgical site, such as tissue properties, for example. In various instances, the power source 80040 comprises a replaceable battery pack configured to be attached directly to the drive module 80010 to supply power to the surgical instrument 80000. The power source 80040 comprises a battery 80042 and a display 80044. In various instances the display 80044 comprises a touch-sensitive display, for example, wherein a user input is sent to the processor 80024.

In various instances, the drive module 80010 comprises a power source interface for attaching the modular power source 80040 thereto. The replaceable connection between the power source 80040 and the drive module 80010 allows for a user to readily change out the power source 80040 without having to disassemble a housing of the drive module 80010. The battery 80042 within the modular power source 80040 comprises a primary cell, but can also include secondary cells. The primary cell battery 80042 is configured to be fully charged once. In other words, the primary cell battery 80042 is configured to be discarded after each surgical procedure. Use of a disposable power supply may, among other things, provide assurance to the clinician that the battery 80042 is fully charged at the beginning of each surgical procedure.

The power source interface supplies the interconnection between the battery 80042 and the connection of the display 80044 upon the attachment of the power source 80040 to the drive module 80010. In other words, no continuous circuits are present within the power source 80040 until the power source 80040 is replaceably attached to the power source interface on the drive module 80010. As such, the power source 80040 can be distributed and sterilized in an uncoupled state. The ability to be in an uncoupled state permits each power source 80040 to be easily sterilized. For example, the modular power source 80040 is compatible with both ethylene oxide and gamma sterilization as no continuous circuits are present in the unattached power source 80040.

Similar to the power source 80040, the drive module 80010 does not have any continuous circuits while unattached to the shaft 80020 and the power source 80040. For at least this reason, the drive module 80010 is able to be sterilized using any desired sterilization protocol following each use. In its unattached configuration, the drive module 80010 is configured to be tolerant of full immersion during the cleaning process.

Further to the above, the control circuit 80022 of the shaft 80020 comprises a processor 80024 configured to receive a user input from the one or more control switches 80012 on the drive module 80010. The shaft 80020 further comprises a motor controller 80028 configured to control the motor 80015 within the drive module 80010 when the shaft 80020 is assembled to the drive module 80010. In various instances, the control circuit 80022 further comprises a safety processor 80024 comprising two controller-based families such as, for example, TMS570 and RM4x known under the trade name Hercules ARM Cortex R4, by Texas Instruments. The safety processor 80026 may be configured specifically for IEC 61508 and ISO 26262 safety critical applications, among others, to provide advanced integrated safety features while delivering scalable performance, connectivity, and memory options. The safety processor 80026 is configured to be in signal communication with the processor 80024 and the motor controller 80028. The motor controller 80028 is configured to be in signal communication with the sensor array 80035 of the end effector 80030 and the motor 80015 within the handle 80010. The motor controller 80028 is configured to send an electrical signal, such as, for example, a voltage signal, indicative of the voltage (or power) to be supplied to the motor 80015. The electrical signal may be determined based off of, for example, user input from the one or more control switches 80012, input received from the sensor array 80035, user input from the display 80044, and/or feedback from the motor 80015. In various instances, the motor controller 80028 may output a PWM control signal to the motor 80015 in order to control the motor 80015.

The shaft 80020 further comprises a memory configured to store control programs which, when executed, prompt the processor to, among other things, command the motor controller 80028 to activate the motor 80015 at a predetermined level. The memory within the control circuit 80022 of each shaft 80020 is configured to store one or more control programs to permit the modular surgical instrument

80000, when fully configured, to perform a desired function. In various instances, the shaft 80020 may comprise a default control program for when the attached shaft 80020 does not comprise a control program and/or a stored control program cannot be read or detected. Such a default control program permits the motor 80015 to be run at a minimum level to allow a clinician to perform basic functions of the modular surgical instrument 80000. In various instances, only basic functions of the modular surgical instrument 80000 are available in the default control program and are performed in a manner that minimizes harm to the tissue in and/or surrounding the surgical site. Storing control program(s) specific to an intended function in each replaceable shaft 80020 minimizes the amount of information that needs to be stored and, thus, relieves the drive module 80010 of the burden of storing all possible control programs, many of which go unused. In various instances, the modular components 80010, 80020, 80030, 80040 of the surgical instrument 80000 can be designed, manufactured, programmed, and/or updated at different times and/or in accordance with different software and/or firmware revisions and updates. Furthermore, individual control programs can be updated more quickly than a collection of numerous control programs. The faster update time makes it more likely that clinicians and/or assistants will update the control program(s) to utilize the most up-to-date program in each surgical procedure. In various instances, the drive module 80010 may not comprise any control programs. In other instances, the drive module 80010 may comprise a default control program as discussed above. In other words, if a clinician intends to perform a first function, the clinician may attach a first shaft comprising a stored first control program to the modular surgical instrument. If the clinician intends to perform a second function that is different from the first function, the clinician may remove the first shaft from the universal drive module and attach a second shaft comprising a stored second control program to the modular surgical instrument. In various instances, if the clinician attaches a shaft without a detectable and/or functional stored control program, the drive module 80010 may comprise a memory storing a default control program to operate the modular surgical instrument 80000 at minimum levels and/or at any suitable level of functionality. The operation and functionality of the stored control programs are described in greater detail in U.S. patent application Ser. No. 14/226,133, now U.S. Patent Application Publication No. 2015/0272557, entitled MODULAR SURGICAL INSTRUMENT SYSTEM, which is incorporated by reference in its entirety herein.

Figure 75:
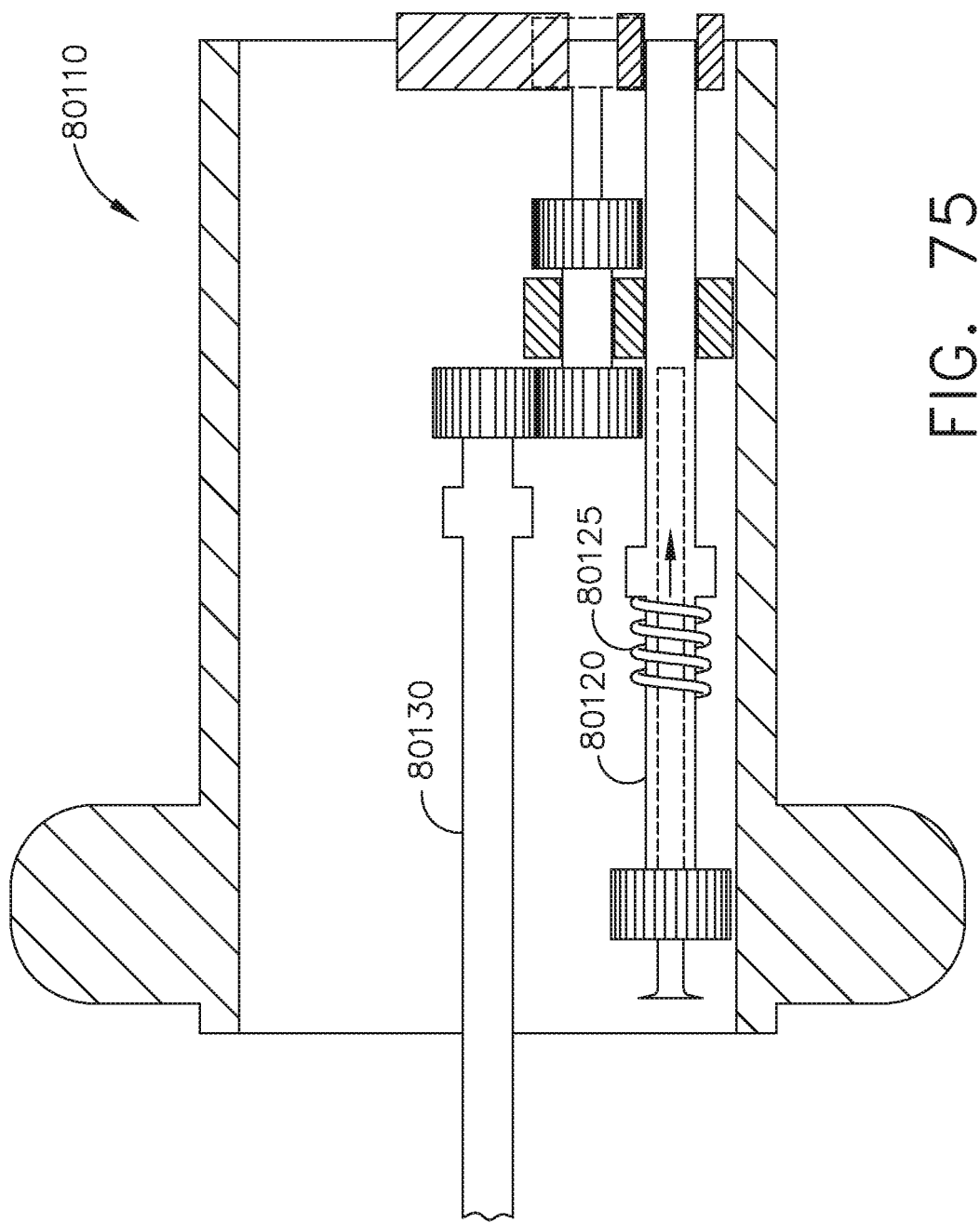
FIG. 75 is a partial cross-sectional perspective view of a handle of the surgical instrument of FIG. 73 in accordance with at least one aspect of the present disclosure.

FIG. 75 depicts a drive module 80110 comprising a plurality of drives configured to interact with corresponding drives in an attached shaft to produce a desired function, such as, for example, rotation and/or articulation of an end effector. For example, the drive module 80110 comprises a rotation drive 80120 configured to rotate an end effector upon actuation. The drive module 80110 of FIG. 75 is configured to operate based on the type of handle attached to the modular shaft. One or more of the plurality of drives is decoupled when a low-functionality handle, such as, for example, a scissor grip handle, is attached to the modular shaft. For example, during the attachment of a low-functionality handle to the modular shaft, an extending lug on the low-functionality handle may cause the rotation drive 80120 to advance distally out of engagement with the low-functionality handle. Such distal advancement results in a decoupling of the rotation drive 80120 from the handle, effectively locking out the functionality of the rotation drive 80120. Upon detachment of the scissor grip handle from the modular shaft, a resilient member 80125, such as, for example, a spring, biases the rotation drive 80120 proximally into its original position. In various instances, all of the drives are decoupled upon the attachment of the low-functionality handle to the modular shaft. In other instances, a first drive, such as, for example, the rotation drive 80120, may be decoupled upon the attachment of the low-functionality handle to the modular shaft, while a second drive 80130 remains in engagement for use with the low-functionality handle.

In various instances, the rotation drive 80120 is in communication with a manual rotation actuator, such as the rotation actuator 1420 described in more detail above with respect to FIGS. 8, 10, and 11. As a clinician rotates the rotation actuator, the position of the rotation actuator can be monitored. For instance, the surgical instrument can comprise an encoder system configured to monitor the position of the rotation actuator. In addition to or in lieu of the encoder system, the drive module 80110 can comprise a sensor system configured to detect a degree of rotation of the rotation actuator. In any event, the detected position of the rotation actuator is communicated to a processor and a motor controller, such as processor 80024 and motor controller 80028 within the shaft 80020. In various instances, the drive module 80110 comprises a handle.

The processor 80024 and the motor controller 80028 are configured to drive a system of the shaft 80020 other than the system being manually driven by the rotation drive 80120 in response to the movement of the rotation drive 80120. In at least one instance, a surgical instrument has a first rotation joint and a second rotation joint where the rotation of the surgical instrument about the first rotation joint is manually driven and the rotation of the surgical instrument about the second rotation joint is driven by an electric motor. In such an instance, the processor 80024 can monitor the rotation of the surgical instrument about the first rotation joint using the encoder and rotate the surgical instrument about the second rotation joint using the motor controller 80028 in order to keep the rotatable components of the surgical instrument aligned, for example.

Figure 76:
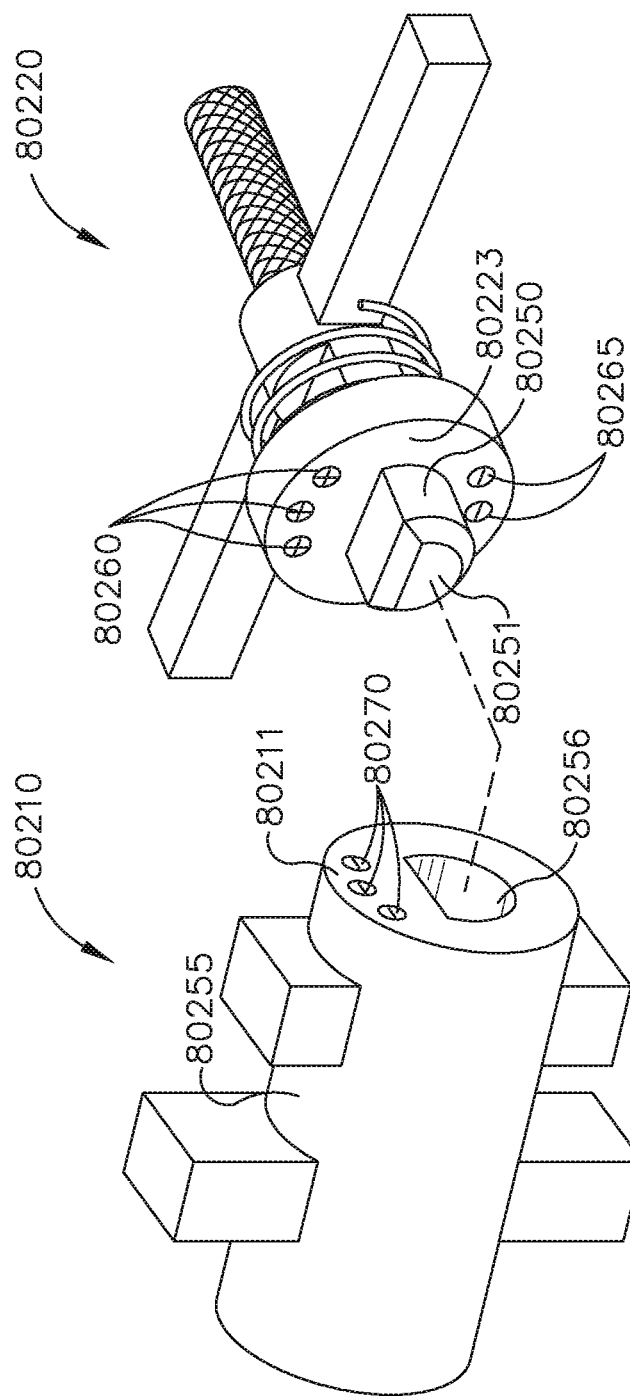
FIG. 76 is a perspective view of a system of magnetic elements arranged on the handle and a shaft of the surgical instrument of FIG. 73 in accordance with at least one aspect of the present disclosure.

FIG. 76 depicts a handle 80210 prior to engagement with an interchangeable shaft 80220. The handle 80210 is usable with several interchangeable shafts and can be referred to as a universal handle. The shaft 80220 comprises a drive rod 80250 configured to mechanically engage a distal nut 80255 of the handle 80210. A proximal end 80251 of the drive rod 80250 comprises a specific geometry configured to fit within a recess 80256 defined in the distal end of the distal nut 80255. The recess 80256 within the distal nut 80255 comprises a geometry that is complementary of the geometry of the proximal end 80251 of the drive rod 80250. In other words, once the clinician and/or the assistant has oriented the shaft 80220 in a manner that allows for the drive rod 80250 to fit within the recess on the distal nut 80255 of the handle 80210, the interchangeable shaft 80220 is successfully aligned with the universal handle 80210 such that there is little, if any, relative lateral movement between the distal nut 80255 and the drive rod 80250.

In various instances, the distal end 80211 of the drive nut 80255 and the proximal end 80223 of the drive rod 80250 comprise a plurality of magnetic elements 80260, 80265, 80270 configured to facilitate alignment of the shaft 80220 with the handle 80210 in addition to or in lieu of the mechanical alignment system described above. The system of magnetic elements 80260, 80265, 80270 allows for self-alignment of the shaft 80220 with the handle 80210. In various instances, the plurality of magnetic elements 80260, 80265, 80270 are permanent magnets. As seen in FIG. 75, the proximal end 80223 of the shaft 80220 comprises a plurality of magnetic elements 80260, 80265 that are oriented asymmetrically, although the magnetic elements 80260, 80265 may be arranged in any suitable manner. The magnetic elements 80260, 80265 are positioned with opposing poles facing outward from the proximal end 80223 of the shaft 80220. More specifically, the magnetic elements 80260 positioned on a first portion of the shaft 80220 are positioned with their positive poles facing outward from the proximal end 80223, while the magnetic elements 80265 positioned on a second, or opposite, portion of the shaft 80220 are positioned with their negative poles facing outward from the proximal end 80223. The distal end 80211 of the drive nut 80255 comprises a plurality of magnetic elements 80270 positioned with their negative poles facing outward from the distal end 80211 of the handle 80210. Such an asymmetric pattern of magnetic elements 80260, 80265 on the shaft 80220 can permit the shaft 80220 and the handle 80210 to be aligned at one or more predefined locations, as described in greater detail below. The use of magnetic elements 80260, 80265, 80270 eliminates the need for a spring mechanism to shift the handle 80210 and the shaft 80220 into predetermined positions.

Further to the above, if the clinician attempts to align the handle 80210 with the shaft 80220 such that the magnetic elements 80270 positioned on the handle 80210 are within the vicinity of the magnetic elements 80260 positioned on a first portion of the shaft 80220, the magnetic elements 80260, 80270 produce an attractive magnetic force, thereby pulling the modular components 80210, 80220 into alignment. However, if the clinician attempts to align the handle 80210 with the shaft 80220 such that the magnetic elements 80270 positioned on the handle 80210 are closer in vicinity to the magnetic elements 80265 positioned on a second portion of the shaft 80220, a repulsive magnetic force will push the modular components 80210, 80220 apart, thereby preventing an improper connection between the handle 80210 and the shaft 80220.

In certain instances, further to the above, only one stable position will exist between the modular components. In various instances, a plurality of magnetic elements are positioned so that their poles alternate in a repeating pattern along the outer circumferences of the distal end of the handle 80210 and the proximal end of the shaft 80220. Such a pattern can be created in order to provide for a plurality of stable alignment positions. The repeating pattern of magnetic elements allows for a series of stable alignments between the shaft and the handle, as an attractive magnetic force draws the modular components 80210, 80220 together at numerous positions. In various instances, the plurality of magnetic elements are oriented in a way to create a bi-stable magnetic network. Such a bi-stable network ensures that the modular components 80210, 80220 end in a stable alignment even when the modular components 80210, 80220 are initially misaligned. In other words, when the handle 80210 and the shaft 80220 are misaligned, the magnetic fields created by the plurality of magnetic elements interact with one another to initiate rotation out of the misaligned position and into the next closest stable alignment. Thus, the repulsive magnetic force experienced by misaligned modular components 80210, 80220 assists in transitioning the modular components 80210, 80220 into alignment. As the modular components 80210, 80220 are pushed apart by the repulsive magnetic force, they rotate into an attractive magnetic field thereby aligning the handle 80210 and the shaft 80220. In various instances, the repulsive magnetic force initiates rotation of the handle with respect to the shaft and vice versa. The pattern of the orientation of the magnetic elements can direct the modular components 80210, 80220 to rotate in a particular direction with respect to one another while also preventing rotation in the opposite direction. For example, in various instances, the magnetic elements are oriented in a pattern that allows for the shaft 80220 and the handle 80210 to achieve alignment by rotating with respect to one another only in a clockwise direction when a repulsive magnetic force is experienced. In other instances, the magnetic elements are oriented in a pattern that allows for the shaft 80220 and the handle 80210 to reach alignment by rotating with respect to one another only in a counterclockwise direction when a repulsive magnetic force is experienced. In various instances, the magnetic elements can impact the speed with which the modular components are brought into alignment. For example, magnetic elements can be arranged based on the strength of their magnetic fields in order to cause acceleration or deceleration into or out of alignment. While the plurality of magnetic elements 80260, 80265, 80270 are described above as being permanent magnets, in certain instances, the plurality of magnetic elements 80260, 80265, 80270 are electromagnets. In such instances, magnetic repulsive and attractive forces can be created by selectively energizing the plurality of magnetic elements 80260, 80265, 80270.

In various instances, the handle 80210 and the shaft 80220 comprise a dominant magnetic element that provides an initial attractive magnetic force, wherein the dominant magnetic elements are configured to pull the modular components 80210, 80220 closer together. After the modular components 80210, 80220 are drawn together by the dominant magnetic elements, the plurality of magnetic elements 80260, 80265, 80270 are configured to finely adjust the orientations of the handle 80210 and the shaft 80220.

Figure 77:
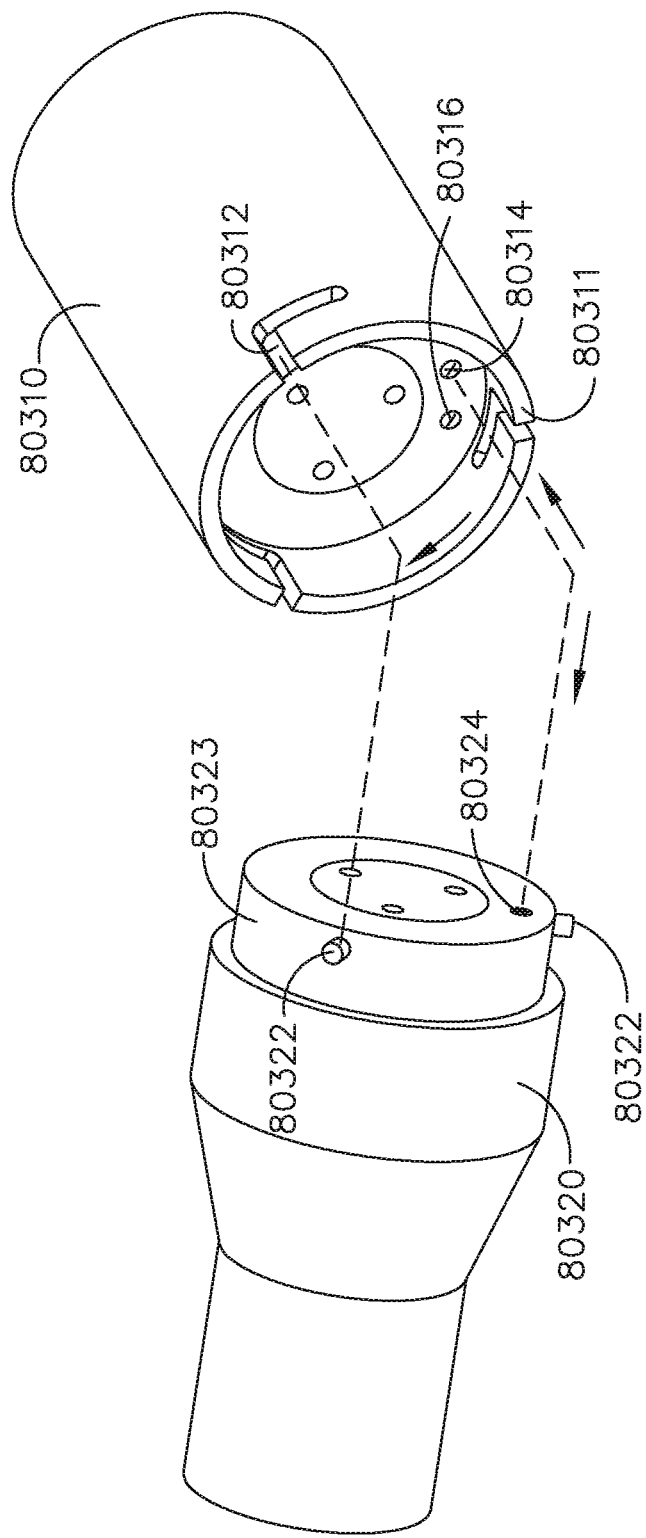
FIG. 77 is a perspective view of a system of magnetic elements arranged on the handle and the shaft of the surgical instrument of FIG. 73 in accordance with at least one aspect of the present disclosure.
Figure 78:
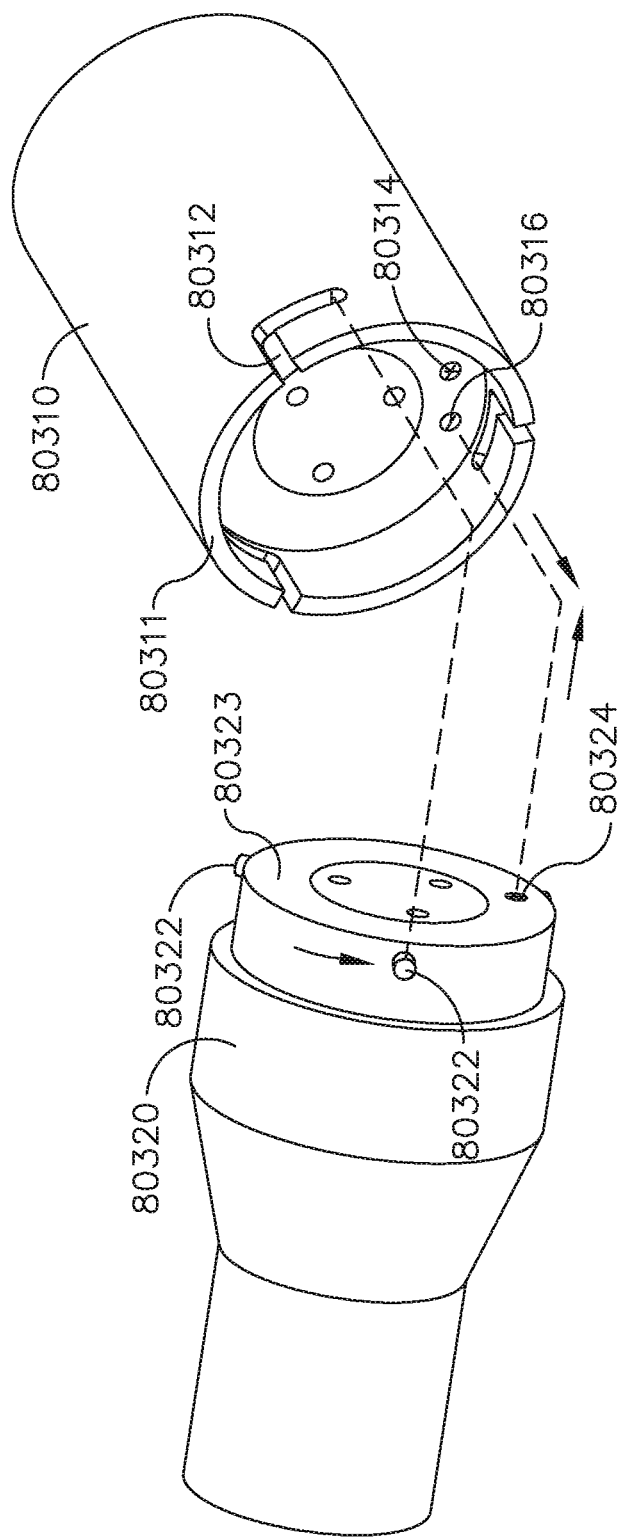
FIG. 78 is a perspective view of the system of magnetic elements of FIG. 77 aligning the shaft with the handle of the surgical instrument in accordance with at least one aspect of the present disclosure.

FIG. 77 depicts a universal handle 80310 prior to being aligned with and attached to a shaft 80320. The proximal end 80323 of the shaft 80320 comprises a pin 80322 configured to engage an L-shaped, or bayonet, slot 80312 cut into the distal end 80311 of the handle 80310. In various instances, a plurality of L-shaped slots 80312 may be cut around the circumference of the distal end 80311 to provide additional attachment support for additional pins 80322. The proximal end 80323 of the shaft 80320 further comprises a frame and a shaft magnetic element 80324 positioned in the frame with its positive pole facing outward. The distal end 80311 of the handle 80310 further comprises a first magnetic element 80314 and a second magnetic element 80316. The first magnetic element 80314 is oriented with its positive pole facing outwardly, and the second magnetic element 80316 is oriented with its negative pole facing outwardly. As the clinician begins aligning the pin 80322 of the shaft 80320 with its corresponding L-shaped slot 80312 in the handle 80310, the first magnetic element 80314 and the shaft magnetic element 80324 interact to produce a repulsive magnetic force. The clinician must overcome this force in order to engage the pin 80322 with the L-shaped slot 80312. Once the pin 80322 is within the L-shaped slot 80312 and/or once the shaft magnetic element 80324 is moved past a threshold distance with respect to the first magnetic element and the second magnetic element 80314 and 80324, the clinician can begin to manually rotate the modular components 80310, 80320 with respect to one another. In addition, as shown in FIG. 78, once the clinician has overcome the repulsive magnetic force to position the pin 80322 within the L-shaped slot 80312, the magnetic elements 80324, 80316 can react to create an attractive magnetic force once the shaft magnetic element 80324 is past the threshold. The attractive magnetic force results in rotation of the shaft 80320 with respect to the handle 80310 and full engagement of the pin 80322 into the L-shaped slot 80312. In such instances, the interaction between the magnetic fields of the shaft magnetic element 80324 and the second magnetic element 80316 on the handle 80310 is strong enough to pull and/or hold the modular components 80310, 80320 together. In various instances, such interaction results in an attractive magnetic force between the shaft magnetic element 80324 and the second magnetic element 80316, resulting in alignment of the modular components 80310, 80320 and full engagement of the pin 80322 within the L-shaped slot 80312. While the orientations of the magnetic elements are specifically described, it is envisioned that the magnetic elements can be oriented in any suitable manner. While the plurality of magnetic elements 80314, 80316, 80324 are described above as being permanent magnets, in certain instances, the plurality of magnetic elements 80314, 80316, 80324 are electromagnets. In such instances, magnetic repulsive and attractive forces can be created by selectively energizing the plurality of magnetic elements 80314, 80316, 80324.

The magnetic elements described above can comprise electromagnets, permanent magnets, or a combination thereof. In instances, such as those described above, a system of permanent magnetic elements may align the shaft and the handle in a plurality of positions. In such instances, an electromagnet can be added to the system of permanent magnetic elements. When activated, the electromagnet is configured to exert a stronger magnetic field than the magnetic fields within the system of permanent magnetic elements. In other words, an electromagnet may be incorporated in order to interrupt, thwart, and/or change the cooperation between the system of permanent magnets. Such an interruption results in the ability to exert selective control over the alignment of the modular components of the surgical instrument. For example, when a system of magnetic elements, such as the magnetic elements 80260, 80265, 82070 in FIG. 76, have drawn the shaft 80220 and the handle 80210 together in a suitably aligned position, a clinician may selectively activate an electromagnet to produce a magnetic field strong enough to overcome the attractive magnetic forces of the permanent magnets and repel the shaft away from the handle. In various instances, activation of the electromagnet repels the handle away from the shaft to release or unlock the shaft from the handle. In various instances, the activation of the electromagnet is configured to not only disrupt the attraction created by the permanent magnets but also to decouple the modular components 80210, 80220.

A modular surgical instrument, such as the surgical instrument 80000 shown in FIG. 73, for example, comprises a plurality of components configured to communicate with one another in order to perform an intended function of the surgical instrument. The communication pathways between the components of the modular surgical instrument are described in detail above. While such communication pathways can be wireless in nature, wired connections are also suitable. In various instances, the end effector and/or shaft of the surgical instrument are configured to be inserted into a patient through a trocar, or cannula, and can have any suitable diameter, such as approximately 5 mm, 8 mm, and/or 12 mm, for example. In addition to size constraints, various modular surgical instruments, such as, for example, a clip applier, comprise end effectors and/or shafts that are configured to rotate and/or articulate, for example. Thus, any wired communication pathway must be compact and have flexibility in order to maintain functionality as the end effector and/or shaft is rotated and/or articulated. In an effort to reduce the size of operational elements within a shaft and/or end effector of a surgical instrument, various micro electro-mechanical functional elements may be utilized. Incorporating micro-electronics such as, for example, a piezo inchworm actuator or a squiggle motor into a surgical instrument assists in reducing the space needed for operational elements, as a squiggle motor, for example, is configured to deliver linear movement without gears or cams.

In various instances, flexibility is built into the wired communication pathway(s) by mounting various electrical traces on a flexible substrate. In various instances, the electrical traces are supported on the flexible substrate in any suitable manner. FIG. 79 depicts a flex circuit 80400 for use in a modular surgical instrument, such as the surgical instrument 1000, for example. The flex circuit 80400 is configured to extend within a housing of a shaft, such as the shaft 80020 of FIG. 73. A distal end 80401 of the flex circuit 80400 is configured to be electrically coupled with conductive electrical traces within an end effector. In at least one instance, the electrical traces are comprised of copper and/or silver, for example. The distal end 80401 is wrapped into a first ring 80402, and the electrical traces 80405 extend around the first ring 80402. A proximal end 80403 of the flex circuit 80400 is configured to be electrically coupled with electrical traces within a handle. The proximal end 80403 is wrapped into a second ring 80404, and the electrical traces 80405 extend around the second ring 80404.

Figure 79A:
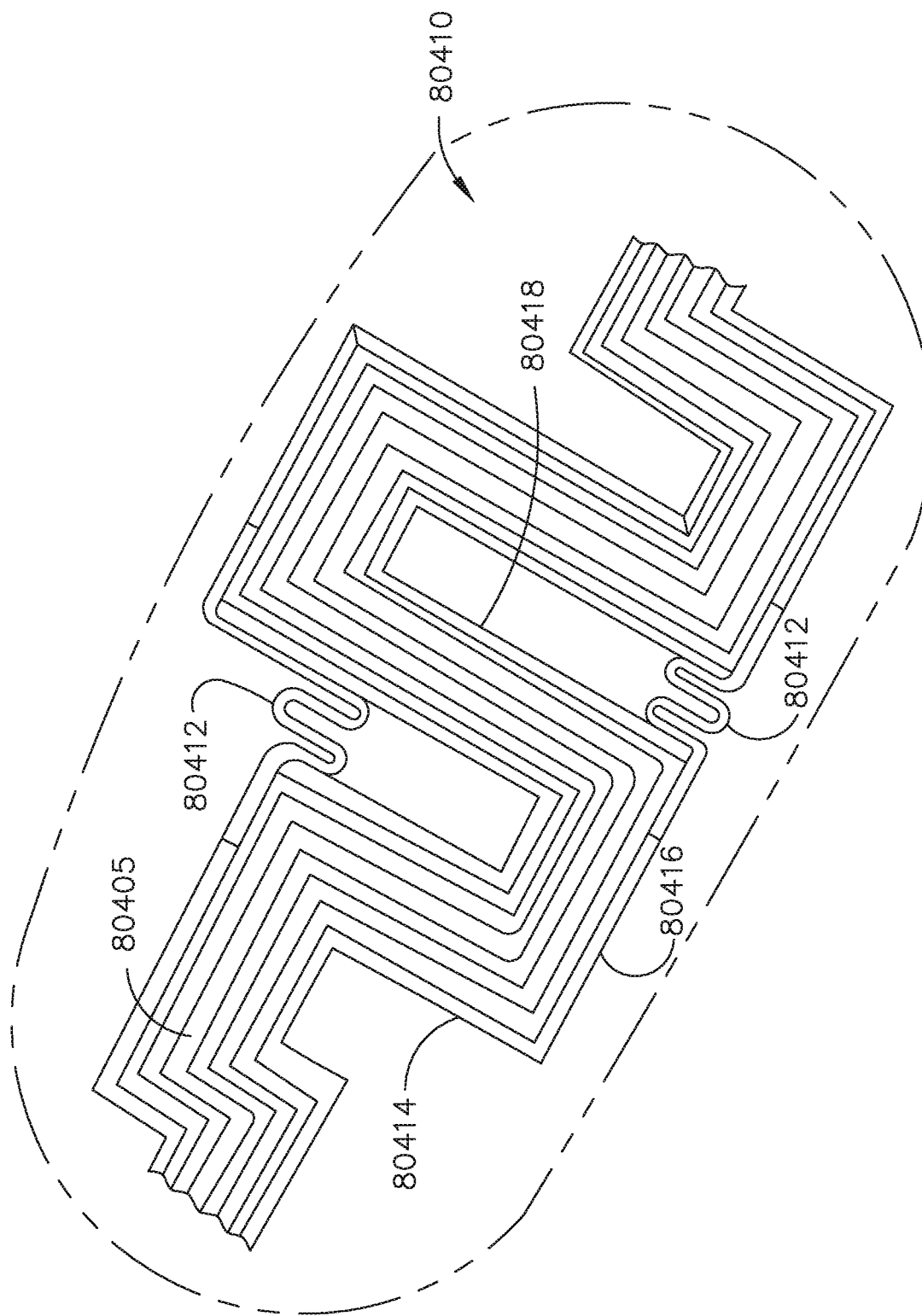
FIG. 79A is a detail perspective view of a primary strain relief portion of the flex circuit of FIG. 79 in accordance with at least one aspect of the present disclosure.

While supporting various electrical traces on the flexible substrate provides for flexibility, additional features may be added to, among other things, increase the longevity of and/or protect the integrity of the flex circuit 80400. As depicted in FIGS. 79 and 79A, a primary strain relief region 80410 is configured to be positioned proximally to an articulation joint. The primary strain relief region 80410 of the flex circuit 80400 experiences the most displacement and/or twisting in response to articulation of the surgical instrument. In an effort to, for example, relieve the strain on the flex circuit 80400 while the surgical instrument is articulated and/or assist the portion of the flex circuit 80400 within the primary strain relief region 80410 to return to its original orientation after the surgical instrument is unarticulated, one or more biasing and/or resilient members 80412 are present for resiliency and/or flexibility. The one or more biasing members 80412 are configured to transition between a flexed state and an un-flexed state, as the surgical instrument is articulated and/or rotated. In various instances, the biasing members 80412 comprise springs. The biasing members 80412 are incorporated into the substrate of the flex circuit 80400 in an effort to, for example, accommodate for motions of surrounding parts. The portion of the flex circuit 80400 within the primary strain relief region 80410 comprises a pattern comprising a first leg 80414, a base 80416, and a second leg 80418. The base 80416 extends between the first leg 80414 and the second leg 80418. The biasing member 80412 extends between and connects the first leg 80414 and the second leg 80418. The biasing member 80412, among other things, permits the first leg 80414 to be deflected relative to the second leg 80418 and then resiliently returns to its unflexed state. The biasing member 80412 is configured to flex into the flexed state when an end effector is articulated, and the biasing member 80412 is configured to resiliently return to the un-flexed state when the end effector is no longer articulated.

Figure 79B:
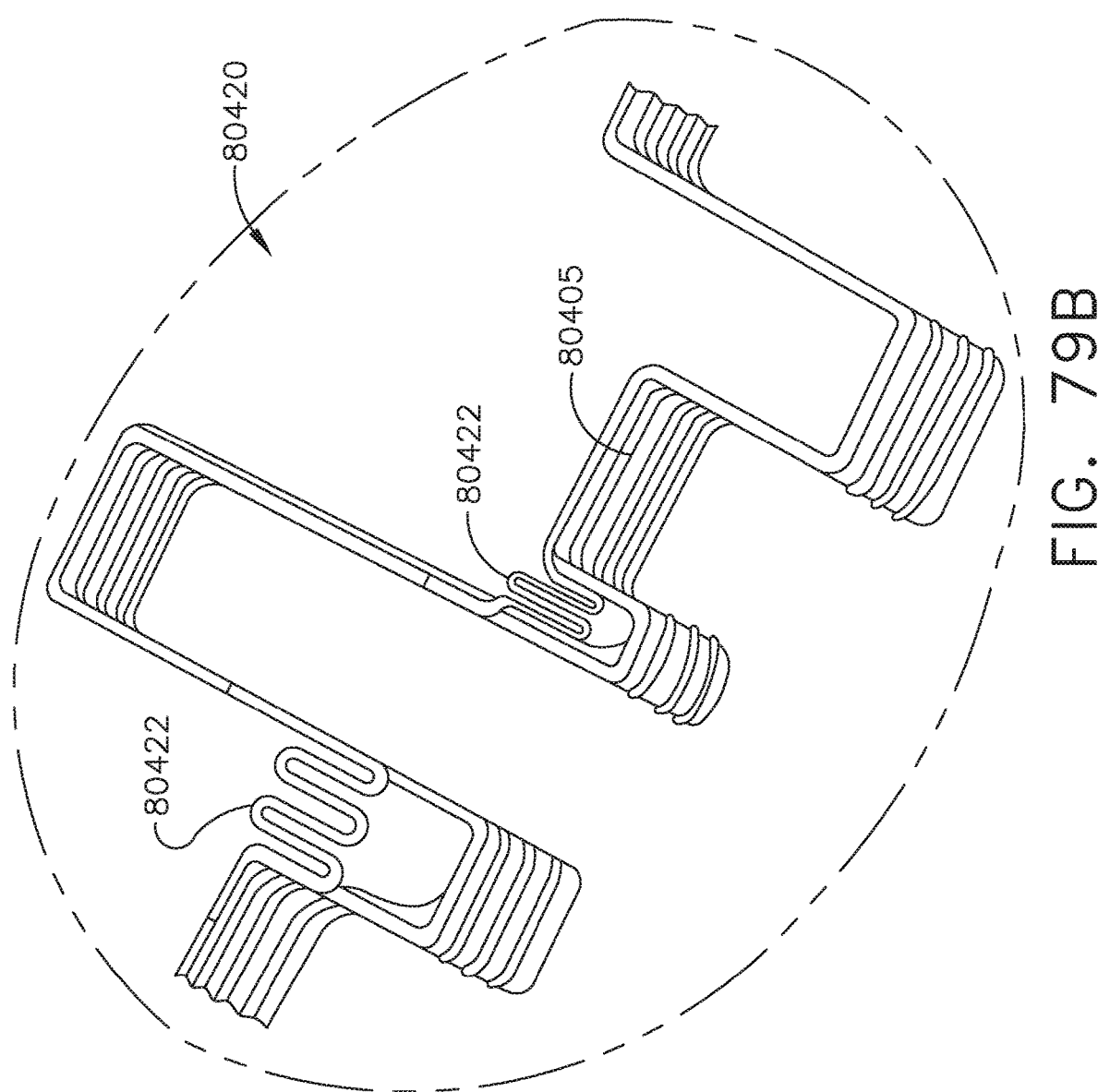
FIG. 79B is a detail perspective view of a secondary strain relief portion of the flex circuit of FIG. 79 in accordance with at least one aspect of the present disclosure.

As seen in FIGS. 79 and 79B, the flex circuit 80400 is manufactured with a secondary strain relief region 80420 whose conductive elements 80405 are separate and not interconnected. Such orientation of the conductive elements 80405 allows for the flex circuit 80400 to be folded. The non-fatiguing and flexible portions of the flex circuit 80400 are positioned perpendicular to the flex circuit 80400 within the primary strain relief region 80410. The secondary strain relief region 80420 comprises one or more biasing members 80422, similar to the biasing members 80412 described in greater detail above. The presence of biasing members 80412 within the primary strain relief region 80410 and the biasing members 80422 within the secondary strain relief portion 80320 allows the flex circuit 80400 to have a stretchable portion in at least two separate planes relative to a longitudinal axis of the shaft, such as the shaft 80020 of FIG. 73, for example. The presence of the primary strain relief portion 80410 in a first plane and a secondary strain relief portion 80320 in a second plane allows for communication between an end effector, a shaft assembly, and a handle of a surgical instrument configured to articulate the end effector, rotate the end effector, and rotate the shaft assembly. In another instance, the flex circuit 80400 can be manufactured flat and subsequently twisted in a portion, such as the primary strain relief region 80410, which correlates to the articulating or actuating portion of the surgical instrument. Such a design may mitigate the need for stress relief of the flex circuit 80400 in general.

Figure 79C:
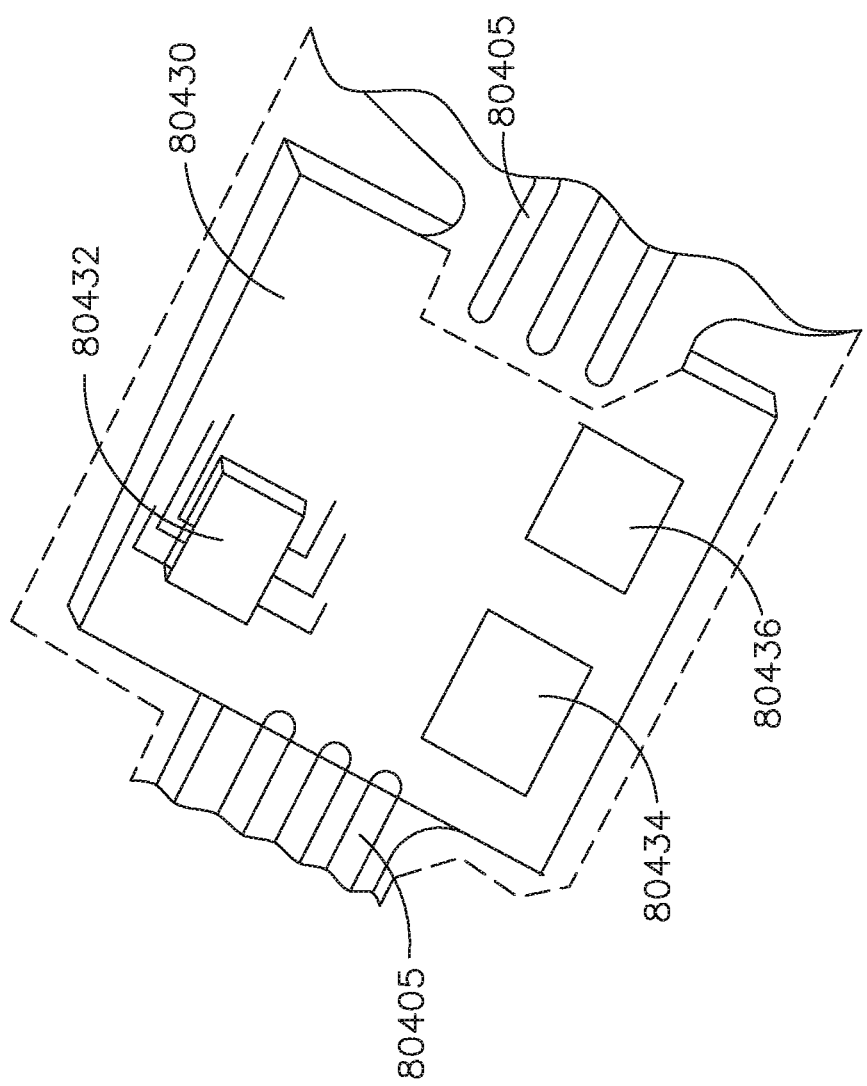
FIG. 79C is a detail perspective view of control circuit components incorporated into a flexible plastic of the flex circuit of FIG. 79 in accordance with at least one aspect of the present disclosure.

FIG. 79C depicts a portion of the flex circuit 80400 of FIG. 79 characterized by a printed circuit board (PCB) integrally formed with the flexible substrate 80430 of the flex circuit 80400. As shown in FIG. 79C, flexible plastic is over molded onto the conductive elements 80405 and various control circuit components 80432, 80434, 80436 are integrally formed with the flexible substrate 80430 of the flex circuit 80400.

Figure 80:
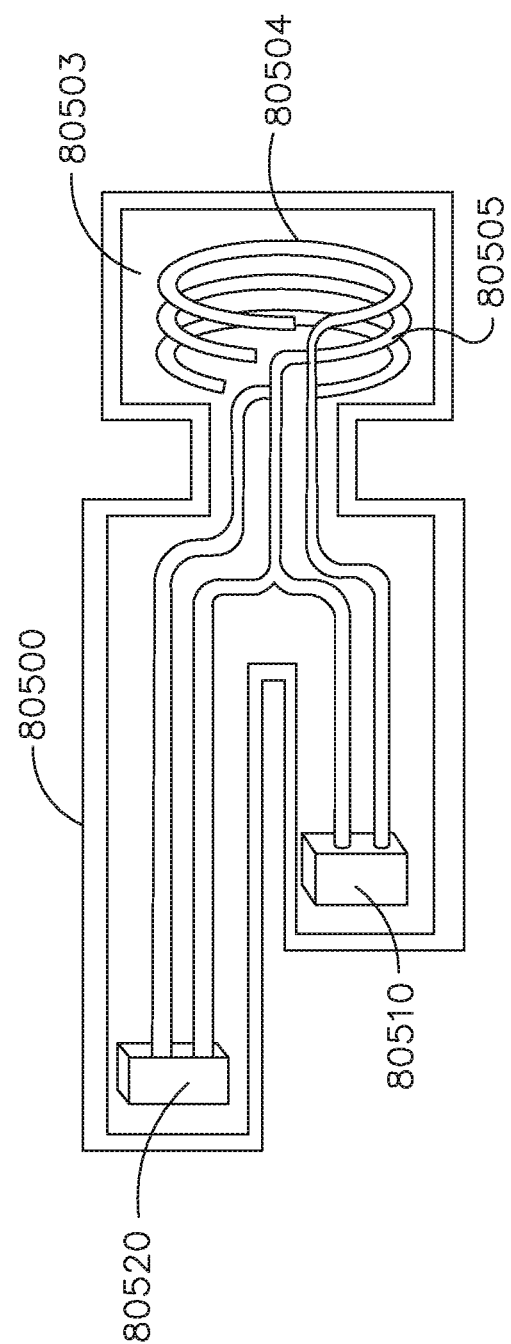
FIG. 80 is a perspective view of a flex circuit for use in combination with the flex circuit of FIG. 79 in accordance with at least one aspect of the present disclosure.
Figure 81A:
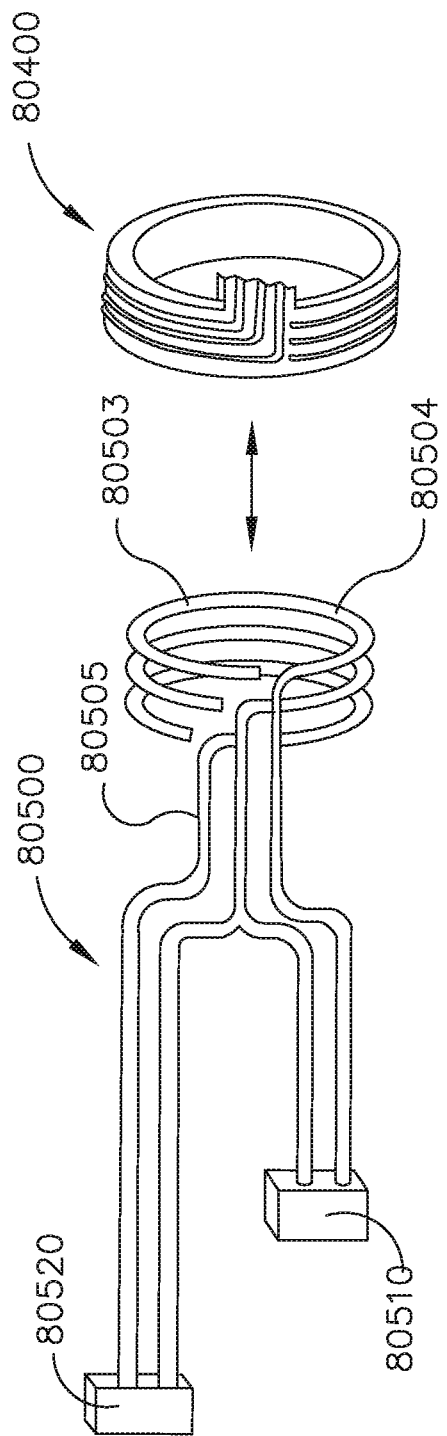
FIG. 81A is a perspective view of the flex circuit of FIG. 79 prior to being electrically coupled with the flex circuit of FIG. 80 in accordance with at least one aspect of the present disclosure.
Figure 81B:
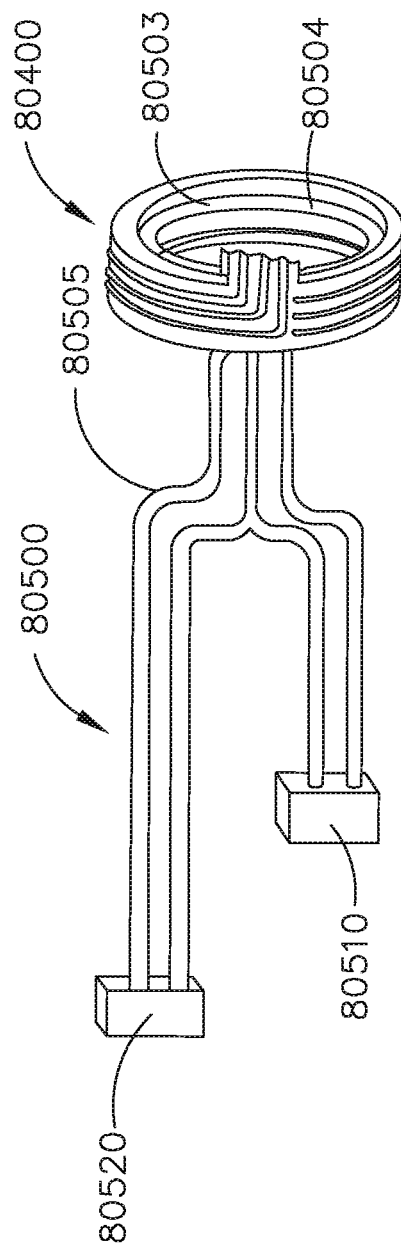
FIG. 81B is a perspective view of the flex circuit of FIG. 79 electrically coupled to the flex circuit of FIG. 80 in accordance with at least one aspect of the present disclosure.

FIG. 80 depicts an end effector flex circuit 80500 configured to extend within an end effector. The end effector flex circuit 80500 is configured to be used with a shaft flex circuit, such as, for example, the flex circuit 80400 shown in FIGS. 79-79C. The end effector flex circuit 80500 comprises electrical traces 80505 supported on a flexible substrate. A distal end 80503 of the end effector flex circuit 80500 is wrapped into a ring 80504. The electrical traces 80505 extend around the ring 80504. As shown in FIGS. 81A and 81B, the ring 80504 is configured to be electrically coupled with the shaft flex circuit, for example, via the first ring 80402 on the distal end 80401 of the flex circuit 80400. One or both of the flex circuits 80400 and 80500 comprise biasing members to maintain electrical contact between the traces at the interface between the flex circuits 80400, 80500. In various instances, the end effector flex circuit 80500 comprises one or more sensors, such as, for example, a clip feed sensor 80510 and/or a clip cam form sensor 80520. Such sensors can detect a parameter of the end effector and communicate the detected parameter to the control circuit components 80432, 80434, 80436 on the shaft flex circuit 80400. In various instances, the control circuit is positioned within a handle of the surgical instrument.

Figure 82:
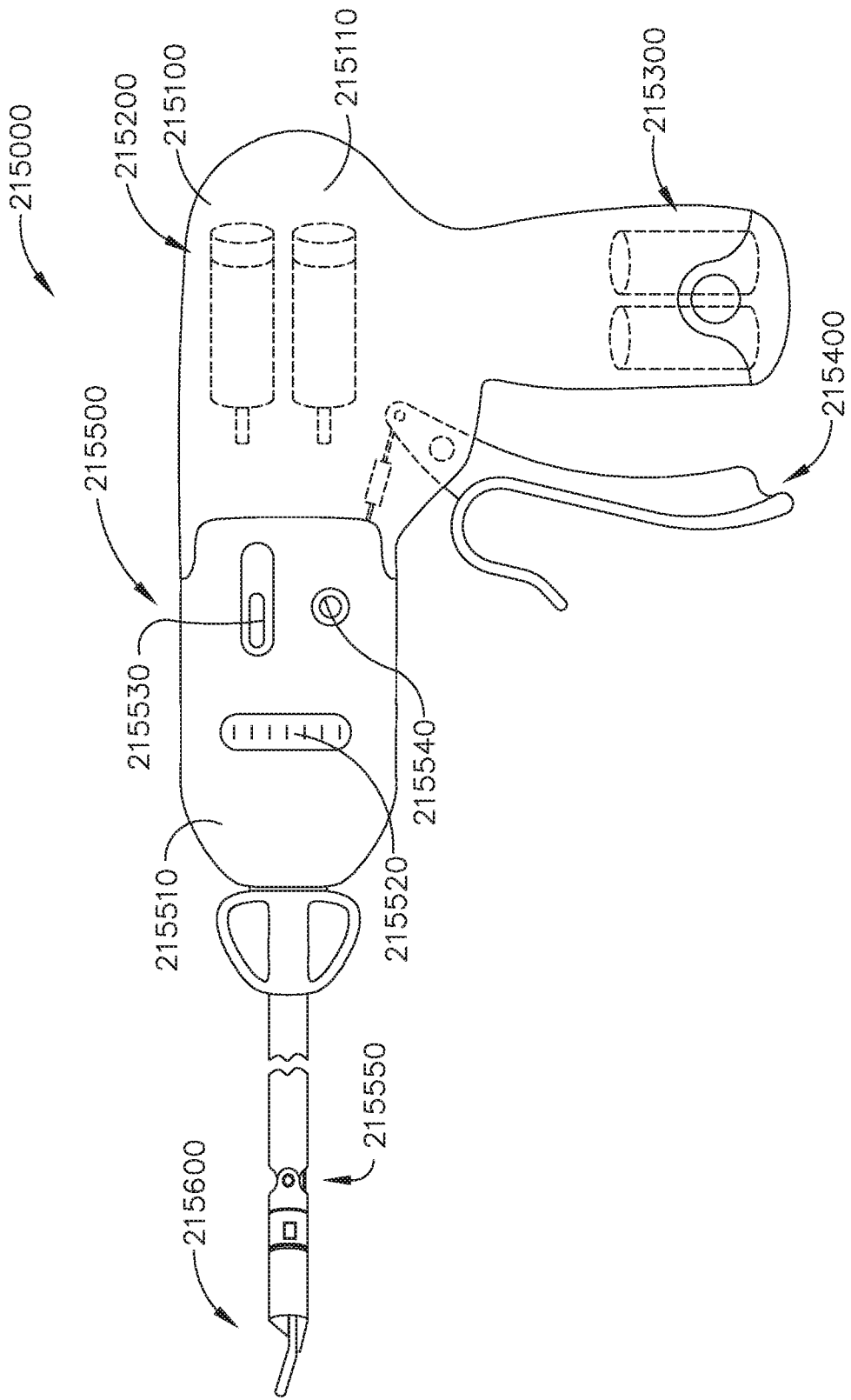
FIG. 82 is an elevational view of a surgical instrument in accordance with at least one embodiment.
Figure 83:
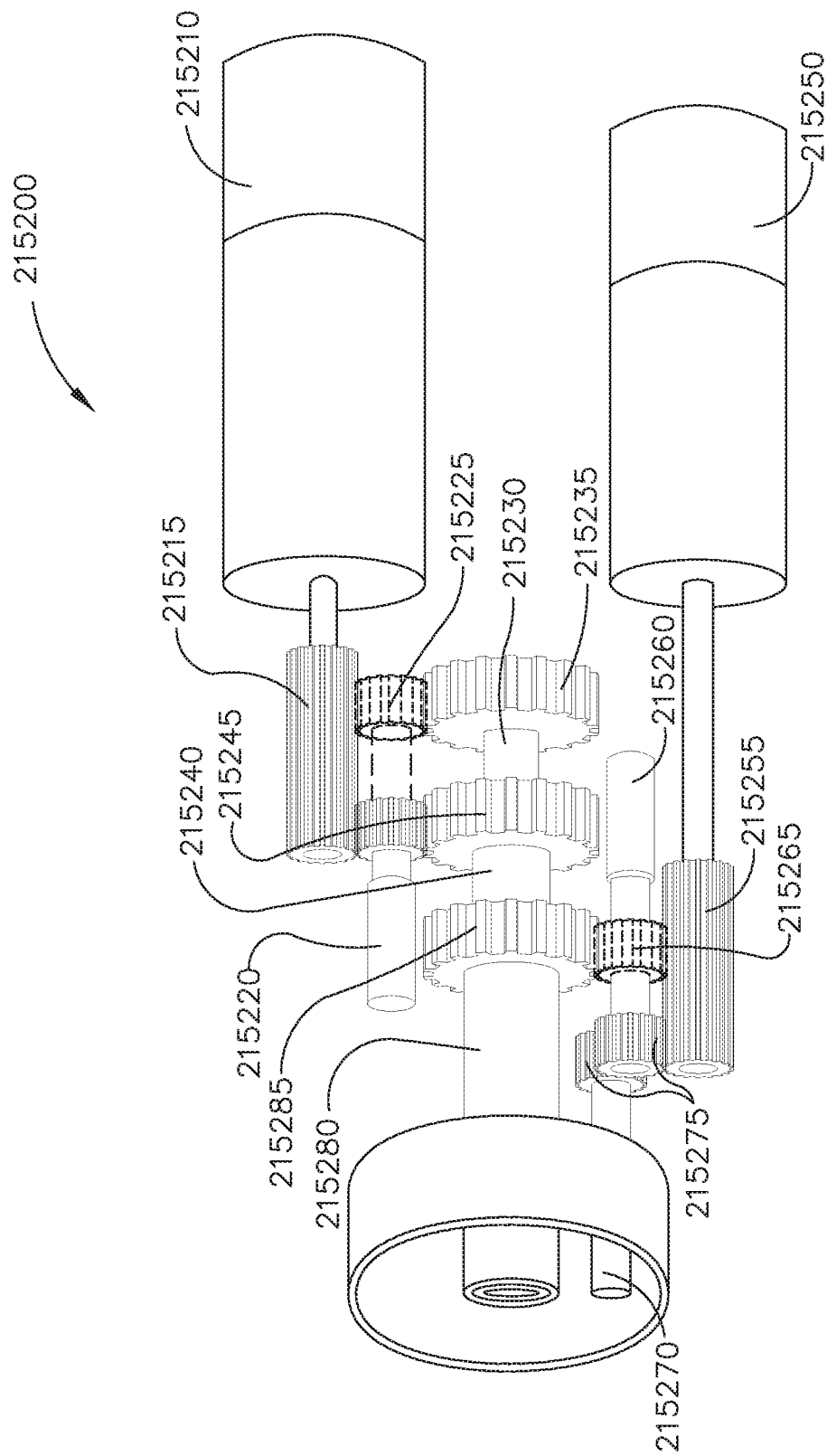
FIG. 83 is a perspective view of a drive system of the surgical instrument of FIG. 82.

Referring to FIG. 82, a surgical instrument 215000 comprises a handle 215100, a shaft assembly 215500 attached to the handle 215100, an end effector 215600, and an articulation joint 215550 rotatably connecting the end effector 215600 to the shaft assembly 215500. The handle 215100 includes a drive system 215200, a power supply 215300, and an actuator 215400. The actuator 215400 is part of a closure drive configured to close the end effector 215600. Referring to FIG. 83, the drive system 215200 comprises a first drive motor 215210, a first shifter motor 215220, a second drive motor 215250, and a second shifter motor 215260. The first drive motor 215210 comprises a rotatable input shaft and an input gear 215215 fixedly mounted to the rotatable input shaft. The first shifter motor 215220 comprises a shifter shaft and a pinion gear 215225 rotatably mounted to the shifter shaft. The pinion gear 215225 is operably intermeshed with the input gear 215215 of the first drive motor 215210 and is translatable between first and second positions by the first shifter motor 215220. When the pinion gear 215225 is in its first position, the pinion gear 215225 is operably intermeshed with the input gear 215215 and an output gear 215235 fixedly mounted to a rotatable output shaft 215230. In such instances, the rotation of the first drive motor 215210 is transferred to the rotatable output shaft 215230 when the first drive motor 215210 is operated. When the pinion gear 215225 is in its second position, the pinion gear 215225 is operably intermeshed with the input gear 215215 and an output gear 215245 fixedly mounted to a rotatable output shaft 215240. In such instances, the rotation of the first drive motor 215210 is transferred to the rotatable output shaft 215240 when the first drive motor 215210 is operated. Notably, the pinion gear 215225 is not engaged with the output gears 215235 and 215245 at the same time and, as a result, the first drive motor 215210 can be used to drive two separate functions of the surgical instrument 215000. In use, a user of the surgical instrument 215000, and/or a control system of the surgical instrument 215000, can select between the two functions by shifting the first shifter motor 215220.

Further to the above, the second drive motor 215250 comprises a rotatable input shaft and an input gear 215255 fixedly mounted to the rotatable input shaft. The second shifter motor 215260 comprises a shifter shaft and a pinion gear 215265 rotatably mounted to the shifter shaft. The pinion gear 215265 is operably intermeshed with the input gear 215255 of the second drive motor 215250 and is translatable between first and second positions by the second shifter motor 215260. When the pinion gear 215265 is in its first position, the pinion gear 215265 is operably intermeshed with the input gear 215255 and an output gear 215275 fixedly mounted to a rotatable output shaft 215270. In such instances, the rotation of the second drive motor 215250 is transferred to the rotatable output shaft 215270 when the second drive motor 215250 is operated. When the pinion gear 215265 is in its second position, the pinion gear 215265 is operably intermeshed with the input gear 215255 and an output gear 215285 fixedly mounted to a rotatable output shaft 215280. In such instances, the rotation of the second drive motor 215250 is transferred to the rotatable output shaft 215280 when the second drive motor 215250 is operated. Notably, the pinion gear 215265 is not engaged with the output gears 215275 and 215285 at the same time and, as a result, the second drive motor 215250 can be used to drive two separate functions of the surgical instrument 215000. In use, a user of the surgical instrument 215000, and/or a control system of the surgical instrument 215000, can select between the two functions by shifting the second shifter motor 215260.

Further to the above, referring again to FIG. 83, the output shafts 215230, 215240, and 215280 comprise rigid shafts and are concentrically nested. In various instances, a bearing is present between the output shaft 215230 and the output shaft 215240 and another bearing is present between the output shaft 215240 and the output shaft 215280. In other instances, the output shafts 215230, 215240, and 215280 are directly supported by one another. Such arrangements can provide a compact design. In various alternative embodiments, none of the output shafts 215230, 215240, and 215280 are nested.

Figure 84:
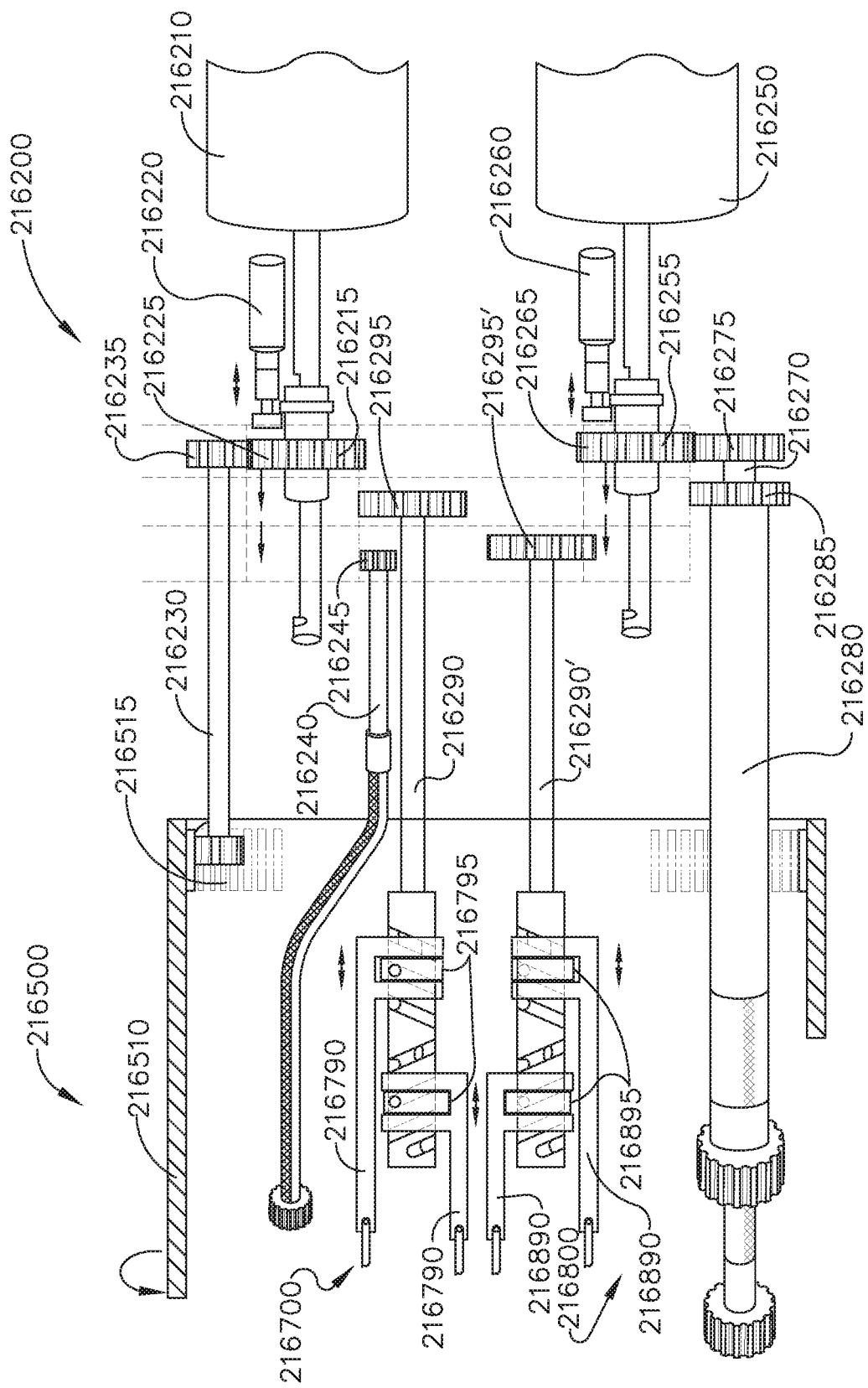
FIG. 84 is a perspective view of a drive system in accordance with at least one embodiment.

Referring to FIG. 84, an alternative drive system 216200 is configured to drive a total of six functions of a surgical instrument. Similar to the above, the drive system 216200 comprises a first drive motor 216210, a first shifter motor 216220, a second drive motor 216250, and a second shifter motor 216260. The first drive motor 216210 comprises a rotatable input shaft and an input gear 216215 fixedly mounted to the rotatable input shaft. The first shifter motor 216220 comprises a shifter shaft and a pinion gear 216225 rotatably mounted to the shifter shaft. The pinion gear 216225 is operably intermeshed with the input gear 216215 of the first drive motor 216210 and is translatable between first, second, and third positions by the first shifter motor 216220. When the pinion gear 216225 is in its first position, the pinion gear 216225 is operably intermeshed with the input gear 216215 and an output gear 216235 fixedly mounted to a rotatable output shaft 216230. In such instances, the rotation of the first drive motor 216210 is transferred to the rotatable output shaft 216230 when the first drive motor 216210 is operated. When the pinion gear 216225 is in its second position, the pinion gear 216225 is operably intermeshed with the input gear 216215 and an output gear 216245 fixedly mounted to a rotatable output shaft 216240. In such instances, the rotation of the first drive motor 216210 is transferred to the rotatable output shaft 216240 when the first drive motor 216210 is operated. When the pinion gear 216225 is in its third position, the pinion gear 216225 is operably intermeshed with the input gear 216215 and an output gear 216295 fixedly mounted to a rotatable output shaft 216290. In such instances, the rotation of the first drive motor 216210 is transferred to the rotatable output shaft 216290 when the first drive motor 216210 is operated. Notably, the pinion gear 216225 is not engaged with more than one output gear 216235, 216245, and 216295 at a time and, as a result, the first drive motor 216210 can be used to drive three separate functions of the surgical instrument. In use, a user of the surgical instrument, and/or a control system of the surgical instrument, can select between the three functions by shifting the first shifter motor 216220.

Further to the above, the output shaft 216230 is operably engaged with a shaft 216500 of the surgical instrument such that the rotation of the output shaft 216230 is transferred to the shaft 216500. More specifically, the distal end of the output shaft 216230 comprises a gear intermeshed with a ring of gear teeth 216515 defined on the interior of the shaft housing 216510. The output shaft 216230 is rotated in a first direction to rotate the shaft 216500 in one direction and an opposite direction to rotate the shaft 216500 in another direction. The output shaft 216240 comprises a flexible cable which can be operably coupled with a jaw clamping drive, a firing drive system, such as a staple firing drive and/or a tissue cutting drive, for example, and/or an end effector rotation drive, for example. The output shaft 216290 is operably engaged with a first articulation drive 216700. The first articulation drive 216700 comprises two translatable articulation drivers 216790, each of which is coupled to a translatable drive nut 216795 threadably engaged with the output shaft 216290. Each drive nut 216795 comprises a pin, or projection, extending into a groove defined in the output shaft 216290 and is constrained from rotating such that the rotation of the output shaft 216290 translates the drive nuts 216795. In use, the output shaft 216290 is rotated in a first direction to rotate an end effector of the surgical instrument about a first articulation joint in one direction and rotated in an opposite direction to rotate the end effector about the first articulation joint in another direction. The thread defined in the output shaft 216290 is configured to push one of the drive nuts 216795 and articulation drivers 216790 distally while it pulls the other drive nut 216795 and articulation driver 216790 proximally. That said, one drive nut and articulation driver 216795 can be sufficient to articulate the end effector about the first articulation joint.

Further to the above, the second drive motor 216250 comprises a rotatable input shaft and an input gear 216255 fixedly mounted to the rotatable input shaft. The second shifter motor 216260 comprises a shifter shaft and a pinion gear 216265 rotatably mounted to the shifter shaft. The pinion gear 216265 is operably intermeshed with the input gear 216255 of the second drive motor 216260 and is translatable between first, second, and third positions by the second shifter motor 216260. When the pinion gear 215665 is in its first position, the pinion gear 216265 is operably intermeshed with the input gear 216255 and an output gear 215675 fixedly mounted to a rotatable output shaft 216270. In such instances, the rotation of the second drive motor 216250 is transferred to the rotatable output shaft 216270. When the pinion gear 216265 is in its second position, the pinion gear 216265 is operably intermeshed with the input gear 216255 and an output gear 216285 fixedly mounted to a rotatable output shaft 216280. In such instances, the rotation of the second drive motor 216250 is transferred to the rotatable output shaft 216280. When the pinion gear 216265 is in its third position, the pinion gear 216265 is operably intermeshed with the input gear 216215 and an output gear 216295' fixedly mounted to a rotatable output shaft 216290'. In such instances, the rotation of the second drive motor 216250 is transferred to the rotatable output shaft 216290'. Notably, the pinion gear 216265 is not engaged with more than one output gear 216275, 216285, and 216295' at a time and, as a result, the second drive motor 216250 can be used to drive three separate functions of the surgical instrument. In use, a user of the surgical instrument, and/or a control system of the surgical instrument, can select between the three functions by shifting the second shifter motor 216260.

Further to the above, the output shaft 216270 and/or the output shaft 216280 can be operably coupled with a jaw clamping drive, a firing drive system, such as a staple firing drive and/or a tissue cutting drive, for example, and/or an end effector rotation drive, for example. The output shaft 216290' is operably engaged with a second articulation drive 216800. The second articulation drive 216800 comprises two translatable articulation drivers 216890, each of which is coupled to a translatable drive nut 216895 threadably engaged with the output shaft 216290'. Each drive nut 216895 comprises a pin, or projection, extending into a thread or groove defined in the output shaft 216290' and is constrained from rotating such that the rotation of the output shaft 216290' displaces the drive nuts 216895. In use, the output shaft 216290' is rotated in a first direction to rotate an end effector of the surgical instrument about a second articulation joint in one direction and rotated in an opposite direction to rotate the end effector about the second articulation joint in another direction. The thread defined in the output shaft 216290' is configured to push one of the drive nuts 216895 and articulation drivers 216890 distally while it pulls the other drive nut 216895 and articulation driver 216890 proximally. That said, one drive nut and articulation driver 216895 can be sufficient to articulate the end effector about the second articulation joint.

As outlined above, the first drive motor 216210 and the first shifter motor 216220 are configured to drive only one of their three functions at a time. Similarly, the second drive motor 216250 and the second shifter motor 216260 are configured to drive only one of their three functions at a time. That said, the drive system 216200 is configured to operate the first drive motor 216210 and the second drive motor 216250 at the same time such that the surgical instrument can perform two functions simultaneously. For instance, the first drive motor 216210 can articulate the end effector about the first articulation joint via the drive shaft 216290 while the second drive motor 216250 can articulate the end effector about the second articulation joint via the drive shaft 216290'. Similarly, the first drive motor 216210 can rotate the shaft 216500 about a longitudinal axis while the second drive motor 216250 rotates the end effector about a longitudinal axis. In some instances, however, the control system of the drive system 216200 can be configured to prevent two end effector functions from being performed at the same time. In at least one such instance, the control system is configured to prevent the end effector from being opened while a staple firing stroke is being performed.

Further to the above, the first shifter motor 216220 can be configured to lock out the two non-coupled drive shafts when it operably couples a drive shaft with the first drive motor 216210. In at least one such instance, the translatable shaft of the first shifter motor 216220 can comprise locks defined thereon which are configured to engage and lock the two non-coupled drive shafts in position. In at least one instance, the first shifter motor 216220 locks the drive shaft 216230 and 216240 when it operably engages the first drive motor 216210 with the drive shaft 216290. Similarly, the second shifter motor 216260 can be configured to lock out the two non-coupled drive shafts when it operably couples a drive shaft with the second drive motor 216250. In at least one such instance, the translatable shaft of the second shifter motor 216260 comprises locks defined thereon which are configured to engage and lock the two non-coupled drive shafts in position. In at least one instance, the second shifter motor 216260 locks the drive shaft 216270 and 216280 when it operably engages the second drive motor 216250 with the drive shaft 216290'. In such instances, the end effector functions not being driven are positively disabled, or locked out. That said, embodiments are envisioned in which the end effector functions do not need to be locked out when they are not being used or coupled with a drive motor. In any event, the first shifter motor 216220 and/or the second shifter motor 216260 can comprise a solenoid, for example, to create the longitudinal displacement of their shafts.

As outlined above, the drive system 215200 is configured to drive four instrument functions and the drive system 216200 is configured to drive six instrument functions. That said, a drive system for the instruments disclosed herein can be configured to drive any suitable number of functions, such as more than six end effector functions, for example.

Figure 85:
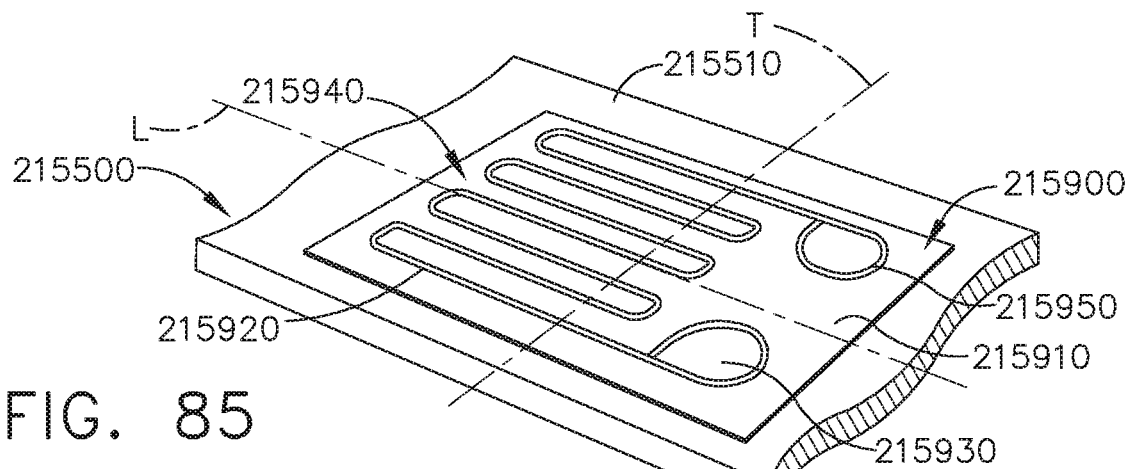
FIG. 85 is a perspective view of a strain gage of the surgical instrument of FIG. 82.

Further to the above, a motor control system of a surgical instrument can adapt the operation of one or more motors of the surgical instrument. Referring to FIG. 85, the surgical instrument 215000 comprises a strain gage circuit 215900 which is in communication with the motor control system of the surgical instrument 215000. The strain gage circuit 215900 comprises a strain gage 215910 mounted to the shroud, or housing, 215510 of the shaft 215500. The strain gage 215910 comprises a base 215920, a first electrical contact 215930 on the base 215920, a circuitous electrical circuit 215940 in electrical communication with the first electrical contact 215930, and a second electrical contact 215950 in electrical communication with the electrical circuit 215940. The electrical contacts 215930 and 215950 are configured to be soldered to, and/or otherwise electrically coupled to, conductive wires and/or traces, for example, to place the strain gage 215910 in communication with the motor control system. The electrical circuit 215940 is comprised of a thin conductive wire, the resistance of which changes when the strain gage 215910 is stretched and/or compressed, as discussed in greater detail below.

Figure 85A:
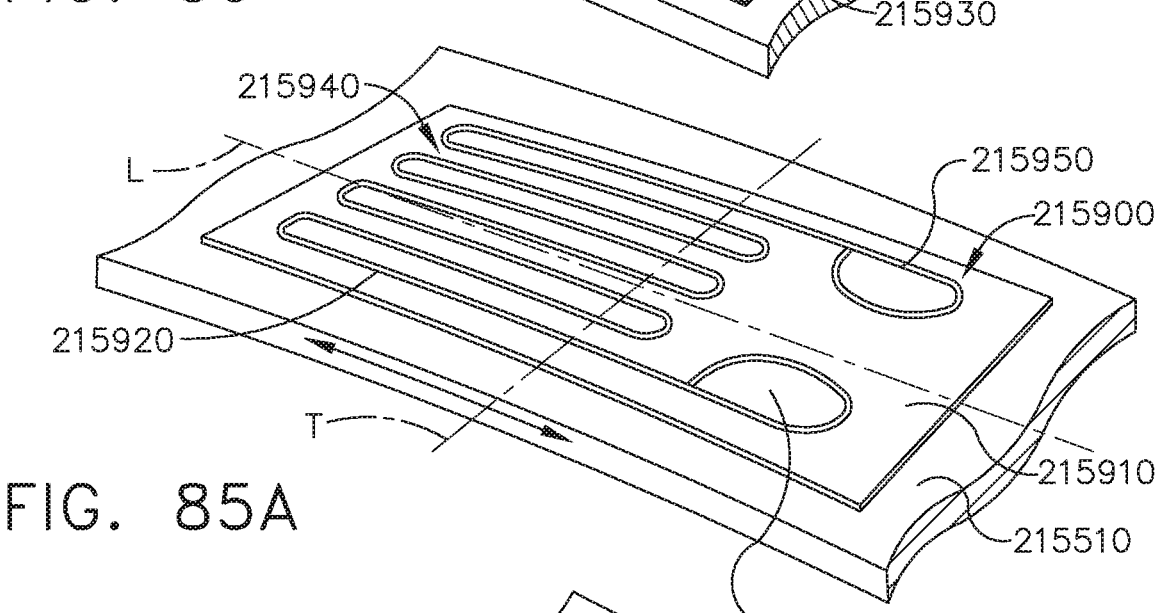
FIG. 85A depicts the strain gage of FIG. 85 in an elongated condition.
Figure 85B:
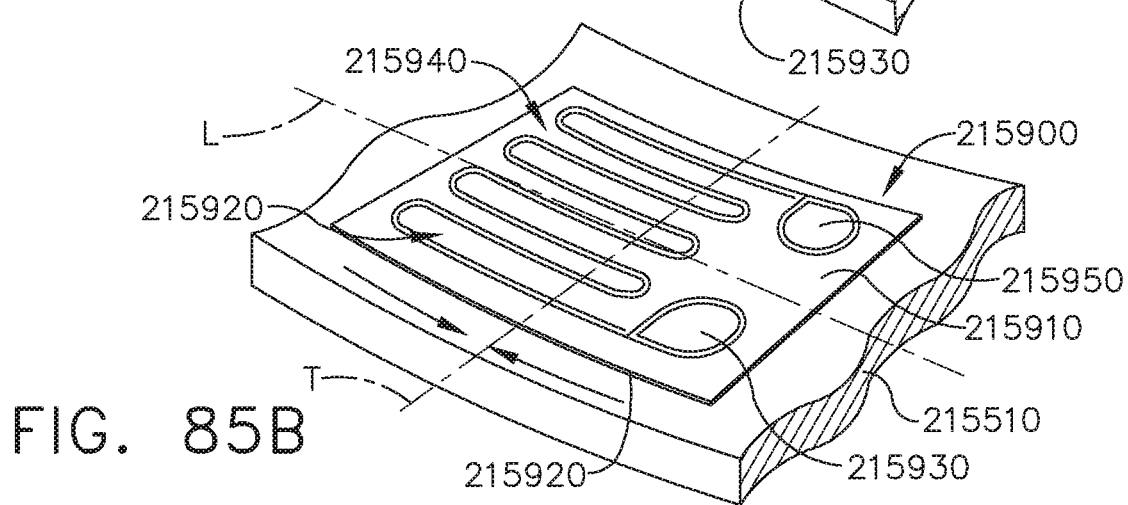
FIG. 85B depicts the strain gage of FIG. 85 in a contracted condition.

Referring again to FIG. 85, the base 215920 of the strain gage 215910 is mounted to the shroud 215510 such that the strain gage 215910 elongates when the shroud 215510 is placed in tension and contracts when the shroud 215510 is compressed. Referring to FIG. 85A, the resistance of the electrical circuit 215940 changes, i.e., increases, when the strain gage 215910 is placed in tension along a longitudinal axis L, which is detectable by the motor control system. Similarly, referring to FIG. 85B, the resistance of the electrical circuit 215940 changes, i.e., decreases, when the strain gage 215910 is compressed along the longitudinal axis L, which is also detectable by the motor control system. The change in resistance of the electrical circuit 215940 is proportional, or at least substantially proportional, to the strain being experienced by the shroud 215510 at the location of the strain gage 215910. In various instances, an increase in strain in the shaft shroud 215510 can indicate that the patient tissue is being over-stressed in some way. With this information, the motor control system of the surgical instrument 215000 can alter the performance of the electric motors of the surgical instrument 215000. For instance, when the strain detected by the strain gage circuit exceeds a predetermined, or threshold, value stored in the memory and/or processor of the motor control system, for example, the motor control system can slow the motor, or motors, being operated at that time. In at least one such instance, the motor control system can slow the electric motor driving a staple firing stroke when the strain threshold is exceeded. In other instances, the motor control system can slow an electric motor driving a clip forming stroke or an electric motor driving a suture stroke, for example, when the strain threshold is exceeded. In various instances, the motor control system can slow an electric motor closing or clamping an end effector and/or articulating the end effector, for example.

Further to the above, the motor control system of the surgical instrument 215000 can adaptively control the speed of one or more electric motors. The motor control system comprises one or more pulse width modulation (PWM) circuits, and/or any other suitable power control circuit, for controlling the speed of the electric motors. A PWM circuit is configured to apply voltage pulses to an electric motor to drive the electric motor at a desired speed—longer voltage pulses drive the electric motor at a faster speed and shorter voltage pulses drive the electric motor at a slower speed. In various instances, the motor control system comprises one or more frequency modulation (FM) circuits and/or voltage transformation circuits for controlling the speed of the electric motors. A FM circuit can apply voltage pulses to a motor at a higher frequency to drive an electric motor at a faster speed and/or a lower frequency to drive an electric motor at a slower speed. PWM circuits and FM circuits are configured to intermittently apply a voltage potential to an electric motor at a constant, or near constant, magnitude; however, various embodiments are envisioned in which the magnitude of the voltage potential can also be changed to adjust the power delivered by the electric motor. Variable resistance circuits, for example, can be used to change the magnitude of the voltage applied to an electric motor.

In addition to or in lieu of adapting the voltage delivered to the electric motors of the surgical instrument 215000 to control the speed of the motors, the current delivered to the electric motors can be adapted to control the drive force delivered by the electric motors. To this end, a surgical instrument can include one or more motor current control circuits.

The strain gage 215910 is an axial strain gage which is well-suited to measuring strain along longitudinal axis L; however, one strain gage 215910 may not provide a complete understanding of the strain occurring within the shroud 215510. Additional strain gages positioned adjacent the strain gage 215910 which are oriented at different directions can provide additional data regarding the strain occurring at that position. For instance, another strain gage can be positioned orthogonally to the strain gage 215910 along the transverse axis T and/or at a 45 degree angle relative to the longitudinal axis L, for example. Various embodiments are envisioned in which the more than one strain gage is provided on a single strain gage base. Such an arrangement can provide a higher resolution of the strain at a particular location. The above being said, any suitable strain gage can be used. For instance, capacitive strain gages, semiconductor strain gages, nanoparticle strain gages, and/or fiber optic strain gages, for example, could be used.

Figure 85C:
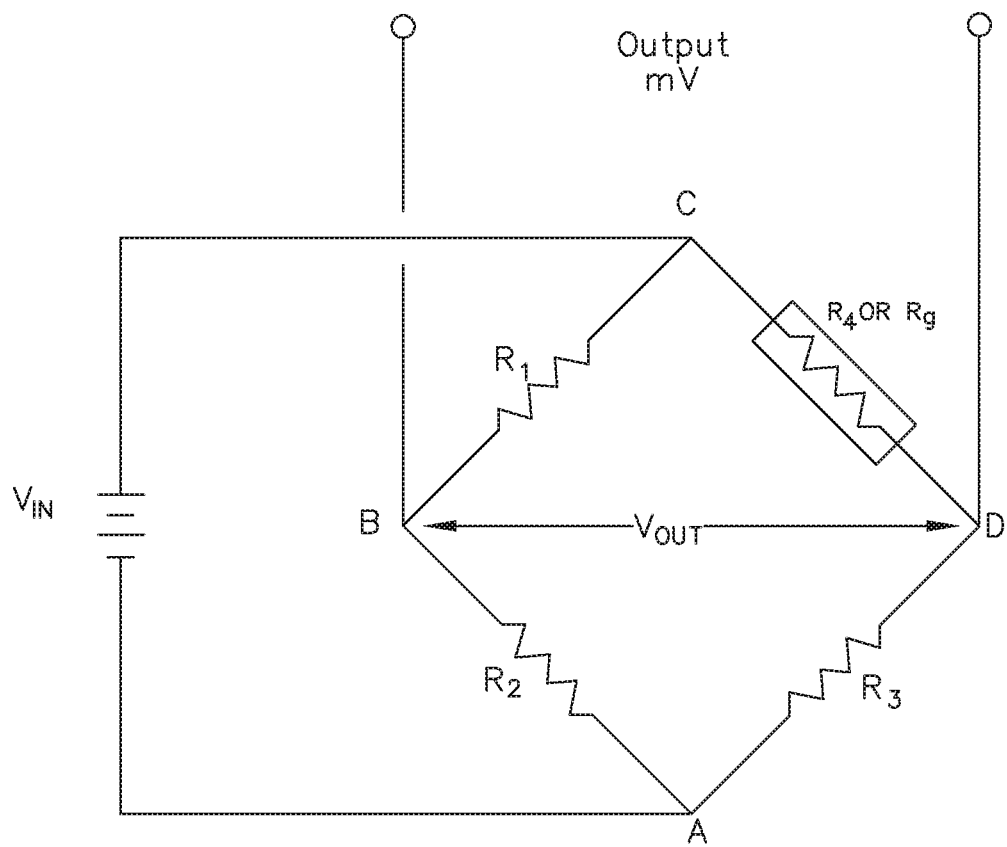
FIG. 85C illustrates a Wheatstone bridge comprising a strain gage in accordance with at least one embodiment.

When one or more resistance strain gages are bonded to a surface to measure strain, as discussed above, the strain gages can be arranged in a Wheatstone bridge circuit, as illustrated in FIG. 85C. A Wheatstone bridge is a divided bridge circuit used for the measurement of static or dynamic electrical resistance. The output voltage of the Wheatstone bridge is often expressed in millivolts output per volt input. Referring to FIG. 85C, if R1, R2, R3, and R4 are equal, and a voltage, $V_{IN}$, is applied between points A and C, then the output between points B and D will show no potential difference. However, if R4 is changed to some value which does not equal R1, R2, and R3, the bridge will become unbalanced and a voltage will exist at the output terminals. In a G-bridge configuration, the variable strain sensor has resistance Rg, while the other arms are fixed value resistors.

A strain gage sensor, however, can occupy one, two, or four arms of the Wheatstone bridge. The total strain, or output voltage of the circuit ($V_{OUT}$) is equivalent to the difference between the voltage drop across R1 and R4, or Rg. The bridge is considered balanced when R1/R2=Rg/R3 and, therefore, $V_{OUT}$ equals zero. Any small change in the resistance of the sensing grid will throw the bridge out of balance, making it suitable for the detection of strain. When the bridge is set up so that Rg is the only active strain gage, a small change in Rg will result in an output voltage from the bridge.

The number of active strain gages that should be connected to the bridge depends on the application. For example, it may be useful to connect strain gages that are on opposite sides of the surgical instrument housing or shroud, one in compression and the other in tension. In this arrangement, the bridge output for the same strain is effectively doubled. In installations where all four of the arms of a Wheatstone bridge are connected to strain gages, temperature compensation is automatic, as resistance change due to temperature variations will be the same for all four arms of the Wheatstone bridge.

In a four-element Wheatstone bridge, further to the above, usually two gages are wired in compression and two in tension, but any suitable arrangement can be used. For example, if R1 and R3 are in tension (positive) and R2 and R4 are in compression (negative), then the output will be proportional to the sum of all the strains measured separately. For gages located on adjacent legs of the Wheatstone bridge, the bridge becomes unbalanced in proportion to the difference in strain. For gages on opposite legs of the Wheatstone bridge, the bridge balances in proportion to the sum of the strains. Whether bending strain, axial strain, shear strain, or torsional strain is being measured, the strain gage arrangement will determine the relationship between the output and the type of strain being measured. As shown in FIG. 85C, if a positive tensile strain occurs on gages R2 and R3, and a negative strain is experienced by gages R1 and R4, the total output, $V_{OUT}$, would be four times the resistance of a single gage.

Other strain gage circuits can be used in addition to or in lieu of the Wheatstone bridges discussed above. Constant current and/or constant voltage arrangements could be used, for instance.

As outlined above, the data provided by the one or more strain gages to the motor control system can be used to modify the operation of one or more electric motors of the surgical instrument. In addition to or in lieu of slowing an electric motor down, the motor control system can stop an electric motor. In at least one instance, the motor control system uses two or more strain thresholds in which the motor control system slows the electric motor down when the measured strain exceeds a first threshold but stops the electric motor when the measured strain exceeds a second, or higher, threshold. In certain instances, the motor control system slows the electric motor down when the measured strain exceeds a first threshold and slows the electric motor down even further when the measured strain exceeds a second, or higher, threshold. In various instances, the motor control system can be configured to speed up an electric motor and/or restore the original speed of the electric motor when the measured strain falls below one or more of the thresholds it exceeded. In any event, the motor control system is configured to receive additional data from an off-instrument surgical hub regarding determining the appropriate reaction to an elevated strain state. Moreover, the motor control system is configured to transmit data to the surgical hub which can store and/or analyze the strain data and emit a return signal regarding the appropriate reaction to an elevated strain state. To this end, the surgical instrument 215000 comprises a wireless signal transmitter and a wireless signal receiver; however, hard-wired embodiments are envisioned.

Further to the above, it should be understood that obtaining accurate strain readings is important. That said, the environment surrounding the surgical instrument 215000 can affect the accuracy of the strain gage readings. Among other things, changes in the temperature of the strain gage 215910 and/or the substrate underlying the strain gage 215190 can affect the strain gage readings. To this end, the surgical instrument 215000 can include a temperature control system for controlling the temperature of the strain gage 215910. In use, the temperature control system is configured to heat and/or cool the strain gage 215910 to control the temperature of the strain gage 215910 relative to a desired or predetermined temperature. In at least one embodiment, the temperature control system comprises a resistive heating electrical circuit to heat the strain gage 215190 and/or the substrate underlying the strain gage 215190. The temperature control system can include a working fluid refrigeration circuit, such as a carbon dioxide refrigeration circuit, for example, to cool the strain gage 215190 and/or the substrate underlying the strain gage 215190. In order to assess the temperature, or temperature change, of a strain gage, the strain gage can include a temperature sensor on the substrate of the strain gage which is in signal communication with the motor control system. Alternatively, a temperature sensor can be adjacent the strain gage. In either event, the motor control system can use the data from a temperature sensor to operate the heating and/or cooling systems discussed above. In addition to or in lieu of actively heating and/or cooling a strain gage, a motor control system can adjust or compensate for the increase in temperature by adjusting the data from the strain gage in view of the data received from the temperature sensor. In at least one instance, the curve relating the voltage of the strain gage to the strain experienced by the underlying substrate can be adjusted for changes in the temperature of the strain gage.

In many instances, further to the above, measuring strain is an excellent proxy for determining the forces that a surgical instrument is experiencing. That said, such strain measurements do not directly measure such forces. In various embodiments, the surgical instrument 215000 comprises one or more force sensors positioned adjacent to the strain gage 215910 to directly measure the forces. In at least one instance, a force sensor comprises a spring element that is stretched and/or contracted along an axis which is parallel to, or at least substantially parallel to, the longitudinal axis of the strain gage 215910. The force sensor is in communication with the motor control system and, as a result, the motor control system can use both the strain gage data and the force sensor data to adapt the operation of the surgical instrument motors.

Further to the above, the strains and/or forces within the shaft shroud 215510 of the surgical instrument 215500 are measurable to control the operation of the surgical instrument 215500. In various instances, elevated strain and/or force readings in the shaft shroud 215510 suggest that the shaft of the surgical instrument 215500 may be pressed against the tissue of the patient. To make the clinician aware of the force being applied to the patient tissue, the surgical instrument 215500 further comprises an indicator in communication with the control system of the surgical instrument 215500 which is activated by the control system when the strain measured by the strain gages and/or the force measured by the force gages in the shaft shroud 215510 exceed a threshold level. The indicator can comprise a light configured to create visible feedback, a speaker configured to create auditory feedback, a vibratory motor configured to create tactile feedback, and/or an icon on a display screen, for example. In certain instances, the control system can reduce the speed of the motor, or motors, in the surgical instrument 215500 when the strain threshold is exceeded. Controlling the electric motors in this manner can prevent the surgical instrument 215500 from over-deflecting and/or breaking, especially when a part of the surgical instrument 215500 is articulating and/or rotating, for example. In at least one instance, the strain gages and/or force sensors can be placed on and/or in a circuit board within the surgical instrument 215500, such as a flex circuit, for example. In such instances, as a result, excessive force loading and/or deflection within the circuitry, especially circuitry mounted to the housing of the surgical instrument, can be prevented. That said, the strains and/or forces within a moving component, such as a rotatable shaft and/or translatable drive member, could also be measured. Such an arrangement allows the motor control system to directly evaluate the strains and/or forces within the drive systems of the surgical instrument 215500 and prevent the electric motors and/or drive components from being overstressed.

The above being said, a surgical instrument can utilize a strain gage in any suitable location. In various instances, a strain gage circuit can comprise a strain gage positioned on the jaw of an end effector. Among other things, such a strain gage can detect the deflection of the jaw, especially when positioned at the distal end of the jaw. With such data, the motor control system can adapt the operation of the surgical instrument to accommodate for an over-flexed jaw, for example. In at least one such instance, the motor control system can slow down the electric motor used to drive a distally-movable tissue cutting knife, such as the knife of a surgical stapler, for example. In use, a jaw will deflect elastically when tissue is captured between the jaws of the end effector, but the jaw can sometimes deflect plastically or permanently. A strain gage positioned on the jaw will allow the motor control system to detect that the jaw has been permanently damaged when the jaw is unclamped. If the permanent damage is above a threshold, the motor control system can limit the functionality of the surgical instrument in some way and/or indicate to the user that the surgical instrument has become damaged and/or indicate the degree of the damage.

Further to the above, a strain gage of a strain gage circuit can be placed on the jaw of a surgical stapler that supports a staple cartridge. When the jaws of the surgical stapler are clamped, the strain gage can detect the strain within the cartridge jaw which can reveal the deflection of the jaw. Along these lines, the deflection of the jaw can reveal the distance between the jaws, or tissue gap. With this information, the motor control system can assess the thickness of the tissue between the jaws and control the speed of the drive motor which drives the tissue cutting knife. For instance, the motor control system can slow down the drive motor when the tissue is thick and/or speed up the drive motor when the tissue is thin. In addition to or in lieu of the above, a strain gage of a strain gage circuit can be placed on the tissue cutting knife. Such a strain gage can provide data relating to the thickness and/or density of the tissue to the motor control system. Similar to the above, the motor control system can slow down the drive motor when the tissue is dense and/or speed up the drive motor when the tissue is less dense, for example. Moreover, the motor control system can stop and/or pause the drive motor which closes the jaw of the end effector when the measured strain has reached a threshold. In many instances, the fluid in the clamped tissue needs time to flow out of the tissue in the end effector after the end effector has been initially clamped and, if the strain falls back below the threshold, the motor control system can be configured to re-start the closure drive motor to compress the tissue a desired amount. Such a strain gage can be placed on one of the end effector jaws and/or the closure drive member, for example.

Figure 82A:
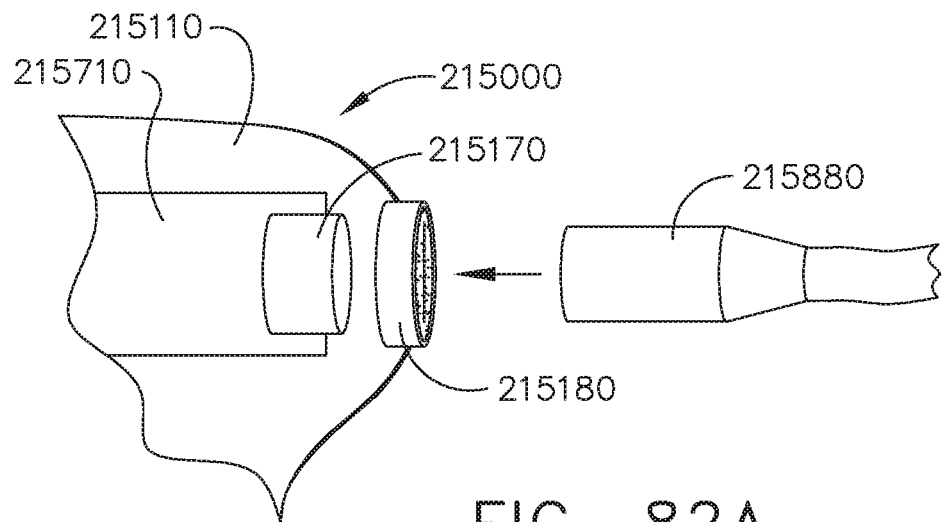
FIG. 82A is a partial detail view of the surgical instrument of FIG. 82.
Figure 82B:
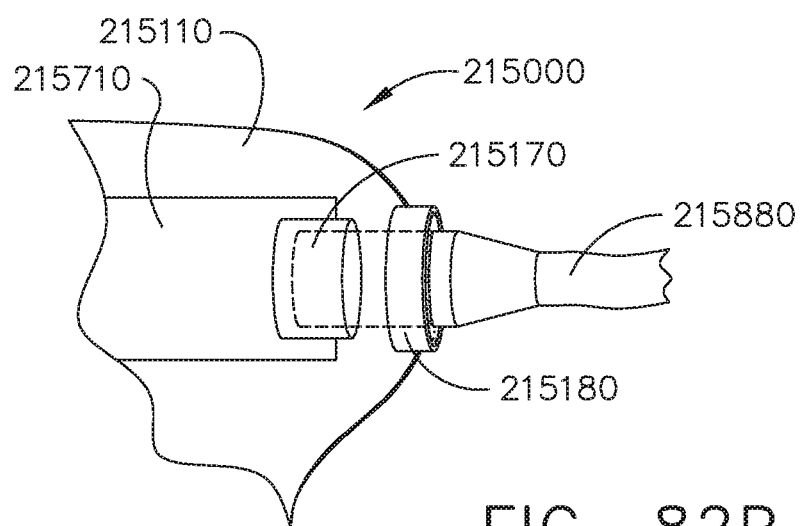
FIG. 82B is a partial detail view of the surgical instrument of FIG. 82 illustrating a probe inserted into a handle of the surgical instrument.
Figure 82C:
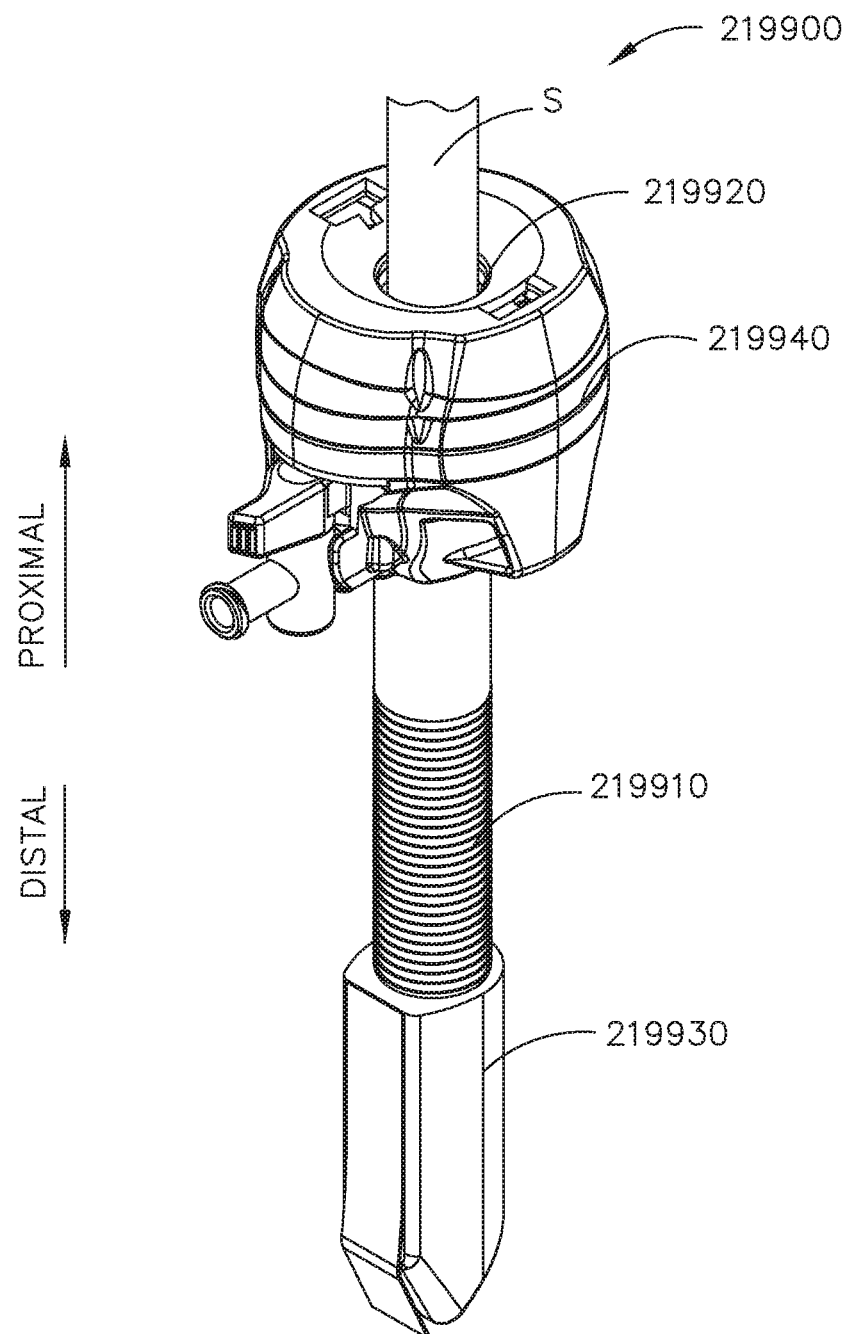
FIG. 82C is a perspective view of a trocar in accordance with at least one embodiment configured to facilitate the insertion of the surgical instrument of FIG. 82, for example, into a patient.

The surgical instruments described herein are insertable into a patient through a trocar, such as the trocar 219900 illustrated in FIG. 82C. A trocar can comprise a long shaft 219910 comprising a longitudinal aperture 219920 extending there through, a sharp distal end 219930 configured to be pushed through an incision in the patient, and a proximal end 219940 comprising a sealable port or opening configured to receive a surgical instrument S. In use, the surgical instrument is passed through the sealable port, through the longitudinal aperture, and into a body cavity of the patient. The sealable port comprises a seal configured to prevent, or at least reduce, the flow of insufflation gas from the patient body cavity through the trocar. The seal is configured to bias itself into a closed, or an at least substantially closed, configuration. Even when a surgical instrument is extending through the sealable port, the seal is biased against the sides of the surgical instrument to create a sealed, or an at least substantially sealed, interface therebetween. In use, the trocar is orientable within the incision to permit the surgical instrument to be properly oriented within the body cavity. In various instances, the clinician using the surgical instrument pushes or pulls the surgical instrument in a desired direction to orient the surgical instrument and, in such instances, the surgical instrument contacts the sidewalls of the longitudinal aperture which also orients the trocar.

In various instances, further to the above, the trocar applies forces to the patient tissue when the trocar is oriented by the surgical instrument. Excessive forces can pinch, bruise, and/or otherwise damage the tissue. To this end, a trocar can comprise one or more force sensor circuits and/or one or more strain gage circuits configured and positioned to detect the forces applied to the trocar by the surgical instrument. In various instances, a force sensor circuit is embedded in a flexible substrate, such as a ribbon, for example, positioned within the longitudinal aperture of the trocar. In at least one such instance, the flexible substrate extends around the inner circumference of the trocar shaft and is attached to the trocar shaft by one or more adhesives, for example. The force sensor circuit comprises one or more transducers supported within the flexible substrate which are compressed by the surgical instrument when the surgical instrument is pushed against the trocar. A transducer, such as a piezoelectric transducer, for example, converts mechanical energy into electrical energy and, when the transducer is compressed between the surgical instrument and the sidewall of the trocar, the force sensor circuit generates a voltage potential. The trocar further comprises a control system in electrical and/or signal communication with the force sensor circuits which is configured to detect the voltage potential, and the magnitude of the voltage potential, created by the transducers in the force sensor circuits.

Further to the above, the control system of the trocar uses an algorithm to determine whether the voltage potentials from the force sensor circuits exceed one or more thresholds. The trocar further comprises at least one haptic feedback generator, such as a light, a speaker, and/or an eccentric motor, for example, in communication with the control system and, when a voltage potential form a force sensor circuit exceeds a predetermined threshold, the control system can actuate the haptic feedback generator to indicate to the clinician that they may be applying an excessive force to the trocar and the patient tissue via the surgical instrument.

Further to the above, the trocar can comprise a wireless signal transmitter in communication with the control system of the trocar. The wireless signal transmitter is configured to emit one or more signals including data regarding the force sensor circuits, especially when a threshold has been exceeded. The surgical instrument inserted through the trocar can comprise a wireless signal receiver in communication with the control system of the surgical instrument which is configured to receive the wireless signals from the trocar and relay the signals, or the data transmitted by the signals, to the instrument control system. The surgical instrument further comprises at least one haptic feedback generator, such as a light, a speaker, and/or an eccentric motor, for example, in communication with the instrument control system and, when a voltage potential from a force sensor circuit exceeds a predetermined threshold, the instrument control system can actuate the haptic feedback generator to indicate to the clinician that they may be applying an excessive force to the trocar and the patient tissue via the surgical instrument.

Further to the above, the trocar and surgical instrument can be part of a surgical hub system. In various instances, the trocar and the surgical instrument communicate with the surgical hub system instead of communicating directly, as discussed above.

The force sensor circuits of the trocar can be used to assess other information regarding the surgical instrument. In at least one instance, the trocar control system can determine that a surgical instrument is present in the trocar when the voltage potential of one or more force sensor circuits changes. In various instances, the trocar control system can determine the direction in which the surgical instrument is being pushed. When the force sensor circuits on one lateral side of the trocar change voltage potential and the force sensor circuits on the opposite lateral side of the trocar do not change voltage potential, or have a lesser voltage potential change, the trocar control system can determine the direction in which the surgical instrument is being pushed. In certain instances, the trocar can comprise a proximal set of transducers and a distal set of transducers which can be used to assess the orientation of the surgical instrument in the trocar. When the proximal transducers on a first lateral side of the trocar have a higher voltage potential than the proximal transducers on a second, or opposite, side of the trocar and the distal transducers on the second side have a higher voltage potential than the distal transducers on the first side, the trocar control system can determine that the surgical instrument is oriented in the second direction within the patient, for example. Such proximal and distal transducers can also be used to assess the torque that the surgical instrument is applying to the trocar and/or patient tissue.

Further to the above, circuits within the trocar and circuits within the surgical instrument can be inductively coupled. In various instances, one or more trocar circuits comprise windings extending around the trocar shaft which generate a field within the trocar which interacts with one or more circuits in the surgical instrument. In at least one such instance, the trocar circuits comprise copper wires embedded in the trocar housing, for example, and the surgical instrument circuits comprise copper wires extending through the shaft of the surgical instrument. In such instances, the trocar can transmit power to the surgical instrument and/or wireless data signals to the surgical instrument via this inductive coupling. The trocar can have its own power supply and/or can receive power from the surgical hub system in the operating room. Alternatively, the circuits of the surgical instrument can be configured and arranged to communicate electrical power and/or wireless signal data to the trocar. In such instances, the sensors, control system, and/or haptic feedback generators can be powered by the surgical instrument positioned in the trocar. In certain instances, the trocar can enter into a low power, or sleep, mode after not being used for a predetermined period of time. The insertion of a surgical instrument into the trocar can be detected by the trocar control system via these inductive circuits which can cause the trocar to enter a full power, or wake, mode. The insertion of a surgical instrument into the trocar can be detected by the instrument control system via these inductive circuits which can cause the instrument to enter a full power, or wake, mode.

In any event, the above-provided discussion regarding the interaction between a trocar and a surgical instrument is applicable to both hand-held surgical instruments and/or surgical instruments operated by a robotic surgical system.

Figure 86:
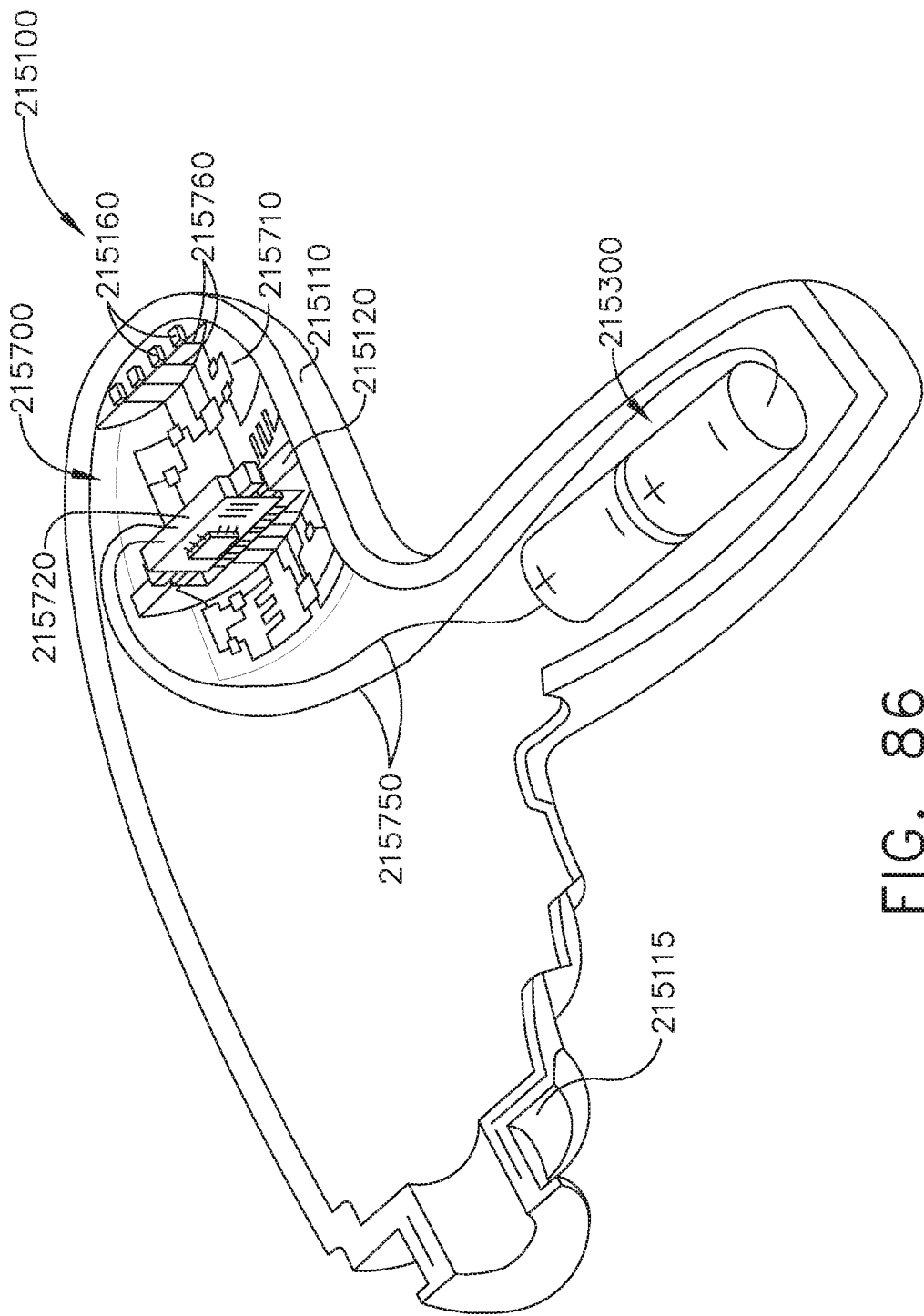
FIG. 86 is a perspective view of one half of a handle housing of the surgical instrument of FIG. 82.

Referring to FIG. 86, the surgical instrument 215000 comprises a motor control system 215700. The motor control system 215700 comprises a first circuit board, i.e., flex circuit 215710, and, as described in greater detail below, a second circuit board, i.e., printed circuit board (PCB) 215720. The flex circuit 215710 comprises a flexible substrate including a non-conductive flexible base and conductive electrical traces defined within and/or on the non-conductive flexible base. The flex circuit 215710 is contourable and is contoured to fit against the interior surface of the handle housing 215110. The interior surface of the handle housing 215110 is generally concave and the flex circuit 215710 has been flexed to match the concave configuration of the handle housing 215110; however, that said, the flex circuit 215710 is contourable to fit any suitable configuration within the handle 215100.

The flexible base is comprised of polyimide and/or polyetheretherketone (PEEK), for example, and can comprise any suitable number of layers. The conductive traces are comprised of copper, silver, and/or conductive polyester, for example. The conductive traces are positioned between the layers of the flexible base and/or embedded within the flexible base and are exposed at specific, pre-determined locations on the flex circuit 215710. The exposed portions of the conductive traces are at least partially covered with a solder coating, such as tin and/or silver, for example, and/or a flux coating, such as an organic flux, for example. The flex circuit 215710 further comprises electronic components mounted to the surface thereof. These surface mount electronic components are mechanically and electrically attached to the exposed portions of the conductive traces of the flex circuit 215710 via soldered connections. Surface mount electronics can be quickly assembled to the flex circuit 215710 using a reflow soldering process, for example. In addition to or in lieu of the surface mount components, the flex circuit 215710 can include electronic components which have through-hole electrical contacts. In such instances, the conductive traces include openings or through-holes which are configured to receive the electrical contacts or pins extending from the electronic devices. These pins can be soldered to the conductive traces using a reflow soldering process and/or a wave soldering process, for example. In addition to the soldered electrical connections, electronic components can be mechanically attached to the flexible base to reduce the possibility of the soldered connections being over-stressed.

Further to the above, the flex circuit 215710 is mounted to the handle housing 215110 using one or more adhesives such that the bottom surface of the flex circuit 215710 is conformed to the handle housing 215110. The flex circuit 215710 can also be at least partially embedded in the handle housing 215110. In at least one such instance, the handle housing 215110 is comprised of plastic which is injection molded over at least a portion of the flex circuit 215710. In certain instances, conductive traces can be directly attached to and/or embedded in the handle housing 215110 without a flexible circuit board. For instance, conductive traces 215760 are defined on the handle housing 215510 which are in electrical communication with electric contacts 215160. When the sides of the handle housing 215110 are assembled together, the electrical contacts 215160 on one side of the handle housing 215110 are electrically connected to corresponding electrical contacts on the other side. In any event, the conductive traces have portions thereof that are exposed such that electrical connections to the conductive traces can be made.

Figure 87:
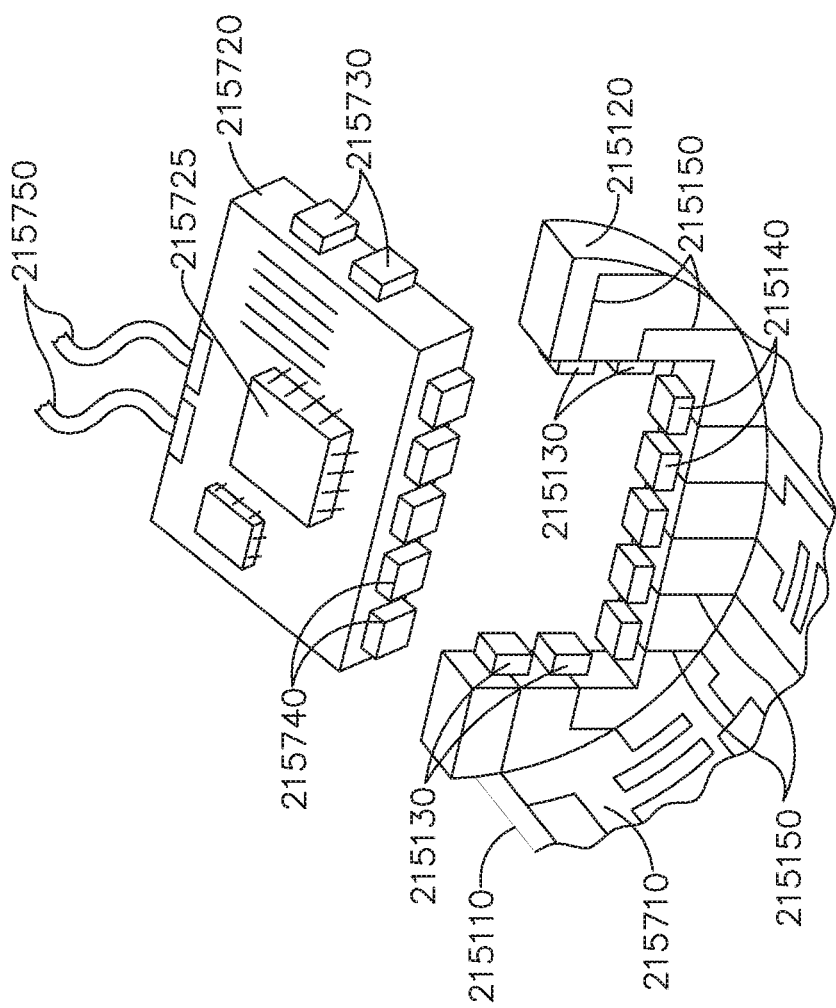
FIG. 87 is a partial perspective view of circuit boards in the handle of FIG. 86.

In use, further to the above, the power source 215300 supplies power to the motor control system 215700. The power source 215300 comprises one or more direct current (DC) batteries, but can comprise any suitable power source such as an alternating current (AC) power source, for example. The power source 215300 can comprise a voltage transformation circuit to provide a desired voltage potential to the motor control system 215700 via electrical wires, or conductors, 215750. Notably, the conductors 215750 are connected to a second circuit board 215720 of the motor control system 215700. The second circuit board 215720 comprises a card and is connected to the first circuit board 215710; however, the second circuit board 215720 can comprise any suitable configuration. Referring to FIG. 87, the second circuit board 215720 is insertable into a card slot 215120 defined in the handle housing 215110. The card slot 215120 is configured to securely receive the second circuit board 215720 such that the second circuit board 215720 does not move, or at least substantially move, relative to the handle housing 215110 once the second circuit board 215720 has been inserted therein. The card slot 215120 comprises electrical contacts 215130 and 215140 mounted on the walls thereof which are in communication with the flexible circuit board 215710 via conductive traces 215150. When the second circuit board 215720 is seated in the card slot 215120, the electrical contacts 215130 and 215140 are electrically coupled to electrical contacts 215730 and 215740 on the second circuit board 215720, respectively.

Further to the above, the second circuit board 215720 comprises a card including a substrate and electronic components positioned on the substrate. The substrate includes a printed circuit board (PCB) comprising a plurality of rigid non-conductive layers and a plurality of conductive traces positioned intermediate and/or on the non-conductive layers. Owing to the rigidity of the second circuit board 215720, the conductive traces can be thick and/or wide which permits the traces to carry large electrical power loads without overheating the materials of the second circuit board 215720. Similar to the above, the second circuit board 215720 comprises surface mount electronic components and/or through-hole-pin electronic components mounted to and electrically coupled to the traces—both of which are designated as electronic components 215725. As a result of the above, the second circuit board 215720 is well-suited to transmit electrical loads between the power source 215300 and the electric motors of the surgical instrument 215000 which are often quite high. As such, the first circuit board 215710 can comprise a flex circuit which can be thinner than a PCB and better suited to transmit lower electrical power loads. That said, a flex circuit can be designed to carry any suitable electrical power loads and can be used for any suitable application in the surgical instrument 215000, for example.

In view of the above, the first circuit board 215710 is designed to have low-power circuits and transmit lower electrical power loads than the second circuit board 215720 which is designed to have high-power circuits. Low-power circuits include signal circuits and/or sensor circuits, such as circuits which are responsive to inputs on the handle 215100 and/or strain gage circuits, for example. High-power circuits include motor control circuits which can comprise PWM and/or FM control circuits, for example. Other high-power circuits include a radio-frequency (RF) generator circuit and/or a transducer drive circuit configured to create a standing wave in an end effector, for example.

Further to the above, the first circuit board 215710 and/or the second circuit board 215720 comprise memory devices configured to store data regarding the operation, state, and/or condition of the surgical instrument 215000, for example. Referring to FIGS. 82A and 82B, the first circuit board 215710 comprises at least one data access terminal and/or contact 215170 which can be used by a clinician to access the data stored in the memory devices. To this end, the handle housing 215110 comprises an access port 215180 configured to permit a connector and/or probe 215880 to be inserted there through to operatively connect to the data access terminal 215170. The access port 215180 comprises a seal including an elastomeric portion comprised of rubber, for example, and a sealed, but openable, aperture extending through the elastomeric portion. The aperture is biased closed, or at least substantially closed, by the elastomeric material of the seal and is openable to permit the probe 215880 to be inserted therethrough. When the probe 215880 is withdrawn from the access port 215180, the seal can re-seal itself.

In addition to or in lieu of the above, the handle housing 215110 comprises a pierceable portion which is configured to be pierced by an electrical probe, for example. The pierceable portion can comprise a thinned portion of the handle housing 215110 which can be readily pierced by the electrical probe to access the circuit boards and/or motor control system in the handle housing 215110. In at least one instance, the handle housing 215110 comprises a demarcation indicating where the handle housing 215110 can be pierced. In at least one instance, the demarcation comprises a colored zone on the handle housing 215110, for example.

Figure 88:
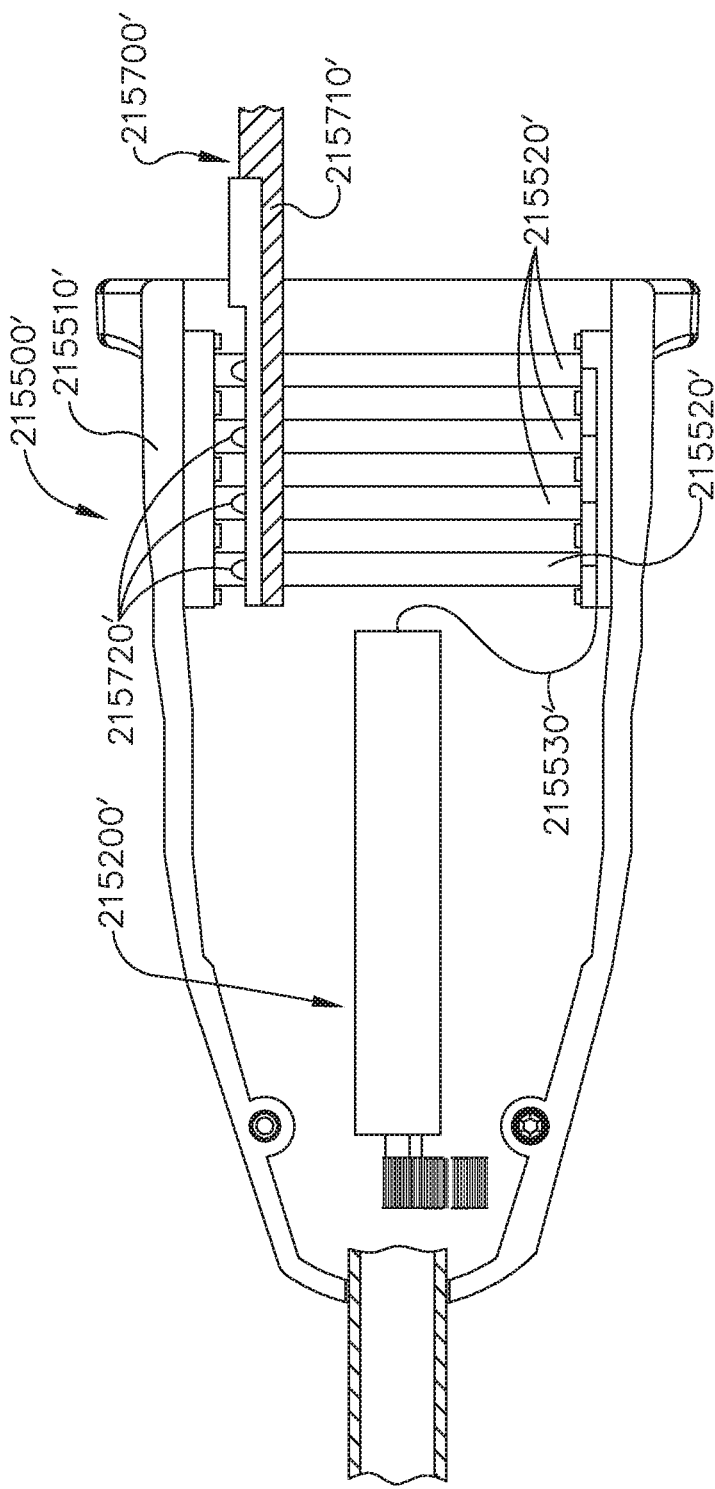
FIG. 88 is a partial cross-sectional view of a surgical instrument in accordance with at least one embodiment.
Figure 89:
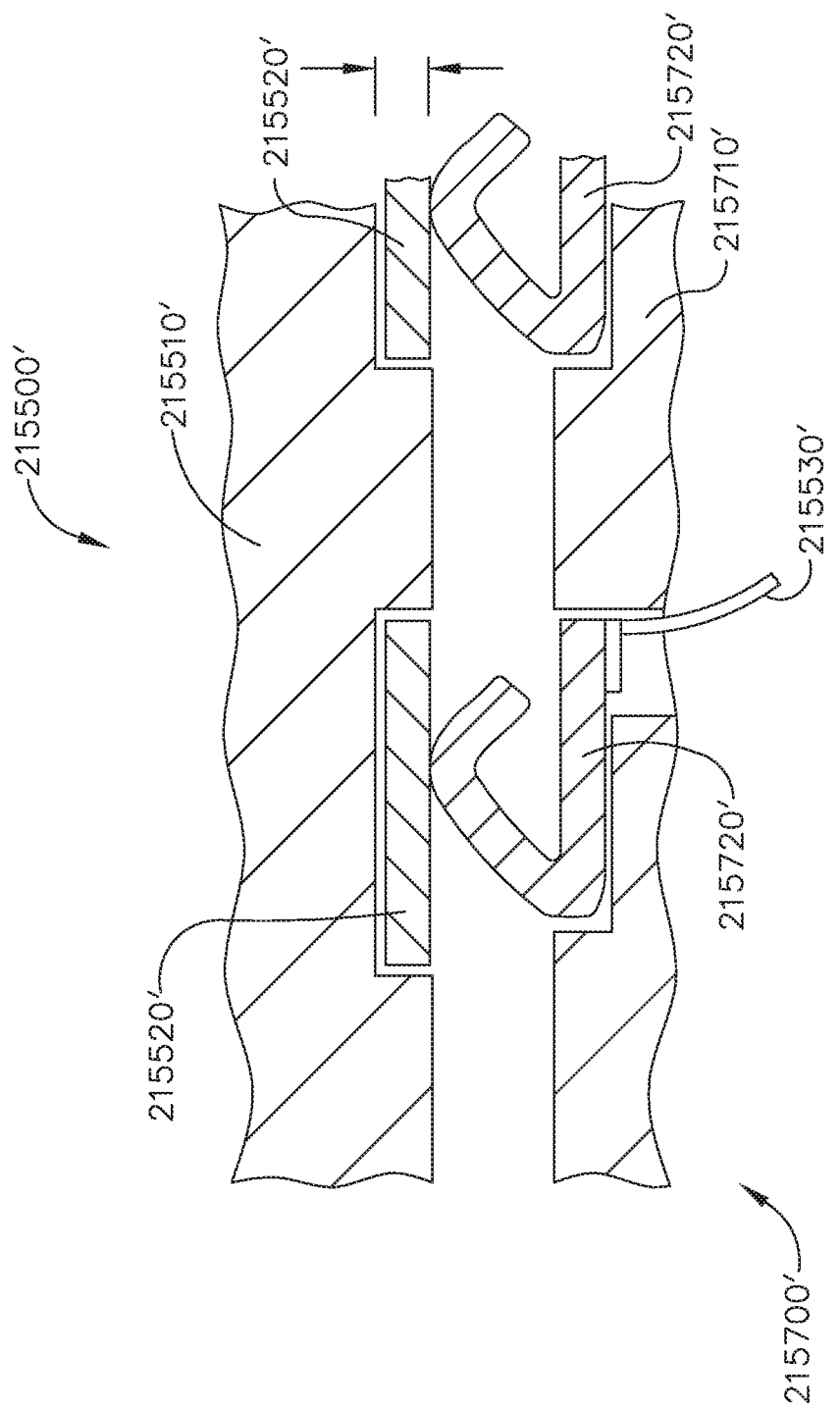
FIG. 89 is a partial detail view of an electrical interface within the surgical instrument of FIG. 88.

Referring to FIGS. 88 and 89, a shaft assembly 215500' is similar to the shaft assembly 215500 in many respects. Like the shaft assembly 215500, the shaft assembly 215500' forms a rotatable interface with a handle, such as the handle 215100, for example, that allows the shaft assembly 215500' to rotate about a longitudinal axis. The shaft assembly 215500' comprises a flex circuit mounted to the interior of the shaft housing, or shroud, 215510' which extends around the entire circumference of the shaft housing 215510' and comprises annular electrical contacts 215520'. The handle comprises a motor control system 215700' including a printed circuit board (PCB) 215710'. The PCB 215710' comprises electrical contacts 215720' which are engaged with and in electrical communication with the annular electrical contacts 215520'. Each electrical contact 215720' comprises a base seated in the PCB 215710' and a compliant or spring member biased into engagement with an annular electrical contact 215520' such that the electrical contacts 215720' are in electrical communication with the annular electrical contacts 215520' regardless of the position in which the shaft assembly 215500' is rotated relative to the handle. The shaft assembly 215500' further comprises wires or conductors 215530' which place the electrical contacts 215520' in electrical communication with an electric motor 215200'. As a result of the above, the electric motor 215200' in the shaft assembly 215500' can be powered by a power source in the handle. Moreover, the interface between the electrical contacts 215520' and 215720' can transmit signals between the shaft assembly 215500' and the handle. Such an arrangement can allow the motor control system in the handle to communicate with one or more sensors, such as strain gauges and/or force sensors, for example, in the shaft assembly 215500', for instance.

Referring to FIG. 90, a handle 217100 is similar to the handle 215100 in many respects. Among other things, the handle 217100 comprises a handle housing 217110, a drive system comprising at least one electric motor and a motor control system, a removable battery 217300 configured to supply power to the motor control system, and an actuation trigger 217400 which, when actuated, closes an end effector of the shaft assembly attached to the handle 217100. In various instances, the electric motor is configured to drive one end effector function, such as closing the end effector, for example. To the extent that other motorized functions are needed, in such instances, the handle 217100 can include other drive motors configured to drive those other end effector functions. Alternatively, a drive motor can be used to drive more than one end effector function, as described above.

Referring again to FIG. 90, the handle 217100 further comprises controls 217140, 217150, and 217160 which are in communication with the motor control system of the handle 217100. The control 217130 is actuatable to operate an electric motor in the handle 217100 which articulates the end effector with respect to a longitudinal axis of the shaft assembly attached to the handle 217100. Referring to FIG. 92, the control 217130 comprises a rocker button including a button shell 217132. The rocker button shell 217132 comprises a first shell portion 217131 and a second shell portion 217133 which are separated by a recessed groove 217135 defined in the rocker button shell 217132. The control 217130 further comprises a first strain gage circuit 217137 attached to and/or embedded in the first shell portion 217131 and a second strain gage circuit 217139 attached to and/or embedded in the second shell portion 217133. The first strain gage circuit 217137 and the second strain gage circuit 217139 are in signal communication with the motor control system via one or more wires or conductors 217136. The wall of the first shell portion 217131 is configured to deflect and/or deform when a clinician depresses the first shell portion 217131 and, in such instances, the motor control system is configured to detect the change in resistance in the first strain gage circuit 217137. Similarly, the wall of the second shell portion 217133 is configured to deflect and/or deform when a clinician depresses the second shell portion 217133 and, in such instances, the motor control system is configured to detect the change in resistance in the second strain gage circuit 217139. When the motor control system detects an increase in resistance in the first strain gage circuit 217137, the motor control system operates the articulation drive motor to articulate the end effector in a first direction. Correspondingly, the motor control system operates the articulation drive motor to articulate the end effector in a second, or opposite, direction when the motor control system detects an increase in resistance in the second strain gage circuit 217139. When the clinician releases or removes their hand from the control 217130, the button shell 217132 will resiliently return to its original configuration and the resistance in the first and second strain gage circuits 217137 and 217139 returns to its original state. This change in the strain gage circuit resistance is detected by the motor control system and, at that point, the motor control system stops driving the articulation drive motor.

Further to the above, the control 217140 is also actuatable to operate the articulation drive motor in the handle 217100. Referring to FIG. 91, the control 217140 comprises a push button including a button shell 217142. The control 217140 further comprises a strain gage circuit 217144 attached to and/or embedded in the button shell 217142. The strain gage circuit 217144 is in signal communication with the motor control system via one or more wires or conductors 217146. The wall of the button shell 217142 is configured to deflect and/or deform when a clinician depresses the button shell 217142 and, in such instances, the motor control system is configured to detect the change in resistance in the strain gage circuit 217144. When the motor control system detects an increase in resistance in the strain gage circuit 217144, the motor control system operates the articulation drive motor to align, of at least substantially re-align, the end effector with the longitudinal axis of the shaft assembly, i.e., move the end effector to a home position. To this end, the motor control system is configured to track the position of the end effector so as to know the direction and amount in which to articulate the end effector to move the end effector to its home position. In at least one embodiment, the motor control system comprises an encoder, for example, to track the position of the end effector. Once the end effector has been re-centered with the longitudinal shaft axis, the motor control system will stop the articulation drive motor. When the clinician releases or removes their hand from the control 217140, the button shell 217142 will resiliently return to its original configuration and the resistance in the strain gage circuit 217144 will return to its original state.

Further to the above, the control 217150 is actuatable to operate a firing drive motor in the handle 217100 to perform, for example, a staple firing stroke, a clip crimping stroke, or a needle suturing stroke—depending on the type of shaft assembly attached to the handle 217100. Referring to FIG. 93, the control 217150 is positioned on the clamping actuator 217400 and comprises a push button including a button shell 217152. The control 217150 further comprises a strain gage circuit 217154 attached to and/or embedded in the button shell 217152. The strain gage circuit 217154 is in signal communication with the motor control system via one or more wires or conductors 217156. The wall of the button shell 217152 is configured to deflect and/or deform when a clinician depresses the button shell 217152 and, in such instances, the motor control system is configured to detect the change in resistance in the strain gage circuit 217154. When the motor control system detects an increase in resistance in the strain gage circuit 217154, the motor control system operates the firing drive motor to drive a firing member distally. To this end, the motor control system is configured to track the position of the firing member so as to know when the firing member has reached the end of its firing stroke and stop the firing drive motor. In at least one embodiment, the motor control system comprises an encoder, for example, to track the position of the firing member. In addition to the above, the motor control system is configured to stop the firing drive motor when the clinician releases or removes their hand from the control 217150. In such instances, similar to the above, the button shell 217152 resiliently returns to its original configuration and the resistance in the strain gage circuit 217154 returns to its original state, which is detected by the motor control system.

Figure 95:
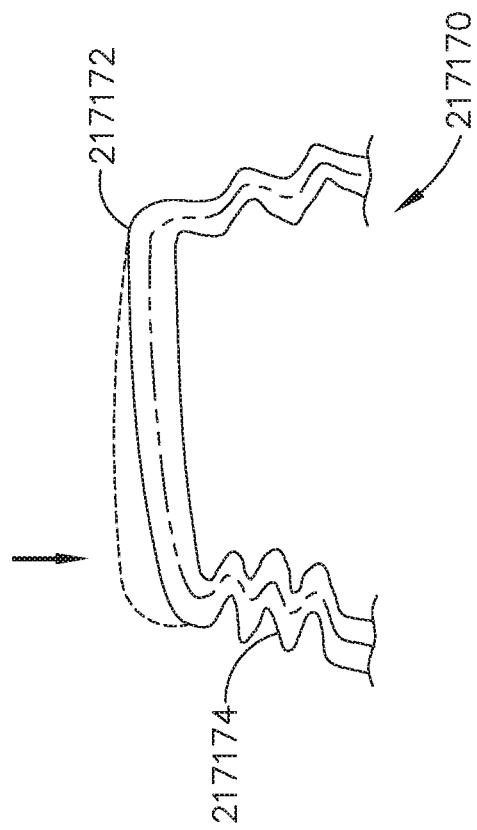
FIG. 95 is a cross-sectional view of a button shell in accordance with at least one embodiment.

As discussed above, the controls 217130, 217140, and 217150 are deformable to actuate a function of the surgical instrument. To the extent that the controls 217130, 217140, and 217150 are readily deformable, they may experience large strains which are readily detectable by their respective strain gage circuits. Referring to FIG. 95, an actuator 217170 comprises a button shell 217172 which has one or more living hinges 217174 defined in the walls of the button shell 217172. Such living hinges 217174 can permit the button shell 217172 to readily deform. Score marks in the button shell 217172 could also be used. In various instances, an actuator can comprise a feature which causes the housing of the actuator to suddenly flex, elastically snap, or give way when a force threshold has been exceeded. That said, such readily deformable controls may be accidentally actuated by the clinician. To this end, the motor control system can utilize one or more measured strain thresholds which can reduce the possibility of the surgical instrument responding to incidental touches of the controls 217130, 217140, and 217150. For instance, for strains measured by the strain gage circuit 217144 of the actuator 217140 which are below a threshold, the motor control system will not actuate the articulation drive motor. Correspondingly, the motor control system will actuate the articulation drive motor for measured strains that meet or exceed the threshold. The motor control system can also include measured strain thresholds for the other controls 217130 and 217150. The measured strain thresholds can be the same for each of the controls 217130, 217140, and 217150 or they can be different. Given that different types of buttons can deform differently, using different measured strain thresholds can be advantageous.

Figure 94:
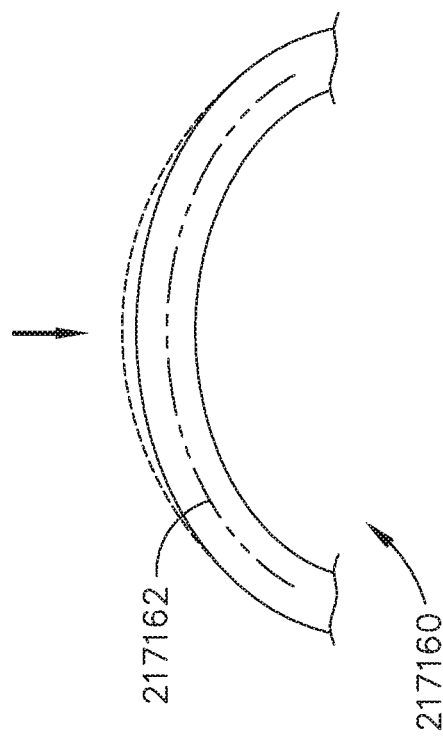
FIG. 94 is a cross-sectional view of a button shell in accordance with at least one embodiment.

Referring to FIG. 94, further to the above, an actuator 217160 comprises a solid button shell 217162. Unlike the button shell 217172, the button shell 217162 is configured such that it does not significantly deform when it is actuated. As a result, the motor control system in communication with the strain gage circuit of the actuator 217160 is configured to be responsive to much lower measured strain values. On the other hand, the actuator 217160 can be used to actuate an important function of the surgical instrument and it may be desirable to have a high measured strain threshold to prevent the accidental actuation of the important function despite having a stiff button wall of the actuator 217160. In such instances, the clinician would have to make a concerted effort to sufficiently depress the actuator 217160 to actuate the important function.

When an actuator is easily deformable, further to the above, the clinician should be able to readily sense that they have actuated the actuator when the wall of the actuator gives way or elastically collapses. When an actuator is stiff, however, a clinician may not be able to intuitively sense that the actuator has been actuated. In either event, a surgical instrument can include a haptic feedback generator in communication with the motor control system. When the motor control system determines that the measured strain in an actuator strain gage circuit has exceeded the predetermined threshold, the motor control system can activate the haptic feedback generator which can notify the clinician that the actuator has been sufficiently actuated. In various instances, the haptic generator comprises at least one visual indicator device, such as a light, for example, at least one auditory indicator device, such as a speaker, for example, and/or at least one vibratory indicator device, such as an electric motor with an eccentric rotational element, for example.

In various embodiments, further to the above, a motor control system can utilize two or more measured strain thresholds in connection with an actuator, such as the actuator 217160, for example, for determining an appropriate action of the surgical instrument. For instance, the motor control system can comprise a first measured strain threshold and a second measured strain threshold which is higher than the first strain threshold. When the measured strain is below the first measured strain threshold and the second measured strain threshold, the motor control system does not drive the electric motor of the drive system associated with the actuator. When the measured strain is at or above the first measured strain threshold but below the second measured strain threshold, the motor control system actuates a first haptic feedback generator, such as a first light, for example, but it does not drive the electric motor. When the measured strain is at or above the second measured strain threshold, the motor control system actuates a second haptic feedback generator, such as a second light, for example, and drives the electric motor. In such instances, the clinician is provided with a warning or notice via the first haptic feedback generator that they are depressing the actuator in some way, intentionally or unintentionally. When the measured strain falls below the second measured strain threshold, but not the first measured strain threshold, the motor control system deactivates the second haptic feedback generator, but not the first haptic feedback generator. The motor control system also stops driving the electric motor in such instances. When the measured strain falls below the first measured strain threshold, the motor control system deactivates the first haptic feedback generator.

Further to the above, the actuators 217130 and 217140 are comprised of a different material than the handle housing 217110. The actuators 217130 and 217140 are comprised of a first plastic material and the handle housing 217110 is comprised of a second plastic material which is different than the first plastic material. The first plastic material is more flexible than the second plastic material so that the actuators can be deformed to actuate the surgical instrument, as described above. In various instances, the first plastic material is selected such that the modulus of elasticity of the first plastic material is lower than the modulus of elasticity of the second plastic material. In any event, the actuators 217130 and 217140 are manufactured separately from the handle housing 217110 and then assembled to the handle housing 217110. The actuators 217130 and 217140 and the handle housing 217110 comprise co-operating features which interlock to connect the actuators 217130 and 217140 to the handle housing 217110. In at least one embodiment, the actuators 217130 and 217140 are placed in a mold and the handle housing 217110 is injection molded around the actuators 217130 and 217140 such that the button housings are held in place, yet sufficiently exposed such that the clinician can actuate them. Similar to the above, interlocking features between the actuators 217130 and 217140 and the handle housing 217110 can be created during the injection molding process which hold the actuators 217130 and 217140 in position relative to the handle housing 217110. In various instances, the actuators 217130 and 217140 are formed during a first shot of an injection molding process and the handle housing 217110 is formed during a second shot of the injection molding process. These arrangements can decrease, if not eliminate, the size of the seam openings between the actuators 217130 and 217140 and the handle housing 217110. The above-provided discussion also applies to the closure actuator 217400 and the actuator 217150 which, once manufactured, can be assembled to the handle housing 217110.

In various alternative embodiments, further to the above, the actuators 217130 and 217140 are comprised of the same material as the handle housing 217110. In at least one such embodiment, the actuators 217130 and 217140 are thinner than the handle housing 217110 such that they can sufficiently deform to actuate the surgical instrument while the handle housing 217110 is sufficiently rigid so as to not deform unacceptably during use. Similar to the above, the actuators 217130 and 217140 can be manufactured separately from the handle housing 217110 and then assembled to the handle housing 217110. In at least one alternative embodiment, the actuators 217130 and 217140 are formed integrally with the handle housing 217110. In such instances, the handle housing 217110 can be formed in two halves which are assembled together by a snap-fit connection, fasteners, and/or one or more adhesives, for example. In at least one embodiment, the actuators 217130 and 217140 and the handle housing 217110 are formed during an injection molding process. In such instances, the strain gage circuits 217134 and 217144 can be positioned in the mold before the melted plastic is injected into the mold such that the strain gage circuits 217134 and 217144 are at least partially embedded in the actuators 217130 and 217140. Otherwise, the strain gage circuits 217134 and 217144 can be applied to the actuators 217130 and 217140, respectively, after the injection molding process. Similar to the above, the actuators 217130 and 217140 are thinner than the handle housing 217110 such that they can sufficiently deform to actuate the surgical instrument while the handle housing 217110 is sufficiently rigid so as to not deform unacceptably during use. Such arrangements can eliminate the seams between the actuators 217130 and 217140 and the handle housing 217110 and create a sealed interface between the actuators 217130 and 217140 and the handle housing 217110. The above-provided discussion also applies to the closure actuator 217400 and the actuator 217150 which, once manufactured, can be assembled to the handle housing 217110.

In various instances, the plastics used to form the actuators 217130 and 217140 and/or the handle housing 217110 are capable of being electroplated. In at least one such instance, conductive traces are electroplated directly onto the actuators 217130 and 217140 and/or the handle housing 217110. The electroplated conductive traces can be comprised of any suitable material, such as tin and/or silver, for example.

In various embodiments, sensors and/or switches other than strain gages can be used to actuate the electric motors of a motor control system. In at least one such embodiment, a handle and/or shaft of a surgical instrument comprises at least one actuator which is deflectable to contact a sensor and/or switch to open and/or close a sensor circuit, as the case may be, to actuate an electric motor of the surgical instrument. Similar to the above, such an actuator can comprise a separate component which is assembled to the handle housing, for example, and is deformable inwardly to contact a sensor and/or switch. Also similar to the above, such an actuator can comprise an integral thin portion of the handle housing which is deformable inwardly to contact a sensor and/or switch. In either event, the sensor and/or switch is positioned behind and aligned with the actuator and can be mounted to a circuit board, for example.

Referring again to FIG. 82, the shaft assembly 215500 comprises actuators 215520, 215530, and 215540 which are configured to operate in the same or similar way as the other actuators described herein. The actuators of the shaft assembly 215500 comprise slide rail actuators, radial actuators, rotational actuators, press-button actuators, and/or any other suitable actuators. In various instances, the shaft assembly 215500 is not meant to be re-used after the surgical procedure and is, thus, disposable. In certain instances, the shaft assembly 215500 can be re-used if it has not exceeded its maximum number of permitted actuations and has been cleaned and re-sterilized. The handle 215100 can also be disposable or re-usable.

In various alternative embodiments, an actuator can be actuated without having to be deflected and/or deformed. In at least one such embodiment, the actuator comprises a capacitive sensor circuit attached to and/or embedded within the handle housing which is in signal communication with the motor control system. The capacitive sensor circuit comprises one or more capacitive sensors which are evaluated by the motor control system for changes in capacitance therein when the clinician places their finger on and/or over one of the capacitive sensors. When the measured capacitance, or capacitance change, exceeds a predetermined threshold, the motor control system actuates the electric motor of the drive system associated with the actuator. When the measured capacitance, or capacitance change, falls below the predetermined threshold, the motor control system no longer drives the electric motor. That said, the motor control system can be configured to perform any suitable action when the measured capacitance, or capacitance change, falls below the predetermined threshold.

In at least one instance, further to the above, the handle housing comprises recesses defined therein and the capacitive sensors are positioned in the recesses. Such an arrangement allows the capacitive sensors to be flush, or at least substantially flush, with the outer surface of the handle housing. In at least one such instance, the capacitive sensors can be a different color than the handle housing such that they are readily observable by the clinician.

In various instances, further to the above, an actuator comprises a membrane switch. In at least one instance, a membrane switch comprises two conductive plates separated by dielectric dots positioned between the conductive plates. One or both of the conductive plates are configured to flex when the membrane switch is depressed and change the electrical state of the membrane switch. The membrane switch can be hermetically sealed so as to prevent water intrusion and/or contaminants from entering the membrane switch which can unintentionally change the electrical properties of the membrane switch.

Further to the above, an actuator can comprise a piezoelectric sensor circuit attached to and/or embedded within the handle housing which is in signal communication with the motor control system. The piezoelectric sensor circuit comprises one or more piezoelectric sensors which are evaluated by the motor control system for changes in electrical properties thereof when the clinician places their finger on and/or taps one of the piezoelectric sensors. When the measured electrical property, or electrical property change, exceeds a predetermined threshold, the motor control system actuates the electric motor of the drive system associated with the actuator. When the measured electrical property, or electrical property change, falls below the predetermined threshold, the motor control system no longer drives the electric motor. That said, the motor control system can be configured to perform any suitable action when the measured electrical property, or electrical property change, falls below the predetermined threshold. In at least one instance, the handle housing comprises recesses defined therein and the piezoelectric sensors are positioned in the recesses. Such an arrangement allows the piezoelectric sensors to be flush, or at least substantially flush, with the outer surface of the handle housing. In at least one such instance, the piezoelectric sensors can be a different color than the handle housing such that they are readily observable by the clinician.

Figure 96:
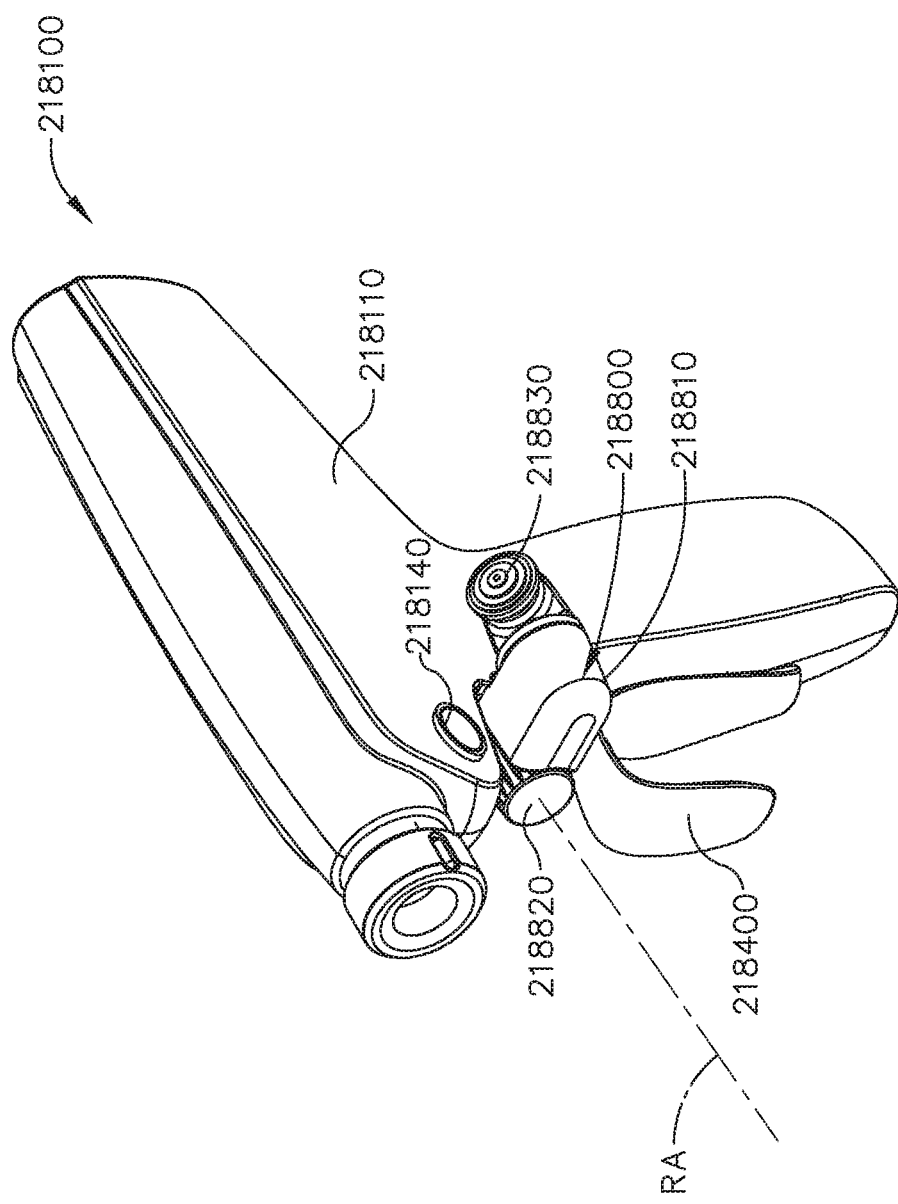
FIG. 96 is a perspective view of a surgical instrument handle in accordance with at least one embodiment.

Referring to FIG. 96, a handle 218100 comprises a handle housing 218110, a button actuator 218140, a rotatable actuator 218400, and a positionable actuator 218800. The positionable actuator 218800 comprises an arm 218810 which is rotatably mounted to the handle housing 218110 about a pivot pin 218820 which defines a rotation axis RA. The pivot pin 218820 is secured to the housing 218110 such that the positionable actuator 218800 does not translate, or at least substantially translate, relative to the housing 218110. Moreover, the pivot pin 218820 fits snugly in an aperture in the housing 218110 such that rotating the arm 218810 about the rotation axis RA requires a concerted effort on the part of the clinician. In at least one instance, the pivot pin 218820 comprises a lock screw which is loosenable to pivot the arm 218810 and tightenable to lock the arm 218810 in position. In any event, the arm 218810 can be pivoted into a comfortable position for the clinician such that a joystick 218830 on the arm 218810 is easily accessible by the clinician. The joystick 218830 comprises one or more sensors in communication with the motor control system of the handle 218100. In use, the motor control system is configured to interpret and use voltages, currents, and/or any other data from the sensors of the joystick 218830 to articulate the end effector of a shaft assembly attached to the handle 218100. The end effector is articulatable in more than one plane and can be articulatable about one or more articulate joints by one or more motor-driven articulation drive systems.

Figure 97:
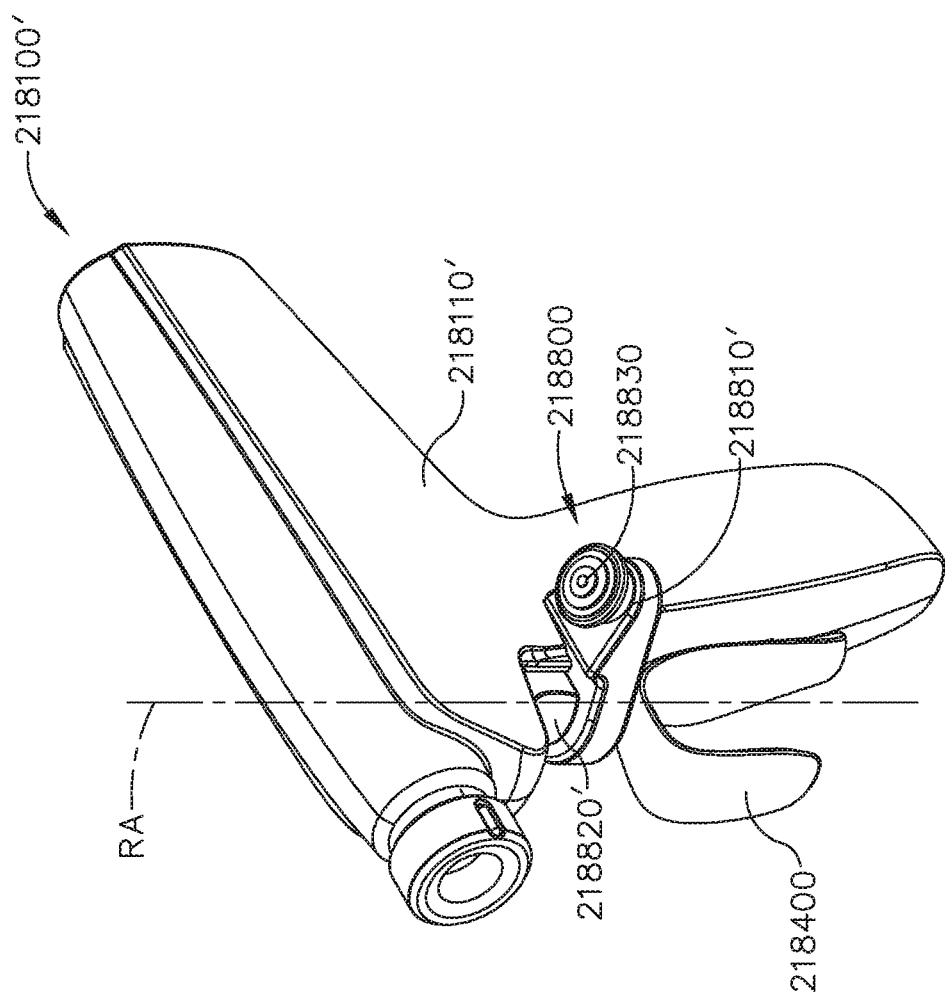
FIG. 97 is a perspective view of a surgical instrument handle in accordance with at least one embodiment.

Referring to FIG. 97, a handle 218100' comprises a handle housing 218110', a button actuator 218140, a rotatable actuator 218400, and a positionable actuator 218800'. The positionable actuator 218800' comprises an arm 218810' which is rotatably mounted to the handle housing 218110' about a pivot pin 218820' which defines a rotation axis RA. The pivot pin 218820' is secured to the housing 218110' such that the positionable actuator 218800' does not translate, or at least substantially translate, relative to the housing 218110'. Moreover, the pivot pin 218820' fits snugly in an aperture in the housing 218110' such that rotating the arm 218810' about the rotation axis RA requires a concerted effort on the part of the clinician. In at least one instance, the pivot pin 218820' comprises a lock screw which is loosenable to pivot the arm 218810' and tightenable to lock the arm 218810' in position. In any event, the arm 218810' can be pivoted into a comfortable position for the clinician such that a joystick 218830 on the arm 218810' is easily accessible by the clinician. For instance, the arm 218810' is rotatable between the left and right sides of the handle 218100'. The joystick 218830 comprises one or more sensors in communication with the motor control system of the handle 218100'. In use, the motor control system is configured to interpret and use voltages, currents, and/or any other data from the sensors of the joystick 218830 to articulate the end effector of a shaft assembly attached to the handle 218100'. The end effector is articulatable in more than one plane and can be articulatable about one or more articulate joints by one or more motor-driven articulation drive systems.

Figure 98:
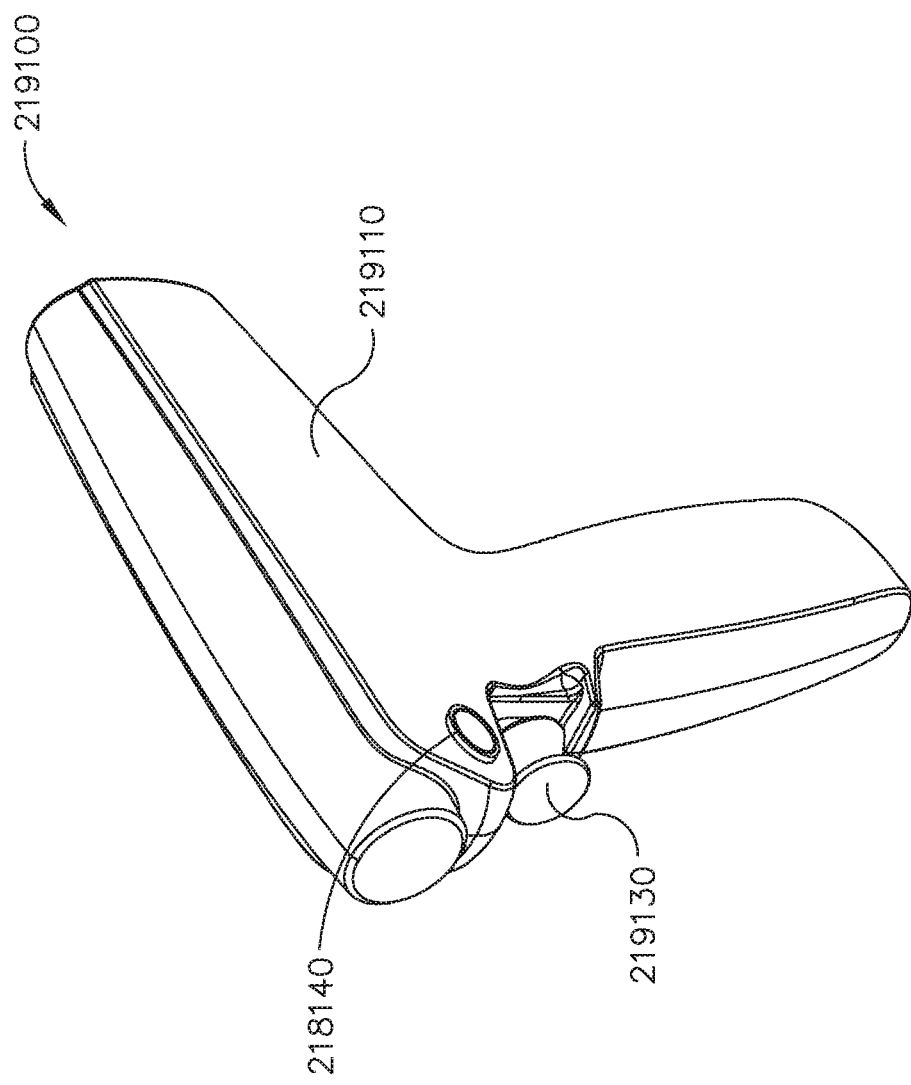
FIG. 98 is a perspective view of a surgical instrument handle in accordance with at least one embodiment.

Referring to FIG. 98, a surgical instrument handle 219100 comprises a handle housing 219110, a button actuator 218140, and a joystick 219130. Unlike the joystick 218130, the joystick 219130 is not mounted on a rotatable arm and is, instead, directly mounted to the handle housing 219110. The joystick 219830 comprises one or more sensors in communication with the motor control system of the handle 219100. In use, the motor control system is configured to interpret and use voltages, currents, and/or any other data from the sensors of the joystick 219830 to articulate the end effector of a shaft assembly attached to the handle 219100. The end effector is articulatable in more than one plane and can be articulatable about one or more articulate joints by one or more motor-driven articulation drive systems.

In addition to or in lieu of a joystick for controlling the articulation of the end effector, a surgical instrument can include a projected capacitive (PCAP) touchscreen for controlling the articulation of the end effector. A PCAP touchscreen comprises electrodes that are aligned in a grid pattern on the sensor side of a touch panel. The electrode grid detects the touch point by sensing the change of electrical charges that occur when a finger of the clinician touches the surface of the touch panel. Such a device can be used in conjunction with a microprocessor of a motor control system which is configured to interpret the touches and/or touch motions on the PCAP touchscreen and move the end effector in a manner which parallels the touches and/or touch motions. The microprocessor is configured to interpret finger taps, finger drags, and/or rotational finger swipes, for example, on the PCAP touchscreen and articulate the end effector in an intuitive manner. For instance, the microprocessor is configured to interpret a finger tap on the PCAP touchscreen as a command to position the end effector in a location which corresponds to where the finger tap occurred on the PCAP touchscreen. A finger tap on the left side of the PCAP touchscreen will cause the end effector to be articulated to the left and a finger tap on the right side of the PCAP touchscreen will cause the end effector to be articulated to the right, for example. A finger tap on the top side of the PCAP touchscreen will cause the end effector to pitch down and a finger tap on the bottom side of the PCAP touchscreen will cause the end effector to pitch up. A finger drag on the PCAP touchscreen will cause the end effector to be articulated in the direction of the finger drag and at the speed of the finger drag, for example. A leftward motion articulates the end effector left, a rightward motion articulates the end effector right, a topward motion pitches the end effector down, and a bottomward motion pitches the end effector up. A fast finger drag will articulate the end effector quickly and a slow finger drag will articulate the end effector slowly. A rotational finger swipe on the PCAP touchscreen will cause the end effector to rotate about a longitudinal axis in the direction of the rotational finger swipe, for example. A clockwise finger swipe will rotate the end effector clockwise and a counter-clockwise finger swipe will rotate the end effector counter-clockwise.

Further to the above, the PCAP touchscreen can include icons thereon which facilitate the use of the PCAP touchscreen and suggest how the finger motions will be interpreted by the microprocessor. A finger tap icon is depicted in FIG. 99. A finger drag icon is depicted in FIG. 100. A rotational finger swipe is depicted in FIG. 101. Such icons could also be positioned on the handle housing.

A surgical theatre is often divided into a sterile field and a non-sterile field. During a surgical procedure, certain clinicians remain in the sterile field while other clinicians remain in the non-sterile field. Typically, surgical instruments within the sterile field are handled by the clinicians in the sterile field. That said, instances are envisioned in which a surgical instrument comprises a sterile barrier that allows a clinician, in the sterile field or non-sterile field, to interact with the surgical instrument. In at least one instance, the sterile barrier comprises a flexible membrane mounted to the surgical instrument. Depending on the surgical instrument and its use, the entirety of the surgical instrument or only a portion of the surgical instrument is protected by the sterile barrier. In at least one instance, the surgical instrument comprises one or more pressure sensitive displays that can be interacted with through the sterile barrier. In use, the surgical instrument in the sterile barrier may generate heat. To this end, the sterile barrier can comprise a heat sink configured to extract heat from within the sterile barrier and dissipate the heat into the surrounding environment. The heat sink can be comprised of any suitable thermally conductive material, such as copper and/or silver, for example. Silver provides an additional advantage owing to its antimicrobial properties. In at least one instance, the heat sink comprises an array of conductive traces extending within the sterile barrier. The conductive traces are embedded within, attached to, and/or printed on the sterile barrier. Such traces can promote conductive heat transfer. In at least one instance, the conductive traces comprise fins that extend from the sterile barrier. Such fins can promote convective heat transfer. In various instances, the materials of the sterile barrier and/or conductive traces are comprised of a material which promotes radiant heat transfer.

As discussed above, a surgical instrument can comprise two or more circuit boards which are operably interconnected by one or more electrical connectors. In many instances, an electrical connection comprises two halves—a male connection half and a female connection half. The male connection half comprises male electrical contacts which can comprise pins, for example, while the female connection half comprises female electrical contacts which can comprise sockets, for example, configured to receive the pins. Each socket comprises one or more deflectable members or tangs configured to engage a pin inserted into the socket and establish one or more electrical contact interfaces therebetween. Even under ideal conditions, such electrical contact interfaces create voltage drops within an electrical circuit. Moreover, an electrical contact interface can degrade over time and/or as a result of use. For instance, the surfaces of the contact interface can oxidize over time and, in such instances, the voltage drop across the contact interface increases as the oxidization increases. In order to reduce such oxidization, the pins and/or sockets can be electroplated with tin, lead, silver, and/or gold, for example. Such electroplating can comprise any suitable thickness, such as between approximately 5 μm and approximately 100 μm, for example. Electroplating having a thickness of approximately 5 μm is often referred to as a "strike" of electroplating and is often used when the plating material is expensive, such as gold, for example. A contact interface can degrade for other reasons, especially when the contact interface carries a high power load. In various instances, a contact interface can develop "whiskers" which grow outwardly from an electroplated surface, especially when tin plating is used without lead intermixed therein. Such whiskers can reduce the distance between adjacent pairs of electrical contacts and, as a result, increase the electromagnetic interference between the adjacent pairs of electrical contacts and/or create a short between the pairs of electrical contacts. That said, various metals can be introduced into the electroplating to reduce the growth of such whiskers. In some instances, a contact interface can develop fretting corrosion within the contact interface as a result of thermocycling, for example. In certain instances, one of the contact tangs can bend or yield when the electrical connectors are engaged with one another.

In view of the above, a control circuit of a surgical instrument comprising one or more electrical interconnections can be configured to assess the contact quality of the electrical interconnections after the components of the surgical instrument have been assembled together and/or during the use of the surgical instrument. The control circuit is configured to assess if the signal across an electrical connection is being distorted by the electrical connection. In at least one instance, the control circuit comprises a signal emitter configured to emit a signal through an electrical circuit including an electrical contact, a signal receiver configured to compare the return signal to the expected return signal, and a digital signal processor for determining if there is signal distortion. Any suitable algorithm can be used to assess signal distortion, such as an algorithm that uses the root mean square of the signal, for example. If the return signal for each of the electrical circuits sufficiently matches their expected return signal, then the control circuit can communicate to the user of the surgical instrument that the signal fidelity within the surgical instrument is sufficient. In at least one instance, the control circuit comprises an indicator light, such as an LED, for example, which is illuminated to indicate there is sufficient signal fidelity in the surgical instrument. If one or more of the return signals does not sufficiently match its expected return signal, the control circuit can communicate to the user of the surgical instrument that the signal fidelity within the surgical instrument may not be sufficient. In such instances, another LED could be illuminated and/or the signal fidelity LED can comprise a two-color LED which can be switched from green to red, for example. In various instances, the control circuit is configured to use more than one signal fidelity threshold—a first threshold above which there is sufficient signal fidelity (or an acceptable amount of noise), a second threshold below the first threshold above which indicates possibly sufficient signal fidelity (or a potentially inappropriate amount of noise), and a third threshold below the second threshold below which there is insufficient signal fidelity (or extensive noise). When the signal fidelity of an electrical circuit is between the first and second thresholds, the control circuit can increase the gain of the power supplied to that circuit to improve the fidelity of the signal. In at least one instance, the magnitude of the voltage is increased. In certain instances, the control circuit can adjust the communication speed across an electrical circuit in view of the signal-noise ratio. For high signal-noise ratios, the control circuit can transmit data across the electrical contact interface at a high rate or with short gaps between the data, or data packets, for example. For low signal-noise ratios, the control circuit can transmit data across the electrical contact interface at a lower rate or with longer gaps between the data, or data packets, for example.

In addition to or in lieu of the above, a control circuit is configured to assess the voltage drop across an electrical contact interface. For instance, when the control circuit detects that a lower-than-expected voltage potential is being delivered to an electronic device within an electrical circuit, for example, the control circuit can increase the gain of the power supplied to that electrical circuit. In at least one such instance, the magnitude of the voltage is increased, for example. To the extent that a short circuit is detected in an electrical circuit, the surgical instrument may be unusable altogether or limited in the functions that it can perform. To this end, the control circuit, a processing circuit and/or an algorithm can be utilized to decide whether or not the short circuit is present on a critical function, whether the surgical instrument can still be used, and what functions can still be used. Upon detecting a short circuit, in various instances, the control circuit can enter into a limp mode that permits only the surgical instrument functions that allow the surgical instrument to be removed from the patient and/or permits the status of the surgical instrument to be monitored by the clinician, for example. In addition to or in lieu of the above, the control circuit can execute an algorithm for assessing whether a detected short circuit is actually a short circuit. In at least one instance, the algorithm operates to increase the gain of the signal in the electrical circuit upon detecting a short circuit and, if the short circuit is still detected after increasing the gain, the control circuit quickly interrupts the power to the electrical circuit comprising the short circuit. However, if increasing the signal gain establishes or re-establishes sufficient signal fidelity, then the control circuit can continue to permit the use of that electrical circuit.

Further to the above, the signal fidelity and/or voltage drop within an electrical circuit can be assessed when the surgical instrument components are assembled. The electrical circuits can also be assessed when the surgical instrument is powered on and/or woken up from a low power, or sleep, mode. The electrical circuits can be assessed intermittently or continuously throughout the operation of the surgical instrument. In various instances, the control circuit of a surgical instrument can enter into a limp mode when the signal distortion and/or voltage drop exceed a predetermined threshold. In various instances, the control circuit can enter into a limp mode that permits only the surgical instrument functions that allow the surgical instrument to be removed from the patient and/or permits the status of the surgical instrument to be monitored by the clinician, for example. The control circuit can also try to fix the signal distortion and/or voltage drop by increasing the signal gain, for example. When there is fluid intrusion into an electrical interface, however, increasing the signal gain may not resolve these issues.

In various instances, further to the above, the surgical instrument can comprise a fan positioned to blow air across the electrical interface when the signal distortion and/or voltage drop within one or more electrical circuits is high, or above a predetermined threshold. In various instances, the fan forms a part of the control circuit. In at least one instance, the fan is positioned proximally with respect to the electrical interface such that air is blown in a proximal-to-distal direction, for example. In certain instances, the surgical instrument can be configured to at least partially insufflate the patient with carbon dioxide, for example. In such instances, the insufflation path can pass over the electrical interface which can dry the electrical interface and/or prevent fluid intrusion in the first place. The control circuit comprises a speed control circuit, such as a pulse width modulation (PWM) circuit, a frequency modulation (FM) circuit, and/or a variable-resistance circuit, for example, configured to operate the fan at different speeds. In such instances, the control circuit is configured to operate the fan at a higher speed when the signal distortion and/or voltage drop is higher and at a lower speed when the signal distortion and/or voltage drop is lower. In various instances, the patient can also be insufflated through one or more trocars, or ports, extending into the patient. In such instances, the control circuit is configured to communicate with a surgical hub system when the fan is turned on, turned off, accelerated, and/or decelerated such that the insufflation amounts can be properly managed by the surgical hub system. When too much insufflation gas is being pushed into the patient by an insufflation system and/or a surgical instrument, and/or when the amount of insufflation gas being pushed into the patient through the surgical instrument is increased too much, the surgical hub system can operate to reduce the amount of insufflation gas being pushed into the patient through the insufflation trocar. When the amount of insufflation gas being pushed into the patient through the surgical instrument is decreased too much, the surgical hub system can operate to increase the amount of insufflation gas being pushed into the patient through the insufflation trocar.

In addition to or in lieu of the above, the surgical instrument comprises a heating circuit positioned and configured to dry the electrical interface when water intrusion in one of the electrical circuits is detected by the control circuit. In at least one such instance, the heating circuit comprises a resistive heating circuit, for example, comprising a heating resistor adjacent the electrical interface. When the signal distortion and/or voltage drop exceeds a predetermined threshold, the control circuit can power the heating circuit and/or increase the current through the heating circuit, for example. When the signal distortion and/or voltage drop falls below the predetermined threshold, the control circuit can turn off the heating circuit immediately, power the heating circuit for a pre-set additional period of time, and/or reduce the current in the heating circuit, for example.

Figure 101A:
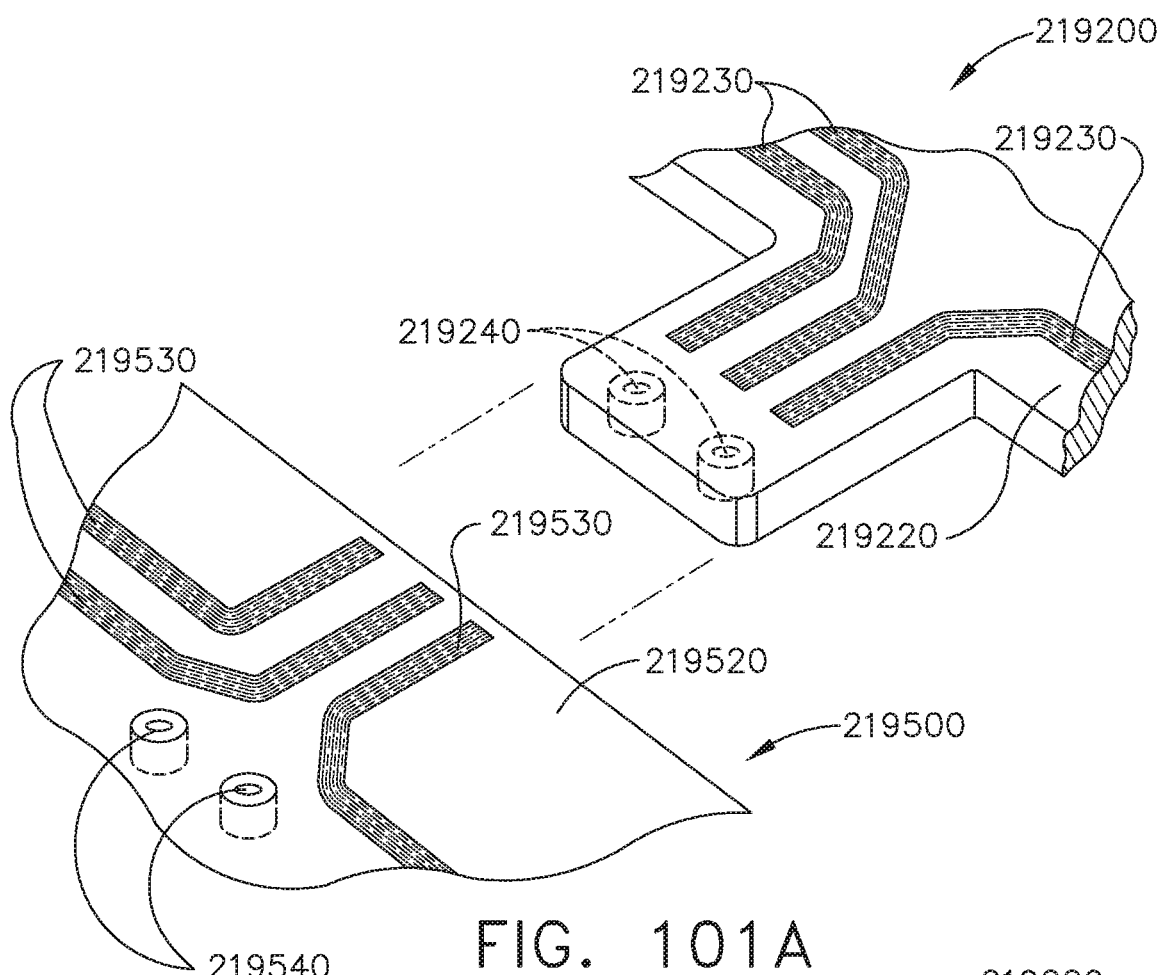
FIG. 101A illustrates a handle flexible circuit and a shaft flexible circuit of a surgical instrument, in accordance with at least one embodiment.
Figure 101B:
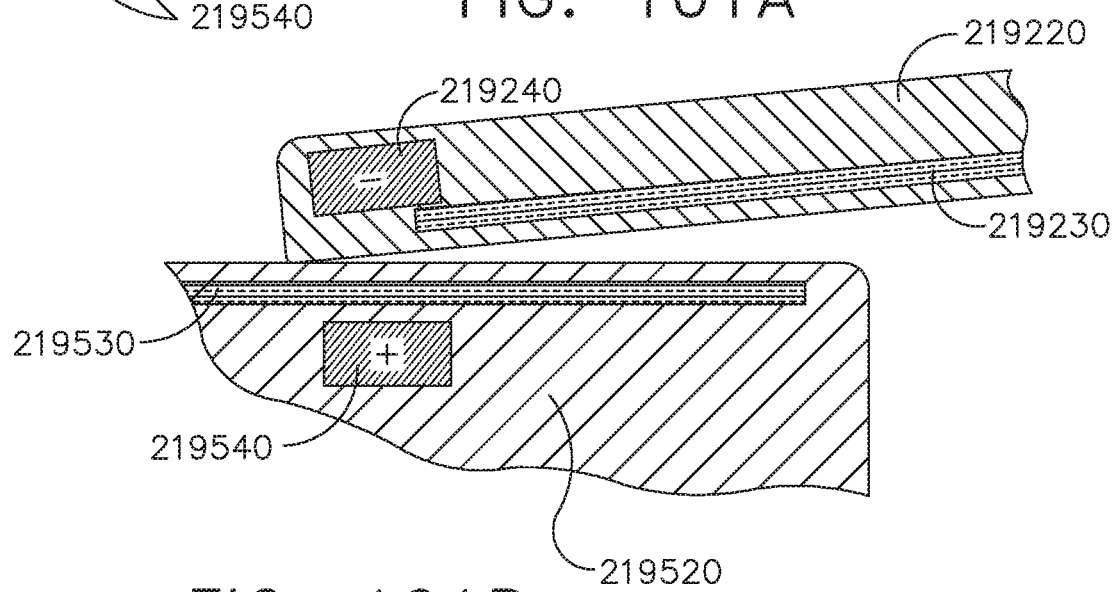
FIG. 101B illustrates a connection between the handle flexible circuit and the shaft flexible circuit of FIG. 101A.

As discussed above, a shaft assembly can be selectively attachable to a handle of a surgical instrument. As also discussed above, the shaft assembly can comprise a shaft flex circuit and the handle can comprise a handle flex circuit. In various instances, the shaft flex circuit and the handle flex circuit comprise electrical connectors which interconnect, or become electrically coupled, when the shaft assembly is mounted to the handle such that the flex circuits are placed in electrical communication with one another. One or both of the electrical connectors can comprise a seal which can seal the electrical interconnection once the electrical connectors are mated; however, one or both of the electrical connectors can comprise unsealed or exposed electrical contacts prior to the interconnection being made. In certain instances, the electrical contacts can be exposed to fluids and/or contaminants. An alternative approach is illustrated in FIG. 101A which depicts a handle flex circuit 219220 and a shaft flex circuit 219520. The handle flex circuit 219220 comprises a flexible substrate and electrical traces 219230 embedded in the flexible substrate. Similarly, the shaft flex circuit 219520 comprises a flexible substrate and electrical traces 219530 embedded in the flexible substrate. Referring to FIG. 101B, the electrical traces 219230 and 219530 are positioned adjacent one another when the shaft assembly is mounted to the handle and are placed in communication with one another. In such instances, the traces 219230 and 219530 form a capacitive and/or inductive connection interface and can communicate electrical signals and/or electrical power across the interface therebetween. As a result, the overlapping traces 219230 and 219250 are enclosed and/or sealed such that their exposure to fluids and/or contaminants is reduced if not eliminated. The walls of the substrate surrounding the traces 219230 and 219530 can be thin and, in various instances, the traces 219230 and 219530 can be printed onto their respective substrates to improve the fidelity of the interconnection therebetween.

As illustrated in FIGS. 101A and 101B, the traces 219230 and 219530 comprise tips which overlap with one another when the flex circuits 219220 and 219520 are interconnected. To facilitate this interconnection, the handle flex circuit 219220 comprises magnets 219240 and the shaft flex circuit 219520 comprises magnets 219540 which arranged in a manner so as to attract one another when brought into close approximation with one another and bring the flex circuits 219220 and 219520 into contact with one another as illustrated in FIG. 101B. The magnets 219240 and 219540 are arranged in two pairs, but can comprise any suitable number and/or arrangement.

A control circuit of a surgical instrument can be utilized to realize variable rate control for a motor-driven system of the surgical instrument. Such motor-driven systems can include, for example, a closing system, a firing system and/or an articulation system of a surgical instrument. In some instances, it is beneficial to utilize a hardware-only implementation of the control circuit to realize the variable rate control of the motor-driven system. For example, a hardware-only implementation can be utilized to provide faster operation than implementations which require software and/or firmware to be executed by a processing device. Also, a hardware-only implementation can be utilized to eliminate the cost and complexity required with processors, software and/or firmware. Additionally, a hardware-only implementation can offer increased reliability, increased durability and an increased life span of the control circuit. Furthermore, a hardware-only implementation can also expand options available for sterilization of the surgical instrument.

In various instances, the rotation of a knob of a surgical instrument and/or the pulling or pressing of an input device of the surgical instrument can cause a proportional position change of the motor. In certain instances, a variable pull of a switch or other input device of the surgical instrument can cause a proportional speed of motor advance.

Figure 102:
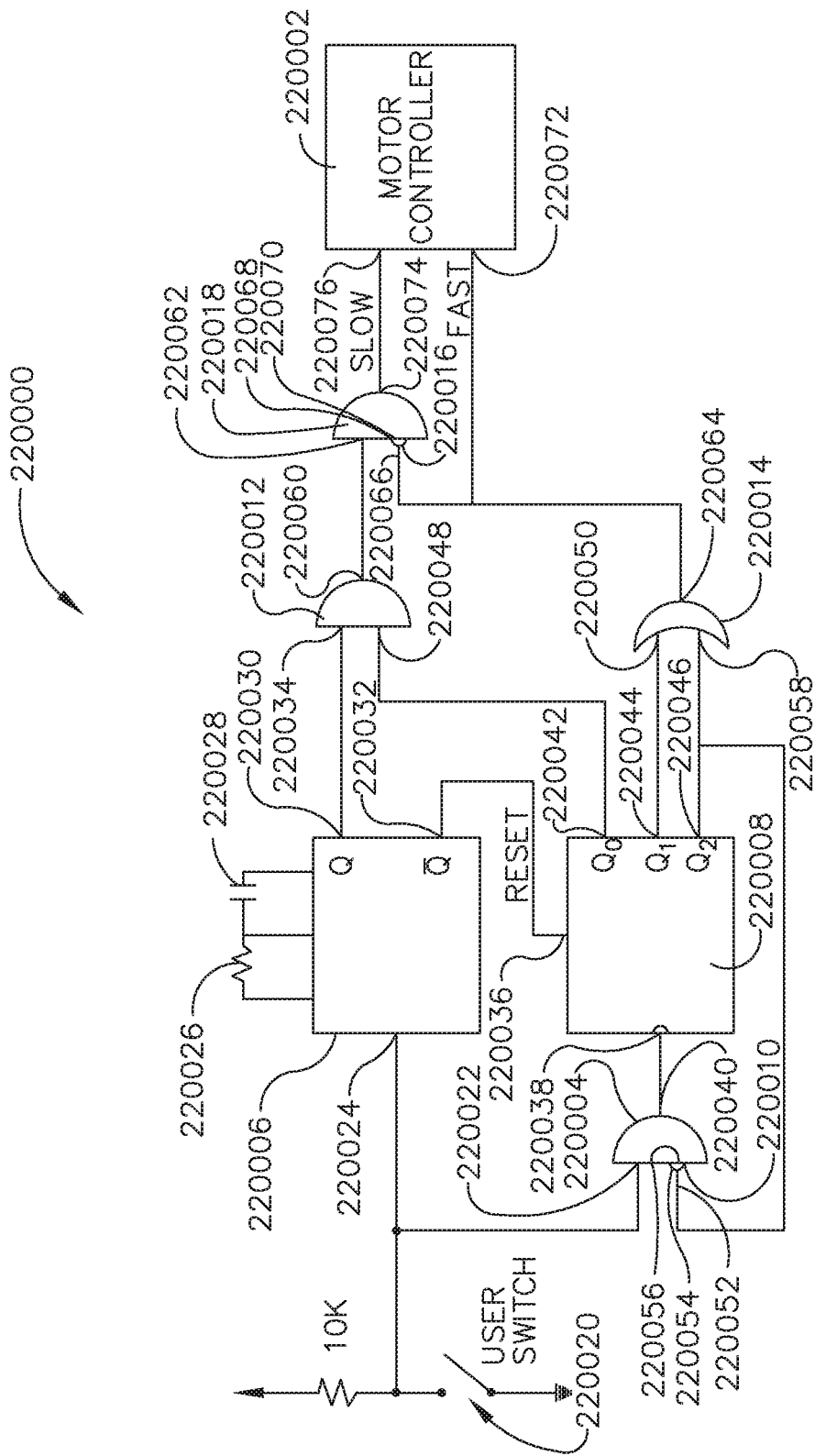
FIG. 102 illustrates a control circuit of a surgical instrument, in accordance with at least one embodiment.

FIG. 102 illustrates a control circuit 220000 of a surgical instrument. The control circuit 220000 is shown as a combinational logic circuit and is utilized to provide input signals and/or waveforms to a motor controller 220002 which controls the speed of rotation of a motor of the surgical instrument. Responsive to the input signals from the control circuit 220000, the motor controller 200002 operates to alter rates of action of a device function based on a parameter that is sensed or tripped as a result of the function that is being performed. For example, in various instances, the device function may be the articulation of an end effector of the surgical instrument, the rate of action may be the speed or velocity of the articulation away from a longitudinal axis of the shaft, and the parameter may be the position of the end effector relative to the longitudinal axis of the shaft. In various instances, the parameter that can be sensed or tripped is the state of an input device, such as a switching device (either open or closed), which can be changed or "bumped" by a user of the surgical instrument.

Further to the above, the control circuit 220000 includes a first AND gate 220004, a monostable multivibrator 220006, an asynchronous counter 220008, a first inverter 220010 (shown as a circle), a second AND gate 220012, an OR gate 220014, a second inverter 220016 (shown as a circle) and a third AND gate 220018. In various instances, the control circuit 220000 also includes the motor controller 22002.

A sensing device 220020, which is shown in FIG. 102 as a user switch, is connected to a first input terminal 220022 of the first AND gate 220004 and to an input terminal 220024 of the monostable multivibrator 220006. In various instances, the control circuit 220000 also includes the sensing device 220020, which may be implemented as a switching device, such as a limit switch, a position sensor, a pressure sensor, and/or a force sensor, among others. According to various aspects, the sensing device 220020 may be implemented as an input device, such as a switching device, which can be actuated or "bumped" by a user of the surgical instrument.

The sensing device 220020 is configured to sense a parameter associated with the surgical instrument and output a signal representative of the sensed parameter. For example, according to various aspects, the sensed parameter can be a user of the surgical instrument "pressing" or "bumping" the sensing device 220020. According to other aspects, the sensed parameter can be the end effector passing through a zone defined around a centered state (e.g., through a zone defined relative to the longitudinal axis of the shaft). The signal output by the sensing device 220020 may be conditioned as needed (not shown) for input to the control circuit 220000. According to various aspects, the sensing device 220020 may output a signal which is representative of a logic "1" or a "high" signal (e.g., 0.5 volts) when the end effector is not in the zone defined around the centered state, and may output a signal which is representative of a logic "0" or a "low" signal (e.g., 0.0 volts) when the end effector is in the zone defined around the centered state. It is to be understood that the above examples of 0.5 volts for a logic "1" or a "high" signal and 0.0 volts for a logic "0" or a "low" signal are merely exemplary. Depending on the specific make and model of the logic components utilized in the control circuit 220000, a voltage other than 0.5 volts may be representative of a logic "1" or a "high" signal and a voltage other than 0.0 volts may be representative of a logic "0" or a "low" signal. As described in more detail hereinbelow, according to various aspects, a plurality of sensing devices 220020 (i.e., two sensing devices, three sensing devices, etc.) may output signals which are for input to the control circuit 220000.

The monostable multivibrator 220006, also known as a "one-shot", includes a resistor 220026 and a capacitor 220028 as depicted in FIG. 102, a first output terminal 220030, and a second output terminal 220032. The signal $\overline{Q}$ which is output from the second output terminal 220032 is a compliment of the signal Q which is output from the first output terminal 220030. The resistor 220026 and the capacitor 220028 collectively form a RC circuit. The monostable multivibrator 220006 is structured to have only one stable state (e.g., a logic "0" output state). When a suitable trigger signal or pulse from the sensing device 220020 is applied to the input terminal 220024 of the monostable vibrator 220006 (e.g., when a user of the surgical instrument presses or bumps the sensing device 220020), the monostable vibrator 220006 generates an output signal Q (e.g., a single output pulse of a specified width) at the first output terminal 220030 for a period of time, and in the process is forced from its stable state (e.g., a logic "0" output state) to another state (e.g., a logic "1" output state). The output signal Q is either a "high" signal or a "low" signal, and the period of time is determined by a time constant of the RC circuit. If no additional "bump" has been applied by the user to the sensing device 220020 and/or no trigger signal or pulse from the sensing device 220020 has been applied to the input terminal 220024 of the monostable multivibrator 220006 during the period of time, the monostable multivibrator 220006 will return to its stable state after the period of time has elapsed (e.g., the output signal Q will go from a logic "1" output state to a logic "0" output state). The first output terminal Q 220030 is connected to a first input terminal 220034 of the second AND gate 220012. The second output terminal 220032 is connected to a reset input terminal 220036 of the asynchronous counter 220008.

As described in more detail hereinbelow, according to various aspects, the monostable multivibrator 220006 can be a retriggerable monostable multivibrator. If the user applies another "bump" to the sensing device 220020 and/or another valid trigger signal or pulse from the sensing device 220020 is applied to the input terminal 220024 of the monostable vibrator 220006 before the output signal Q has returned to the stable state (e.g., a logic "0" state), the width of the pulse of the output signal Q will be increased. Stated differently, the output signal Q will remain in its unstable state (e.g., a logic "1" state) for a longer period of time. Any number of user-initiated "bumps" of the sensing device 220020 and/or any number of valid trigger signals or pulses from a plurality of sensing devices 220020 can be applied to the input terminal 220024 of the monostable vibrator 220006 before the output signal Q has returned to the stable state, with each application operating to further increase the width of the pulse of the output signal Q.

The asynchronous counter 220008 includes a plurality of flip-flops (not shown), where the first one of the flip-flops is clocked by an external clock and each of the subsequent flip-flops are clocked by the output of the preceding flip-flop. Since the external clock signal accumulates propagation delays as it ripples through the plurality of flip-flops, the asynchronous counter 220008 is also known as a ripple counter. As shown in FIG. 102, the asynchronous counter 220008 includes a first input terminal 220038 which is connected to an output terminal 220040 of the first AND gate 220004, a reset input terminal 220036 which is connected to the second output terminal 220032 of the monostable multivibrator 220006, a first output terminal 220042, a second output terminal 220044, and a third output terminal 220046. The first output terminal 220042 of the asynchronous counter 220008 is connected to a second input terminal 220048 of the second AND gate 220012. The second output terminal 220044 of the asynchronous counter 220006 is connected to a first input terminal 220050 of the OR gate 220014. The third output terminal 220046 of the asynchronous counter 220006 is connected to an input terminal 220052 of the first inverter 220010 (shown as a circle) which has an output terminal 220054 which is connected to a second input terminal 220056 of the first AND gate 220004. According to various aspects, the first inverter 220010 is incorporated into the first AND gate 220004. The third output terminal 220046 of the asynchronous counter 220008 is also connected to a second input terminal 220058 of the OR gate 220014.

The output terminal 220060 of the second AND gate 220012 is connected to a first input terminal 220062 of the third AND gate 220018. The output terminal 220064 of the OR gate 220014 is connected to an input terminal 220066 of the second inverter 220016 (shown as a circle) which has an output terminal 220068 which is connected to a second input terminal 220070 of the third AND gate 220018. According to various aspects, the second inverter 220016 is incorporated into the third AND gate 220018. The output terminal 220064 of the OR gate 220014 is also connected to a "fast" input terminal 220072 of the motor controller 220002. The output terminal 220074 of the third AND gate 220018 is connected to a "slow" input terminal 220076 of the motor controller 220002. According to various aspects, when the "slow" input terminal 220074 of the motor controller 220002 receives a "high" signal, the motor controller 220002 operates to run a motor (e.g., an articulation motor) of the surgical instrument at a low speed. Similarly, when the "fast" input terminal 220072 of the motor controller 220002 receives a high signal, the motor controller 200002 operates to run a motor (e.g., an articulation motor) of the surgical instrument at a high speed.

Although the control circuit 220000 is shown as a specific configuration of a hardware-only control circuit in FIG. 102, it will be appreciated that according to other aspects the functionality of the control circuit 220000 (e.g., realizing proportional speed control for a motor-driven system of the surgical instrument) can be implemented with other logic elements and/or other arrangements of logic elements.

Figure 103:
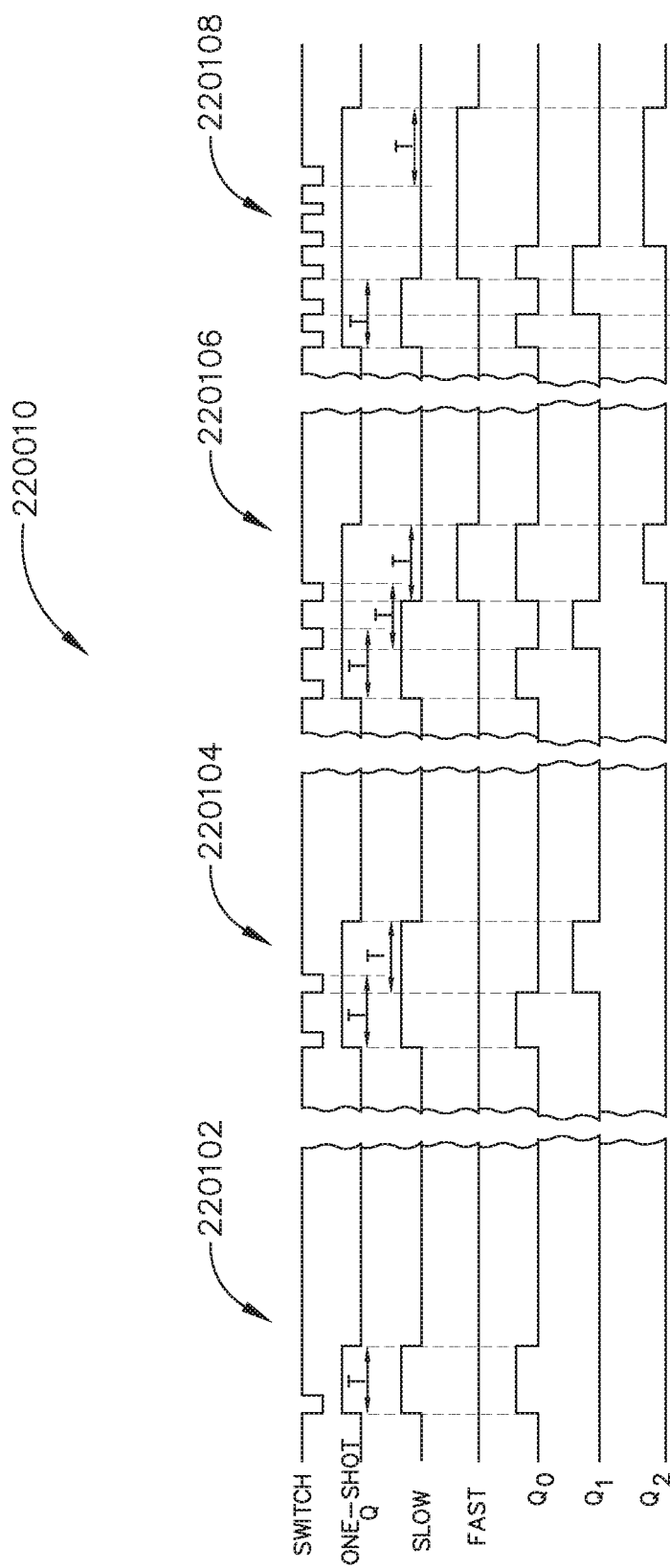
FIG. 103 illustrates timing diagrams associated with the control circuit of FIG. 102, in accordance with at least one embodiment.

FIG. 103 illustrates timing diagrams 220100 associated with the control circuit 220000 of FIG. 102, in accordance with at least one aspect of the present disclosure. The first timing diagram 220102 is shown at the far left side of FIG. 103, and is representative of an instance when a user of the surgical instrument "bumps" the sensing device 220020 a single time, or when a single trigger signal or pulse from the sensing device 220020 is applied to the input terminal 220024 of the monostable vibrator 220006.

When the monostable multivibrator 220006 is in a stable state (e.g., when the user has not yet "bumped" the sensing device 220020 or the sensing device 200020 is in an open condition) as shown on the left-most side of FIG. 103, the output signal Q at the first output terminal 220030 of the monostable multivibrator 220006 is a low signal, the output signals $Q_0$, $Q_1$ and $Q_2$ at the first, second and third output terminals 220042, 220044, 220046 of the asynchronous counter 220008 are low signals, and the signals at the "slow" and "fast" input terminals 220076, 220072 to the motor controller 220002 are low signals.

When the user "bumps" the sensing device 220020 a single time or the sensing device 220020 is triggered a single time and/or transitions, a signal associated with the sensing device 220020 changes, and the changed signal (e.g., in the form of a pulse going from high to low and then back to high as shown in FIG. 103) is input at the input terminal 220024 to the monostable multivibrator 220006. Responsive to the leading edge of the pulse of the input signal, the Q output signal at the first output terminal 220030 of the monostable multivibrator 220006 transitions from a low signal to a high signal in the form of a pulse having a duration of T. The asynchronous counter 220008 recognizes this first change (e.g., a change in count from 0 to 1) and operates to transition the output signal $Q_0$ at the first output terminal 220042 of the asynchronous counter 220008 from a low signal to a high signal in the form of a pulse having a duration of T. The $Q_1$ and $Q_2$ signals at the second and third output terminals 220044, 220046 of the asynchronous counter 220008 are not affected by the first change in the signal associated with the sensing device 220020 and remain as low signals.

By having high signals at the first and second input terminals 220034, 220048 of the second AND gate 220012, a high signal is at the output terminal 220060 of the second AND gate 220012, and this high signal is also at the first input terminal 220062 of the third AND gate 220018. By having low signals at the first and second input terminals 220050, 220058 of the OR gate 220014, the signals at the output terminal 220064 of the OR gate 220064 and at the "fast" terminal of the motor controller 220002 are also low signals. The low signal from the output terminal 220064 of the OR gate is converted from a low signal to a high signal by the second inverter 220016, and this high signal is at second input terminal 220070 of the third AND gate 220018. By having high signals at the first and second input terminals 220062, 220070 of the third AND gate 220018, the signal at the output terminal 220074 of the third AND gate is a high signal, and this high signal (in the form of a pulse having a duration of T) is also at the "slow" input terminal 220076 of the motor controller 220002. Thus, when a user "bumps" the sensing device 220020 a single time or a single trigger signal or pulse from the sensing device 220020 is applied to the input terminal 220024 of the monostable vibrator 220006, the motor controller 220002 causes the motor of the surgical instrument to run at a "slow" speed for a time T.

The second timing diagram 220104 is shown to the immediate right of the first timing diagram 220102, and is representative of an instance when a user "bumps" the sensing device twice or two trigger signals or pulses from the sensing device 220020 (or from sensing devices 220020) are applied to the input terminal 220024 of the monostable vibrator 220006, where the second of the "bumps" or of the trigger signals or pulses is applied to the input terminal 220024 of the monostable vibrator 220006 before the output signal Q has returned to the stable state (e.g., a logic "0" state). The second timing diagram 22104 is the same as the first timing diagram 220102 up until the time that the second "bump" or the second trigger signal or pulse occurs. As the second of the "bumps" or of the trigger signal or pulse occurs before the output signal Q has returned to the stable state (e.g., a logic "0" state), the width of the pulse of the output signal Q is increased (the output signal Q remains a high signal for a period of time), and the width of the pulse of the signal input to the "slow" input terminal 220076 of the motor controller 220002 is increased (the signal remains a high signal for a period of time), which results in the motor running at the "slow" speed from the time of the first "bump" or of the trigger signal or pulse until the occurrence of the falling edge of the output signal Q.

Additionally, the asynchronous counter 220008 recognizes this second change (e.g., a change in count from 1 to 2) and operates to transition the output signal $Q_0$ at the first output terminal 220042 of the asynchronous counter 220008 from a high signal back to a low signal, and to transition the output signal $Q_1$ at the second output terminal 220044 of the asynchronous counter 220008 from a low signal to a high signal in the form of a pulse having a duration of T. The $Q_2$ signal at the third output terminal 220046 of the asynchronous counter 220008 is not affected by the second change in the signal associated with the sensing device 220020 and remains a low signal. Thus, when two user-initiated "bumps" of the sensing device 220002 or two trigger signals or pulses from the sensing device 220020 (or from a plurality of sensing devices 220020) are applied to the input terminal 220024 of the monostable vibrator 220006, where the second of the two "bumps" or of the trigger signals or pulses is applied while the output signal Q is still high, the motor controller 220002 operates to cause the motor of the surgical instrument to run at a "slow" speed for a time greater than T. In this instance, the time greater than T is the sum of the time T shortened by the leading edge of the second "bump" or of the second trigger signal or pulse plus the time T.

The third timing diagram 220106 is shown to the immediate right of the second timing diagram 220104, and is representative of an instance when three "bumps" are applied to the sensing device 220020 or three trigger signals or pulses from the sensing device 220020 (or from sensing devices 220020) are applied to the input terminal 220024 of the monostable vibrator 220006, where the second and third of the "bumps" or of the trigger signals or pulses are applied to the input terminal 220024 of the monostable vibrator 220006 before the output signal Q has returned to the stable state (e.g., a logic "0" state). The third timing diagram 22106 is the same as the second timing diagram 220104 up until the time that the third "bump" or trigger signal or pulse occurs. As the third "bump" or trigger signal or pulse occurs before the output signal Q has returned to the stable state (e.g., a logic "0" state), the width of the pulse of the output signal Q is increased (the output signal Q remains a high signal for a period of time). This causes the motor controller 220002 to run the motor at a "slow" speed during the time associated with the first and second "bumps" or trigger signals or pulses until the occurrence of the rising edge of the output signal $Q_0$, the falling edge of the output signal $Q_1$ and the rising edge of the output signal $Q_2$. Thereafter, the motor controller 220002 operates to run the motor at a "fast" speed for the time T after the third "bump" or trigger signal or pulse until the occurrence of the falling edge of the output signal Q, the falling edge of the signal $Q_0$ and the falling edge of the output signal $Q_2$.

The asynchronous counter 220008 recognizes this third change (e.g., a change in count from 2 to 3) and operates to transition the output signal $Q_1$ at the second output terminal 220044 of the asynchronous counter 220008 from a high signal back to a low signal, to transition the output signal $Q_0$ at the first output terminal 220042 of the asynchronous counter 220008 from a low signal to a high signal in the form of a pulse having a duration of T, and to transition the output signal $Q_2$ at the third output terminal 220046 of the asynchronous counter 220008 from a low signal to a high signal in the form of a pulse. As shown in FIG. 103, due to some propagation delay, the output signal $Q_2$ transitions somewhat later than the output signal $Q_0$ does, and thus has a duration somewhat less than T. The transitions of the $Q_0$ output signal, the $Q_1$ output signal and the $Q_2$ output signal operate to cause the signal at the slow input terminal 220076 of the motor controller 220002 to transition from a high signal back to a low signal, and to cause the signal at the "fast" input terminal 220072 of the motor controller 220002 to transition from a low signal to a high signal (e.g., in the form of a pulse having a duration of T). Thus, when three "bumps" or trigger signals or pulses from the sensing device 220020 (or from a plurality of sensing devices 220020) are applied to the input terminal 220024 of the monostable vibrator 220006, where the second and third of the three "bumps" or trigger signals or pulses are applied while the Q output signal is still high, the motor controller 220002 operates to cause the motor of the surgical instrument to run at a "slow" speed for a time greater than T (i.e., the sum of the time T shortened by the leading edge of the second trigger signal or pulse plus the time T), then to run at a "fast" speed for the time T.

The fourth timing diagram 220108 is shown to the immediate right of the third timing diagram 220106, and is representative of an instance when multiple (e.g., more than three) "bumps" are applied to the sensing device 220020 or multiple trigger signals or pulses from the sensing device 220020 (or from sensing devices 200020) are applied to the input terminal 220024 of the monostable vibrator 220006, where each of the "bumps" or trigger signals or pulses occur after the first "bump" is applied to the sensing device 220020 or after the first trigger signal or pulse is applied to the input terminal 220024 of the monostable vibrator 220006 before the output signal Q has returned to the stable state (e.g., a logic "0" state). The fourth timing diagram 22108 is the same as the third timing diagram 220106 up until the time that the fourth "bump" or trigger signal or pulse occurs. As the fourth "bump" or trigger signal or pulse occurs before the output signal Q has returned to the stable state (e.g., a logic "0" state), the width of the pulse of the output signal Q is increased (the output signal Q remains a high signal for a period of time). This causes the motor controller 220002 to cause the motor to continue to run at a "fast" speed as long as the Q output signal is high (e.g. for the time T after the fourth "bump", trigger signal or pulse). The asynchronous counter 220008 is reset on the falling edge of the output signal Q2.

The asynchronous counter 220008 recognizes this fourth change (e.g., a change in count from 3 to 4) and operates to extend the width of the pulse of the output signal $Q_1$ at the second output terminal 220044 of the asynchronous counter 220008, and to shorten the duration of the second pulse of the output signal $Q_0$ at the first output terminal 220042 of the asynchronous counter 220006.

As shown in the timing diagram 220108, as additional "bumps" (e.g., a fifth "bump", a sixth "bump", etc.) are applied to the sensing device 220020 or additional trigger signals or pulses (e.g., a fifth trigger signal or pulse, a sixth trigger signal or pulse, etc.) from the sensing device 220020 (or from sensing devices 200020) are applied to the input terminal 220024 of the monostable vibrator 220006 before the output signal Q has returned to the stable state (e.g., a logic "0" state), the width of the pulse of the output signal $Q_2$ is extended until a time T has elapsed after the last "bump", trigger signal or pulse has been applied before the output signal Q has returned to the stable state (e.g., a logic "0" state). Thus, when four or more "bumps" or trigger signals or pulses have occurred, where the second, third, fourth, etc. of the four or more "bumps" or trigger signals or pulses are applied while the Q output signal is still high, the motor controller 220002 operates to cause the motor of the surgical instrument to run at a "slow" speed for a time greater than T (i.e., the sum of the time T shortened by the leading edge of the second trigger signal or pulse plus the time T), then to run at a "fast" speed until a time T has elapsed after the last "bump", trigger signal or pulse is applied before the output signal Q has returned to the stable state. The $Q_2$ output signal remains high until the asynchronous counter 220008 is reset on the falling edge of the output signal Q.

In some applications, the control circuit 220000 does not have to be as sophisticated as is shown in FIG. 102. For example, in some applications, it may be desirable to run the motor at a "slow" speed initially for a short period of time then allow the motor to speed up to a faster speed or to a full speed. This can be useful, for example, when articulating an end effector of a surgical instrument. For example, according to various aspects, a control circuit for the articulation system of the surgical instrument can be implemented with an "end-of-stoke" switch that allows the articulation motor to be operated in the reverse direction but not any further in the forward direction while the "end-of-stroke" switch is tripped. In other applications, it may be desirable to change the speed of the motor from a slow speed to a fast speed, or from a fast speed to a slow speed, for a controllable period of time.

Figure 104:
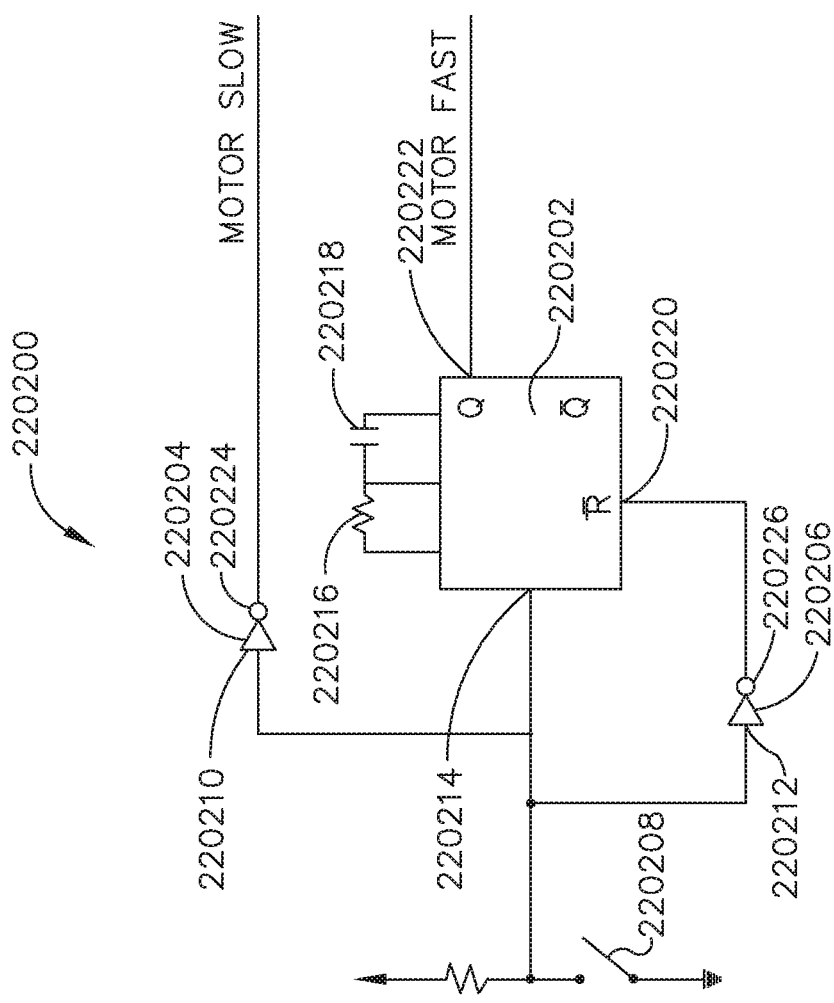
FIG. 104 illustrates a control circuit of a surgical instrument, in accordance with at least one embodiment.

FIG. 104 illustrates a control circuit 220200 of a surgical instrument. The control circuit 220200 is shown as a combinational logic circuit and may be utilized to provide input signals and/or waveforms to a motor controller (not shown for purposes of simplicity in FIG. 104). Responsive to the input signals from the control circuit 220200, the motor controller operates to change the motor speed when an input device of the surgical instrument is held in a given position for a period of time.

The control circuit 220200 is similar to the control circuit 220000 of FIG. 102 in that the control circuit 220200 includes a monostable multivibrator 220202, a first inverter 220204, and a second inverter 220206, but is different in that it does not include the other components of control circuit 220000 and has a different functionality. According to various aspects, the control circuit 220200 includes the motor controller, which may be similar or identical to the motor controller 220002 of FIG. 102.

A sensing device 220208, which is shown in FIG. 104 as a switching device, is connected to an input terminal 220210 of the first inverter 220204, to an input terminal 220212 of the second inverter 220206, and to a first input terminal 220214 of the monostable multivibrator 220202. According to various aspects, the control circuit 220200 also includes the sensing device 220208, which may be implemented as a trigger, a switching device, such as a push button, a limit switch, a position sensor, a pressure sensor, and/or a force sensor, among others.

The monostable multivibrator 220202 can be similar or identical to the monostable vibrator 220006, and includes a resistor 220216 and a capacitor 220218 as depicted in FIG. 104, the first input terminal 220214, a reset input terminal 220220, and a first output terminal 220222. The resistor 220216 and the capacitor 220218 collectively form a RC circuit. The first output terminal 220222 of the monostable multivibrator 220202 is connected to a "motor fast" input terminal of the motor controller.

The first inverter 220204 also includes an output terminal 220224 which is connected to a "motor slow" input terminal of the motor controller. The second inverter 220206 also includes an output terminal 220226 which is connected to the reset input terminal 220220 of the monostable multivibrator 220202.

In operation, when the sensing device 220208 is changed from an open position as shown in FIG. 104 to a closed position and held in place for a period of time (e.g., by a user of the surgical instrument), a "low" signal is applied to the input terminal 220210 of the first inverter 220204, to the input terminal 220212 of the second inverter 220206, and to the first input terminal 220214 of the monostable multivibrator 220202. The first inverter 220204 operates to invert the "low" signal to a "high" signal at the output terminal 220224 of the first inverter 220204, which results in a "high" signal being at the "motor slow" input terminal of the motor controller, resulting in a motor (e.g., an articulation motor) of the surgical instrument being operated at a "slow" speed. The second inverter 220206 also operates to invert the "low" signal to a "high" signal at the output terminal 220226 of the second inverter 220206, which results in a "high" signal being at the reset input terminal 220220 of the monostable multivibrator 220202. Once the sensing device 220208 is released from its "held" position, after a period of time determined by a time constant of the RC circuit, the monostable multivibrator 220202 operates to generate a "high" signal (the output signal Q) at the output terminal 220222 of the monostable multivibrator 220202, which results in a "high" signal being at the "motor fast" input terminal of the motor controller. The time constant can be on the order of approximately 0.5 seconds to 1.0 seconds, for example. The "high" signal at the "motor fast" input terminal of the motor controller results in the motor of the surgical instrument changing from a "slow" speed of rotation to a "fast" of "full" speed of rotation. The timer of the monostable multivibrator 220202 is reset once the sensing device 220208 changes from a closed state back to an open state (e.g., by releasing the push button). Thus, in cooperation with the sensing device 220208, the control circuit 220200 can be utilized to create a "slow" motor speed for a controllable period of time, followed by the speed of the motor then being increased to a "fast" motor speed or all the way up to a "full" motor speed.

Although the control circuit 220200 is described above in the context of a controllable "slow" speed followed by a "fast" speed, it will be appreciated that the control circuit 220200 can also be configured to realize a controllable "fast" speed followed by a "slower" speed. It will be appreciated that the control circuit 220200 can be implemented with solid state circuits configured to create different motor speeds. According to various aspects, the surgical instrument can include a switching system configured to slow the articulation motor as it passes thru a predefined portion of the articulation arc. According to various aspects, the surgical instrument can also include a switching system configured to rotate an anvil to an open position at a relatively fast speed. For example, a switch could be located on the anvil at point where positive opening tabs contact, and the closing of the switch can operate to cause a fast period of opening when the switch is tripped. According to various aspects, the control circuit can be configured to prevent a single point failure in motor control circuit.

As discussed above, a control circuit is configured to control the power delivered to an electric motor. In some instances, a light emitting diode (LED) array can be configured as a proportional display to show motor speed or current. For example, a display driver such as the LM3914 by Texas Instruments can be utilized to drive a display that is proportional to current. Different colors, different placement or different LEDs (or even skipping some LEDs on the display array) can be utilized to emphasize that the current is proportional to the load on the motor system.

FIG. 104A illustrates a control circuit 220400 configured to indicate the power being delivered to the electric motor. The control circuit 220400 comprises a power supply 220410, a motor control circuit 220420, a LM3914 integrated circuit (or similar display driver) 220430, and a segmented display 220450 in communication with a plurality of gates or contacts 220440 defined on the integrated circuit 220430. The integrated circuit 220430 comprises ten comparators and a resistor scaling network, for example; however, the integrated circuit 220430 can comprise any suitable arrangement to drive a graduated display (See FIG. 104B) which indicates the current being drawn by the electric motor. The segmented display 220450 comprises ten light emitting diodes (LEDs), i.e., 220451-220460, which are each in communication with one of the contacts 220440. For the control circuit 220400, the LEDs 220451-220460 light up in proportion to the motor current being drawn, which is in proportion to the torque applied/delivered by the motor, either in the forward direction or the reverse direction.

Each LED represents 10 percent of the maximum applicable current to the electric motor. Thus, the LED 220541 is illuminated when the electric motor is drawing more than 10 percent of the total current available (and when the motor is applying/delivering a low torque). If the motor current draw does not exceed 20 percent, however, the second LED 220452 is not illuminated—nor are the LEDs 220453-220460. When the electric motor is drawing more than 20 percent of the total current available, the second LED 220452 is illuminated, and so forth. When the electric motor is drawing 100% of the available current, all of the LEDs 220451-220460 are illuminated (and when the motor is applying/delivering a high torque).

In at least one alternative aspect, some of the LEDs, such as the ninth and tenth LEDs 220459 and 220460 represent an overdrive condition of the electric motor. Moreover, while ten LEDs provide a conveniently understandable display, any suitable number of LEDs could be used, such as three LEDs, for example. In such instances, a first LED, when illuminated, would represent a low torque condition, a second LED, when illuminated, would represent a mid-torque condition, and a third LED, when illuminated, would represent a high-torque condition, for example. Although FIGS. 104A and 104B are described in the context of current being drawn by the motor, it will be appreciated that similar circuitry could be utilized to provide an indication of motor speed by measuring and displaying motor voltage instead of motor current.

Figure 104C:
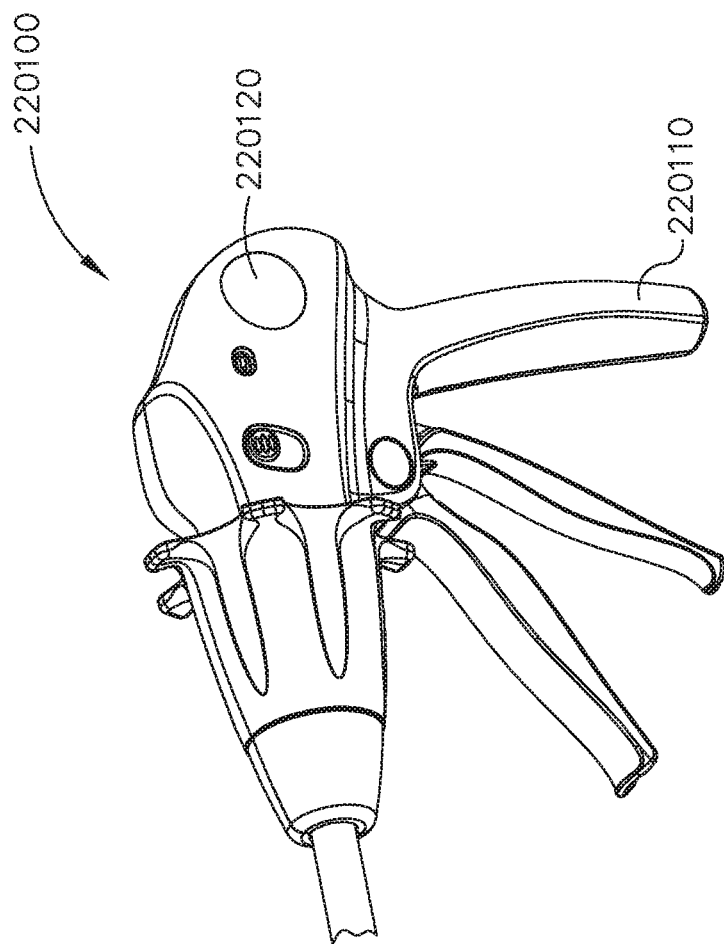
FIG. 104A illustrates a control circuit configured to indicate the power being delivered to an electric motor, in accordance with at least one embodiment.

FIG. 104C illustrates a surgical instrument comprising a handle 220100. The handle 220100 comprises a handle housing 220110, actuators, and a control system configured to operate the surgical instrument. Similar to other surgical instruments disclosed herein, the control system of the handle 220100 is configured to communicate with a surgical hub system. While the handle 220100 can be configured to communicate wirelessly with the surgical hub system via electromagnetic waves, the handle 220100 comprises an acoustic speaker and/or an acoustic sensor configured to communicate with the surgical hub system. The surgical hub system also comprises an acoustic speaker and/or an acoustic sensor in the same room, or at least within sufficient auditory range, as the surgical instrument so as to communicate with the surgical instrument. Such data communication is wireless, and can comprise various chirps, for example, which may or may not be within the auditory range of a human being. The signals can be above, within, and/or below the auditory range of a human being. An acoustic system advantageously does not rely on emitting electromagnetic waves which may interfere with the operation of a surgical instrument and/or system, for example, in the same operating room.

In some instances, it is desirable to configure a circuit to determine the suitability of the circuit before the circuit is energized. For example, it would be desirable to detect the return path capacity of an electrosurgical circuit, and if the return path capacity is not sufficient, limit the amount of electrosurgical energy to be applied to a patient without exceeding a predefined localized current threshold. According to various aspects, the surface area and the resistance levels of the grounding pad are used to determine the return path capacity, and if the return path capacity is found to be insufficient, the output of the monopolar generator is limited to a level below the localized current level threshold. In practice, it is beneficial to maximize the generator coupling to patient for the highest efficiency and to realize the best electrosurgical performance while limiting the power when the patient contact quality is changed or goes below a threshold where a burn is possible. According to various aspects, a printed flex circuit of the electrosurgical system includes a predefined zone with an altered area which acts as a fuse to define the maximum capacity of the return path.

FIG. 105 illustrates a surgical system 220300, in accordance with at least one aspect of the present disclosure. The surgical system 220300 includes a surgical hub 220302, an electro-surgical instrument 220304, a capacitive return pad 220306, and a cable or cord 220308 which connects the capacitive return pad 220306 with the surgical hub 220302. The capacitive return pad 220306 and the cable or cord 220308 collectively form a return path for the electrosurgical energy applied to the patient via the electrosurgical instrument 220304. When applying electrosurgical energy to a patient, it is important to ensure that the current-carrying capacity of the return path is sufficient to handle the amount of electrosurgical energy applied to the patient.

The surgical hub 220302 includes a monopolar generator module 220310, and the monopolar generator module 220310 includes a sensing device (see FIG. 106) configured to sense electrical continuity in the return path for the electrosurgical energy. Various aspects of a surgical hub are described in more detail in U.S. patent application Ser. No. 15/940,629, entitled COMPUTER IMPLEMENTED INTERACTIVE SURGICAL SYSTEMS, filed on Mar. 29, 2018, the disclosure of which is hereby incorporated by reference in its entirety. Various aspects of a electro-surgical instrument and a capacitive return pad are described in more detail in U.S. patent application Ser. No. 16/024,090, entitled CAPACITIVE COUPLED RETURN PAD WITH SEPARABLE ARRAY ELEMENTS, filed on Jun. 29, 2018, the disclosure of which is hereby incorporated by reference in its entirety.

As described in more detail hereinbelow, the surgical system 220300 is configured to detect the current-carrying capacity of the return path (by sensing the continuity of the return path) and limit the maximum amount of electrosurgical energy applied to the patient (by controlling the electrosurgical energy delivered by the monopolar generator module 220310), without exceeding a predefined localized current threshold.

Figure 106:
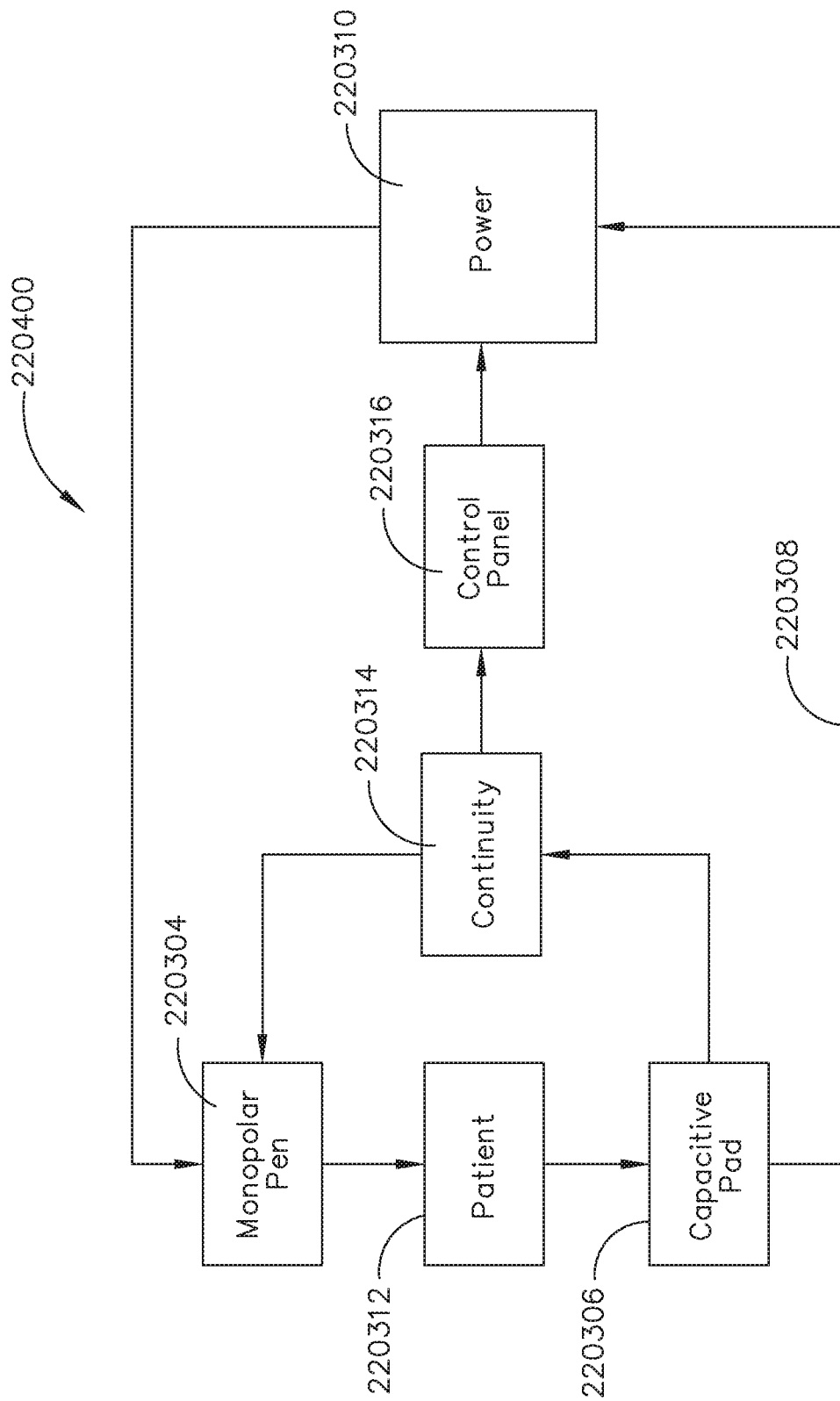

FIG. 106 illustrates a schematic diagram 220400 which is representative of current and signal paths of the surgical system 220300 of FIG. 105, in accordance with at least one aspect of the present disclosure. Electrosurgical current is supplied by the monopolar generator module 220310 of the surgical hub 220302 to the electro-surgical instrument 220304, where is it selectively applied to a patient 220312. The applied electrosurgical current passes through the body of the patient 220312 and is received by the capacitive return pad 220306, then subsequently passes through the cable or cord 220308 back to the monopolar generator module 220310 of the surgical hub 220302 to complete the path followed by the electrosurgical current.

Although the sensing device 220314 of the monopolar generator module 220310 of the surgical hub 220302 is shown schematically in FIG. 106 as sensing the electrical continuity between the capacitive return pad 220306 and the electrosurgical instrument 220304, it will be appreciated that the sensing device 220314 senses the electrical continuity from the capacitive return pad 220306 and the cable or cord 220308 to the electrosurgical instrument 220304 via the sensing device 220314 positioned within the monopolar generator module 220310. The sensing device 220314 operates to monitor the continuity, and is configured to generate an output signal which is representative of the integrity and/or current carrying-capacity of the return path. The output signal generated by the sensing device 220314 is passed to a control system 220316 of the monopolar generator module 220310, and the control system 220316 operates to control the amount of electrosurgical energy delivered to the electrosurgical instrument 220304. In instances where the continuity of the return path is less than absolute (e.g., where the integrity of the return path varies from absolute), the control system 220316 operates to limit the amount of electrosurgical energy delivered to the electrosurgical instrument 220304, without exceeding a predefined localized current threshold.

Figure 107:
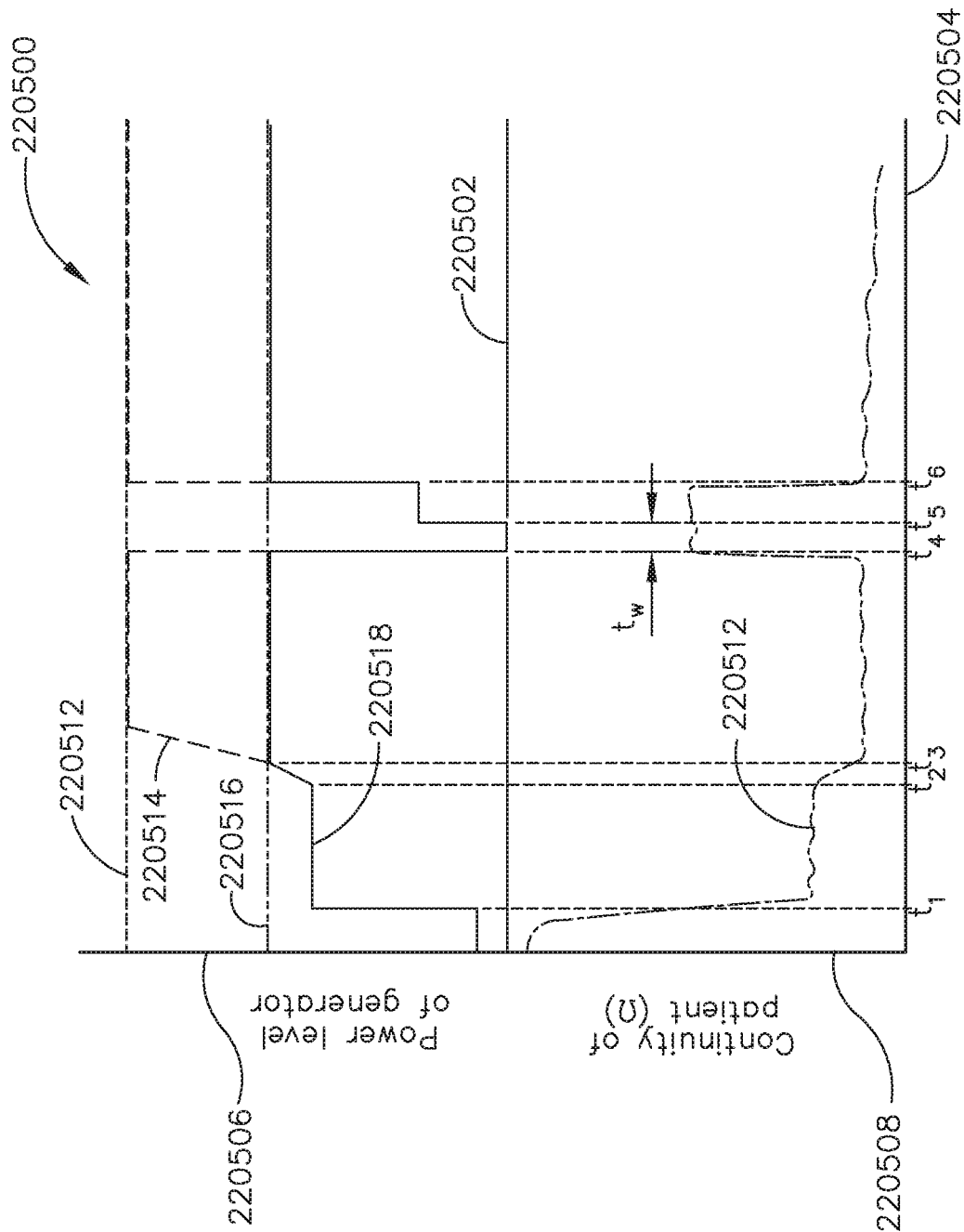

FIG. 107 illustrates a graph 220500 which shows a relationship between a continuity level of the patient 220312 and the level of electrosurgical power supplied by the monopolar generator module 220310 of the surgical system 220300 of FIG. 105, in accordance with at least one aspect of the present disclosure. The continuity level of the patient 220312, as measured by the resistance of the patient 220312, can serve as a proxy for the continuity level of the return path of the surgical system 220300. The graph 220500 includes two horizontal axes—an "upper" horizontal axis 220502 and a "lower" horizontal axis 220504. The time t is shown along the "lower" horizontal axis 220504, but is not shown along the "upper" x-axis 220502 for purposes of clarity. However, as indicated by the vertical dashed lines shown in FIG. 107, the "upper" horizontal axis 220502 and the "lower" horizontal axis 220504 are aligned with one another. The graph 220500 also includes two vertical axes— an "upper" vertical axis 220506 and a "lower" vertical axis 220508. The level of electrosurgical power supplied by the monopolar generator module 220310 of the surgical system 220300 is shown along the "upper" y-axis 220506 and the continuity level of the patient 220312, as measured by the resistance of the patient 220312, is shown along the "lower" y-axis 220508.

The graph 220500 further includes a maximum power threshold 220510 for the monopolar generator module 220310, a potential power level 220514 available at the electrosurgical instrument 220304 for application to the patient 220312, a user setting 220516 for the power level supplied by the monopolar generator module 220310, the actual power level 220518 of electrosurgical energy applied by the electrosurgical instrument 220304, and the electrical continuity 220520 of the patient 220312, as measured by the resistance of the patient 220312. As described in more detail hereinbelow, as the continuity of the patient 220312 varies (which corresponds to variations of the detected return path integrity), the level of electrosurgical energy supplied by the monopolar generator module 220310 varies.

Starting at time t=0 at the left hand side of the "lower" horizontal axis 220504, as well as at the left hand side of the "upper" horizontal axis 220502, and moving toward time $t_1$, as the continuity of the patient 220312 begins to increase, the level of power supplied by the monopolar generator module 220310 begins to increase. From time $t_1$ to time $t_2$, as the continuity of the patient 220312 levels off and remains relatively constant, the level of power supplied by the monopolar generator module 220310 levels off and remains relatively constant. From time $t_2$ to time $t_3$, as the continuity of the patient 220312 further increases, the level of power supplied by the monopolar generator module 220310 further increases and reaches the user setting 220516 for the monopolar generator module 220310. From time $t_3$ to time $t_4$, as the continuity of the patient 220312 levels off and remains relatively constant, the level of power supplied by the monopolar generator module 220310 levels off and remains relatively constant. At time $t_4$, as the continuity level of the patient 220312 decreases, the level of power supplied by the monopolar generator module 220310 decreases. As shown in FIG. 107, according to various aspects, if a loss of integrity of the return path is detected, the power supplied by the monopolar generator module 220310 can be turned off (the level of power supplied by the monopolar generator module 220310 decreases to zero) for a period of time to allow for the integrity of the return path to be verified (e.g., by the control system 220316 of the monopolar generator module 220310) before allowing for the power to start being supplied again by the monopolar generator module 220310. In FIG. 107, the period of time is represented by the wait time $t_w$ which is shown as the period of time between time $t_4$ and time $t_5$.

From time $t_4$ to time $t_5$, while the power supplied by the monopolar generator module 220310 is shown as zero, the continuity of the patient 220312 levels off and remains relatively constant. At time $t_5$, once the wait time $t_w$ has been reached, the power to the monopolar generator module 220310 is restored and the power supplied by the monopolar generator module 220310 increases. From time $t_5$ to time $t_6$, as the continuity of the patient 220312 continues to remain relatively constant, the level of power supplied by the monopolar generator module 220310 levels off and remains relatively constant. At time $t_6$, as the continuity level of the patient increases again, the level of power supplied by the monopolar generator module 220310 increases again, in this case up to but not exceeding the power level associated with the user setting 220516. After time $t_6$, as the continuity of the patient 220312 levels off and then continues to remain relatively constant, the level of power supplied by the monopolar generator module 220310 levels off at the power level associated with the user setting 220516 and then remains relatively constant.

According to various aspects, to more easily accomplish certain functions (e.g., articulation), the surgical instrument includes one or more flexible circuits. According to various aspects, the flexible circuits are configured such that (1) the impact of any vibration on the flexible circuit is minimized, (2) solid chip attachment locations are sealed off from fluids and/or (3) the flexible circuits are easily inner-connectable to one another. According to various aspects, the substrates of one or more of the flexible circuits are bio-compatible with tissue of the patient, and such flexible circuits can be implanted within the patient. According to various aspects, the flexible circuits can have tubular part features for housing leads from the flexible circuit while the flexible circuit is being assembled but not necessarily at the final assembly locations. According to various aspects, electrical and/or mechanical sensors can be integrated into the flexible circuits.

Shielding can be integrated with/built into the flexible circuits to prevent unwanted radio-frequency (RF) interference from affecting the performance of the flexible circuits. In certain aspects, the flexible circuits can include various configurations of twisted pair wiring. In addition to providing for the transmission of power and/or signals within the surgical instrument, the twisted pair wiring can be configured to provide one or more secondary functions. Such secondary functions can include, for example, shielding the twisted pair wiring from electromagnetic interference, short-circuit detection, and/or contamination detection.

Figure 108:
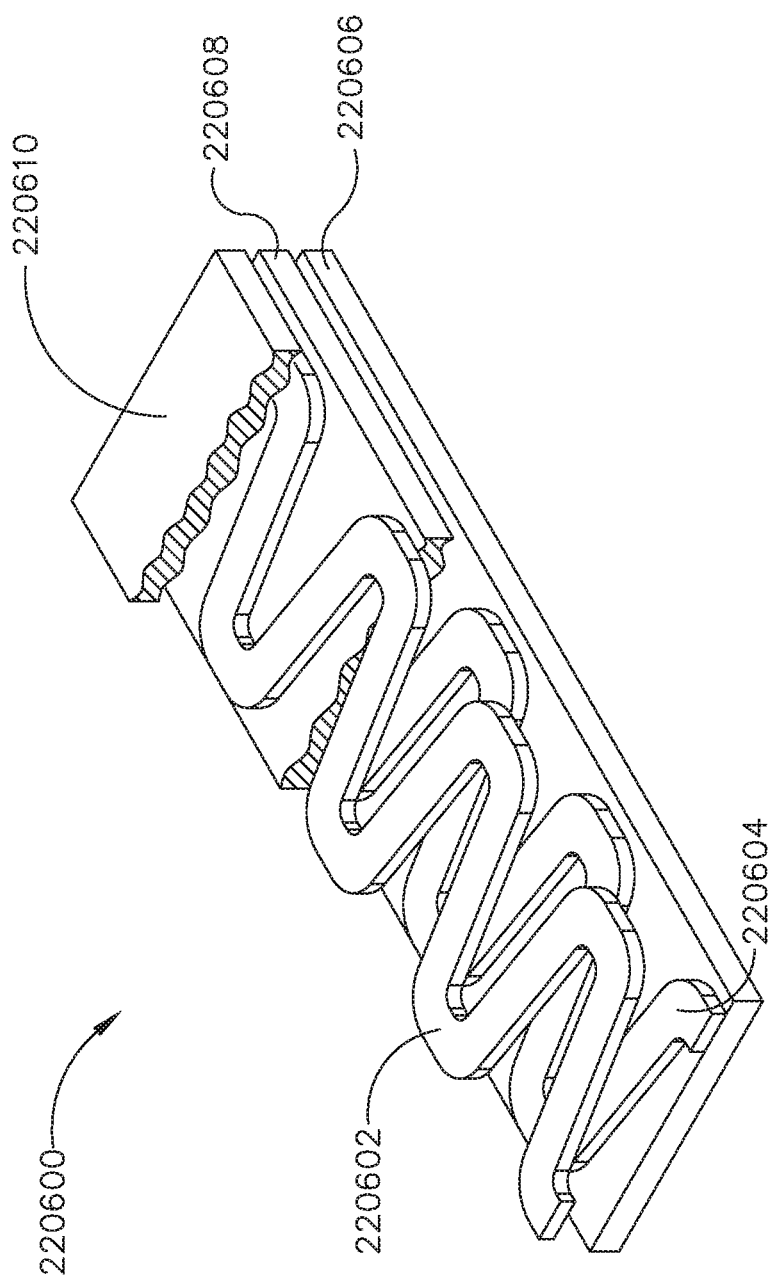

FIG. 108 illustrates a flexible circuit 220600 of a surgical instrument. The flexible circuit 220600 includes a twisted pair of conductors, where the twisted pair of conductors includes a "top" conductive trace 220602 and a "bottom" conductive trace 220604. As shown in FIG. 108, the "top" and "bottom" conductive traces 220602, 220604 overlap one another at regular intervals. When a current or a signal is being carried through the twisted pair of conductors, the overlapped configuration of the "top" and "bottom" conductive traces 220602, 220604 operates to better protect the current or signal from potential interference from an external electromagnetic field. This is particularly true when the primary macro-direction of the flexible circuit 220600 is parallel to the source of the electromagnetic field which can cause the potential interference.

The flexible circuit 220600 also includes a first layer 220606 of an insulative material, a second layer 220608 of an insulative material and a third layer 220610 of an insulative material. The first layer 220606 of the insulative material is positioned "below" the "bottom" conductive trace 220604. The second layer 220608 is positioned "above" the "bottom" conductive trace 220604 and "below" the "top" conductive trace 220602 (i.e., between the "top" and "bottom" conductive traces 220602, 220604). The third insulative layer 220610 is positioned "above" the "top" conductive trace 220602. According to various aspects, the "bottom" conductive trace 220604 is formed directly on the first layer 220606 of the insulative material, and the "top" conductive trace 220602 is formed directly on either the second layer 220608 of the insulative material or the third layer 220610 of the insulative material. According to various aspects, the first layer 220606, the second layer 220608 and the third layer 220610 each comprise a polymer such as, for example, a polyimide.

Figure 109:
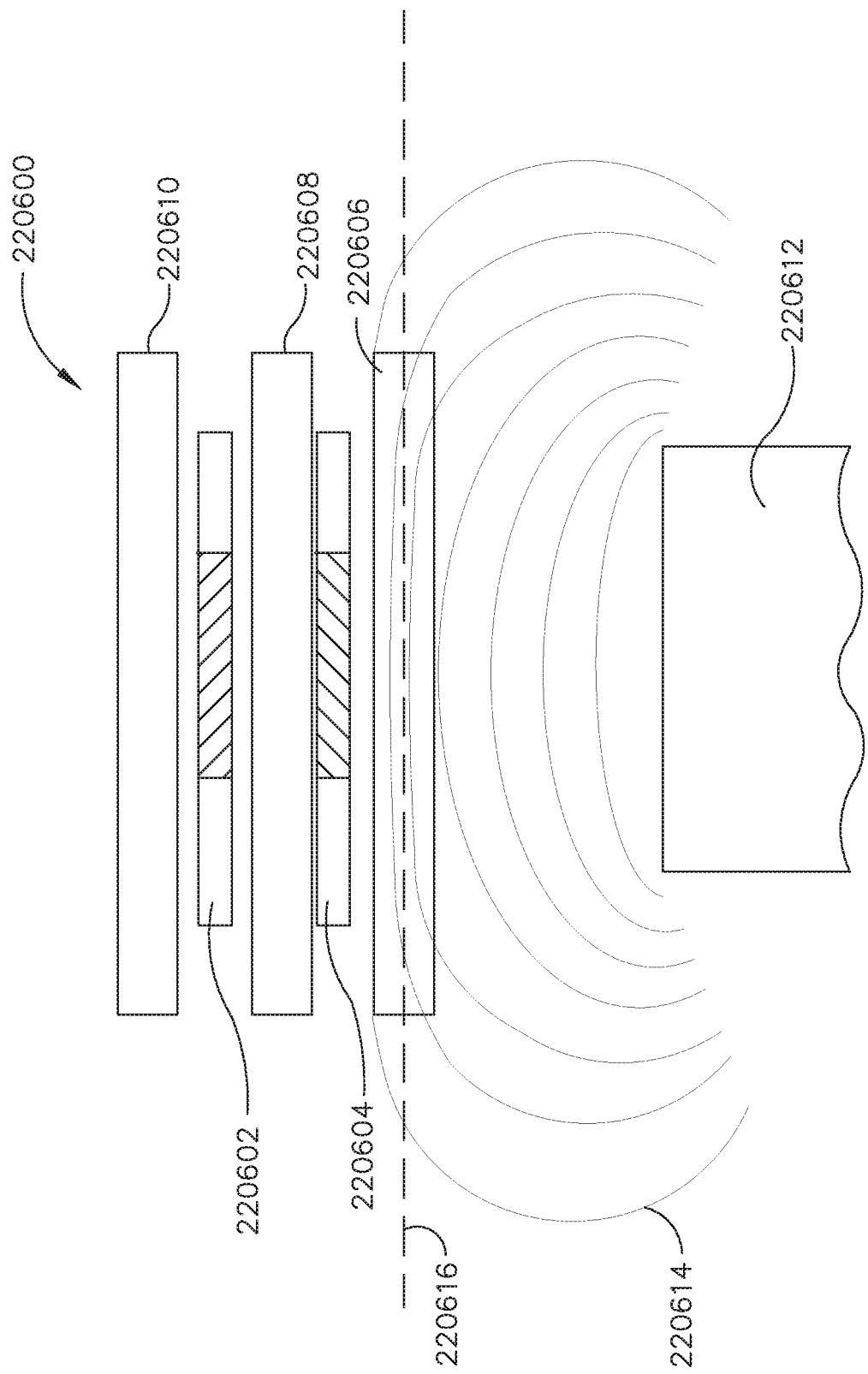

FIG. 109 illustrates a cross-section of the flexible circuit 220600 of FIG. 108. The hatched areas shown on the "top" and "bottom" conductive traces 220602, 220604 represent the areas where the "top" and "bottom" conductive traces 220602, 220604 overlap one another. As shown in FIG. 109, when a source 220612 generates an electromagnetic field 220614 (shown as electromagnetic field lines), the overlapped configuration of the "top" and "bottom" conductive traces 220602, 220604 operate to block or reject the electromagnetic field 220614 which can cause the potential interference, especially so along the direction of the dashed line 220616. According to various aspects, flexible circuits other than those with twisted pairs of conductors can be configured to provide the above-mentioned secondary functions.

Figure 110:
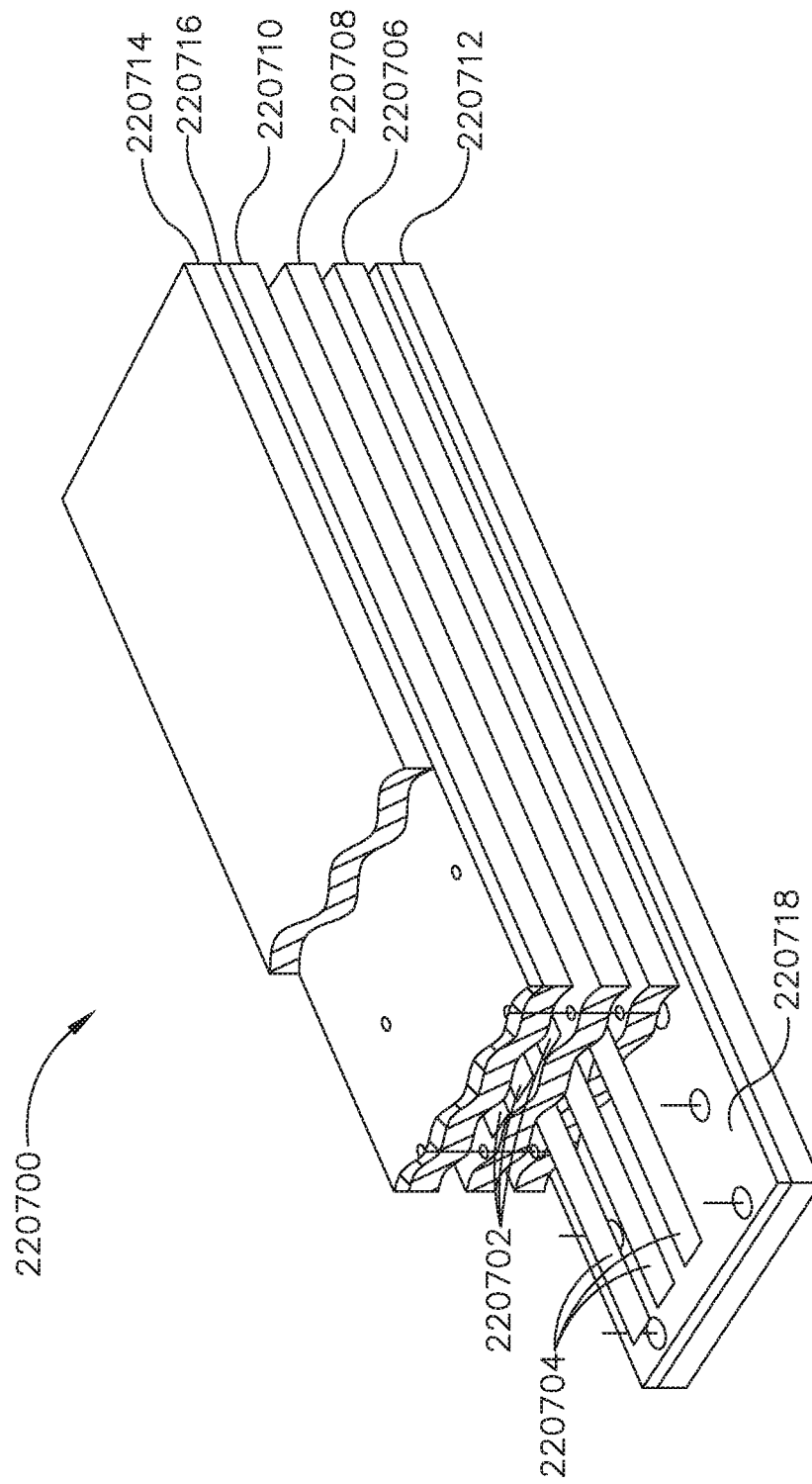

FIG. 110 illustrates a flexible circuit 220700 of a surgical instrument. The flexible circuit 220700 includes a first plurality of conductive traces 220702 and a second plurality of conductive traces 220704, where the first and second pluralities of conductive traces 220702, 220704 are positioned at different layers of the flexible circuit 220700. The flexible circuit 220700 also includes a first layer 220706 of an insulative material, a second layer 220708 of an insulative material, a third layer 220710 of an insulative material, a fourth layer 22712 of an insulative material, and a fifth layer 22714 of an insulative material. The first layer 220706 of the insulative material is positioned "below" the second plurality of conductive traces 220704. The second layer 220708 is positioned "above" the second plurality of conductive traces 220704 and "below" the first plurality of conductive traces 220702 (i.e., between the first and second pluralities of conductive traces 220702, 220704). The third insulative layer 220610 is positioned "above" the first plurality of conductive traces 220702. According to various aspects, the second plurality of conductive traces 220704 is formed directly on the first layer 220706 of the insulative material, and the first plurality of conductive traces 220702 is formed directly on either the second layer 220708 of the insulative material or the third layer 220710 of the insulative material. According to various aspects, the first layer 220706, the second layer 220708, the third layer 220710, the fourth layer 220712 and the fifth layer 220714 each comprise a polymer such as, for example, a polyimide.

Figure 111:
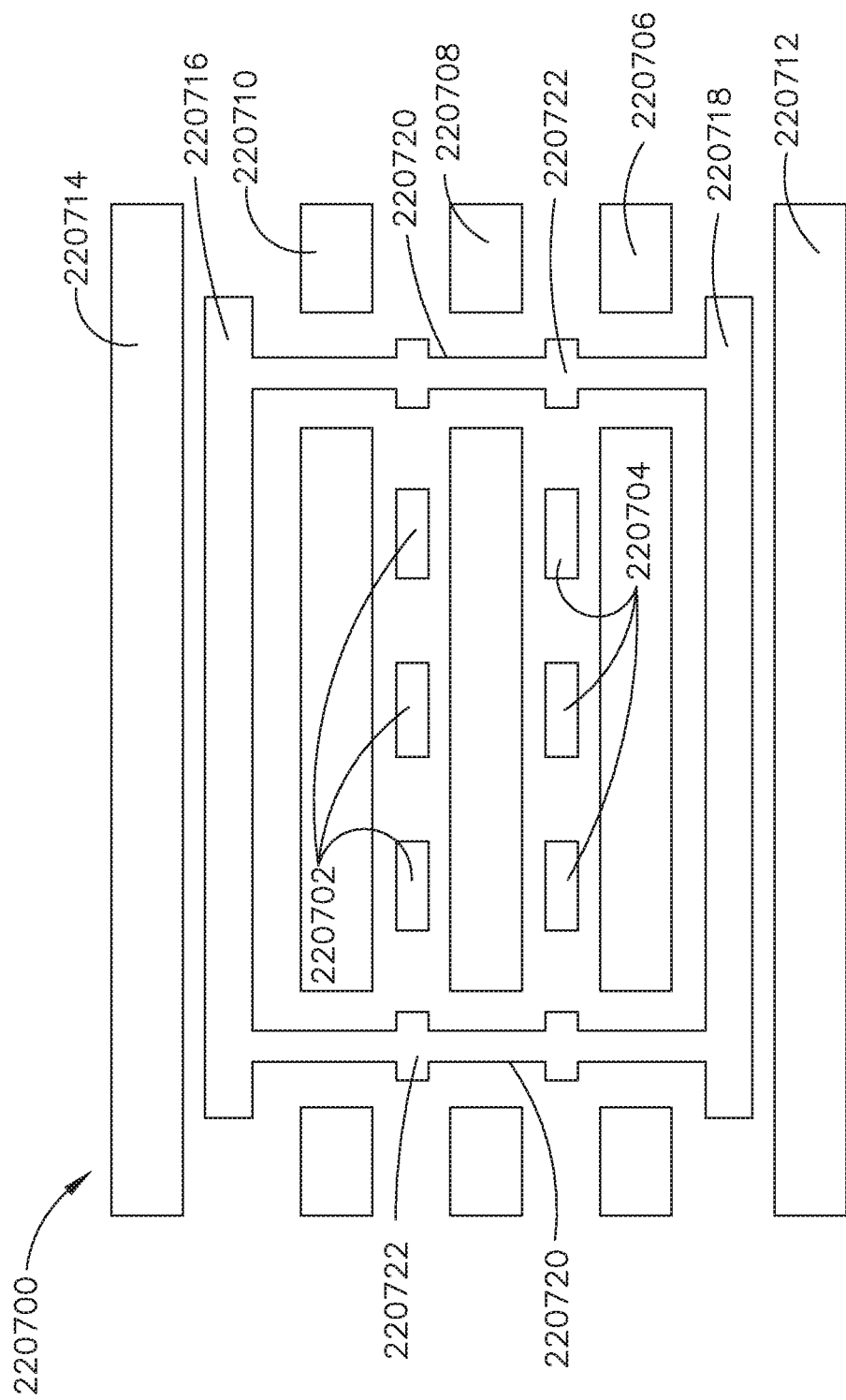

Referring to FIG. 111, the flexible circuit 220700 further includes a first shield layer 220716, a second shield layer 220718, and vertical shields 220720. The vertical shields 220720 are formed through vias in the first, second and third layers 220706, 220708, 220710 of the insulative material. The first shield layer 220716, the second shield layer 220718, and the vertical shields 220720 collectively operate to better protect currents or signals being carried through the first and/or second pluralities of conductive traces 220702, 220704 from potential interference from an external electromagnetic field. The first shield layer 220716 is positioned "above" the third layer 220710 of insulative material and "below" the fifth layer 220714 of insulative material (i.e., between the third and fifth layers 220710, 220714 of insulative material). The second shield layer 220718 is positioned "above" the fourth layer 220712 of insulative material and "below" the first layer 220706 of insulative material (i.e., between the fifth and first layers 220712, 220706 of insulative material). The vertical shields 220720 are connected to the first and second shield layers 220712, 220714, and surround the "left" and "right" sides of the first and second pluralities of conductive traces 220702, 220704. As the first shield layer 220712 covers the "bottom" of the second plurality of conductive traces 220704 and the second shield layer 220714 covers the "top" of the first plurality of conductive traces 220702, the first shield layer 220712, the second shield layer 220714 and the vertical shields 220720 collectively cooperate to form an electromagnetic shield which surrounds a cross-section of the first and second pluralities of conductive traces 220702, 220704.

Further to the above, the flexible circuit 220700 can additionally include shield traces 220722 (see FIG. 111) which can be positioned alongside and along the length of the "left" and "right" sides of the first and second pluralities of conductive traces 220702, 220704 such that the first shield layer 220712, the second shield layer 220714, the vertical shields 220720 and the trace shields 220722 collectively cooperate to form an electromagnetic shield which surrounds a length of the first and second pluralities of conductive traces 220702, 220704. The position and arrangement of the first, second, third, fourth and/or fifth layers 220706, 220708, 220710, 220712, 220714 of insulative material provide the secondary function of providing short-circuit protection between the first and second pluralities of conductive traces 220702, 220704 and/or between the electromagnetic shield and the first and second pluralities of conductive traces 220702, 220704. By effectively surrounding a length of the first and second pluralities of conductive traces 220702, 220704, the first shield layer 220712, the second shield layer 220714, the vertical shields 220720 and the trace shields 220722 collectively operate to protect the flexible circuit 220700 from potential interference from an external electromagnetic field.

Figure 111A:
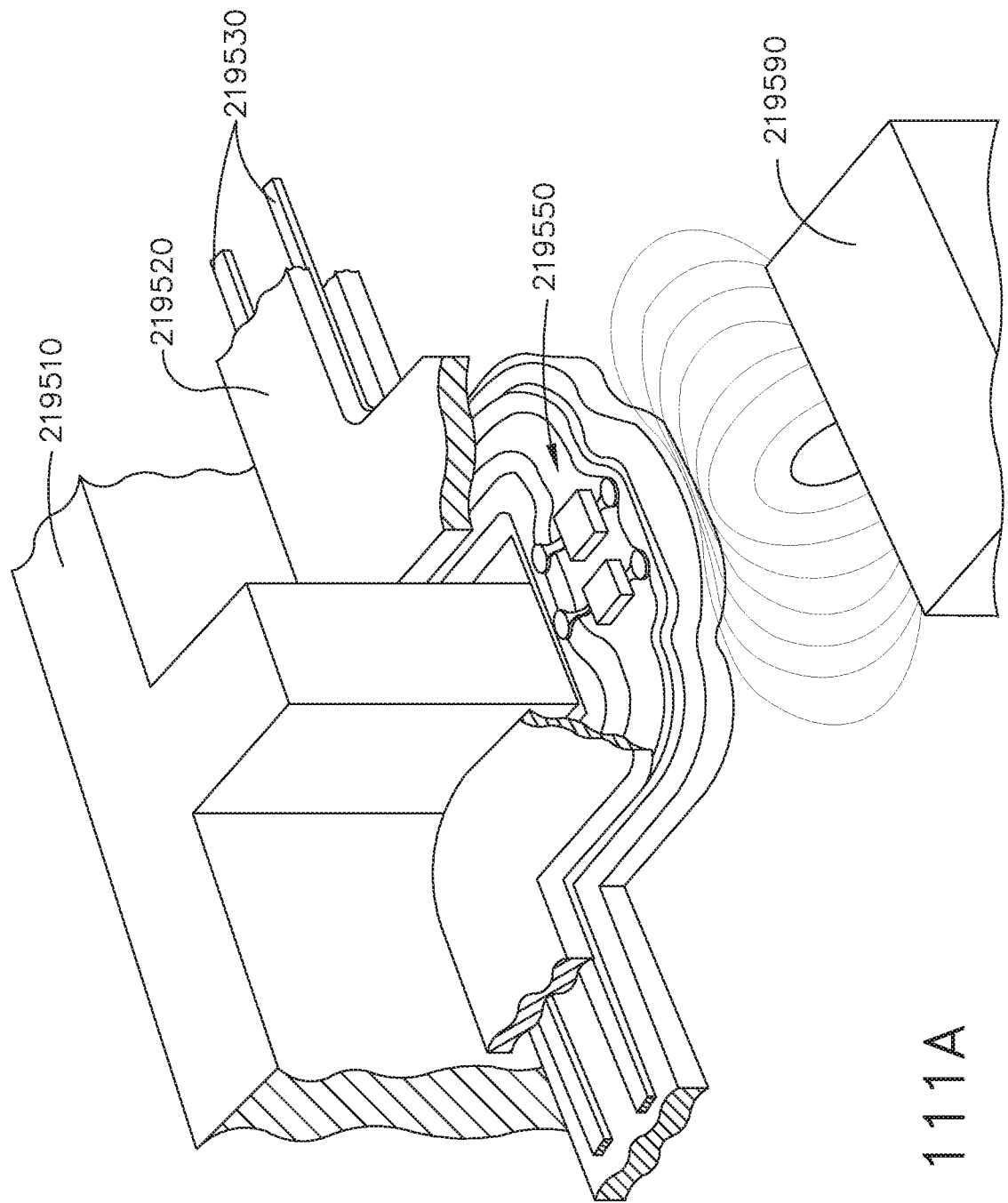

Further to the above, a flex circuit of a surgical instrument can comprise components configured to absorb, distribute, and/or otherwise address electromagnetic interference (EMI) from components within the surgical instrument and/or an adjacent surgical instrument, for example. Referring to FIG. 111A, a circuitous flex circuit 219520 extends alongside a shaft shroud 219510 and, in certain instances, passes closely to an EMI emitting component, such as 219590, for example. The flex circuit further comprises components 219550, such as ferrites, inductors, capacitors, and/or snubber networks, for example, where they are needed. Smaller components can be used if the burden of absorbing the EMI is shared across multiple components. In certain instances, the components 219550 bridge or extend between two or more conductive traces 219530 in the flex circuit 219520.

The aspects which provide for provide short-circuit detection and/or contamination detection are described with reference to FIGS. 101A and 101B hereinabove.

A control circuit of a surgical instrument can be utilized to control one or more motor-driven systems of the surgical instrument. Such motor-driven systems can include an end effector closing system, an end effector articulation system, and/or a firing system, for example. In some instances, it is beneficial to utilize a parameter of a motor-driven system to control the motor-driven system. For example, as explained in greater detail below, a parameter such as acoustic data, vibration data, and/or acceleration data associated with the motor-driven system can provide an indication that one or more components of the motor-driven system is experiencing degradation, operating in a damaged state, and/or heading toward failure, for example, and can be utilized to control the motor-driven system in light of these potential issues.

Figure 112:
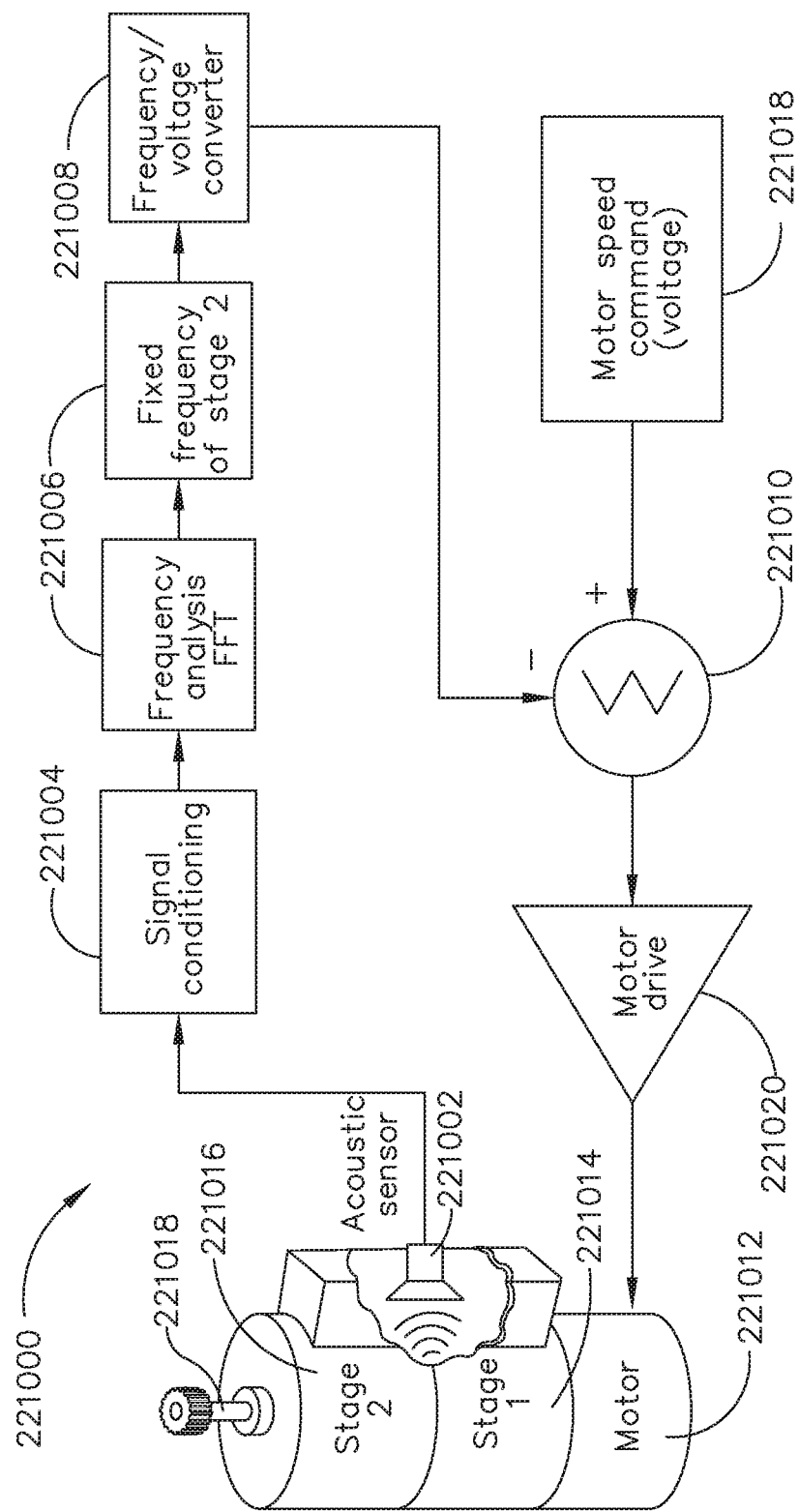

FIG. 112 illustrates a control circuit 221000 of a surgical instrument. The control circuit 221000 is configured as a closed-loop system which utilizes an acoustic measurement to control the rotation speed of an electric motor, such as a drive motor, for example, of the surgical instrument. As the rotation speed of an electric motor has a distinct relationship to the torque applied/delivered by the electric motor (the speed and the torque can be inversely proportional to one another), the control circuit 221000 can also be considered as being configured as a closed-loop system which utilizes an acoustic measurement to control the torque applied/ delivered by an electric motor, such as a drive motor, for example, of the surgical instrument. For purposes of simplicity, the control circuit 221000 will be described hereinafter in the context of controlling the rotation speed of the electric motor of the surgical instrument.

The control circuit 221000 includes at least one acoustic sensor 221002, at least one signal conditioner 221004, at least one Fast Fourier Transform (FFT) circuit 221006, at least one frequency-to-voltage converter 221008, and at least one summing amplifier 221010. The control circuit 221000 further comprises a motor drive circuit 221020 which is configured to control the electric motor, as described in greater detail below. In various instances, the control circuit 221000 forms a part of another control circuit of the surgical instrument. For example, the control circuit 221000 can form a part of the control circuit which includes a main processing circuit and/or main processor of the surgical instrument, and/or one or more memory devices, for example.

The acoustic sensor 221002 is configured to sense acoustic information, in the form of vibration energy, associated with an electric motor 221012, gearboxes 221014, 221016 operably coupled to the motor 221012, and/or a drive train 221018 operably coupled with the gearboxes 221014, 221016. The electric motor 221012, the gearboxes 221014, 221016 and the drive train 221018 collectively form a drive system of the surgical instrument. Thus, the acoustic sensor can be considered as being configured to measure a parameter of the drive system of the surgical instrument. In various instances, the acoustic sensor 221002 comprises a piezoelectric pickup, for example, responsive to the acoustic forces transmitted by the soundwaves emitted from the motor 221012, the gearboxes 221014, 221016, and/or the drive train 221018. The acoustic sensor 221002 is configured to convert the mechanical energy from the sound waves into electrical energy in the form of electric signals or voltage potentials within the circuitry of the acoustic sensor 221002. Notably, the acoustic information sensed by the acoustic sensor 221002 is not limited to vibrations within the range of human hearing. Vibrations above or below the range of human hearing can also be sensed by the acoustic sensor 221002 and converted into electrical energy.

Further to the above, the gearboxes 221014, 221016 comprise speed reduction gearboxes configured to produce a rotational output which is slower than the output speed of the electric motor 221012. As a result, the electric motor 221012 and the drive train 221018 rotate at different speeds and, accordingly, have different acoustic signatures. The input of the first gearbox 221014 rotates at the speed of the electric motor 221012 while the output of the first gearbox 221014 rotates at a slower speed than the electric motor 221012 and, as such, the first gearbox 221014 has a different acoustic signature than the electric motor 221012. Similarly, the input of the second gearbox 221016 rotates at the speed of the first gearbox 221014 output and the output of the second gearbox 221016 rotates at a different speed than its input. As such, the second gearbox 22106 has a different acoustic signature than the first gearbox 221014. Each of these acoustic signatures has a frequency content, including wavelength and amplitude/magnitude, which is related to the speed of the respective component.

The signal conditioner 221004 is configured to receive the acoustic information (e.g., electric signals or voltage potentials) from the acoustic sensor 221002 and convert the acoustic information into another type of electrical signals. For example, in various instances, the signal conditioner 221004 may amplify the magnitude of the electrical signals from the acoustic sensor 221002, filter out noise within the electrical signals from the acoustic filter 221002, etc. The fast Fourier transform (FFT) circuit 221006 executes a FFT algorithm which analyzes the electrical signals from the signal conditioner 221004 and converts the electrical signals from a time domain to a representation in the frequency domain. In various instances, a main processing circuit of the surgical instrument can execute the FFT algorithm. The converted electrical signals may be considered frequency component signals. The frequency-to-voltage converter 221008 is configured to convert the frequency component signals provided by the FFT circuit 221006 to a proportional voltage signal. The proportional voltage signal is used as a feedback signal which is input into the summing amplifier 221010. The summing amplifier 221010 compares the proportional voltage signal to a motor speed command signal (which is a voltage signal) provided by a motor controller 221018, and adjusts the motor speed command signal as needed. For example, if the proportional voltage signal from the frequency-to-voltage converter 221008 is the same as the motor speed command signal provided by the motor controller 221018, no adjustment of the motor speed command signal is needed. However, if the proportional voltage signal from the frequency-to-voltage converter 221008 is different from the motor speed command signal provided by the motor controller 221018 (e.g., less than or greater than), the summation amplifier 221010 will increase or decrease the motor speed command signal so that the motor can realize the desired speed of rotation. The adjusted motor speed command signal is passed to the motor drive circuit 221020, which operates to provide a voltage to the motor, where the voltage varies in accordance with a desired speed of rotation of the motor as called for by the adjusted motor speed command signal. In various instances, the motor controller 221018 and/or the motor drive circuit 221020 are part of the control circuit 221000, or they can comprise separate circuits in communication with the control circuit 22100. In certain instances, the motor controller 221018 and/or the motor drive circuit 221020 are part of a control circuit which includes the main processor of the surgical instrument.

Further to the above, the control circuit 221000 is configured to discern between the different acoustic signatures of various electric motors, gearboxes, and/or drive trains of the surgical instrument using a single acoustic sensor. In various other instances, the control circuit 221000 can comprise a plurality of acoustic sensors 221002. In at least one such instance, each acoustic sensor 221002 is exclusively dedicated to pick up the acoustic waves of a single component of the surgical instrument, such as an electric motor, gearbox, or drive train, for example. In any event, baselines for the respective acoustic signatures of the rotatable components of a surgical instrument can be established during the assembly of the surgical instrument, and such baselines serve as references for the control circuit 221000 to associate the sensed acoustic signatures with the correct components and, also, determine whether or not the surgical instrument is operating normally. Moreover, by utilizing one or more acoustic sensors 221002 in this way, the speed of a motor and/or gearbox can be sensed/measured, the start of travel by a translatable member can be detected, and/or the end of travel by the translatable member can be detected during use, for example.

In various instances, further to the above, utilizing acoustic information allows for the remote sensing of motor speed, thereby eliminating the need for directly coupled sensors and/or encoders, for example. In various instances, the cost of the acoustic sensor 221002 can be considerably less than an encoder and the assembly, wiring, and electronics to support the encoder. Moreover, the acoustic sensor 221002 and the FFT circuit 221006 can be part of a redundant system that confirms readings from other systems. Such an arrangement can be useful for mitigating risks and can create single point failure tolerant designs, for example. Furthermore, as indicated above, the acoustic sensor 221002 and the FFT circuit 221006 can provide various indications of failure, wear, etc. of the drive components of the surgical instrument. Additional details regarding the detection of drive train failure can be found, for example, in U.S. patent application Ser. No. 15/131,963, entitled METHOD FOR OPERATING A SURGICAL INSTRUMENT, filed Apr. 18, 2016, now U.S. Patent Application Publication No. 2017/0296173, the disclosure of which is hereby incorporated by reference in its entirety. The entire disclosure of U.S. patent application Ser. No. 15/043,289, entitled MECHANISMS FOR COMPENSATING FOR DRIVETRAIN FAILURE IN POWERED SURGICAL INSTRUMENTS, filed on Feb. 12, 2016, now U.S. Patent Application Publication No. 2017/0231628 is incorporated by reference herein.

Although the control circuit 221000 was described above in terms of the acoustic sensor 221002, it should be appreciated that other parameters of a surgical instrument can be sensed/measured to provide motor speed control. For example, an accelerometer and/or vibration sensor, for example, can be utilized in addition to or in lieu of the acoustic sensor 221002 to sense/measure acceleration data, vibration data, etc. associated with a motor-driven system of the surgical instrument. Such data can be utilized to control the speed of rotation of the motor, as described in greater detail below.

Further to the above, the functionality of the control circuit 221000 is utilized to implement one or more methods for identifying the degradation and/or failure of the drive components of the surgical instrument. Such drive components include, for example, the motor 221012, the first gearbox 221014, the second gearbox 221016, and/or the drive train 221018 which can include a rack and pinion 221022 (see FIG. 115) arrangement, for example.

Figure 113:
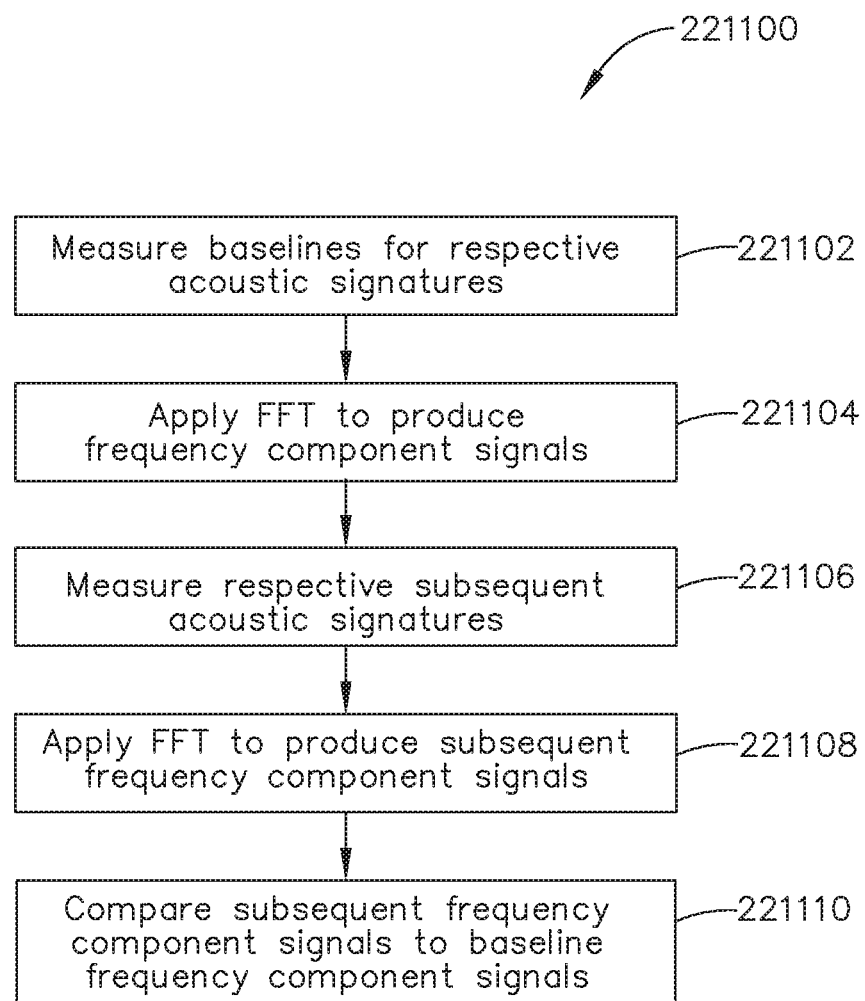

FIG. 113 illustrates a method 221100 for identifying the degradation or failure of components of a surgical instrument. As an initial step, i.e., step 221102, baseline measurements of the respective acoustic signatures of the motor 221012, the first gearbox 221014, the second gearbox 221016, and/or the drive train 221018 are made. At step 221104, the FFT circuit 221006 produces the frequency component signals which are representative of the baseline measurements of the respective acoustic signatures. This sequence may be repeated any number of different times for various speed and load conditions. Referring to FIG. 114, a graph 221200 shows, in at least one instance, the frequency component signals representative of the baseline measurements of the respective acoustic signatures broken down by component. More specifically, the graph 221200 shows the frequency profile 221012a for the motor 221012, the frequency profile 221014a for the first gearbox 221014, the frequency profile 221016a for the second gearbox 221016, and the frequency profile 221018a for the drive train 221018. As illustrated in the composite frequency profile in FIG. 114, none of the frequency profiles 221012a, 221014a, 221016a, and 221018a overlap with one another; however, circumstances can arise where there is a partial overlap between adjacent frequency profiles. These frequency profiles, or their respective component signals, are recorded and stored on one or more memory devices, such as solid state memory devices, for example, of the control circuit which includes the main processor of the surgical instrument. The stored frequency profiles can be accessed by the control circuit 221000. As explained in greater detail below, the "baseline" frequency component signals are utilized to determine if the motor-drive system of the surgical instrument has experienced any degradation or failure.

After the baseline frequency component signals have been established and recorded at step 221404, the surgical instrument is thereafter operated and the frequency profiles of the acoustic signatures associated with such operation of the surgical instrument are determined and monitored during the operation of the surgical instrument at step 221106. The frequency profiles associated with the operation of the surgical instrument can be monitored by the control circuit 221000 and/or the control circuit which includes the main processor of the surgical instrument. At step 221018, the frequency profiles are converted to their respective frequency component signals by the FFT circuit 221006. At step 221110, the respective frequency component signals from step 221108 are compared to the baseline frequency component signals from step 221104 to determine whether any of the components of the motor-driven system have experienced any degradation. This comparison can be implemented by the control circuit 221000, by the control circuit which includes the main processor of the surgical instrument and/or an algorithm of the surgical instrument, for example. As shown in the graph 221300 of FIG. 115, the frequency component signal of the second gearbox 221016 indicates possible fatigue and/or damage to the second gearbox 221016 as it deviates from the baseline established at step 221404. It should be understood that a certain amount of deviation from the established baseline is to be expected, or normal, and thus not indicative of degradation and/or failure. To this end, the control circuit 221000, the control circuit which includes the main processor of the surgical instrument and/or the algorithm utilizes one or more predetermined thresholds for delineating between a non-consequential deviation from the baseline and a consequential deviation from the baseline.

Although the method 221100 was described in the context of determining the degradation or failure of the motor 221012, the first gearbox 221014, the second gearbox 221016, and/or the drive train 221018, it should be appreciated that the method 221100 could also be utilized to determine the degradation or failure of other components of the surgical instrument.

FIG. 116 illustrates a method 221400 for identifying the degradation or failure of the drive components of a surgical instrument. As an initial step, baseline measurements of the current being drawn by the motor 221012 are made over time at step 221402. The baseline current measurements can be made in any suitable manner, such as by a current sensor circuit, for example, and can provide an indication of the amount of current being drawn by the motor 221012 when the motor-driven system of the surgical instrument is operating in a normal manner, i.e., when the motor 221012, the gearboxes 221014 and 221016, and the drive train 221018 have not yet experienced any degradation and/or damage. At step 221404, a FFT circuit, which can be similar or identical to the FFT circuit 221006, produces frequency component signals which are representative of the baseline measurements of the current being drawn by the motor 221012. This sequence may be repeated any number of different times for various speed and load conditions. As explained in greater detail below, the "baseline" frequency component signals can be utilized to determine if the motor-drive system of the surgical instrument has experienced any degradation or failure.

After step 221404, the current being drawn by the motor 221012 is sensed/measured by the current sensor circuit, for example, at step 221406, and converted to the respective frequency component signals by the FFT circuit at step 221408. At step 221410, the respective frequency component signals from step 221408 are compared to the baseline frequency component signals from step 221404 to determine whether any of the components of the motor-driven system have experienced any degradation. This comparison can be implemented by the control circuit 221000, by the control circuit which includes the main processor of the surgical instrument and/or an algorithm of the surgical instrument, for example. In various instances, the control circuit 221000, the control circuit which includes the main processor of the surgical instrument and/or the algorithm look for repetitious events on a frequency which could be indicative of a spinning failure such as, for example, a chipped tooth on a gear of a gearbox.

Referring to FIG. 117, a graph 221500 shows the baseline measurements 221502 (solid line) and the subsequent measurements 221504 (dashed line) of the current drawn by the motor 221102. The graph 221500 also shows the baseline frequency component signals 221506 (forward slash bars) and the subsequent frequency component signals 221508 (back slash bars) representative of the baseline measurements and the subsequent measurements of the current drawn by the motor 221102. The graph 221500 includes two horizontal axes—an "upper" horizontal axis 221510 and a "lower" horizontal axis 220512. The time t is shown along the "upper" horizontal axis 221510, and the frequency Hz is along the "lower" horizontal axis 221512. The graph 221500 also includes two vertical axes—an "upper" vertical axis 220514 and a "lower" vertical axis 221516. The current is shown along the "upper" vertical axis 220514 and the magnitude of the fast Fourier transforms is shown along the "lower" vertical axis 221516. As discussed below, this information is used by the control circuit 221000, the control circuit which includes the main processor of the surgical instrument and/or an algorithm of the surgical instrument to evaluate repetitive anomalous current draws and/or acoustic events.

Referring again to FIG. 117, the subsequent current measurements represented by the dashed line 221504 indicate three different instances of an abnormal event being experienced by the motor 221012. These abnormal events comprise spikes in the motor current draw and are represented by three peaks in the dashed line 221504. The control circuit 221000, the control circuit which includes the main processor of the surgical instrument and/or the algorithm operate to differentiate between the baseline current draw and the anomalous current draw peaks. In at least one instance, the algorithm determines that an anomalous current draw peak has occurred when the current draw exceeds a threshold difference relative to the baseline current draw. In various instances, the threshold difference is 50% above the baseline current draw, for example. In other instances, the threshold difference is 100% above the baseline current draw, for example, although any suitable threshold can be used. In various instances, the algorithm can use the motor current draw threshold alone to determine whether an anomalous event has occurred. In certain instances, the algorithm can use other parameters in addition to the motor current draw threshold for assessing anomalous events. For instance, the algorithm can use the time between the anomalous events to determine whether or not the anomalous events are repetitive. If a repeating time period between the repeating events can be established by the algorithm, then the algorithm can determine that there may be degradation and/or damage in one of the rotating components in the drive system even though the current peaks do not exceed the threshold. That said, the lack of an established time period between the repetitive events does not necessarily indicate that degradation and/or damage hasn't occurred. Instead, in such instances, it can be an early indication of degradation and/or damage. In at least one instance, the threshold for determining whether motor current draws are abnormal is lower if a consistent time period between the peaks can be established. Correspondingly, the threshold is higher if a consistent time period can't be established.

Notably, the above-discussed anomalous current draws may or may not correspond with a corresponding variation in the baseline acoustic frequency profile. For instance, in FIG. 117, the frequency components of the baseline current and the subsequent current are within the normal expected range during the three motor current spikes discussed above, which is shown in three grouping comparisons 221518 delineated by dashed lines. If, however, there is also an anomalous repetitive event within the frequency components that corresponds in time with the measured motor current peaks, the algorithm can apply a lower threshold for determining anomalous motor current draws indicative of drive component degradation and/or damage. The above being said, an anomalous repetitive event within the frequency components without corresponding motor current spikes can also be indicative of drive component degradation and/or damage. FIG. 117 depicts such an abnormal additional frequency 221520. When the magnitude of the anomalous frequency exceeds a predetermined threshold, the algorithm can determine that degradation and/or damage has occurred. In various instances, the algorithm can use a lower threshold for the frequency magnitude when corresponding motor spikes are present and a higher threshold for the frequency magnitude when corresponding motor spikes are not present. As such, the algorithm can determine that degradation and/or damage has occurred with or without corresponding anomalous motor current draws, and vice versa.

Although the method 221400 of FIG. 116 was described in the context of determining the degradation or failure of the motor-driven system based on a comparison of currents being drawn by the motor 221012, it will be appreciated that similar methods which utilize other comparisons could also be utilized to determine the degradation or failure of the drive components of the surgical instrument. For example, a measured motor load could be compared to measured shaft power over time, and changes in losses between the two can be utilized to identify possible fatigue and/or damage to a component of the motor-drive system of the surgical instrument. Additionally, methods similar to those of the method 221100 and/or the method 221400 can be utilized for purposes of heat management within a sterile barrier of the surgical instrument.

FIG. 118 illustrates a method 221600 for adjusting a motor control algorithm of a surgical instrument. An algorithm refers to a self-consistent sequence of steps leading to a desired result, where a "step" refers to a manipulation of physical quantities, which may take the form of electrical or magnetic signals capable of being stored, transferred, combined, compared, and otherwise manipulated. In the context of the motor control algorithm, the motor control algorithm is utilized to control the speed of a motor of the surgical instrument. The method 221600 may be utilized to adjust the motor control algorithm to minimize or limit damage of a drive whenever degradation or failure of the drive has been detected. Prior to the start of the method 221600, the method 221100, the method 221400, and/or similar methods can be utilized to detect the degradation and/or damage of the motor-driven system.

If degradation or failure is detected, referring again to FIG. 118, a control circuit of the surgical instrument (e.g., the control circuit which includes the main processor of the surgical instrument) adjusts the motor control algorithm to adjust or control the speed of the electric motor at step 221602 to try to reduce the noise, vibration, and/or wear on a component of the motor-drive system. In various instances, the speed control can be adjusted by adjusting the pulse width modulation (PWM) duty cycle to speed up or slow down the motor speed given an experienced torque (load) on the system. Adjusting the PWM duty cycle to increase the voltage of the motor speed command signal provided by the motor controller operates to increase the voltage applied to the motor, which in turn operates to increase the motor speed. Adjusting the PWM duty cycle to decrease the voltage of the motor speed command signal provided by the motor controller 221018 operates to decrease the voltage applied to the motor, which in turn operates to decrease the motor speed. Decreasing the motor speed allows for the acoustic sensing of the motor-drive system to be moved to lower frequency levels. Increasing or decreasing the motor speed can move the operation of the motor drive system away from the natural resonance, or natural frequency harmonics, of the motor drive system.

After the PWM duty cycle has been adjusted at step 221602, the motor drive system is checked once again at step 221604 to determine whether or not any degradation or failure of the motor drive system has occurred. The determination can be made by utilizing the method 221100, the method 221400, and/or similar methods. In various instances, such determinations are made on a periodic basis, or on a continuous basis, whenever the motor drive system is in use. If degradation or failure is detected at step 221604, the control circuit adjusts the motor control algorithm to adjust a current limit of the motor controller at step 221606 proportionate to the detected wear level of the motor-drive system to try to minimize the likelihood of further wear or catastrophic failure. By lowering the amount of current available to be drawn by the motor, the force or torque applied/delivered by the motor is also limited. Thus, by lowering the current limit of the motor controller proportionate to the detected wear level of the motor drive system, the power of the motor is decreased commensurate with the detected wear level of the motor-drive system.

After the current limit of the motor controller 221108 has been adjusted at step 221606, the motor-drive system is checked once again at step 221608 to determine whether or not any degradation or failure of the motor-drive system has been detected. The determination can be made by utilizing the method 221100, the method 221400 or similar methods.

In various instances, such determinations are made on a periodic basis, or on a continuous basis whenever the motor-drive system is in use.

If degradation or failure is detected at step 221608, the control circuit adjusts the motor control algorithm to oscillate adjustment of the speed control of the surgical instrument or the current limit of the motor controller at step 221610 to coincide with a detected failing point of the motor-drive system to try to compensate for the detected damage. For example, if a tooth on a gear has failed, is cracked, or is partially damaged, the acoustic sensor 221002 could detect the clatter resulting from the damage. The decomposition provided by a fast Fourier transform circuit, such as the fast Fourier transform circuit 221006, for example, could define the period of the disturbance, and then the motor control algorithm could adjust the current limit of the motor controller, the motor speed command signal (a voltage) provided by the motor controller, and/or the PWM duty cycle synchronized to that period to reduce overall system vibration and further overstress of the motor-driven system.

After the speed control of the surgical instrument and/or the current limit of the motor controller has been adjusted in an oscillating manner at step 221610, the motor drive system is checked once again at step 221612 to monitor the degradation and/or failure of the motor drive system. This determination can be made by utilizing the method 221100, the method 221400, and/or similar methods. Such determinations are made on a periodic basis, or on a continuous basis whenever the motor-drive system is in use. If additional degradation or failure is detected at step 221612, the above-described process can repeat itself, and can be repeated any number of times. If degradation or failure is detected at step 221612 which exceeds a threshold, as described in greater detail below, the process may end. Although a specific order of steps has been described for the method 221600, it will be appreciated that the order of the steps can be different. For example, the current threshold can be adjusted before the speed control is adjusted and/or at the same time that the speed control is adjusted.

If a motor-driven system failure initiates during a surgical procedure but the motor-drive system or a component thereof does not entirely fail, the motor control algorithm can operate to reduce the performance of the motor-drive system (e.g., speed, capability, load) to allow the clinician to continue without delaying the surgical procedure and allow for a different surgical instrument to be obtained. Responsive to the partial failure, the control circuit and/or an algorithm can generate one or more warnings to the user. Such warnings can be in the form of an audible warning, a visual warning, a tactile warning, and/or combinations thereof, for example, and can indicate that the surgical instrument will experience an impending failure, is being operated in a limp mode, and/or will need to be serviced soon, for example. The control circuit and/or the algorithm could also include a countdown as a percent of damage, time since damage, and/or performance degradation to help the clinician know how much time is remaining until servicing of the surgical instrument is required.

Further to the above, the control circuit and/or the algorithm can provide an assessment regarding the severity of the failure. The assessment can inform multiple decision outcomes that ensure patient safety while balancing the delay to the procedure and/or the cost of using another surgical instrument, for example. If the severity of the failure is deemed catastrophic by the control circuit and/or the algorithm, the control circuit and/or the algorithm can inform the clinician of the determination by an appropriate feedback generator. If the severity of the failure is deemed nearly catastrophic such that a procedure step cannot be completed, the control circuit and/or the algorithm can operate to inform the user that the user must pursue appropriate steps to safely release the surgical instrument from the patient. When the surgical instrument is a motor-driven tissue cutting stapling instrument, for example, the control circuit and/or the algorithm can operate to only allow the drive motor to reverse the knife direction, if possible, and/or revert to manual bailout to retract the knife. If the severity of the failure is deemed severe damage, but not catastrophic, the control circuit and/or the algorithm can operate to inform the clinician of the damage level and allow the clinician to complete the procedure step, but disable use of the surgical instrument after the procedure step is complete and the surgical instrument is safely removed from the patient. If the severity of the failure is deemed damaged, but not severely, the control circuit and/or the algorithm can operate to inform the clinician that damage has occurred and that functionality of the surgical instrument may be altered, but that it is possible to continue the procedure beyond the current procedural step.

In various instances, the control circuit and/or an algorithm is configured to use situational awareness to perform a risk assessment of a damaged surgical instrument and the remaining procedure steps to inform the clinician of a recommended course of action. In a bariatric procedure, for example, a surgical stapling and cutting instrument is used to transect and staple a portion of a patient's stomach. Notably, stomach tissue can vary in thickness along the transection and stapling path. In fact, the tissue thickness variation along this path is usually quite predictable. In a revisional bariatric procedure removing a gastric band, for example, the first stapling firing of the surgical stapling and cutting instrument is on the antrum of the stomach, i.e., where the stomach tissue is thickest. In such instances, as a result, the drive train of the surgical stapling and cutting instrument will likely experience a high loading, stress, and strain during this first stapling firing. Thus, if the instrument is damaged in some way before this first stapling firing, it is possible that the first stapling firing may further damage, if not catastrophically damage, the instrument. With this in mind, in various instances, the surgical instrument comprises a wireless and/or wired signal transmitter and receiver that is in communication with a surgical hub system and is configured to receive a notification from the surgical hub system that the surgical instrument is about to be used in this type of bariatric procedure. In such instances, the control circuit and/or an algorithm is configured to inform the user of the surgical instrument of the damaged condition of and/or the current damage to the surgical instrument and the possibility of further damage. Moreover, the control circuit and/or the algorithm can be configured to limit the current available to the electric motor so as to reduce the possibility of catastrophic failure and optionally allow the clinician to override the lower current limit. The control circuit and/or algorithm can be further configured to re-evaluate the condition of the drive system of the surgical instrument after this first stapling firing for additional damage. If the current damage is still below an acceptable threshold, the control circuit and/or the algorithm can allow the subsequent staple firings of the surgical instrument needed to complete the tissue incision and stapling path. If the current damage is above the acceptable threshold, the control circuit and/or the algorithm can recommend that the surgical instrument be replaced to complete the procedure. Thus, as a result of data from the surgical hub system, the instrument is situationally aware of the tissue thickness, density, and/or quality that is about to be transected and stapled. Moreover, the data from the surgical hub system can include data regarding previous surgical procedures involving the stomach tissue such as the presence of previous stapling lines, the presence of the gastric band, and/or tissue scarring which, when transected and stapled by the instrument, may increase the stress on the instrument drive system. The control circuit and/or the algorithm can operate in a similar manner to the above-described process to assess the current degradation or damage of the instrument drive system, notify the clinician of this degradation or damage, and offer options to the clinician as how to proceed further in the surgical procedure.

Additional details regarding situational awareness are described, for example, in U.S. patent application Ser. No. 15/940,654, entitled SURGICAL HUB SITUATIONAL AWARENESS, filed on Mar. 29, 2018, the disclosure of which is herein incorporated by reference in its entirety.

In various instances, the condition of the motor-driven system is communicated to a surgical hub system on a periodic basis, or on a continuous basis. Thus, the condition of the motor-driven system prior to a detected failure is known by the surgical hub system. A surgical hub system is described in more detail in U.S. patent application Ser. No. 15/940,629, entitled COMPUTER IMPLEMENTED INTERACTIVE SURGICAL SYSTEMS, filed on Mar. 29, 2018, the disclosure of which is hereby incorporated by reference in its entirety. An algorithm, executed by a control circuit and/or processor of the surgical hub system, can utilize the history of the use of the surgical instrument in the current case, the life history of the surgical instrument and the surgical hub's situational awareness to more fully diagnose the potential for failure of the surgical instrument in the current case, an actual failure of the surgical instrument in the current case, and better predict similar failures in similar surgical instruments used in other cases. It will be appreciated that the knowledge provided by the functionality of the surgical hub system can provide a better understanding of the failure mode, allow for future failures to be predicted and/or avoided based on the data and analysis, and provide direction to design improvements of the surgical instrument to improve lifecycles and avoid future failures. When the surgical hub system determines a failure of a surgical instrument is impending, the surgical hub system can communicate this information to a user of the surgical instrument via a display and/or a speaker of the surgical hub system.

In various instances, a handle of the surgical instrument can be configured to provide the electrical system within the handle with improved durability and robustness to the surgical environment. For example, touch-less controls which can be entirely sealed and which require no force to cause a switch of state can be incorporated into the design of the handle. Also, reusable handles can be provided with improved replaceable switch and control elements.

In many surgical procedures, more than one surgical instrument is utilized to complete the surgical procedure. In many instances, at least two surgical instruments can be positioned within the patient at the same time, and it is possible for the two surgical instruments to come into contact and/or close proximity with one another. In some circumstances, this does not cause a major concern. In other circumstances, such as when one of the surgical instruments is an electrosurgical instrument or an ultrasonic surgical instrument, for example, it is desirable to keep another surgical instrument from coming into contact with the electrosurgical instrument or the ultrasonic surgical instrument.

FIG. 119 illustrates an environment 222000 of a surgical procedure. The environment 222000 includes a first surgical instrument 222002, a second surgical instrument 222004, a patient 222006, and a grounding pad 222008 in contact with the patient 222006. The first and second surgical instruments 222002, 222004 are shown as positioned within the patient 222006, i.e., within an abdominal cavity, for example, who is lying on the grounding pad 220008. The first surgical instrument 222002 can be any of a variety of different surgical instruments. For example, the first surgical instrument 222002 can be an endocutter, or a tissue cutting and stapling instrument, comprising a shaft 222010 and an end effector comprising jaws 222012. An external surface of the shaft 222010 and/or the jaws 222012 of the endocutter 222002 includes an electrically conductive material such as, for example, a stainless steel and/or any other suitable metal.

The second surgical instrument 222004 is a monopolar instrument which can receive high-frequency electrosurgical energy from a source, and apply the high-frequency electrosurgical energy to the patient 222006 in a manner well-known in the art. For example, the high-frequency electrosurgical energy is applied by an electrode tip 222013 of the second surgical instrument 222004. The source can be, for example, a monopolar generator such as the monopolar generator module 220310 of the surgical hub 220302. Under normal circumstances, the electrosurgical energy applied to the patient 222006 passes through the patient 222006 to the grounding pad 220008, where it is then returned back to the source of the electrosurgical energy via electrical conductors of a return path (not shown) to complete an electrosurgical electrical circuit.

Due to the proximity of the first surgical instrument 222002 to the second surgical instrument 222004 within the patient 222006 at certain times during the surgical procedure, there is a risk that too much of the high frequency electrosurgical energy applied to the patient 222006 by the second surgical instrument 222004 during the surgical procedure will be diverted through the patient 222006 to the first surgical instrument 222002 owing to the high conductivity of the shaft 222010 and/or the jaws 222012 as opposed to the grounding pad 222008 as intended. The closer the first surgical instrument 222002 comes to the second surgical instrument 222004 within the patient 222006, the higher the risk of too much of the high frequency electrosurgical energy passing through the patient 222206 to the first surgical instrument 222002. In a worst case scenario, where the electrically conductive portion of the first surgical instrument 222002 comes into direct contact with the electrode tip of the second surgical instrument 222004, an electrical short-circuit is established from the second surgical instrument 222004 directly to the first surgical instrument 222002.

In order to mitigate the chance of too much of the high frequency electrosurgical energy passing through the patient 222006 to the first surgical instrument 222002, the second surgical instrument 222004 is configured to apply a low current to the patient 222006 as a test current prior to the second surgical instrument 222004 applying the full level of electrosurgical energy to the patient 222006. The source of the test current can be, for example, a monopolar generator such as the monopolar generator module 220310 of the surgical hub 220302. In order to apply the test current, the second surgical instrument 222004 includes electrical terminations 222014 (see FIGS. 120, 121, and 122) on the shaft 222018 of the second surgical instrument 222004. The electrical terminations 222014 are electrically connected to the source of the electrosurgical energy, and/or a battery, and can apply the test current to the patient 222006. In a way, the electrical terminations 222014 are being utilized as continuity sensors to help determine electrical continuity along a path from the second surgical instrument 222004, through the patient 222006, and to the grounding pad 222008. According to various aspects, the electrical terminations 222014 form a portion of a control circuit of the second surgical instrument 222004, and the control circuit and/or an algorithm can be utilized to apply the test current to the patient 222006.

The test current may only be applied for a brief period of time, such as for a few milliseconds, for example, in order to adequately determine if a sufficient instrument-patient-pad continuity is present as described above. According to various aspects, the continuity can be determined by a sensing device incorporated into the grounding pad 222008, a sensing device incorporated in the cord or cable of the return path and/or by a monopolar generator such as the monopolar generator module 220310 of the surgical hub 220302. Moreover, the test current may comprise an amperage of only a few milliamps, for example. If the application of the test current does not indicate the presence of a short circuit or significant shunt between the first surgical instrument 222002 and the second surgical instrument 222004, the control circuit operates to allow the second surgical instrument 222004 to be provided with the full level of electrosurgical energy which can then be applied to the patient 222006. However, if the application of the test current indicates the presence of a short circuit or significant shunt between the first surgical instrument 222002 and second surgical instrument 222004, the control circuit operates to prevent the second surgical instrument 222004 from being provided with the full level of electrosurgical energy, effectively preventing or locking out the second surgical instrument 222004 from applying the full level of electrosurgical energy to the patient 220006 until the instruments 222002 and 222004 are sufficiently separated to eliminate the short circuit or shunt therebetween. According to various aspects, the test current can also be applied periodically or continuously throughout a surgical procedure, and the electrosurgical energy being applied to the patient 222006 during the surgical procedure can be decreased or even interrupted based on the sensing and/or detection of short-circuits and/or significant shunts between the first surgical instrument 222002 and the second surgical instrument 222004.

Referring to FIGS. 120-122, the signals 222016 shown as being emitted from the electrical terminations 222014 are representations of the test current exiting from the electrical terminations 222014. Although the electrical terminations 222014 are only shown as being positioned on the shaft 222018 of the second surgical instrument 222004, the electrical terminations 222014 are also positioned on the body 222020 of the second surgical instrument 222004. Such an arrangement provides for potential leakage paths from the body 222020 of the second surgical instrument 222004 to the shaft 222010 and/or jaws 222012 of the first surgical instrument 222002, as well as from the shaft 222018 of the second surgical instrument 222004 to the shaft 222010 and/or jaws 222012 of the first surgical instrument 222002, for example.

FIG. 123 illustrates a graph 222100 which shows a relationship between the leakage current 222102 of the surgical instrument 222004 and the proximity of other objects in the surgical environment 222000 to the surgical instrument 222004. The time t is shown along the horizontal axis 222104 and the leakage current is shown along the vertical axis 222106. When nothing but air is within approximately 5 centimeters from the second surgical instrument 222004, there is very little, if any, current loss from the second surgical instrument 222004. In fact, the current loss in such instances is below a first threshold which can be interpreted by the control circuit of the surgical instrument 222004 that the surgical instrument 222004 is not in contact with the patient or another surgical instrument. The surgical instrument 222004 further comprises a first indicator, such as a light and/or a symbol on a screen of the surgical instrument 222004, for example, in communication with the control circuit that, when actuated by the control circuit, indicates to the clinician that the surgical instrument 222004 is not in a position in which it can affect the patient tissue and/or short out against and/or contact another surgical instrument, for example. In at least one instance, the first indicator comprises a green LED, for example.

When the surgical instrument 222004 is moved close to the patient, referring again to FIG. 123, the leakage current increases above the first threshold. In at least one such instance, close can be approximately 3 cm, for example. The surgical instrument 222004 further comprises a second indicator, such as a light and/or a symbol on a screen of the surgical instrument 222004, for example, in communication with the control circuit that is activated by the control circuit when the leakage current exceeds the first threshold. In at least one instance, the second indicator comprises a yellow LED, for example. The actuation of the second indicator indicates to the clinician that the surgical instrument 222004 may be in a position in which it can affect the patient tissue. Because the leakage current is still below a second threshold, however, a third indicator in communication with the control circuit, such as a light and/or a symbol on a screen of the surgical instrument 222004, for example, is not actuated. In such instances, the clinician can understand that the surgical instrument 222004 is not in a position to short out against and/or contact another surgical instrument, for example. In at least one instance, the third indicator comprises a red LED, for example. When the surgical instrument 222004 is in contact with the patient, but not another surgical instrument, the leakage current is above the first threshold but still below the second threshold unless the surgical instrument 222004 is moved close to another surgical instrument, as discussed below.

When the surgical instrument 222004 is moved close to another surgical instrument, referring again to FIG. 123, the leakage current increases above the second threshold. In at least one such instance, close can be approximately 3 cm, for example. In such instances, the control circuit of the surgical instrument 222004 actuates the third indicator. In such instances, the clinician can understand that the surgical instrument 222004 may be in a position to short out against and/or contact another surgical instrument, for example. When the surgical instrument 222004 moves even closer to another surgical instrument, such as within approximately 1 cm, for example, the current leakage can increase significantly. In such instances, the control circuit can produce an audible warning via a speaker in the surgical instrument 222004 in communication with the control circuit, for example. Such an audible warning could also be created when the surgical instrument 222004 contacts the other surgical instrument. If the surgical instrument 222004 is moved away from the other surgical instrument and the leakage current decreases, the control circuit will deactivate the audible warning. If the leakage current falls below the second threshold, the control circuit will deactivate the third indicator. If the leakage current falls below the first threshold, the control circuit will deactivate the second indicator.

As a result of the above, a clinician can understand the positioning of the surgical instrument 222004 relative to its environment.

In order to mitigate false warnings of unwanted contact, it is beneficial to establish thresholds which can be utilized to differentiate contact between, one, the second surgical instrument 222004 and the body of the patient 222006 or a trocar, two, the second surgical instrument 222004 and the target tissue of the patient 222006 and, three, the second surgical instrument 222004 and the first surgical instrument 222002 or another surgical instrument within the environment 222000 of the surgical procedure.

FIG. 124 illustrates a graph 222200 which shows the direct current (DC) output voltage 222202 of the test current of the second surgical instrument 222004 during a surgical procedure. The time t of the surgical procedure is shown along the horizontal axis 222204 and the voltage v of the test current is shown along the vertical axis 222206. At time $t_1$, the voltage 222202 of the test current crosses a $v_1$ voltage threshold 222208 which is indicative of the second surgical instrument 222004 coming into contact with the trocar as the second surgical instrument 222004 is inserted into the patient. The voltage v of the test current then spikes upward for a brief period of time as the continuity sensors 222014 of the second surgical instrument 222014 are passing through the trocar. Thereafter, the voltage of the test current returns back to the lower level once the sensors 222014 have passed through the trocar and the second surgical instrument 222004 is further inserted into the patient. At time $t_2$, the voltage 222202 of the test current crosses a $v_2$ voltage threshold 222210 which is indicative of the second surgical instrument 222004 coming into contact with, or close approximation with, the tissue of the patient 222006. The voltage 222202 thereafter stays above the $v_2$ voltage threshold 22210 as the surgical instrument 222004 is moved and manipulated relative to the patient tissue. At time $t_3$, the voltage 222202 of the test current crosses the $v_3$ voltage threshold 222212, which is indicative of the second surgical instrument 222004 coming into contact with, or close approximation with, the first surgical instrument 222004 or another surgical instrument within the environment 222000 of the surgical procedure. The voltage 222202 of the test current returns to a lower level as the second surgical instrument 222004 is moved away from the adjacent instrument. The $v_1$ voltage threshold 222208 can be considered an instrument-to-trocar contact threshold, the $v_2$ voltage threshold 222210 can be considered an instrument-to-target tissue contact threshold, and the $v_3$ voltage threshold 222210 can be considered an instrument-to-instrument contact threshold.

In various instances, a control circuit and/or an algorithm can be utilized to analyze the DC output voltage v on an ongoing or continuous basis. The control circuit and/or the algorithm takes into account the magnitude of DC output voltage 222202, the slope of the DC output voltage 222202, and/or the rate of change of the slope of the DC output voltage 222202, for example. Using such data, the control circuit and/or the algorithm can provide a more accurate indication of when the second surgical instrument 222004 actually comes into contact with a trocar or the body of the patient 222006, the target tissue of the patient 222006, and the first surgical instrument 222002 or another surgical instrument within the environment 222000 of the surgical procedure. The more accurate indication provided by the control circuit and/or the algorithm operates to mitigate false warnings of unwanted contact.

Further to the above, various forms of current leakage or interaction can occur between two or more surgical instruments in a surgical environment. For example, when a fluid is present around a staple cartridge jaw of an endocutter positioned in a patient, an exposed set of electrical contacts of the endocutter can interfere with the sensing of an adjacent powered dissector. Therefore, it is desirable to sense and monitor the electrical interaction between adjacent powered surgical devices. In various instances, the electrical potential of one or more circuit boards in a surgical instrument and/or the interconnected metal shaft components of a powered surgical instrument can be sensed and monitored. In certain instances, the electric potential is sensed by the source of the high frequency electrosurgical power. In at least one instance, the electrical potential is sensed by respective sensing devices of the powered surgical instruments. Based on the sensed electrical potentials, respective control circuits and/or algorithms of the powered surgical instruments can determine if any of the powered surgical instruments are bleeding current or have a parasitic interaction and could be inadvertently exposing the adjacent surgical devices to false signals.

FIG. 125 illustrates a powered surgical instrument 222300. The shaft of the powered surgical instrument 222300 includes an electrical sensing grid 222302 and electrical insulation 222304. The electrical sensing grid 222302 is configured to detect electrical potential relative to ground. The electrical insulation 222304 surrounds the electrical sensing grid 222302 and operates to electrically isolate the electrical sensing grid 222302 from the environment which is external to the powered surgical instrument 222300. In at least one instance, the electrical sensing grid 222302 is sealed against the shroud of the shaft to prevent, or reduce the possibility of, fluids contacting the sensing grid 222302.

FIG. 126 illustrates a graph 222400 which shows the electrical potential 222402 associated with the powered surgical instrument 222300 of FIG. 125, in accordance with at least one aspect of the present disclosure. The time t is shown along the horizontal axis 222404 and the electrical potential $v_{ext}$ is shown along the vertical axis 222406. The low value of the electrical potential 222402 shown along the bottom left of the graph 222400 is indicative of some parasitic or exposed current being present between the electrical components which are internal to the powered surgical instrument 222300. As the powered surgical instrument 222300 comes closer to an external electrical source, such as another powered surgical instrument, for example, the electrical potential 222402 begins to increase. The electrical potential 222402 increases more and more as the powered surgical instrument 222300 gets closer and closer to the external electrical source. The slope of the increased electrical potential, which is represented by the dashed line 222408, can be utilized to indicate the presence and/or proximity of the external electrical source. In various instances, a control circuit and/or an algorithm can be utilized to analyze the electrical potential 222402, and taking into account the magnitude of the electrical potential 222402, the slope of the electrical potential 222402, and/or the rate of change of the slope of the electrical potential 222402, for example, the control circuit and/or the algorithm can provide an accurate determination of how close the powered surgical instrument 222300 is to an external electrical source.

FIG. 127 illustrates an active transmission and sensing scheme 222500 utilized by first and second surgical instruments 222502, 222504. The first surgical instrument 222502 is a "smart" surgical instrument and includes a transmitter 222506 (which can be a magnetic transmitter) and a receiving circuit 222508 which collectively operate to provide magnetic emission and detection along the shaft 222510 and/or the end effector 222512 of the first surgical instrument 222502. The first surgical instrument 222502 comprises an endocutter including a staple cartridge jaw and an anvil jaw, but can comprise any suitable surgical instrument. The second surgical instrument 222504 is a "non-transmission enabled" surgical instrument and includes first and second sensing devices 222514, 222516 which are positioned opposite one another on the shaft or body 222518 of the second surgical instrument 222504. The second surgical instrument 222504 comprises a clampable jaw and, in addition, a blade in communication with a standing vibration transducer configured to cut and/or coagulate tissue. The first sensing device 222514 is positioned on the "blade side" of the second surgical instrument 222504 while the second sensing device 222516 is positioned on the "jaw side" of the second surgical instrument 222504. The first and second sensing devices 222514, 222516 are magnetic sensors, for example. By being positioned opposite one another on opposite sides of the shaft or body 222518, the first and second sensing devices 222514, 222516 allow for the first surgical instrument 222502 to determine the position and orientation of the second surgical instrument 222504 relative to the first surgical instrument 222502.

The transmitter 222506 and the receiving circuit 222508 extend along the length of the shaft 222510 and/or the end effector 222512 of the first surgical instrument 222502. The transmitter 222506 and the receiving circuit 222508 are positioned within a flexible circuit at any suitable location in the shaft 222510 and/or the end effector 222512, and can be active at the same time, either continuously or intermittently, as described in greater detail below. The transmitter 222506 is configured to transmit a signal 222519 in the form of a magnetic field which is reflected by the first and second sensing devices 222514, 222516 of the second surgical instrument 222504 to form respective return signals 222520, 222522, which are also in the form of magnetic fields. That said, signals other than magnetic fields could be emitted and reflected in other aspects. The receiving circuit 222508 is configured to receive the return signals 222520, 222522. According to various aspects, the receiving circuit 222508 either incorporates or may be considered a magnetic sensing device. In various instances, the receiving circuit 222508 is configured to look for a response from the transmitter 222506 after the transmitter emits the signal 222519, as also described in greater detail below.

In various instances, a magnetic power source of the transmitter 222506 generates randomly sequenced on-off pulses. Stated another way, the magnetic fields emitted by the transmitter 222506 are not periodic; instead, the magnetic fields are emitted at random times as determined by a control circuit and/or an algorithm of the first surgical instrument 222502. That said, the magnetic fields are emitted at an average rate of approximately 10 times per second and at a frequency of around 1 kHz, for example. Moreover, the duration of the magnetic field pulses are randomized. In between the pulses, the receiving circuit 222508 can be switched in and is configured to listen for the return signals 222520, 222522. The receiver circuit 222508 receives the return signals 222520, 222522 and passes information representative of the return signals 222520, 222522 to a control circuit and/or an algorithm of the first surgical instrument 222502. The control circuit may also have information representative of the signals 222519 emitted by the transmitter 222506. Based on the information representative of the signals 222519 and the information representative of the return signals 222520, 222522, the control circuit and/or the algorithm can determine the position and orientation of the second surgical instrument 222504 relative to the first surgical instrument 222502. If, for some reason, the receiver circuit 222508 only receives one of the return signals 222520, 222522, the control circuit and/or the algorithm would be able to determine the position of the second surgical instrument 222504 relative to the first surgical instrument 222502, but not its orientation.

In instances where another magnetic signal-emitting surgical instrument is present in the surgical field of the first and second surgical instruments 222502, 222504, it is likely that the receiver circuit 222508 of the first surgical instrument 222502 will receive the magnetic signals of the other signal-emitting surgical instrument. Without more, the control circuit and/or the algorithm may not be able to properly analyze the position and/or orientation of the second surgical instrument 222504 relative to the first surgical instrument 222502. Such a situation could be avoided if the other signal-emitting surgical instrument emitted its signals at a frequency which can be filtered out by one or more low-pass and/or high-pass filters in the receiver circuit 222508. Such a situation could also likely be avoided if the other signal-emitting surgical instrument also emits a signal in the form of a magnetic field at an average rate of approximately 10 times per second and at a frequency of around 1 kHz, for example. Owing to the randomness of the pulse duration and rate of the signals emitted by the first surgical instrument 222502 and the other signal-emitting surgical instrument, and also to the randomness of switching in the receiver circuit 222508 and a corresponding receiver circuit in the other signal-emitting surgical instrument, a situation where the magnetic emissions from the two signal-emitting surgical instruments are in perfect synchrony is mitigated and/or avoided. Thus, it will be appreciated that the active transmission and sensing scheme 222500 described above can also be utilized with two surgical instruments which both have active transmission and sensing means.

FIG. 128 illustrates a graph 222600 of signals transmitted and received by the first surgical instrument 222502 of FIG. 127. The transmitted signals 222602 are representative of the signal transmitted by the transmitter 222506 and are shown with back slashes. The received signals 222604 are representative of the return signals 222520, 222522 and are shown with forward slashes. The time t is shown along the horizontal axis 222608 and the amplitude of the transmitted and received signals 222602, 222604 is shown along the vertical axis 222606. As shown in FIG. 128, the amplitude of each of the transmitted signals 222602 is within a given band relative to the 1 kHz emission frequency. The given amplitude band is shown as being bounded by the dashed lines 222605A, 222605B. That said, the amplitudes of only some of the received signals 222604 are within the given band. As described in more detail below, by analyzing the difference between the transmitted signal 222602 and the received signal 222604 of each signal set and the differences between each consecutive signal set, the control circuit and/or an algorithm of the first surgical instrument 222502 can determine the proximity and orientation of the second surgical instrument 222504 relative to the first surgical instrument 222502.

FIG. 129 illustrates a graph 222700 which shows the proximity measurements 222702 of the first sensing device 222514 and the proximity measurements 222704 of the second sensing device 222516 of the second surgical instrument 222504 relative to the first surgical instrument 222502. The proximity measurements 222702 of the first sensing device 222514 are shown with back slashes and the proximity measurements 222704 of the second sensing device 222516 are shown with forward slashes. The time t is shown along the horizontal axis 222706 and the distance in centimeters is shown along the vertical axis 222708. According to the first set of "proximity bars" near the left-hand side of the graph 222700 taken during a first sample, the second surgical instrument 220504 is located somewhere around 10 centimeters relative to the first surgical device 222502 at a somewhat angled orientation. According to the second set of "proximity bars" just to the right of the first set taken during a second sample, the second surgical instrument 220504 is somewhere within 7-9 centimeters of the first surgical device 222502 at a somewhat angled orientation. According to the third set of "proximity bars" just to the right of the second set taken during a third sample, the second sensing device 222516 positioned on the "jaw side" of the second surgical instrument 222504 is within 1 centimeter of the first surgical device 222502; however, the second surgical instrument 222504 is angled at a steep angle relative to the first surgical instrument 222502. According to the fourth set of "proximity bars" at the right-hand side of the graph 222700 which were taken during a fourth sample, the first sensing device 222514 positioned opposite the "blade side" of the second surgical instrument 220504 is within 1 centimeter of the first surgical device 222502. As the proximities of both the first and second sensing devices 222514, 222516 are determined relative to the first surgical instrument 222502, it will be appreciated that the orientation of the second surgical instrument 222504 relative to the first surgical instrument 222502 is also determined in this manner.

In addition to or in lieu of active sensing, passive sensing such as inductive sensing and/or capacitive sensing, for example, can be utilized to determine the proximity of one surgical instrument relative to another surgical instrument.

FIG. 130 illustrates a passive sensing scheme 222800 utilized by a first surgical instrument 222801 and a second surgical instrument 222804. The first surgical instrument 222802 includes a magnetic transmitter 222806 and a transducer 222808. The transducer 222808 is configured to vary its output voltage in response to a magnetic field. The transducer 222808 comprises a Hall-effect sensor, but could comprise any suitable sensor. As described in more detail below, the Hall-effect sensor 222808 may be considered an inductive proximity sensor. The magnetic transmitter 222806 operates to generate a primary magnetic field 222810 which emanates outwardly from the magnetic transmitter 222806. When the second surgical instrument 222804 gets within a certain distance of the first surgical instrument 222802, the primary magnetic field 222810 induces a current in a conductive material of the second surgical instrument 222804. In at least one instance, the shaft and/or a jaw of the second surgical instrument 222804, for example, comprises the conductive material. The induced current in the conductive material of the second surgical instrument 222804 operates to generate a secondary magnetic field 222812 which emanates out from the conductive material of the second surgical instrument 222804. The secondary magnetic field 222812 tends to oppose the primary magnetic field 222810 and has a weakening effect on the primary magnetic field 222810. The net strength of the magnetic field at the Hall-effect sensor 222808, in both an unaffected condition (where the second surgical instrument 222804 is so far away from the first surgical instrument 222802 so as to have no effect on the primary magnetic field 222810) as well as in an affected condition (where the second surgical instrument 222804 is close enough to the first surgical instrument 222802 to have an effect on the primary magnetic field 222810) is sensed by the Hall-effect sensor 222808, which generates an output signal or Hall current representative of the strength of the net magnetic field at the Hall-effect sensor 222808, and thus of the proximity of the second surgical instrument 222804 to the first surgical instrument 222802.

FIG. 131 illustrates the primary magnetic field 222810 in an unaffected condition proximate the Hall-effect sensor 222808. When there is no object close enough to the first surgical instrument 222802 so as to have an effect on the primary magnetic field 222810, the condition of the primary magnetic field 222810 is considered to be in an unaffected condition. Thus, the field lines 222814 shown in FIG. 130 may be considered representative of an unaffected condition of the primary magnetic field 222810 and what is expected to be received by a receiving circuit of the first surgical instrument 222802 absent the presence of another instrument.

FIG. 132 illustrates the primary magnetic field 222810 in an affected condition proximate the Hall-effect sensor 222808. When an object is close enough to the first surgical instrument 222802 so as to have an effect on the primary magnetic field 222810, the condition of the primary magnetic field 222810 is considered to be in an affected condition. The field lines 222816 of the primary magnetic field 222810 shown in FIG. 131, which are different from the field lines 222814 of FIG. 130 and are shown as broken dashed lines, may be considered representative of an affected condition of the primary magnetic field 222810, and are not what is expected to be received by a receiving circuit of the first surgical instrument 222802.

FIG. 133 illustrates a graph 222900 which shows the Hall current 222902 output by the Hall-effect sensor 222808 of the first surgical instrument 222802 of FIG. 130. The strength of the net magnetic field sensed by the Hall-effect sensor 222808, whether magnetic field strength H or magnetic flux density B, is shown along the horizontal axis 222904, and the current I is shown along the vertical axis 222906. As the strength of the net magnetic field sensed by the Hall-effect sensor 222808 increases, the magnitude of the Hall current 222902 decreases. The high magnitude of the Hall current 222902 shown along the left-had side of the graph 222900 is indicative of no other electrically conductive object, such as the second surgical instrument 222804, for example, being in close proximity to the first surgical instrument 222802. The decrease in the magnitude of the Hall-current between the 1 and the 2 of the magnetic field strength is indicative of the second surgical instrument 222804 being at some distance from the first surgical instrument 222802. The further decrease in the magnitude of the Hall-current between the 2 and the 3 of the magnetic field strength is indicative of the second surgical instrument 222804 approaching the first surgical instrument 222802. The even further decrease in the magnitude of the Hall-current between the 3 and the 4 of the magnetic field strength is indicative of the second surgical instrument 222804 being at close proximity to the first surgical instrument 222802. The Hall current can be passed to a control circuit of the first surgical instrument 222802, and the control circuit and/or an algorithm can analyze the magnitude of the Hall current, the slope of the Hall current, and/or the rate of change of the slope of the Hall current, for example, to provide an indication of the proximity of the first surgical instrument 222802 to the second surgical instrument 222804.

FIGS. 134 and 135 illustrate a passive sensing scheme 223000 utilized by a first surgical instrument 223002 and a second surgical instrument 223004. In this passive sensing scheme 223000, the first surgical instrument 223002 includes first and second capacitor plates 223006, 223008 housed in a sensing head of the first surgical instrument 223002. In a parallel-plate capacitor arrangement like the one shown in FIGS. 134 and 135, when a voltage is applied between the first and second capacitor plates 223006, 223008, a uniform electric field is created between the first and second capacitor plates 223006, 223008. The strength of the electric field is directly proportional to the voltage applied and inversely proportional to the distance between the first and second capacitor plates 223006, 223008. When there is no object close enough to the first surgical instrument 223002 so as to have an effect on the electric field, the condition of the electric field is considered to be in an unaffected condition. Thus, the field lines 223010 shown in FIG. 134 may be considered representative of an unaffected condition of the electric field and what is expected to be received by a receiving circuit of the first surgical instrument 223002.

When an object is close enough to the first surgical instrument 222802 so as to have an effect on the electric field, the condition of the electric field is considered to be in an affected condition. As another electrically conductive object, such as the second surgical instrument 223004, for example, approaches the first surgical instrument 223002 as shown in FIG. 135, the capacitance associated with the first and second capacitor plates 223006, 223008 of the first surgical instrument 223002 increases. The increased capacitance is shown conceptually by the additional field lines 223012 in FIG. 135, and the electric field in FIG. 135 is different from the electric field in FIG. 134. The electric field shown in FIG. 135 may be considered representative of an affected condition of the electric field, and is not what is expected to be received by a receiving circuit of the first surgical instrument 223002 absent the presence of another surgical instrument. According to various aspects, a sensing device such as a capacitive sensor can sense the capacitance and generate an output signal representative of the sensed capacitance. The output signal can be converted to a voltage signal which is representative of the sensed capacitance, and the voltage signal can be passed to a control circuit of the first surgical instrument 223002. Based on the voltage signals which are representative of the sensed capacitance, the control circuit and/or an algorithm can monitor the sensed capacitances, and analyze the change in the capacitance and/or the change in the electric field to provide an indication of the proximity of the first surgical instrument 223002 to the second surgical instrument 223004. The capacitive sensor can thus be considered a capacitive proximity sensor.

In various aspects, instead of utilizing inductive proximity sensing or capacitive proximity sensing as described above, a surgical instrument may utilize a different proximity sensing scheme. FIG. 136 illustrates a surgical instrument 223100 which includes a direct current (DC) power source 223102, an oscillator 223104, a coil 223106, and a current sensor 223108. The DC power source 223102 provides direct current (DC) power to the oscillator 223104. The oscillator 223104 is configured to convert the direct current (DC) power to an alternating current (AC) signal which is passed to the coil 223106. As the alternating current is fed to the coil 22306, the coil 223106 generates a changing magnetic field 223110 which induces a current in the coil 223106. The current from the coil 223106 is sensed/measured by the current sensor 223108. As an electrically conductive object, such as another surgical instrument, for example, approaches the surgical instrument 223100, the other surgical instrument can affect the strength of the magnetic field 223110, which in turn affects the magnitude of the induced current. By sensing/measuring the induced current, a control circuit and/or an algorithm of the surgical instrument 223100 can determine when another object is approaching and/or is in close proximity.

FIG. 137 illustrates a graph 223200 which shows the induced current 223202 measured by the current sensor 223108 of the surgical instrument 223100 of FIG. 136, in at least one instance. The time t is shown along the horizontal axis 223204, and the current I is shown along the vertical axis 223206. When the magnitude of the induced current 223202 is relatively constant as shown for the period of time shown on the left-hand side of FIG. 137, the induced current 223202 is indicative of a situation where no other object/surgical instrument is approaching or proximate to the surgical instrument 223100. When the magnitude of the induced current 223202 is increasing as shown for the period of time shown on the right-hand side of FIG. 137, the induced current 223202 is indicative of a situation where another object/surgical instrument is approaching and/or proximate to the surgical instrument 223100. A control circuit and/or an algorithm of the surgical instrument 223100 can analyze the magnitude of the measured current, the slope of the measured current, and/or the rate of change of the slope of the measured current, for example, to provide an indication of the proximity of the surgical instrument 223100 to another electrically conductive object/surgical instrument.

There are many surgical instruments which include electrical components in the end effector and/or shaft of the surgical instrument. In certain surgical procedures, a surgical instrument being utilized can come into contact with various liquids which are either from the patient or introduced into the patient during the surgical procedure. In some cases, the liquid can come into contact with the electrical components in the end effector and/or shaft of the surgical instrument. When this occurs, the performance of the electrical components, and thus the performance of the surgical instrument, can be affected to varying degrees. The degradation of the performance of the electrical components and/or the surgical instrument due to the exposure to the liquid is often referred to as liquid contamination.

In some instances, when liquid contamination occurs, the electrical components can still perform their primary function, but not necessarily as well as would be possible otherwise. In other instances, one or more of the electrical components can no longer perform their primary function, which can lead to the failure of the surgical instrument. Due to the potential performance issues associated with liquid contamination, it is desirable to sense and detect liquid contamination of an electrical component of a surgical instrument, and take actions to adjust for the liquid contamination.

FIG. 138 illustrates a surgical instrument 223300 including an end effector 223302, a shaft 223304, a sensing array which includes a first pair of sensing devices 223306A, 223306B and a second pair of sensing devices 223308A, 223308B, and a fluid detection circuit 223310. The surgical instrument 223300 also includes an electrically insulative material 223312 and an absorption material 223314. The shaft 223304 includes one or more openings 223316 through an external housing/shroud 223318 of the shaft 223304 which may allow for fluid and/or other contaminants 223320 to pass from an environment which is external to the shaft 223304 to a position within the shaft 223304.

The first pair of sensing devices 223306A, 223306B and the second pair of sensing devices 223308A, 223308B are positioned within the shaft 223304 and are surrounded by the shroud 223318 of the shaft 223304. As shown in FIG. 138, the sensing device 223306A is spaced apart from the sensing device 223306B, the sensing device 223308A is spaced apart from the sensing device 223308B, and the first and second pairs of sensing devices 223306A, 223306B, 223308A, 223308B are spaced apart from one another. Each of the sensing devices 223306A, 223306B, 223308A, 223308B is connected to the fluid detection circuit 223310. Based on the configuration of the first and second pairs of sensing devices 223306A, 223306B, 223308A, 223308B, the sensing devices 223306A, 223306B, 223308A, 223308B and their respective connection paths to the fluid detection circuit 223310 may be considered a ladder circuit, where two "rungs" of the ladder are represented by the respective first and second pairs of sensing devices 223306A, 223306B, 223308A, 223308B and the two "rails" of the ladder are represented by their respective connection paths to the fluid detection circuit 223310. Although only two pairs of sensing devices are shown in FIG. 138, it will be appreciated that the surgical instrument 223300 may include any number of pairs of sensing devices which are spaced apart from one another and connected to the fluid detection circuit 223310 in a manner like the first and/or second pair of sensing devices 223306A, 223306B, 223308A, 223308B, and/or any other suitable manner.

The sensing devices 223306A, 223306B, 223308A, 223308B comprise conductivity electrodes which are electrically insulated from each other by the electrically insulative material 223312. The electrically insulative material 223312 can include four or more openings corresponding to the positions of the sensing devices 223306A, 223306B, 223308A, 223308B which allow for fluid within the shaft 223304 to pass therethrough and come into contact with the sensing devices 223306A, 223306B, 223308A, 223308B. When the first pair of the sensing devices 223306A, 223306B are electrically isolated from one another owing to an absence of fluid between the sensing devices 223036A and 223306B, the fluid detection circuit 223310 outputs a signal which is indicative of the interior volume of the shaft 223304 being dry enough for the normal operation of the surgical instrument 223300. The signal is then passed to a control circuit (not shown) of the surgical instrument 223300, where the signal is interpreted as being indicative of a condition where the interior volume of the shaft 223304 is sufficiently dry as to allow for the normal operation of the surgical instrument 223300. The control circuit can include a shaft processing circuit and/or a handle processing circuit which includes a main processor of the surgical instrument 223300. Alternatively, the fluid detection circuit 223310 may not output a signal when the first pair of the sensing devices 223306A, 223306B, are electrically isolated from one another, and the control circuit may interpret this lack of a signal as being indicative of a condition where the interior volume of the shaft 223304 is sufficiently dry as to allow for the normal operation of the surgical instrument 223300.

When the fluid within the shaft 223304 is of a sufficient volume which allows for the first pair of sensing devices 223306A, 223306B to be electrically connected to one another via the fluid, the fluid detection circuit 223310 recognizes the electrical connection between the first pair of sensing devices 223306A, 223306B and outputs a signal which is indicative of a liquid contamination condition proximate the positions of the first pair of sensing devices 223306A, 223306B. The signal is then passed to the control circuit. Responsive to the liquid contamination signal, the control circuit issues one or more control signals which serve to adjust the operation of the surgical instrument 223300. For example, the control circuit can issue one or more control signals which serve to lower the amount of power available to the surgical instrument 223300, lock out or disable one or more functions of the surgical instrument 223300, and/or lock out or disable one or more electrical traces which are susceptible to signal loss or short-circuiting, for example. Also, for example, the fluid detection circuit 223310 may not output a signal when the sensing devices 223306A, 223306B are electrically connected to one another via the fluid, and the control circuit may interpret this lack of a signal as being indicative of a liquid contamination condition. The electrical connection between the sensing devices 223306A, 223306B provides an indication whether or not the fluid has intruded a first distance into the surgical instrument 223300, where the first distance corresponds to the positions of the sensing devices 223306A, 223306B within the shaft 223304.

When the second pair of the sensing devices 223308A, 223308B are electrically isolated from one another, the fluid detection circuit 223310 can output a signal which is indicative of the interior volume of the shaft 223304 being dry enough for continued operation of the surgical instrument 223300. The signal is then passed to the control circuit of the surgical instrument 223300, where the signal is interpreted as being indicative of a condition where the interior volume of the shaft 223304 proximate the positions of the sensing devices 223308A, 223308B is sufficiently dry as to allow for the continued operation of the surgical instrument 223300. Alternatively, the fluid detection circuit 223310 may not output a signal when the second pair of the sensing devices 223308A, 223308B, are electrically isolated from one another, and the control circuit may interpret this lack of a signal as being indicative of a condition where the interior volume of the shaft 223304 is sufficiently dry as to allow for the continued operation of the surgical instrument 223300.

When the fluid within the shaft 223304 is of a sufficient volume which allows for the second pair of sensing devices 2233086A, 223308B to be electrically connected to one another via the fluid, the fluid detection circuit 223310 recognizes the electrical connection between the second pair of sensing devices 223308A, 223308B and outputs a signal which is indicative of a liquid contamination condition proximate to the positions of the sensing devices 2233086A, 223308B. The signal is then passed to the control circuit. Responsive to the liquid contamination signal, the control circuit issues one or more control signals which serve to adjust the operation of the surgical instrument 223300. For example, the control circuit can issue one or more control signals which serve to lower the amount of power available to the surgical instrument 223300, lock out or disable one or more functions the surgical instrument 223300, and/or lock out or disable one or more electrical traces which are susceptible to signal loss or short-circuiting, for example. Alternatively, the fluid detection circuit 223310 may not output a signal when the sensing devices 223308A, 223308B are electrically connected to one another via the fluid, and the control circuit may interpret this lack of a signal as being indicative of a liquid contamination condition. The electrical connection between the sensing devices 223308A, 223308B provides an indication whether or not the fluid has further intruded to a second distance into the surgical instrument 223300, where the second distance corresponds to the positions of the sensing devices 223308A, 223308B within the shaft 223304.

In various instances, the sensing devices 223306A, 223306B, 223308A, 223308B, the electrically insulative material 223312, and/or the fluid detection circuit 223310 can form portions of a flex circuit 223322 which is positioned within the shaft 223004 and can conform to the interior surface of the external housing or shroud 223318 of the shaft 223004. That said, the sensing devices 223306A, 223306B, 223308A, 223308B, the electrically insulative material 223312, and/or the fluid detection circuit 223310 can be arranged in any suitable manner.

The absorption material 223314 is configured to absorb the fluid within the shaft 223004. By absorbing the fluid, the absorption material 223314 slows the ingress of the fluid into the surgical instrument 223300; however, the fluid will ultimately wick through the absorption material 223314 toward the second pair of sensing devices 223308A, 223308B. Notably, the first pair of sensing devices 223306A, 223306B are positioned distally with respect to the absorption material 223314 and, as a result, any initial fluid intrusion will quickly reach the first pair of sensing devices 223306A, 223306B. On the other hand, at least a portion of the absorption material 223314 is present between the first pair of sensing devices 223306A, 223306B and the second pair of sensing devices 223308A, 223308B and, as a result, the fluid intrusion may or may not reach the second pair of sensing devices 223308A, 223308B. As a result, the fluid detection circuit 223310 is configured to use the electrical connection between the first pair of sensing devices 223306A, 223306B as a fluid intrusion/contamination warning which does not necessarily change any operation of the surgical instrument 223300, and to use the electrical connection between the second pair of sensing devices 223308A, 223308B as a fluid intrusion/contamination warning which does change the operation of the surgical instrument 223300.

As shown in FIG. 138, the absorption material 223314 may be configured in the form of a ring or cylinder which is concentric with the external housing/shroud 223318 of the shaft 223004. The second pair of sensing devices 223308A, 223308B are positioned between the absorption material 223314 and the external housing/shroud 223318 which further limits and controls the potential ingress of the fluid into the surgical instrument 223300.

In various instances, the above-described sensing array and/or another similar sensing array can be used in concert with the absorption material 223314 to not only detect the presence of fluid within the shaft 223304, but also to detect when the fluid has reached an amount which can no longer be adequately handled by various electrical components of the surgical instrument 223300. Stated differently, this combination can help determine how much fluid is in the shaft 223304. It will be appreciated that some electrical components of the surgical instrument 223300 can perform their primary function better than other electrical components of the surgical instrument 223300 can when both are exposed to the same volume of fluid. Similarly, some electrical components of the surgical instrument 223300 will fail before other electrical components of the surgical instrument 223300 will fail when both are exposed to the same volume of fluid.

FIG. 139 illustrates an electrical circuit 223400 of the surgical instrument 223300 of FIG. 138. The electrical circuit 223400, or at least a portion of the electrical circuit 223400, can be positioned within the absorption material 223314 of the surgical instrument 223300 and can be utilized to determine when fluid in the shaft 223004 has reached a volume which can no longer be adequately handled by one or more electrical components of the surgical instrument 223300. The electrical circuit 223400 includes a sensing array which includes a first pair of sensing devices 223402A, 223402B and a second pair of sensing devices 223404A, 223404B. The first and second pairs of sensing devices 223402A, 223402B, 223404A, 223404B can be the first and second pairs of sensing devices 223306A, 223306B, 223308A, 223308B shown in FIG. 138, respectively, or additional sensing devices. Thus, it should be appreciated that the electrical circuit 223400 can form a part of the flexible circuit 223322 and can also be electrically connected to the fluid detection circuit 223310.

The electrical circuit 223400 also includes a first comparator 223406 which is electrically connected to the first pair of sensing devices 223402A, 223402B, and a second comparator 223408 which is electrically connected to the second pair of sensing devices 223404A, 223404B. As explained in greater detail below, the first and second comparators 223406, 223408 are utilized to determine whether an input has reached some predetermined value. In various instances, the first and second comparators 223406, 223408 are realized with operational amplifiers. In certain instances, the first and second comparators 223406, 223408 are realized with a dedicated comparator integrated circuit. The electrical circuit 223400 further includes a first resistive element 223410 which is electrically connected to the first pair of sensing devices 223402A, 223402B, and a second resistive element 223412 which is electrically connected to the second pair of sensing devices 223404A, 223404B.

Based on the configuration of the first and second pairs of sensing devices 223402A, 223402B, 223404A, 223404B and their respective connection paths back to the power source V, at least part of the electrical circuit 223400 may be considered a ladder circuit, where two rungs of the ladder are represented by the respective first and second pairs of sensing devices 223402A, 223402B, 223404A, 223404B and the two rails of the ladder are represented by their respective connection paths back to the power source V. Although only two pair of sensing devices are shown in FIG. 139, it should be appreciated that the electrical circuit 223400 may include any number of pairs of sensing devices, which are spaced apart from one another and connected to the power source V in a manner like the first and/or second pair of sensing devices 223402A, 223402B, 223404A, 223404B, as well as any number of corresponding comparators.

In operation, when a sufficient amount of fluid within the shaft 223004 causes the first pair of sensing devices 223402A, 223402B to be electrically connected to one another via the fluid, the first pair of sensing devices 223402A, 223402B provide a voltage signal to a first input (e.g., the negative-input) of the first comparator 223406. The first comparator 223406 then compares the voltage signal from the first pair of sensing devices 223402A, 223402B with a reference voltage which is connected to a second input (e.g., the positive+input) of the first comparator 223406. Based on which voltage is larger, the first comparator 223406 then outputs either a "high" signal or a "low" signal. For example, when the reference voltage is greater than the voltage signal from the first pair of sensing devices 223402A, 223402B, the first comparator 223406 outputs a "low" signal which is an indication that the volume of fluid within the shaft 223004 proximate to the first pair of sensing devices 223402A, 223402B has not yet reached a level that cannot be adequately handled by the electrical components of the surgical instrument 223300. This would also be the case when the sensing devices 223402A, 223402B are electrically isolated from one another. On the other hand, when the voltage signal from the first pair of sensing devices 223402A, 223402B, is greater than the reference voltage, the first comparator 223406 outputs a "high" signal which is an indication that the amount of fluid proximate to the first pair of sensing devices 223402A, 223402B has reached a level within the shaft 223304 which can no longer be adequately handled by one or more electrical components of the surgical instrument 223300. In either case, the signal output by the first comparator 223406 may be passed to the control circuit of the surgical instrument 223300 for further action.

Similarly, when the absorption material 223314 has absorbed a sufficient amount of fluid from within the shaft 223004 to cause the second pair of sensing devices 223404A, 223404B to be electrically connected to one another via the absorbed fluid, the second pair of sensing devices 223404A, 223404B provide a voltage signal to a first input (e.g., the negative-input) of the second comparator 223408. The first comparator 223408 then compares the voltage signal from the second pair of sensing devices 223404A, 223404B with a reference voltage which is connected to a second input (e.g., the positive+input) of the second comparator 223408. Based on which voltage is larger, the second comparator 223408 then outputs either a "high" signal or a "low" signal. For example, when the reference voltage is greater than the voltage signal from the second pair of sensing devices 223404A, 223404B, the second comparator 223408 outputs a "low" signal which is an indication that the volume of fluid within the shaft 223004 has not yet reached a level that cannot be adequately handled by the electrical components of the surgical instrument 223300. This would also be the case when the sensing devices 223404A, 223404B are electrically isolated from one another. On the other hand, when the voltage signal from the second pair of sensing devices 223404A, 223404B, is greater than the reference voltage, the second comparator 223408 outputs a "high" signal which is an indication that the amount of fluid absorbed by the absorption material 223314 has reached a saturation level, which is an indication that the volume of fluid within the shaft 223004 can no longer be adequately handled by one or more electrical components of the surgical instrument 223300. In either case, the signal output by the second comparator 223408 may be passed to the control circuit of the surgical instrument 223300 for further action.

Responsive to a "high" output signal from the first comparator 223406 and/or the second comparator 223408, the control circuit can issue one or more control signals which serve to issue a signal degradation warning, issue a component and/or sub-system failure warning, lower the amount of power available to the surgical instrument 223300, lock out or disable one or more functional features of the surgical instrument 223300, and/or lock out or disable one or more electrical traces which are susceptible to signal loss or short-circuiting, for example.

Although the same reference voltage is shown in FIG. 139 as being applied to the first comparator 223406 as well as to the second comparator 223408, it will be appreciated that a first reference voltage can be applied to the first comparator 223406 and a second reference voltage can be applied to the second comparator 223408, where the first and second voltage references are different from one another. For example, if the first reference voltage is lower than the second reference voltage, the output signal from the first comparator 223406 can provide an indication that a "level 1" fluid contamination level has been reached in the shaft 223004 where electrical signals are degraded and/or the performance of at least one electrical component of the surgical instrument 223000 is in danger of being affected, and the output signal from the second comparator 223408 can provide an indication that a "level 2" fluid contamination level has been reached in the shaft 223004 where electrical signals are even further degraded and/or the performance of at least one other electrical component of the surgical instrument 223000 is in danger of being affected. Based on the different meanings of the output signals passed to the control circuit of the surgical instrument 223300, the control circuit can issue control signals which serve to adjust the operations of the surgical instrument 223300 differently and/or adjust different operations of the surgical instrument 223000. For example, when a "level 1" fluid contamination level signal is output from the first comparator 223406, the control circuit issues one or more control signals which serve to lower the amount of power available to the surgical instrument 223300. When a "level 2" fluid contamination level signal is output from the second comparator 223408, the control circuit issues one or more control signals which serve to further lower the amount of power available to the surgical instrument 223300, lock out or disable one or more functional features of the surgical instrument 223300, and/or lock out or disable one or more electrical traces which are susceptible to signal loss or short-circuiting, for example.

Furthermore, although the sensing devices 223402A, 223402B, 223404A, 223404B are shown in FIG. 139 as being in an "open" position (e.g., not electrically connected to one another), the above-described functionality of the electrical circuit 223400 can also be realized with the sensing devices 223402A, 223402B, 223404A, 223404B being in a "closed" position. As long as the sensing devices 223402A, 223402B, 223404A, 223404B remain in the "closed" position and pass respective voltage signals to the first and second comparators 223406, 223408, the output signals of the first comparator 223406 and/or the second comparator 223408 would be an indication that the volume of fluid within the shaft 223004 has not yet reached a level that cannot be adequately handled by the electrical components of the surgical instrument 223300. As more and more fluid comes into the shaft 223004 and is absorbed by the absorption material 223314, the absorption material 223314 further expands, eventually reaching the point where the electrical connection between the second pair of sensing devices sensing 223404A, 223404B is broken/pulled apart, thereby breaking/altering the electrical continuity/conductivity within the electrical circuit 223400. The breaking/altering in the continuity/conductivity changes the respective voltage signals applied to the first inputs (e.g., the negative-inputs) of the first and second comparators 223406, 223408, which in turn changes the meaning of the signals output by the first and second comparators 223406, 223408.

When a surgical instrument is used during a surgical procedure, the density of the air associated with the environment in which the surgical procedure is taking place can have an effect on the performance of the surgical instrument. In most case, the altitude the surgical procedure is taking place at can be a proxy for the air density. For example, a surgical instrument being used in a high altitude location where the air is generally less dense than at sea level can perform differently than when the surgical instrument is used at or near sea level. Due to performance issues associated with air density/altitude, it is desirable to sense/detect the air density/altitude which the surgical instrument is operating at, and adjust various thresholds, control parameters and/or sensed values to compensate for differences in altitude.

Heat dissipation within a surgical instrument is one performance characteristic which changes with altitude. As the altitude increases, there is less air for a given volume and, as a result, the atmospheric pressure decreases. As the atmospheric pressure decreases, air molecules spread out further and the temperature decreases. There are certain parts of a surgical instrument which rely on convection cooling to dissipate heat generated by the operation of the surgical instrument. With convection cooling, the heat generated by the operation of the surgical instrument is transferred from the surgical instrument to the air surrounding the surgical instrument. At higher altitudes, where the atmospheric pressure is lower and there is less air (the air density is lower), the convection cooling is less efficient due to there being less air, and it is more difficult to dissipate the waste heat generated by the electronics of the surgical instrument which drive motors, generate high frequency electrosurgical energy for radio-frequency (RF), and/or ultrasonic type applications, for example, due to the convection cooling being less efficient. This is why motor heat dissipation efficiency decreases with increasing altitudes.

Air volume delivered by a compressor pump in a smoke evacuation system utilized with a surgical procedure is another performance characteristic which changes with altitude. The compressor pump will deliver the same volume of air regardless of the weight or density of the air (as altitude increases, the weight and density of the air becomes lower and lower). However, since the weight of the air is lower at higher altitudes, the compressor pump requires less electrical power to deliver the same volume of air at higher altitudes. Stated differently, to deliver a given volume of air at a higher altitude, the motor speed of the compressor pump can be decreased. That said, to deliver a given weight of air at a higher altitude, the motor speed of the compressor pump is increased.

In view of the above, it will be appreciated why it is desirable to sense/detect the altitude (as a proxy for the air density) which the surgical instrument is operating at, and adjust various thresholds, control parameters and/or sensed values to compensate for differences in altitude. The altitude can be sensed/detected in a number of different ways. For example, the surgical instrument can include a sensing device which senses and measures atmospheric/barometric pressure, such as a barometric pressure sensor, for example. The sensed atmospheric pressure is a proxy for the altitude. Based on the sensed atmospheric pressure, a control circuit and/or algorithm of the surgical instrument can issue one or more control signals which operate to alter/adjust the normal operation of the surgical instrument to account for the altitude/air density. In addition to or in lieu of taking direct readings of the atmospheric pressure, the surgical instrument can include a global positioning system (GPS) receiver which determines the precise position of the receiver. In such instances, the control circuit and/or algorithm can correlate the GPS readings with a GPS location, the known altitude and average atmospheric barometric readings at the GPS location, and issue one or more control signals to alter/adjust the normal operation of the surgical instrument to account for the altitude/air density at that location. There are also several ways to estimate/calculate a de-rating factor which can be applied to the various thresholds, control parameters and/or sensed values to account for changes in altitude/air density.

FIG. 140 illustrates a graph 223500 which shows relationships between altitude, atmospheric pressure 223502 and electrical power 223504 utilized by a surgical instrument, in various instances. The graph 223500 can be utilized to determine de-rating factors corresponding to different sensed/detected altitudes, where the altitudes are proxies for different air densities. The altitude is shown along a first horizontal axis 223506 as elevation from sea level. A second horizontal axis 223508 is aligned with the first horizontal axis 223506 and also represents the elevation from sea level. A power percentage is shown along a first vertical axis 223510 and a scaled atmospheric pressure is shown along a second vertical axis 223512. As shown in FIG. 140, as the elevation increases, the atmospheric pressure 223502 decreases and the electrical power 223504 utilized by the surgical instrument decreases. At sea level (elevation=0), the atmospheric pressure 223502 is at the scaled level of 1, and the electrical power 223504 is at 100% power (full power). At an elevation of 10,000 feet above sea level, the atmospheric pressure 223502 is at the scaled level of approximately 0.20, and the electrical power 223504 is at 70% power (30% less than full power). Stated differently, at an atmospheric pressure 223502 associated with an elevation of 10,000 feet above sea level, temperature thresholds associated with the surgical instrument can be de-rated by 30%. Similar de-rating percentages can be determined for other elevations by simply determining where a vertical line aligned with a given elevation on the first horizontal axis 223506 crosses the electrical power 223504 and the atmospheric pressure 223502. In various instances, the de-rating percentages can be stored as a look-up table in a memory device of a control circuit of the surgical instrument, and can be utilized by the control circuit and/or an algorithm to apply de-rating factors to the various thresholds, control parameters and/or sensed values to account for the sensed/detected air densities.

Another method for determining de-rating factors and/or other applicable adjustments for differences in altitude can be found, for example, in a white paper entitled A METHOD FOR APPROXIMATING COMPONENT TEMPERATURES AT ALTITUDE CONDITIONS BASED ON CFD ANALYSIS AT SEA LEVEL CONDITIONS authored by Bruno Zoccali, the disclosure of which is hereby incorporated by reference in its entirety. The white paper was publicly available on the website of TDMG Inc. (www.tdmginc.com) as of Dec. 6, 2018.

The surgical instruments disclosed herein are configured to include temperature sensors positioned within a handle assembly and/or a shaft of the surgical instrument. The surgical instrument can be any of the surgical instruments described herein. The temperature sensors are positioned to sense the temperature of certain components and/or sub-systems positioned within the handle assembly and/or the shaft of the surgical instrument. For example, the temperature sensors may be positioned to sense the temperature of an electric motor, power circuitry, and/or communication circuitry, for example. The sensed temperatures may be utilized by a control circuit of the surgical instrument, such as a main processor in a handle assembly of the surgical instrument, for example, and/or an algorithm to adjust/adapt the operation of the surgical instrument.

In various instances, thermal sensing devices can be built into flex circuits within different parts of the surgical instrument, and the temperatures measured/sensed by the thermal sensing devices can be utilized by the control circuit and/or an algorithm to determine if a temperature of a given component and/or sub-system is in a warning or danger zone. Once the sensed/measured temperature of a given component and/or sub-system is determined to be above the warning level, the control circuit and/or the algorithm can further operate to begin reducing the level of power supplied to the highest heat creating components and/or systems. For example, the level of power supplied to the drive motor of the surgical instrument can be reduced.

Once the sensed/measured temperature of a given component and/or sub-system is determined to be over a predetermined critical threshold, the control circuit and/or the algorithm can act to place the surgical instrument into a shut down condition, where the electronics of the surgical instrument which function to provide communication with a surgical hub stay energized but the surgical instrument is otherwise prevented from performing certain functionalities, such as closing jaws, firing staples, and/or delivering high frequency electrosurgical energy, for example. By keeping the electronics which function to provide communication with the surgical hub energized, the surgical hub can continue to keep a user of the surgical instrument informed regarding the operational status of the surgical instrument. Various aspects of a surgical hub are described in more detail in U.S. patent application Ser. No. 15/940,629, entitled COMPUTER IMPLEMENTED INTERACTIVE SURGICAL SYSTEMS, filed on Mar. 29, 2018, the disclosure of which is hereby incorporated by reference in its entirety.

In order to manage the temperatures of the components and/or sub-systems of the surgical instrument and the continued operation of the surgical instrument in heavy use conditions, in various instances, the priority of operation can be based on the importance level of the component, subsystem and/or task to be performed. Therefore, in certain circumstances the surgical instrument can be controlled such that the highest heat generator can go unregulated or only be regulated after a critical task is accomplished.

In some instances, when a component and/or subsystem of the surgical instrument is being regulated, a control circuit of the surgical instrument, such as a main processor in a handle assembly of the surgical instrument, for example, can communicate with the surgical hub in order to receive more information on how best to proceed. In some instances, the situational awareness functionality of the surgical hub can operate to inform the control circuit of the surgical instrument that the surgical instrument is in the middle of a critical task, and the control circuit and/or an algorithm can then control the surgical instrument to either ignore the heat warning or reprioritize the importance of the component and/or sub-system that was being regulated. Various aspects of situational awareness functionality are described, for example, in U.S. patent application Ser. No. 15/940,654, entitled SURGICAL HUB SITUATIONAL AWARENESS, filed on Mar. 29, 2018, the disclosure of which is herein incorporated by reference in its entirety.

In some instances, the surgical instrument can be controlled to proportionally limit motor power use based on the sensed/measured temperatures or on estimated temperatures. For example, as predetermined temperature thresholds are exceeded and/or the rate of temperature rise exceeds a predetermined threshold and/or a modeled heat build-up is approaching a predetermined threshold, the surgical instrument can be controlled to reduce the level of power made available to the motor as a first priority, then reduce the power available for the energy modality (e.g., electrosurgical energy, ultrasonic energy), if any.

FIG. 141 illustrates a method 223600 for determining heat flux from sensed/measured temperatures over time to predict an occurrence of a predefined temperature threshold being exceeded. At step 223602, the temperatures of the components and/or sub-systems positioned within the handle assembly and/or the shaft of the surgical instrument are sensed/measured by a temperature sensing device. At step 223604, the energy delivered to each motor and to the power circuitry of the surgical instrument is measured over time by an energy measuring device. At step 223606, the accumulated heat built-up inside the surgical instrument is estimated based on the information determined at steps 223602 and 223604. At step 223608, the rate of the temperature rise within the surgical instrument is determined by a control circuit and/or algorithm of the surgical instrument. Based on the determined rate of the temperature rise at step 223608, the time at which the predefined temperature threshold will be exceeded can be determined at step 223610 by the control circuit and/or an algorithm of the surgical instrument. In some instances, the method 223600 further comprises a step 223612, wherein the rate of temperature rise determined at step 223608 can be compared to a rate of temperature rise predicted by a modeled heat build-up to establish a higher level of confidence of the accuracy of the determined rate of temperature rise. This comparison can be performed by the control circuit of the surgical instrument.

FIG. 142 illustrates a graph 223700 which shows a relationship between a sensed temperature 223702, an approximated temperature 223704, and an energy usage 223706 of the surgical instrument. The time t is shown along a first horizontal axis 223708 and along a third horizontal axis 223712. A second horizontal axis 223710 also represents time t. A first vertical axis 223714 is associated with the approximated temperature 223704, a second vertical axis 223716 is associated with the sensed temperature 223702, and a third vertical axis 223718 is associated with the energy usage 223706. In various instances, the sensed temperature 223702 is a temperature sensed within a handle assembly of the surgical instrument, the approximated temperature is a temperature which is estimated by a heat build-up model, and the energy usage 223706 represents the total of all energy consumed by the surgical instrument during its use in a surgical procedure.

As shown in FIG. 142, when the surgical instrument is first energized, the level of energy 223706 used by the surgical instrument is very low. The small increase in the sensed temperature 223702 can be attributed to the electrical circuits within the surgical instrument being energized. From time $t_1$ to time $t_2$, when an end effector of the surgical instrument is being articulated, the energy usage 223706 increases and the sensed temperature 223702 increases. The approximated temperature 223704 is shown increasing at time $t_2$. As the articulation is paused between time $t_2$ and time $t_3$, the energy usage 223706 stays the same, the sensed temperature 223702 continues to increase, and the approximated temperature 223704 stays the same. From time $t_3$ to time $t_4$, when the end effector is further articulated, the energy usage 223706 increases and the sensed temperature 223702 increases. The approximated temperature 223704 is shown increasing at time $t_4$.

As the articulation is paused again between time $t_4$ and time $t_5$, the energy usage 223706 stays the same, the sensed temperature 223702 continues to increase and the approximated temperature 223704 stays the same. At time $t_5$, the energy modality of the surgical instrument, such as the application of mechanical energy, electrosurgical energy, and/or ultrasonic energy, for example, is energized, the energy usage 223706 begins to increase significantly, the sensed temperature 223702 reaches the motor temperature threshold 223720 (which is the same for the sensed temperature 223702 and the approximated temperature 223704), and the approximated temperature 223704 increases and passes the motor threshold 223720 in the process.

From time $t_5$ to time $t_6$, as the energy modality continues to be energized, the energy usage 223706 increases significantly, the sensed temperature 223702 increases significantly, exceeding the motor threshold 223720 at approximately time $t_5$ and reaching the energy threshold 223722 at time $t_6$. As a result of the sensed temperature 223702 exceeding the motor threshold 223720 at approximately time $t_5$, a control circuit and/or an algorithm of the surgical instrument, such as a main processor in a handle assembly of the surgical instrument, for example, and/or an algorithm acts to limit the power delivered to the motor (or motors) of the surgical instrument. This limiting remains in effect until the sensed temperature 223702 falls back below the motor threshold 223720 at approximately time $t_{10}$.

At approximately time $t_6$, the sensed temperature 223702 passes the energy threshold 223722. As a result of the sensed temperature 223702 exceeding the energy threshold 223722 at approximately time $t_6$, the control circuit and/or the algorithm acts to limit the power delivered to the energy modality of the surgical instrument. This limiting remains in effect until the sensed temperature 223702 falls back below the energy threshold 223722 at approximately time $t_7$. Once the limiting of the power delivered to the energy modality 223702 is halted at time $t_7$, the sensed temperature 223702 begins to decrease. From time $t_8$ to time $t_9$, although the sensed temperature 223702 is still above the motor threshold 223720, the control circuit and/or the algorithm may allow the end effector to be articulated once again because the sensed temperature 223702 is decreasing.

According to various aspects, the motor threshold 223720 and the energy threshold 223722 can be altered/adjusted by the control circuit and/or an algorithm to compensate for differences in air density, altitude and/or atmospheric pressure as described above.

The devices, systems, and methods disclosed in the Subject application can be used with the devices, systems, and methods disclosed in U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Pat. No. 10,022,120, entitled SURGICAL NEEDLE WITH RECESSED FEATURES; and U.S. patent application Ser. No. 14/740,724, now U.S. Pat. No. 9,888,914, entitled SUTURING INSTRUMENT WITH MOTORIZED NEEDLE DRIVE, which are incorporated by reference in their entireties herein.

The devices, systems, and methods disclosed in the Subject application can be used with the devices, systems, and methods disclosed in U.S. Provisional Patent Application Ser. No. 62/659,900, entitled METHOD OF HUB COMMUNICATION, filed on Apr. 19, 2018, U.S. Provisional Patent Application Ser. No. 62/611,341, entitled INTERACTIVE SURGICAL PLATFORM, filed on Dec. 28, 2017, U.S. Provisional Patent Application Ser. No. 62/611,340, entitled CLOUD-BASED MEDICAL ANALYTICS, filed on Dec. 28, 2017, and U.S. Provisional Patent Application Ser. No. 62/611,339, entitled ROBOT ASSISTED SURGICAL PLATFORM, filed on Dec. 28, 2017, which are incorporated by reference in their entireties herein. The devices, systems, and methods disclosed in the Subject application can also be used with the devices, systems, and methods disclosed in U.S. patent application Ser. No. 15/908,021, entitled SURGICAL INSTRUMENT WITH REMOTE RELEASE, filed on Feb. 28, 2018, U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed on Feb. 28, 2018, U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,058, entitled SURGICAL INSTRUMENT WITH MODULAR POWER SOURCES, filed on Feb. 28, 2018, and U.S. patent application Ser. No. 15/908,143, entitled SURGICAL INSTRUMENT WITH SENSOR AND/OR CONTROL SYSTEMS, filed on Feb. 28, 2018, which are incorporated by reference in their entireties herein. The devices, systems, and methods disclosed in the Subject application can also be used with the devices, systems, and methods disclosed in U.S. patent application Ser. No. 14/226,133, now U.S. Patent Application Publication No. 2015/0272557, entitled MODULAR SURGICAL INSTRUMENT SYSTEM, filed on Mar. 26, 2014, which is incorporated by reference in its entirety herein.

Various aspects of the subject matter described herein are set out in the following example sets.

Example Set 1

Example 1

A method for controlling a surgical instrument. The method comprising operating a drive system driven by an electric motor and a motor control circuit, sensing strain within the surgical instrument via a strain gage circuit in communication with the motor control circuit, and changing the speed of the electric motor via the motor control circuit based on input from the strain gage circuit.

Example 2

The method of Example 1, wherein the changing step comprises slowing the speed of the electric motor when the strain measured by the strain gage circuit exceeds a threshold limit.

Example 3

The method of Example 2, wherein the changing step comprises increasing the speed of the electric motor if the strain measured by the strain gage circuit returns below the threshold limit.

Example 4

The method of Example 1, wherein the surgical instrument comprises a shaft and an end effector rotatably connected to the shaft, and wherein the operating step comprises rotating the end effector relative to the shaft.

Example 5

The method of Examples 1, 2, or 3, wherein the surgical instrument comprises an end effector including a movable jaw, and wherein the operating step comprises moving the jaw.

Example 6

The method of Examples 1, 2, 3, 4, or 5, wherein the surgical instrument comprises a firing system including a movable firing member, and wherein the operating step comprises moving the firing member.

Example 7

The method of Examples 1, 2, 3, 4, 5, or 6, wherein the surgical instrument comprises a shroud, and wherein the strain gage circuit comprises a strain gage attached to the shroud.

Example 8

The method of Examples 1, 2, 3, 4, 5, or 6, wherein the surgical instrument comprises a shroud, and wherein the strain gage circuit comprises a strain gage attached to the shroud.

Example 9

The method of Examples 1, 2, 3, 4, 5, or 6, wherein the surgical instrument comprises a shroud, and wherein the strain gage circuit comprises a strain gage embedded in the shroud.

Example 10

The method of Examples 1, 2, 3, 4, 5, 6, 7, 8, or 9, wherein the surgical instrument comprises a handle including a handle housing, wherein the strain gage circuit comprises a strain gage attached to the handle housing, and wherein the method further comprises pressing the handle housing to control the speed of the electric motor.

Example 11

The method of Examples 1, 2, 3, 4, 5, 6, 7, 8, or 9, wherein the surgical instrument comprises a handle including a handle housing, wherein the strain gage circuit comprises a strain gage embedded in the handle housing, and wherein the method further comprises pressing the handle housing to control the speed of the electric motor.

Example 12

The method of Examples 1, 2, 3, 4, 5, 6, 7, 8, 9, 10, or 11, wherein the drive system comprises a drive shaft, and wherein at least a portion of the strain gage circuit is mounted to the drive shaft.

Example 13

The method of Examples 1, 2, 3, 4, 5, 6, 7, 8, 9, 10, 11, or 12, wherein the motor control circuit comprises default operating controls, wherein the strain gage circuit provides data to the motor control circuit, and wherein the motor control circuit modifies the default operating controls based on the data from the strain gage circuit.

Example 14

A method for controlling a surgical instrument. The method comprising operating a drive system driven by an electric motor and a motor control system, sensing strain within the surgical instrument via a strain gage circuit in communication with the motor control system, and changing the speed of the electric motor via the motor control system based on data from the strain gage circuit.

Example 15

The method of Example 14, wherein the motor control system comprises default operating controls, and wherein the motor control system modifies the default operating controls based on the data from the strain gage circuit.

Example 16

The method of Examples 14 or 15, wherein the surgical instrument comprises a handle including a handle housing, wherein the strain gage circuit comprises a strain gage attached to the handle housing, and wherein the method further comprises pressing the handle housing to control the speed of the electric motor.

Example 17

The method of Examples 14 or 15, wherein the surgical instrument comprises a handle including a handle housing, wherein the strain gage circuit comprises a strain gage embedded in the handle housing, and wherein the method further comprises pressing the handle housing to control the speed of the electric motor.

Example 18

A method for controlling a surgical instrument. The method comprising operating the surgical instrument using a control system, wherein the surgical instrument comprises a shroud, sensing a parameter of the shroud using a sensor circuit in communication with the control system, and modifying the operation of the surgical instrument based on data from the sensor circuit.

Example 19

The method of Example 18, wherein the control system comprises default operating controls, and wherein the control system modifies the default operating controls based on the data from the sensor circuit.

Example Set 2

Example 1

A surgical instrument comprising a handle, a shaft extending from the handle, an end effector extending from the shaft, a drive electric motor, and a shifter electric motor configurable in a first configuration, a second configuration, and a third configuration. The surgical instrument further comprises a first drive system configured to perform a first end effector function. The first drive system is drivable by the drive electric motor when the shifter electric motor is in the first configuration. The surgical instrument further comprises a second drive system configured to perform a second end effector function. The second drive system is drivable by the drive electric motor when the shifter electric motor is in the second configuration. The surgical instrument further comprises a third drive system configured to perform a third end effector function. The third drive system is drivable by the drive electric motor when the shifter electric motor is in the third configuration. The second drive system and the third drive system are not drivable by the drive electric motor when the shifter electric motor is in the first configuration. The first drive system and the third drive system are not drivable by the drive electric motor when the shifter electric motor is in the second configuration. The first drive system and the second drive system are not drivable by the drive electric motor when the shifter electric motor is in the third configuration.

Example 2

The surgical instrument of Example 1, wherein the shifter electric motor comprises a solenoid.

Example 3

The surgical instrument of Examples 1 or 2, wherein the drive electric motor comprises a rotatable drive output shaft and a drive output gear mounted to the drive output shaft, wherein the shifter electric motor comprises a translatable shifter shaft and a rotatable shifter gear, wherein the shifter gear is operably engaged with the drive output gear and selectively engageable with the first drive system, the second drive system, and the third drive system.

Example 4

The surgical instrument of Examples 1, 2, or 3, wherein the first drive system comprises a first rotatable drive shaft, wherein the second drive system comprises a second rotatable drive shaft, wherein the third drive system comprises a third rotatable drive shaft, and wherein the first rotatable drive shaft, the second rotatable drive shaft, and the third rotatable drive shaft are nested along a longitudinal axis.

Example 5

The surgical instrument of Examples 1, 2, 3, or 4, further comprising an articulation joint rotatably connecting the end effector to the shaft, wherein the end effector comprises a clampable jaw and a translatable firing member, wherein the first end effector function comprises articulating the end effector relative to the shaft, wherein the second end effector function comprises moving the jaw into a clamped position, and wherein the third end effector function comprises moving the firing member through a firing stroke.

Example 6

The surgical instrument of Example 5, further comprising a staple cartridge including staples removably stored therein, wherein the firing member is configured to deploy the staples from the staple cartridge during the firing stroke.

Example 7

The surgical instrument of Examples 5 or 6, further comprising a second drive motor configured to drive a fourth drive system to perform the second end effector function.

Example 8

The surgical instrument of Examples 1, 2, 3, or 4, further comprising a second drive motor configured to drive a fourth drive system to perform the second end effector function.

Example 9

The surgical instrument of Examples 7 or 8, wherein the drive electric motor and the second drive motor are operable at the same time.

Example 10

The surgical instrument of Examples 7, 8, or 9, wherein the drive electric motor and the second drive motor are operable at different times.

Example 11

The surgical instrument of Examples 1, 2, 3, 4, 5, 6, 7, 8, 9, or 10, further comprising a staple cartridge.

Example 12

A surgical system comprising a housing, a shaft extending from the housing, an end effector extending from the shaft, a drive electric motor, and a shifter electric motor configurable in a first configuration, a second configuration, and a third configuration. The surgical system further comprises a first drive system configured to perform a first end effector function. The first drive system is drivable by the drive electric motor when the shifter electric motor is in the first configuration. The surgical system further comprises a second drive system configured to perform a second end effector function. The second drive system is drivable by the drive electric motor when the shifter electric motor is in the second configuration. The surgical system further comprises a third drive system configured to perform a third end effector function. The third drive system is drivable by the drive electric motor when the shifter electric motor is in the third configuration. The second drive system and the third drive system are not drivable by the drive electric motor when the shifter electric motor is in the first configuration. The first drive system and the third drive system are not drivable by the drive electric motor when the shifter electric motor is in the second configuration. The first drive system and the second drive system are not drivable by the drive electric motor when the shifter electric motor is in the third configuration.

Example 13

The surgical system of Example 12, wherein the housing comprises a handle.

Example 14

The surgical system of Examples 12 or 13, wherein the housing is configured to be attached to a robotic surgical system.

Example 15

The surgical system of Example 14, further comprising the robotic surgical system.

Example 16

A surgical system comprising a housing, a shaft extending from the housing, an end effector extending from the shaft, a first drive electric motor, a first shifter electric motor configurable in a first configuration and a second configuration, and a first drive system configured to perform a first end effector function. The first drive system is drivable by the first drive electric motor when the first shifter electric motor is in the first configuration. The surgical system further comprises a second drive system configured to perform a second end effector function. The second drive system is drivable by the first drive electric motor when the first shifter electric motor is in the second configuration. The second drive system is not drivable by the first drive electric motor when the first shifter electric motor is in the first configuration. The first drive system is not drivable by the first drive electric motor when the first shifter electric motor is in the second configuration. The surgical system further comprises a second drive electric motor, a second shifter electric motor, and a third drive system. The second shifter electric motor is configurable in a third configuration and a fourth configuration. The third drive system is configured to perform a third end effector function. The third drive system is drivable by the second drive electric motor when the second shifter electric motor is in the third configuration. The surgical system further comprises fourth drive system configured to perform a fourth end effector function. The fourth drive system is drivable by the second drive electric motor when the second shifter electric motor is in the fourth configuration. The fourth drive system is not drivable by the second drive electric motor when the second shifter electric motor is in the third configuration. The third drive system is not drivable by the second drive electric motor when the second shifter electric motor is in the fourth configuration.

Example 17

The surgical system of Example 16, wherein the housing comprises a handle.

Example 18

The surgical system of Examples 16 or 17, wherein the housing is configured to be attached to a robotic surgical system.

Example 19

The surgical system of Example 18, further comprising the robotic surgical system.

Example 20

The surgical system of Examples 16, 17, 18, or 19, wherein the first drive electric motor and the second drive electric motor are operable at the same time.

Example 21

The surgical system of Examples 16, 17, 18, 19, or 20, wherein the first drive electric motor and the second drive electric motor are operable at different times.

Example Set 3

Example 1

A surgical instrument comprising a handle, a shaft extending from the handle, an end effector extending from the shaft, and a drive system. The drive system comprises an electric motor, a drive shaft operably coupled to the electric motor, a motor control system in communication with the electric motor, and a strain gage circuit embedded in the drive shaft. The strain gage circuit is in signal communication with the motor control system. The motor control system is configured to control the operation of the electric motor to perform an end effector function based on a signal from the strain gage circuit.

Example 2

The surgical instrument of Example 1, wherein the strain gage circuit is configured to measure the strain in the drive shaft, and wherein the motor control system comprises a processor and an algorithm configured to stop the electric motor when the measured strain exceeds a predetermined threshold.

Example 3

The surgical instrument of Example 2, wherein the drive system further comprises an actuator and an actuation sensor, wherein the actuation sensor is in communication with the motor control system, wherein the actuator is movable between an unactuated position and an actuated position, and wherein an actuation of the actuator re-starts the electric motor after being stopped by the motor control system.

Example 4

The surgical instrument of Example 1, wherein the strain gage circuit is configured to measure the strain in the drive shaft, and wherein the motor control system comprises a processor and an algorithm configured to slow the electric motor when the measured strain exceeds a predetermined threshold.

Example 5

The surgical instrument of Example 4, wherein the drive system further comprises an actuator and an actuation sensor, wherein the actuation sensor is in communication with the motor control system, wherein the actuator is movable between an unactuated position and an actuated position, and wherein an actuation of the actuator speeds up the electric motor after being slowed by the motor control system.

Example 6

The surgical instrument of Examples 1, 2, 3, 4, or 5, further comprising means for regulating the temperature of the strain gage circuit.

Example 7

The surgical instrument of Example 6, wherein the means is configured to minimize the temperature variations in the strain gage circuit relative to a predetermined temperature.

Example 8

The surgical instrument of Example 7, wherein the predetermined temperature is independent of the ambient temperature surrounding the surgical instrument.

Example 9

The surgical instrument of Example 6, wherein the means is configured to hold the temperature of the strain gage circuit at a constant temperature.

Example 10

The surgical instrument of Example 9, wherein the constant temperature is different than the ambient temperature surrounding the surgical instrument.

Example 11

The surgical instrument of Examples 1, 2, 3, 4, 5, 6, 7, 8, 9, or 10, further comprising a transmitter and a receiver. The transmitter is in signal communication with the motor control system. The transmitter is configured to emit a wireless signal to a surgical instrument system. The receiver is in signal communication with the motor control system. The receiver is configured to receive a wireless signal from the surgical instrument system.

Example 12

The surgical instrument of Examples 1, 2, 3, 4, 5, 6, 7, 8, 9, 10, or 11, further comprising an articulation joint rotatably connecting the end effector to the shaft, wherein the end effector function comprises rotating the end effector about the articulation joint, and wherein the motor control system is configured to stop the articulation of the end effector when the strain in the drive shaft exceeds a threshold level.

Example 13

The surgical instrument of Examples 1, 2, 3, 4, 5, 6, 7, 8, 9, 10, or 11, further comprising an articulation joint rotatably connecting the end effector to the shaft, wherein the end effector function comprises rotating the end effector about the articulation joint, and wherein the motor control system is configured to stop the articulation of the end effector when the measured strain in the drive shaft exceeds a threshold level.

Example 14

The surgical instrument of Examples 1, 2, 3, 4, 5, 6, 7, 8, 9, 10, or 11, further comprising an articulation joint rotatably connecting the end effector to the shaft, wherein the end effector function comprises rotating the end effector about the articulation joint, and wherein the motor control system is configured to slow the articulation of the end effector when the measured strain in the drive shaft exceeds a threshold level.

Example 15

The surgical instrument of Examples 1, 2, 3, 4, 5, 6, 7, 8, 9, 10, or 11, wherein the end effector comprises a rotatable jaw, wherein the end effector function comprises rotating the jaw, and wherein the motor control system is configured to stop the rotation of the jaw when the measured strain in the drive shaft exceeds a threshold level.

Example 16

The surgical instrument of Examples 1, 2, 3, 4, 5, 6, 7, 8, 9, 10, or 11, wherein the end effector comprises a rotatable jaw, wherein the end effector function comprises rotating the jaw, and wherein the motor control system is configured to slow the rotation of the jaw when the measured strain in the drive shaft exceeds a threshold level.

Example 17

The surgical instrument of Examples 1, 2, 3, 4, 5, 6, 7, 8, 9, 10, or 11, wherein the end effector comprises a tissue cutting member, wherein the end effector function comprises displacing the tissue cutting member through a cutting stroke, and wherein the motor control system is configured to stop the translation of the tissue cutting member when the measured strain in the drive shaft exceeds a threshold level.

Example 18

The surgical instrument of Examples 1, 2, 3, 4, 5, 6, 7, 8, 9, 10, or 11, wherein the end effector comprises a tissue cutting member, wherein the end effector function comprises displacing the tissue cutting member through a cutting stroke, and wherein the motor control system is configured to slow the translation of the tissue cutting member when the measured strain in the drive shaft exceeds a threshold level.

Example 19

The surgical instrument of Examples 1, 2, 3, 4, 5, 6, 7, 8, 9, 10, 11, 12, 13, 14, 15, 16, 17, or 18, wherein the end effector comprises a staple cartridge including staples removably stored therein.

Example 20

A surgical instrument comprising a handle, a shaft extending from the handle, an end effector extending from the shaft, and a drive system. The drive system comprises an electric motor, a drive shaft operably coupled to the electric motor, and a motor control system in communication with the electric motor. The surgical instrument further comprises a strain gage circuit in signal communication with the motor control system. The motor control system is configured to control the operation of the electric motor to perform an end effector function based on a signal from the strain gage circuit.

Example 21

A surgical system comprising a housing, a shaft extending from the housing, an end effector extending from the shaft, and a drive system. The drive system comprises an electric motor, a drive shaft operably coupled to the electric motor, and a motor control system in communication with the electric motor. The surgical system further comprises a strain gage circuit in signal communication with the motor control system. The motor control system is configured to control the operation of the electric motor to perform an end effector function based on a signal from the strain gage circuit.

Example 22

The surgical system of Example 21, further comprising a force measurement circuit in signal communication with the motor control system, wherein the motor control system is configured to control the operation of the electric motor to perform the end effector function based on a signal from the force measurement circuit.

Example 23

The surgical system of Example 21, further comprising a force measurement circuit in signal communication with the motor control system, wherein the motor control system is configured to control the operation of the electric motor to perform a different end effector function based on a signal from the force measurement circuit.

Example 24

The surgical system of Examples 22 or 23, wherein the force measurement circuit comprises a spring element.

Example 25

A surgical system comprising a first instrument and a second instrument. The first instrument comprises a strain gage circuit and a transmitter in communication with the strain gage circuit. The second instrument comprises an electric motor, a drive shaft operably coupled to the electric motor, and a motor control system in communication with the electric motor and the transmitter. The motor control system is configured to control the operation of the electric motor based on a signal from the strain gage circuit.

Example 26

The surgical system of Example 25, further comprising a surgical data hub, wherein the motor control system is in communication with the transmitter via the surgical data hub.

Example Set 4

Example 1

A surgical instrument comprising a handle and a shaft assembly extending from the handle. The handle comprises a housing, a circuit board positioned in the housing, and a port defined in the housing. The circuit board comprises an electrical connector. The port comprises a seal. The seal comprises a self-sealing aperture. The port is configured to permit a communications probe to be inserted through the self-sealing aperture to engage the electrical connector.

Example 2

The surgical instrument of Example 1, wherein the circuit board comprises a flex circuit mounted to the housing.

Example 3

The surgical instrument of Example 2, further comprising a second circuit board in communication with the flex circuit, wherein the second circuit board comprises a laminate circuit board.

Example 4

The surgical instrument of Example 3, wherein the flex circuit conducts electrical currents below a threshold amperage but not above the threshold amperage, and wherein the laminate circuit board conducts electrical currents above the threshold amperage.

Example 5

The surgical instrument of Example 1, wherein the circuit board comprises a first circuit board, wherein the surgical instrument further comprises a second circuit board, wherein the housing comprises a card slot defined therein, and wherein the second circuit board comprises a card removably retained in the card slot.

Example 6

The surgical instrument of Example 5, wherein the first circuit board conducts electrical currents below a threshold amperage but not above the threshold amperage, and wherein the second circuit board conducts electrical currents above the threshold amperage.

Example 7

The surgical instrument of Examples 5 or 6, further comprising electrical contacts in the card slot, wherein the electrical contacts place the second circuit board in communication with the first circuit board when the second circuit board is seated in the card slot.

Example 8

The surgical instrument of Example 1, wherein the circuit board comprises a first circuit board, wherein the surgical instrument further comprises a second circuit board, wherein the first circuit board conducts electrical currents below a threshold amperage but not above the threshold amperage, wherein the second circuit board conducts electrical currents above the threshold amperage, wherein the surgical instrument further comprises an electric motor, and wherein the second circuit board comprises a motor controller configured to control the electric motor.

Example 9

The surgical instrument of Example 1, wherein the circuit board comprises a first circuit board, wherein the surgical instrument further comprises a second circuit board, wherein the first circuit board conducts electrical currents below a threshold amperage but not above the threshold amperage, wherein the second circuit board conducts electrical currents above the threshold amperage, wherein the surgical instrument further comprises an RF generator, and wherein the second circuit board comprises a controller configured to control the RF generator.

Example 10

The surgical instrument of Example 1, wherein the circuit board comprises a first circuit board, wherein the surgical instrument further comprises a second circuit board, wherein the first circuit board conducts electrical currents below a threshold amperage but not above the threshold amperage, wherein the second circuit board conducts electrical currents above the threshold amperage, wherein the surgical instrument further comprises a transducer configured to convert electrical energy into mechanical energy, and wherein the second circuit board comprises a controller configured to control the transducer.

Example 11

The surgical instrument of Example 1, wherein the circuit board comprises electrical traces printed on the housing.

Example 12

The surgical instrument of Example 11, wherein the circuit board further comprises solid state components surface mounted on the electrical traces.

Example 13

The surgical instrument of Example 1, wherein the circuit board comprises electrical traces embedded in the housing, and wherein the housing has been etched to at least partially expose the electrical traces.

Example 14

The surgical instrument of Example 1, wherein the circuit board comprises a flex circuit embedded in the housing.

Example 15

The surgical instrument of Examples 2 or 14, further comprising a second circuit board in communication with the flex circuit, wherein the second circuit board comprises a laminate circuit board.

Example 16

The surgical instrument of Example 15, wherein the flex circuit conducts electrical currents below a threshold amperage but not above the threshold amperage, and wherein the laminate circuit board conducts electrical currents above the threshold amperage.

Example 17

The surgical instrument of Examples 1, 2, 3, 4, 5, 6, 7, 8, 9, 10, 11, 12, 13, 14, 15, or 16, further comprising a staple cartridge including staples removably stored therein.

Example 18

The surgical instrument of Examples 1, 2, 3, 4, 5, 6, 7, 8, 9, 10, 11, 12, 13, 14, 15, 16, or 17, wherein the port is comprised of an elastomeric material.

Example 19

A surgical instrument comprising a handle housing, a first circuit board embedded in the handle housing, and a second circuit board in communication with the first circuit board. The first circuit board conducts electrical currents below a threshold amperage but not above the threshold amperage. The second circuit board conducts electrical currents above the threshold amperage.

Example 20

The surgical instrument of Example 19, wherein the first circuit board comprises a flex circuit.

Example 21

The surgical instrument of Examples 19 or 20, wherein the handle housing comprises a card slot defined therein, and wherein the second circuit board comprises a card removably retained in the card slot.

Example 22

The surgical instrument of Examples 19, 20, or 21, further comprising an electric motor, wherein the second circuit board comprises a motor controller configured to control the electric motor.

Example 23

The surgical instrument of Examples 19, 20, 21, or 22, further comprising an RF generator, wherein the second circuit board comprises a controller configured to control the RF generator.

Example 24

The surgical instrument of Examples 19, 20, 21, or 22, further comprising a transducer configured to convert electrical energy into mechanical energy, wherein the second circuit board comprises a controller configured to control the transducer.

Example 25

The surgical instrument of Examples 19, 20, 21, 22, 23, or 24, wherein the first circuit board comprises electrical traces printed on the handle housing.

Example 26

The surgical instrument of Examples 25 or 26, wherein the first circuit board further comprises solid state components surface mounted on the electrical traces.

Example 27

The surgical instrument of Examples 25 or 26, wherein the handle housing has been etched to at least partially expose the electrical traces.

Example 28

The surgical instrument of Examples 19, 20, 21, 22, 23, 24, 25, 26, or 27, further comprising a port defined in the handle housing, wherein the port comprises a seal, wherein the seal comprises a self-sealing aperture, wherein the first circuit board comprises an electrical contact, and wherein the port is configured to permit a communications probe to be inserted through the self-sealing aperture to engage the electrical contact.

Example 29

A surgical instrument comprising a handle housing. The handle housing comprises a rotation interface and an electric interface defined on the rotation interface. The handle housing has been etched to at least partially expose the electrical interface. The surgical instrument further comprises a shaft rotatably mounted to the handle housing at the rotation interface. The shaft comprises electrical contacts engaged with the electrical interface.

Example 30

The surgical instrument of Example 29, wherein the electrical interface comprises a flex circuit.

Example Set 5

Example 1

A surgical instrument handle comprising a housing, a control circuit positioned in the housing, a button shell, and a flex circuit at least partially embedded in the button shell. The flex circuit is in electrical communication with the control circuit.

Example 2

The surgical instrument handle of Example 1, wherein the button shell has been etched to expose at least a portion of the flex circuit.

Example 3

The surgical instrument handle of Examples 1 or 2, wherein the button shell is molded over at least a portion of the flex circuit.

Example 4

The surgical instrument handle of Examples 1, 2, or 3, wherein the button shell and the housing comprise an assembly.

Example 5

The surgical instrument handle of Examples 1, 2, 3, or 4, wherein the button shell is integrally-formed with the housing.

Example 6

The surgical instrument handle of Examples 1, 2, 3, 4, or 5, wherein the flex circuit comprises a capacitive switch element.

Example 7

The surgical instrument handle of Example 6, wherein the button shell comprises an outer surface accessible by a user of the surgical instrument handle, wherein the capacitive switch element is mounted to the outer surface.

Example 8

The surgical instrument handle of Examples 1, 2, 3, 4, or 5, wherein the flex circuit comprises a force-sensitive piezoelectric switch element.

Example 9

The surgical instrument handle of Example 8, wherein the button shell comprises an outer surface accessible by a user of the surgical instrument handle, wherein the force-sensitive piezoelectric switch element is mounted to the outer surface.

Example 10

The surgical instrument handle of Examples 1, 2, 3, 4, or 5, wherein the flex circuit comprises a strain gage.

Example 11

The surgical instrument handle of Example 10, wherein the strain gage is contained within the button shell.

Example 12

The surgical instrument handle of Examples 1, 2, 3, 4, or 5, wherein the button shell comprises a compliant section configured to permit the button shell to observably deflect when depressed by a user of the surgical instrument handle.

Example 13

The surgical instrument handle of Example 12, wherein the flex circuit comprises a switch positioned adjacent the button shell such that the button shell contacts the switch when the button shell is deflected by the user.

Example 14

The surgical instrument handle of Examples 12 or 13, wherein the button shell comprises a living hinge.

Example 15

The surgical instrument handle of Examples 12 or 13, wherein the button shell comprises scoring configured to permit the button shell to observably deflect.

Example 16

The surgical instrument handle of Examples 1, 2, 3, 4, 5, 6, 7, 8, 9, 10, 11, 12, 13, 14, or 15, wherein the button shell is constructed to resist observable deflection when depressed by the user of the surgical instrument handle.

Example 17

The surgical instrument handle of Example 16, wherein the control circuit comprises a haptic feedback generator, and wherein the control circuit actuates the haptic feedback generator when the button shell is depressed.

Example 18

The surgical instrument handle of Examples 1, 2, 3, 4, 5, 6, 7, 8, 9, 10, 11, 12, 13, 14, 15, 16, or 17, wherein the housing and the button shell are comprised of the same material.

Example 19

The surgical instrument handle of Examples 1, 2, 3, 4, 5, 6, 7, 8, 9, 10, 11, 12, 13, 14, 15, 16, or 17, wherein the housing and the button shell are comprised of different materials.

Example 20

A surgical instrument comprising a housing, a control circuit positioned in the housing, a button shell, and an actuation circuit formed with the button shell. The actuation circuit is in electrical communication with the control circuit.

Example 21

The surgical instrument of Example 20, wherein the actuation circuit is at least partially embedded in the button shell.

Example 22

The surgical instrument of Example 20, wherein the actuation circuit is at least partially attached to the button shell.

Example 23

The surgical instrument of Example 20, wherein the actuation circuit is at least partially printed on the button shell.

Example 24

The surgical instrument of Examples 20, 21, 22, or 23, wherein the actuation circuit comprises electrical traces and surface mount components connected to the electrical traces.

Example 25

A surgical instrument comprising a housing, a control circuit, and a button wall. The control circuit is at least partially formed with the button wall.

Example 26

The surgical instrument of Example 25, wherein the control circuit is at least partially embedded in the button wall.

Example 27

The surgical instrument of Example 25, wherein the control circuit is at least partially attached to the button wall.

Example 28

The surgical instrument of Example 25, wherein the control circuit is at least partially printed on the button wall.

Example 29

The surgical instrument of Examples 25, 26, 27, or 28, wherein the control circuit comprises electrical traces and surface mount components connected to the electrical traces.

Example Set 6

Example 1

A surgical instrument comprising an electric motor and a control circuit. The control circuit comprises a plurality of logic gates and a monostable multivibrator connected to a first one of the logic gates. The control circuit is configured to alter a rate of action of a function of the surgical instrument by controlling a speed of rotation of the electric motor based on a sensed parameter.

Example 2

The surgical instrument of Example 1, wherein the plurality of logic gates includes at least one of the following; (1) an AND gate, (2) an OR gate, and (3) an inverter gate.

Example 3

The surgical instrument of Examples 1 or 2, wherein the monostable multivibrator comprises a retriggerable monostable multivibrator.

Example 4

The surgical instrument of Examples 1, 2, or 3, wherein the function of the surgical instrument comprises an articulation of an end effector of the surgical instrument.

Example 5

The surgical instrument of Examples 1, 2, 3, or 4, wherein the rate of action comprises a speed of an articulation of an end effector away from a longitudinal axis of a shaft of the surgical instrument.

Example 6

The surgical instrument of Example 5, wherein the speed of the articulation is slowed as the end effector passes through a zone defined around a centered state of a shaft of the surgical instrument.

Example 7

The surgical instrument of Examples 1, 2, 3, 4, 5, or 6, wherein the sensed parameter comprises a sensed position of an end effector relative to a longitudinal axis of a shaft of the end effector.

Example 8

The surgical instrument of Examples 1, 2, 3, 4, 5, 6, or 7, wherein the sensed parameter comprises a state of a switching device.

Example 9

The surgical instrument of Examples 1, 2, 3, 4, 5, 6, 7, or 8, wherein the control circuit further comprises an asynchronous counter connected to the monostable multivibrator.

Example 10

The surgical instrument of Example 9, wherein the asynchronous counter comprises a ripple counter.

Example 11

The surgical instrument of Examples 1, 2, 3, 4, 5, 6, 7, 8, 9, or 10, further comprising a sensing device connected to the monostable multivibrator.

Example 12

The surgical instrument of Examples 1, 2, 3, 4, 5, 6, 7, 8, 9, 10, or 11, further comprising a motor controller configured to control the speed of rotation of the electric motor.

Example 13

A surgical instrument comprising a flexible circuit comprising at least two conductors. The flexible circuit is configured to transfer electrical power within the flexible circuit, carry a signal within the flexible circuit, and provide a secondary function.

Example 14

The surgical instrument of Example 13, wherein the flexible circuit comprises a multilayer flexible circuit.

Example 15

The surgical instrument of Examples 12 or 13, wherein the at least two conductors comprises a twisted pair of conductors which overlap one another at regular intervals.

Example 16

The surgical instrument of Example 15, wherein the twisted pair of conductors are configured to mitigate interference from an electromagnetic field from an external source.

Example 17

The surgical instrument of Examples 13, 14, 15, or 16, wherein the at least two conductors comprises first and second pluralities of conductors.

Example 18

The surgical instrument of Example 17, wherein the flexible circuit further comprises an electromagnetic shield which surrounds the first and second pluralities of conductors.

Example 19

The surgical instrument of Examples 13, 14, 15, 16, 17, or 18, wherein the secondary function comprises electromagnetic shielding.

Example 20

The surgical instrument of Examples 13, 14, 15, 16, 17, or 18, wherein the secondary function comprises short-circuit protection.

Example 21

The surgical instrument of Examples 13, 14, 15, 16, 17, or 18, wherein the secondary function comprises contamination detection.

Example Set 7

Example 1

A surgical instrument comprising a drive system and a control circuit. The drive system comprises an electric motor. The control circuit comprises an acoustic sensor. The control circuit is configured to utilize a parameter of the drive system measured by the acoustic sensor to control a speed of the electric motor.

Example 2

The surgical instrument of Example 1, wherein the drive system further comprises a gear box and a drive train.

Example 3

The surgical instrument of Examples 1 or 2, wherein the control circuit further comprises at least one of the following; (1) a fast Fourier transform circuit and (2) a fast Fourier transform algorithm executable by a processor of the control circuit.

Example 4

The surgical instrument of Examples 1, 2, or 3, wherein the control circuit is further configured to determine a degradation of the drive system.

Example 5

The surgical instrument of Example 4, wherein the control circuit is further configured to adjust a motor control algorithm in response to the determined degradation of the drive system.

Example 6

The surgical instrument of Example 5, wherein the motor control algorithm, when executed by the surgical instrument, is configured to adjust at least one of the following; (1) the speed of the electric motor, (2) a motor speed command signal provided by a motor controller of the surgical instrument, (3) a voltage applied to the electric motor, (4) a pulse width modulation duty cycle, and (5) a current limit of a motor controller of the surgical instrument.

Example 7

The surgical instrument of Examples 1, 2, 3, 4, 5, or 6, wherein the control circuit is further configured to provide an indication of an impending failure of the surgical instrument.

Example 8

A surgical instrument comprising a drive system and a control circuit. The drive system comprises an electric motor. The control circuit comprises an acoustic sensor. The control circuit is configured to utilize a parameter of the drive system measured by the acoustic sensor to control a torque applied by the electric motor.

Example 9

The surgical instrument of Example 8, wherein the drive system further comprises a gear box and a drive train.

Example 10

The surgical instrument of Examples 8 or 9, wherein the control circuit further comprises a fast Fourier transform circuit.

Example 11

The surgical instrument of Examples 8, 9, or 10, wherein the control circuit is further configured to determine a degradation of the drive system.

Example 12

The surgical instrument of Example 11, wherein the control circuit is further configured to adjust a motor control algorithm in response to the determined degradation of the drive system.

Example 13

The surgical instrument of Example 12, wherein the motor control algorithm, when executed by the surgical instrument, is configured to adjust at least one of the following; (1) the speed of the electric motor, (2) a motor speed command signal provided by a motor controller of the surgical instrument, (3) a voltage applied to the electric motor, (4) a pulse width modulation duty cycle, and (5) a current limit of a motor controller of the surgical instrument.

Example 14

The surgical instrument of Examples 8, 9, 10, 11, 12, or 13, wherein the control circuit is further configured to provide an indication of an impending failure of the surgical instrument.

Example 15

A surgical system comprising a surgical instrument and a surgical hub system. The surgical instrument comprises a drive system and a control circuit. The drive system comprises an electric motor. The control circuit comprises a sensing device. The control circuit is configured to utilize a parameter of the drive system sensed by the sensing device to control a speed of the electric motor. The surgical hub system is in communication with the surgical instrument. The surgical hub system is configured to supply a second parameter to the control circuit. The control circuit is further configured to utilize the second parameter to modify an operation of the surgical instrument.

Example 16

The surgical system of Example 15, wherein the sensing device comprises at least one of the following; (1) an acoustic sensor, (2) a vibration sensor, and (3) an accelerometer.

Example 17

The surgical system of Examples 15 or 16, wherein the control circuit further comprises a fast Fourier transform circuit.

Example 18

The surgical system of Examples 15, 16, or 17, wherein the second parameter comprises the presence of a previous stapling line in the tissue of the patient.

Example 19

The surgical system of Examples 15, 16, or 17, wherein the second parameter comprises the presence of a gastric band in the tissue of the patient.

Example 20

The surgical system of Examples 15, 16, or 17, wherein the second parameter comprises the presence of scarred tissue from a previous surgical procedure.

Example 21

The surgical system of Examples 15, 16, 17, 18, 19, or 20, wherein the surgical hub system is further configured to predict a failure of the surgical instrument.

Example 22

The surgical system of Examples 15, 16, 17, 18, 19, or 20, wherein the surgical hub system is further configured to provide a notification of a predicted failure of the surgical instrument.

Example 23

The surgical system of Examples 15, 16, 17, 18, 19, or 20, wherein the surgical hub system is further configured to communicate a predicted failure of the surgical instrument to the surgical instrument.

Example Set 8

Example 1

A surgical instrument comprising a body, a shaft, and a control circuit comprising at least one sensing device. The control circuit is configured to determine a presence of another surgical instrument proximate to the surgical instrument within an environment of a surgical procedure.

Example 2

The surgical instrument of Example 1, wherein the surgical instrument comprises a monopolar surgical instrument.

Example 3

The surgical instrument of Examples 1 or 2, wherein the at least one sensing device comprises a passive sensing device.

Example 4

The surgical instrument of Example 3, wherein the passive sensing device is configured to be activated by a magnetic field associated with the another surgical instrument.

Example 5

The surgical instrument of Examples 3 or 4, wherein the passive sensing device is configured to be activated by an electric field associated with the another surgical instrument.

Example 6

The surgical instrument of Example 2, wherein the at least one sensing device comprises a continuity sensor and is positioned on at least one of the following; (1) a body of the monopolar surgical instrument and (2) a shaft of the monopolar surgical instrument.

Example 7

The surgical instrument of Examples 1, 2, 3, 4, 5, or 6, wherein the at least one sensing device comprises a proximity sensor configured to detect the presence of the another surgical instrument within the environment of the surgical procedure.

Example 8

The surgical instrument of Example 7, wherein the proximity sensor comprises one of the following; (1) an inductive proximity sensor and (2) a capacitive proximity sensor.

Example 9

The surgical instrument of Examples 1, 2, 3, 4, 5, 6, 7, or 8, wherein the at least one sensing device comprises an electrical sensing grid.

Example 10

The surgical instrument of Examples 1, 2, 3, 4, 5, 6, 7, 8, or 9, wherein the control circuit is further configured to determine electrical continuity within the surgical instrument.

Example 11

The surgical instrument of Examples 1, 2, 3, 4, 5, 6, 7, 8, 9, or 10, wherein the control circuit is further configured to determine electrical continuity within an electrical circuit configured to carry electrosurgical energy.

Example 12

A surgical instrument comprising a transmitter, a receiver, and a control circuit. The transmitter is configured to transmit a signal. The receiver is configured to receive a reflected signal associated with the transmitted signal. The control circuit is configured to determine a proximity of another surgical instrument to the surgical instrument based on the reflected signal.

Example 13

The surgical instrument of Example 12, wherein the transmitter comprises a magnetic transmitter.

Example 14

The surgical instrument of Examples 12 or 13, wherein the transmitter is further configured to generate random sequenced on-off pulses.

Example 15

The surgical instrument of Examples 12, 13, or 14, wherein at least one of the following forms a part of a flexible circuit; (1) the transmitter and (2) the receiver.

Example 16

A surgical instrument comprising a transmitter and a transducer. The transmitter is configured to transmit a signal.

The transducer is configured to sense a primary magnetic field associated with the transmitter. The surgical instrument further comprises means for determining a proximity of another surgical instrument to the surgical instrument based on a condition of the primary magnetic field.

Example 17

The surgical instrument of Example 16, wherein the transmitter comprises a magnetic transmitter.

Example 18

The surgical instrument of Examples 16 or 17, wherein the transducer comprises a Hall-effect sensor.

Example 19

The surgical instrument of Examples 16, 17, or 18, wherein the condition comprises one of the following; (1) an unaffected condition which is indicative of there being no object comprising a metal proximate to the surgical instrument and (2) an affected condition which is indicative of there being an object comprising a metal proximate to the surgical instrument.

Example 20

The surgical instrument of Example 19, wherein the object comprises the another surgical instrument.

Example Set 9

Example 1

A surgical instrument comprising a shaft, a sensing array positioned within the shaft, and a detection circuit electrically coupled to the sensing array. The detection circuit is configured to determine when a fluid originating from an environment external to the shaft is present within the shaft.

Example 2

The surgical instrument of Example 1, wherein the sensing array forms a part of a flexible circuit.

Example 3

The surgical instrument of Examples 1 or 2, wherein the sensing array comprises first and second sensing devices.

Example 4

The surgical instrument of Example 3, wherein the first and second sensing devices comprise electrically conductive electrodes.

Example 5

The surgical instrument of Example 3, wherein the sensing array further comprises third and fourth sensing devices.

Example 6

The surgical instrument of Example 3, further comprising an electrically insulative material positioned between the first and second sensing devices.

Example 7

The surgical instrument of Example 6, wherein the electrically insulative material forms a part of a flexible circuit.

Example 8

The surgical instrument of Examples 1, 2, 3, 4, 5, 6, or 7, further comprising an absorption material positioned within the shaft.

Example 9

The surgical instrument of Example 8, wherein the absorption material comprises a ring of absorption material which is concentric with the shaft.

Example 10

The surgical instrument of Examples 1, 2, 3, 4, 5, 6, 7, 8, or 9, further comprising an electrical circuit electrically connected to the sensing array, wherein the electrical circuit is configured to determine whether an amount of the fluid within the shaft is greater than a threshold amount.

Example 11

The surgical instrument of Example 10, wherein the electrical circuit comprises at least one comparator.

Example 12

The surgical instrument of Example 10, wherein the electrical circuit comprises a plurality of comparators.

Example 13

The surgical instrument of Examples 1, 2, 3, 4, 5, 6, 7, 8, 9, 10, 11, or 12, further comprising a control circuit couplable to the detection circuit, wherein the control circuit is configured to adjust an operation of the surgical instrument based on a signal from the detection circuit.

Example 14

A surgical instrument comprising a sensing device and a control circuit. The sensing device is configured to sense an atmospheric pressure. The control circuit is configured to determine an altitude of the surgical instrument based on the sensed atmospheric pressure. The control circuit is further configured to adjust at least one of the following based on the sensed atmospheric pressure; (1) a threshold utilized by the control circuit and (2) a control parameter of the surgical instrument.

Example 15

The surgical instrument of Example 14, wherein the threshold comprises at least one of the following; (1) a temperature threshold and (2) an energy threshold.

Example 16

The surgical instrument of Examples 14 or 15, wherein the control parameter comprises a motor speed.

Example 17

The surgical instrument of Examples 14, 15, or 16, wherein the control circuit is further configured to determine a de-rating factor based on the sensed atmospheric pressure.

Example 18

A surgical instrument comprising a handle assembly, at least one sensing device, and a control circuit. The handle assembly comprises a housing. The at least one sensing device is positioned within the housing and is configured to measure a temperature. The control circuit is configured to determine whether at least one of the following is operating in a danger zone based on the measured temperature: (1) an electrical component of the surgical instrument and (2) a sub-assembly of the surgical instrument.

Example 19

The surgical instrument of Example 18, wherein the at least one sensing device forms a part of a flexible circuit.

Example 20

The surgical instrument of Examples 18 or 19, wherein the control circuit is further configured to adjust an operation of the surgical instrument based on the measured temperature.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

The surgical instrument systems described herein can be used in connection with the deployment and deformation of staples. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

The entire disclosures of:

U.S. patent application Ser. No. 11/013,924, entitled TROCAR SEAL ASSEMBLY, now U.S. Pat. No. 7,371,227;

U.S. patent application Ser. No. 11/162,991, entitled ELECTROACTIVE POLYMER-BASED ARTICULATION MECHANISM FOR GRASPER, now U.S. Pat. No. 7,862,579;

U.S. patent application Ser. No. 12/364,256, entitled SURGICAL DISSECTOR, now U.S. Patent Application Publication No. 2010/0198248;

U.S. patent application Ser. No. 13/536,386, entitled EMPTY CLIP CARTRIDGE LOCKOUT, now U.S. Pat. No. 9,282,974;

U.S. patent application Ser. No. 13/832,786, entitled CIRCULAR NEEDLE APPLIER WITH OFFSET NEEDLE AND CARRIER TRACKS, now U.S. Pat. No. 9,398,905;

U.S. patent application Ser. No. 12/592,174, entitled APPARATUS AND METHOD FOR MINIMALLY INVASIVE SUTURING, now U.S. Pat. No. 8,123,764;

U.S. patent application Ser. No. 12/482,049, entitled ENDOSCOPIC STITCHING DEVICES, now U.S. Pat. No. 8,628,545;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 14/200,111, entitled CONTROL SYSTEMS FOR SURGICAL INSTRUMENTS, now U.S. Pat. No. 9,629,629;

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;

U.S. patent application Ser. No. 14/248,587, entitled POWERED SURGICAL STAPLER, now U.S. Pat. No. 9,867,612;

U.S. patent application Ser. No. 12/945,748, entitled SURGICAL TOOL WITH A TWO DEGREE OF FREEDOM WRIST, now U.S. Pat. No. 8,852,174;

U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;

International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Pat. No. 10,117,702;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
an electric motor; and
a control circuit, comprising:
a plurality of logic gates; and
a monostable multivibrator connected to a first one of the logic gates, wherein the control circuit is configured to alter a rate of action of a function of the surgical instrument by controlling a speed of rotation of the electric motor based on a sensed parameter, wherein the function of the surgical instrument comprises an articulation of an end effector of the surgical instrument, and wherein controlling the speed of rotation of the electric motor comprises controlling the speed of rotation of the electric motor to articulate the end effector at a first non-zero speed or a second non-zero speed greater than the first non-zero speed.

2. The surgical instrument of claim 1, wherein the plurality of logic gates includes at least one of the following:
an AND gate;
an OR gate; and
an inverter gate.

3. The surgical instrument of claim 1, wherein the monostable multivibrator comprises a retriggerable monostable multivibrator.

4. The surgical instrument of claim 1, wherein the rate of action comprises a speed of the articulation of the end effector away from a longitudinal axis of a shaft of the surgical instrument.

5. The surgical instrument of claim 4, wherein the speed of the articulation is slowed as the end effector passes through a zone defined around a centered state of a shaft of the surgical instrument.

6. The surgical instrument of claim 1, wherein the sensed parameter comprises a sensed position of the end effector relative to a longitudinal axis of a shaft of the end effector.

7. The surgical instrument of claim 1, wherein the sensed parameter comprises a state of a switching device.

8. The surgical instrument of claim 1, wherein the control circuit further comprises an asynchronous counter connected to the monostable multivibrator.

9. The surgical instrument of claim 1, wherein the control circuit further comprises a ripple counter connected to the monostable multivibrator.

10. The surgical instrument of claim 1, further comprising a sensing device connected to the monostable multivibrator.

11. The surgical instrument of claim 1, further comprising a motor controller configured to control the speed of rotation of the electric motor.

12. A surgical instrument, comprising:
an end effector;
an electric motor; and
a control circuit, comprising:
a logic gate; and a monostable multivibrator connected to the logic gate, wherein the control circuit is configured to alter a rate of action of a function of the surgical instrument by controlling a speed of rotation of the electric motor based on a sensed parameter, wherein the function of the surgical instrument comprises a rotation of the end effector about an axis, wherein controlling the speed of rotation of the electric motor comprises controlling the speed of rotation of the electric motor to rotate the end effector about the axis at a first non-zero speed or a second non-zero speed greater than the first non-zero speed.

13. The surgical instrument of claim 12, wherein the logic gate includes at least one of the following:
an AND gate;
an OR gate; and
an inverter gate.

14. The surgical instrument of claim 12, wherein the monostable multivibrator comprises a retriggerable monostable multivibrator.

15. The surgical instrument of claim 12, wherein the rate of action comprises a speed of the rotation of the end effector.

16. The surgical instrument of claim 15, wherein the speed of the rotation is slowed as the end effector passes through a pre-identified zone.

17. The surgical instrument of claim 12, wherein the sensed parameter comprises a sensed position of the end effector relative to a pre-identified position.

18. The surgical instrument of claim 12, wherein the sensed parameter comprises a state of a switching device.

19. The surgical instrument of claim 12, wherein the control circuit further comprises an asynchronous counter connected to the monostable multivibrator.

20. The surgical instrument of claim 12, wherein the control circuit further comprises a ripple counter connected to the monostable multivibrator.

21. The surgical instrument of claim 12, further comprising a sensing device connected to the monostable multivibrator.

22. The surgical instrument of claim 12, further comprising a motor controller configured to control the speed of rotation of the electric motor.

* * * * *